(12) United States Patent
Shinohata et al.

(10) Patent No.: US 9,145,357 B2
(45) Date of Patent: Sep. 29, 2015

(54) N-SUBSTITUTED CARBAMIC ACID ESTER PRODUCTION METHOD, ISOCYANATE PRODUCTION METHOD USING SUCH N-SUBSTITUTED CARBAMIC ACID ESTER, AND COMPOSITION FOR TRANSFER AND STORAGE OF N-SUBSTITUTED CARBAMIC ACID ESTER COMPRISING N-SUBSTITUTED CARBAMIC ACID ESTER AND AROMATIC HYDROXY COMPOUND

(71) Applicant: Asahi Kasei Chemicals Corporation, Tokyo (JP)

(72) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 14/151,178

(22) Filed: Jan. 9, 2014

(65) Prior Publication Data

US 2014/0194650 A1 Jul. 10, 2014

Related U.S. Application Data

(62) Division of application No. 12/810,668, filed as application No. PCT/JP2009/005007 on Sep. 29, 2009, now Pat. No. 8,658,819.

(30) Foreign Application Priority Data

Aug. 21, 2009 (JP) .................. 2009-192250
Aug. 21, 2009 (JP) .................. 2009-192268

(51) Int. Cl.
| | | |
|---|---|---|
| C07C 263/00 | (2006.01) | |
| C07C 263/04 | (2006.01) | |
| C07C 275/40 | (2006.01) | |
| C07C 269/00 | (2006.01) | |
| C07C 269/04 | (2006.01) | |
| C07C 271/54 | (2006.01) | |
| C07C 271/56 | (2006.01) | |
| C07C 271/58 | (2006.01) | |

(52) U.S. Cl.
CPC ............. *C07C 275/40* (2013.01); *C07C 263/04* (2013.01); *C07C 269/00* (2013.01); *C07C 269/04* (2013.01); *C07C 271/54* (2013.01); *C07C 271/56* (2013.01); *C07C 271/58* (2013.01); *C07C 2101/14* (2013.01)

(58) Field of Classification Search
CPC .......................... C07C 263/00; C07C 263/04
See application file for complete search history.

(56) References Cited

U.S. PATENT DOCUMENTS

| | | |
|---|---|---|
| 2,145,242 A | 1/1939 | Arnold |
| 2,409,701 A | 10/1946 | Loth |
| 2,409,712 A | 10/1946 | Schweitzer |
| 2,677,698 A | 5/1954 | Deutschman, Jr. et al. |
| 2,692,275 A | 10/1954 | Bortnick |
| 3,466,346 A | 9/1969 | Graff et al. |
| 3,734,941 A | 5/1973 | Sydor |
| 3,873,553 A | 3/1975 | Hearsey |
| 3,992,430 A | 11/1976 | Baeskai |
| 3,993,430 A | 11/1976 | Forker |
| 4,081,472 A | 3/1978 | Tsumura et al. |
| 4,097,676 A | 6/1978 | Romano |
| 4,290,970 A | 9/1981 | Merger et al. |
| 4,297,501 A | 10/1981 | Becker et al. |
| 4,381,404 A | 4/1983 | Buysch et al. |
| 4,388,238 A | 6/1983 | Heitkamper et al. |
| 4,388,246 A | 6/1983 | Sundermann et al. |

(Continued)

FOREIGN PATENT DOCUMENTS

| | | |
|---|---|---|
| CA | 2033634 A1 | 7/1991 |
| CA | 2094484 A1 | 10/1993 |

(Continued)

OTHER PUBLICATIONS

Office Action issued in related Canadian Patent Application No. 2707336 dated Feb. 27, 2012.

(Continued)

*Primary Examiner* — Samantha Shterengarts
(74) *Attorney, Agent, or Firm* — Morgan, Lewis & Bockius LLP

(57) ABSTRACT

The present invention is a method for producing an N-substituted carbamic acid ester derived from an organic amine from an organic amine, a carbonic acid derivative and a hydroxy composition containing one or more types of hydroxy compounds, wherein the organic amine, the carbonic acid derivative and the hydroxy composition are reacted using a urethane production reaction vessel provided with a condenser, a gas containing the hydroxy composition, the compound having the carbonyl group derived from the carbonic acid derivative, and an ammonia formed as a by-product in the reaction, is introduced into the condenser provided in the urethane production reaction vessel, and the hydroxy composition and the compound having the carbonyl group derived from the carbonic acid derivative are condensed, and wherein a stoichiometric ratio of a hydroxy compound contained in the condensed hydroxy composition to the condensed compound having the carbonyl group derived from the carbonic acid derivative is 1 or more, and a ratio of number of carbonyl groups (—C(=O)—) contained in the compound having the carbonyl group derived from the carbonic acid derivative and number of ammonia molecules contained in the ammonia recovered as a gas from the condenser is 1 or less.

11 Claims, 29 Drawing Sheets

(56) References Cited

U.S. PATENT DOCUMENTS

| | | | |
|---|---|---|---|
| 4,388,426 | A | 6/1983 | Schure et al. |
| 4,430,505 | A | 2/1984 | Heitkamper et al. |
| 4,480,110 | A | 10/1984 | Heitkamper et al. |
| 4,482,499 | A | 11/1984 | Merger et al. |
| 4,497,963 | A | 2/1985 | Merger et al. |
| 4,514,339 | A | 4/1985 | Romano et al. |
| 4,611,079 | A | 9/1986 | Merger et al. |
| 4,692,550 | A | 9/1987 | Engbert et al. |
| 4,713,476 | A | 12/1987 | Merger et al. |
| 4,925,971 | A | 5/1990 | Aoki et al. |
| 5,087,739 | A | 2/1992 | Bohmholdt et al. |
| 5,360,931 | A | 11/1994 | Bohmholdt et al. |
| 5,386,053 | A | 1/1995 | Otterbach et al. |
| 5,744,633 | A | 4/1998 | Wilmes et al. |
| 6,111,138 | A | 8/2000 | Van Wijck et al. |
| 7,122,697 | B2 | 10/2006 | Yoshida et al. |
| 2006/0025626 | A1 | 2/2006 | Kohlstruk et al. |
| 2008/0227999 | A1 | 9/2008 | Molzahn |
| 2010/0029981 | A1 | 2/2010 | Shinohata et al. |
| 2010/0036154 | A1 | 2/2010 | Michalczak et al. |
| 2010/0069665 | A1 | 3/2010 | Shinohata et al. |
| 2010/0113823 | A1 | 5/2010 | Shinohata et al. |
| 2010/0274046 | A1 | 10/2010 | Kloetzer et al. |
| 2013/0178643 | A1 | 7/2013 | Shinohata et al. |

FOREIGN PATENT DOCUMENTS

| | | |
|---|---|---|
| CA | 2707336 A1 | 2/2011 |
| CN | 1251088 A | 4/2000 |
| CN | 101234998 A | 8/2008 |
| CN | 101374802 A | 2/2009 |
| DE | 1042891 B | 11/1956 |
| DE | 3928595 A1 | 3/1991 |
| EP | 0355443 A2 | 2/1990 |
| EP | 0566925 A2 | 10/1993 |
| EP | 0568782 A2 | 11/1993 |
| EP | 0657420 A1 | 6/1995 |
| JP | 52-071433 A | 6/1977 |
| JP | 56-103152 A | 8/1981 |
| JP | 56-103153 A | 8/1981 |
| JP | 57-112363 A | 7/1982 |
| JP | 59-108754 | 6/1984 |
| JP | H01-203356 A | 8/1989 |
| JP | 2000759 A | 1/1990 |
| JP | H02-000262 A | 1/1990 |
| JP | 03-020254 A | 1/1991 |
| JP | 03-184947 A | 8/1991 |
| JP | 04-164060 | 6/1992 |
| JP | H04-221359 A | 8/1992 |
| JP | 05-310677 A | 11/1993 |
| JP | 06-41045 A | 2/1994 |
| JP | 06-192204 | 7/1994 |
| JP | 06-239826 | 8/1994 |
| JP | 07-157463 A | 6/1995 |
| JP | 08-109118 A | 4/1996 |
| JP | 08-277255 A | 10/1996 |
| JP | H08-277257 A | 10/1996 |
| JP | H09-255630 A | 9/1997 |
| JP | 2804132 B2 | 7/1998 |
| JP | 2804232 B2 | 7/1998 |
| JP | 3382289 B2 | 12/2002 |
| JP | 57-091967 A | 1/2009 |
| TW | 200930693 A | 7/2009 |
| WO | 2008/059953 A1 | 5/2008 |
| WO | 2008/084824 A1 | 7/2008 |
| WO | 2008/120645 A1 | 10/2008 |

OTHER PUBLICATIONS

Office Action issued in related Chinese Patent Application No. 200980124092.1 dated Dec. 28, 2012.

Office Action issued in related Chinese Patent Application No. 200980160125.8 dated May 22, 2013.

Search Report issued in related International Patent Application No. PCT/JP2012/054148 dated May 15, 2012.

Office Action issued in related Japanese Patent Application No. 2012-088122 dated Jun. 1, 2012.

Office Action issued in related Japanese Patent Application No. 2010-53996 dated Feb. 23, 2010.

Office Action issued in related Taiwanese Patent Application No. 101105787 dated Oct. 17, 2013.

Office Action issued in related U.S. Appl. No. 13/001,238 dated Apr. 29, 2013.

Office Action issued in related U.S. Appl. No. 13/821,818 dated Dec. 19, 2013.

Office Action issued in related Taiwanese Patent Application No. 098134456 dated Apr. 13, 2012.

Yadav et al., "Three Component Coupling Strategy for Expeditious Synthesis of 4-Aminobenzolxazinones on Mineral Support," SYNLETT, 3055-3058 (2005).

Harris et al., "Thermal oligomerization of N,N-(1,6-hexanediyl)bisurea," Polymer, 35: 3766-3768 (1994).

Katchalski et al., "The Chemical Structure of Some Diamine Carbamates," Journal of American Chemical Society, 73: 1829-1831 (1951).

Hoffman, "Ueber die aromatischen Cyanate," Berchte der Deutechen Chemiscen Gesellschaft, 3: 653-658 (1870).

Schiff, "Ueber die aromatischen Cyanate," Berchte der Deutechen Chemiscen Gesellschaft, 3: 649-652 (1870).

Bayer, "Das Diisocyanat-Polyadditionsverfahren," Historische Entwicklung und chemische Grundlagen (1963).

Miyake, "Reactions of Amines with Urea and its Derivatives, III, Reactions of Urea with Diamines," Journal of Synthetic Organic Chemistry, 20: 1003-1008 (1962).

Yukikagaku-Seikagaku Meimeihou, Organic Chemistry and Biochemistry Nomenclature (2nd revision published in Japan in 1992 by Nonkodo Co., Ltd.

Recommendations 1979, IUPAC Nomenclature of Organic Chemistry, Advanced Chemistry Development, Inc., Oxford: Pergamon Press, 1979.

Recommendations 1993, IUPAC Nomenclature of Organic Chemistry, Blackwell Scientific Publications, 1993.

Gittos et al., "A New Synthesis of Isocyantes," Journal of the Chemical Society, Perkin Transactions I: Organic and Bio-Organic Chemistry (1972-1999) 141-143 (1976).

Stedman et al., :The Methylurethanes of the Isomerie a-Hydroxyphenylethyldimethylamines and their Miotic Acticity, Journal of the Chemical Society, 609-617 (1929).

Dyer et al., "Thermal Degradation of Alkyl N-Phenylcarbamates," Journal of the American Chemical Society, 81: 2138-2143 (1959).

N-SUBSTITUTED CARBAMIC ACID ESTER PRODUCTION METHOD, ISOCYANATE PRODUCTION METHOD USING SUCH N-SUBSTITUTED CARBAMIC ACID ESTER, AND COMPOSITION FOR TRANSFER AND STORAGE OF N-SUBSTITUTED CARBAMIC ACID ESTER COMPRISING N-SUBSTITUTED CARBAMIC ACID ESTER AND AROMATIC HYDROXY COMPOUND

TECHNICAL FIELD

The present invention relates to a method for producing N-substituted carbamic acid ester, a method for producing isocyanate that uses that N-substituted carbamic acid ester, and a composition for transferring and storing N-substituted carbamic acid ester comprising an N-substituted carbamic acid ester and an aromatic hydroxy compound.

BACKGROUND ART

Isocyanates are widely used as production raw materials of such products as polyurethane foam, paints and adhesives. The main industrial production method of isocyanates comprises reacting an amine with phosgene (phosgene method), and nearly the entire amount of isocyanates produced throughout the world are produced according to the phosgene method. However, the phosgene method has numerous problems.

Firstly, this method requires the use of a large amount of phosgene as raw material. Phosgene is extremely toxic and requires special handling precautions to prevent exposure of handlers thereof, and also requires special apparatuses to detoxify waste.

Secondly, since highly corrosive hydrogen chloride is produced in large amounts as a by-product of the phosgene method, in addition to requiring a process for detoxifying the hydrogen chloride, in many cases hydrolytic chlorine is contained in the isocyanates produced, which may have a detrimental effect on the weather resistance and heat resistance of polyurethane products in the case of using isocyanates produced using the phosgene method.

On the basis of this background, a method for producing isocyanate compounds is sought that does not use phosgene.

Although examples of such methods include a method for synthesizing aliphatic isocyanate from an aliphatic nitro compound and carbon monoxide, and a method for converting an aliphatic amide compound to isocyanate by Hoffmann decomposition, both of these methods have poor yield and are inadequate for industrial application.

Methods for obtaining an isocyanate and a hydroxy compound by thermal decomposition of N-substituted carbamic acid ester have long been known, an example of which may include the method of A. W. Hoffmann (see Non-Patent Document 1). This method enables a high yield to be achieved more easily than the methods described above, and the basic reactions employed in this method are indicated below:

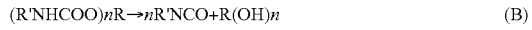

(wherein R represents an organic residue having a valence of n, R' represents a monovalent organic residue, and n represents an integer of 1 or more). Thermal decomposition represented by the above general formulas is reversible, and although the equilibrium thereof is biased towards the N-substituted carbamic acid ester on the left side at low temperatures, the side with the isocyanate and hydroxy compound is advantageous at high temperatures.

In this manner, thermal decomposition of N-substituted carbamic acid ester is associated with harsh reaction conditions, such as being carried out at high temperatures, as well as the concomitant occurrence of various irreversible side reactions.

As indicated in the publication by Schiff (see Non-Patent Document 2) and the research by E. Dyer and G. C. Wright (see Non-Patent Document 3), examples of such side reactions may include those resulting in the formation of substituted ureas, biurets, urethodiones, carbodiimides and isocyanurates.

These side reactions not only cause decreases in selectivity and yield of the target isocyanate, but also induce the formation of polymers during the production of polyisocyanate in particular, and depending on the case, can cause a situation that makes long-term operation difficult, such as causing the reactor to be clogged by precipitation of polymeric solids.

The majority of undesirable side reactions occur at higher temperatures, have a long reaction time, and the formed isocyanate tends to increase the longer the duration of contact with each component of the reaction mixture.

Various methods have been proposed thus far relating to the obtaining of a favorable isocyanate yield by inhibiting the formation of products of undesirable side reactions during thermal decomposition of N-substituted carbamic acid esters.

First, with respect to methods for producing an intermediate in the form of N-substituted carbamic acid ester, several methods have been disclosed for producing N-substituted carbamic acid ester that do not use phosgene. For example, Patent Document 1 describes a method for oxidative urethanation from a primary amine, carbon monoxide and an aliphatic alcohol or aromatic hydroxy compound using a precious metal catalyst. However, since this method uses highly toxic carbon monoxide and an expensive precious metal catalyst, it has problems such as requiring a complicated procedure and excessive cost to recover the catalyst from the product in the form of N-substituted carbamic acid ester.

In addition, Patent Document 2 describes a method for producing N-substituted carbamic acid-O-aryl ester by reacting an N-alkyl-N,N'-dialkyl urea, an aromatic hydroxy compound and hydrogen chloride gas. However, this method uses corrosive hydrogen chloride gas, consumes an expensive and uncommon urea compound, and has the problem of requiring a complicated procedure and excessive cost to recover the N-substituted carbamic acid-O-aryl ester from a hydrochloride of N,N'-dialkylamine formed as a by-product.

Methods using urea or a carbonic acid derivative (such as carbonic acid ester or carbamic acid ester) have been proposed as methods for producing N-substituted carbamic acid ester that are alternatives to methods using expensive raw materials or catalysts and the like in the manner of the methods described above.

Patent Document 3 describes a method for producing aliphatic N-substituted carbamic acid ester that does not use phosgene in which a 1,3-di-substituted urea is produced from a primary amine and urea in a first stage, and an N-substituted carbamic acid ester is produced by reacting the 1,3-di-substituted urea with a hydroxy compound followed by separating and recovering the primary amine produced as a by-product and returning it to the first stage in a second stage. However, not only is the yield of the N-substituted carbamic acid ester formed low, but recycling equipment is required for the primary amine, thereby making the process extremely complicated and making this method unsatisfactory for industrial application.

An example of a method for producing N-substituted carbamic acid-O-alkyl ester using urea or a carbonic acid derivative is disclosed in Patent Document 4 in which a diamine, an alcohol and urea are reacted to convert to an N-substituted carbamic acid-O-alkyl ester. Patent Document 5 discloses a method for producing N-substituted carbamic acid-O-alkyl ester after first producing bis-urea from an aliphatic primary polyamine, urea and alcohol, while Patent Document 6 discloses a method for producing N-substituted carbamic acid-O-alkyl ester by partially reacting urea and alcohol in a first step and then supplying a diamine in a subsequent second step.

However, since the N-substituted carbamic acid-O-alkyl esters produced by these methods are thermally extremely stable, a thermal decomposition reaction that produces isocyanates from these N-substituted carbamic acid-O-alkyl esters requires a high temperature that causes the formation of polymers due to undesirable side reactions (for example those represented by the formulas (C) to (E) indicated below). In addition, although urea is generally added in excess to obtain N-(aliphatic)-substituted-O-alkyl urethane at high yield, since the residual excess urea itself undergoes a thermal decomposition reaction at temperatures of 130° C. or higher, isocyanic acid and ammonia gas are generated (see, for example formula (F) indicated below), or the isocyanic acid forms biurets that further undergo thermal decomposition at temperatures of 200° C. or higher (see, for example, formulas (G) and (H) indicated below), thereby contributing to the formation of polymers and the like (see, for example, formulas (I) to (L) indicated below). Since these polymers and the like have extremely low solubility in solvents and the like, they frequently adhere or solidify to the reaction vessel, thereby making these methods industrially unsatisfactory. In addition, since there is no description regarding recovery of the urea or carbonic acid derivative used in excess, increases in the amount of urea or carbonic acid derivative used were unable to be avoided.

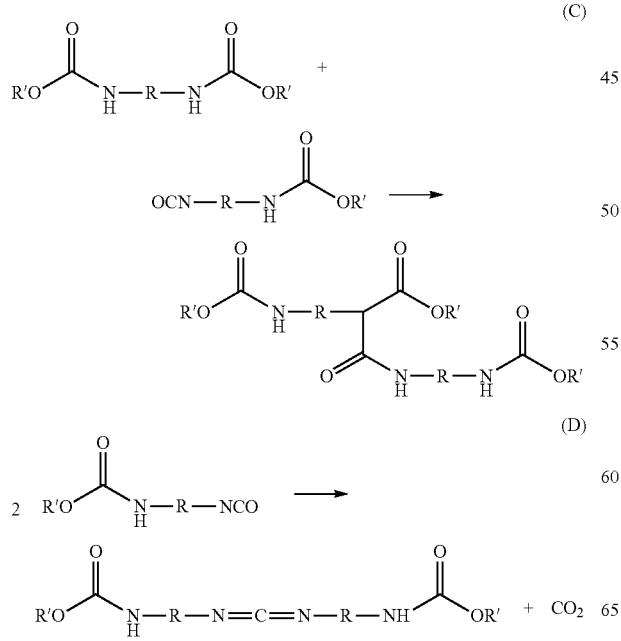

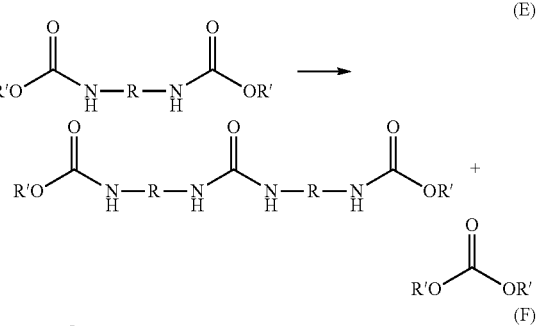

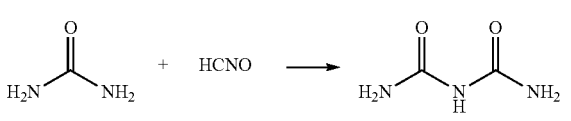

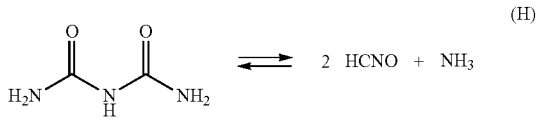

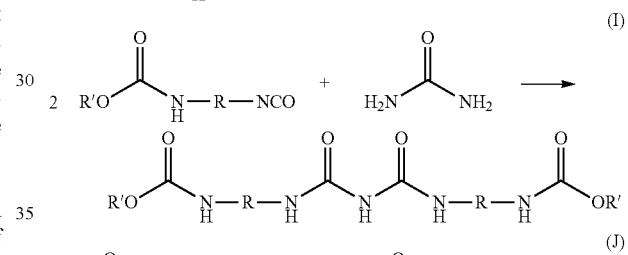

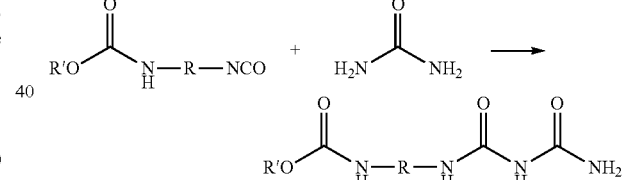

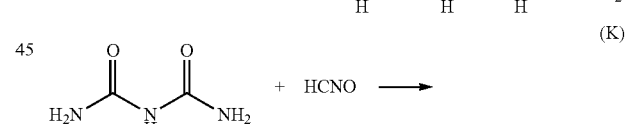

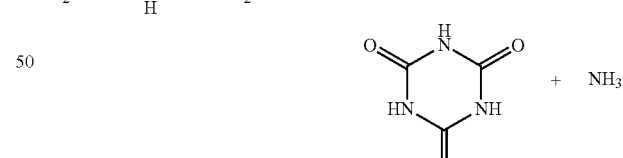

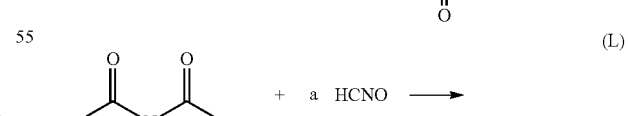

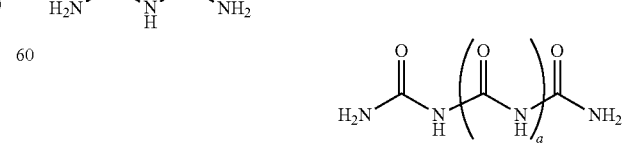

(wherein R represents an organic residue, R' represents an aliphatic group, and a represents an integer of 0 or more.)

Furthermore, for the sake of simplifying the explanation, although the above formulas indicate reactions in the case R represents a divalent organic residue and R' represents a monovalent organic residue, it can be easily surmised that similar reactions proceed even in the case both R and R' have a valence of 2 or more.

With respect to this point, N-substituted carbamic acid-O-aryl esters are known to easily decompose to their corresponding isocyanates and aromatic hydroxy compounds (see, for example, Non-Patent Document 4), and several methods for producing N-substituted carbamic acid-O-aryl esters have been disclosed.

Patent Document 7 discloses a method for producing an aliphatic N-substituted carbamic acid-O-aryl ester by a one-step reaction of urea, an aromatic hydroxy compound and an aliphatic primary amine. Patent Document 8 discloses a method for producing an N-substituted carbamic acid-O-aryl ester by reacting urea and an aromatic hydroxy compound in a first step followed by reacting with a primary amine in a second step.

In these methods as well, it is necessary to use an excess amount of urea or carbonic acid derivative with respect to the amino group of the aliphatic amine in order to improve yield based on the comparatively expensive aliphatic amine. However, since these patent documents also do not describe recovery of the urea or carbonic acid derivative used in excess, increases in the amounts of urea or carbonic acid derivative used were unable to be avoided.

Patent Document 9 discloses a method for producing an aliphatic N-substituted carbamic acid-O-aryl ester from an aliphatic primary polyamine, an aromatic hydroxy compound and urea and/or non-N-substituted carbamic acid-O-aryl compound, wherein the non-N-substituted carbamic acid-O-aryl compound is recovered from the resulting urethanation reaction solution and recycled as a raw material of the urethanation reaction. According to this method, an attempt is made to inhibit increases in basic units of the urea or non-N-substituted carbamic acid-O-aryl compound. This method comprises obtaining an aromatic hydroxy compound and isocyanic acid by thermal decomposition of a non-N-substituted carbamic acid-O-aryl compound contained in an urethanation reaction solution, reabsorbing the isocyanic acid formed by decomposition into the aromatic hydroxy compound, and then reacting with the aromatic hydroxy compound to recover the non-N-substituted carbamic acid-O-aryl compound. However, in addition to the procedure being complicated, the recovery rate of the non-N-substituted carbamic acid-O-aryl compound was unable to be made adequately satisfactory.

In the case of all of the methods described above, it is difficult to quantitatively obtain N-substituted carbamic acid-O-aryl ester by using urea and a non-N-substituted carbamic acid ester as raw materials, and not only are various structures of polymers formed (and in many cases containing polymers for which the structures thereof are unable to be identified), these polymers adhere to the reaction vessel or, as a result of these compounds being formed, there was the problem of increases in the amounts of urea and amine compounds used. In addition, when producing isocyanates by applying N-substituted carbamic acid-O-aryl ester to a thermal decomposition reaction, these polymers additionally form other polymers by reacting with isocyanates formed by thermal decomposition, which may also cause problems due to adhering to or solidifying in the reaction vessel.

Therefore, methods have been disclosed for enabling a solvent to be present during thermal decomposition of N-substituted carbamic acid-O-aryl esters or N-substituted carbamic acid-O-alkyl esters, for example, to avoid the problem of adhesion and solidification of polymers to the reaction vessel.

For example, according to the description of Patent Document 10, thermal decomposition of an aliphatic, alicyclic or aromatic polycarbamate is carried out at 150 to 350° C. and 0.001 to 20 bar in the presence of an inert solvent and in the presence or absence of a catalyst, auxiliary agent in the form of hydrogen chloride, organic acid chloride, alkylating agent or organic tin chloride. By-products formed can be removed continuously from the reaction vessel together with the reaction solution, for example, and a corresponding amount of fresh solvent or recovered solvent is added simultaneously. However, a disadvantage of this method is that, for example, a decrease in the production efficiency of polyisocyanate occurs due to the use of a refluxing solvent, and what is more, a large amount of energy is required, including that for recovering the solvent, for example. Moreover, the auxiliary agent used is volatile under the reaction conditions, thereby potentially contaminating the decomposition product. In addition, the amount of residue is large based on the amount of polyisocyanate formed, thereby making economic efficiency and reliability as an industrial method suspect.

Patent Document 11 describes one method for continuous thermal decomposition of a carbamate, such as an alicyclic diurethane in the form of 5-(ethoxycarbonylamino)-1-(ethoxycarbonylaminomethyl)-1,3,3-trimethylcyclohexane, supplied along the inner surface of a tubular reaction vessel in a liquid form in the presence of a high boiling point solvent. This method has the disadvantages of low yield and low selectivity during production of a (cyclic) aliphatic diisocyanate. In addition, there is no description of a continuous method accompanying recovery of rebonded or partially decomposed carbamate, and post-treatment of solvent containing by-products and catalyst is also not mentioned.

On the other hand, the description of Patent Document 12, for example, relates to a circulation method for producing (cyclic) aliphatic diisocyanate by converting a corresponding diamine to an N-substituted carbamic acid-O-alkyl ester followed by thermal decomposition of this N-substituted carbamic acid-O-alkyl ester as an example of a method for carrying out thermal decomposition of an N-substituted carbamic acid ester without using a solvent. This method minimizes the decrease in yield by recirculating the product from an N-substituted carbamic acid ester decomposition step to an N-substituted carbamic acid-O-alkyl ester formation step following reaction with alcohol. By-products that are unable to be recirculated are removed by distillative separation of a reaction mixture of the N-substituted carbamic acid-O-alkyl ester formation step. In this case, worthless residue forms in the form of bottom products while all comparatively low boiling point components, including N-substituted carbamic acid-O-alkyl ester, are removed from the top of the column. However, this method has the disadvantage of using a large amount of energy. This is because all of the N-substituted carbamic acid-O-alkyl ester is required to be evaporated in the presence of a catalyst, and this N-substituted carbamic acid-O-alkyl ester must also be evaporated at a temperature level within a range of the decomposition temperature of the N-substituted carbamic acid-O-alkyl ester. Isocyanate groups formed in useful products react with residual carbamic acid ester groups, frequently resulting in the formation of comparatively high molecular weight by-products that cause a reduction in yield, thereby continuing to fail to solve the problem of adhesion and solidification of polymers to the reaction vessel.

In addition, according to the description of Patent Document 13, a method is disclosed whereby worthless by-products are partially removed prior to carrying out thermal decomposition of N-substituted carbamic acid ester. The disadvantage of this method is that the yield of isocyanate decreases as a result of N-substituted carbamic acid ester being contained in the partially removed by-products. In addition, since polymeric compounds form and adhere to the reaction vessel as a result of heating of by-products remaining in the reaction vessel without being discharged from the reaction vessel, the problem of adhesion and solidification of polymers to the reaction vessel remains unsolved, and long-term, continuous operation is difficult.

As has been described above, a method for thermally decomposing a non-N-substituted carbamic acid-O-aryl ester contained in a reaction solution of an N-substituted carbamic acid ester production step to obtain an aromatic hydroxy compound and isocyanic acid, reabsorbing the isocyanic acid formed by decomposition in the aromatic hydroxy compound, and recovering a non-N-substituted carbamic acid-O-aryl compound by reacting with the aromatic hydroxy compound (see Patent Document 9) and a method for purifying by crystallization (see Patent Document 14) have been developed as described above to solve the problems. However, in the case of the former method, it is difficult to adequately reduce the amount of non-N-substituted carbamic acid-O-aryl compound in the reaction solution of the N-substituted carbamic acid ester production step. In addition, in the latter method employing crystallization as well, it is difficult to selectively crystallize compounds having a similar structure at high yield, while also resulting in the problem of consuming energy to separate a solid-solution and recover the crystallization solvent. In addition, a method has been disclosed for removing urea and carbonic acid derivatives from a reaction solution of an N-substituted carbamic acid ester production step more easily in which an amine compound, urea and alcohol are reacted, the resulting solution of N-substituted carbamic acid-O-alkyl ester is introduced into a distillation column, and urea and carbonic acid ester are recovered from the distillation column (see Patent Document 15). However, due to the low boiling point of the alcohol used, there are limitations on the set temperature and set pressure of the distillation column, thereby reducing the amount of urea in the N-substituted carbamic acid-O-alkyl ester solution, while the effect of inhibiting formation of by-products is not necessarily clear.

For example, it is described in Patent Document 16 that when an O-alkyl urethane obtained by reacting carbonic acid ester and organic amine is subjected to thermal decomposition in the presence of an aromatic hydroxy compound, a minute amount of carbonic acid derivatives are also present. Here, the effect of the carbonic acid derivatives is to improve thermal stability of the aromatic hydroxy compound, and is not intended to have an effect on an N-substituted carbamic acid-O-alkyl ester or an isocyanate formed during thermal decomposition. Moreover, there is no description regarding an effect on N-substituted carbamic acid-O-aryl ester. In addition, although Patent Document 15 describes a composition for transfer and storage of N-substituted carbamic acid-O-aryl ester that maintains the stability thereof by inhibiting a thermal denaturation reaction of N-substituted carbamic acid-O-alkyl ester, as well as an isocyanate production process that uses that composition, there is no mention of residual urea of urea-derived compounds as described above in that composition, and there is also no mention made of N-substituted carbamic acid-O-aryl ester.

Patent Document 1: U.S. Pat. No. 4,297,501
Patent Document 2: U.S. Pat. No. 3,873,553
Patent Document 3: U.S. Pat. No. 2,677,698
Patent Document 4: U.S. Pat. No. 4,713,476
Patent Document 5: European Patent Application No. 0568782
Patent Document 6: European Patent Application No. 0657420
Patent Document 7: U.S. Pat. No. 4,925,971
Patent Document 8: Japanese Patent Application Laid-open No. H4-164060
Patent Document 9: Japanese Patent Application Laid-open No. H7-157463
Patent Document 10: U.S. Pat. No. 4,388,246
Patent Document 11: U.S. Pat. No. 4,692,550
Patent Document 12: European Patent Application No. 0355443
Patent Document 13: Japanese Patent No. 3382289
Patent Document 14: Japanese Patent No. 2804232
Patent Document 15: WO 2008/120645
Patent Document 16: WO 2008/084824
Non-Patent Document 1: Berchte der Deutechen Chemischen Gesellschaft, Vol. 3, p. 653, 1870
Non-Patent Document 2: Berchte der Deutechen Chemischen Gesellschaft, Vol. 3, p. 649, 1870
Non-Patent Document 3: Journal of American Chemical Society, Vol. 81, p. 2138, 1959
Non-Patent Document 4: O. Bayer, Das Diisocyanat-Polyaditions Verfahren, p. 12, 1963
Non-Patent Document 5: Journal of Synthetic Organic Chemistry, Japan, Vol. 20, No. 11, p. 1003, 1962

DISCLOSURE OF INVENTION

Problems to be Solved by the Invention

In this manner, problems involving the formation of polymers by residual urea and urea-derived compounds and the adhesion of these polymers to the reaction vessel have yet to be solved in the production of isocyanates by thermal decomposition of N-substituted carbamic acid esters, and particularly N-substituted carbamic acid-O-aryl compounds.

In addition, urea and carbonic acid derivatives, which are used in excess during production of N-substituted carbamic acid ester, have also been determined to cause other problems as well.

In production methods of N-substituted carbamic acid-O-alkyl esters or N-substituted carbamic acid-O-aryl esters that use urea and carbonic acid derivatives, ammonia formed as a by-product must be extracted outside the system in order to increase the yield of the N-substituted carbamic acid ester (see, for example, Patent Document 7). In many cases, by-product ammonia is removed from the system by providing a line for discharging ammonia in the reaction vessel for producing the N-substituted carbamic acid ester. Urea and carbonic acid derivatives themselves undergo a thermal decomposition reaction as previously described and become involved in the formation of polymers due to the formation of isocyanic acid and the isocyanic acid forming biurets. Although the majority of these compounds derived from urea and carbonic acid derivatives are condensed and returned to the reaction system together with the alcohol and aromatic hydroxy compound, a portion thereof may be discharged as gas components together with the by-product ammonia. When operation is carried out for a long period of time, these compounds adhere and accumulate on the inner walls of the ammonia discharge line, and have been determined to cause clogging of the ammonia discharge line.

However, there are no examples in the prior art as described above of an examination of means for solving the problem of clogging of the ammonia discharge line, and technology enabling long-term operation of N-substituted carbamic acid ester production equipment has yet to be established.

In this manner, there are still numerous problems involving the production of N-substituted carbamic acid ester for use as an isocyanate precursor and the production of isocyanates, and since a method to serve as an alternative to the phosgene method has yet to be established, there is a strong desire for these problems to be solved.

As has been described above, various methods have been proposed for the production of N-substituted carbamic acid-O-alkyl esters or N-substituted carbamic acid-O-aryl esters that use urea or carbonic acid derivatives. There are many cases in which the urea or carbonic acid derivatives added in excess to obtain N-substituted carbamic acid esters at high yield in these methods cause the formation of polymers and the like as described above, which in turn adhere to and solidify on the reaction vessel.

In addition, there were also many cases in which polymers formed by side reactions and excess urea or carbonic acid derivatives additionally formed different types of polymers due to the occurrence of side reactions with isocyanate as previously described during the production of isocyanate by a thermal decomposition reaction of N-substituted carbamic acid-O-alkyl ester or N-substituted carbamic acid-O-aryl ester, resulting in the problem of these polymers also adhering to or solidifying in the reaction vessel. In addition, there was also the problem of increases in the amounts of urea, carbonic acid derivatives and amines used due to the formation of these polymers. However, there are no descriptions of methods for efficiently recovering and reusing the excess urea and carbonic acid derivatives, and increases in the amount of urea or carbonic acid derivatives used have been unable to be avoided.

Although ammonia is formed as a by-product in the case of producing N-substituted carbamic acid-O-alkyl ester or N-substituted carbamic acid-O-aryl ester using urea and carbonic acid derivatives, there are also problems with the discharge of this ammonia. In order to increase the yield of N-substituted carbamic acid-O-alkyl ester or N-substituted carbamic acid-O-aryl ester, although by-product ammonia is frequently discharged by providing a line for discharging ammonia in the reaction vessel for producing the N-substituted carbamic acid ester, there were many cases in which solids adhered to and solidified on the inner walls of the ammonia discharge line, thereby impairing long-term operation.

An object of the present invention is to provide a method for producing N-substituted carbamic acid ester, a method for producing isocyanate by thermal decomposition of the N-substituted carbamic acid ester, and a composition for transfer and storage of N-substituted carbamic acid ester comprising an N-substituted carbamic acid ester and an aromatic hydroxy compound that is suitable for transfer and storage of the N-substituted carbamic acid ester, and particularly N-substituted carbamic acid-O-aryl ester, as well as suitable for the production of isocyanate.

Means for Solving the Problems

Therefore, as a result of conducting extensive studies of the above-mentioned problems, the inventors of the present invention found that the problems are solved by a method for producing N-substituted carbamic acid ester from an organic amine, a carbonic acid derivative and a hydroxy composition, wherein the reaction between the organic amine, the carbonic acid derivative and the hydroxy composition is carried out using a reaction vessel equipped with a condenser, the number of carbonyl groups contained in compounds having carbonyl groups derived from the carbonic acid derivative contained in the ammonia recovered as a gas from the condenser is made to be a specific amount or less, and the recovered carbonic acid derivative is reused in production of N-substituted carbamic acid ester; a method for producing an isocyanate by a thermal decomposition reaction of the N-substituted carbamic acid ester produced by the above-described method; and a specific composition containing an N-substituted carbamic acid ester and an aromatic hydroxy composition, thereby leading to completion of the present invention.

Namely, in a first aspect thereof, the present invention provides:

[1] A method for producing an N-substituted carbamic acid ester derived from an organic amine from an organic amine, a carbonic acid derivative and a hydroxy composition containing one or more types of hydroxy compounds, wherein the organic amine, the carbonic acid derivative and the hydroxy composition are reacted using a urethane production reaction vessel provided with a condenser, a gas containing the hydroxy composition, a compound having a carbonyl group derived from the carbonic acid derivative, and ammonia formed as a by-product in the reaction, is introduced into the condenser provided in the urethane production reaction vessel, and the hydroxy composition and the compound having the carbonyl group derived from the carbonic acid derivative are condensed, and wherein a stoichiometric ratio of a hydroxy compound contained in the condensed hydroxy composition to the condensed compound having the carbonyl group derived from the carbonic acid derivative is 1 or more, and a ratio of number of carbonyl groups (—C(=O)—) contained in the compound having the carbonyl group derived from the carbonic acid derivative and number of ammonia molecules contained in ammonia recovered as a gas from the condenser is 1 or less.

[2] The production method according to item [1] above, wherein the hydroxy compound is an alcohol or aromatic hydroxy compound.

[3] The production method according to item [1] above, wherein the hydroxy composition and/or the compound having the carbonyl group derived from the carbonic acid derivative which have been condensed by the condenser is reused in the reaction.

[4] The production method according to item [1] above, wherein the hydroxy composition and the compound having the carbonyl group derived from the carbonic acid derivative which have been condensed by the condenser are circulated within the urethane production reaction vessel.

[5] The production method according to item [1] above, wherein the carbonic acid derivative is urea and/or carbamic acid ester.

[6] The production method according to item [1] above, wherein the N-substituted carbamic acid ester is produced by a process comprising the following steps (a) and (b):

step (a): a step of obtaining a reaction mixture containing a compound having an ureido group by reacting the organic amine and the carbonic acid derivative; and step (b): a step of producing the N-substituted carbamic acid ester by reacting the compound having the ureido group, which is obtained in the step (a), and the hydroxy composition using the urethane production reaction vessel provided with the condenser, wherein a gas containing the hydroxy composition, the compound having the carbonyl group derived from the carbonic acid derivative and an ammonia produced as a by-product in the reaction is introduced into the condenser provided in the urethane production reaction vessel, and the hydroxy composition and the compound having the carbonyl group derived from the carbonic acid derivative are condensed.

[7] The production method according to item [6] above, wherein the hydroxy compound is an alcohol or aromatic hydroxy compound.

[8] The production method according to item [6] above, wherein the carbonic acid derivative of the step (a) is urea and/or a carbamic acid ester.

[9] The production method according to item [6] above, wherein the reaction of the step (a) is carried out in the presence of at least one type of compound selected from the group consisting of water, an alcohol and an aromatic hydroxy compound.

[10] The production method according to item [6] above, wherein the hydroxy composition and/or the compound having the carbonyl group derived from the carbonic acid derivative, which have been condensed by the condenser in the step (b), is reused in the reaction of step (a).

[11] The production method according to item [5] or [8] above, wherein the carbamic acid ester is a carbamic acid ester produced according to the following step (c):

step (c): a step of producing the carbamic acid ester by reacting a hydroxy composition c (wherein the hydroxy composition c represents a composition comprising one or more types of hydroxy compounds) and urea.

[12] The production method according to item [11] above, wherein the hydroxy compound that composes the hydroxy composition c is an alcohol and/or an aromatic hydroxy compound.

[13] The production method according to item [1] or [6] above, wherein the condensed hydroxy composition and/or the compound having the carbonyl group derived from the carbamic acid ester is reused in the step (c).

In a second aspect thereof, the present invention also provides:

[14] A method for producing an N-substituted carbamic acid ester from an organic amine, a carbonic acid derivative and a hydroxy composition containing one or more types of hydroxy compounds, the method comprising following steps (a) and (b):

step (a): a step of obtaining a reaction mixture containing a compound having an ureido group by reacting the organic amine and the carbonic acid derivative; and step (b): a step of producing the N-substituted carbamic acid ester by reacting the compound having the ureido group, which is obtained in the step (a), and the hydroxy composition using a urethane production reaction vessel provided with a condenser, wherein a gas containing the hydroxy composition, the compound having the carbonyl group derived from the carbonic acid derivative and an ammonia produced as a by-product in the reaction is introduced into the condenser provided in the urethane production reaction vessel, and a hydroxy composition and the compound having the carbonyl group derived from the carbonic acid derivative are condensed.

[15] The production method according to item [14] above, wherein the hydroxy compound is an alcohol and/or aromatic hydroxy compound.

[16] The production method according to item [14] above, wherein the carbonic acid derivative of the step (a) is urea and/or a carbamic acid ester.

[17] The production method according to item [14] above, wherein the reaction of the step (a) is carried out in the presence of at least one type of compound selected from the group consisting of water, an alcohol and an aromatic hydroxy compound.

[18] The production method according to item [14] above, wherein the hydroxy composition and/or the compound having the carbonyl group derived from the carbonic acid derivative, which have been condensed by the condenser in the step (b), is reused in the step (a).

[19] The production method according to item [16] above, wherein the carbamic acid ester is a carbamic acid ester produced according to the following step (c):

step (c): a step of producing the carbamic acid ester by reacting the hydroxy composition c and urea.

[20] The production method according to item [19] above, wherein a hydroxy compound that composes the hydroxy composition c is an alcohol and/or aromatic hydroxy compound.

[21] The production method according to item [19] above, wherein the condensed hydroxy composition and/or the compound having the carbonyl group derived from the carbonic acid derivative is reused in the step (c).

[22] The production method according to item [1] or [14] above, wherein the urethane production reaction vessel is a tank type and/or a column type reaction vessel provided with a condenser.

[23] The production method according to item [1] or [14] above, wherein the urethane production reaction vessel has a gas phase containing the hydroxy composition, the compound having the carbonyl group derived from the carbonic acid derivative and the ammonia formed as a by-product in the reaction, and a liquid phase in which the reaction is carried out, and the volumetric content of the liquid phase in the urethane production reaction vessel is 50% or less.

[24] The production method according to any one of items [2], [7] or [15] above, wherein the hydroxy compound is an aromatic hydroxy compound, the organic amine is a compound represented by the following formula (1), and the N-substituted carbamic acid ester produced is an N-substituted carbamic acid-O—Ar ester represented by the following formula (2):

(1)

(2)

(wherein $R^1$ represents an organic group which has 1 to 85 carbon atoms and which is substituted with a amino groups, Ar represents a group derived from an aromatic hydroxy compound that is a residue in which a single hydroxy group bonded to an aromatic ring of the aromatic hydroxy compound has been removed, a represents an integer of from 1 to 10, and b represents an integer of from 1 to a).

[25] The production method according to any one of items [2], [7] or [15] above, wherein the hydroxy compound is an alcohol, the organic amine is a compound represented by the following formula (3), and the N-substituted carbamic acid ester produced is an N-substituted carbamic acid-O—R² ester represented by the following formula (4):

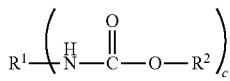

(wherein
R¹ represents an organic group which has 1 to 85 carbon atoms and which is substituted with a amino groups,
R² represents a group derived from an alcohol that is a residue in which a single hydroxy group bonded to a saturated carbon atom of the alcohol has been removed from the alcohol,
a represents an integer of from 1 to 10, and
c represents an integer of from 1 to a).
[26] The production method according to item [25] above, wherein an N-substituted carbamic acid-O—Ar ester represented by the following formula (5) and having an ester group derived from the aromatic hydroxy compound is produced by reacting the N-substituted carbamic acid-O—R² ester represented by formula (4) above and the aromatic hydroxy compound:

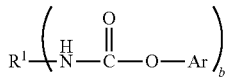

(wherein
R¹ represents an organic group which has 1 to 85 carbon atoms and which is substituted with a amino groups,
Ar represents a group derived from an aromatic hydroxy compound that is a residue in which a single hydroxy group bonded to an aromatic ring of the aromatic hydroxy compound has been removed from the aromatic hydroxy compound, and
b represents an integer of from 1 to a (wherein the a is the same as defined in formula (3) above, and represents an integer of from 1 to 10)).
In addition, in a third aspect thereof, the present invention provides:
[27] A composition for transfer and storage of an N-substituted carbamic acid-O—Ar ester comprising the N-substituted carbamic acid-O—Ar ester represented by the following formula (6), and an aromatic hydroxy composition containing one or more types of aromatic hydroxy compounds, wherein
a ratio of number of molecules of the aromatic hydroxy compound that composes the aromatic hydroxy composition (B) to number of ester groups that compose the N-substituted carbamic acid-O—Ar ester (A) is within a range of from 1 to 100:

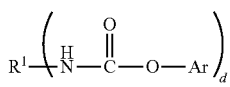

(wherein
R¹ represents an organic group which has 1 to 85 carbon atoms and which is substituted with a amino groups,
Ar represents a residue in which a single hydroxy group bonded to an aromatic ring of an aromatic hydroxy compound has been removed from the aromatic hydroxy compound (and the aromatic hydroxy compound may be the same or different from the aromatic hydroxy compound that composes the aromatic hydroxy composition), and
d represents an integer of from 1 to 10).
[28] The composition for transfer and storage according to item [27] above, wherein the N-substituted carbamic acid-O—Ar ester is an N-substituted carbamic acid-O—Ar ester produced from the organic amine, the carbonic acid derivative and the aromatic hydroxy composition, and the composition for transfer and storage is a composition containing at least one type of compound that is urea and/or carbamic acid ester and/or biuret and/or compound that has a terminal biuret group, (—NH—(C=O)—NH—(C=O)—NH₂), is derived from an organic amine and is formed in a reaction of the organic amine, the carbonic acid derivative and the aromatic hydroxy composition.
[29] The composition for transfer and storage according to item [27] above, wherein the composition for transfer and storage contains a carbonic acid ester derived from the aromatic hydroxy composition.

Additionally, in a preferable aspect thereof, the present invention provides:
[30] The production method according to item [24] or [26] above, wherein the aromatic hydroxy compound is a monovalent to trivalent (namely, number of hydroxy groups bonded to the aromatic ring is an integer from 1 to 3) aromatic hydroxy compound.
[31] The production method according to item [30] above, wherein the aromatic hydroxy compound is an aromatic hydroxy compound represented by the following formula (7):

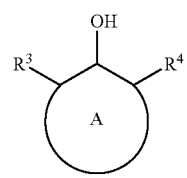

(wherein
ring A represents an optionally substituted single or multiple aromatic hydrocarbon ring,
R³ and R⁴ respectively and independently represent a hydrogen atom or organic group,
number of carbon atoms that compose the aromatic hydroxy compound is an integer of from 6 to 50, and
R³ and R⁴ may form a ring structure by bonding with A).
[32] The production method according to item [31] above, wherein at least one of the aromatic hydroxy compounds that compose the hydroxy composition is an aromatic hydroxy compound represented by the following formula (8):

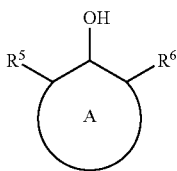

(8)

(wherein
ring A represents an optionally substituted single or multiple aromatic hydrocarbon ring,
$R^5$ and $R^6$ respectively and independently represent any group defined in (i) to (v) below,
number of carbon atoms that compose the aromatic hydroxy compound is an integer of from 6 to 50, and
$R^5$ and $R^6$ may form a ring structure by bonding with A:
(i) a hydrogen atom,
(ii) a halogen atom,
(iii) a group in which the atom at the α position is a nitrogen atom and number of carbon atoms is from 1 to 44, and which does not contain active hydrogen (excluding the hydrogen bonded to the α position nitrogen atom), the nitrogen atom being a secondary nitrogen atom (namely, a nitrogen atom that forms an —NH— bond),
(iv) a group in which the atom at the α position is a carbon atom and the number of carbon atoms is from 1 to 44, and which does not contain active hydrogen, the carbon atom being a primary or secondary carbon atom (namely, a carbon of a methyl group or a carbon that forms a —CH₂— bond), provided that in the case the $R^5$ and/or $R^6$ form a saturated and/or unsaturated condensed ring structure with the aromatic ring A and the condensed ring has 6 members or less, the carbon atom at the α position may be a tertiary or quaternary carbon atom, and in the case the α position carbon forms a double bond or triple bond with a β position atom (atom that forms the $R^5$ and $R^6$ and that is also adjacent to an atom bonded to the aromatic ring of ring A) as well, the α position carbon atom may be a tertiary or quaternary carbon atom, and
(v) a group in which the atom at the β position is an oxygen atom, and number of carbons is from 1 to 44, and which does not contain active hydrogen).
[33] The production method according to item [32] above, wherein the hydroxy composition contains an aromatic hydroxy compound represented by the above formula (8) together with an aromatic hydroxy compound represented by the following formula (9):

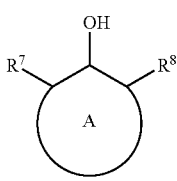

(9)

(wherein
ring A represents an optionally substituted single or multiple aromatic hydrocarbon ring,
$R^7$ and $R^8$ respectively and independently represent any group defined in (i) to (v) below,
number of carbon atoms that compose the aromatic hydroxy compound is an integer of from 6 to 50, and $R^7$ and $R^8$ may form a ring structure by bonding with A:
(i) a hydrogen atom,
(ii) a halogen atom,
(iii) a group in which the atom at the α position is a nitrogen atom and the number of carbon atoms is from 1 to 44, and which does not contain active hydrogen, the nitrogen atom being a tertiary nitrogen atom (namely, a nitrogen atom that does not have a hydrogen atom),
(iv) a group in which the atom at the α position is a carbon atom and number of carbon atoms is from 1 to 44, and which does not contain active hydrogen, the carbon atom at the α position being a tertiary or quaternary carbon atom (namely, a carbon atom that forms a —CH— bond or a carbon atom not bonded to hydrogen); in the case $R^7$ and/or $R^8$ form a saturated and/or unsaturated condensed ring structure with the ring A, and the condensed ring has 7 members or more, the carbon atom at the α position may be a primary or secondary carbon atom (namely, a carbon atom of a methyl group or a carbon atom that forms a —CH₂— bond); in the case the α position carbon forms a double bond with a β position atom, the α position carbon is quaternary carbon; and groups in which the α position carbon forms a triple bond with a β position atom are excluded, and
(v) a group in which the atom at the α position is an oxygen atom and the number of carbons is from 1 to 24, and which does not contain active hydrogen).
[34] The production method according to any one of items [31], [32] or [33] above, wherein a standard boiling point of the aromatic hydroxy compound represented by the formula (7), the formula (8) or the formula (9) differs by 10° C. or more from the standard boiling point of an isocyanate in which all amino groups of the organic amine are substituted with isocyanate groups (—NCO groups).

Further, in a preferable aspect thereof, the present invention provides:

[35] The composition according to item [27] above, wherein the aromatic hydroxy compound that composes the aromatic hydroxy composition is a monovalent to trivalent (namely, the number of hydroxy groups bonded to the aromatic ring is an integer from 1 to 3) aromatic hydroxy compound.

[36] The composition according to item [35] above, wherein the aromatic hydroxy compound that composes the aromatic hydroxy composition is an aromatic hydroxy compound represented by the following formula (7):

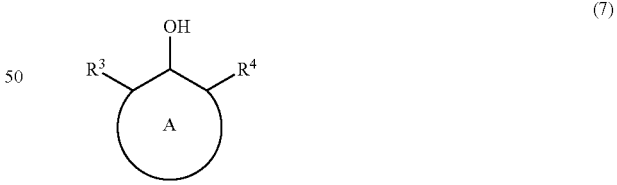

(7)

(wherein
ring A represents an optionally substituted single or multiple aromatic hydrocarbon ring,
$R^3$ and $R^4$ respectively and independently represent a hydrogen atom or organic group,
number of carbon atoms that compose the aromatic hydroxy compound is an integer of from 6 to 50, and
$R^3$ and $R^4$ may form a ring structure by bonding with A).
[37] The composition according to item [36] above, wherein at least one of the aromatic hydroxy compounds that compose the aromatic hydroxy composition is an aromatic hydroxy compound represented by the following formula (8):

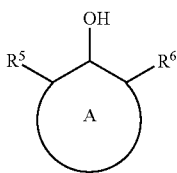

(8)

(wherein ring A represents an optionally substituted single or multiple aromatic hydrocarbon ring, $R^5$ and $R^6$ respectively and independently represent any group defined in (i) to (v) below, number of carbon atoms that compose the aromatic hydroxy compound is an integer of from 6 to 50, and $R^5$ and $R^6$ may form a ring structure by bonding with A:

(i) a hydrogen atom, (ii) a halogen atom, (iii) a group in which the atom at the α position is a nitrogen atom and the number of carbon atoms is from 1 to 44, and which does not contain active hydrogen (excluding the hydrogen bonded to the α position nitrogen atom), the nitrogen atom being a secondary nitrogen atom (namely, a nitrogen atom that forms an —NH— bond), (iv) a group in which the atom at the α position is a carbon atom and number of carbon atoms is from 1 to 44, and which does not contain active hydrogen, the carbon atom being a primary or secondary carbon atom (namely, a carbon of a methyl group or a carbon that forms a —CH$_2$— bond), provided that in the case the $R^5$ and/or $R^6$ form a saturated and/or unsaturated condensed ring structure with the aromatic ring A, and the condensed ring has 6 members or less, the carbon atom at the α position may be a tertiary or quaternary carbon atom, and in the case the α position carbon forms a double bond or triple bond with a β position atom (atom that forms the $R^5$ and $R^6$ and that is also adjacent to an atom bonded to the aromatic ring of ring A) as well, the α position carbon atom may be a tertiary or quaternary carbon atom, and (v) a group in which the atom at the α position is an oxygen atom and the number of carbons is from 1 to 44, and which does not contain active hydrogen).

[38] The composition according to item [37] above, wherein the aromatic hydroxy composition contains an aromatic hydroxy compound represented by the above formula (8) together with an aromatic hydroxy compound represented by the following formula (9):

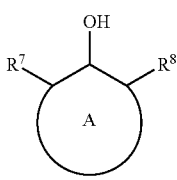

(9)

(wherein ring A represents an optionally substituted single or multiple aromatic hydrocarbon ring, $R^7$ and $R^8$ respectively and independently represent any group defined in (i) to (v) below, number of carbon atoms that compose the aromatic hydroxy compound is an integer from 6 to 50, and $R^7$ and $R^8$ may form a ring structure by bonding with A:

(i) a hydrogen atom, (ii) a halogen atom, (iii) a group in which the atom at the α position is a nitrogen atom and the number of carbon atoms is from 1 to 44, and which does not contain active hydrogen, the nitrogen atom being a tertiary nitrogen atom (namely, a nitrogen atom that does not have a hydrogen atom), (iv) a group in which the atom at the α position is a carbon atom and the number of carbon atoms is from 1 to 44, and which does not contain active hydrogen, the carbon atom at the α position being a tertiary or quaternary carbon atom (namely, a carbon atom that forms a —CH— bond or a carbon atom not bonded to hydrogen); in the case $R^7$ and/or $R^8$ form a saturated and/or unsaturated condensed ring structure with the ring A, and the condensed ring has 7 members or more, the carbon atom at the α position may be a primary or secondary carbon atom (namely, a carbon atom of a methyl group or a carbon atom that forms a —CH$_2$— bond); in the case the α position carbon forms a double bond with a β position atom, the α position carbon is quaternary carbon; and groups in which the α position carbon forms a triple bond with a β position atom are excluded, and (v) a group in which the atom at the α position is an oxygen atom and the number of carbons is from 1 to 24, and which does not contain active hydrogen).

[39] The composition according to any one of items [36], [37] or [38] above, wherein a standard boiling point of the aromatic hydroxy compound represented by the formula (7), the formula (8) or the formula (9) differs by 10° C. or more from the standard boiling point of an isocyanate in which all amino groups of the organic amine are substituted with isocyanate groups (—NCO groups).

Furthermore, in a preferable aspect thereof, the present invention provides:

[40] The production method according to item [24] or [26] above, wherein the organic amine is an organic monoamine represented by the following formula (10), the N-substituted carbamic acid mono (—O—Ar ester) represented by the following formula (11) is obtained, and the N-substituted carbamic acid mono (—O—Ar ester) is used to obtain the N-substituted carbamic acid poly (—O—Ar ester) represented by the following formula (12) by carrying out the following step (X):

step (X): the N-substituted carbamic acid mono (—O—Ar ester) and a methylenating agent are reacted to crosslink aromatic groups derived from the organic monoamine contained in the N-substituted carbamic acid mono (—O—Ar ester) with methylene groups (—CH$_2$—) so as to obtain the N-substituted carbamic acid poly (—O—Ar ester) represented by the following formula (12):

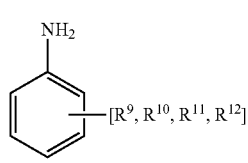 (10)

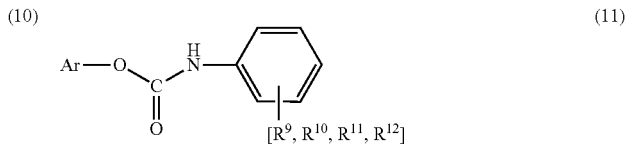 (11)

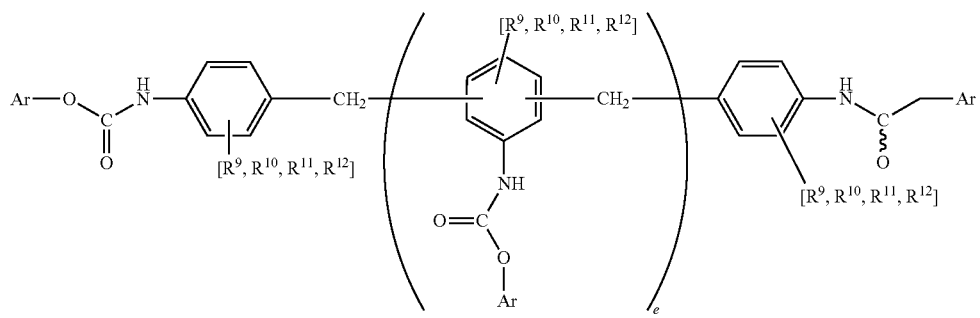 (12)

(wherein

Ar represents a group derived from an aromatic hydroxy compound that is a residue in which a single hydroxy group bonded to an aromatic ring of the aromatic hydroxy compound has been removed, $R^9$ to $R^{12}$ may respectively and independently substitute the aromatic ring, $R^9$ to $R^{12}$ may mutually bond to form a ring with the aromatic ring, and represent a hydrogen atom or a group composed of groups in which an alkyl group, cycloalkyl group, aryl group or group selected from the group consisting of these groups is bonded by saturated hydrocarbon bonds and/or ether bonds, e represents 0 or a positive integer, and a total number of carbon atoms that compose the organic monoamine represented by formula (10) is an integer of from 6 to 50).

[41] The production method according to item [25] above, wherein the organic amine is an organic monoamine represented by the following formula (13), the N-substituted carbamic acid mono (—O—$R^2$ ester) represented by the following formula (14) is obtained, and the N-substituted carbamic acid mono (—O—$R^2$ ester) is used to obtain an N-substituted carbamic acid poly (—O—Ar ester) represented by the following formula (16) by carrying out the following steps (X) and (Y):

step (X): the N-substituted carbamic acid mono (—O—$R^2$ ester) and a methylenating agent are reacted to crosslink aromatic groups derived from the organic monoamine contained in the N-substituted carbamic acid mono (—O—$R^2$ ester) with methylene groups (—$CH_2$—) so as to obtain the N-substituted carbamic acid poly (—O—$R^2$ ester) represented by the following formula (15); and, step (Y): the N-substituted carbamic acid poly (—O—$R^2$ ester) produced in step (X) is reacted with an aromatic hydroxy compound to produce an N-substituted carbamic acid poly (—O—Ar ester) having ester groups derived from the aromatic hydroxy compound represented by the following formula (16):

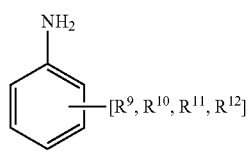 (13)

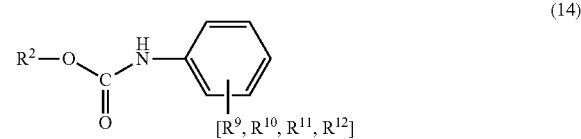 (14)

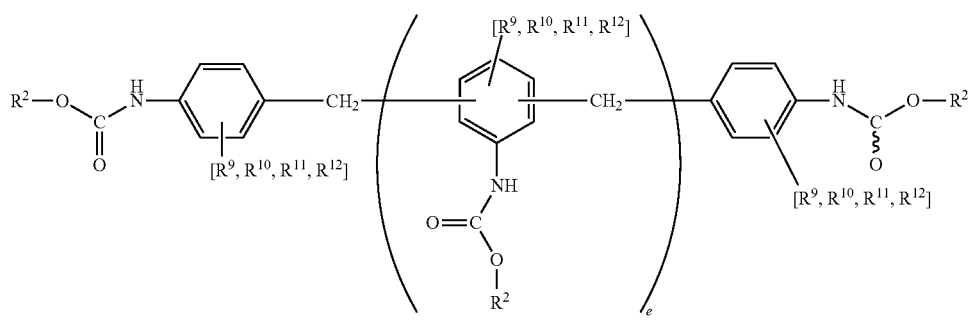 (15)

-continued

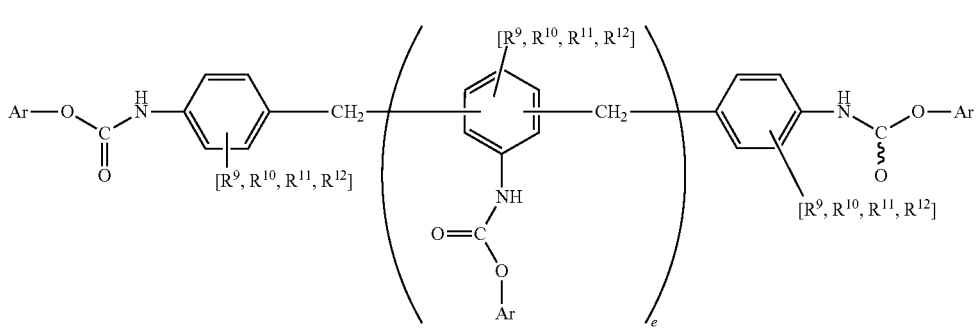

(16)

(wherein $R^9$ to $R^{12}$ may respectively and independently substitute the aromatic ring, $R^9$ to $R^{12}$ may mutually bond to form a ring with the aromatic ring, and represent hydrogen atoms or groups composed of groups in which an alkyl group, cycloalkyl group, aryl group or group selected from the group consisting of these groups is bonded by saturated hydrocarbon bonds and/or ether bonds, $R^2$ represents a group derived from an alcohol that is a residue in which a single hydroxy group bonded to a saturated carbon atom of the alcohol has been removed from the alcohol, Ar represents a group derived from an aromatic hydroxy compound that is a residue in which a single hydroxy group bonded to an aromatic ring of the aromatic hydroxy compound has been removed from the aromatic hydroxy compound;

e represents 0 or a positive integer, and a total number of carbon atoms that compose the organic monoamine represented by formula (13) is an integer of from 6 to 50).

Moreover, in a fourth aspect thereof, the present invention provides:

[42] An isocyanate production method, comprising: recovering an isocyanate and an aromatic hydroxy compound that are formed by subjecting the N-substituted carbamic acid-O—Ar ester according to any one of items [24], [26], [40] and [41] above to a thermal decomposition reaction.

[43] An isocyanate production method, comprising: recovering an isocyanate and an aromatic hydroxy compound that are formed by transferring the composition for transfer and storage of an N-substituted carbamic acid-O—Ar ester according to any one of items [27] to [29] above to a thermal decomposition reaction vessel, and subjecting the N-substituted carbamic acid ester to a thermal decomposition reaction.

[44] The production method according to item [42] or [43] above, wherein the recovered aromatic hydroxy compound according to item [42] or [43] above is reused as the aromatic hydroxy compound according to item [2] above, and/or the aromatic hydroxy compound according to item [7] above, and/or the aromatic hydroxy compound according to item [9] above, and/or the aromatic hydroxy compound according to item [12] above, and/or the aromatic hydroxy compound according to item [15] above, and/or the aromatic hydroxy compound according to item [17] above, and/or the aromatic hydroxy compound according to item [20] above.

[45] The production method according to item [42] or [43] above, wherein a residual liquid containing unreacted N-substituted carbamic acid-O—Ar ester recovered from a bottom of the thermal decomposition reaction vessel is again transferred to the thermal decomposition reaction vessel, and the N-substituted carbamic acid-O—Ar ester is subjected to a thermal decomposition reaction.

[46] The production method according to item [42] or [43] above, wherein the isocyanate produced in the production method according to item [42] or [43] above contains 1 to 1000 ppm of the aromatic hydroxy compound that composes the aromatic hydroxy composition based on the isocyanate.

[47] The production method according to any one of items [1], [11], [14] or [19] above, wherein the ammonia recovered in the form of a gas is reacted with carbon dioxide to produce urea, and the urea is reused.

Advantageous Effects of the Invention

According to the present invention, N-substituted carbamic acid ester can be advantageously produced in terms of basic units of urea. In addition, the N-substituted carbamic acid ester can be preferably used as a production raw material of isocyanate.

Further, according to the present invention, production of N-substituted carbamic acid ester can be realized over a long period of time by being able to avoid adhesion and accumulation of polymeric by-products to the reaction vessel during production of N-substituted carbamic acid ester, as well as clogging of a line for discharging ammonia formed as a by-product during production of N-substituted carbamic acid ester.

MODE FOR CARRYING OUT THE INVENTION

Figure 1:
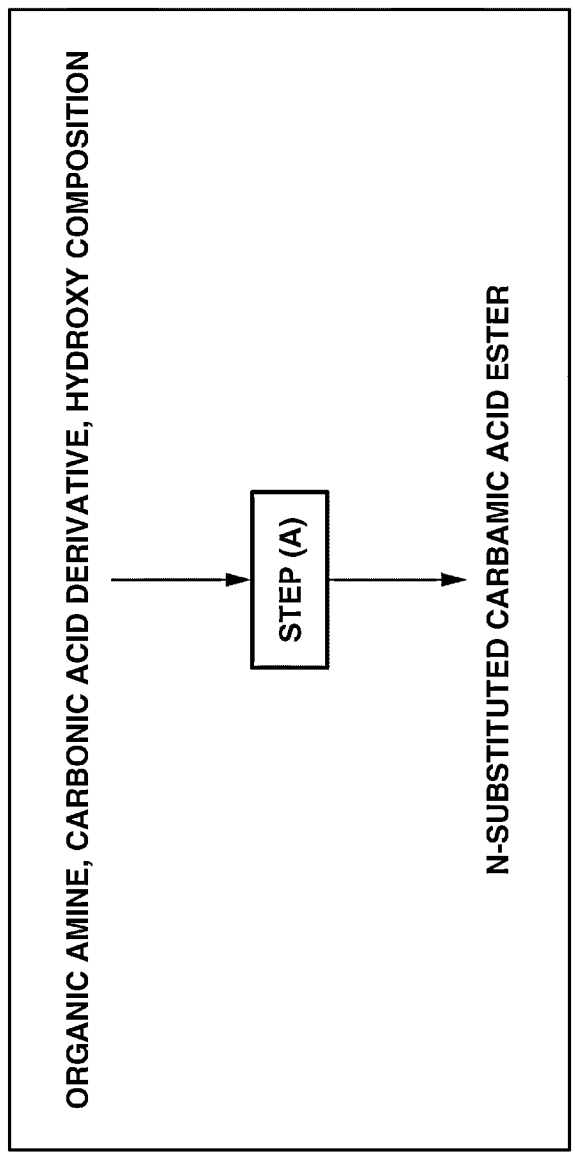
FIG. 1 shows a conceptual drawing depicting one aspect of the present embodiment in the form of a production method of N-substituted carbamic acid ester according to step (A)

The following provides a detailed explanation of the mode for carrying out the present invention (to be referred to as "present embodiment"). Furthermore, the present invention is not limited to the following present embodiment, but rather can be modified in various ways within the scope of the gist thereof.

An explanation is first given of compounds used in the production method of the present embodiment, and compounds that compose the composition for transfer and storage of the present embodiment.

<Organic Amine>

An organic primary amine is preferably used for the organic amine in the present embodiment. Here, an organic primary amine refers to a "primary amine" (mono primary amines and poly primary amines) as defined in rule C-8 of the nomenclature (IUPAC Nomenclature of Organic Chemistry) stipulated by the International Union of Pure and Applied Chemistry (IUPAC). This organic amine is represented by the following formula (29). This rule is based on Recommendations on Organic & Biochemical Nomenclature. Hereinafter, in the case of referring to IUPAC rules in the present application as well as subsequently indicated nomenclature rules defined by IUPAC (with the exception of cases specially citing IUPAC recommendations of other years), such referrals cite "Yukikagaku • Seikagaku Meimeihou" (Organic Chemistry and Biochemistry Nomenclature) (2nd revision published in Japan in 1992 by Nankodo Co., Ltd.), which is based on an edition containing all rules of organic chemistry and biochemistry, along with transliteration rules for Japanese, published as a supplement to "Chemical Fields" in 1980 based on the Recommendations 1979, as well as all subsequent revisions and recommendations. The term "organic" refers generically to a group of compounds considered to be subject to the nomenclature disclosed in the above publications. The subjects may be subjects described in recommendations published in 1993. However, "organic" compounds covered by the nomenclature described above include organometallic compounds and metal complexes. In the present embodiment, although the following provides explanations of "organic", and/or "organic groups", and/or "substituents" and the like, as well as compounds used in the present embodiment, when not specifically explained, these are composed of atoms that do not include metal atoms and/or semimetals. More preferably, "organic compounds", "organic groups" and "substituents" composed of atoms selected from H (hydrogen atoms), C (carbon atoms), N (nitrogen atoms), O (oxygen atoms), S (sulfur atoms), Cl (chlorine atoms), Br (bromine atoms) and I (iodine atoms) are used in the present embodiment.

In addition, the terms "aliphatic" and "aromatic" are frequently used in the following explanations. According to the above-mentioned IUPAC rules, organic compounds are described as being classified into aliphatic compounds and aromatic compounds. Aliphatic compounds refer to the definitions of groups in accordance with aliphatic compounds based on the 1995 IUPAC recommendations. Aliphatic compounds are defined in these recommendations as "acyclic or cyclic saturated or unsaturated carbon compounds, excluding aromatic compounds". In addition, aliphatic compounds used in the explanation of the present embodiment include saturated and unsaturated as well as linear and cyclic aliphatic compounds, and refer to "organic compounds", "organic groups" and "substituents" composed of atoms selected from the above-mentioned H (hydrogen atoms); C (carbon atoms); N (nitrogen atoms); O (oxygen atoms); S (sulfur atoms); Si (silicon atoms); and halogen atoms selected from Cl (chlorine atoms), Br (bromine atoms) and I (iodine atoms).

In addition, in the case an aromatic group such as an aralkyl group is bonded to an aliphatic group, such groups are frequently denoted in the manner of "aliphatic group substituted with an aromatic group" or "group composed of an aliphatic group bonded to an aromatic group". This is based on the reactivity in the present embodiment, and because properties relating to reactions of groups in the manner of aralkyl groups closely resemble the reactivity of aliphatic groups and not aromatic groups. In addition, non-aromatic reactive groups including groups such as aralkyl groups and alkyl groups are frequently denoted as "aliphatic groups optionally substituted with an aromatic group", "aliphatic group substituted with an aromatic group" or "aliphatic group bonded to an aromatic group" and the like.

Furthermore, although definitions in accordance with the nomenclature rules stipulated by IUPAC as described above are used when explaining general formulas of compounds used in the present specification, common names are frequently used for the names of specific groups or the names of compounds listed as examples. In addition, although numbers of atoms, numbers of substituents and numbers of compounds are frequently described in the present specification, these are all represented with integers.

(wherein $R^1$ represents an organic group which has 1 to 85 carbon atoms, and which is substituted with n amino groups, and a represents an integer of 1 to 10.)

In formula (29) above, $R^1$ represents an aliphatic group, an aromatic group or a group bonded to an aliphatic group and an aromatic group, and represents a group composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a heterocrosslinked ring group or heterocyclic group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (30) to (38).

  (30)

  (31)

  (32)

  (33)

(34)

  (35)

  (36)

  (37)

  (38)

Among these $R^1$ groups, $R^1$ groups that can be preferably used in the present embodiment in consideration of less susceptibility to the occurrence of side reactions contain groups selected from the group consisting of acyclic hydrocarbon groups and cyclic hydrocarbon groups selected from aliphatic groups, aromatic groups and groups bonded to aliphatic groups and aromatic groups (such as a monocyclic hydrocarbon group, condensed polycyclic hydrocarbon group, crosslinked cyclic hydrocarbon group, spirohydrocarbon group, ring-assembling hydrocarbon group or cyclic hydrocarbon group having a side chain), and groups bonded to at least one type of group selected from this group (mutually substituted groups), having 1 to 85 carbon atoms. In consideration of fluidity and the like, the number of carbon atoms is preferably from 1 to 70 and more preferably from 1 to 13.

Preferable examples of organic amines composed by the $R^1$ group may include:

1) optionally aliphatic- and/or aromatic-substituted aromatic organic mono primary amines in which the $R^1$ group has 6 to 85 carbon atoms and contains one or more types of an aromatic ring optionally substituted with an aliphatic group and/or aromatic group, an aromatic group in the $R^1$ group is substituted with an $NH^2$ group, and a is 1, 2) aromatic organic poly primary amines in which the $R^1$ group has 6 to 85 carbon atoms and contains one or more types of an aromatic ring optionally substituted with an aliphatic group and/or aromatic group, an aromatic group in the $R^1$ group is substituted with an $NH_2$ group, and a is 2 or more, and 3) aliphatic organic poly primary amines in which the $R^1$ group is an aliphatic group having 1 to 85 carbon atoms optionally substituted with an aromatic group, and a is 2 or 3.

In the above descriptions, atoms bonded to an $NH_2$ group (and preferably carbon atoms) that are contained in an aromatic ring are denoted as aromatic organic amines, while cases of bonding to atoms not in an aromatic ring (mainly carbon) are denoted as aliphatic organic amines. More preferable aliphatic groups are linear hydrocarbon groups, cyclic hydrocarbon groups and at least one type of group selected from the linear hydrocarbon groups and cyclic hydrocarbon groups (referring to, for example, cyclic hydrocarbon groups substituted with a linear hydrocarbon group or linear hydrocarbon groups substituted with a cyclic hydrocarbon group) having 6 to 70 carbon atoms.

The following lists specific examples of preferable organic primary amines.

1) Aromatic Organic Monoamines

Optionally aliphatic- and/or aromatic-substituted aromatic organic mono primary amines in which the $R^1$ group is a group having 6 to 85 carbon atoms and contains one or more types of an aromatic ring optionally substituted with an aliphatic group and/or aromatic group, an aromatic group in the $R^1$ group is substituted with an $NH_2$ group and a is 1, preferably aromatic organic monoamines in which the $R^1$ group is a group having 6 to 70 carbon atoms and a is 1, and more preferably in consideration of fluidity and the like, aromatic organic monoamines in which the $R^1$ group has 6 to 13 carbon atoms and contains one or more types of "$NH_2$ group-substituted" aromatic rings and a is 1, which are aromatic organic monoamines represented by the following formula (39).

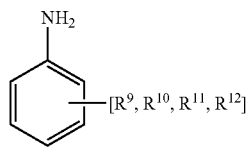

(39)

At least one position of the ortho position and/or para position of the $NH_2$ group of the aromatic organic mono primary amine represented by formula (39) is not substituted, $R^9$ to $R^{12}$ respectively represent a group substituted at an arbitrary position that retains aromatic properties of the ring, $R^9$ to $R^{12}$ may respectively and independently substitute the aromatic ring, $R^9$ to $R^{12}$ may mutually bond to form a ring with the aromatic ring, and represent hydrogen atoms or groups composed of groups in which an alkyl group, a cycloalkyl group, an aryl group or group selected from the group consisting of these groups is bonded by saturated hydrocarbon bonds and/or ether bonds, the number of carbon atoms of $R^9$ to $R^{12}$ is an integer within a range of from 0 to 7, and the total number of carbon atoms that compose an aromatic organic mono primary amine represented by formula (39) is 6 to 13.

Preferable examples of aromatic organic mono primary amines represented by formula (39) may include those in which the $R^9$ to $R^{12}$ groups are hydrogen atoms or groups selected from alkyl groups such as a methyl group or an ethyl group, and examples of such aromatic organic mono primary amines may include aniline, aminotoluene (including isomers), dimethylaniline (including isomers), diethylaniline (including isomers), dipropylaniline (including isomers), aminonaphthalene (including isomers), aminomethylnaphthalene (including isomers), dimethylnaphthylamine (including isomers) and trimethylnaphthylamine (including isomers), with aniline being used more preferably.

2) Aromatic Organic Poly Primary Amines

Aromatic organic poly primary amines in which the $R^1$ group is a group having 6 to 85 carbon atoms and containing one or more aromatic rings optionally substituted with an aliphatic group and/or aromatic group, an aromatic group in the $R^1$ group is substituted with an $NH_2$ group and a is 2 or more, preferably aromatic organic polyamines in which the $R^1$ group is a group having 6 to 70 carbon atoms and a is 2 or more, and more preferably in consideration of fluidity and the like, aromatic organic polyamines in which the $R^1$ group has 6 to 13 carbon atoms and contains one or more types of "$NH_2$ group-substituted" aromatic rings, the aromatic ring may be further substituted with an alkyl group, an aryl group or an aralkyl group, and a is 2 or more. Examples of such aromatic organic polyamines may include diaminobenzene (including isomers), diaminotoluene (including isomers), methylenedianiline (including isomers), diaminomesitylene (including isomers), diaminobiphenyl (including isomers), diaminodibenzyl (including isomers), bis(aminophenyl) propane (including isomers), bis(aminophenyl) ether (including isomers), bis(aminophenoxyethane) (including isomers), diaminoxylene (including isomers), diaminoanisole (including isomers), diaminophenetol (including isomers), diaminonaphthalene (including isomers), diamino-methylbenzene (including isomers), diamino-methylpyridine (including isomers), diamino-methylnaphthalene (including isomers) and polymethylene polyphenyl polyamines represented by the following formula (40):

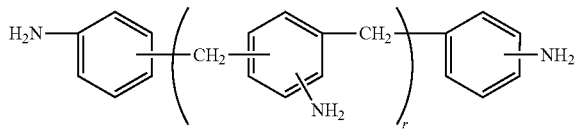

(40)

(wherein
f represents an integer of 0 to 6).

3) Aliphatic Organic Polyamines

Aliphatic organic polyamines in which the $R^1$ group of an organic amine represented by formula (29) is an aliphatic group in which the number of carbon atoms is an integer within a range of from 1 to 85 and which may be substituted with an aromatic group, and n is 2 or 3. More preferable organic amines are aliphatic organic primary amines in which the aliphatic group is a linear hydrocarbon group, cyclic hydrocarbon group or group to which is bonded at least one type of group selected from the linear hydrocarbon groups and the cyclic hydrocarbon groups (such as cyclic hydrocarbon group substituted with a linear hydrocarbon group or a linear hydrocarbon group substituted with a cyclic hydrocarbon group). More preferably, the organic amine is an aliphatic organic polyamine in which the $R^1$ group is an aliphatic group that is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 1 to 70 carbon atoms, and a is 2 or 3. In consideration of fluidity and the like during large-volume industrial production, the organic amine is most preferably an aliphatic organic poly primary amine in which the $R^1$ group is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 6 to 13 carbon atoms and composed of carbon atoms and hydrogen atoms. Namely, this refers to the case in which the R1 group is a linear and/or branched alkyl group, a cycloalkyl group or a group composed of the alkyl groups and cycloalkyl groups. Examples of these organic amines may include aliphatic di-primary amines such as ethylenediamine, diaminopropane (including isomers), diaminobutane (including isomers), diaminopentane (including isomers), diaminohexane (including isomers) or diaminodecane (including isomers); aliphatic triamines such as triaminohexane (including isomers), triaminononane (including isomers) or triaminodecane (including isomers); and, substituted cyclic aliphatic polyamines such as diaminocyclobutane (including isomers), diaminocyclohexane (including isomers), 3-aminomethyl-3,5,5-trimethylcyclohexylamine (cis and/or trans forms) or methylenebis(cyclohexylamine) (including isomers).

<Carbonic Acid Derivative>

The carbonic acid derivative in the present embodiment refers to a compound represented by the following formula (41). It is a component that is used as a raw material for producing N-substituted carbamic acid ester together with the organic amine and the aromatic hydroxy composition. In addition, it is a component that may be contained in the composition for transfer and storage of N-substituted carbamic acid ester.

(41)

(wherein

X represents an amino group having 0 to 20 carbon atoms, and

Y represents an organic group having 1 to 20 carbon atoms or an amino group having 0 to 20 carbon atoms.)

Examples of compounds represented by formula (41) above may include urea compounds and carbamic acid esters.

Urea compounds refer to compounds having at least one urea bond in a molecule thereof, and are preferably compounds having one urea bond represented by the following formula (42):

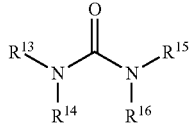

(42)

(wherein $R^{13}$, $R^{14}$, $R^{15}$ and $R^{16}$ respectively and independently represent an aliphatic group having 1 to 20 carbon atoms, an aliphatic group having 7 to 20 carbon atoms substituted with an aromatic compound, an aromatic group having 6 to 20 carbon atoms, or a hydrogen atom, the total number of carbon atoms that compose $R^{13}$ and $R^{14}$ is an integer of 0 to 20, and the total number of carbon atoms that compose $R^{15}$ and $R^{16}$ is an integer of 0 to 20).

Examples of $R^{13}$, $R^{14}$, $R^{15}$ and $R^{16}$ may include a hydrogen atom, alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers) or a nonadecyl group (including isomers); aryl groups in which the number of carbon atoms that compose the group is 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); and, aralkyl groups in which the number of carbon atoms that compose the group is 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers).

Specific examples may include urea, methylurea, ethylurea, propylurea (including isomers), butylurea (including isomers), pentylurea (including isomers), hexylurea (including isomers), heptylurea (including isomers), octylurea (including isomers), nonylurea (including isomers), decylurea (including isomers), undecylurea (including isomers), dodecylurea (including isomers), tridecylurea (including isomers), tetradecylurea (including isomers), pentadecylurea (including isomers), hexadecylurea (including isomers), heptadecylurea (including isomers), octadecylurea (including isomers), nonadecylurea (including isomers), phenylurea, N-(methylphenyl) urea (including isomers), N-(ethylphenyl) urea (including isomers), N-(propylphenyl) urea (including isomers), N-(butylphenyl) urea (including isomers), N-(pentylphenyl) urea (including isomers), N-(hexylphenyl) urea (including isomers), N-(heptylphenyl) urea (including isomers), N-(octylphenyl) urea (including isomers), N-(nonylphenyl) urea (including isomers), N-(decylphenyl) urea (including isomers), N-biphenyl urea (including isomers), N-(dimethylphenyl) urea (including isomers), N-(diethylphenyl) urea (including isomers), N-(dipropylphenyl) urea (including isomers), N-(dibutylphenyl) urea (including isomers), N-(dipentylphenyl) urea (including isomers), N-(dihexylphenyl) urea (including isomers), N-(diheptylphenyl) urea (including isomers), N-terphenyl urea (including isomers), N-(trimethylphenyl) urea (including isomers), N-(triethylphenyl) urea (including isomers), N-(tripropylphenyl)

urea (including isomers), N-(tributylphenyl) urea (including isomers), N-(phenylmethyl) urea, N-(phenylethyl) urea (including isomers), N-(phenylpropyl) urea (including isomers), N-(phenylbutyl) urea (including isomers), N-(phenylpentyl) urea (including isomers), N-(phenylhexyl) urea (including isomers), N-(phenylheptyl) urea (including isomers), N-(phenyloctyl) urea (including isomers), N-(phenylnonyl) urea (including isomers), dimethylurea (including isomers), diethylurea (including isomers), dipropylurea (including isomers), dibutylurea (including isomers), dipentylurea (including isomers), dihexylurea (including isomers), diheptylurea (including isomers), dioctylurea (including isomers), dinonylurea (including isomers), didecylurea (including isomers), diundecylurea (including isomers), didodecylurea (including isomers), ditridecylurea (including isomers), ditetradecylurea (including isomers), dipentadecylurea (including isomers), dihexadecylurea (including isomers), diheptadecylurea (including isomers), dioctadecylurea (including isomers), dinonadecylurea (including isomers), diphenylurea (including isomers), di(methylphenyl) urea (including isomers), di(ethylphenyl) urea (including isomers), di(propylphenyl) urea (including isomers), di(butylphenyl) urea (including isomers), di(pentylphenyl) urea (including isomers), di(hexylphenyl) urea (including isomers), di(heptylphenyl) urea (including isomers), di(octylphenyl) urea (including isomers), di(nonylphenyl) urea (including isomers), di(decylphenyl) urea (including isomers), di(biphenyl) urea (including isomers), di(dimethylphenyl) urea (including isomers), di(diethylphenyl) urea (including isomers), di(dipropylphenyl) urea (including isomers), di(dibutylphenyl) urea (including isomers), di(dipentylphenyl) urea (including isomers), di(dihexylphenyl) urea (including isomers), di(diheptylphenyl) urea (including isomers), di(terphenyl) urea (including isomers), di(trimethylphenyl) urea (including isomers), di(triethylphenyl) urea (including isomers), di(tripropylphenyl) urea (including isomers), di(tributylphenyl) urea (including isomers), di(phenylmethyl) urea (including isomers), di(phenylethyl) urea (including isomers), di(phenylpropyl) urea (including isomers), di(phenylbutyl) urea (including isomers), di(phenylpentyl) urea (including isomers), di(phenylhexyl) urea (including isomers), di(phenylheptyl) urea (including isomers), di(phenyloctyl) urea (including isomers) and di(phenylnonyl) urea (including isomers). Among these, urea in which $R^{13}$, $R^{14}$, $R^{15}$ and $R^{16}$ in formula (42) above are hydrogen atoms is used preferably.

A non-N-substituted carbamic acid ester represented by the following formula (43) is preferably used for the carbamic acid ester:

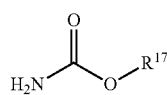

(43)

(wherein $R^{17}$ represents an aliphatic group having 1 to 50 carbon atoms, an aralkyl group having 7 to 50 carbon atoms or an aromatic group having 6 to 50 carbon atoms).

Examples of aliphatic groups of $R^{17}$ may include groups composed of specific non-metal atoms (carbon, oxygen, nitrogen, sulfur, silicon or halogen atoms). Preferable examples of these aliphatic groups may include groups in which the aliphatic group is a linear hydrocarbon group, a cyclic hydrocarbon group or a group to which is bonded at least one type of group selected from the linear hydrocarbon groups and the cyclic hydrocarbon groups (such as a cyclic hydrocarbon group substituted with a linear hydrocarbon group or a linear hydrocarbon group substituted with a cyclic hydrocarbon group). In addition, examples in the case of an aralkyl group refer to groups in which a linear and/or branched alkyl group is substituted with an aromatic group, and represent groups in which the alkyl group having 1 to 44 carbon atoms is substituted with the aromatic group having 6 to 49 carbon atoms. As was previously explained, the aromatic group preferably refers to a group composed of specific non-metal atoms (carbon, oxygen, nitrogen, sulfur, silicon or halogen atoms), examples of which may include a monocyclic aromatic group, a condensed polycyclic aromatic group, a crosslinked cyclic aromatic group, a ring-assembling aromatic group and a heterocyclic aromatic group, and is more preferably a substituted and/or unsubstituted phenyl group, substituted and/or unsubstituted naphthyl group, or substituted and/or unsubstituted anthryl group.

Examples of aromatic groups of $R^{17}$ may include groups composed of specific non-metal atoms (carbon, oxygen, nitrogen, sulfur, silicon or halogen atoms), examples of which may include a monocyclic aromatic group, a condensed polycyclic aromatic group, a crosslinked cyclic aromatic group, a ring-assembling aromatic group and a heterocyclic aromatic group, and is more preferably a substituted and/or unsubstituted phenyl group, a substituted and/or unsubstituted naphthyl group, or a substituted and/or unsubstituted anthryl group. Substituents may be substituted with hydrogen atoms, aliphatic groups (linear hydrocarbon groups, cyclic hydrocarbon groups and groups bonded to at least one type of group selected from the linear hydrocarbon groups and the cyclic hydrocarbon groups (such as a cyclic hydrocarbon group substituted with a linear hydrocarbon group or a linear hydrocarbon group substituted with a cyclic hydrocarbon group)) or the above-mentioned aromatic groups, and may also be groups composed of the above-mentioned aliphatic groups and aromatic groups.

Examples of this $R^{17}$ may include alkyl groups in which the number of carbon atoms comprising the group is 1 to 50, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers) or an eicosyl group (including isomers); aryl groups in which the number of carbon atoms comprising the group is 6 to 50, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); and, aralkyl groups in which the number of carbon atoms comprising the group is 7 to 50, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers).

Specific examples may include methyl carbamate, ethyl carbamate, propyl carbamate (including isomers), butyl carbamate (including isomers), pentyl carbamate (including isomers), hexyl carbamate (including isomers), heptyl carbamate (including isomers), octyl carbamate (including isomers), nonyl carbamate (including isomers), decyl carbamate (including isomers), undecyl carbamate (including isomers), dodecyl carbamate (including isomers), tridecyl carbamate (including isomers), tetradecyl carbamate (including isomers), pentadecyl carbamate (including isomers), hexadecyl carbamate (including isomers), heptadecyl carbamate (including isomers), octadecyl carbamate (including isomers), nonadecyl carbamate (including isomers), phenyl carbamate, (methylphenyl) carbamate (including isomers), (ethylphenyl) carbamate (including isomers), (propylphenyl) carbamate (including isomers), (butylphenyl) carbamate (including isomers), (pentylphenyl) carbamate (including isomers), (hexylphenyl) carbamate (including isomers), (heptylphenyl) carbamate (including isomers), (octylphenyl) carbamate (including isomers), (nonylphenyl) carbamate (including isomers), (decylphenyl) carbamate (including isomers), (biphenyl) carbamate (including isomers), (dimethylphenyl) carbamate (including isomers), (diethylphenyl) carbamate (including isomers), (dipropylphenyl) carbamate (including isomers), (dibutylphenyl) carbamate (including isomers), (dipentylphenyl) carbamate (including isomers), (dihexylphenyl) carbamate (including isomers), (diheptylphenyl) carbamate (including isomers), (terphenyl) carbamate (including isomers), (trimethylphenyl) carbamate (including isomers), (triethylphenyl) carbamate (including isomers), (tripropylphenyl) carbamate (including isomers), (tributylphenyl) carbamate (including isomers), (phenylmethyl) carbamate (including isomers), (phenylethyl) carbamate (including isomers), (phenylpropyl) carbamate (including isomers), (phenylbutyl) carbamate (including isomers), (phenylpentyl) carbamate (including isomers), (phenylhexyl) carbamate (including isomers), (phenylheptyl) carbamate (including isomers), (phenyloctyl) carbamate (including isomers) and (phenylnonyl) carbamate (including isomers).

The N-substituted carbamic acid ester contained in the composition for transfer and storage of the present embodiment is preferably produced from an organic amine, a carbonic acid derivative and an aromatic hydroxy composition. In this case, there are many cases in which a non-N-substituted carbamic acid ester contained in the composition for transfer and storage is a non-N-substituted carbamic acid ester in which an ester group of the non-N-substituted carbamic acid ester is derived from the aromatic hydroxy composition.

<Carbonic Acid Ester>

A carbonic acid ester is a component preferably contained in a specific amount in the composition for transfer and storage of the present embodiment.

A carbonic acid ester refers to a compound in which one or two of the two hydrogen atoms of carbonic acid $CO(OH)_2$ is substituted with an aliphatic group or an aromatic group. In the present embodiment, a compound represented by the following formula (44) is used preferably:

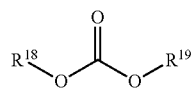

(44)

(wherein $R^{18}$ and $R^{19}$ respectively and independently represent an aliphatic group having 1 to 20 carbon atoms, an aralkyl group having 7 to 50 carbon atoms, or an aromatic group having 6 to 50 carbon atoms).

Examples of aliphatic groups of $R^{18}$ and $R^{19}$ may include groups composed of specific non-metal atoms (carbon, oxygen, nitrogen, sulfur, silicon or halogen atoms). Preferable examples of these aliphatic groups may include groups in which the aliphatic group is a linear hydrocarbon group, a cyclic hydrocarbon group or a group to which is bonded at least one type of group selected from the linear hydrocarbon groups and the cyclic hydrocarbon groups (such as a cyclic hydrocarbon group substituted with a linear hydrocarbon group or a linear hydrocarbon group substituted with a cyclic hydrocarbon group). In addition, examples in the case of an aralkyl group refer to groups in which a linear and/or branched alkyl group is substituted with an aromatic group, and represent groups in which the alkyl group having 1 to 44 carbon atoms is substituted with the aromatic group having 6 to 49 carbon atoms. As was previously explained, the aromatic group preferably refers to a group composed of specific non-metal atoms (carbon, oxygen, nitrogen, sulfur, silicon or halogen atoms), examples of which may include a monocyclic aromatic group, a condensed polycyclic aromatic group, a crosslinked cyclic aromatic group, a ring-assembling aromatic group and a heterocyclic aromatic group, and is more preferably a substituted and/or unsubstituted phenyl group, a substituted and/or unsubstituted naphthyl group, or a substituted and/or unsubstituted anthryl group.

Examples of aromatic groups of $R^{18}$ and $R^{19}$ may include groups composed of specific non-metal atoms (carbon, oxygen, nitrogen, sulfur, silicon or halogen atoms), examples of which may include a monocyclic aromatic group, a condensed polycyclic aromatic group, a crosslinked cyclic aromatic group, a ring-assembling aromatic group and a heterocyclic aromatic group, and is more preferably a substituted and/or unsubstituted phenyl group, a substituted and/or unsubstituted naphthyl group, or a substituted and/or unsubstituted anthryl group. Substituents may be substituted with hydrogen atoms, aliphatic groups (linear hydrocarbon groups, cyclic hydrocarbon groups and groups bonded to at least one type of group selected from the linear hydrocarbon groups and the cyclic hydrocarbon groups (such as a cyclic hydrocarbon group substituted with a linear hydrocarbon group or a linear hydrocarbon group substituted with a cyclic hydrocarbon group)) or the above-mentioned aromatic groups, and may also be groups composed of the above-mentioned aliphatic groups and aromatic groups.

Examples of these $R^{18}$ and $R^{19}$ may include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers) or an eicosyl group (including isomers); aryl groups such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); and, aralkyl groups such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers).

Specific examples may include dimethyl carbonate, diethyl carbonate, dipropyl carbonate (including isomers), dibutyl carbonate (including isomers), dipentyl carbonate (including isomers), dihexyl carbonate (including isomers), diheptyl carbonate (including isomers), dioctyl carbonate (including isomers), dinonyl carbonate (including isomers), didecyl carbonate (including isomers), diundecyl carbonate (including isomers), didodecyl carbonate (including isomers), ditridecyl carbonate (including isomers), ditetradecyl carbonate (including isomers), dipentadecyl carbonate (including isomers), dihexadecyl carbonate (including isomers), diheptadecyl carbonate (including isomers), dioctadecyl carbonate (including isomers), dinonadecyl carbonate (including isomers), diphenyl carbonate (including isomers), di(methylphenyl) carbonate (including isomers), di(ethylphenyl) carbonate (including isomers), di(propylphenyl) carbonate (including isomers), di(butylphenyl) carbonate (including isomers), di(pentylphenyl) carbonate (including isomers), di(hexylphenyl) carbonate (including isomers), di(heptylphenyl) carbonate (including isomers), di(octylphenyl) carbonate (including isomers), di(nonylphenyl) carbonate (including isomers), di(decylphenyl) carbonate (including isomers), di(biphenyl) carbonate (including isomers), di(dimethylphenyl) carbonate (including isomers), di(diethylphenyl) carbonate (including isomers), di(dipropylphenyl) carbonate (including isomers), di(dibutylphenyl) carbonate (including isomers), di(dipentylphenyl) carbonate (including isomers), di(dihexylphenyl) carbonate (including isomers), di(diheptylphenyl) carbonate (including isomers), di(phenylphenyl) carbonate (including isomers), di(trimethylphenyl) carbonate (including isomers), di(triethylphenyl) carbonate (including isomers), di(tripropylphenyl) carbonate (including isomers), di(tributylphenyl) carbonate (including isomers), di(phenylmethyl) carbonate (including isomers), di(phenylethyl) carbonate (including isomers), di(phenylpropyl) carbonate (including isomers), di(phenylbutyl) carbonate (including isomers), di(phenylpentyl) carbonate (including isomers), di(phenylhexyl) carbonate (including isomers), di(phenylheptyl) carbonate (including isomers), di(phenyloctyl) carbonate (including isomers) di(phenylnonyl) carbonate (including isomers), (methyl)(ethyl) carbonate, (methyl)(propyl) carbonate (including isomers), (methyl)(butyl) carbonate (including isomers), (methyl)(pentyl) carbonate (including isomers), (methyl)(hexyl) carbonate (including isomers), (methyl)(heptyl) carbonate (including isomers), (methyl)(octyl) carbonate (including isomers), (methyl)(nonyl) carbonate (including isomers), (methyl)(decyl) carbonate (including isomers), (methyl)(undecyl) carbonate (including isomers), (methyl)(dodecyl) carbonate (including isomers), (methyl)(tridecyl) carbonate (including isomers), (methyl)(tetradecyl) carbonate (including isomers), (methyl)(pentadecyl) carbonate (including isomers), (methyl)(hexadecyl) carbonate (including isomers), (methyl)(heptadecyl) carbonate (including isomers), (methyl)(octadecyl) carbonate (including isomers), (methyl)(nonadecyl) carbonate (including isomers), (methyl)(phenyl) carbonate (including isomers), (methyl)(methylphenyl) carbonate (including isomers), (methyl)(ethylphenyl) carbonate (including isomers), (methyl)(propylphenyl) carbonate (including isomers), (methyl)(butylphenyl) carbonate (including isomers), (methyl)(pentylphenyl) carbonate (including isomers), (methyl)(hexylphenyl) carbonate (including isomers), (methyl)(heptylphenyl) carbonate (including isomers), (methyl)(octylphenyl) carbonate (including isomers), (methyl)(nonylphenyl) carbonate (including isomers), (methyl)(decylphenyl) carbonate (including isomers), (methyl)(biphenyl) carbonate (including isomers), (methyl)(dimethylphenyl) carbonate (including isomers), (methyl)(diethylphenyl) carbonate (including isomers), (methyl)(dipropylphenyl) carbonate (including isomers), (methyl)(dibutylphenyl) carbonate (including isomers), (methyl)(dipentylphenyl) carbonate (including isomers), (methyl)(dihexylphenyl) carbonate (including isomers), (methyl)(diheptylphenyl) carbonate (including isomers), (methyl)(phenylphenyl) carbonate (including isomers), (methyl)(trimethylphenyl) carbonate (including isomers), (methyl)(triethylphenyl) carbonate (including isomers), (methyl)(tripropylphenyl) carbonate (including isomers), (methyl)(tributylphenyl) carbonate (including isomers), (methyl)(phenylmethyl) carbonate (including isomers), (methyl)(phenylethyl) carbonate (including isomers), (methyl)(phenylpropyl) carbonate (including isomers), (methyl)(phenylbutyl) carbonate (including isomers), (methyl)(phenylpentyl) carbonate (including isomers), (methyl)(phenylhexyl) carbonate (including isomers), (methyl)(phenylheptyl) carbonate (including isomers), (methyl)(phenyloctyl) carbonate (including isomers), (methyl)(phenylnonyl) carbonate (including isomers), (ethyl)(propyl) carbonate (including isomers), (ethyl)(butyl) carbonate (including isomers), (ethyl)(pentyl) carbonate (including isomers), (ethyl)(hexyl) carbonate (including isomers), (ethyl)(heptyl) carbonate (including isomers), (ethyl)(octyl) carbonate (including isomers), (ethyl)(nonyl) carbonate (including isomers), (ethyl)(decyl) carbonate (including isomers), (ethyl)(undecyl) carbonate (including isomers), (ethyl)(dodecyl) carbonate (including isomers), (ethyl)(tridecyl) carbonate (including isomers), (ethyl)(tetradecyl) carbonate (including isomers), (ethyl)(pentadecyl) carbonate (including isomers), (ethyl)(hexadecyl) carbonate (including isomers), (ethyl)(heptadecyl) carbonate (including isomers), (ethyl)(octadecyl) carbonate (including isomers), (ethyl)(nonadecyl) carbonate (including isomers), (ethyl)(phenyl) carbonate (including isomers), (ethyl)(methylphenyl) carbonate (including isomers), (ethyl)(ethylphenyl) carbonate (including isomers), (ethyl)(propylphenyl) carbonate (including isomers), (ethyl)(butylphenyl) carbonate (including isomers), (ethyl)(pentylphenyl) carbonate (including isomers), (ethyl)(hexylphenyl) carbonate (including isomers), (ethyl)(heptylphenyl) carbonate (including isomers), (ethyl)(octylphenyl) carbonate (including isomers), (ethyl)(nonylphenyl) carbonate (including isomers), (ethyl)(decylphenyl) carbonate (including isomers), (ethyl)(biphenyl) carbonate (including isomers), (ethyl)(dimethylphenyl) carbonate (including isomers), (ethyl)(diethylphenyl) carbonate (including isomers), (ethyl)(dipropylphenyl) carbonate (including isomers), (ethyl)(dibutylphenyl) carbonate (including isomers), (ethyl)(dipentylphenyl) carbonate (including isomers), (ethyl)(dihexylphenyl) carbonate (including isomers), (ethyl)(diheptylphenyl) carbonate (including isomers), (ethyl)(phenylphenyl) carbonate (including isomers), (ethyl)(trimethylphenyl) carbonate (including isomers), (ethyl)(triethylphenyl) carbonate (including isomers), (ethyl)(tripropylphenyl) carbonate (including isomers), (ethyl)(tributylphenyl) carbonate (including isomers), (ethyl)(phenylmethyl) carbonate (including isomers), (ethyl)(phenylethyl) carbonate (including isomers), (ethyl)(phenylpropyl) carbonate (including isomers), (ethyl)(phenylbutyl) carbonate (including isomers), (ethyl)(phenylpentyl) carbonate (including isomers), (ethyl)(phenylhexyl) carbonate (including isomers), (ethyl)(phenylheptyl) carbonate (including isomers), (ethyl)(phenyloctyl) carbonate (including isomers), (ethyl)(phenylnonyl) carbonate (including isomers), (propyl)(butyl) carbonate (including isomers), (propyl)(pentyl) carbonate (including isomers), (propyl)(hexyl) carbonate (including isomers), (propyl)(heptyl) carbonate (including isomers), (propyl)(octyl) carbonate (including isomers), (propyl)(nonyl) carbonate (including isomers), (propyl)(decyl) carbonate (including isomers), (propyl)(undecyl) carbonate (including isomers), (propyl)(dodecyl) carbonate (including isomers), (propyl)(tridecyl) carbonate (including isomers), (propyl)(tetradecyl) carbonate (including isomers), (propyl)(pentadecyl) carbonate (including isomers), (propyl)(hexadecyl) carbonate (including isomers), (propyl)(heptadecyl) carbonate (including isomers), (propyl)(octadecyl) carbonate (including isomers), (propyl)(nonadecyl) carbonate (including isomers), (propyl)(phenyl) carbonate (including isomers), (propyl)(methylphenyl) carbonate (including isomers), (propyl)(ethylphenyl) carbonate (including isomers), (propyl)(propylphenyl) carbonate (including isomers), (propyl)(butylphenyl) carbonate (including isomers), (propyl)(pentylphenyl) carbonate (including isomers), (propyl)(hexylphenyl) carbonate (including isomers), (propyl)(heptylphenyl) carbonate (including isomers), (propyl)(octylphenyl) carbonate (including isomers), (propyl)(nonylphenyl) carbonate (including isomers), (propyl)(decylphenyl) carbonate (including isomers), (propyl)(biphenyl) carbonate (including isomers), (propyl)(dimethylphenyl) carbonate (including isomers), (propyl)(diethylphenyl) carbonate (including isomers), (propyl)(dipropylphenyl) carbonate (including isomers), (propyl)(dibutylphenyl) carbonate (including isomers), (propyl)(dipentylphenyl) carbonate (including isomers), (propyl)(dihexylphenyl) carbonate (including isomers), (propyl)(diheptylphenyl) carbonate (including isomers), (propyl)(phenylphenyl) carbonate (including isomers), (propyl)(trimethylphenyl) carbonate (including isomers), (propyl)(triethylphenyl) carbonate (including isomers), (propyl)(tripropylphenyl) carbonate (including isomers), (propyl)(tributylphenyl) carbonate (including isomers), (propyl)(phenylmethyl) carbonate (including isomers), (propyl)(phenylethyl) carbonate (including isomers), (propyl)(phenylpropyl) carbonate (including isomers), (propyl)(phenylbutyl) carbonate (including isomers), (propyl)(phenylpentyl) carbonate (including isomers), (propyl)(phenylhexyl) carbonate (including isomers), (propyl)(phenylheptyl) carbonate (including isomers), (propyl)(phenyloctyl) carbonate (including isomers), (propyl)(phenylnonyl) carbonate (including isomers), (butyl)(pentyl) carbonate (including isomers), (butyl)(hexyl) carbonate (including isomers), (butyl)(heptyl) carbonate (including isomers), (butyl)(octyl) carbonate (including isomers), (butyl)(nonyl) carbonate (including isomers), (butyl)(decyl) carbonate (including isomers), (butyl)(undecyl) carbonate (including isomers), (butyl)(dodecyl) carbonate (including isomers), (butyl)(tridecyl) carbonate (including isomers), (butyl)(tetradecyl) carbonate (including isomers), (butyl)(pentadecyl) carbonate (including isomers), (butyl)(hexadecyl) carbonate (including isomers), (butyl)(heptadecyl) carbonate (including isomers), (butyl)(octadecyl) carbonate (including isomers), (butyl)(nonadecyl) carbonate (including isomers), (butyl)(phenyl) carbonate (including isomers), (butyl)(methylphenyl) carbonate (including isomers), (butyl)(ethylphenyl) carbonate (including isomers), (butyl)(propylphenyl) carbonate (including isomers), (butyl)(butylphenyl) carbonate (including isomers), (butyl)(pentylphenyl) carbonate (including isomers), (butyl)(hexylphenyl) carbonate (including isomers), (butyl)(heptylphenyl) carbonate (including isomers), (butyl)(octylphenyl) carbonate (including isomers), (butyl)(nonylphenyl) carbonate (including isomers), (butyl)(decylphenyl) carbonate (including isomers), (butyl)(biphenyl) carbonate (including isomers), (butyl)(dimethylphenyl) carbonate (including isomers), (butyl)(diethylphenyl) carbonate (including isomers), (butyl)(dipropylphenyl) carbonate (including isomers), (butyl)(dibutylphenyl) carbonate (including isomers), (butyl)(dipentylphenyl) carbonate (including isomers), (butyl)(dihexylphenyl) carbonate (including isomers), (butyl)(diheptylphenyl) carbonate (including isomers), (butyl)(phenylphenyl) carbonate (including isomers), (butyl)(trimethylphenyl) carbonate (including isomers), (butyl)(triethylphenyl) carbonate (including isomers), (butyl)(tripropylphenyl) carbonate (including isomers), (butyl)(tributylphenyl) carbonate (including isomers), (butyl)(phenylmethyl) carbonate (including isomers), (butyl)(phenylethyl) carbonate (including isomers), (butyl)(phenylpropyl) carbonate (including isomers), (butyl)(phenylbutyl) carbonate (including isomers), (butyl)(phenylpentyl) carbonate (including isomers), (butyl)(phenylhexyl) carbonate (including isomers), (butyl)(phenylheptyl) carbonate (including isomers), (butyl)(phenyloctyl) carbonate (including isomers), (butyl)(phenylnonyl) carbonate (including isomers), (pentyl)(hexyl) carbonate (including isomers), (pentyl)(heptyl) carbonate (including isomers), (pentyl)(octyl) carbonate (including isomers), (pentyl)(nonyl) carbonate (including isomers), (pentyl)(decyl) carbonate (including isomers), (pentyl)(undecyl) carbonate (including isomers), (pentyl)(dodecyl) carbonate (including isomers), (pentyl)(tridecyl) carbonate (including isomers), (pentyl)(tetradecyl) carbonate (including isomers), (pentyl)(pentadecyl) carbonate (including isomers), (pentyl)(hexadecyl) carbonate (including isomers), (pentyl)(heptadecyl) carbonate (including isomers), (pentyl)(octadecyl) carbonate (including isomers), (pentyl)(nonadecyl) carbonate (including isomers), (pentyl)(phenyl) carbonate (including isomers), (pentyl)(methylphenyl) carbonate (including isomers), (pentyl)(ethylphenyl) carbonate (including isomers), (pentyl)(propylphenyl) carbonate (including isomers), (pentyl)(butylphenyl) carbonate (including isomers), (pentyl)(pentylphenyl) carbonate (including isomers), (pentyl)(hexylphenyl) carbonate (including isomers), (pentyl)(heptylphenyl) carbonate (including isomers), (pentyl)(octylphenyl) carbonate (including isomers), (pentyl)(nonylphenyl) carbonate (including isomers), (pentyl)(decylphenyl) carbonate (including isomers), (pentyl)(biphenyl) carbonate (including isomers), (pentyl)(dimethylphenyl) carbonate (including isomers), (pentyl)(diethylphenyl) carbonate (including isomers), (pentyl)(dipropylphenyl) carbonate (including isomers), (pentyl)(dibutylphenyl) carbonate (including isomers), (pentyl)(dipentylphenyl) carbonate (including isomers), (pentyl)(dihexylphenyl) carbonate (including isomers), (pentyl)(diheptylphenyl) carbonate (including isomers), (pentyl)(phenylphenyl) carbonate (including isomers), (pentyl)(trimethylphenyl) carbonate (including isomers), (pentyl)(triethylphenyl) carbonate (including isomers), (pentyl)(tripropylphenyl) carbonate (including isomers), (pentyl)(tributylphenyl) carbonate (including isomers), (pentyl)(phenylmethyl) carbonate (including isomers), (pentyl)(phenylethyl) carbonate (including isomers), (pentyl)(phenylpropyl) carbonate (including isomers), (pentyl)(phenylbutyl) carbonate (including isomers), (pentyl)(phenylpentyl) carbonate (including isomers), (pentyl)(phenylhexyl) carbonate (including isomers), (pentyl)(phenylheptyl) carbonate (including isomers), (pentyl)(phenyloctyl) carbonate (including isomers), (pentyl)(phenylnonyl) carbonate (including isomers), (hexyl)(heptyl) carbonate (including isomers), (hexyl)(octyl) carbonate (including isomers), (hexyl)(nonyl) carbonate (including isomers), (hexyl)(decyl) carbonate (including isomers), (hexyl)(undecyl) carbonate (including isomers), (hexyl)(dodecyl) carbonate (including isomers), (hexyl)(tridecyl) carbonate (including isomers), (hexyl)(tetradecyl) carbonate (including isomers), (hexyl)(pentadecyl) carbonate (including isomers), (hexyl)(hexadecyl) carbonate (including isomers), (hexyl)(heptadecyl) carbonate (including isomers), (hexyl)(octadecyl) carbonate (including isomers), (hexyl)(nonadecyl) carbonate (including isomers), (hexyl)(phenyl) carbonate (including isomers), (hexyl)(methylphenyl) carbonate (including isomers), (hexyl)(ethylphenyl) carbonate (including isomers), (hexyl)(propylphenyl) carbonate (including isomers), (hexyl)(butylphenyl) carbonate (including isomers), (hexyl)(pentylphenyl) carbonate (including isomers), (hexyl)(hexylphenyl) carbonate (including isomers), (hexyl)(heptylphenyl) carbonate (including isomers), (hexyl)(octylphenyl) carbonate (including isomers), (hexyl)(nonylphenyl) carbonate (including isomers), (hexyl)(decylphenyl) carbonate (including isomers), (hexyl)(biphenyl) carbonate (including isomers), (hexyl)(dimethylphenyl) carbonate (including isomers), (hexyl)(diethylphenyl) carbonate (including isomers), (hexyl)(dipropylphenyl) carbonate (including isomers), (hexyl)(dibutylphenyl) carbonate (including isomers), (hexyl)(dipentylphenyl) carbonate (including isomers), (hexyl)(dihexylphenyl) carbonate (including isomers), (hexyl)(diheptylphenyl) carbonate (including isomers), (hexyl)(phenylphenyl) carbonate (including isomers), (hexyl)(trimethylphenyl) carbonate (including isomers), (hexyl)(triethylphenyl) carbonate (including isomers), (hexyl)(tripropylphenyl) carbonate (including isomers), (hexyl)(tributylphenyl) carbonate (including isomers), (hexyl)(phenylmethyl) carbonate (including isomers), (hexyl)(phenylethyl) carbonate (including isomers), (hexyl)(phenylpropyl) carbonate (including isomers), (hexyl)(phenylbutyl) carbonate (including isomers), (hexyl)(phenylpentyl) carbonate (including isomers), (hexyl)(phenylhexyl) carbonate (including isomers), (hexyl)(phenylheptyl) carbonate (including isomers), (hexyl)(phenyloctyl) carbonate (including isomers), (hexyl)(phenylnonyl) carbonate (including isomers), (heptyl)(octyl) carbonate (including isomers), (heptyl)(nonyl) carbonate (including isomers), (heptyl)(decyl) carbonate (including isomers), (heptyl)(undecyl) carbonate (including isomers), (heptyl)(dodecyl) carbonate (including isomers), (heptyl)(tridecyl) carbonate (including isomers), (heptyl)(tetradecyl) carbonate (including isomers), (heptyl)(pentadecyl) carbonate (including isomers), (heptyl)(hexadecyl) carbonate (including isomers), (heptyl)(heptadecyl) carbonate (including isomers), (heptyl)(octadecyl) carbonate (including isomers), (heptyl)(nonadecyl) carbonate (including isomers), (heptyl)(phenyl) carbonate (including isomers), (heptyl)(methylphenyl) carbonate (including isomers), (heptyl)(ethylphenyl) carbonate (including isomers), (heptyl)(propylphenyl) carbonate (including isomers), (heptyl)(butylphenyl) carbonate (including isomers), (heptyl)(pentylphenyl) carbonate (including isomers), (heptyl)(hexylphenyl) carbonate (including isomers), (heptyl)(heptylphenyl) carbonate (including isomers), (heptyl)(octylphenyl) carbonate (including isomers), (heptyl)(nonylphenyl) carbonate (including isomers), (heptyl)(decylphenyl) carbonate (including isomers), (heptyl)(biphenyl) carbonate (including isomers), (heptyl)(dimethylphenyl) carbonate (including isomers), (heptyl)(diethylphenyl) carbonate (including isomers), (heptyl)(dipropylphenyl) carbonate (including isomers), (heptyl)(dibutylphenyl) carbonate (including isomers), (heptyl)(dipentylphenyl) carbonate (including isomers), (heptyl)(dihexylphenyl) carbonate (including isomers), (heptyl)(diheptylphenyl) carbonate (including isomers), (heptyl)(phenylphenyl) carbonate (including isomers), (heptyl)(trimethylphenyl) carbonate (including isomers), (heptyl)(triethylphenyl) carbonate (including isomers), (heptyl)(tripropylphenyl) carbonate (including isomers), (heptyl)(tributylphenyl) carbonate (including isomers), (heptyl)(phenylmethyl) carbonate (including isomers), (heptyl)(phenylethyl) carbonate (including isomers), (heptyl)(phenylpropyl) carbonate (including isomers), (heptyl)(phenylbutyl) carbonate (including isomers), (heptyl)(phenylpentyl) carbonate (including isomers), (heptyl)(phenylhexyl) carbonate (including isomers), (heptyl)(phenylheptyl) carbonate (including isomers), (heptyl)(phenyloctyl) carbonate (including isomers), (heptyl)(phenylnonyl) carbonate (including isomers), (octyl)(nonyl) carbonate (including isomers), (octyl)(decyl) carbonate (including isomers), (octyl)(undecyl) carbonate (including isomers), (octyl)(dodecyl) carbonate (including isomers), (octyl)(tridecyl) carbonate (including isomers), (octyl)(tetradecyl) carbonate (including isomers), (octyl)(pentadecyl) carbonate (including isomers), (octyl)(hexadecyl) carbonate (including isomers), (octyl)(heptadecyl) carbonate (including isomers), (octyl)(octadecyl) carbonate (including isomers), (octyl)(nonadecyl) carbonate (including isomers), (octyl)(phenyl) carbonate (including isomers), (octyl)(methylphenyl) carbonate (including isomers), (octyl)(ethylphenyl) carbonate (including isomers), (octyl)(propylphenyl) carbonate (including isomers), (octyl)(butylphenyl) carbonate (including isomers), (octyl)(pentylphenyl) carbonate (including isomers), (octyl)(hexylphenyl) carbonate (including isomers), (octyl)(heptylphenyl) carbonate (including isomers), (octyl)(octylphenyl) carbonate (including isomers), (octyl)(nonylphenyl) carbonate (including isomers), (octyl)(decylphenyl) carbonate (including isomers), (octyl)(biphenyl) carbonate (including isomers), (octyl)(dimethylphenyl) carbonate (including isomers), (octyl)(diethylphenyl) carbonate (including isomers), (octyl)(dipropylphenyl) carbonate (including isomers), (octyl)(dibutylphenyl) carbonate (including isomers), (octyl)(dipentylphenyl) carbonate (including isomers), (octyl)(dihexylphenyl) carbonate (including isomers), (octyl)(diheptylphenyl) carbonate (including isomers), (octyl)(phenylphenyl) carbonate (including isomers), (octyl)(trimethylphenyl) carbonate (including isomers), (octyl)(triethylphenyl) carbonate (including isomers), (octyl)(tripropylphenyl) carbonate (including isomers), (octyl)(tributylphenyl) carbonate (including isomers), (octyl)(phenylmethyl) carbonate (including isomers), (octyl)(phenylethyl) carbonate (including isomers), (octyl)(phenylpropyl) carbonate (including isomers), (octyl)(phenylbutyl) carbonate (including isomers), (octyl)(phenylpentyl) carbonate (including isomers), (octyl)(phenylhexyl) carbonate (including isomers), (octyl)(phenylheptyl) carbonate (including isomers), (octyl)(phenyloctyl) carbonate (including isomers), (octyl)(phenylnonyl) carbonate (including isomers), (methylphenyl)(ethylphenyl) carbonate (including isomers), (methylphenyl)(propylphenyl) carbonate (including isomers), (methylphenyl)(butylphenyl) carbonate (including isomers), (methylphenyl)(pentylphenyl) carbonate (including isomers), (methylphenyl)(hexylphenyl) carbonate (including isomers), (methylphenyl)(heptylphenyl) carbonate (including isomers), (methylphenyl)(octylphenyl) carbonate (including isomers), (methylphenyl)(nonylphenyl) carbonate (including isomers), (methylphenyl)(decylphenyl) carbonate (including isomers), (methylphenyl)(biphenyl) carbonate (including isomers), (methylphenyl)(dimethylphenyl) carbonate (including isomers), (methylphenyl)(diethylphenyl) carbonate (including isomers), (methylphenyl)(dipropylphenyl) carbonate (including isomers), (methylphenyl)(dibutylphenyl) carbonate (including isomers), (methylphenyl)(dipentylphenyl) carbonate (including isomers), (methylphenyl)(dihexylphenyl) carbonate (including isomers), (methylphenyl)(diheptylphenyl) carbonate (including isomers), (methylphenyl)(phenylphenyl) carbonate (including isomers), (methylphenyl)(trimethylphenyl) carbonate (including isomers), (methylphenyl)(triethylphenyl) carbonate (including isomers), (methylphenyl)(tripropylphenyl) carbonate (including isomers), (methylphenyl)(tributylphenyl) carbonate (including isomers), (methylphenyl)(phenylmethyl) carbonate (including isomers), (methylphenyl)(phenylethyl) carbonate (including isomers), (methylphenyl)(phenylpropyl) carbonate (including isomers), (methylphenyl)(phenylbutyl) carbonate (including isomers), (methylphenyl)(phenylpentyl) carbonate (including isomers), (methylphenyl)(phenylhexyl) carbonate (including isomers), (methylphenyl)(phenylheptyl) carbonate (including isomers), (methylphenyl)(phenyloctyl) carbonate (including isomers), (methylphenyl)(phenylnonyl) carbonate (including isomers), (ethylphenyl)(propylphenyl) carbonate (including isomers), (ethylphenyl)(butylphenyl) carbonate (including isomers), (ethylphenyl)(pentylphenyl) carbonate (including isomers), (ethylphenyl)(hexylphenyl) carbonate (including isomers), (ethylphenyl)(heptylphenyl) carbonate (including isomers), (ethylphenyl)(octylphenyl) carbonate (including isomers), (ethylphenyl)(nonylphenyl) carbonate (including isomers), (ethylphenyl)(decylphenyl) carbonate (including isomers), (ethylphenyl)(biphenyl) carbonate (including isomers), (ethylphenyl)(dimethylphenyl) carbonate (including isomers), (ethylphenyl)(diethylphenyl) carbonate (including isomers), (ethylphenyl)(dipropylphenyl) carbonate (including isomers), (ethylphenyl)(dibutylphenyl) carbonate (including isomers), (ethylphenyl)(dipentylphenyl) carbonate (including isomers), (ethylphenyl)(dihexylphenyl) carbonate (including isomers), (ethylphenyl)(diheptylphenyl) carbonate (including isomers), (ethylphenyl)(phenylphenyl) carbonate (including isomers), (ethylphenyl)(trimethylphenyl) carbonate (including isomers), (ethylphenyl)(triethylphenyl) carbonate (including isomers), (ethylphenyl)(tripropylphenyl) carbonate (including isomers), (ethylphenyl)(tributylphenyl) carbonate (including isomers), (ethylphenyl)(phenylmethyl) carbonate, (ethylphenyl)(phenylethyl) carbonate (including isomers), (ethylphenyl)(phenylpropyl) carbonate (including isomers), (ethylphenyl)(phenybutyl) carbonate (including isomers), (ethylphenyl)(phenylpentyl) carbonate (including isomers), (ethylphenyl)(phenyhexyl) carbonate (including isomers), (ethylphenyl)(phenylheptyl) carbonate (including isomers), (ethylphenyl)(phenyloctyl) carbonate (including isomers), (ethylphenyl)(phenylnonyl) carbonate (including isomers), (propylphenyl)(propylphenyl) carbonate (including isomers), (propylphenyl)(butylphenyl) carbonate (including isomers), (propylphenyl)(pentylphenyl) carbonate (including isomers), (propylphenyl)(hexylphenyl) carbonate (including isomers), (propylphenyl)(heptylphenyl) carbonate (including isomers), (propylphenyl)(octylphenyl) carbonate (including isomers), (propylphenyl)(nonylphenyl) carbonate (including isomers), (propylphenyl)(decylphenyl) carbonate (including isomers), (propylphenyl)(biphenyl) carbonate (including isomers), (propylphenyl)(dimethylphenyl) carbonate (including isomers), (propylphenyl)(diethylphenyl) carbonate (including isomers), (propylphenyl)(dipropylphenyl) carbonate (including isomers), (propylphenyl)(dibutylphenyl) carbonate (including isomers), (propylphenyl)(dipentylphenyl) carbonate (including isomers), (propylphenyl)(dihexylphenyl) carbonate (including isomers), (propylphenyl)(diheptylphenyl) carbonate (including isomers), (propylphenyl)(phenylphenyl) carbonate (including isomers), (propylphenyl)(trimethylphenyl) carbonate (including isomers), (propylphenyl)(triethylphenyl) carbonate (including isomers), (propylphenyl)(tripropylphenyl) carbonate (including isomers), (propylphenyl)(tributylphenyl) carbonate (including isomers), (propylphenyl)(phenylmethyl) carbonate (including isomers), (propylphenyl)(phenylethyl) carbonate (including isomers), (propylphenyl)(phenylpropyl) carbonate (including isomers), (propylphenyl)(phenybutyl) carbonate (including isomers), (propylphenyl)(phenylpentyl) carbonate (including isomers), (propylphenyl)(phenyhexyl) carbonate (including isomers), (propylphenyl)(phenylheptyl) carbonate (including isomers), (propylphenyl)(phenyloctyl) carbonate (including isomers), (propylphenyl)(phenylnonyl) carbonate (including isomers), (butylphenyl)(pentylphenyl) carbonate (including isomers), (butylphenyl)(hexylphenyl) carbonate (including isomers), (butylphenyl)(heptylphenyl) carbonate (including isomers), (butylphenyl)(octylphenyl) carbonate (including isomers), (butylphenyl)(nonylphenyl) carbonate (including isomers), (butylphenyl)(decylphenyl) carbonate (including isomers), (butylphenyl)(biphenyl) carbonate (including isomers), (butylphenyl)(dimethylphenyl) carbonate (including isomers), (butylphenyl)(diethylphenyl) carbonate (including isomers), (butylphenyl)(dipropylphenyl) carbonate (including isomers), (butylphenyl)(dibutylphenyl) carbonate (including isomers), (butylphenyl)(dipentylphenyl) carbonate (including isomers), (butylphenyl)(dihexylphenyl) carbonate (including isomers), (butylphenyl)(diheptylphenyl) carbonate (including isomers), (butylphenyl)(phenylphenyl) carbonate (including isomers), (butylphenyl)(trimethylphenyl) carbonate (including isomers), (butylphenyl)(triethylphenyl) carbonate (including isomers), (butylphenyl)(tripropylphenyl) carbonate (including isomers), (butylphenyl)(tributylphenyl) carbonate (including isomers), (butylphenyl)(phenylmethyl) carbonate (including isomers), (butylphenyl)(phenylethyl) carbonate (including isomers), (butylphenyl)(phenylpropyl) carbonate (including isomers), (butylphenyl)(phenybutyl) carbonate (including isomers), (butylphenyl)(phenylpentyl) carbonate (including isomers), (butylphenyl)(phenyhexyl) carbonate (including isomers), (butylphenyl)(phenylheptyl) carbonate (including isomers), (butylphenyl)(phenyloctyl) carbonate (including isomers), (butylphenyl)(phenylnonyl) carbonate (including isomers), (pentylphenyl)(hexylphenyl) carbonate (including isomers), (pentylphenyl)(heptylphenyl) carbonate (including isomers), (pentylphenyl)(octylphenyl) carbonate (including isomers), (pentylphenyl)(nonylphenyl) carbonate (including isomers), (pentylphenyl)(decylphenyl) carbonate (including isomers), (pentylphenyl)(biphenyl) carbonate (including isomers), (pentylphenyl)(dimethylphenyl) carbonate (including isomers), (pentylphenyl)(diethylphenyl) carbonate (including isomers), (pentylphenyl)(dipropylphenyl) carbonate (including isomers), (pentylphenyl)(dibutylphenyl) carbonate (including isomers), (pentylphenyl)(dipentylphenyl) carbonate (including isomers), (pentylphenyl)(dihexylphenyl) carbonate (including isomers), (pentylphenyl)(diheptylphenyl) carbonate (including isomers), (pentylphenyl)(phenylphenyl) carbonate (including isomers), (pentylphenyl)(trimethylphenyl) carbonate (including isomers), (pentylphenyl)(triethylphenyl) carbonate (including isomers), (pentylphenyl)(tripropylphenyl) carbonate (including isomers), (pentylphenyl)(tributylphenyl) carbonate (including isomers), (pentylphenyl)(phenylmethyl) carbonate (including isomers), (pentylphenyl)(phenylethyl) carbonate (including isomers), (pentylphenyl)(phenylpropyl) carbonate (including isomers), (pentylphenyl)(phenybutyl) carbonate (including isomers), (pentylphenyl)(phenylpentyl) carbonate (including isomers), (pentylphenyl)(phenyhexyl) carbonate (including isomers), (pentylphenyl)(phenylheptyl) carbonate (including isomers), (pentylphenyl)(phenyloctyl) carbonate (including isomers), (pentylphenyl)(phenylnonyl) carbonate (including isomers), (hexylphenyl)(heptylphenyl) carbonate (including isomers), (hexylphenyl)(octylphenyl) carbonate (including isomers), (hexylphenyl)(nonylphenyl) carbonate (including isomers), (hexylphenyl)(decylphenyl) carbonate (including isomers), (hexylphenyl)(biphenyl) carbonate (including isomers), (hexylphenyl)(dimethylphenyl) carbonate (including isomers), (hexylphenyl)(diethylphenyl) carbonate (including isomers), (hexylphenyl)(dipropylphenyl) carbonate (including isomers), (hexylphenyl)(dibutylphenyl) carbonate (including isomers), (hexylphenyl)(dipentylphenyl) carbonate (including isomers), (hexylphenyl)(dihexylphenyl) carbonate (including isomers), (hexylphenyl)(diheptylphenyl) carbonate (including isomers), (hexylphenyl)(phenylphenyl) carbonate (including isomers), (hexylphenyl)(trimethylphenyl) carbonate (including isomers), (hexylphenyl)(triethylphenyl) carbonate (including isomers), (hexylphenyl)(tripropylphenyl) carbonate (including isomers), (hexylphenyl)(tributylphenyl) carbonate (including isomers), (hexylphenyl)(phenylmethyl) carbonate (including isomers), (hexylphenyl)(phenylethyl) carbonate (including isomers), (hexylphenyl)(phenylpropyl) carbonate (including isomers), (hexylphenyl)(phenybutyl) carbonate (including isomers), (hexylphenyl)(phenylpentyl) carbonate (including isomers), (hexylphenyl)(phenyhexyl) carbonate (including isomers), (hexylphenyl)(phenylheptyl) carbonate (including isomers), (hexylphenyl)(phenyloctyl) carbonate (including isomers), (hexylphenyl)(phenylnonyl) carbonate (including isomers), (dimethylphenyl)(diethylphenyl) carbonate (including isomers), (dimethylphenyl)(dipropylphenyl) carbonate (including isomers), (dimethylphenyl)(dibutylphenyl) carbonate (including isomers), (dimethylphenyl)(dipentylphenyl) carbonate (including isomers), (dimethylphenyl)(dihexylphenyl) carbonate (including isomers), (dimethylphenyl)(diheptylphenyl) carbonate (including isomers), (dimethylphenyl)(phenylphenyl) carbonate (including isomers), (dimethylphenyl)(trimethylphenyl) carbonate (including isomers), (dimethylphenyl)(triethylphenyl) carbonate (including isomers), (dimethylphenyl)(tripropylphenyl) carbonate (including isomers), (dimethylphenyl)(tributylphenyl) carbonate (including isomers), (dimethylphenyl)(phenylmethyl) carbonate (including isomers), (dimethylphenyl)(phenylethyl) carbonate (including isomers), (dimethylphenyl)(phenylpropyl) carbonate (including isomers), (dimethylphenyl)(phenybutyl) carbonate (including isomers), (dimethylphenyl)(phenylpentyl) carbonate (including isomers), (dimethylphenyl)(phenyhexyl) carbonate (including isomers), (dimethylphenyl)(phenylheptyl) carbonate (including isomers), (dimethylphenyl)(phenyloctyl) carbonate (including isomers), (dimethylphenyl)(phenylnonyl) carbonate (including isomers), (diethylphenyl)(dipropylphenyl) carbonate (including isomers), (diethylphenyl)(dibutylphenyl) carbonate (including isomers), (diethylphenyl)(dipentylphenyl) carbonate (including isomers), (diethylphenyl)(dihexylphenyl) carbonate (including isomers), (diethylphenyl)(diheptylphenyl) carbonate (including isomers), (diethylphenyl)(phenylphenyl) carbonate (including isomers), (diethylphenyl)(trimethylphenyl) carbonate (including isomers), (diethylphenyl)(triethylphenyl) carbonate (including isomers), (diethylphenyl)(tripropylphenyl) carbonate (including isomers), (diethylphenyl)(tributylphenyl) carbonate (including isomers), (diethylphenyl)(phenylmethyl) carbonate (including isomers), (diethylphenyl)(phenylethyl) carbonate (including isomers), (diethylphenyl)(phenylpropyl) carbonate (including isomers), (diethylphenyl)(phenybutyl) carbonate (including isomers), (diethylphenyl)(phenylpentyl) carbonate (including isomers), (diethylphenyl)(phenyhexyl) carbonate (including isomers), (diethylphenyl)(phenylheptyl) carbonate (including isomers), (diethylphenyl)(phenyloctyl) carbonate (including isomers), (diethylphenyl)(phenylnonyl) carbonate (including isomers), (dipropylphenyl)(dibutylphenyl) carbonate (including isomers), (dipropylphenyl)(dipentylphenyl) carbonate (including isomers), (dipropylphenyl)(dihexylphenyl) carbonate (including isomers), (dipropylphenyl)(diheptylphenyl) carbonate (including isomers), (dipropylphenyl)(phenylphenyl) carbonate (including isomers), (dipropylphenyl)(trimethylphenyl) carbonate (including isomers), (dipropylphenyl)(triethylphenyl) carbonate (including isomers), (dipropylphenyl)(tripropylphenyl) carbonate (including isomers), (dipropylphenyl)(tributylphenyl) carbonate (including isomers), (dipropylphenyl)(phenylmethyl) carbonate (including isomers), (dipropylphenyl)(phenylethyl) carbonate (including isomers), (dipropylphenyl)(phenylpropyl) carbonate (including isomers), (dipropylphenyl)(phenybutyl) carbonate (including isomers), (dipropylphenyl)(phenylpentyl) carbonate (including isomers), (dipropylphenyl)(phenyhexyl) carbonate (including isomers), (dipropylphenyl)(phenylheptyl) carbonate (including isomers), (dipropylphenyl)(phenyloctyl) carbonate (including isomers), (dipropylphenyl)(phenylnonyl) carbonate (including isomers), (dibutylphenyl)(dipentylphenyl) carbonate (including isomers), (dibutylphenyl)(dihexylphenyl) carbonate (including isomers), (dibutylphenyl)(diheptylphenyl) carbonate (including isomers), (dibutylphenyl)(phenylphenyl) carbonate (including isomers), (dibutylphenyl)(trimethylphenyl) carbonate (including isomers), (dibutylphenyl)(triethylphenyl) carbonate (including isomers), (dibutylphenyl)(tripropylphenyl) carbonate (including isomers), (dibutylphenyl)(tributylphenyl) carbonate (including isomers), (dibutylphenyl)(phenylmethyl) carbonate (including isomers), (dibutylphenyl)(phenylethyl) carbonate (including isomers), (dibutylphenyl)(phenylpropyl) carbonate (including isomers), (dibutylphenyl)(phenybutyl) carbonate (including isomers), (dibutylphenyl)(phenylpentyl) carbonate (including isomers), (dibutylphenyl)(phenyhexyl) carbonate (including isomers), (dibutylphenyl)(phenylheptyl) carbonate (including isomers), (dibutylphenyl)(phenyloctyl) carbonate (including isomers), (dibutylphenyl)(phenylnonyl) carbonate (including isomers), (dipentylphenyl)(dihexylphenyl) carbonate (including isomers), (dipentylphenyl)(diheptylphenyl) carbonate (including isomers), (dipentylphenyl)(phenylphenyl) carbonate (including isomers), (dipentylphenyl)(trimethylphenyl) carbonate (including isomers), (dipentylphenyl)(triethylphenyl) carbonate (including isomers), (dipentylphenyl)(tripropylphenyl) carbonate (including isomers), (dipentylphenyl)(tributylphenyl) carbonate (including isomers), (dipentylphenyl)(phenylmethyl) carbonate (including isomers), (dipentylphenyl)(phenylethyl) carbonate (including isomers), (dipentylphenyl)(phenylpropyl) carbonate (including isomers), (dipentylphenyl)(phenybutyl) carbonate (including isomers), (dipentylphenyl)(phenylpentyl) carbonate (including isomers), (dipentylphenyl)(phenyhexyl) carbonate (including isomers), (dipentylphenyl)(phenylheptyl) carbonate (including isomers), (dipentylphenyl)(phenyloctyl) carbonate (including isomers), (dipentylphenyl)(phenylnonyl) carbonate (including isomers), (trimethylphenyl)(triethylphenyl) carbonate (including isomers), (trimethylphenyl)(tripropylphenyl) carbonate (including isomers), (trimethylphenyl)(tributylphenyl) carbonate (including isomers), (trimethylphenyl)(phenylmethyl) carbonate (including isomers), (trimethylphenyl)(phenylethyl) carbonate (including isomers), (trimethylphenyl)(phenylpropyl) carbonate (including isomers), (trimethylphenyl)(phenybutyl) carbonate (including isomers), (trimethylphenyl)(phenylpentyl) carbonate (including isomers), (trimethylphenyl)(phenyhexyl) carbonate (including isomers), (trimethylphenyl)(phenylheptyl) carbonate (including isomers), (trimethylphenyl)(phenyloctyl) carbonate (including isomers) and (trimethylphenyl)(phenylnonyl) carbonate (including isomers).

The N-substituted carbamic acid ester contained in the composition for transfer and storage of the present embodiment is preferably produced by reacting an organic amine, a carbonic acid derivative and an aromatic hydroxy composition. In this case, the carbonic acid ester contained in the composition for transfer and storage is a carbonic acid ester in which an ester group of the carbonic acid ester is a group derived from the aromatic hydroxy composition.

In addition to being contained in the composition for transfer and storage of the present embodiment, the above-mentioned carbonic acid ester may be contained in a compound having a carbonyl group derived from the carbonic acid derivative that is recovered during production of the N-substituted carbamic acid ester. The carbonic acid ester in that case is a carbonic acid ester in which an ester group of the carbonic acid ester is an ester group derived from an aromatic hydroxy compound used in production of the N-substituted carbamic acid ester.

The recovered compound having a carbonyl group derived from a carbonic acid derivative can also be reused as a raw material for producing N-substituted carbamic acid ester. At that time, in addition to the previously described urea compounds, carbamic acid esters and carbonic acid esters, although urea compounds, biurets or nurates and the like of complex substituted monomers or polymers may also be contained as compounds having a carbonyl group derived from the carbonic acid derivative, the containing of such compounds does not present a problem.

<Hydroxy Composition>

The hydroxy composition in the present embodiment refers to a composition that contains one type or a plurality of types of hydroxy compounds. Although a hydroxy compound refers to a compound having a hydroxy group (—OH group), hydroxy compounds that compose the hydroxy composition are compounds in which a hydroxy group (—OH group) is bonded to a carbon atom in the form of an alcohol and/or aromatic hydroxy compound are used preferably.

<Hydroxy Composition: Alcohol>

According to the IUPAC definition (Rule C-201), alcohols are "compounds in which a hydroxy group, —OH, is attached to a saturated carbon atom: $R_3COH$", and refer to a hydroxy compound represented by the following formula (45):

$$R^{20}(-OH)_g \tag{45}$$

(wherein $R^{20}$ represents a group composed of an aliphatic group having 1 to 50 carbon atoms substituted with g hydroxy groups or an aliphatic group having 7 to 50 carbon atoms to which is bonded an aromatic group, an OH group of the alcohol represented by formula (45) is an OH group not bonded to an aromatic group, and g represents an integer of 1 to 5, provided that $R^{20}$ is a group that does not have an active hydrogen other than that of the hydroxy group.)

Although the term "active hydrogen" is used in the above explanation, an "active hydrogen" refers to a hydrogen atom bonded to an oxygen atom, sulfur atom, nitrogen atom or silicon atom and the like (excluding aromatic hydroxy groups), and a hydrogen atom of a terminal methine group. Examples of these active hydrogens may include hydrogen contained in an atomic group such as an —OH group, —C(=O)OH group, —C(=O)H group, —SH group, —SO$_3$H group, —SO$_2$H group, —SOH group, —NH$_2$ group, —NH— group, —SiH group or —C≡CH group. Although a hydroxy group (—OH groups) also contains an active hydrogen, since the hydroxy group is contained in the composition or reaction raw materials of the present embodiment and does not have a detrimental effect thereon, unless specifically indicated otherwise, hydroxy groups are excluded from groups containing active hydrogen. Although the term "active hydrogen" is frequently used in other locations of the present embodiment, the definition described above also applies thereto.

Examples of aliphatic hydrocarbon groups of $R^{20}$ may include aliphatic hydrocarbon groups in which atoms other than hydrogen atoms that compose the group are specific non-metal atoms (carbon, oxygen, nitrogen, sulfur, silicon or halogen atoms). Preferable examples of aliphatic groups may include groups in which the aliphatic group is a linear hydrocarbon group, a cyclic hydrocarbon group or a group to which is bonded at least one type of group selected from the linear hydrocarbon groups and the cyclic hydrocarbon groups (such as a cyclic hydrocarbon group substituted with a linear hydrocarbon group or a linear hydrocarbon group substituted with a cyclic hydrocarbon group). In addition, examples of aliphatic groups to which is bonded an aromatic group may include groups in which a linear and/or branched alkyl group or cycloalkyl group is substituted with an aromatic group, and groups in which the alkyl group having 1 to 44 carbon atoms is substituted with the aromatic group having 6 to 49 carbon atoms. As was previously explained, the aromatic group preferably refers to an aromatic group in which atoms other than hydrogen atoms that compose the aromatic group are specific non-metal atoms (carbon, oxygen, nitrogen, sulfur, silicon or halogen atoms), examples of which may include a monocyclic aromatic group, a condensed polycyclic aromatic group, a crosslinked cyclic aromatic group, a ring-assembling aromatic group and a heterocyclic aromatic group, and is more preferably a substituted and/or unsubstituted phenyl group, a substituted and/or unsubstituted naphthyl group, or a substituted and/or unsubstituted anthryl group.

Examples of this $R^{20}$ may include alkyl groups and/or cycloalkyl groups and/or cycloalkyl groups substituted with an alkyl group and/or alkyl groups substituted with a cycloalkyl group such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers), cyclopentyl group, cyclohexyl group, cycloheptyl group, cyclooctyl group, methylcyclopentyl group (including isomers), ethylcyclopentyl group (including isomers), methylcyclohexyl group (including isomers), ethylcyclohexyl group (including isomers), propylcyclohexyl group (including isomers), butylcyclohexyl group (including isomers), pentylcyclohexyl group (including isomers), hexylcyclohexyl group (including isomers), dimethylcyclohexyl group (including isomers), diethylcyclohexyl group (including isomers) or dibutylcyclohexyl group (including isomers); and, aralkyl groups such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers).

Among these alcohols, alcohols having one or two alcoholic hydroxy groups (hydroxy groups directly added to a carbon atom other than that of an aromatic group that composes the hydroxy compound) are preferable in consideration of industrial use due to their typically low viscosity, while monoalcohols in which the number of the alcoholic hydroxy groups is 1 are more preferable.

Specific examples may include alkyl alcohols and/or cycloalkyl alcohols and/or cycloalkyl alcohols substituted with an alkyl group and/or alkyl alcohols substituted with a cycloalkyl group such as methanol, ethanol, propanol (including isomers), butanol (including isomers), pentanol (including isomers), hexanol (including isomers), heptanol (including isomers), octanol (including isomers), nonanol (including isomers), decanol (including isomers), dodecanol (including isomers), octadecanol (including isomers), cyclopentanol, cyclohexanol, cycloheptanol, cyclooctanol, methylcyclopentanol (including isomers), ethylcyclopentanol (including isomers), methylcyclohexanol (including isomers), ethylcyclohexanol (including isomers), propylcyclohexanol (including isomers), butylcyclohexanol (including isomers), pentylcyclohexanol (including isomers), hexylcyclohexanol (including isomers), dimethylcyclohexanol (including isomers), diethylcyclohexanol (including isomers) or dibutylcyclohexanol; and alkyl alcohols substituted with an aryl group such as phenylmethanol, phenylethanol (including isomers), phenylpropanol (including isomers), phenylbutanol (including isomers), phenylpentanol (including isomers), phenylhexanol (including isomers), phenylheptanol (including isomers), phenyloctanol (including isomers) or phenylnonanol (including isomers).

Among these, alkyl alcohols having 1 to 20 carbon atoms are used preferably from the viewpoints of ease of acquisition, solubility of raw materials and products and the like.

<Hydroxy Composition: Aromatic Hydroxy Compound>

The following provides an explanation of the case in which the hydroxy compound that composes the hydroxy composition is an aromatic hydroxy compound. In this case, the hydroxy composition frequently refers to an aromatic hydroxy composition. Here, aromatic hydroxy compounds are classified as phenols and refer to "compounds having one or more hydroxy groups attached to a benzene or other arene ring" as stated in the IUPAC definition (Rule C-202).

The aromatic hydroxy compound is preferably a monovalent to trivalent aromatic hydroxy compound (namely, that in which the number of hydroxy groups bonded to the aromatic ring is an integer of from 1 to 3) in consideration of industrial use due to the typically low viscosity thereof, while a monovalent aromatic hydroxy compound (namely, that in which the number of hydroxy groups bonded to the aromatic ring is 1) is more preferable.

An aromatic hydroxy compound that composes (or is contained in) the aromatic hydroxy composition is at least one type of aromatic hydroxy compound represented by the following formula (46):

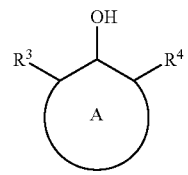

(46)

(wherein ring A represents an optionally substituted aromatic hydrocarbon ring and may be monocyclic or polycyclic, $R^3$ and $R^4$ respectively and independently represent a hydrogen atom or organic group, the number of carbon atoms that compose the aromatic hydroxy compound is an integer of from 6 to 50, and $R^3$ and $R^4$ may bond with A to form a ring structure).

Examples of substituents that substitute an aromatic group of an aromatic hydroxy compound represented by formula (46) above may include groups selected from a hydrogen atom, a halogen atom, an aliphatic group and an aromatic group that are composed of acyclic hydrocarbon groups or cyclic hydrocarbon groups (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a hetero-crosslinked ring group or a heterocyclic group), groups bonded to one or more types of groups selected from the acyclic hydrocarbon groups and the cyclic hydrocarbon groups, and groups in which the above-mentioned groups are bonded through a covalent bond with a specific non-metal atom (carbon, oxygen, nitrogen, sulfur or silicon atom). In addition, covalent bonding with a specific non-metal atom as described above (carbon, oxygen, nitrogen, sulfur or silicon atom) refers to a state in which, for example, a group represented by the following formulas (47) to (54) and the above-mentioned groups are bonded with a covalent bond.

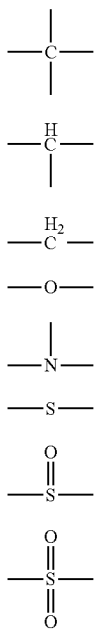

(47)
(48)
(49)
(50)
(51)
(52)
(53)
(54)

Among such substituents, substituents that can be preferably used in the present embodiment in consideration of less susceptibility to the occurrence of side reactions contain groups selected from the group consisting of acyclic hydrocarbon groups and cyclic hydrocarbon groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups).

In formula (46) above, $R^3$ and $R^4$ are preferably groups defined by the following (i) to (v):

(i) a hydrogen atom, (ii) a halogen atom, (iii) a group in which the atom at the α position is a nitrogen atom and the nitrogen atom is a secondary or tertiary nitrogen atom (namely, a nitrogen atom that forms an —NH— bond or nitrogen that does not bond to hydrogen), and which does not contain active hydrogen (excluding the hydrogen bonded to the α position nitrogen atom), (iv) a group in which the atom at the α position is a carbon atom and which does not contain active hydrogen, and (v) a group in which the atom at the α position is an oxygen atom and which does not contain active hydrogen.

Although the term "atom at the α position" is used in the preceding explanation, an "atom at the α position" refers to an atom that composes the $R^3$ and $R^4$ that is adjacent to a carbon atom on the aromatic hydrocarbon ring to which the $R^3$ and $R^4$ groups are bonded.

Although previously explained, an "active hydrogen" refers to a hydrogen atom bonded to an oxygen atom, a sulfur atom, a nitrogen atom or a silicon atom and the like (excluding aromatic hydroxy groups), and a hydrogen atom of a terminal methine group. Examples of these active hydrogens may include hydrogen contained in an atomic group such as an —OH group, a —C(=O)OH group, a —C(=O)H group, a —SH group, a —SO$_3$H group, a —SO$_2$H group, a —SOH group, a —NH$_2$ group, a —NH— group, a —SiH group or a —C≡CH group. Although an aromatic hydroxy group (—OH group directly bonded to an aromatic ring) also contains an active hydrogen, since the hydroxy group is contained in the composition or reaction raw materials of the present embodiment and does not have a detrimental effect thereon, aromatic hydroxy groups are excluded from groups containing active hydrogen.

In the case of transferring a composition containing an N-substituted carbamic acid ester at a high temperature or in the case of reacting an organic amine, a carbonic acid derivative and an aromatic hydroxy compound and obtaining an N-substituted carbamic acid-O-aryl ester at a high temperature, an aromatic hydroxy compound in which the substituent that substitutes ring A of the aromatic hydroxy compound (excluding $R^3$ and $R^4$) is an inactive substituent is preferable. An inactive substituent here refers to a group in which the inactive substituent does not contain an active hydrogen as previously described (although it may have an aromatic hydroxy group).

Examples of such substituents that substitute ring A (excluding $R^3$ and $R^4$) may include a group selected from the group consisting of an alkyl group, a cycloalkyl group, an aryl group, an aralkyl group and an ether group (substituted and/or unsubstituted alkyl ether and/or aryl ether and/or aralkyl ether); a group to which is bonded a group selected from one or more types of the above-mentioned groups; a group selected from groups in which a group selected from one or more types of the above-mentioned groups is selected from groups composed of a group bonded with a saturated hydrocarbon bond and/or a ether bond; and, a group which is a halogen atom and in which the total of the number of carbon atoms that compose ring A and the number of carbon atoms that compose all substituents that substitute ring A is an integer of from 6 to 50.

Furthermore, in above-mentioned definition (iii), the case is described in which a nitrogen atom at the α position of $R^3$ and $R^4$ is a nitrogen atom that forms an —NH— bond. According to the definition of an "active hydrogen" as previously described, a hydrogen atom of this —NH— bond is also an active hydrogen. However, as a result of studies conducted by the inventors of the present invention, a hydrogen atom bonded to a nitrogen atom at the α position has low reactivity, and in the present embodiment, was determined to have hardly any detrimental effects. The inventors of the present invention surmised that this is due to steric hindrance attributable to a hydroxy group.

In formula (46) above, examples of ring A may include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring and an acephenanthrylene ring. More preferably, ring A has a structure that contains at least one structure selected from a benzene ring and a naphthalene ring.

Moreover, in consideration of industrial use, an aromatic hydroxy compound that is easily acquirable and has benzene skeleton thereof is preferable. Preferable examples of such an aromatic hydroxy compound may include aromatic hydroxy compounds represented by the following formula (55):

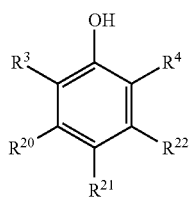

(55)

(wherein $R^3$, $R^4$, $R^{20}$, $R^{21}$ and $R^{22}$ respectively and independently represent a group selected from the group consisting of an alkyl group, a cycloalkyl group, an aryl group, an aralkyl group and an ether group (substituted and/or unsubstituted alkyl ether and/or aryl ether and/or aralkyl ether); a group to which is bonded a group selected from one or more types of the above groups; a group selected from groups in which one or more types of the above groups is composed of a group bonded with a saturated aliphatic bond and/or ether bond; a halogen atom; or a hydrogen atom, and the total number of carbon atoms that compose the $R^3$, $R^4$, $R^{20}$, $R^{21}$ and $R^{22}$ is an integer of from 0 to 44).

In formula (55) above, $R^3$, $R^4$, $R^{20}$, $R^{21}$ and $R^{22}$ are preferably groups independently selected from groups indicated in the following (i) to (v):

(i) a hydrogen atom, (ii) a halogen atom, (iii) a group in which the atom at the α position is a carbon atom, the number of carbon atoms is from 1 to 44, and the three groups bonded to the carbon atom at the α position are respectively and independently selected from an alkyl group having 1 to 43 carbon atoms, a cycloalkyl group having 1 to 43 carbon atoms, an alkoxy group having 1 to 43 carbon atoms, a polyoxyalkylene alkyl ether group having 2 to 43 atoms and does not have an OH group on the terminal thereof, an aryl group having 6 to 43 carbon atoms, an aralkyl group having 7 to 43 carbon atoms, an aralkyloxy group having 7 to 43 carbon atoms, a group to which is bonded one or more types of the above groups and a hydrogen atom, (iv) an aryl group having 1 to 44 carbon atoms, wherein the aryl group is substituted by a substituent, the aryl group may be substituted with 1 to 5 of the substituents indicated below, and the substituent is a group selected from a hydrogen atom, an alkyl group having 1 to 38 carbon atoms, a cycloalkyl group having 4 to 38 carbon atoms, an alkoxy group having 1 to 38 carbon atoms, a polyoxyalkylene alkyl ether group having 2 to 38 carbons that does not have an OH group on the terminal thereof, an aryl group having 6 to 38 carbon atoms, an aralkyl group having 7 to 38 carbon atoms, an aralkyloxy group having 7 to 38 carbon atoms and a group to which is bonded one or more types of the above groups, and (v) a group in which the atom at the α position is an oxygen atom, the number of carbon atoms is from 1 to 44, and the group bonded to the oxygen atom at the α position is a group selected from an alkyl group having 1 to 44 carbon atoms, a cycloalkyl group having 1 to 44 carbon atoms, an alkoxy group having 1 to 44 carbon atoms, a polyoxyalkylene alkyl ether group having 2 to 44 carbon atoms that does not have an OH group on the terminal thereof, an aryl group having 6 to 44 carbon atoms, an aralkyl group having 7 to 44 carbon atoms, an aralkyloxy group having 7 to 44 carbon atoms, and a group to which is bonded one or more types of the above groups.

Furthermore, although the term "atom at the α position" is used in the preceding explanation of formula (55) above, an "atom at the α position" refers to an atom that composes the $R^3$, $R^4$, $R^{20}$, $R^{21}$ and $R^{22}$ that is adjacent to a carbon atom on the aromatic hydrocarbon ring to which the $R^3$, $R^4$, $R^{20}$, $R^{21}$ and $R^{22}$ groups are bonded.

In addition, although the term "aralkyloxy group" is used in the above explanation, an "aralkyloxy group" represents a group in which an oxygen atom is bonded to a previously defined aralkyl group.

Examples of these $R^3$, $R^4$, $R^{20}$, $R^{21}$ and $R^{22}$ may include alkyl groups and/or cycloalkyl groups and/or cycloalkyl groups substituted with an alkyl group and/or alkyl groups substituted with a cycloalkyl group such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers), cyclopentyl group, cyclohexyl group, cycloheptyl group, cyclooctyl group, methylcyclopentyl group (including isomers), ethylcyclopentyl group (including isomers), methylcyclohexyl group (including isomers), ethylcyclohexyl group (including isomers), propylcyclohexyl group (including isomers), butylcyclohexyl group (including isomers), pentylcyclohexyl group (including isomers), hexylcyclohexyl group (including isomers), dimethylcyclohexyl group (including isomers), diethylcyclohexyl group (including isomers) or dibutylcyclohexyl group (including isomers); alkoxy groups and/or cycloalkoxy groups and/or cycloalkoxy groups substituted with an alkoxy group and/or alkoxy groups substituted with a cycloalkoxy group such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers), an octadecyloxy group (including isomers), a cyclopentyloxy group (including isomers), a cyclohexyloxy group (including isomers), a cycloheptyloxy group (including isomers), a cyclooctyloxy group (including isomers), a methylcyclopentyloxy group (including isomers), an ethylcyclopentyloxy group (including isomers), a methylcyclohexyloxy group (including isomers), an ethylcyclohexyloxy group (including isomers), a propylcyclohexyloxy group (including isomers), a butylcyclohexyloxy group (including isomers), a pentylcyclohexyloxy group (including isomers), a hexylcyclohexyloxy group (including isomers), a dimethylcyclohexyloxy group (including isomers), a diethylcyclohexyloxy group (including isomers) or a dibutylcyclohexyloxy group (including isomers); substituted or unsubstituted aryl groups such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); substituted or unsubstituted aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and, aralkyloxy groups such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers).

Among these aromatic hydroxy compounds, aromatic hydroxy compounds in which $R^{20}$ and $R^{22}$ are hydrogen atoms are used preferably.

Preferable examples of aromatic hydroxy compounds represented by the previously indicated formula (46) as well as specific examples of aromatic hydroxy compounds represented by the above-mentioned formula (55) may include chlorophenol (including isomers), bromophenol (including isomers), dichlorophenol (including isomers), dibromophenol (including isomers), trichlorophenol (including isomers), tribromophenol (including isomers), phenol, methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), octadecylphenol (including isomers), dimethylphenol (including isomers), diethylphenol (including isomers), dipropylphenol (including isomers), dibutylphenol (including isomers), dipentylphenol (including isomers), dihexylphenol (including isomers), diheptylphenol (including isomers), dioctylphenol (including isomers), dinonylphenol (including isomers), didecylphenol (including isomers), didodecylphenol (including isomers), dioctadecylphenol (including isomers), trimethylphenol (including isomers), triethylphenol (including isomers), tripropylphenol (including isomers), tributylphenol (including isomers), tripentylphenol (including isomers), trihexylphenol (including isomers), triheptylphenol (including isomers), trioctylphenol (including isomers), trinonylphenol (including isomers), tridecylphenol (including isomers), tridodecylphenol (including isomers), trioctadecylphenol (including isomers), (methoxymethyl) phenol (including isomers), (ethoxymethyl) phenol (including isomers), (propoxymethyl) phenol (including isomers), (butyloxymethyl) phenol (including isomers), (pentyloxymethyl) phenol (including isomers), (hexyloxymethyl) phenol (including isomers), (heptyloxymethyl) phenol (including isomers), (octyloxymethyl) phenol (including isomers), (nonyloxymethyl) phenol (including isomers), (decyloxymethyl) phenol (including isomers), (dodecyloxymethyl) phenol (including isomers), (octadecyloxymethyl) phenol (including isomers), (cyclopentyloxymethyl) phenol (including isomers), (cyclohexyloxymethyl) phenol (including isomers), (cycloheptyloxymethyl) phenol (including isomers), (cyclooctyloxymethyl) phenol (including isomers), (methylcyclopentyloxymethy) phenol (including isomers), (ethylcyclopentyloxymethyl) phenol (including isomers), (methylcyclohexyloxymethyl) phenol (including isomers), (ethylcyclohexyloxymethyl) phenol (including isomers), (propylcyclohexyloxymethyl) phenol (including isomers), (butylcyclohexyloxymethyl) phenol (including isomers), (pentylcyclohexyloxymethyl) phenol (including isomers), (hexylcyclohexyloxymethyl) phenol (including isomers), (dimethylcyclohexyloxymethyl) phenol (including isomers), (diethylcyclohexyloxymethyl) phenol (including isomers), (dibutylcyclohexyloxymethyl) phenol (including isomers), (phenoxymethyl) phenol, (methylphenoxymethyl) phenol (including isomers), (ethylphenoxymethyl) phenol (including isomers), (propylphenoxymethyl) phenol (including isomers), (butylphenoxymethyl) phenol (including isomers), (pentylphenoxymethyl) phenol (including isomers), (hexylphenoxymethyl) phenol (including isomers), (heptylphenoxymethyl) phenol (including isomers), (octylphenoxymethyl) phenol (including isomers), (nonylphenoxymethyl) phenol (including isomers), (decylphenoxymethyl) phenol (including isomers), (phenylphenoxymethyl) phenol (including isomers), (dimethylphenoxymethyl) phenol (including isomers), (diethylphenoxymethyl) phenol (including isomers), (dipropylphenoxymethyl) phenol (including isomers), (dibutylphenoxymethyl) phenol (including isomers), (dipentylphenoxymethyl) phenol (including isomers), (dihexylphenoxymethyl) phenol (including isomers), (diheptylphenoxymethyl) phenol (including isomers), (diphenylphenoxymethyl) phenol (including isomers), (trimethylphenoxymethyl) phenol (including isomers), (triethylphenoxymethyl) phenol (including isomers), (tripropylphenoxymethyl) phenol (including isomers), (tributylphenoxymethyl) phenol (including isomers), (phenylmethoxymethyl) phenol (including isomers), (phenylethoxymethyl) phenol (including isomers), (phenylpropyloxymethyl) phenol (including isomers), (phenylbutyloxymethyl) phenol (including isomers), (phenylpentyloxymethyl) phenol (including isomers), (phenylhexyloxymethyl) phenol (including isomers), (phenylheptyloxymethyl) phenol (including isomers), (phenyloctyloxymethyl) phenol (including isomers), (phenylnonyloxymethyl) phenol (including isomers), di(methoxymethyl) phenol, di(ethoxymethyl) phenol, di(propoxymethyl) phenol (including isomers), di(butyloxymethyl) phenol (including isomers), di(pentyloxymethyl) phenol (including isomers), di(hexyloxymethyl) phenol (including isomers), di(heptyloxymethyl) phenol (including isomers), di(octyloxymethyl) phenol (including isomers), di(nonyloxymethyl) phenol (including isomers), di(decyloxymethyl) phenol (including isomers), di(dodecyloxymethyl) phenol (including isomers), di(octadecyloxymethyl) phenol (including isomers), di(cyclopentyloxymethyl) phenol (including isomers), di(cyclohexyloxymethyl) phenol (including isomers), di(cycloheptyloxymethyl) phenol (including isomers), di(cyclooctyloxymethyl) phenol (including isomers), di(methylcyclopentyloxymethy) phenol (including isomers), di(ethylcyclopentyloxymethyl) phenol (including isomers), di(methylcyclohexyloxymethyl) phenol (including isomers), di(ethylcyclohexyloxymethyl) phenol (including isomers), di(propylcyclohexyloxymethyl) phenol (including isomers), di(butylcyclohexyloxymethyl) phenol (including isomers), di(pentylcyclohexyloxymethyl) phenol (including isomers), di(hexylcyclohexyloxymethyl) phenol (including isomers), bis(dimethylcyclohexyloxymethyl) phenol (including isomers), bis(diethylcyclohexyloxymethyl) phenol (including isomers), bis(dibutylcyclohexyloxymethyl) phenol (including isomers), di(phenoxymethyl) phenol, di(methylphenoxymethyl) phenol (including isomers), di(ethylphenoxymethyl) phenol (including isomers), di(propylphenoxymethyl) phenol (including isomers), di(butylphenoxymethyl) phenol (including isomers), di(pentylphenoxymethyl) phenol (including isomers), di(hexylphenoxymethyl) phenol (including isomers), di(heptylphenoxymethyl) phenol (including isomers), di(octylphenoxymethyl) phenol (including isomers), di(nonylphenoxymethyl) phenol (including isomers), di(decylphenoxymethyl) phenol (including isomers), di(phenylphenoxymethyl) phenol (including isomers), bis(dimethylphenoxymethyl) phenol (including isomers), bis(diethylphenoxymethyl) phenol (including isomers), bis(dipropylphenoxymethyl) phenol (including isomers), bis(dibutylphenoxymethyl) phenol (including isomers), bis(dipentylphenoxymethyl) phenol (including isomers), bis(dihexylphenoxymethyl) phenol (including isomers), bis(diheptylphenoxymethyl) phenol (including isomers), bis(diphenylphenoxymethyl) phenol (including isomers), di(trimethylphenoxymethyl) phenol (including isomers), di(triethylphenoxymethyl) phenol (including isomers), di(tripropylphenoxymethyl) phenol (including isomers), di(tributylphenoxymethyl) phenol (including isomers), di(phenylmethoxymethyl) phenol (including isomers), di(phenylethoxymethyl) phenol (including isomers), di(phenylpropyloxymethyl) phenol (including isomers), di(phenylbutyloxymethyl) phenol (including isomers), di(phenylpentyloxymethyl) phenol (including isomers), di(phenylhexyloxymethyl) phenol (including isomers), di(phenylheptyloxymethyl) phenol (including isomers), di(phenyloctyloxymethyl) phenol (including isomers), di(phenylnonyloxymethyl) phenol (including isomers), tri(methoxymethyl) phenol, tri(ethoxymethyl) phenol, tri(propoxymethyl) phenol (including isomers), tri(butyloxymethyl) phenol (including isomers), tri(pentyloxymethyl) phenol (including isomers), tri(hexyloxymethyl) phenol (including isomers), tri(heptyloxymethyl) phenol (including isomers), tri(octyloxymethyl) phenol (including isomers), tri(nonyloxymethyl) phenol (including isomers), tri(decyloxymethyl) phenol (including isomers), tri(dodecyloxymethyl) phenol (including isomers), tri(octadecyloxymethyl) phenol (including isomers), tri(cyclopentyloxymethyl) phenol (including isomers), tri(cyclohexyloxymethyl) phenol (including isomers), tri(cycloheptyloxymethyl) phenol (including isomers), tri(cyclooctyloxymethyl) phenol (including isomers), tri(methylcyclopentyloxymethy) phenol (including isomers), tri(ethylcyclopentyloxymethyl) phenol (including isomers), tri(methylcyclohexyloxymethyl) phenol (including isomers), tri(ethylcyclohexyloxymethyl) phenol (including isomers), tri(propylcyclohexyloxymethyl) phenol (including isomers), tri(butylcyclohexyloxymethyl) phenol (including isomers), tri(pentylcyclohexyloxymethyl) phenol (including isomers), tri(hexylcyclohexyloxymethyl) phenol (including isomers), bis(dimethylcyclohexyloxymethyl) phenol (including isomers), bis(diethylcyclohexyloxymethyl) phenol (including isomers), bis(dibutylcyclohexyloxymethyl) phenol (including isomers), tri(phenoxymethyl) phenol, tri(methylphenoxymethyl) phenol (including isomers), tri(ethylphenoxymethyl) phenol (including isomers), tri(propylphenoxymethyl) phenol (including isomers), tri(butylphenoxymethyl) phenol (including isomers), tri(pentylphenoxymethyl) phenol (including isomers), tri(hexylphenoxymethyl) phenol (including isomers), tri(heptylphenoxymethyl) phenol (including isomers), tri(octylphenoxymethyl) phenol (including isomers), tri(nonylphenoxymethyl) phenol (including isomers), tri(decylphenoxymethyl) phenol (including isomers), tri(phenylphenoxymethyl) phenol (including isomers), bis(dimethylphenoxymethyl) phenol (including isomers), bis(diethylphenoxymethyl) phenol (including isomers), bis(dipropylphenoxymethyl) phenol (including isomers), bis(dibutylphenoxymethyl) phenol (including isomers), bis(dipentylphenoxymethyl) phenol (including isomers), bis(dihexylphenoxymethyl) phenol (including isomers), bis(diheptylphenoxymethyl) phenol (including isomers), bis(diphenylphenoxymethyl) phenol (including isomers), tri(trimethylphenoxymethyl) phenol (including isomers), tri(triethylphenoxymethyl) phenol (including isomers), tri(tripropylphenoxymethyl) phenol (including isomers), tri(tributylphenoxymethyl) phenol (including isomers), tri(phenylmethoxymethyl) phenol, tri(phenylethoxymethyl) phenol (including isomers), tri(phenylpropyloxymethyl) phenol (including isomers), tri(phenylbutyloxymethyl) phenol (including isomers), tri(phenylpentyloxymethyl) phenol (including isomers), tri(phenylhexyloxymethyl) phenol (including isomers), tri(phenylheptyloxymethyl) phenol (including isomers), tri(phenyloctyloxymethyl) phenol (including isomers), tri(phenylnonyloxymethyl) phenol (including isomers), (phenylmethyl) phenol (including isomers), ((methylphenyl)methyl) phenol (including isomers), ((ethylphenyl)methyl) phenol (including isomers), ((propylphenyl)methyl) phenol (including isomers), ((butylphenyl)methyl) phenol (including isomers), ((pentylphenyl)methyl) phenol (including isomers), ((hexylphenyl)methyl) phenol (including isomers), ((heptylphenyl)methyl) phenol (including isomers), ((octylphenyl)methyl) phenol (including isomers), ((nonylphenyl)methyl) phenol (including isomers), ((decylphenyl)methyl) phenol (including isomers), ((biphenyl)methyl) phenol (including isomers), ((dimethylphenyl)methyl) phenol (including isomers), ((diethylphenyl)methyl) phenol (including isomers), ((dipropylphenyl)methyl) phenol (including isomers), ((dibutylphenyl)methyl) phenol (including isomers), ((dipentylphenyl)methyl) phenol (including isomers), ((dihexylphenyl)methyl) phenol (including isomers), ((diheptylphenyl)methyl) phenol (including isomers), ((terphenyl)methyl) phenol (including isomers), ((trimethylphenyl)methyl) phenol (including isomers), ((triethylphenyl)methyl) phenol (including isomers), ((tripropylphenyl)methyl) phenol (including isomers), ((tributylphenyl)methyl) phenol (including isomers), di(phenylmethyl) phenol (including isomers), di((methylphenyl)methyl) phenol (including isomers), di((ethylphenyl)methyl) phenol (including isomers), di((propylphenyl)methyl) phenol (including isomers), di((butylphenyl)methyl) phenol (including isomers), di((pentylphenyl)methyl) phenol (including isomers), di((hexylphenyl)methyl) phenol (including isomers), di((heptylphenyl)methyl) phenol (including isomers), di((octylphenyl)methyl) phenol (including isomers), di((nonylphenyl)methyl) phenol (including isomers), di((decylphenyl)methyl) phenol (including isomers), di((biphenyl)

methyl) phenol (including isomers), di((dimethylphenyl)methyl) phenol (including isomers), di((diethylphenyl)methyl) phenol (including isomers), di((dipropylphenyl)methyl) phenol (including isomers), di((dibutylphenyl)methyl) phenol (including isomers), di((dipentylphenyl)methyl) phenol (including isomers), di((dihexylphenyl)methyl) phenol (including isomers), di((diheptylphenyl)methyl) phenol (including isomers), di((terphenyl)methyl) phenol (including isomers), di((trimethylphenyl)methyl) phenol (including isomers), di((triethylphenyl)methyl) phenol (including isomers), di((tripropylphenyl)methyl) phenol (including isomers), di((tributylphenyl)methyl) phenol (including isomers), tri (phenylmethyl) phenol (including isomers), tri((methylphenyl)methyl) phenol (including isomers), tri((ethylphenyl)methyl) phenol (including isomers), tri((propylphenyl)methyl) phenol (including isomers), tri((butylphenyl)methyl) phenol (including isomers), tri((pentylphenyl)methyl) phenol (including isomers), tri((hexylphenyl)methyl) phenol (including isomers), tri((heptylphenyl)methyl) phenol (including isomers), tri((octylphenyl)methyl) phenol (including isomers), tri((nonylphenyl)methyl) phenol (including isomers), tri((decylphenyl)methyl) phenol (including isomers), tri((biphenyl)methyl) phenol (including isomers), tri((dimethylphenyl)methyl) phenol (including isomers), tri((diethylphenyl)methyl) phenol (including isomers), tri ((dipropylphenyl)methyl) phenol (including isomers), tri ((dibutylphenyl)methyl) phenol (including isomers), tri ((dipentylphenyl)methyl) phenol (including isomers), tri ((dihexylphenyl)methyl) phenol (including isomers), tri ((diheptylphenyl)methyl) phenol (including isomers), tri ((terphenyl)methyl) phenol (including isomers), tri ((trimethylphenyl)methyl) phenol (including isomers), tri ((triethylphenyl)methyl) phenol (including isomers), tri ((tripropylphenyl)methyl) phenol (including isomers), tri ((tributylphenyl)methyl) phenol (including isomers), phenylethylphenol (including isomers), phenyl-n-propylphenol (including isomers), phenyl-n-butylphenol (including isomers), phenyl-n-pentylphenol (including isomers), phenyl-n-hexylphenol (including isomers), phenyl-n-heptylphenol (including isomers), phenyl-n-octylphenol (including isomers), phenyl-n-nonylphenol (including isomers), (methylamino) phenol, (ethylamino) phenol, (propylamino) phenol (including isomers), (butylamino) phenol (including isomers), (pentylamino) phenol (including isomers), (hexylamino) phenol (including isomers), (heptylamino) phenol (including isomers), (octylamino) phenol (including isomers), (nonylamino) phenol (including isomers), (decylamino) phenol (including isomers), (dodecylamino) phenol (including isomers), (octadecylamino) phenol (including isomers), di(methylamino) phenol, di(ethylamino) phenol, di(propylamino) phenol (including isomers), di(butylamino) phenol (including isomers), di(pentylamino) phenol (including isomers), di(hexylamino) phenol (including isomers), di(heptylamino) phenol (including isomers), di(octylamino) phenol (including isomers), di(nonylamino) phenol (including isomers), di(decylamino) phenol (including isomers), di(dodecylamino) phenol (including isomers), di(octadecylamino) phenol (including isomers), tri(methylamino) phenol, tri(ethylamino) phenol, tri(propylamino) phenol (including isomers), tri(butylamino) phenol (including isomers), tri (pentylamino) phenol (including isomers), tri(hexylamino) phenol (including isomers), tri(heptylamino) phenol (including isomers), tri(octylamino) phenol (including isomers), tri (nonylamino) phenol (including isomers), tri(decylamino) phenol (including isomers), tri(dodecylamino) phenol (including isomers), tri(octadecylamino) phenol (including isomers), methoxyphenol (including isomers), ethoxyphenol (including isomers), propyloxyphenol (including isomers), butyloxyphenol (including isomers), pentyloxyphenol (including isomers), hexyloxyphenol (including isomers), heptyloxyphenol (including isomers), octyloxyphenol (including isomers), nonyloxyphenol (including isomers), decyloxyphenol (including isomers), dodecyloxyphenol (including isomers), octadecyloxyphenol (including isomers), cyclopentyloxyphenol (including isomers), cyclohexyloxyphenol (including isomers), cycloheptyloxyphenol (including isomers), cyclooctyloxyphenol (including isomers), (methylcyclopentyloxy) phenol (including isomers), (ethylcyclopentyloxy) phenol (including isomers), (methylcyclohexyloxy) phenol (including isomers), (ethylcyclohexyloxy) phenol (including isomers), (propylcyclohexyloxy) phenol (including isomers), (butylcyclohexyloxy) phenol (including isomers), (pentylcyclohexyloxy) phenol (including isomers), (hexylcyclohexyloxy) phenol (including isomers), (dimethylcyclohexyloxy) phenol (including isomers), (diethylcyclohexyloxy) phenol (including isomers), (dibutylcyclohexyloxy) phenol (including isomers), phenoxyphenol, (methylphenyloxy) phenol (including isomers), (ethylphenyloxy) phenol (including isomers), (propylphenyloxy) phenol (including isomers), (butylphenyloxy) phenol (including isomers), (pentylphenyloxy) phenol (including isomers), (hexylphenyloxy) phenol (including isomers), (heptylphenyloxy) phenol (including isomers), (octylphenyloxy) phenol (including isomers), (nonylphenyloxy) phenol (including isomers), (decylphenyloxy) phenol (including isomers), biphenyloxyphenol (including isomers), (dimethylphenyloxy) phenol (including isomers), (diethylphenyloxy) phenol (including isomers), (dipropylphenyloxy) phenol (including isomers), (dibutylphenyloxy) phenol (including isomers), (dipentylphenyloxy) phenol (including isomers), (dihexylphenyloxy) phenol (including isomers), (diheptylphenyloxy) phenol (including isomers), terphenyloxyphenol (including isomers), (trimethylphenyloxy) phenol (including isomers), (triethylphenyloxy) phenol (including isomers), (tripropylphenyloxy) phenol (including isomers), (tributylphenyloxy) phenol (including isomers), (phenylmethyloxy) phenol, (phenylethyloxy) phenol (including isomers), (phenylpropyloxy) phenol (including isomers), (phenylbutyloxy) phenol (including isomers), (phenylpentyloxy) phenol (including isomers), (phenylhexyloxy) phenol (including isomers), (phenylheptyloxy) phenol (including isomers), (phenyloctyloxy) phenol (including isomers), (phenylnonyloxy) phenol (including isomers), dimethoxyphenol (including isomers), diethoxyphenol (including isomers), dipropyloxyphenol (including isomers), dibutyloxyphenol (including isomers), dipentyloxyphenol (including isomers), dihexyloxyphenol (including isomers), diheptyloxyphenol (including isomers), dioctyloxyphenol (including isomers), dinonyloxyphenol (including isomers), didecyloxyphenol (including isomers), didodecyloxyphenol (including isomers), dioctadecyloxyphenol (including isomers), dicyclopentyloxyphenol (including isomers), dicyclohexyloxyphenol (including isomers), dicycloheptyloxyphenol (including isomers), dicyclooctyloxyphenol (including isomers), di(methylcyclopentyloxy) phenol (including isomers), di(ethylcyclopentyloxy) phenol (including isomers), di(methylcyclohexyloxy) phenol (including isomers), di(ethylcyclohexyloxy) phenol (including isomers), di(propylcyclohexyloxy) phenol (including isomers), di(butylcyclohexyloxy) phenol (including isomers), di(pentylcyclohexyloxy) phenol (including isomers), di(hexylcyclohexyloxy) phenol (including isomers), bis (dimethylcyclohexyloxy) phenol (including isomers), bis(diethylcyclohexyloxy) phenol (including isomers), bis(dibutylcyclohexyloxy) phenol (including isomers), phenyloxyphenol, di(methylphenyloxy) phenol (including isomers), di(ethylphenyloxy) phenol (including isomers), di(propylphenyloxy) phenol (including isomers), di(butylphenyloxy) phenol (including isomers), di(pentylphenyloxy) phenol (including isomers), di(hexylphenyloxy) phenol (including isomers), di(heptylphenyloxy) phenol (including isomers), di(octylphenyloxy) phenol (including isomers), di(nonylphenyloxy) phenol (including isomers), di(decylphenyloxy) phenol (including isomers), dibiphenyloxyphenol (including isomers), bis(dimethylphenyloxy) phenol (including isomers), bis(diethylphenyloxy) phenol (including isomers), bis(dipropylphenyloxy) phenol (including isomers), bis(dibutylphenyloxy) phenol (including isomers), bis(dipentylphenyloxy) phenol (including isomers), bis(dihexylphenyloxy) phenol (including isomers), bis(diheptylphenyloxy) phenol (including isomers), diterphenyloxyphenol (including isomers), di(trimethylphenyloxy) phenol (including isomers), di(triethylphenyloxy) phenol (including isomers), di(tripropylphenyloxy) phenol (including isomers), di(tributylphenyloxy) phenol (including isomers), di(phenylmethyloxy) phenol, di(phenylethyloxy) phenol (including isomers), di(phenylpropyloxy) phenol (including isomers), di(phenylbutyloxy) phenol (including isomers), di(phenylpentyloxy) phenol (including isomers), di(phenylhexyloxy) phenol (including isomers), di(phenylheptyloxy) phenol (including isomers), di(phenyloctyloxy) phenol (including isomers), di(phenylnonyloxy) phenol (including isomers), trimethoxyphenol (including isomers), triethoxyphenol (including isomers), tripropyloxyphenol (including isomers), tributyloxyphenol (including isomers), tripentyloxyphenol (including isomers), trihexyloxyphenol (including isomers), triheptyloxyphenol (including isomers), trioctyloxyphenol (including isomers), trinonyloxyphenol (including isomers), tridecyloxyphenol (including isomers), tridodecyloxyphenol (including isomers), trioctadecyloxyphenol (including isomers), tricyclopentyloxyphenol (including isomers), tricyclohexyloxyphenol (including isomers), tricycloheptyloxyphenol (including isomers), tricyclooctyloxyphenol (including isomers), tri(methylcyclopentyloxy) phenol (including isomers), tri(ethylcyclopentyloxy) phenol (including isomers), tri(methylcyclohexyloxy) phenol (including isomers), tri(ethylcyclohexyloxy) phenol (including isomers), tri(propylcyclohexyloxy) phenol (including isomers), tri(butylcyclohexyloxy) phenol (including isomers), tri(pentylcyclohexyloxy) phenol (including isomers), tri(hexylcyclohexyloxy) phenol (including isomers), tri(dimethylcyclohexyloxy) phenol (including isomers), tri(diethylcyclohexyloxy) phenol (including isomers), tri(dibutylcyclohexyloxy) phenol (including isomers), phenyloxyphenol, tri(methylphenyloxy) phenol (including isomers), tri(ethylphenyloxy) phenol (including isomers), tri(propylphenyloxy) phenol (including isomers), tri(butylphenyloxy) phenol (including isomers), tri(pentylphenyloxy) phenol (including isomers), tri(hexylphenyloxy) phenol (including isomers), tri(heptylphenyloxy) phenol (including isomers), tri(octylphenyloxy) phenol (including isomers), tri(nonylphenyloxy) phenol (including isomers), tri(decylphenyloxy) phenol (including isomers), tribiphenyloxyphenol (including isomers), tri(dimethylphenyloxy) phenol (including isomers), tri(diethylphenyloxy) phenol (including isomers), tri(dipropylphenyloxy) phenol (including isomers), tri(dibutylphenyloxy) phenol (including isomers), tri(dipentylphenyloxy) phenol (including isomers), tri(dihexylphenyloxy) phenol (including isomers), tri(diheptylphenyloxy) phenol (including isomers), triterphenyloxyphenol (including isomers), tri(trimethylphenyloxy) phenol (including isomers), tri(triethylphenyloxy) phenol (including isomers), tri(tripropylphenyloxy) phenol (including isomers), tri(tributylphenyloxy) phenol (including isomers), tri(phenylmethyloxy) phenol, tri(phenylethyloxy) phenol (including isomers), tri(phenylpropyloxy) phenol (including isomers), tri(phenylbutyloxy) phenol (including isomers), tri(phenylpentyloxy) phenol (including isomers), tri(phenylhexyloxy) phenol (including isomers), tri(phenylheptyloxy) phenol (including isomers), tri(phenyloctyloxy) phenol (including isomers), tri(phenylnonyloxy) phenol (including isomers), phenylphenol (including isomers), hydroxyphenyl phenol (including isomers), hydroxyphenoxy phenol (including isomers), hydroxyphenylpropyl phenol (including isomers) and naphthol (including isomers).

More preferable examples of the aromatic hydroxy compounds listed above may include those in which the number of carbon atoms that compose the $R^3$, $R^4$, $R^{20}$, $R^{21}$ and $R^{22}$ is 0 to 13 due to the ease of transfer thereof. More preferably, the aromatic hydroxy compound is an aromatic hydroxy compound in which $R^3$, $R^4$, $R^{20}$, $R^{21}$ and $R^{22}$ are groups having 0 to 9 carbon atoms selected from a hydrogen atom, a linear or branched alkyl group, a cycloalkyl group, an optionally substituted aryl group, a linear or branched alkoxy group, an optionally substituted aryloxy group and an optionally substituted aralkyl group.

In addition, the aromatic hydroxy compound forms an N-substituted carbamic acid-O—Ar ester (the details of which are described hereinafter), and the N-substituted carbamic acid-O—Ar ester is used in the form of an isocyanate derivative. Although details of a method for producing an isocyanate derived from an N-substituted carbamic acid-O—Ar ester from the N-substituted carbamic acid-O—Ar ester will be described hereinafter, this method involves obtaining an aromatic hydroxy compound derived from the N-substituted carbamic acid-O—Ar ester and an isocyanate by thermal decomposition of the N-substituted carbamic acid-O—Ar ester. In consideration of the reaction formula, the aromatic hydroxy compound formed at that time is an aromatic hydroxy compound contained in the aromatic hydroxy composition used when producing the N-substituted carbamic acid-O—Ar ester. Namely, an aromatic hydroxy compound of formula (46), and preferably formula (55), is produced as a by-product together with isocyanate during thermal decomposition of the N-substituted carbamic acid-O—Ar ester. In one of the present embodiments, although depending on the particular case, the aromatic hydroxy compound and isocyanate are separated by distillation following the thermal decomposition step, and the separated aromatic hydroxy compound may be recycled in the form of an aromatic hydroxy composition in the reaction between the organic amine, carbonic acid derivative and aromatic hydroxy compound. Thus, in consideration of the process through the isocyanate production step, it is necessary to take into consideration the separability of the aromatic hydroxy compound serving as a raw material of the N-substituted carbamic acid-O—Ar ester and the isocyanate formed from the N-substituted carbamic acid-O—Ar ester. Although it is difficult to generally define separability, it is defined on the basis of the finding that generally two components to be separated can be adequately separated by distillation industrially if the standard boiling points thereof are 10° C. or more apart. Thus, this definition refers to a value that is limited by currently known separation means, and is not intended to serve as a basis of the present embodiment.

The following Table (1) indicates the standard boiling points of aromatic hydroxy compounds or boiling points at reduced pressure in the case measurement thereof is difficult at normal pressure. Although the reactivity of the aromatic hydroxy compound that composes the aromatic hydroxy composition used in the present embodiment with a compound containing a ureido group and/or an N-substituted carbamic acid-O—$R^2$ ester (details regarding this N-substituted carbamic acid-O—$R^2$ ester will be described hereinafter) and/or urea is important, the standard boiling point is also an important selection index with respect to separation of each component. As shown in the following Table (1), the types and numbers of substituents, the locations of substituents and the like have a considerable influence on the boiling point of the aromatic hydroxy compound. Boiling point is a physical property that is also dependent on intermolecular forces, and is commonly known among persons with ordinary skill in the art to be unable to be defined by the structure of a single molecule. Thus, selection of an aromatic hydroxy compound according to an important aspect of the present invention in the form of standard boiling point is carried out by measuring or investigating the structure and properties (standard boiling point) of the desired N-substituted carbamic acid-O—Ar ester (the details of which will be described hereinafter) and/or isocyanate. Measurement of standard boiling point can be carried out with known methods, and can be routinely carried out by a researcher with ordinary skill in the relevant technical field. As has been described above, it is difficult to define separation of aromatic hydroxy compounds used in the present invention with a structure such as a general formula, and the intended method of the present embodiment is not to predict the standard boiling point of an aromatic hydroxy compound. Thus, a person with ordinary skill in the art is able to carry out the present embodiment by referring to or measuring standard boiling point corresponding to the compound used as previously described.

TABLE 1

| Aromatic Hydroxy Compounds | Boiling Point ° C. (values in parentheses indicate pressure during measurement, and the absence of values in parentheses means that measurement was carried out at normal pressure) |
|---|---|
| Phenol | 182 |
| 2-methylphenol | 191 |
| 3-methylphenol | 203 |
| 4-methylphenol | 202 |
| 2,4-dimethylphenol | 211 |
| 2,6-dimethylphenol | 203 |
| 2,5-dimethylphenol | 212 |
| 3,4-dimethylphenol | 227 |
| 3,5-dimethyphenol | 222 |
| 2,4,6-trimethylphenol | 220 |
| 4-propylphenol | 232 |
| 2-propylphenol | 225 |
| 2-(propan-2-yl) phenol | 212 |
| 4-(propan-2-yl) phenol | 212 |
| 3-(propan-2-yl) phenol | 228 |
| 2,6-dierylphenol | 219 |
| 4-butylphenol | 138-139 (2.40 kPa) |
| 4-pentylphenol | 250 |
| 2-(2-methylbutan-2-yl) phenol | 92 (0.53 kPa) |
| 2,4-bis(propan-2-yl) phenol | 249 |
| 2,6-bis(propan-2-yl) phenol | 256 |
| 2-(phenylmethyl) phenol | 312 |
| 3,5-dimethoxyphenol | 172 (2.27 kPa) |
| 2,6-dimethoxyphenol | 167 (1.33 kPa) |
| 2-ethoxyphenol | 216 |
| 4-heptylphenol | 156 (1.20 kPa) |
| 4-octylphenol | 150 (0.53 kPa) (lit.) |
| 4-butoxyphenol | 278 |
| 4-(2,4,4-trimethylpentan-2-yl) phenol | 175 (4.00 kPa) |
| 2,4-bis(2-methylbutan-2-yl) phenol | 170 (0.267 kPa) |

TABLE 1-continued

| Aromatic Hydroxy Compounds | Boiling Point ° C. (values in parentheses indicate pressure during measurement, and the absence of values in parentheses means that measurement was carried out at normal pressure) |
|---|---|
| Naphthalen-2-ol | 285 |
| Naphthalen-1-ol | 278 |
| Pyrocatechol | 245 |
| Resorcinol | 178 (2.13 kPa) |
| Hydroquinone | 285 |
| Pyrogallol | 309 |
| 2-bromophenol | 195 |
| 3-bromophenol | 236 |
| 4-bromophenol | 235-236 |
| 2-chlorophenol | 175-176 |
| 3-chlorophenol | 214 |
| 4-chlorophenol | 220 |
| 4-chloro-2-methylphenol | 220-225 |
| 2-chloro-4-methylphenol | 195-196 |

Next, an explanation is given of an active aromatic hydroxy compound. The aromatic hydroxy compounds represented by the above-mentioned formula (46) and/or formula (55) can be preferably used as aromatic hydroxy compounds that compose the aromatic hydroxy composition used in the composition for transfer and storage of N-substituted carbamic acid-O—Ar ester. In addition, these aromatic hydroxy compounds can also be preferably used as aromatic hydroxy compounds that compose the aromatic hydroxy composition used when producing N-substituted carbamic acid-O—Ar ester by reacting the organic amine, the carbonic acid derivative and the aromatic hydroxy composition or by reacting the compound having the ureido groups and the aromatic hydroxy composition. Although the latter aromatic hydroxy compounds that compose the aromatic hydroxy composition used to produce an N-substituted carbamic acid-O—Ar ester are included in those represented by the above-mentioned formula (46) and/or formula (55), they preferably include aromatic hydroxy compounds represented by the following formula (56) in particular (aromatic hydroxy compounds represented by the following formula (56) are frequently referred to as "active aromatic hydroxy compounds" in the present specification in order to indicate their ease of reaction). These active aromatic hydroxy compounds represented by the following formula (56) are not only used to produce N-substituted carbamic acid-O—Ar ester, but may also be used alone as an aromatic hydroxy compound that composes the aromatic hydroxy composition used in the composition for transfer and storage of N-substituted carbamic acid-O—Ar ester, or can also be used as one type of aromatic hydroxy compound that composes the aromatic hydroxy composition.

As a result of studies conducted by the inventors of the present invention, in the production of N-substituted carbamic acid-O—Ar ester from the organic amine, the carbonic acid derivative and the aromatic hydroxy composition, there was determined to be cases in which the formation rate of the N-substituted carbamic acid-O—Ar ester varies considerably depending on the aromatic hydroxy compound used. As a result of further conducting more extensive studies, it was found that the formation rate of the N-substituted carbamic acid-O—Ar ester depends on the type of substituent at the ortho position relative to the hydroxy group of the aromatic hydroxy compound used, and that when the aromatic hydroxy compound is used that has a specific substituent at the ortho position, the formation rate of N-substituted carbamic acid-O—Ar ester is much higher than in the case of using other aromatic hydroxy compounds. This finding of the specific aromatic hydroxy compound demonstrating such an effect is not found in the prior art and is surprising. Although the mechanism by which this effect is demonstrated is not clear, the inventors of the present invention surmised that hydroxy groups serving as reaction sites are sterically inhibited in the case the size of a group bonded to an atom at the α position is equal to or greater than a specific size.

The active aromatic hydroxy compounds are aromatic hydroxy compounds represented by the following formula (56):

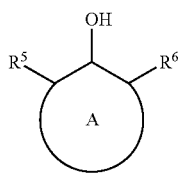

(56)

(wherein ring A represents an optionally substituted single or multiple aromatic hydrocarbon ring, $R^5$ and $R^6$ respectively and independently represent any group defined in (i) to (v) below, the number of carbon atoms that compose the aromatic hydroxy compound is an integer of from 6 to 50, and $R^5$ and $R^6$ may form a ring structure by bonding with A:

(i) a hydrogen atom, (ii) a halogen atom, (iii) a group in which the atom at the α position is a nitrogen atom and the number of carbon atoms is from 1 to 44, and which does not contain active hydrogen (excluding the hydrogen bonded to the α position nitrogen atom), the nitrogen atom being a secondary nitrogen atom (namely, a nitrogen atom that forms an —NH— bond), (iv) a group in which the atom at the α position is a carbon atom and the number of carbon atoms is from 1 to 44, and which does not contain active hydrogen, the carbon atom being a primary or secondary carbon atom (namely, a carbon of a methyl group or a carbon that forms a —CH$_2$— bond), provided that in the case the $R^5$ and/or $R^6$ form a saturated and/or unsaturated condensed ring structure with the aromatic ring A, and the condensed ring has 6 members or less, the carbon atom at the α position may be a tertiary or quaternary carbon atom as in the case of, for example, the following formula (57) or formula (58), and in the case the α position carbon forms a double bond or triple bond with a β position atom (atom that forms the $R^5$ and $R^6$ and that is also adjacent to an atom bonded to the aromatic ring of ring A) as well, the α position carbon atom may be a tertiary or quaternary carbon atom:

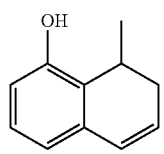

(57)

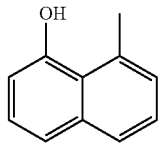

(58)

and, (v) a group in which the atom at the α position is an oxygen atom and the number of carbons is from 1 to 44, and which does not contain active hydrogen).

Furthermore, although the term "atom at the α position" is used in the preceding explanation of the formula (56), an "atom at the α position" refers to an atom that composes the $R^5$ and $R^6$ that is adjacent to a carbon atom on the aromatic hydrocarbon ring to which the $R^5$ and $R^6$ groups are bonded.

A substituent that substitutes an aromatic group of an aromatic hydroxy compound represented by formula (56) above (excluding $R^5$ and $R^6$) is selected from a hydrogen atom, a halogen atom, an aliphatic group and an aromatic group, is a group composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a hetero-crosslinked ring group or heterocyclic ring group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (59) to (66).

(59)

(60)

(61)

(62)

(63)

(64)

(65)

-continued

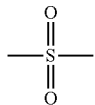
(66)

Among such substituents, examples of substituents that can be preferably used in the present embodiment in consideration of less susceptibility to the occurrence of side reactions may include groups selected from the group consisting of acyclic hydrocarbon groups and cyclic hydrocarbon groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups).

In the case of transferring a composition containing an N-substituted carbamic acid-O—Ar ester at a high temperature or in the case of reacting an organic amine, a carbonic acid derivative and an aromatic hydroxy compound and obtaining an N-substituted carbamic acid-O—Ar ester at a high temperature, the substituent that substitutes ring A of the aromatic hydroxy compound (excluding $R^5$ and $R^6$) is preferably an inactive substituent in the form of an aromatic hydroxy compound. An inactive substituent here refers to a group in which the inactive substituent does not contain an active hydrogen as previously described (although it may have an aromatic hydroxy group).

Examples of such substituents that substitute ring A (excluding $R^5$ and $R^6$) may include a group selected from the group consisting of an alkyl group, a cycloalkyl group, an aryl group, an aralkyl group and an ether group (substituted and/or unsubstituted alkyl ether and/or aryl ether and/or aralkyl ether); a group to which is bonded a group selected from one or more types of the above-mentioned groups; a group selected from groups in which a group selected from one or more types of the above-mentioned groups is selected from groups composed of a group bonded with a saturated hydrocarbon bond and/or ether bond; and a group which is a halogen atom and in which the total of the number of carbon atoms that compose ring A and the number of carbon atoms that compose all substituents that substitute ring A is an integer of from 6 to 50.

Furthermore, in above-mentioned definition (iii), the case is described in which a nitrogen atom at the α position of $R^5$ and $R^6$ is a nitrogen atom that forms an —NH— bond. According to the definition of the "active hydrogen" as previously described, a hydrogen atom of this —NH— bond is also an active hydrogen. However, as a result of studies conducted by the inventors of the present invention, a hydrogen atom bonded to a nitrogen atom at the α position has low reactivity, and in the present embodiment, was determined to have hardly any detrimental effects. The inventors of the present invention surmised that this is due to steric hindrance attributable to a hydroxy group.

In formula (56) above, examples of ring A may include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring and an acephenanthrylene ring. More preferably, ring A has a structure that contains at least one structure selected from a benzene ring and a naphthalene ring.

Moreover, in consideration of industrial use, an aromatic hydroxy compound that is easily acquirable and has benzene skeleton thereof is preferable. Preferable examples of such an aromatic hydroxy compound may include aromatic hydroxy compounds represented by the following formula (67):

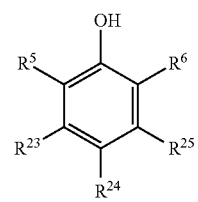
(67)

(wherein $R^5$ and $R^6$ are the groups defined above, $R^{23}$, $R^{24}$ and $R^{25}$ respectively and independently represent a group selected from the group consisting of an alkyl group, a cycloalkyl group, an aryl group, an aralkyl group and an ether group (substituted and/or unsubstituted alkyl ether and/or aryl ether and/or aralkyl ether); a group to which is bonded a group selected from one or more types of the above groups; a group selected from groups in which one or more types of the above groups is composed of a group bonded with a saturated aliphatic bond and/or an ether bond; a halogen atom; or a hydrogen atom, and the total number of carbon atoms that compose the $R^5$, $R^6$, $R^{23}$, $R^{24}$ and $R^{25}$ is an integer of from 0 to 44).

In formula (67) above, $R^5$ and $R^6$ are preferably groups independently selected from groups indicated in (i) to (v) below:

(i) a hydrogen atom, (ii) a halogen atom, (iii) a group in which the atom at the α position is a nitrogen atom and the number of carbon atoms is from 1 to 44, and which does not contain active hydrogen (excluding the hydrogen bonded to the α position nitrogen atom), the nitrogen atom being a secondary nitrogen atom (namely, a nitrogen atom that forms an —NH— bond), and the group bonded to the α position nitrogen atom is selected from an alkyl group having 1 to 44 carbon atoms, a cycloalkyl group having 1 to 44 carbon atoms, an aryl group having 6 to 44 carbon atoms, an aralkyl group having 7 to 44 carbon atoms and a group to which is bonded one or more types of the above-mentioned groups, (iv) a group in which the atom at the α position is a carbon atom and the number of carbon atoms is from 1 to 44, and which does not contain active hydrogen, the carbon atom being a primary or secondary carbon atom (namely, a carbon of a methyl group or a carbon that forms a —CH$_2$— bond), provided that in the case the $R^5$ and/or $R^6$ form a saturated and/or unsaturated condensed ring structure with the aromatic ring A and the condensed ring has 6 members or less, the carbon atom at the α position may be a tertiary or quaternary carbon atom as in the case of, for example, the following formula (68) or formula (69). Also in the case the α position carbon forms a double bond or triple bond with a β position atom (atom that forms the $R^5$ and $R^6$ and that is also adjacent to an atom bonded to the aromatic ring of ring A) as well, the α position carbon atom may be a tertiary or quaternary carbon atom:

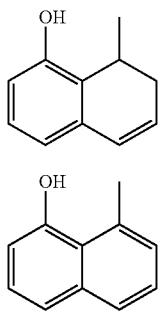

(68)

(69)

and a group other than a hydrogen atom that is bonded to the α position carbon atom is respectively and independently a group selected from an alkyl group having 1 to 43 carbon atoms, a cycloalkyl group having 1 to 43 carbon atoms, an alkoxy group having 1 to 43 carbon atoms, a polyoxyalkylene alkyl ether group having 2 to 43 atoms and does not have an OH group on the terminal thereof, an aryl group having 6 to 43 carbon atoms, an aralkyl group having 7 to 43 carbon atoms, an aralkyloxy group having 7 to 43 carbon atoms, and a group to which is bonded one or more types of the above groups, and (v) a group in which the atom at the α position is an oxygen atom and the number of carbon atoms is 1 to 20, and which does not contain active hydrogen, and the group bonded to the oxygen atom at the α position is a group selected from an alkyl group having 1 to 44 carbon atoms, a cycloalkyl group having 1 to 44 carbon atoms, a polyoxyalkylene alkyl ether group having 2 to 44 carbon atoms that does not have an OH group on the terminal thereof, an aryl group having 6 to 44 carbon atoms, an aralkyl group having 7 to 44 carbon atoms, and a group to which is bonded one or more types of the above groups.

Moreover, $R^{23}$, $R^{24}$ and $R^{25}$ are preferably groups independently selected from groups indicated in (vi) to (x) below:

(vi) a hydrogen atom, (vii) a halogen atom, (viii) a group in which the atom at the α position is a carbon atom, the number of carbon atoms is from 1 to 44, and three groups bonded to the α position carbon atom are respectively and independently selected from an alkyl group having 1 to 43 carbon atoms, a cycloalkyl group having 1 to 43 carbon atoms, an alkoxy group having 1 to 43 carbon atoms, a polyoxyalkylene alkyl ether group having 2 to 43 atoms and does not have an OH group on the terminal thereof, an aryl group having 6 to 43 carbon atoms, an aralkyl group having 7 to 43 carbon atoms, an aralkyloxy group having 7 to 43 carbon atoms, a group to which is bonded one or more types of the above groups, and a hydrogen atom, (ix) an aryl group having 1 to 44 carbon atoms, wherein the aryl group is substituted by a substituent, the aryl group may be substituted with 1 to 5 of the substituents indicated below, and the substituent is a group selected from a hydrogen atom, an alkyl group having 1 to 38 carbon atoms, a cycloalkyl group having 4 to 38 carbon atoms, an alkoxy group having 1 to 38 carbon atoms, a polyoxyalkylene alkyl ether group having 2 to 38 carbons that does not have an OH group on the terminal thereof, an aryl group having 6 to 38 carbon atoms, an aralkyl group having 7 to 38 carbon atoms, an aralkyloxy group having 7 to 38 carbon atoms and a group to which is bonded one or more types of the above groups, and (x) a group in which the atom at the α position is an oxygen atom, the number of carbon atoms is 1 to 44, and the group bonded to the oxygen atom at the α position is a group selected from an alkyl group having 1 to 44 carbon atoms, a cycloalkyl group having 1 to 44 carbon atoms, an alkoxy group having 1 to 44 carbon atoms, a polyoxyalkylene alkyl ether group having 2 to 44 carbon atoms that does not have an OH group on the terminal thereof, an aryl group having 6 to 44 carbon atoms, an aralkyl group having 7 to 44 carbon atoms, an aralkyloxy group having 7 to 44 carbon atoms, and a group to which is bonded one or more types of the above groups.

Furthermore, although the term "atom at the α position" is used in the preceding explanation of formula (67) above, an "atom at the α position" refers to an atom that composes the $R^5$, $R^6$, $R^{23}$, $R^{24}$ and $R^{25}$ that is adjacent to a carbon atom on the aromatic hydrocarbon ring to which the $R^5$, $R^6$, $R^{23}$, $R^{24}$ and $R^{25}$ groups are bonded.

Examples of such $R^{23}$, $R^{24}$ and $R^{25}$ groups may include alkyl groups and/or cycloalkyl groups and/or cycloalkyl groups substituted with an alkyl group and/or alkyl groups substituted with a cycloalkyl group such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers), cyclopentyl group, cyclohexyl group, cycloheptyl group, cyclooctyl group, methylcyclopentyl group (including isomers), ethylcyclopentyl group (including isomers), methylcyclohexyl group (including isomers), ethylcyclohexyl group (including isomers), propylcyclohexyl group (including isomers), butylcyclohexyl group (including isomers), pentylcyclohexyl group (including isomers), hexylcyclohexyl group (including isomers), dimethylcyclohexyl group (including isomers), diethylcyclohexyl group (including isomers) or dibutylcyclohexyl group (including isomers); alkoxy groups and/or cycloalkoxy groups and/or cycloalkoxy groups substituted with an alkoxy group and/or alkoxy groups substituted with a cycloalkoxy group such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers), an octadecyloxy group (including isomers), a cyclopentyloxy group, a cyclohexyloxy group, a cycloheptyloxy group, a cyclooctyloxy group, a methylcyclopentyloxy group (including isomers), an ethylcyclopentyloxy group (including isomers), a methylcyclohexyloxy group (including isomers), an ethylcyclohexyloxy group (including isomers), a propylcyclohexyloxy group (including isomers), a butylcyclohexyloxy group (including isomers), a pentylcyclohexyloxy group (including isomers), a hexylcyclohexyloxy group (including isomers), a dimethylcyclohexyloxy group (including isomers), a diethylcyclohexyloxy group (including isomers) or a dibutylcyclohexyloxy group (including isomers); optionally substituted aryl groups such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); optionally substituted aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and, aralkyloxy groups such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers).

Preferable examples of aromatic hydroxy compounds represented by formula (56) above may include the compounds listed below, while specific examples of aromatic hydroxy compounds represented by formula (67) above are also listed below.

More specifically, examples of these compounds may include chlorophenol (including isomers), bromophenol (including isomers), dichlorophenol (including isomers), dibromophenol (including isomers), trichlorophenol (including isomers), tribromophenol (including isomers), phenol, methylphenol (including isomers), ethylphenol (including isomers), 2-n-propylphenol (including isomers), 2-n-butylphenol (including isomers), 2-n-pentylphenol (including isomers), 2-n-hexylphenol (including isomers), 2-n-heptylphenol (including isomers), 2-n-octylphenol (including isomers), 2-n-nonylphenol (including isomers), 2-n-decylphenol (including isomers), 2-n-dodecylphenol (including isomers), 2-n-octadecylphenol (including isomers), 3-propylphenol (including isomers), 3-butylphenol (including isomers), 3-pentylphenol (including isomers), 3-hexylphenol (including isomers), 3-heptylphenol (including isomers), 3-octylphenol (including isomers), 3-nonylphenol (including isomers), 3-decylphenol (including isomers), 3-dodecylphenol (including isomers), 3-octadecylphenol (including isomers), 4-propylphenol (including isomers), 4-butylphenol (including isomers), 4-pentylphenol (including isomers), 4-hexylphenol (including isomers), 4-heptylphenol (including isomers), 4-octylphenol (including isomers), 4-nonylphenol (including isomers), 4-decylphenol (including isomers), 4-dodecylphenol (including isomers), 4-octadecylphenol (including isomers), 4-phenylphenol (including isomers), dimethylphenol (including isomers), diethylphenol (including isomers), di(n-propyl) phenol (including isomers), di(n-butyl) phenol (including isomers), di(n-pentyl) phenol (including isomers), di(n-hexyl) phenol (including isomers), di(n-heptyl) phenol (including isomers), di(n-octyl) phenol (including isomers), di(n-nonyl) phenol (including isomers), di(n-decyl) phenol (including isomers), di(n-dodecyl) phenol (including isomers), di(n-octadecyl) phenol (including isomers), trimethylphenol (including isomers), triethylphenol (including isomers), tri(n-propyl) phenol (including isomers), tri(n-butyl) phenol (including isomers), tri(n-pentyl) phenol (including isomers), tri(n-hexyl) phenol (including isomers), tri(n-heptyl) phenol (including isomers), tri(n-octyl) phenol (including isomers), tri(n-nonyl) phenol (including isomers), tri(n-decyl) phenol (including isomers), tri(n-dodecyl) phenol (including isomers), tri(n-octadecyl) phenol (including isomers), (methoxymethyl) phenol, (ethoxymethyl) phenol, (propoxymethyl) phenol (including isomers), (butyloxymethyl) phenol (including isomers), (pentyloxymethyl) phenol (including isomers), (hexyloxymethyl) phenol (including isomers), (heptyloxymethyl) phenol (including isomers), (octyloxymethyl) phenol (including isomers), (nonyloxymethyl) phenol (including isomers), (decyloxymethyl) phenol (including isomers), (dodecyloxymethyl) phenol (including isomers), (octadecyloxymethyl) phenol (including isomers), (cyclopentyloxymethyl) phenol, (cyclohexyloxymethyl) phenol, (cycloheptyloxymethyl) phenol, (cyclooctyloxymethyl) phenol, (methylcyclopentyloxymethy) phenol (including isomers), (ethylcyclopentyloxymethyl) phenol (including isomers), (methylcyclohexyloxymethyl) phenol (including isomers), (ethylcyclohexyloxymethyl) phenol (including isomers), (propylcyclohexyloxymethyl) phenol (including isomers), (butylcyclohexyloxymethyl) phenol (including isomers), (pentylcyclohexyloxymethyl) phenol (including isomers), (hexylcyclohexyloxymethyl) phenol (including isomers), (dimethylcyclohexyloxymethyl) phenol (including isomers), (diethylcyclohexyloxymethyl) phenol (including isomers), (dibutylcyclohexyloxymethyl) phenol (including isomers), (phenoxymethyl) phenol, (methylphenoxymethyl) phenol (including isomers), (ethylphenoxymethyl) phenol (including isomers), (propylphenoxymethyl) phenol (including isomers), (butylphenoxymethyl) phenol (including isomers), (pentylphenoxymethyl) phenol (including isomers), (hexylphenoxymethyl) phenol (including isomers), (heptylphenoxymethyl) phenol (including isomers), (octylphenoxymethyl) phenol (including isomers), (nonylphenoxymethyl) phenol (including isomers), (decylphenoxymethyl) phenol (including isomers), (phenylphenoxymethyl) phenol (including isomers), (dimethylphenoxymethyl) phenol (including isomers), (diethylphenoxymethyl) phenol (including isomers), (dipropylphenoxymethyl) phenol (including isomers), (dibutylphenoxymethyl) phenol (including isomers), (dipentylphenoxymethyl) phenol (including isomers), (dihexylphenoxymethyl) phenol (including isomers), (diheptylphenoxymethyl) phenol (including isomers), (diphenylphenoxymethyl) phenol (including isomers), (trimethylphenoxymethyl) phenol (including isomers), (triethylphenoxymethyl) phenol (including isomers), (tripropylphenoxymethyl) phenol (including isomers), (tributylphenoxymethyl) phenol (including isomers), (phenylmethoxymethyl) phenol (including isomers), (phenylethoxymethyl) phenol (including isomers), (phenylpropyloxymethyl) phenol (including isomers), (phenylbutyloxymethyl) phenol (including isomers), (phenylpentyloxymethyl) phenol (including isomers), (phenylhexyloxymethyl) phenol (including isomers), (phenylheptyloxymethyl) phenol (including isomers), (phenyloctyloxymethyl) phenol (including isomers), (phenylnonyloxymethyl) phenol (including isomers), di(methoxymethyl) phenol, di(ethoxymethyl) phenol, di(propoxymethyl) phenol (including isomers), di(butyloxymethyl) phenol (including isomers), di(pentyloxymethyl) phenol (including isomers), di(hexyloxymethyl) phenol (including isomers), di(heptyloxymethyl) phenol (including isomers), di(octyloxymethyl) phenol (including isomers), di(nonyloxymethyl) phenol (including isomers), di(decyloxymethyl) phenol (including isomers), di(dodecyloxymethyl) phenol (including isomers), di(octadecyloxymethyl) phenol (including isomers), di(cyclopentyloxymethyl) phenol (including isomers), di(cyclohexyloxymethyl) phenol (including isomers), di(cycloheptyloxymethyl) phenol (including isomers), di(cyclooctyloxymethyl) phenol (including isomers), di(methylcyclopentyloxymethy) phenol (including isomers), di(ethylcyclopentyloxymethyl) phenol (including isomers), di(methylcyclohexyloxymethyl) phenol (including isomers), di(ethylcyclohexyloxymethyl) phenol (including isomers), di(propylcyclohexyloxymethyl) phenol (including isomers), di(butylcyclohexyloxymethyl) phenol (including isomers), di(pentylcyclohexyloxymethyl) phenol (including isomers), di(hexylcyclohexyloxymethyl) phenol (including isomers), bis(dimethylcyclohexyloxymethyl) phenol (including isomers), bis(diethylcyclohexyloxymethyl) phenol (including isomers), bis(dibutylcyclohexyloxymethyl) phenol (including isomers), di(phenoxymethyl) phenol, di(methylphenoxymethyl) phenol (including isomers), di(ethylphenoxymethyl) phenol (including isomers), di(propylphenoxymethyl) phenol (including isomers), di(butylphenoxymethyl) phenol (including isomers), di(pentylphenoxymethyl) phenol (including isomers), di(hexylphenoxymethyl) phenol (including isomers), di(heptylphenoxymethyl) phenol (including isomers), di(octylphenoxymethyl) phenol (including isomers), di(nonylphenoxymethyl) phenol (including isomers), di(decylphenoxymethyl) phenol (including isomers), di(phenylphenoxymethyl) phenol (including isomers), bis(dimethylphenoxymethyl) phenol (including isomers), bis(diethylphenoxymethyl) phenol (including isomers), bis(dipropylphenoxymethyl) phenol (including isomers), bis(dibutylphenoxymethyl) phenol (including isomers), bis(dipentylphenoxymethyl) phenol (including isomers), bis(dihexylphenoxymethyl) phenol (including isomers), bis(diheptylphenoxymethyl) phenol (including isomers), bis(diphenylphenoxymethyl) phenol (including isomers), di(trimethylphenoxymethyl) phenol (including isomers), di(triethylphenoxymethyl) phenol (including isomers), di(tripropylphenoxymethyl) phenol (including isomers), di(tributylphenoxymethyl) phenol (including isomers), di(phenylmethoxymethyl) phenol, di(phenylethoxymethyl) phenol (including isomers), di(phenylpropyloxymethyl) phenol (including isomers), di(phenylbutyloxymethyl) phenol (including isomers), di(phenylpentyloxymethyl) phenol (including isomers), di(phenylhexyloxymethyl) phenol (including isomers), di(phenylheptyloxymethyl) phenol (including isomers), di(phenyloctyloxymethyl) phenol (including isomers), di(phenylnonyloxymethyl) phenol (including isomers), tri(methoxymethyl) phenol, tri(ethoxymethyl) phenol, tri(propoxymethyl) phenol (including isomers), tri(butyloxymethyl) phenol (including isomers), tri(pentyloxymethyl) phenol (including isomers), tri(hexyloxymethyl) phenol (including isomers), tri(heptyloxymethyl) phenol (including isomers), tri(octyloxymethyl) phenol (including isomers), tri(nonyloxymethyl) phenol (including isomers), tri(decyloxymethyl) phenol (including isomers), tri(dodecyloxymethyl) phenol (including isomers), tri(octadecyloxymethyl) phenol (including isomers), tri(cyclopentyloxymethyl) phenol (including isomers), tri(cyclohexyloxymethyl) phenol (including isomers), tri(cycloheptyloxymethyl) phenol (including isomers), tri(cyclooctyloxymethyl) phenol (including isomers), tri(methylcyclopentyloxymethy) phenol (including isomers), tri(ethylcyclopentyloxymethyl) phenol (including isomers), tri(methylcyclohexyloxymethyl) phenol (including isomers), tri(ethylcyclohexyloxymethyl) phenol (including isomers), tri(propylcyclohexyloxymethyl) phenol (including isomers), tri(butylcyclohexyloxymethyl) phenol (including isomers), tri(pentylcyclohexyloxymethyl) phenol (including isomers), tri(hexylcyclohexyloxymethyl) phenol (including isomers), bis(dimethylcyclohexyloxymethyl) phenol (including isomers), bis(diethylcyclohexyloxymethyl) phenol (including isomers), bis(dibutylcyclohexyloxymethyl) phenol (including isomers), tri(phenoxymethyl) phenol, tri(methylphenoxymethyl) phenol (including isomers), tri(ethylphenoxymethyl) phenol (including isomers), tri(propylphenoxymethyl) phenol (including isomers), tri(butylphenoxymethyl) phenol (including isomers), tri(pentylphenoxymethyl) phenol (including isomers), tri(hexylphenoxymethyl) phenol (including isomers), tri(heptylphenoxymethyl) phenol (including isomers), tri(octylphenoxymethyl) phenol (including isomers), tri(nonylphenoxymethyl) phenol (including isomers), tri(decylphenoxymethyl) phenol (including isomers), tri(phenylphenoxymethyl) phenol (including isomers), bis(dimethylphenoxymethyl) phenol (including isomers), bis(diethylphenoxymethyl) phenol (including isomers), bis(dipropylphenoxymethyl) phenol (including isomers), bis(dibutylphenoxymethyl) phenol (including isomers), bis(dipentylphenoxymethyl) phenol (including isomers), bis(dihexylphenoxymethyl) phenol (including isomers), bis(diheptylphenoxymethyl) phenol (including isomers), bis(diphenylphenoxymethyl) phenol (including isomers), tri(trimethylphenoxymethyl) phenol (including isomers), tri(triethylphenoxymethyl) phenol (including isomers), tri(tripropylphenoxymethyl) phenol (including isomers), tri(tributylphenoxymethyl) phenol (including isomers), tri(phenylmethoxymethyl) phenol, tri(phenylethoxymethyl) phenol (including isomers), tri(phenylpropyloxymethyl) phenol (including isomers), tri(phenylbutyloxymethyl) phenol (including isomers), tri(phenylpentyloxymethyl) phenol (including isomers), tri(phenylhexyloxymethyl) phenol (including isomers), tri(phenylheptyloxymethyl) phenol (including isomers), tri(phenyloctyloxymethyl) phenol (including isomers), tri(phenylnonyloxymethyl) phenol (including isomers), (phenylmethyl) phenol (including isomers), ((methylphenyl)methyl) phenol (including isomers), ((ethylphenyl)methyl) phenol (including isomers), ((propylphenyl)methyl) phenol (including isomers), ((butylphenyl)methyl) phenol (including isomers), ((pentylphenyl)methyl) phenol (including isomers), ((hexylphenyl)methyl) phenol (including isomers), ((heptylphenyl)methyl) phenol (including isomers), ((octylphenyl)methyl) phenol (including isomers), ((nonylphenyl)methyl) phenol (including isomers), ((decylphenyl)methyl) phenol (including isomers), ((biphenyl)methyl) phenol (including isomers), ((dimethylphenyl)methyl) phenol (including isomers), ((diethylphenyl)methyl) phenol (including isomers), ((dipropylphenyl)methyl) phenol (including isomers), ((dibutylphenyl)methyl) phenol (including isomers), ((dipentylphenyl)methyl) phenol (including isomers), ((dihexylphenyl)methyl) phenol (including isomers), ((diheptylphenyl)methyl) phenol (including isomers), ((terphenyl)methyl) phenol (including isomers), ((trimethylphenyl)methyl) phenol (including isomers), ((triethylphenyl)methyl) phenol (including isomers), ((tripropylphenyl)methyl) phenol (including isomers), ((tributylphenyl)methyl) phenol (including isomers), di(phenylmethyl) phenol (including isomers), di((methylphenyl)methyl) phenol (including isomers), di((ethylphenyl)methyl) phenol (including isomers), di((propylphenyl)methyl) phenol (including isomers), di((butylphenyl)methyl) phenol (including isomers), di((pentylphenyl)methyl) phenol (including isomers), di((hexylphenyl)methyl) phenol (including isomers), di((heptylphenyl)methyl) phenol (including isomers), di((octylphenyl)methyl) phenol (including isomers), di((nonylphenyl)methyl) phenol (including isomers), di((decylphenyl)methyl) phenol (including isomers), di((biphenyl)methyl) phenol (including isomers), di((dimethylphenyl)methyl) phenol (including isomers), di((diethylphenyl)methyl) phenol (including isomers), di((dipropylphenyl)methyl) phenol (including isomers), di((dibutylphenyl)methyl) phenol (including isomers), di((dipentylphenyl)methyl) phenol (including isomers), di((dihexylphenyl)methyl) phenol (including isomers), di((diheptylphenyl)methyl) phenol (including isomers), di((terphenyl)methyl) phenol (including isomers), di((trimethylphenyl)methyl) phenol (including isomers), di((triethylphenyl)methyl) phenol (including isomers), di((tripropylphenyl)methyl) phenol (including isomers), di((tributylphenyl)methyl) phenol (including isomers), tri (phenylmethyl) phenol (including isomers), tri((methylphenyl)methyl) phenol (including isomers), tri((ethylphenyl)methyl) phenol (including isomers), tri((propylphenyl)methyl) phenol (including isomers), tri((butylphenyl)methyl) phenol (including isomers), tri((pentylphenyl)methyl) phenol (including isomers), tri((hexylphenyl)methyl) phenol (including isomers), tri((heptylphenyl)methyl) phenol (including isomers), tri((octylphenyl)methyl) phenol (including isomers), tri((nonylphenyl)methyl) phenol (including isomers), tri((decylphenyl)methyl) phenol (including isomers), tri((biphenyl)methyl) phenol (including isomers), tri((dimethylphenyl)methyl) phenol (including isomers), tri((diethylphenyl)methyl) phenol (including isomers), tri((dipropylphenyl)methyl) phenol (including isomers), tri((dibutylphenyl)methyl) phenol (including isomers), tri((dipentylphenyl)methyl) phenol (including isomers), tri((dihexylphenyl)methyl) phenol (including isomers), tri((diheptylphenyl)methyl) phenol (including isomers), tri((terphenyl)methyl) phenol (including isomers), tri((trimethylphenyl)methyl) phenol (including isomers), tri((triethylphenyl)methyl) phenol (including isomers), tri((tripropylphenyl)methyl) phenol (including isomers), tri((tributylphenyl)methyl) phenol (including isomers), phenylethylphenol (including isomers), phenyl-n-propylphenol (including isomers), phenyl-n-butylphenol (including isomers), phenyl-n-pentylphenol (including isomers), phenyl-n-hexylphenol (including isomers), phenyl-n-heptylphenol (including isomers), phenyl-n-octylphenol (including isomers), phenyl-n-nonylphenol (including isomers), (methylamino) phenol, (ethylamino) phenol, (propylamino) phenol (including isomers), (butylamino) phenol (including isomers), (pentylamino) phenol (including isomers), (hexylamino) phenol (including isomers), (heptylamino) phenol (including isomers), (octylamino) phenol (including isomers), (nonylamino) phenol (including isomers), (decylamino) phenol (including isomers), (dodecylamino) phenol (including isomers), (octadecylamino) phenol (including isomers), di(methylamino) phenol, di(ethylamino) phenol, di(propylamino) phenol (including isomers), di(butylamino) phenol (including isomers), di(pentylamino) phenol (including isomers), di(hexylamino) phenol (including isomers), di(heptylamino) phenol (including isomers), di(octylamino) phenol (including isomers), di(nonylamino) phenol (including isomers), di(decylamino) phenol (including isomers), di(dodecylamino) phenol (including isomers), di(octadecylamino) phenol (including isomers), tri(methylamino) phenol, tri(ethylamino) phenol, tri(propylamino) phenol (including isomers), tri(butylamino) phenol (including isomers), tri (pentylamino) phenol (including isomers), tri(hexylamino) phenol (including isomers), tri(heptylamino) phenol (including isomers), tri(octylamino) phenol (including isomers), tri (nonylamino) phenol (including isomers), tri(decylamino) phenol (including isomers), tri(dodecylamino) phenol (including isomers), tri(octadecylamino) phenol (including isomers), methoxyphenol (including isomers), ethoxyphenol (including isomers), propyloxyphenol (including isomers), butyloxyphenol (including isomers), pentyloxyphenol (including isomers), hexyloxyphenol (including isomers), heptyloxyphenol (including isomers), octyloxyphenol (including isomers), nonyloxyphenol (including isomers), decyloxyphenol (including isomers), dodecyloxyphenol (including isomers), octadecyloxyphenol (including isomers), cyclopentyloxyphenol (including isomers), cyclohexyloxyphenol (including isomers), cycloheptyloxyphenol (including isomers), cyclooctyloxyphenol (including isomers), (methylcyclopentyloxy) phenol (including isomers), (ethylcyclopentyloxy) phenol (including isomers), (methylcyclohexyloxy) phenol (including isomers), (ethylcyclohexyloxy) phenol (including isomers), (propylcyclohexyloxy) phenol (including isomers), (butylcyclohexyloxy) phenol (including isomers), (pentylcyclohexyloxy) phenol (including isomers), (hexylcyclohexyloxy) phenol (including isomers), (dimethylcyclohexyloxy) phenol (including isomers), (diethylcyclohexyloxy) phenol (including isomers), (dibutylcyclohexyloxy) phenol (including isomers), phenoxyphenol, (methylphenyloxy) phenol (including isomers), (ethylphenyloxy) phenol (including isomers), (propylphenyloxy) phenol (including isomers), (butylphenyloxy) phenol (including isomers), (pentylphenyloxy) phenol (including isomers), (hexylphenyloxy) phenol (including isomers), (heptylphenyloxy) phenol (including isomers), (octylphenyloxy) phenol (including isomers), (nonylphenyloxy) phenol (including isomers), (decylphenyloxy) phenol (including isomers), biphenyloxyphenol (including isomers), (dimethylphenyloxy) phenol (including isomers), (diethylphenyloxy) phenol (including isomers), (dipropylphenyloxy) phenol (including isomers), (dibutylphenyloxy) phenol (including isomers), (dipentylphenyloxy) phenol (including isomers), (dihexylphenyloxy) phenol (including isomers), (diheptylphenyloxy) phenol (including isomers), terphenyloxyphenol (including isomers), (trimethylphenyloxy) phenol (including isomers), (triethylphenyloxy) phenol (including isomers), (tripropylphenyloxy) phenol (including isomers), (tributylphenyloxy) phenol (including isomers), (phenylmethyloxy) phenol, (phenylethyloxy) phenol (including isomers), (phenylpropyloxy) phenol (including isomers), (phenylbutyloxy) phenol (including isomers), (phenylpentyloxy) phenol (including isomers), (phenylhexyloxy) phenol (including isomers), (phenylheptyloxy) phenol (including isomers), (phenyloctyloxy) phenol (including isomers), (phenylnonyloxy) phenol (including isomers), dimethoxyphenol (including isomers), diethoxyphenol (including isomers), dipropyloxyphenol (including isomers), dibutyloxyphenol (including isomers), dipentyloxyphenol (including isomers), dihexyloxyphenol (including isomers), diheptyloxyphenol (including isomers), dioctyloxyphenol (including isomers), dinonyloxyphenol (including isomers), didecyloxyphenol (including isomers), didodecyloxyphenol (including isomers), dioctadecyloxyphenol (including isomers), dicyclopentyloxyphenol (including isomers), dicyclohexyloxyphenol (including isomers), dicycloheptyloxyphenol (including isomers), dicyclooctyloxyphenol (including isomers), di(methylcyclopentyloxy) phenol (including isomers), di(ethylcyclopentyloxy) phenol (including isomers), di(methylcyclohexyloxy) phenol (including isomers), di(ethylcyclohexyloxy) phenol (including isomers), di(propylcyclohexyloxy) phenol (including isomers), di(butylcyclohexyloxy) phenol (including isomers), di(pentylcyclohexyloxy) phenol (including isomers), di(hexylcyclohexyloxy) phenol (including isomers), bis(dimethylcyclohexyloxy) phenol (including isomers), bis(diethylcyclohexyloxy) phenol (including isomers), bis(dibutylcyclohexyloxy) phenol (including isomers), diphenyloxyphenol, di(methylphenyloxy) phenol (including isomers), di(ethylphenyloxy) phenol (including isomers), di(propylphenyloxy) phenol (including isomers), di(butylphenyloxy) phenol (including isomers), di(pentylphenyloxy) phenol (including isomers), di(hexylphenyloxy) phenol (including isomers), di(heptylphenyloxy) phenol (including isomers), di(octylphenyloxy) phenol (including isomers), di(nonylphenyloxy) phenol (including isomers), di(decylphenyloxy) phenol (including isomers), dibiphenyloxyphenol (including isomers), bis(dimethylphenyloxy) phenol (including isomers), bis(diethylphenyloxy) phenol (including isomers), bis(dipropylphenyloxy) phenol (including isomers), bis(dibutylphenyloxy) phenol (including isomers), bis(dipentylphenyloxy) phenol (including isomers), bis(dihexylphenyloxy) phenol (including isomers), bis(diheptylphenyloxy) phenol (including isomers), diterphenyloxyphenol (including isomers), di(trimethylphenyloxy) phenol (including isomers), di(triethylphenyloxy) phenol (including isomers), di(tripropylphenyloxy) phenol (including isomers), di(tributylphenyloxy) phenol (including isomers), di(phenylmethyloxy) phenol, di(phenylethyloxy) phenol (including isomers), di(phenylpropyloxy) phenol (including isomers), di(phenylbutyloxy) phenol (including isomers), di(phenylpentyloxy) phenol (including isomers), di(phenylhexyloxy) phenol (including isomers), di(phenylheptyloxy) phenol (including isomers), di(phenyloctyloxy) phenol (including isomers), di(phenylnonyloxy) phenol (including isomers), trimethoxyphenol (including isomers), triethoxyphenol (including isomers), tripropyloxyphenol (including isomers), tributyloxyphenol (including isomers), tripentyloxyphenol (including isomers), trihexyloxyphenol (including isomers), triheptyloxyphenol (including isomers), trioctyloxyphenol (including isomers), trinonyloxyphenol (including isomers), tridecyloxyphenol (including isomers), tridodecyloxyphenol (including isomers), trioctadecyloxyphenol (including isomers), tricyclopentyloxyphenol (including isomers), tricyclohexyloxyphenol (including isomers), tricycloheptyloxyphenol (including isomers), tricyclooctyloxyphenol (including isomers), tri(methylcyclopentyloxy) phenol (including isomers), tri(ethylcyclopentyloxy) phenol (including isomers), tri(methylcyclohexyloxy) phenol (including isomers), tri(ethylcyclohexyloxy) phenol (including isomers), tri(propylcyclohexyloxy) phenol (including isomers), tri(butylcyclohexyloxy) phenol (including isomers), tri(pentylcyclohexyloxy) phenol (including isomers), tri(hexylcyclohexyloxy) phenol (including isomers), tri(dimethylcyclohexyloxy) phenol (including isomers), tri(diethylcyclohexyloxy) phenol (including isomers), tri(dibutylcyclohexyloxy) phenol (including isomers), phenyloxyphenol, tri(methylphenyloxy) phenol (including isomers), tri(ethylphenyloxy) phenol (including isomers), tri(propylphenyloxy) phenol (including isomers), tri(butylphenyloxy) phenol (including isomers), tri(pentylphenyloxy) phenol (including isomers), tri(hexylphenyloxy) phenol (including isomers), tri(heptylphenyloxy) phenol (including isomers), tri(octylphenyloxy) phenol (including isomers), tri(nonylphenyloxy) phenol (including isomers), tri(decylphenyloxy) phenol (including isomers), tribiphenyloxyphenol (including isomers), tri(dimethylphenyloxy) phenol (including isomers), tri(diethylphenyloxy) phenol (including isomers), tri(dipropylphenyloxy) phenol (including isomers), tri(dibutylphenyloxy) phenol (including isomers), tri(dipentylphenyloxy) phenol (including isomers), tri(dihexylphenyloxy) phenol (including isomers), tri(diheptylphenyloxy) phenol (including isomers), triterphenyloxyphenol (including isomers), tri(trimethylphenyloxy) phenol (including isomers), tri(triethylphenyloxy) phenol (including isomers), tri(tripropylphenyloxy) phenol (including isomers), tri(tributylphenyloxy) phenol (including isomers), (phenylmethyloxy) phenol, tri(phenylethyloxy) phenol (including isomers), tri(phenylpropyloxy) phenol (including isomers), tri(phenylbutyloxy) phenol (including isomers), tri (phenylpentyloxy) phenol (including isomers), tri(phenylhexyloxy) phenol (including isomers), tri(phenylheptyloxy) phenol (including isomers), tri(phenyloctyloxy) phenol (including isomers), tri(phenylnonyloxy) phenol (including isomers), and naphthol (including isomers).

More preferable examples of the aromatic hydroxy compounds listed above may include those in which the number of carbon atoms that compose the $R^5$, $R^6$, $R^{23}$, $R^{24}$ and $R^{25}$ is from 0 to 13 due to the ease of transfer thereof. More preferably, the aromatic hydroxy compound is an aromatic hydroxy compound in which $R^5$, $R^6$, $R^{23}$, $R^{24}$ and $R^{25}$ are groups having 0 to 9 carbon atoms selected from a hydrogen atom, linear or branched alkyl group, cycloalkyl group, optionally substituted aryl group, linear or branched alkoxy group, optionally substituted aryloxy group and optionally substituted aralkyl group.

In addition, the aromatic hydroxy compound forms an N-substituted carbamic acid-O—Ar ester, and the N-substituted carbamic acid-O—Ar ester is used in the form of an isocyanate derivative. Although details of a method for producing an isocyanate derived from an N-substituted carbamic acid-O—Ar ester from the N-substituted carbamic acid-O—Ar ester will be described hereinafter, this method involves obtaining an aromatic hydroxy compound derived from the N-substituted carbamic acid-O—Ar ester and an isocyanate by thermal decomposition of the N-substituted carbamic acid ester. In consideration of the reaction scheme, the aromatic hydroxy compound formed at that time is an aromatic hydroxy compound contained in the aromatic hydroxy composition used when producing the N-substituted carbamic acid-O—Ar ester. Namely, an aromatic hydroxy compound of formula (56), and preferably formula (67), is produced as a by-product together with isocyanate during thermal decomposition of the N-substituted carbamic acid-O—Ar ester. In one of the present embodiments, although depending on the particular case, the aromatic hydroxy compound and isocyanate are separated by distillation following the thermal decomposition step, and the separated aromatic hydroxy compound may be recycled in the form of an aromatic hydroxy composition in the reaction between the organic amine, carbonic acid derivative and aromatic hydroxy compound. Thus, in consideration of the process through the isocyanate production step, it is necessary to take into consideration the separability of the aromatic hydroxy compound serving as a raw material of the N-substituted carbamic acid-O—Ar ester and the isocyanate formed from the N-substituted carbamic acid ester. Although it is difficult to generally define separability, it is defined on the basis of the finding that generally two components to be separated can be adequately separated by distillation industrially if the standard boiling points thereof are 10° C. or more apart. Thus, this definition refers to a value that is limited by currently known separation means, and is not intended to serve as a basis of the present embodiment.

As has been described above, an aromatic hydroxy compound having a specific structure is preferably used from the viewpoint of reactivity during production of N-substituted carbamic acid-O—Ar ester.

Conversely, the inventors of the present invention found that, in the case a group bonded to the atom at the α position of a substituent of at least one ortho position of the aromatic hydroxy compound is a bulky substituent, the formation rate of N-substituted carbamic acid-O—Ar ester decreases considerably. More specifically, this refers to an aromatic hydroxy compound in which a substituent in which the atom at the α position is a tertiary or quaternary carbon atom or tertiary nitrogen atom is bonded to at least one ortho position relative to a hydroxy group of the aromatic hydroxy compound. The demonstration of such an effect by this aromatic hydroxy compound is also not found in the prior art. Hereinafter, an aromatic hydroxy compound for which the formation rate of N-substituted carbamic acid-O—Ar ester is low is frequently referred to as a low activity aromatic hydroxy compound.

Moreover, as a result of focusing on the fact that the formation rate of N-substituted carbamic acid ether differs depending on the type of aromatic hydroxy compound as described above, the inventors of the present invention conceived of and completed an N-substituted carbamic acid-O—Ar ester production method that uses an aromatic hydroxy composition composed of a plurality of types of aromatic hydroxy compounds. This N-substituted carbamic acid-O—Ar ester production that uses an aromatic hydroxy composition composed of a plurality of types of aromatic hydroxy compounds will be described later.

The aromatic hydroxy composition composed of a plurality of types of aromatic hydroxy compounds is composed by containing an aromatic hydroxy compound represented by the above-mentioned formula (56) and/or formula (67) (active aromatic hydroxy compound) together with a low activity aromatic hydroxy compound represented by the following formula (70):

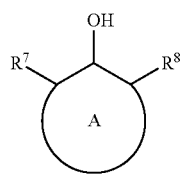

(wherein ring A represents an optionally substituted single or multiple aromatic hydrocarbon ring, $R^7$ and $R^8$ respectively and independently represent any group defined in (i) to (v) below, the number of carbon atoms that compose the aromatic hydroxy compound is an integer of from 6 to 50, and $R^7$ and $R^8$ may form a ring structure by bonding with A:

(i) a hydrogen atom, (ii) a halogen atom, (iii) a group in which the atom at the α position is a nitrogen atom and the number of carbon atoms is from 1 to 44, and which does not contain active hydrogen, the nitrogen atom being a tertiary nitrogen atom (namely, a nitrogen atom that does not have a hydrogen atom), (iv) a group in which the atom at the α position is a carbon atom and the number of carbon atoms is from 1 to 44, and which does not contain active hydrogen, the carbon atom at the α position being a tertiary or quaternary carbon atom (namely, a carbon atom that forms a —CH— bond or a carbon atom not bonded to hydrogen); in the case $R^7$ and/or $R^8$ form a saturated and/or unsaturated condensed ring structure with the ring A, and the condensed ring has 7 members or more, the carbon atom at the α position may be a primary or secondary carbon atom (namely, a carbon atom of a methyl group or a carbon atom that forms a —CH$_2$— bond); in the case the α position carbon forms a double bond with a β position atom, the α position carbon is quaternary carbon; and groups in which the α position carbon forms a triple bond with a β position atom are excluded, and (v) a group in which the atom at the α position is an oxygen atom and the number of carbons is from 1 to 24, and which does not contain active hydrogen).

Furthermore, although the term "atom at the α position" is used in the preceding explanation of formula (70) above, an "atom at the α position" refers to an atom that composes the $R^7$ and $R^8$ that is adjacent to a carbon atom on the aromatic hydrocarbon ring to which the Wand $R^8$ groups are bonded.

Examples of substituents that substitute an aromatic group of the aromatic hydroxy compound represented by formula (70) above (excluding $R^7$ and $R^8$) may include groups selected from a hydrogen atom, a halogen atom, an aliphatic group and an aromatic group that are composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a heterocrosslinked ring group or a heterocyclic ring group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (71) to (78).

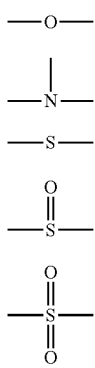

(74)

(75)

(76)

(77)

(89)

Among these substituents, examples of substituents that can be preferably used in the present embodiment in consideration of less susceptibility to the occurrence of side reactions may include groups selected from the group consisting of acyclic hydrocarbon groups and cyclic hydrocarbon groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups).

In the case of transferring a composition containing an N-substituted carbamic acid-O—Ar ester at a high temperature or in the case of reacting an organic amine, a carbonic acid derivative and an aromatic hydroxy compound and obtaining an N-substituted carbamic acid-O—Ar ester at a high temperature, the substituent that substitutes ring A of the aromatic hydroxy compound (excluding $R^7$ and $R^8$) is preferably an inactive substituent in the form of an aromatic hydroxy compound. An inactive substituent here refers to a group in which the inactive substituent does not contain an active hydrogen as previously described (although it may have an aromatic hydroxy group).

Examples of such substituents that substitute ring A (excluding $R^7$ and $R^8$) may include a group selected from the group consisting of an alkyl group, a cycloalkyl group, an aryl group, an aralkyl group and an ether group (substituted and/or unsubstituted alkyl ether and/or aryl ether and/or aralkyl ether); a group to which is bonded a group selected from one or more types of the above-mentioned groups; a group selected from groups in which a group selected from one or more types of the above-mentioned groups is selected from groups composed of a group bonded with a saturated hydrocarbon bond and/or an ether bond; and a group which is a halogen atom and in which the total of the number of carbon atoms that compose ring A and the number of carbon atoms that compose all substituents that substitute ring A is an integer of from 6 to 50.

In formula (70) above, examples of ring A may include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring and an acephenanthrylene ring. More preferably, ring A has a structure that contains at least one structure selected from a benzene ring and a naphthalene ring.

Moreover, in consideration of industrial use, an aromatic hydroxy compound that is easily acquirable and has benzene skeleton thereof is preferable. Preferable examples of such an aromatic hydroxy compound may include aromatic hydroxy compounds represented by the following formula (79):

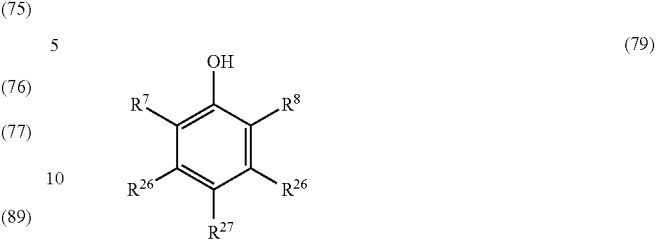

(79)

(wherein
$R^7$ and $R^8$ are the groups defined above,
$R^{26}$, $R^{27}$ and $R^{28}$ respectively and independently represent a group selected from the group consisting of an alkyl group, a cycloalkyl group, an aryl group, an aralkyl group and an ether group (substituted and/or unsubstituted alkyl ether and/or aryl ether and/or aralkyl ether); a group to which is bonded a group selected from one or more types of the above groups; a group selected from groups in which one or more types of the above groups is composed of a group bonded with a saturated aliphatic bond and/or an ether bond; a halogen atom; or a hydrogen atom, and the total number of carbon atoms that compose the $R^7$, $R^8$, $R^{26}$, $R^{27}$ and $R^{28}$ is an integer of from 0 to 44).

In formula (79) above, $R^7$ and $R^8$ are preferably groups independently selected from groups indicated in (i) to (vi) below:

(i) a hydrogen atom, (ii) a halogen atom, (iii) a group in which the atom at the α position is a nitrogen atom, the number of carbon atoms is from 1 to 44, the nitrogen atom is a tertiary nitrogen atom (namely, a nitrogen atom that does not have a hydrogen atom), and a group bonded to the α position nitrogen atom is respectively and independently selected from an alkyl group having 1 to 44 carbon atoms, a cycloalkyl group having 1 to 44 carbon atoms, a polyoxyalkylene alkyl ether group having 2 to 44 atoms and does not have an OH group on the terminal thereof, an aryl group having 6 to 44 carbon atoms, an aralkyl group having 7 to 44 carbon atoms, and a group to which is bonded one or more types of the above groups, (iv) an optionally substituted aryl group having 6 to 44 carbon atoms that does not contain active hydrogen, (v) a group in which the atom at the α position is a carbon atom and the number of carbon atoms is from 1 to 44, and which does not contain active hydrogen, the carbon atom at the α position being a tertiary or quaternary carbon atom (namely, a carbon atom that forms a —CH— bond or a carbon atom not bonded to hydrogen); in the case $R^7$ and/or $R^8$ form a saturated and/or unsaturated condensed ring structure with the ring A, and the condensed ring has 7 members or more, the carbon atom at the α position may be a primary or secondary carbon atom (namely, a carbon atom of a methyl group or a carbon atom that forms a —CH$_2$— bond); in the case the α position carbon forms a double bond with a β position atom, the α position carbon is quaternary carbon; and groups in which the α position carbon forms a triple bond with a β position atom are excluded, and a group other than a hydrogen atom that is bonded to the α position carbon atom is respectively and independently a group selected from an alkyl group having 1 to 43 carbon atoms, a cycloalkyl group having 1 to 43 carbon atoms, an alkoxy group having 1 to 43 carbon atoms, a polyoxyalkylene alkyl ether group having 2 to 43 atoms and does not have an OH group on the terminal thereof, an aryl group having 6 to 43 carbon atoms, an aralkyl group having 7 to 43 carbon atoms, an aralkyloxy group having 7 to 43 carbon atoms, and a group to which is bonded one or more types of the above groups, and (vi) a group in which the atom at the α position is an oxygen atom, the number of carbons is from 1 to 24, and which does not contain active hydrogen, and the group bonded to the oxygen atom at the α position is a group respectively and independently selected from an alkyl group having 1 to 44 carbon atoms, a cycloalkyl group having 1 to 44 carbon atoms, a polyoxyalkylene alkyl ether group having 2 to 44 carbon atoms that does not have an OH group on the terminal thereof, an aralkyl group having 7 to 44 carbon atoms, and a group to which is bonded one or more types of the above groups.

Moreover, $R^{26}$, $R^{27}$ and $R^{28}$ are preferably groups independently selected from groups indicated in (vii) to (xi) below:

(vii) a hydrogen atom, (viii) a halogen atom, (ix) a group in which the atom at the α position is a carbon atom, the number of carbon atoms is from 1 to 44, and three groups bonded to the α position carbon atom are respectively and independently selected from an alkyl group having 1 to 43 carbon atoms, a cycloalkyl group having 1 to 43 carbon atoms, an alkoxy group having 1 to 43 carbon atoms, a polyoxyalkylene alkyl ether group having 2 to 43 atoms and does not have an OH group on the terminal thereof, an aryl group having 6 to 43 carbon atoms, an aralkyl group having 7 to 43 carbon atoms, an aralkyloxy group having 7 to 43 carbon atoms, a group to which is bonded one or more types of the above groups, and a hydrogen atom, (x) an aryl group having 1 to 44 carbon atoms, wherein the aryl group is substituted by a substituent, the aryl group may be substituted with 1 to 5 of the substituents indicated below, and the substituent is a group selected from a hydrogen atom, an alkyl group having 1 to 38 carbon atoms, a cycloalkyl group having 4 to 38 carbon atoms, an alkoxy group having 1 to 38 carbon atoms, a polyoxyalkylene alkyl ether group having 2 to 38 carbons that does not have an OH group on the terminal thereof, an aryl group having 6 to 38 carbon atoms, an aralkyl group having 7 to 38 carbon atoms, an aralkyloxy group having 7 to 38 carbon atoms and a group to which is bonded one or more types of the above groups, and (xi) a group in which the atom at the α position is an oxygen atom, the number of carbon atoms is from 1 to 44, and the group bonded to the oxygen atom at the α position is a group selected from an alkyl group having 1 to 44 carbon atoms, a cycloalkyl group having 1 to 44 carbon atoms, an alkoxy group having 1 to 44 carbon atoms, a polyoxyalkylene alkyl ether group having 2 to 44 carbon atoms that does not have an OH group on the terminal thereof, an aryl group having 6 to 44 carbon atoms, an aralkyl group having 7 to 44 carbon atoms, an aralkyloxy group having 7 to 44 carbon atoms, and a group to which is bonded one or more types of the above groups.

Furthermore, although the term "atom at the α position" is used in the preceding explanation of formula (79) above, an "atom at the α position" refers to an atom that composes the $R^7$, $R^8$, $R^{26}$, $R^{27}$ and $R^{28}$ that is adjacent to a carbon atom on the aromatic hydrocarbon ring to which the $R^7$, $R^8$, $R^{26}$, $R^{27}$ and $R^{28}$ groups are bonded.

Examples of such $R^{26}$, $R^{27}$ and $R^{28}$ groups may include alkyl groups and/or cycloalkyl groups and/or cycloalkyl groups substituted with an alkyl group and/or alkyl groups substituted with a cycloalkyl group such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers), cyclopentyl group, cyclohexyl group, cycloheptyl group, cyclooctyl group, methylcyclopentyl group (including isomers), ethylcyclopentyl group (including isomers), methylcyclohexyl group (including isomers), ethylcyclohexyl group (including isomers), propylcyclohexyl group (including isomers), butylcyclohexyl group (including isomers), pentylcyclohexyl group (including isomers), hexylcyclohexyl group (including isomers), dimethylcyclohexyl group (including isomers), diethylcyclohexyl group (including isomers) or dibutylcyclohexyl group (including isomers); alkoxy groups and/or cycloalkoxy groups and/or cycloalkoxy groups substituted with an alkyl group and/or alkoxy groups substituted with a cycloalkoxy group such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers), an octadecyloxy group (including isomers), a cyclopentyloxy group, a cyclohexyloxy group, a cycloheptyloxy group, a cyclooctyloxy group, a methylcyclopentyloxy group (including isomers), an ethylcyclopentyloxy group (including isomers), a methylcyclohexyloxy group (including isomers), an ethylcyclohexyloxy group (including isomers), a propylcyclohexyloxy group (including isomers), a butylcyclohexyloxy group (including isomers), a pentylcyclohexyloxy group (including isomers), a hexylcyclohexyloxy group (including isomers), a dimethylcyclohexyloxy group (including isomers), a diethylcyclohexyloxy group (including isomers) or a dibutylcyclohexyloxy group (including isomers); optionally substituted aryl groups such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); optionally substituted aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and, aralkyloxy groups such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers).

Preferable examples of aromatic hydroxy compounds represented by formula (70) above may include the compounds listed below, while specific examples of aromatic hydroxy compounds represented by formula (79) above are also listed below.

More specifically, examples of these compounds may include 2-isopropylphenol (including isomers), 2-tert-butylphenol (including isomers), 2-tert-pentylphenol (including isomers), 2-tert-hexylphenol (including isomers), 2-tert-heptylphenol (including isomers), 2-tert-octylphenol (including isomers), 2-tert-nonylphenol (including isomers), 2-tert-decylphenol (including isomers), 2-tert-dodecylphenol (including isomers), 2-tert-octadecylphenol (including isomers), 2-sec-propylphenol (including isomers), 2-sec-butylphenol (including isomers), 2-sec-pentylphenol (including isomers), 2-sec-hexylphenol (including isomers), 2-sec-heptylphenol (including isomers), 2-sec-octylphenol (including isomers), 2-sec-nonylphenol (including isomers), 2-sec-decylphenol (including isomers), 2-sec-dodecylphenol (including isomers), 2-sec-octadecylphenol (including isomers), 2-phenylphenol, 2,4-di-tert-propylphenol (including isomers), 2,4-di-tert-butylphenol (including isomers), 2,4-di-tert-pentylphenol (including isomers), 2,4-di-tert-hexylphenol (including isomers), 2,4-di-tert-heptylphenol (including isomers), 2,4-di-tert-octylphenol (including isomers), 2,4-di-tert-nonylphenol (including isomers), 2,4-di-tert-decylphenol (including isomers), 2,4-di-tert-dodecylphenol (including isomers), 2,4-di-tert-octadecylphenol (including isomers), 2,4-di-sec-propylphenol (including isomers), 2,4-di-sec-butylphenol (including isomers), 2,4-di-sec-pentylphenol (including isomers), 2,4-di-sec-hexylphenol (including isomers), 2,4-di-sec-heptylphenol (including isomers), 2,4-di-sec-octylphenol (including isomers), 2,4-di-sec-nonylphenol (including isomers), 2,4-di-sec-decylphenol (including isomers), 2,4-di-sec-dodecylphenol (including isomers), 2,4-di-sec-octadecylphenol (including isomers), 2,6-di-tert-propylphenol (including isomers), 2,6-di-tert-butylphenol (including isomers), 2,6-di-tert-pentylphenol (including isomers), 2,6-di-tert-hexylphenol (including isomers), 2,6-di-tert-heptylphenol (including isomers), 2,6-di-tert-octylphenol (including isomers), 2,6-di-tert-nonylphenol (including isomers), 2,6-di-tert-decylphenol (including isomers), 2,6-di-tert-dodecylphenol (including isomers), 2,6-di-tert-octadecylphenol (including isomers), 2,6-di-sec-propylphenol (including isomers), 2,6-di-sec-butylphenol (including isomers), 2,6-di-sec-pentylphenol (including isomers), 2,6-di-sec-hexylphenol (including isomers), 2,6-di-sec-heptylphenol (including isomers), 2,6-di-sec-octylphenol (including isomers), 2,6-di-sec-nonylphenol (including isomers), 2,6-di-sec-decylphenol (including isomers), 2,6-di-sec-dodecylphenol (including isomers), 2,6-di-sec-octadecylphenol (including isomers), 2,4-diphenylphenol, 2,6-diphenylphenol, 2,4,6-tri-tert-propylphenol (including isomers), 2,4,6-tri-tert-butylphenol (including isomers), 2,4,6-tri-tert-pentylphenol (including isomers), 2,4,6-tri-tert-hexylphenol (including isomers), 2,4,6-tri-tert-heptylphenol (including isomers), 2,4,6-tri-tert-octylphenol (including isomers), 2,4,6-tri-tert-nonylphenol (including isomers), 2,4,6-tri-tert-decylphenol (including isomers), 2,4,6-tri-tert-dodecylphenol (including isomers), 2,4,6-tri-tert-octadecylphenol (including isomers), 2,4,6-tri-sec-propylphenol (including isomers), 2,4,6-tri-sec-butylphenol (including isomers), 2,4,6-tri-sec-pentylphenol (including isomers), 2,4,6-tri-sec-hexylphenol (including isomers), 2,4,6-tri-sec-heptylphenol (including isomers), 2,4,6-tri-sec-octylphenol (including isomers), 2,4,6-tri-sec-nonylphenol (including isomers), 2,4,6-tri-sec-decylphenol (including isomers), 2,4,6-tri-sec-dodecylphenol (including isomers), 2,4,6-tri-sec-octadecylphenol (including isomers), (2-methoxy-2-methylethyl) phenol, (2-ethoxy-2-methylethyl) phenol, (2-propoxy-2-methylethyl) phenol (including isomers), (2-butyloxy-2-methylethyl) phenol (including isomers), (2-pentyloxy-2-methylethyl) phenol (including isomers), (2-hexyloxy-2-methylethyl) phenol (including isomers), (2-heptyloxy-2-methylethyl) phenol (including isomers), (2-octyloxy-2-methylethyl) phenol (including isomers), (2-nonyloxy-2-methylethyl) phenol (including isomers), (2-decyloxy-2-methylethyl) phenol (including isomers), (2-dodecyloxy-2-methylethyl) phenol (including isomers), (2-octadecyloxy-2-methylethyl) phenol (including isomers), (2-cyclopentyloxy-2-methylethyl) phenol (including isomers), (2-cyclohexyloxy-2-methylethyl) phenol (including isomers), (2-cycloheptyloxy-2-methylethyl) phenol (including isomers), (2-cyclooctyloxy-2-methylethyl) phenol (including isomers), (2-(methylcyclopentyloxy)-2-methylethyl) phenol (including isomers), (2-(ethylcyclopentyloxy)-2-methylethyl) phenol (including isomers), (2-(methylcyclohexyloxy)-2-methylethyl) phenol (including isomers), (2-(ethylcyclohexyloxy)-2-methylethyl) phenol (including isomers), (2-(propylcyclohexyloxy)-2-methylethyl) phenol (including isomers), (2-(butylcyclohexyloxy)-2-methylethyl) phenol (including isomers), (2-(pentylcyclohexyloxy)-2-methylethyl) phenol (including isomers), (2-(hexylcyclohexyloxy)-2-methylethyl) phenol (including isomers), (2-(dimethylcyclohexyloxy)-2-methylethyl) phenol (including isomers), (2-(diethylcyclohexyloxy)-2-methylethyl) phenol (including isomers), (2-(dibutylcyclohexyloxy)-2-methylethyl) phenol (including isomers), (2-phenoxy-2-methylethyl) phenol (including isomers), (2-(methylphenoxy)-2-methylethyl) phenol (including isomers), (2-(ethylphenoxy)-2-methylethyl) phenol (including isomers), (2-(propylphenoxy)-2-methylethyl) phenol (including isomers), (2-(butylphenoxy)-2-methylethyl) phenol (including isomers), (2-(pentylphenoxy)-2-methylethyl) phenol (including isomers), (2-(hexylphenoxy)-2-methylethyl) phenol (including isomers), (2-(heptylphenoxy)-2-methylethyl) phenol (including isomers), (2-(octylphenoxy)-2-methylethyl) phenol (including isomers), (2-(nonylphenoxy)-2-methylethyl) phenol (including isomers), (2-(decylphenoxy)-2-methylethyl) phenol (including isomers), (2-(phenylphenoxy)-2-methylethyl) phenol (including isomers), (2-(dimethylphenoxy)-2-methylethyl) phenol (including isomers), (2-(diethylphenoxy)-2-methylethyl) phenol (including isomers), (2-(dipropylphenoxy)-2-methylethyl) phenol (including isomers), (2-(dibutylphenoxy)-2-methylethyl) phenol (including isomers), (2-(dipentylphenoxy)-2-methylethyl) phenol (including isomers), (2-(dihexylphenoxy)-2-methylethyl) phenol (including isomers), (2-(diheptylphenoxy)-2-methylethyl) phenol (including isomers), (2-(diphenylphenoxy)-2-methylethyl) phenol (including isomers), (2-(trimethylphenoxy)-2-methylethyl) phenol (including isomers), (2-(triethylphenoxy)-2-methylethyl) phenol (including isomers), (2-(tripropylphenoxy)-2-methylethyl) phenol (including isomers), (2-(tributylphenoxy)-2-methylethyl) phenol (including isomers), (2-(phenylmethoxy)-2-methylethyl) phenol (including isomers), (2-(phenylethoxy)-2-methylethyl) phenol (including isomers), (2-(phenylpropyloxy)-2-methylethyl) phenol (including isomers), (2-(phenylbutyloxy)-2-methylethyl) phenol (including isomers), (2-(phenylpentyloxy)-2-methylethyl) phenol (including isomers), (2-(phenylhexyloxy)-2-methylethyl) phenol (including isomers), (2-(phenylheptyloxy)-2-methylethyl) phenol (including isomers), (2-(phenyloctyloxy)-2-methylethyl) phenol (including isomers), (2-(phenylnonyloxy)-2-methylethyl) phenol (including isomers), (2-methoxy-2-methylpropyl) phenol, (2-ethoxy-2-methylpropyl) phenol, (2-propoxy-2-methylpropyl) phenol (including isomers), (2-butyloxy-2-methylpropyl) phenol (including isomers), (2-pentyloxy-2-methylpropyl) phenol (including isomers), (2-hexyloxy-2-methylpropyl) phenol (including isomers), (2-heptyloxy-2-methylpropyl) phenol (including isomers), (2-octyloxy-2-methylpropyl) phenol (including isomers), (2-nonyloxy-2-methylpropyl) phenol (including isomers), (2-decyloxy-2-methylpropyl) phenol (including isomers), (2-dodecyloxy-2-methylpropyl) phenol (including isomers), (2-octadecyloxy-2-methylpropyl) phenol (including isomers), (2-cyclopentyloxy-2-methylpropyl) phenol (including isomers), (2-cyclohexyloxy-2-methylpropyl) phenol (including isomers), (2-cycloheptyloxy-2-methylpropyl) phenol (including isomers), (2-cyclooctyloxy-2-methylpropyl) phenol (including isomers), (2-(methylcyclopentyloxy)-2-methylpropyl) phenol (including isomers), (2-(ethylcyclopentyloxy)-2-methylpropyl) phenol (including isomers), (2-(methylcyclohexyloxy)-2-methylpropyl) phenol (including isomers), (2-(ethylcyclohexyloxy)-2-methylpropyl) phenol (including isomers), (2-(propylcyclohexyloxy)-2-methylpropyl) phenol (including isomers), (2-(butylcyclohexyloxy)-2-methylpropyl) phenol (including isomers), (2-(pentylcyclohexyloxy)-2-methylpropyl) phenol (including isomers), (2-(hexylcyclohexyloxy)-2-methylpropyl) phenol (including isomers), (2-(dimethylcyclohexyloxy)-2-methylpropyl) phenol (including isomers), (2-(diethylcyclohexyloxy)-2-methylpropyl) phenol (including isomers), (2-(dibutylcyclohexyloxy)-2-methylpropyl) phenol (including isomers), (2-phenoxy-2-methylpropyl) phenol (including isomers), (2-(methylphenoxy)-2-methylpropyl) phenol (including isomers), (2-(ethylphenoxy)-2-methylpropyl) phenol (including isomers), (2-(propylphenoxy)-2-methylpropyl) phenol (including isomers), (2-(butylphenoxy)-2-methylpropyl) phenol (including isomers), (2-(pentylphenoxy)-2-methylpropyl) phenol (including isomers), (2-(hexylphenoxy)-2-methylpropyl) phenol (including isomers), (2-(heptylphenoxy)-2-methylpropyl) phenol (including isomers), (2-(octylphenoxy)-2-methylpropyl) phenol (including isomers), (2-(nonylphenoxy)-2-methylpropyl) phenol (including isomers), (2-(decylphenoxy)-2-methylpropyl) phenol (including isomers), (2-(phenylphenoxy)-2-methylpropyl) phenol (including isomers), (2-(dimethylphenoxy)-2-methylpropyl) phenol (including isomers), (2-(diethylphenoxy)-2-methylpropyl) phenol (including isomers), (2-(dipropylphenoxy)-2-methylpropyl) phenol (including isomers), (2-(dibutylphenoxy)-2-methylpropyl) phenol (including isomers), (2-(dipentylphenoxy)-2-methylpropyl) phenol (including isomers), (2-(dihexylphenoxy)-2-methylpropyl) phenol (including isomers), (2-(diheptylphenoxy)-2-methylpropyl) phenol (including isomers), (2-(diphenylphenoxy)-2-methylpropyl) phenol (including isomers), (2-(trimethylphenoxy)-2-methylpropyl) phenol (including isomers), (2-(triethylphenoxy)-2-methylpropyl) phenol (including isomers), (2-(tripropylphenoxy)-2-methylpropyl) phenol (including isomers), (2-(tributylphenoxy)-2-methylpropyl) phenol (including isomers), (2-(phenylmethoxy)-2-methylpropyl) phenol (including isomers), (2-(phenylethoxy)-2-methylpropyl) phenol (including isomers), (2-(phenylpropyloxy)-2-methylpropyl) phenol (including isomers), (2-(phenylbutyloxy)-2-methylpropyl) phenol (including isomers), (2-(phenylpentyloxy)-2-methylpropyl) phenol (including isomers), (2-(phenylhexyloxy)-2-methylpropyl) phenol (including isomers), (2-(phenylheptyloxy)-2-methylpropyl) phenol (including isomers), (2-(phenyloctyloxy)-2-methylpropyl) phenol (including isomers), (2-(phenylnonyloxy)-2-methylpropyl) phenol (including isomers), di(2-methoxy-2-methylethyl) phenol (including isomers), di(2-ethoxy-2-methylethyl) phenol (including isomers), di(2-propoxy-2-methylethyl) phenol (including isomers), di(2-butyloxy-2-methylethyl) phenol (including isomers), di(2-pentyloxy-2-methylethyl) phenol (including isomers), di(2-hexyloxy-2-methylethyl) phenol (including isomers), di(2-heptyloxy-2-methylethyl) phenol (including isomers), di(2-octyloxy-2-methylethyl) phenol (including isomers), di(2-nonyloxy-2-methylethyl) phenol (including isomers), di(2-decyloxy-2-methylethyl) phenol (including isomers), di(2-dodecyloxy-2-methylethyl) phenol (including isomers), di(2-octadecyloxy-2-methylethyl) phenol (including isomers), di(2-cyclopentyloxy-2-methylethyl) phenol (including isomers), di(2-cyclohexyloxy-2-methylethyl) phenol (including isomers), di(2-cycloheptyloxy-2-methylethyl) phenol (including isomers), di(2-cyclooctyloxy-2-methylethyl) phenol (including isomers), di(2-(methylcyclopentyloxy)-2-methylethyl) phenol (including isomers), di(2-(ethylcyclopentyloxy)-2-methylethyl) phenol (including isomers), di(2-(methylcyclohexyloxy)-2-methylethyl) phenol (including isomers), di(2-(ethylcyclohexyloxy)-2-methylethyl) phenol (including isomers), di(2-(propylcyclohexyloxy)-2-methylethyl) phenol (including isomers), di(2-(butylcyclohexyloxy)-2-methylethyl) phenol (including isomers), di(2-(pentylcyclohexyloxy)-2-methylethyl) phenol (including isomers), di(2-(hexylcyclohexyloxy)-2-methylethyl) phenol (including isomers), di(2-(dimethylcyclohexyloxy)-2-methylethyl) phenol (including isomers), di(2-(diethylcyclohexyloxy)-2-methylethyl) phenol (including isomers), di(2-(dibutylcyclohexyloxy)-2-methylethyl) phenol (including isomers), di(2-phenoxy-2-methylethyl) phenol (including isomers), di(2-(methylphenoxy)-2-methylethyl) phenol (including isomers), di(2-(ethylphenoxy)-2-methylethyl) phenol (including isomers), di(2-(propylphenoxy)-2-methylethyl) phenol (including isomers), di(2-(butylphenoxy)-2-methylethyl) phenol (including isomers), di(2-(pentylphenoxy)-2-methylethyl) phenol (including isomers), di(2-(hexylphenoxy)-2-methylethyl) phenol (including isomers), di(2-(heptylphenoxy)-2-methylethyl) phenol (including isomers), di(2-(octylphenoxy)-2-methylethyl) phenol (including isomers), di(2-(nonylphenoxy)-2-methylethyl) phenol (including isomers), di(2-(decylphenoxy)-2-methylethyl) phenol (including isomers), di(2-(phenylphenoxy)-2-methylethyl) phenol (including isomers), di(2-(dimethylphenoxy)-2-methylethyl) phenol (including isomers), di(2-(diethylphenoxy)-2-methylethyl) phenol (including isomers), di(2-(dipropylphenoxy)-2-methylethyl) phenol (including isomers), di(2-(dibutylphenoxy)-2-methylethyl) phenol (including isomers), di(2-(dipentylphenoxy)-2-methylethyl) phenol (including isomers), di(2-(dihexylphenoxy)-2-methylethyl) phenol (including isomers), di(2-(diheptylphenoxy)-2-methylethyl) phenol (including isomers), di(2-(diphenylphenoxy)-2-methylethyl) phenol (including isomers), di(2-(trimethylphenoxy)-2-methylethyl) phenol (including isomers), di(2-(triethylphenoxy)-2-methylethyl) phenol (including isomers), di(2-(tripropylphenoxy)-2-methylethyl) phenol (including isomers), di(2-(tributylphenoxy)-2-methylethyl) phenol (including isomers), di(2-(phenylmethoxy)-2-methylethyl) phenol (including isomers), di(2-(phenylethoxy)-2-methylethyl) phenol (including isomers), di(2-(phenylpropyloxy)-2-methylethyl) phenol (including isomers), di(2-(phenylbutyloxy)-2-methylethyl) phenol (including isomers), di(2-(phenylpentyloxy)-2-methylethyl) phenol (including isomers), di(2-(phenylhexyloxy)-2-methylethyl) phenol (including isomers), di(2-(phenylheptyloxy)-2-methylethyl) phenol (including isomers), di(2-(phenyloctyloxy)-2-methylethyl) phenol (including isomers), di(2-(phenylnonyloxy)-2-methylethyl) phenol (including isomers), di(2-methoxy-2-methylpropyl) phenol (including isomers), di(2-ethoxy-2-methylpropyl) phenol (including isomers), di(2-propoxy-2-methylpropyl) phenol (including isomers), di(2-butyloxy-2-methylpropyl) phenol (including isomers), di(2-pentyloxy-2-methylpropyl) phenol (including isomers), di(2-hexyloxy-2-methylpropyl) phenol (including isomers), di(2-heptyloxy-2-methylpropyl) phenol (including isomers), di(2-octyloxy-2-methylpropyl) phenol (including isomers), di(2-nonyloxy-2-methylpropyl) phenol (including isomers), di(2-decyloxy-2-methylpropyl) phenol (including isomers), di(2-dodecyloxy-2-methylpropyl) phenol (including isomers), di(2-octadecyloxy-2-methylpropyl) phenol (including isomers), di(2-cyclopentyloxy-2-methylpropyl) phenol (including isomers), di(2-cyclohexyloxy-2-methylpropyl) phenol (including isomers), di(2-cycloheptyloxy-2-methylpropyl) phenol (including isomers), di(2-cyclooctyloxy-2-methylpropyl) phenol (including isomers), di(2-(methylcyclopentyloxy)-2-methylpropyl) phenol (including isomers), di(2-(ethylcyclopentyloxy)-2-methylpropyl) phenol (including isomers), di(2-(methylcyclohexyloxy)-2-methylpropyl) phenol (including isomers), di(2-(ethylcyclohexyloxy)-2-methylpropyl) phenol (including isomers), di(2-(propylcyclohexyloxy)-2-methylpropyl) phenol (including isomers), di(2-(butylcyclohexyloxy)-2-methylpropyl) phenol (including isomers), di(2-(pentylcyclohexyloxy)-2-methylpropyl) phenol (including isomers), di(2-(hexylcyclohexyloxy)-2-methylpropyl) phenol (including isomers), di(2-(dimethylcyclohexyloxy)-2-methylpropyl) phenol (including isomers), di(2-(diethylcyclohexyloxy)-2-methylpropyl) phenol (including isomers), di(2-(dibutylcyclohexyloxy)-2-methylpropyl) phenol (including isomers), di(2-phenoxy-2-methylpropyl) phenol (including isomers), di(2-(methylphenoxy)-2-methylpropyl) phenol (including isomers), di(2-(ethylphenoxy)-2-methylpropyl) phenol (including isomers), di(2-(propylphenoxy)-2-methylpropyl) phenol (including isomers), di(2-(butylphenoxy)-2-methylpropyl) phenol (including isomers), di(2-(pentylphenoxy)-2-methylpropyl) phenol (including isomers), di(2-(hexylphenoxy)-2-methylpropyl) phenol (including isomers), di(2-(heptylphenoxy)-2-methylpropyl) phenol (including isomers), di(2-(octylphenoxy)-2-methylpropyl) phenol (including isomers), di(2-(nonylphenoxy)-2-methylpropyl) phenol (including isomers), di(2-(decylphenoxy)-2-methylpropyl) phenol (including isomers), di(2-(phenylphenoxy)-2-methylpropyl) phenol (including isomers), di(2-(dimethylphenoxy)-2-methylpropyl) phenol (including isomers), di(2-(diethylphenoxy)-2-methylpropyl) phenol (including isomers), di(2-(dipropylphenoxy)-2-methylpropyl) phenol (including isomers), di(2-(dibutylphenoxy)-2-methylpropyl) phenol (including isomers), di(2-(dipentylphenoxy)-2-methylpropyl) phenol (including isomers), di(2-(dihexylphenoxy)-2-methylpropyl) phenol (including isomers), di(2-(diheptylphenoxy)-2-methylpropyl) phenol (including isomers), di(2-(diphenylphenoxy)-2-methylpropyl) phenol (including isomers), di(2-(trimethylphenoxy)-2-methylpropyl) phenol (including isomers), di(2-(triethylphenoxy)-2-methylpropyl) phenol (including isomers), di(2-(tripropylphenoxy)-2-methylpropyl) phenol (including isomers), di(2-(tributylphenoxy)-2-methylpropyl) phenol (including isomers), di(2-(phenylmethoxy)-2-methylpropyl) phenol (including isomers), di(2-(phenylethoxy)-2-methylpropyl) phenol (including isomers), di(2-(phenylpropyloxy)-2-methylpropyl) phenol (including isomers), di(2-(phenylbutyloxy)-2-methylpropyl) phenol (including isomers), di(2-(phenylpentyloxy)-2-methylpropyl) phenol (including isomers), di(2-(phenylhexyloxy)-2-methylpropyl) phenol (including isomers), di(2-(phenylheptyloxy)-2-methylpropyl) phenol (including isomers), di(2-(phenyloctyloxy)-2-methylpropyl) phenol (including isomers), di(2-(phenylnonyloxy)-2-methylpropyl) phenol (including isomers), tri(2-methoxy-2-methylethyl) phenol (including isomers), tri(2-ethoxy-2-methylethyl) phenol (including isomers), tri(2-propoxy-2-methylethyl) phenol (including isomers), tri(2-butyloxy-2-methylethyl) phenol (including isomers), tri(2-pentyloxy-2-methylethyl) phenol (including isomers), tri(2-hexyloxy-2-methylethyl) phenol (including isomers), tri(2-heptyloxy-2-methylethyl) phenol (including isomers), tri(2-octyloxy-2-methylethyl) phenol (including isomers), tri(2-nonyloxy-2-methylethyl) phenol (including isomers), tri(2-decyloxy-2-methylethyl) phenol (including isomers), tri(2-dodecyloxy-2-methylethyl) phenol (including isomers), tri(2-octadecyloxy-2-methylethyl) phenol (including isomers), tri(2-cyclopentyloxy-2-methylethyl) phenol (including isomers), tri(2-cyclohexyloxy-2-methylethyl) phenol (including isomers), tri(2-cycloheptyloxy-2-methylethyl) phenol (including isomers), tri(2-cyclooctyloxy-2-methylethyl) phenol (including isomers), tri(2-(methylcyclopentyloxy)-2-methylethyl) phenol (including isomers), tri(2-(ethylcyclopentyloxy)-2-methylethyl) phenol (including isomers), tri(2-(methylcyclohexyloxy)-2-methylethyl) phenol (including isomers), tri(2-(ethylcyclohexyloxy)-2-methylethyl) phenol (including isomers), tri(2-(propylcyclohexyloxy)-2-methylethyl) phenol (including isomers), tri(2-(butylcyclohexyloxy)-2-methylethyl) phenol (including isomers), tri(2-(pentylcyclohexyloxy)-2-methylethyl) phenol (including isomers), tri(2-(hexylcyclohexyloxy)-2-methylethyl) phenol (including isomers), tri(2-(trimethylcyclohexyloxy)-2-methylethyl) phenol (including isomers), tri(2-(triethylcyclohexyloxy)-2-methylethyl) phenol (including isomers), tri(2-(tributylcyclohexyloxy)-2-methylethyl) phenol (including isomers), tri(2-phenoxy-2-methylethyl) phenol (including isomers), tri(2-(methylphenoxy)-2-methylethyl) phenol (including isomers), tri(2-(ethylphenoxy)-2-methylethyl) phenol (including isomers), tri(2-(propylphenoxy)-2-methylethyl) phenol (including isomers), tri(2-(butylphenoxy)-2-methylethyl) phenol (including isomers), tri(2-(pentylphenoxy)-2-methylethyl) phenol (including isomers), tri(2-(hexylphenoxy)-2-methylethyl) phenol (including isomers), tri(2-(heptylphenoxy)-2-methylethyl) phenol (including isomers), tri(2-(octylphenoxy)-2-methylethyl) phenol (including isomers), tri(2-(nonylphenoxy)-2-methylethyl) phenol (including isomers), tri(2-(decylphenoxy)-2-methylethyl) phenol (including isomers), tri(2-(phenylphenoxy)-2-methylethyl) phenol (including isomers), tri(2-(trimethylphenoxy)-2-methylethyl) phenol (including isomers), tri(2-(triethylphenoxy)-2-methylethyl) phenol (including isomers), tri(2-(tripropylphenoxy)-2-methylethyl) phenol (including isomers), tri(2-(tributylphenoxy)-2-methylethyl) phenol (including isomers), tri(2-(tripentylphenoxy)-2-methylethyl) phenol (including isomers), tri(2-(trihexylphenoxy)-2-methylethyl) phenol (including isomers), tri(2-(triheptylphenoxy)-2-methylethyl) phenol (including isomers), tri(2-(triphenylphenoxy)-2-methylethyl) phenol (including isomers), tri(2-(trimethylphenoxy)-2-methylethyl) phenol (including isomers), tri(2-(triethylphenoxy)-2-methylethyl) phenol (including isomers), tri(2-(tripropylphenoxy)-2-methylethyl) phenol (including isomers), tri(2-(tributylphenoxy)-2-methylethyl) phenol (including isomers), tri(2-(phenylmethoxy)-2-methylethyl) phenol (including isomers), tri (2-(phenylethoxy)-2-methylethyl) phenol (including isomers), tri(2-(phenylpropyloxy)-2-methylethyl) phenol (including isomers), tri(2-(phenylbutyloxy)-2-methylethyl) phenol (including isomers), tri(2-(phenylpentyloxy)-2-methylethyl) phenol (including isomers), tri(2-(phenylhexyloxy)-2-methylethyl) phenol (including isomers), tri(2-(phenylheptyloxy)-2-methylethyl) phenol (including isomers), tri(2-(phenyloctyloxy)-2-methylethyl) phenol (including isomers), tri(2-(phenylnonyloxy)-2-methylethyl) phenol (including isomers), tri(2-methoxy-2-methylpropyl) phenol (including isomers), tri(2-ethoxy-2-methylpropyl) phenol (including isomers), tri(2-propoxy-2-methylpropyl) phenol (including isomers), tri(2-butyloxy-2-methylpropyl) phenol (including isomers), tri(2-pentyloxy-2-methylpropyl) phenol (including isomers), tri(2-hexyloxy-2-methylpropyl) phenol (including isomers), tri(2-heptyloxy-2-methylpropyl) phenol (including isomers), tri(2-octyloxy-2-methylpropyl) phenol (including isomers), tri(2-nonyloxy-2-methylpropyl) phenol (including isomers), tri(2-decyloxy-2-methylpropyl) phenol (including isomers), tri(2-dodecyloxy-2-methylpropyl) phenol (including isomers), tri(2-octadecyloxy-2-methylpropyl) phenol (including isomers), tri(2-cyclopentyloxy-2-methylpropyl) phenol (including isomers), tri(2-cyclohexyloxy-2-methylpropyl) phenol (including isomers), tri(2-cycloheptyloxy-2-methylpropyl) phenol (including isomers), tri(2-cyclooctyloxy-2-methylpropyl) phenol (including isomers), tri(2-(methylcyclopentyloxy)-2-methylpropyl) phenol (including isomers), tri(2-(ethylcyclopentyloxy)-2-methylpropyl) phenol (including isomers), tri(2-(methylcyclohexyloxy)-2-methylpropyl) phenol (including isomers), tri(2-(ethylcyclohexyloxy)-2-methylpropyl) phenol (including isomers), tri(2-(propylcyclohexyloxy)-2-methylpropyl) phenol (including isomers), tri(2-(butylcyclohexyloxy)-2-methylpropyl) phenol (including isomers), tri(2-(pentylcyclohexyloxy)-2-methylpropyl) phenol (including isomers), tri (2-(hexylcyclohexyloxy)-2-methylpropyl) phenol (including isomers), tri(2-(trimethylcyclohexyloxy)-2-methylpropyl) phenol (including isomers), tri(2-(triethylcyclohexyloxy)-2-methylpropyl) phenol (including isomers), tri(2-(tributylcyclohexyloxy)-2-methylpropyl) phenol (including isomers), tri(2-phenoxy-2-methylpropyl) phenol (including isomers), tri(2-(methylphenoxy)-2-methylpropyl) phenol (including isomers), tri(2-(ethylphenoxy)-2-methylpropyl) phenol (including isomers), tri(2-(propylphenoxy)-2-methylpropyl) phenol (including isomers), tri(2-(butylphenoxy)-2-methylpropyl) phenol (including isomers), tri(2-(pentylphenoxy)-2-methylpropyl) phenol (including isomers), tri(2-(hexylphenoxy)-2-methylpropyl) phenol (including isomers), tri(2-(heptylphenoxy)-2-methylpropyl) phenol (including isomers), tri(2-(octylphenoxy)-2-methylpropyl) phenol (including isomers), tri(2-(nonylphenoxy)-2-methylpropyl) phenol (including isomers), tri(2-(decylphenoxy)-2-methylpropyl) phenol (including isomers), tri(2-(phenylphenoxy)-2-methylpropyl) phenol (including isomers), tri(2-(trimethylphenoxy)-2-methylpropyl) phenol (including isomers), tri (2-(triethylphenoxy)-2-methylpropyl) phenol (including isomers), tri(2-(tripropylphenoxy)-2-methylpropyl) phenol (including isomers), tri(2-(tributylphenoxy)-2-methylpropyl) phenol (including isomers), tri(2-(tripentylphenoxy)-2-methylpropyl) phenol (including isomers), tri(2-(trihexylphenoxy)-2-methylpropyl) phenol (including isomers), tri (2-(triheptylphenoxy)-2-methylpropyl) phenol (including isomers), tri(2-(triphenylphenoxy)-2-methylpropyl) phenol (including isomers), tri(2-(trimethylphenoxy)-2-methylpropyl) phenol (including isomers), tri(2-(triethylphenoxy)-2-methylpropyl) phenol (including isomers), tri(2-(tripropylphenoxy)-2-methylpropyl) phenol (including isomers), tri (2-(tributylphenoxy)-2-methylpropyl) phenol (including isomers), tri(2-(phenylmethoxy)-2-methylpropyl) phenol (including isomers), tri(2-(phenylethoxy)-2-methylpropyl) phenol (including isomers), tri(2-(phenylpropyloxy)-2-methylpropyl) phenol (including isomers), tri(2-(phenylbutyloxy)-2-methylpropyl) phenol (including isomers), tri(2-(phenylpentyloxy)-2-methylpropyl) phenol (including isomers), tri(2-(phenylhexyloxy)-2-methylpropyl) phenol (including isomers), tri(2-(phenylheptyloxy)-2-methylpropyl) phenol (including isomers), tri(2-(phenyloctyloxy)-2-methylpropyl) phenol (including isomers), tri(2-(phenylnonyloxy)-2-methylpropyl) phenol (including isomers), (dimethylamino) phenol, (diethylamino) phenol, (dipropylamino) phenol (including isomers), (dibutylamino) phenol (including isomers), (dipentylamino) phenol (including isomers), (dihexylamino) phenol (including isomers), (diheptylamino) phenol (including isomers), (dioctylamino) phenol (including isomers), (dinonylamino) phenol (including isomers), (didecylamino) phenol (including isomers), (didodecylamino) phenol (including isomers), (dioctadecylamino) phenol (including isomers), bis(dimethylamino) phenol, bis (diethylamino) phenol, bis(dipropylamino) phenol (including isomers), bis(dibutylamino) phenol (including isomers), bis(dipentylamino) phenol (including isomers), bis(dihexylamino) phenol (including isomers), bis(diheptylamino) phenol (including isomers), bis(dioctylamino) phenol (including isomers), bis(dinonylamino) phenol (including isomers), bis (didecylamino) phenol (including isomers), bis(didodecylamino) phenol (including isomers), bis(dioctadecylamino) phenol (including isomers), (2-phenyl-2-methylethyl) phenol (including isomers), (2-(methylphenyl)-2-methylethyl) phenol (including isomers), (2-(ethylphenyl)-2-methylethyl) phenol (including isomers), (2-(propylphenyl)-2-methylethyl) phenol (including isomers), (2-(butylphenyl)-2-methylethyl) phenol (including isomers), (2-(pentylphenyl)-2-methylethyl) phenol (including isomers), (2-(hexylphenyl)-2-methylethyl) phenol (including isomers), (2-(heptylphenyl)-2-methylethyl) phenol (including isomers), (2-(octylphenyl)-2-methylethyl) phenol (including isomers), (2-(nonylphenyl)-2-methylethyl) phenol (including isomers), (2-(decylphenyl)-2-methylethyl) phenol (including isomers), (2-(biphenyl)-2-methylethyl) phenol (including isomers), (2-(dimethylphenyl)-2-methylethyl) phenol (including isomers), (2-(diethylphenyl)-2-methylethyl) phenol (including isomers), (2-(dipropylphenyl)-2-methylethyl) phenol (including isomers), (2-(dibutylphenyl)-2-methylethyl) phenol (including isomers), (2-(dipentylphenyl)-2-methylethyl phenol (including isomers), (2-(dihexylphenyl)-2-methylethyl) phenol (including isomers), (2-(diheptylphenyl)-2-methylethyl) phenol (including isomers), (2-(terphenyl)-2-methylethyl) phenol (including isomers), (2-(trimethylphenyl)-2-methylethyl) phenol (including isomers), (2-(triethylphenyl)-2-methylethyl) phenol (including isomers), (2-(tripropylphenyl)-2-methylethyl) phenol (including isomers), (2-(tributylphenyl)-2-methylethyl) phenol (including isomers), di(2-phenyl-2-methylethyl) phenol (including isomers), di(2-(methylphenyl)-2-methylethyl) phenol (including isomers), di(2-(ethylphenyl)-2-methylethyl) phenol (including isomers), di(2-(propylphenyl)-2-methylethyl) phenol (including isomers), di(2-(butylphenyl)-2-methylethyl) phenol (including isomers), di(2-(pentylphenyl)-2-methylethyl) phenol (including isomers), di(2-(hexylphenyl)-2-methylethyl) phenol (including isomers), di(2-(heptylphenyl)-2-methylethyl) phenol (including isomers), di(2-(octylphenyl)-2-methylethyl) phenol (including isomers), di(2-(nonylphenyl)-2-methylethyl) phenol (including isomers), di(2-(decylphenyl)-2-methylethyl) phenol (including isomers), di(2-(biphenyl)-2-methylethyl) phenol (including isomers), di(2-(dimethylphenyl)-2-methylethyl) phenol (including isomers), di(2-(diethylphenyl)-2-methylethyl) phenol (including isomers), di(2-(dipropylphenyl)-2-methylethyl) phenol (including isomers), di(2-(dibutylphenyl)-2-methylethyl) phenol (including isomers), di(2-(dipentylphenyl)-2-methylethyl) phenol (including isomers), di(2-(dihexylphenyl)-2-methylethyl) phenol (including isomers), di(2-(diheptylphenyl)-2-methylethyl) phenol (including isomers), di(2-(terphenyl)-2-methylethyl) phenol (including isomers), di(2-(trimethylphenyl)-2-methylethyl) phenol (including isomers), di(2-(triethylphenyl)-2-methylethyl) phenol (including isomers), di(2-(tripropylphenyl)-2-methylethyl) phenol (including isomers), di(2-(tributylphenyl)-2-methylethyl) phenol (including isomers), tri(2-phenyl-2-methylethyl) phenol (including isomers), tri(2-(methylphenyl)-2-methylethyl) phenol (including isomers), tri(2-(ethylphenyl)-2-methylethyl) phenol (including isomers), tri(2-(propylphenyl)-2-methylethyl) phenol (including isomers), tri(2-(butylphenyl)-2-methylethyl) phenol (including isomers), tri(2-(pentylphenyl)-2-methylethyl) phenol (including isomers), tri(2-(hexylphenyl)-2-methylethyl) phenol (including isomers), tri(2-(heptylphenyl)-2-methylethyl) phenol (including isomers), tri(2-(octylphenyl)-2-methylethyl) phenol (including isomers), tri(2-(nonylphenyl)-2-methylethyl) phenol (including isomers), tri(2-(decylphenyl)-2-methylethyl) phenol (including isomers), tri(2-(biphenyl)-2-methylethyl) phenol (including isomers), tri(2-(dimethylphenyl)-2-methylethyl) phenol (including isomers), tri(2-(diethylphenyl)-2-methylethyl) phenol (including isomers), tri(2-(dipropylphenyl)-2-methylethyl) phenol (including isomers), tri(2-(dibutylphenyl)-2-methylethyl) phenol (including isomers), tri(2-(dipentylphenyl)-2-methylethyl) phenol (including isomers), tri(2-(dihexylphenyl)-2-methylethyl) phenol (including isomers), tri(2-(diheptylphenyl)-2-methylethyl) phenol (including isomers), tri(2-(terphenyl)-2-methylethyl) phenol (including isomers), tri(2-(trimethylphenyl)-2-methylethyl) phenol (including isomers), tri(2-(triethylphenyl)-2-methylethyl) phenol (including isomers), tri(2-(tripropylphenyl)-2-methylethyl) phenol (including isomers), tri(2-(tributylphenyl)-2-methylethyl) phenol (including isomers), (2-phenyl-2-methylpropyl) phenol (including isomers), (2-(methylphenyl)-2-methylpropyl) phenol (including isomers), (2-(ethylphenyl)-2-methylpropyl) phenol (including isomers), (2-(propylphenyl)-2-methylpropyl) phenol (including isomers), (2-(butylphenyl)-2-methylpropyl) phenol (including isomers), (2-(pentylphenyl)-2-methylpropyl) phenol (including isomers), (2-(hexylphenyl)-2-methylpropyl) phenol (including isomers), (2-(heptylphenyl)-2-methylpropyl) phenol (including isomers), (2-(octylphenyl)-2-methylpropyl) phenol (including isomers), (2-(nonylphenyl)-2-methylpropyl) phenol (including isomers), (2-(decylphenyl)-2-methylpropyl) phenol (including isomers), (2-(biphenyl)-2-methylpropyl) phenol (including isomers), (2-(dimethylphenyl)-2-methylpropyl) phenol (including isomers), (2-(diethylphenyl)-2-methylpropyl) phenol (including isomers), (2-(dipropylphenyl)-2-methylpropyl) phenol (including isomers), (2-(dibutylphenyl)-2-methylpropyl) phenol (including isomers), (2-(dipentylphenyl)-2-methylpropyl) phenol (including isomers), (2-(dihexylphenyl)-2-methylpropyl) phenol (including isomers), (2-(diheptylphenyl)-2-methylpropyl) phenol (including isomers), (2-(terphenyl)-2-methylpropyl) phenol (including isomers), (2-(trimethylphenyl)-2-methylpropyl) phenol (including isomers), (2-(triethylphenyl)-2-methylpropyl) phenol (including isomers), (2-(tripropylphenyl)-2-methylpropyl) phenol (including isomers), (2-(tributylphenyl)-2-methylpropyl) phenol (including isomers), di(2-phenyl-2-methylpropyl) phenol (including isomers), di(2-(methylphenyl)-2-methylpropyl) phenol (including isomers), di(2-(ethylphenyl)-2-methylpropyl) phenol (including isomers), di(2-(propylphenyl)-2-methylpropyl) phenol (including isomers), di(2-(butylphenyl)-2-methylpropyl) phenol (including isomers), di(2-(pentylphenyl)-2-methylpropyl) phenol (including isomers), di(2-(hexylphenyl)-2-methylpropyl) phenol (including isomers), di(2-(heptylphenyl)-2-methylpropyl) phenol (including isomers), di(2-(octylphenyl)-2-methylpropyl) phenol (including isomers), di(2-(nonylphenyl)-2-methylpropyl) phenol (including isomers), di(2-(decylphenyl)-2-methylpropyl) phenol (including isomers), di(2-(biphenyl)-2-methylpropyl) phenol (including isomers), di(2-(dimethylphenyl)-2-methylpropyl) phenol (including isomers), di(2-(diethylphenyl)-2-methylpropyl) phenol (including isomers), di(2-(dipropylphenyl)-2-methylpropyl) phenol (including isomers), di(2-(dibutylphenyl)-2-methylpropyl) phenol (including isomers), di(2-(dipentylphenyl)-2-methylpropyl) phenol (including isomers), di(2-(dihexylphenyl)-2-methylpropyl) phenol (including isomers), di(2-(diheptylphenyl)-2-methylpropyl) phenol (including isomers), di(2-(terphenyl)-2-methylpropyl) phenol (including isomers), di(2-(trimethylphenyl)-2-methylpropyl) phenol (including isomers), di(2-(triethylphenyl)-2-methylpropyl) phenol (including isomers), di(2-(tripropylphenyl)-2-methylpropyl) phenol (including isomers), di(2-(tributylphenyl)-2-methylpropyl) phenol (including isomers), tri(2-phenyl-2-methylpropyl) phenol (including isomers), tri(2-(methylphenyl)-2-methylpropyl) phenol (including isomers), tri(2-(ethylphenyl)-2-methylpropyl) phenol (including isomers), tri(2-(propylphenyl)-2-methylpropyl) phenol (including isomers), tri(2-(butylphenyl)-2-methylpropyl) phenol (including isomers), tri(2-(pentylphenyl)-2-methylpropyl) phenol (including isomers), tri(2-(hexylphenyl)-2-methylpropyl) phenol (including isomers), tri(2-(heptylphenyl)-2-methylpropyl) phenol (including isomers), tri(2-(octylphenyl)-2-methylpropyl) phenol (including isomers), tri(2-(nonylphenyl)-2-methylpropyl) phenol (including isomers), tri(2-(decylphenyl)-2-methylpropyl) phenol (including isomers), tri(2-(biphenyl)-2-methylpropyl) phenol (including isomers), tri(2-(dimethylphenyl)-2-methylpropyl) phenol (including isomers), tri(2-(diethylphenyl)-2-methylpropyl) phenol (including isomers), tri(2-(dipropylphenyl)-2-methylpropyl) phenol (including isomers), tri(2-(dibutylphenyl)-2-methylpropyl) phenol (including isomers), tri(2-(dipentylphenyl)-2-methylpropyl) phenol (including isomers), tri(2-(dihexylphenyl)-2-methylpropyl) phenol (including isomers), tri(2-(diheptylphenyl)-2-methylpropyl) phenol (including isomers), tri(2-(terphenyl)-2-methylpropyl) phenol (including isomers), tri(2-(trimethylphenyl)-2-methylpropyl) phenol (including isomers), tri(2-(triethylphenyl)-2-methylpropyl) phenol (including isomers), tri(2-(tripropylphenyl)-2-methylpropyl) phenol (including isomers), tri(2-(tributylphenyl)-2-methylpropyl) phenol (including isomers), tri(dipropylamino) phenol (including isomers), tri(dibutylamino) phenol (including isomers), tri(dipentylamino) phenol (including isomers), tri(dihexylamino) phenol (including isomers), tri(diheptylamino) phenol (including isomers), tri(dioctylamino) phenol (including isomers), tri(dinonylamino) phenol (including isomers), tri(didecylamino) phenol (including isomers), tri(didodecylamino) phenol (including isomers) and tri(dioctadecylamino) phenol (including isomers).

More preferable examples of the aromatic hydroxy compounds listed above may include those in which the number of carbon atoms that compose the $R^7$, $R^8$, $R^{26}$, $R^{27}$ and $R^{28}$ is from 0 to 13 due to the ease of transfer thereof. More preferably, the aromatic hydroxy compound is an aromatic hydroxy compound in which $R^7$, $R^8$, $R^{26}$, $R^{27}$ and $R^{28}$ are groups having 0 to 9 carbon atoms selected from a hydrogen atom, a linear or branched alkyl group, a cycloalkyl group, an optionally substituted aryl group, a linear or branched alkoxy group, an optionally substituted aryloxy group and an optionally substituted aralkyl group.

In addition, the aromatic hydroxy compound forms an N-substituted carbamic acid ester, and the N-substituted carbamic acid ester is used in the form of an isocyanate precursor. Although details of a method for producing an isocyanate derived from an N-substituted carbamic acid ester from the N-substituted carbamic acid ester will be described hereinafter, this method involves obtaining an aromatic hydroxy compound derived from the N-substituted carbamic acid ester and an isocyanate by thermal decomposition of the N-substituted carbamic acid ester. In consideration of the reaction formula, the aromatic hydroxy compound formed at that time is an aromatic hydroxy compound contained in the aromatic hydroxy composition used when producing the N-substituted carbamic acid ester. Namely, an aromatic hydroxy compound of formula (70), and preferably formula (79), is produced as a by-product together with isocyanate during thermal decomposition of the N-substituted carbamic acid ester. In one of the present embodiments, although depending on the particular case, the aromatic hydroxy compound and isocyanate are separated by distillation following the thermal decomposition step, and the separated aromatic hydroxy compound may be recycled in the form of an aromatic hydroxy composition in the reaction between the organic amine, carbonic acid derivative and aromatic hydroxy compound. Thus, in consideration of the process through the isocyanate production step, it is necessary to take into consideration the separability of the aromatic hydroxy compound serving as a raw material of the N-substituted carbamic acid ester and the isocyanate formed from the N-substituted carbamic acid ester. Although it is difficult to generally define separability, it is defined on the basis of the finding that generally two components to be separated can be adequately separated by distillation industrially if the standard boiling points thereof are 10° C. or more apart. Thus, this definition refers to a value that is limited by currently known separation means, and is not intended to serve as a basis of the present embodiment.

<Compound Having Ureido Group>

A compound having an ureido group is a compound that is produced by reacting with organic amine and carbonic acid derivative in one of several methods for producing N-substituted carbamic acid ester from organic amine, carbonic acid derivative and a hydroxy composition. In this method, the compound having the ureido group and the hydroxy composition are reacted to produce N-substituted carbamic acid ester.

The compound having the ureido group is a compound represented by the following formula (80):

(wherein
$R^1$ represents an organic group which has 1 to 85 carbon atoms and which is substituted by h number of ureido groups, and
h represents an integer of 1 to 10).

A compound having the ureido group represented by formula (80) above is a compound having "ureido group" as defined in nomenclature rule C-971 stipulated by IUPAC.

In formula (80) above, $R^1$ represents an aliphatic group, an aromatic group or a group bonded to an aliphatic group and an aromatic group, and represents a group composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a heterocrosslinked ring group or heterocyclic ring group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (81) to (89).

-continued

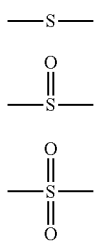

Among these R$^1$ groups, R$^1$ groups that can be preferably used in the present embodiment in consideration of less susceptibility to the occurrence of side reactions contain groups selected from the group consisting of acyclic hydrocarbon groups and cyclic hydrocarbon groups selected from aliphatic groups and aromatic groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups), having 1 to 85 carbon atoms. In consideration of fluidity and the like, the number of carbon atoms is preferably from 1 to 70 and more preferably from 1 to 13.

Preferable examples of compounds having a ureido group composed by the R$^1$ group may include:

1) N-substituted aromatic organic monoureas in which the R$^1$ group has 6 to 85 carbon atoms and contains one or more types of an aromatic ring optionally substituted with an aliphatic group and/or an aromatic group, an aromatic group in the R$^1$ group is substituted with an ureido group, and h is 1, 2) N-substituted aromatic organic polyureas in which the R$^1$ group has 6 to 85 carbon atoms and contains one or more types of an aromatic ring optionally substituted with an aliphatic group and/or an aromatic group, an aromatic group in the R$^1$ group is substituted with a ureido group, and h is 2 or more, and 3) N-substituted aliphatic organic polyureas in which the R$^1$ group is an aliphatic group having 1 to 85 carbon atoms optionally substituted with an aromatic group, and h is 2 or 3.

In the above descriptions, compounds in which atoms bonded to a ureido group (mainly carbon atoms) that are contained in an aromatic ring are denoted as N-substituted aromatic organic ureas, while cases of bonding to atoms not in an aromatic ring (mainly carbon atoms) are denoted as N-substituted aliphatic organic ureas.

Although h in the above formula (80) is an integer of from 1 to 10, in the case of using an organic amine of the aforementioned formula (29) as a starting substance, h is an integer that does not exceed a of the organic amine represented by formula (29).

The following indicates preferable examples of compounds having a ureido group.

1) N-Aromatic Organic Monoureas

N-substituted aromatic organic monoureas in which the R$^1$ group is a group having 6 to 85 carbon atoms and containing one or more types of an aromatic ring optionally substituted with an aliphatic group and/or an aromatic group, an aromatic group in the R$^1$ group is substituted with a ureido group and h is 1, preferably N-aromatic organic ureas in which the R$^1$ group is a group having 6 to 70 carbon atoms and h is 1, and more preferably in consideration of fluidity and the like, N-aromatic organic monoureas in which the R$^1$ group has 6 to 13 carbon atoms and h is 1, which are N-aromatic organic monoureas represented by the following formula (90).

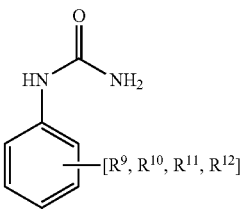

At least one position of the ortho position and/or para position of the ureido group of the N-substituted aromatic organic monourea represented by formula (90) is not substituted, groups R$^9$ to R$^{12}$ respectively represent a group substituted at an arbitrary position that retains aromatic properties of the ring, groups R$^9$ to R$^{12}$ may respectively and independently substitute the aromatic ring, groups R$^9$ to R$^{12}$ may mutually bond to form a ring with the aromatic ring, and represent hydrogen atoms, groups selected from the group consisting of an alkyl group, a cycloalkyl group, an aryl group and an aryl group having a hydroxy group, or groups selected from groups in which a group selected from the aforementioned group is composed of groups bonded by saturated aliphatic bonds and/or ether bonds, the number of carbon atoms of groups R$^9$ to R$^{12}$ is an integer within a range of from 0 to 7, and the total number of carbon atoms that compose an N-aromatic organic monourea represented by formula (90) is from 6 to 13.

Preferable examples of N-aromatic organic monoureas represented by formula (90) may include those in which the R$^9$ to R$^{12}$ groups are hydrogen atoms or groups selected from alkyl groups such as a methyl group or an ethyl group, and examples of such N-aromatic organic monoureas may include N-phenyl urea, N-(methylphenyl) urea (including isomers), N-(dimethylphenyl) urea (including isomers), N-(diethylphenyl) urea (including isomers), N-(dipropylphenyl) urea (including isomers), N-naphthyl urea (including isomers), N-(methylnaphthyl) urea (including isomers), N-dimethylnaphthyl urea (including isomers) and N-trimethylnaphthyl urea (including isomers). Among these, N-phenyl urea is more preferable.

2) N-Substituted Aromatic Organic Polyureas

N-substituted aromatic organic polyureas in which the R$^1$ group is a group having 6 to 85 carbon atoms that contains one or more aromatic rings optionally substituted with an aliphatic group and/or an aromatic group, an aromatic group in the R$^1$ group is substituted with a ureido group and h is 2 or more, preferably N-substituted aromatic organic polyureas in which the R$^1$ group is a group having 6 to 70 carbon atoms and h is 2 or more, and more preferably in consideration of fluidity and the like, N-substituted aromatic organic polyureas in which the R$^1$ group contains one or more types of aromatic rings, the aromatic ring has 6 to 13 carbon atoms and may be further substituted with an alkyl group, an aryl group or an aralkyl group, and h is 2 or more. Examples of such N-substituted aromatic organic polyureas may include N,N'-phenylene diurea (including isomers), N,N'-methylphenylene diurea (including isomers), N,N'-methylenediphenylene diurea (including isomers), N,N'-mesitylene diurea (including isomers), N,N'-biphenylene diurea (including isomers), N,N'-diphenylene diurea (including isomers), N,N'-propylenediphenylene diurea (including isomers), N,N'-oxydiphenylene diurea (including isomers), bis(ureidophenoxyethane) (including isomers), N,N'-xylene diurea (including isomers), N,N'-methoxyphenyl diurea (including isomers), N,N'-ethoxyphenyl diurea (including isomers), N,N'-naphthalene diurea (including isomers), N,N'-methylnaphthalene diurea (including isomers), and polymethylene polyphenyl polyureas represented by the following formula (91):

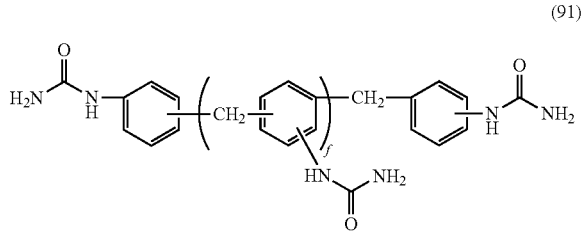

(91)

(wherein
f represents an integer of from 0 to 6).

3) N-Substituted Aliphatic Organic Polyureas

N-substituted aliphatic organic polyureas in which the $R^1$ group of a compound having the ureido group represented by formula (80) is an aliphatic group having 1 to 85 carbon atoms and may be substituted with an aromatic group, and h is 2 or 3. More preferable N-aliphatic organic polyureas are N-organic polyureas in which the aliphatic group is a linear hydrocarbon group, a cyclic hydrocarbon group or a group to which is bonded at least one type of group selected from the linear hydrocarbon groups and the cyclic hydrocarbon groups (such as a cyclic hydrocarbon group substituted with a linear hydrocarbon group or a linear hydrocarbon group substituted with a cyclic hydrocarbon group). More preferably, the N-substituted aromatic organic polyurea is an N-substituted aromatic organic polyurea in which the $R^1$ group is an aliphatic group that is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 1 to 70 carbon atoms, and h is 2 or 3. In consideration of fluidity and the like during large-volume industrial production, the N-substituted aliphatic organic polyurea is most preferably an N-aliphatic organic polyurea in which the $R^1$ group is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 6 to 13 carbon atoms and composed of carbon atoms and hydrogen atoms. Namely, this refers to the case in which the $R^1$ group is a linear or branched alkyl group, a cycloalkyl group or a group composed of the alkyl groups and cycloalkyl groups. Examples of these may include N-aliphatic diureas such as N,N'-ethylene diurea, N,N'-propylene diurea (including isomers), N,N'-butylene diurea (including isomers), N,N'-pentamethylene diurea (including isomers), N,N'-hexamethylene diurea (including isomers) or N,N'-decamethylene diurea (including isomers); N-aliphatic triureas such as N,N',N''-hexamethylene triurea (including isomers), N,N',N''-nonamethylene triurea (including isomers) or N,N',N''-decamethylene triurea (including isomers); and, substituted N-alicyclic polyureas such as N,N'-cyclobutylene diurea (including isomers), N,N'-methylenedi-cyclohexyl diurea (including isomers), 3-ureidomethyl-3,5,5-trimethylcyclohexyl urea (cis and/or trans form) or methylenebis(cyclohexylurea) (including isomers).

<N-Substituted Carbamic Acid Ester>

N-substituted carbamic acid-O—Ar ester and N-substituted carbamic acid-O—$R^2$ ester are compounds that are produced from an organic amine, a carbonic acid derivative and a hydroxy compound according to the production method of the present embodiment. In addition, N-substituted carbamic acid-O—Ar ester is also a compound contained in a composition for transfer and storage of the N-substituted carbamic acid-O—Ar ester. Furthermore, N-substituted carbamic acid-O—Ar ester and N-substituted carbamic acid-O—$R^2$ ester may simply be collectively referred to as N-substituted carbamic acid ester.

First, an explanation is given of the N-substituted carbamic acid-O—$R^2$ ester. The N-substituted carbamic acid-O—$R^2$ ester is the N-substituted carbamic acid-O—$R^2$ ester obtained in the case of using an alcohol as a hydroxy compound that composes a hydroxy composition in the reaction between the organic amine, the carbonic acid derivative and the hydroxy composition, and is represented by the following formula (92):

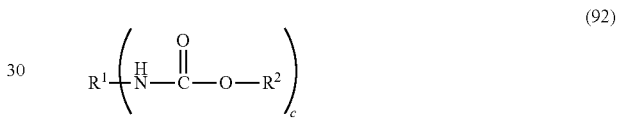

(92)

(wherein $R^1$ represents an organic group which has 1 to 85 carbon atoms and which is substituted with a number of amino groups, $R^2$ represents a group derived from an alcohol that is a residue in which a single hydroxy group bonded to a saturated carbon atom of the alcohol has been removed from the alcohol, c represents an integer equal to or greater than 1 and equal to or less than a or equal to or greater than 1 and equal to or less than h, and a and h are the same as previously defined).

In formula (92) above, $R^1$ represents an aliphatic group, an aromatic group or a group bonded to an aliphatic group and an aromatic group, and represents a group composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a heterocrosslinked ring group or heterocyclic ring group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (93) to (101).

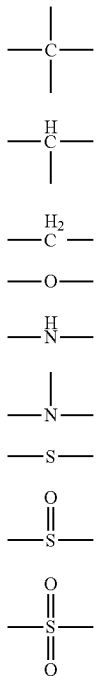

(93)
(94)
(95)
(96)
(97)
(98)
(99)
(100)
(101)

Among these $R^1$ groups, $R^1$ groups that can be preferably used in the present embodiment in consideration of less susceptibility to the occurrence of side reactions contain groups selected from the group consisting of acyclic hydrocarbon groups and cyclic hydrocarbon groups selected from aliphatic groups and aromatic groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups), having 1 to 85 carbon atoms. In consideration of fluidity and the like, the number of carbon atoms is preferably from 1 to 70 and more preferably from 1 to 13.

Preferable examples of N-substituted carbamic acid esters composed by the $R^1$ group may include:

1) N-aromatic organic monocarbamic acid esters in which the $R^1$ group has 6 to 85 carbon atoms and contains one or more types of an aromatic ring, and c is 1, 2) N-aromatic organic polycarbamic acid esters in which the $R^1$ group has 6 to 85 carbon atoms and contains one or more types of an aromatic ring, and c is 2 or more, and 3) N-aliphatic organic polycarbamic acid esters in which the $R^1$ group is an aliphatic group having 1 to 85 carbon atoms, and c is 2 or 3.

Moreover, more preferable aliphatic groups are linear hydrocarbon groups, cyclic hydrocarbon groups and a group bonded by at least one type of group selected from the linear hydrocarbon groups and cyclic hydrocarbon groups (referring to, for example, cyclic hydrocarbon groups substituted with a linear hydrocarbon group or linear hydrocarbon groups substituted with a cyclic hydrocarbon group) having 6 to 70 carbon atoms.

In addition, although c in the above formula (92) is an integer of from 1 to 10, in the case of using an organic amine of the aforementioned formula (29) as a starting substance, and is an integer that does not exceed a of the organic amine represented by formula (29).

The following indicates specific examples of N-substituted carbamic acid-O—$R^2$ esters.

1) N-Aromatic Organic Monocarbamic Acid Ester

N-aromatic organic monocarbamic acid ester in which the $R^1$ group is a group having 6 to 85 carbon atoms and containing one or more types of "carbamic acid ester group-substituted" aromatic rings and c is 1, preferably N-aromatic organic monocarbamic acid esters in which the $R^1$ group is a group having 6 to 70 carbon atoms and containing one or more types of "carbamic acid ester group-substituted" aromatic rings and c is 1, and more preferably in consideration of fluidity and the like, N-aromatic organic monocarbamic acid esters in which the $R^1$ group is a group having 6 to 13 carbon atoms and contains one or more types of "carbamic acid ester group-substituted" aromatic rings and c is 1, which are N-aromatic organic monocarbamic acid esters represented by the following formula (102).

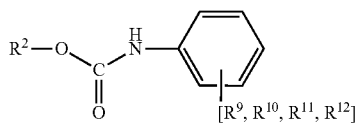

(102)

The $R^1$ group of N-aromatic organic monocarbamic acid esters represented by formula (102) above is the same as previously defined. Groups $R^9$ to $R^{12}$ respectively represent a group substituted at an arbitrary position that retains aromatic properties of the ring, groups $R^9$ to $R^{12}$ may respectively and independently substitute the aromatic ring, groups $R^9$ to $R^{12}$ may mutually bond to form a ring with the aromatic ring, and represent hydrogen atoms, groups selected from the group consisting of an alkyl group, a cycloalkyl group, an aryl group and an aryl group having a hydroxy group, or groups selected from groups in which a group selected from the aforementioned group is composed of groups bonded by saturated aliphatic bonds and/or ether bonds, and the total number of carbon atoms that compose an N-aromatic organic monocarbamic acid ester represented by formula (102) is from 7 to 63.

Preferable examples of N-aromatic organic monocarbamic acid-O—$R^2$ esters represented by formula (102) may include those in which the $R^9$ to $R^{12}$ groups are hydrogen atoms or groups selected from alkyl groups such as a methyl group or an ethyl group.

2) N-Aromatic Organic Polycarbamic Acid Ester

N-aromatic organic polycarbamic acid-O—$R^2$ esters in which the $R^1$ group is a group having 6 to 85 carbon atoms that contains one or more types of "carbamic acid ester group-substituted" aromatic rings and c is 2 or more, preferably N-aromatic organic polycarbamic acid-O—$R^2$ esters in which the $R^1$ group is a group having 6 to 70 carbon atoms that contains one or more types of "carbamic acid ester group-substituted" aromatic rings and c is 2 or more, and more preferably in consideration of fluidity and the like, N-aromatic organic polycarbamic acid-O—$R^2$ esters in which the $R^1$ group contains one or more types of "carbamic acid ester group-substituted" aromatic rings, the aromatic ring has 6 to 13 carbon atoms and may be further substituted with an alkyl group, an aryl group or an aralkyl group, and c is 2 or more.

In addition, examples may include polymethylene polyphenyl polycarbamic acid-O—R² esters represented by the following formula (103):

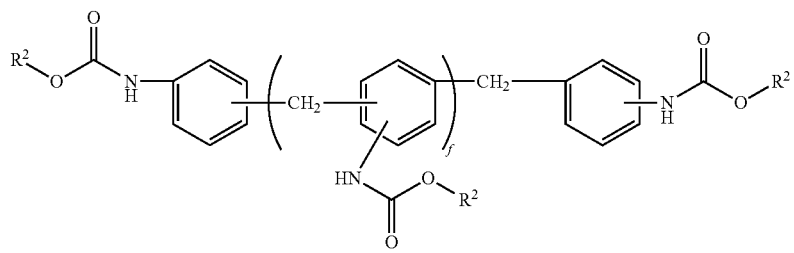

(wherein
R² is the same as previously defined, and
f represents an integer of 0 to 6).

3) N-Aliphatic Organic Polycarbamic Acid-O—R² Ester

N-aliphatic organic polycarbamic acid-O—R² ester in which the R¹ group of an N-substituted carbamic acid ester represented by formula (92) is an aliphatic group having 1 to 85 carbon atoms and c is 2 or 3. More preferable N-substituted carbamic acid-O—R² esters are N-substituted carbamic acid-O—R² esters in which the aliphatic group is a linear hydrocarbon group, a cyclic hydrocarbon group or a group to which is bonded at least one type of group selected from the linear hydrocarbon groups and the cyclic hydrocarbon groups (such as a cyclic hydrocarbon group substituted with a linear hydrocarbon group or a linear hydrocarbon group substituted with a cyclic hydrocarbon group). More preferably, the N-aliphatic organic polycarbamic acid ester is an N-aliphatic organic polycarbamic acid ester in which the R¹ group is an aliphatic group that is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 1 to 70 carbon atoms, and c is 2 or 3. In consideration of fluidity and the like during large-volume industrial production, the N-aliphatic organic polycarbamic acid ester is most preferably an N-aliphatic organic polycarbamic acid ester in which the R¹ group is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 6 to 13 carbon atoms and composed of carbon atoms and hydrogen atoms. Namely, this refers to the case in which the R¹ group is a linear and/or branched alkyl group, a cycloalkyl group or a group composed of the alkyl groups and cycloalkyl groups.

Although all examples of N-substituted carbamic acid-O—R² esters cannot be listed since the specific structure thereof is determined by the type of organic amine used and the type of alcohol that composes the hydroxy composition, examples include N,N'-hexanediyl-di(carbamic acid methyl ester) (including isomers), N,N'-hexanediyl-di(carbamic acid ethyl ester) (including isomers), N,N'-hexanediyl-di(carbamic acid propyl ester) (including isomers), N,N'-hexanediyl-di(carbamic acid butyl ester) (including isomers), N,N'-hexanediyl-di(carbamic acid pentyl ester) (including isomers), N,N'-hexanediyl-di(carbamic acid hexyl ester) (including isomers), N,N'-hexanediyl-di(carbamic acid heptyl ester) (including isomers), N,N'-hexanediyl-di(carbamic acid octyl ester) (including isomers), N,N'-hexanediyl-di(carbamic acid nonyl ester) (including isomers), N,N'-hexanediyl-di(carbamic acid decyl ester) (including isomers), N,N'-hexanediyl-di(carbamic acid dodecyl ester) (including isomers), N,N'-hexanediyl-di(carbamic acid octadecyl ester) (including isomers), N,N'-methylenediphenylene-di(carbamic acid methyl ester) (including isomers), N,N'-methylenediphenylene-di(carbamic acid ethyl ester) (including isomers), N,N'-methylenediphenylene-di(carbamic acid propyl ester) (including isomers), N,N'-methylenediphenylene-di(carbamic acid butyl ester) (including isomers), N,N'-methylenediphenylene-di(carbamic acid pentyl ester) (including isomers), N,N'-methylenediphenylene-di(carbamic acid hexyl ester) (including isomers), N,N'-methylenediphenylene-di(carbamic acid heptyl ester) (including isomers), N,N'-methylenediphenylene-di(carbamic acid octyl ester) (including isomers), N,N'-methylenediphenylene-di(carbamic acid nonyl ester) (including isomers), N,N'-methylenediphenylene-di(carbamic acid decyl ester) (including isomers), N,N'-methylenediphenylene-di(carbamic acid dodecyl ester) (including isomers), N,N'-methylenediphenylene-di(carbamic acid octadecyl ester) (including isomers), 3-(methoxycarbonylamino-methyl)-3,5,5-trimethylcyclohexyl carbamic acid methyl ester (including isomers), 3-(ethoxycarbonylamino-methyl)-3,5,5-trimethylcyclohexyl carbamic acid ethyl ester (including isomers), 3-(propyloxycarbonylamino-methyl)-3,5,5-trimethylcyclohexyl carbamic acid propyl ester (including isomers), 3-(butyloxycarbonylamino-methyl)-3,5,5-trimethylcyclohexyl carbamic acid butyl ester (including isomers), 3-(pentyloxycarbonylamino-methyl)-3,5,5-trimethylcyclohexyl carbamic acid pentyl ester (including isomers), 3-(hexyloxycarbonylamino-methyl)-3,5,5-trimethylcyclohexyl carbamic acid hexyl ester (including isomers), 3-(heptyloxycarbonylamino-methyl)-3,5,5-trimethylcyclohexyl carbamic acid heptyl ester (including isomers), 3-(octyloxycarbonylamino-methyl)-3,5,5-trimethylcyclohexyl carbamic acid octyl ester (including isomers), 3-(nonyloxycarbonylamino-methyl)-3,5,5-trimethylcyclohexyl carbamic acid nonyl ester (including isomers), 3-(decyloxycarbonylamino-methyl)-3,5,5-trimethylcyclohexyl carbamic acid decyl ester (including isomers), 3-(dodecyloxycarbonylamino-methyl)-3,5,5-trimethylcyclohexyl carbamic acid dodecyl ester (including isomers), 3-(octadecyloxycarbonylamino-methyl)-3,5,5-trimethylcyclohexyl carbamic acid octadecyl ester (including isomers), toluene-di(carbamic acid methyl ester) (including isomers), toluene-di(carbamic acid ethyl ester) (including isomers), toluene-di(carbamic acid propyl ester) (including isomers), toluene-di(carbamic acid butyl ester) (including isomers), toluene-di(carbamic acid pentyl ester) (including isomers), toluene-di(carbamic acid hexyl ester) (including isomers), toluene-di(carbamic acid heptyl ester) (including isomers), toluene-di(carbamic acid octyl ester) (including isomers), toluene-di(carbamic acid nonyl ester) (including isomers), toluene-di(carbamic acid decyl ester) (including isomers), toluene-di(carbamic acid dodecyl ester) (including isomers), toluene-di(carbamic acid octadecyl ester) (including isomers), N,N'-methylenedicyclohexyl-di(carbamic acid methyl ester) (including isomers), N,N'-methylenedicyclohexyl-di(carbamic acid ethyl ester) (including isomers), N,N'-methylenedicyclohexyl-di(carbamic acid propyl ester) (including isomers), N,N'-methylenedicyclohexyl-di(carbamic acid butyl ester) (including isomers), N,N'-methylenedicyclohexyl-di(carbamic acid pentyl ester) (including isomers), N,N'-methylenedicyclohexyl-di(carbamic acid hexyl ester) (including isomers), N,N'-methylenedicyclohexyl-di(carbamic acid heptyl ester) (including isomers), N,N'-methylenedicyclohexyl-di(carbamic acid octyl ester) (including isomers), N,N'-methylenedicyclohexyl-di(carbamic acid nonyl ester) (including isomers), N,N'-methylenedicyclohexyl-di(carbamic acid decyl ester) (including isomers), N,N'-methylenedicyclohexyl-di(carbamic acid dodecyl ester) (including isomers), N,N'-methylenedicyclohexyl-di(carbamic acid octadecyl ester) (including isomers), N-phenyl carbamic acid methyl ester (including isomers), N-phenyl carbamic acid ethyl ester (including isomers), N-phenyl carbamic acid propyl ester (including isomers), N-phenyl carbamic acid butyl ester (including isomers), N-phenyl carbamic acid pentyl ester (including isomers), N-phenyl carbamic acid hexyl ester (including isomers), N-phenyl carbamic acid heptyl ester (including isomers), N-phenyl carbamic acid octyl ester (including isomers), N-phenyl carbamic acid nonyl ester (including isomers), N-phenyl carbamic acid decyl ester (including isomers), N-phenyl carbamic acid dodecyl ester (including isomers), N-phenyl carbamic acid octadecyl ester (including isomers), N-dimethylphenyl carbamic acid methyl ester (including isomers), N-dimethylphenyl carbamic acid ethyl ester (including isomers), N-dimethylphenyl carbamic acid propyl ester (including isomers), N-dimethylphenyl carbamic acid butyl ester (including isomers), N-dimethylphenyl carbamic acid pentyl ester (including isomers), N-dimethylphenyl carbamic acid hexyl ester (including isomers), N-dimethylphenyl carbamic acid heptyl ester (including isomers), N-dimethylphenyl carbamic acid octyl ester (including isomers), N-dimethylphenyl carbamic acid nonyl ester (including isomers), N-dimethylphenyl carbamic acid decyl ester (including isomers), N-dimethylphenyl carbamic acid dodecyl ester (including isomers) and N-dimethylphenyl carbamic acid octadecyl ester (including isomers).

Next, an explanation is given of the N-substituted carbamic acid-O—Ar ester. The N-substituted carbamic acid-O—Ar ester is the N-substituted carbamic acid-O—Ar ester obtained in the case of using an aromatic hydroxy compound as a hydroxy compound that composes a hydroxy composition in the reaction between an organic amine, a carbonic acid derivative and a hydroxy composition, and is represented by the following formula (104):

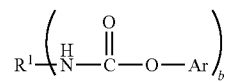

(104)

(wherein $R^1$ represents an organic group which has 1 to 85 carbon atoms and which is substituted with a number of amino groups, Ar represents a group derived from an aromatic hydroxy compound that is a residue in which a single hydroxy group bonded to an aromatic ring of the aromatic hydroxy compound has been removed from the aromatic hydroxy compound, and b represents an integer of 1 to 10).

In formula (104) above, $R^1$ represents an aliphatic group or an aromatic group, a group composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a hetero-crosslinked ring group or a heterocyclic group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (105) to (113).

(105)

(106)

(107)

(108)

(109)

(110)

(111)

(112)

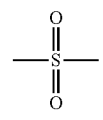

(113)

Among these R¹ groups, R¹ groups that can be preferably used in the present embodiment in consideration of less susceptibility to the occurrence of side reactions contain groups selected from the group consisting of acyclic hydrocarbon groups and cyclic hydrocarbon groups selected from aliphatic groups or aromatic groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups), having 1 to 85 carbon atoms. In consideration of fluidity and the like, the number of carbon atoms is preferably from 1 to 70 and more preferably from 1 to 13.

Preferable examples of N-substituted carbamic acid-O—Ar esters composed by the R¹ group may include:

1) N-aromatic organic monocarbamic acid esters in which the R¹ group has 6 to 85 carbon atoms and contains one or more types of "carbamic acid ester group-substituted" aromatic rings, and b is 1, 2) N-aromatic organic polycarbamic acid esters in which the R¹ group has 6 to 85 carbon atoms and contains one or more types of "carbamic acid ester group-substituted" aromatic rings, and b is 2 or more, and 3) N-aliphatic organic polycarbamic acid esters in which the R¹ group is an aliphatic group having 1 to 85 carbon atoms, and b is 2 or 3. More preferable aliphatic groups are linear hydrocarbon groups, cyclic hydrocarbon groups and at least one type of group selected from the linear hydrocarbon groups and cyclic hydrocarbon groups (referring to, for example, cyclic hydrocarbon groups substituted with a linear hydrocarbon group or linear hydrocarbon groups substituted with a cyclic hydrocarbon group) having 6 to 70 carbon atoms.

In addition, although b in the above formula (104) is an integer of from 1 to 10, in the case of using an organic amine of the aforementioned formula (29) as a starting substance, b is an integer that does not exceed a of the organic amine represented by formula (29).

The following indicates specific examples of N-substituted carbamic acid esters.

1) N-Aromatic Organic Monocarbamic Acid Ester

N-aromatic organic monocarbamic acid ester in which the R¹ group is a group having 6 to 85 carbon atoms and containing one or more types of aromatic rings and b is 1, preferably N-aromatic organic monocarbamic acid esters in which the R¹ group is a group having 6 to 70 carbon atoms and containing one or more types of "carbamic acid ester group-substituted" aromatic rings and b is 1, and more preferably in consideration of fluidity and the like, N-aromatic organic monocarbamic acid esters in which the R¹ group has 6 to 13 carbon atoms and contains one or more types of "carbamic acid ester group-substituted" aromatic rings and b is 1, which are N-aromatic organic monocarbamic acid esters represented by the following formula (114).

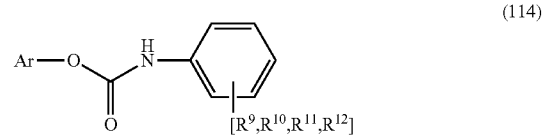

(114)

The R¹ group of N-aromatic organic monocarbamic acid esters represented by formula (114) above is the same as previously defined. Groups R⁹ to R¹² respectively represent a group substituted at an arbitrary position that retains aromatic properties of the ring, groups R⁹ to R¹² may respectively and independently substitute the aromatic ring, groups R⁹ to R¹² may mutually bond to form a ring with the aromatic ring, and represent hydrogen atoms, groups selected from the group consisting of an alkyl group, a cycloalkyl group, an aryl group and an aryl group having a hydroxy group, or groups selected from groups in which a group selected from the aforementioned group is composed of groups bonded by saturated aliphatic bonds and/or ether bonds, and the total number of carbon atoms that compose an N-aromatic organic monocarbamic acid ester represented by formula (114) is from 7 to 63.

Preferable examples of N-aromatic organic monocarbamic acid-O—Ar esters represented by formula (114) may include those in which the R⁹ to R¹² groups are hydrogen atoms or groups selected from alkyl groups such as a methyl group or an ethyl group.

2) N-Aromatic Organic Polycarbamic Acid Ester

N-aromatic organic polycarbamic acid-O—Ar ester in which the R¹ group is a group having 6 to 85 carbon atoms that contains one or more types of "carbamic acid ester group-substituted" aromatic rings and b is 2 or more, preferably N-aromatic organic polycarbamic acid-O—Ar ester in which the R¹ group is a group having 6 to 70 carbon atoms that contains one or more types of "carbamic acid ester group-substituted" aromatic rings and b is 2 or more, and more preferably in consideration of fluidity and the like, N-aromatic organic polycarbamic acid-O—Ar esters in which the R¹ group contains one or more types of "carbamic acid ester group-substituted" aromatic rings, the aromatic ring has 6 to 13 carbon atoms and may be further substituted with an alkyl group, aryl group or aralkyl group, and b is 2 or more.

In addition, examples may include polymethylene polyphenyl polycarbamic acid-O—Ar esters represented by the following formula (115):

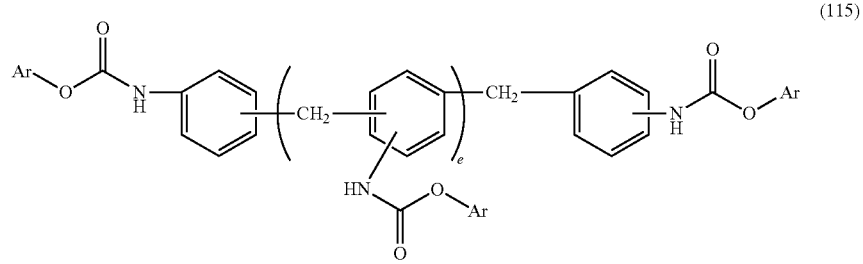

(115)

(wherein

Ar is the same as previously defined, and f represents an integer of 0 to 6).

3) N-Aliphatic Organic Polycarbamic Acid-O—Ar Ester

N-aliphatic organic polycarbamic acid-O—Ar ester in which the $R^1$ group of an organic amine represented by formula (29) is an aliphatic group having 1 to 85 carbon atoms and b is 2 or 3. More preferable N-substituted carbamic acid-O—Ar esters are N-substituted carbamic acid-O—Ar esters in which the aliphatic group is a linear hydrocarbon group, a cyclic hydrocarbon group or a group to which is bonded at least one type of group selected from the linear hydrocarbon groups and the cyclic hydrocarbon groups (such as a cyclic hydrocarbon group substituted with a linear hydrocarbon group or a linear hydrocarbon group substituted with a cyclic hydrocarbon group). More preferably, the N-aliphatic organic polycarbamic acid ester is an N-aliphatic organic polycarbamic acid ester in which the $R^1$ group is an aliphatic group that is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 1 to 70 carbon atoms, and b is 2 or 3. In consideration of fluidity and the like during large-volume industrial production, the N-aliphatic organic polycarbamic acid ester is most preferably an N-aliphatic organic polycarbamic acid ester in which the $R^1$ group is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 6 to 13 carbon atoms and composed of carbon atoms and hydrogen atoms. Namely, this refers to the case in which the $R^1$ group is a linear and/or branched alkyl group, a cycloalkyl group or a group composed of the alkyl groups and cycloalkyl groups.

Although all examples of N-substituted carbamic acid-O—Ar esters cannot be listed since the specific structure thereof is determined by the type of organic amine used and the type of aromatic hydroxy compound that composes the hydroxy composition, examples may include N,N'-hexanediyl-di(carbamic acid phenyl ester), N,N'-hexanediyl-di(carbamic acid (methylphenyl) ester) (including isomers), N,N'-hexanediyl-di(carbamic acid (ethylphenyl) ester) (including isomers), N,N'-hexanediyl-di(carbamic acid (propylphenyl) ester) (including isomers), N,N'-hexanediyl-di(carbamic acid (butylphenyl) ester) (including isomers), N,N'-hexanediyl-di(carbamic acid (pentylphenyl) ester) (including isomers), N,N'-hexanediyl-di(carbamic acid (hexylphenyl) ester) (including isomers), N,N'-hexanediyl-di(carbamic acid (heptylphenyl) ester) (including isomers), N,N'-hexanediyl-di(carbamic acid (octylphenyl) ester) (including isomers), N,N'-hexanediyl-di(carbamic acid (nonylphenyl) ester) (including isomers), N,N'-hexanediyl-di(carbamic acid (decylphenyl) ester) (including isomers), N,N'-hexanediyl-di(carbamic acid (dodecylphenyl) ester) (including isomers), N,N'-hexanediyl-di(carbamic acid (octadecylphenyl) ester) (including isomers), N,N'-hexanediyl-bis(carbamic acid (dimethylphenyl) ester) (including isomers), N,N'-hexanediyl-bis(carbamic acid (diethylphenyl) ester) (including isomers), N,N'-hexanediyl-bis(carbamic acid (dipropylphenyl) ester) (including isomers), N,N'-hexanediyl-bis(carbamic acid (dibutylphenyl) ester) (including isomers), N,N'-hexanediyl-bis(carbamic acid (dipentylphenyl) ester) (including isomers), N,N'-hexanediyl-bis(carbamic acid (dihexylphenyl) ester) (including isomers), N,N'-hexanediyl-bis(carbamic acid (diheptylphenyl) ester) (including isomers), N,N'-hexanediyl-bis(carbamic acid (dioctylphenyl) ester) (including isomers), N,N'-hexanediyl-bis(carbamic acid (dinonylphenyl) ester) (including isomers), N,N'-hexanediyl-bis(carbamic acid (didecylphenyl) ester) (including isomers), N,N'-hexanediyl-bis(carbamic acid (didodecylphenyl) ester) (including isomers), N,N'-hexanediyl-bis(carbamic acid (dioctadecylphenyl) ester) (including isomers), N,N'-methylenediphenylene-di(carbamic acid phenyl ester) (including isomers) N,N'-methylenediphenylene-di(carbamic acid (methylphenyl) ester) (including isomers), N,N'-methylenediphenylene-di(carbamic acid (ethylphenyl) ester) (including isomers), N,N'-methylenediphenylene-di(carbamic acid (propylphenyl) ester) (including isomers), N,N'-methylenediphenylene-di(carbamic acid (butylphenyl) ester) (including isomers), N,N'-methylenediphenylene-di(carbamic acid (pentylphenyl) ester) (including isomers), N,N'-methylenediphenylene-di(carbamic acid (hexylphenyl) ester) (including isomers), N,N'-methylenediphenylene-di(carbamic acid (heptylphenyl) ester) (including isomers), N,N'-methylenediphenylene-di(carbamic acid (octylphenyl) ester) (including isomers), N,N'-methylenediphenylene-di(carbamic acid (nonylphenyl) ester) (including isomers), N,N'-methylenediphenylene-di(carbamic acid (decylphenyl) ester) (including isomers), N,N'-methylenediphenylene-di(carbamic acid (dodecylphenyl) ester) (including isomers), N,N'-methylenediphenylene-di(carbamic acid (octadecylphenyl ester) (including isomers), N,N'-methylenediphenylene-bis(carbamic acid (dimethylphenyl) ester) (including isomers), N,N'-methylenediphenylene-bis(carbamic acid (diethylphenyl) ester) (including isomers), N,N'-methylenediphenylene-bis(carbamic acid (dipropylphenyl) ester) (including isomers), N,N'-methylenediphenylene-bis(carbamic acid (dibutylphenyl) ester) (including isomers), N,N'-methylenediphenylene-bis(carbamic acid (dipentylphenyl) ester) (including isomers), N,N'-methylenediphenylene-bis(carbamic acid (dihexylphenyl) ester) (including isomers), N,N'-methylenediphenylene-bis(carbamic acid (diheptylphenyl) ester) (including isomers), N,N'-methylenediphenylene-bis(carbamic acid (dioctylphenyl) ester) (including isomers), N,N'-methylenediphenylene-bis(carbamic acid (dinonylphenyl) ester) (including isomers), N,N'-methylenediphenylene-bis(carbamic acid (didecylphenyl) ester) (including isomers), N,N'-methylenediphenylene-bis(carbamic acid (didodecylphenyl) ester) (including isomers), N,N'-methylenediphenylene-bis(carbamic acid (dioctadecylphenyl ester) (including isomers), 3-(phenoxycarbonylamino-methyl)-3,5,5-trimethylcyclohexyl carbamic acid phenyl ester, 3-((methylphenoxy)carbonylamino-methyl)-3,5,5-trimethylcyclohexyl carbamic acid (methylphenyl) ester (including isomers), 3-((ethylphenoxy)carbonylamino-methyl)-3,5,5-trimethylcyclohexyl carbamic acid (ethylphenyl) ester (including isomers), 3-((propylphenoxy)carbonylamino-methyl)-3,5,5-trimethylcyclohexyl carbamic acid (propylphenyl) ester (including isomers), 3-((butylphenoxycarbonyl)amino-methyl)-3,5,5-trimethylcyclohexyl carbamic acid (butylphenyl) ester (including isomers), 3-((pentylphenoxy)carbonylamino-methyl)-3,5,5-trimethylcyclohexyl carbamic acid (pentylphenyl) ester (including isomers), 3-((hexylphenoxy)carbonylamino-methyl)-3,5,5-trimethylcyclohexyl carbamic acid (hexylphenyl) ester (including isomers), 3-((heptylphenoxy)carbonylamino-methyl)-3,5,5-trimethylcyclohexyl carbamic acid (heptylphenyl) ester (including isomers), 3-((octylphenoxy)carbonylamino-methyl)-3,5,5-trimethylcyclohexyl carbamic acid (octylphenyl) ester (including isomers), 3-((nonylphenoxy)carbonylamino-methyl)-3,5,5-trimethylcyclohexyl carbamic acid (nonylphenyl) ester (including isomers), 3-((decylphenoxy)carbonylamino-methyl)-3,5,5-trimethylcyclohexyl carbamic acid (decylphenyl) ester (including isomers), 3-((dodecylphenoxy)carbonylamino-methyl)-3,5,5-trimethylcyclohexyl carbamic acid (dodecylphenyl) ester (including isomers), 3-((octadecylphenoxy)carbonylamino-methyl)-3,5,5-trimethylcyclohexyl carbamic acid (octadecylphenyl) ester (including isomers), 3-((dimethylphenoxy)carbonylamino-methyl)-3,5,5-trimethylcyclohexyl carbamic acid (dimethylphenyl) ester (including isomers), 3-((diethylphenoxy)carbonylamino-methyl)-3,5,5-trimethylcyclohexyl carbamic acid (diethylphenyl) ester (including isomers), 3-((dipropylphenoxy)carbonylamino-methyl)-3,5,5-trimethylcyclohexyl carbamic acid (dipropylphenyl) ester (including isomers), 3-((dibutylphenoxycarbonyl)amino-methyl)-3,5,5-trimethylcyclohexyl carbamic acid (dibutylphenyl) ester (including isomers), 3-((dipentylphenoxy)carbonylamino-methyl)-3,5,5-trimethylcyclohexyl carbamic acid (dipentylphenyl) ester (including isomers), 3-((dihexylphenoxy)carbonylamino-methyl)-3,5,5-trimethylcyclohexyl carbamic acid (dihexylphenyl) ester (including isomers), 3-((diheptylphenoxy)carbonylamino-methyl)-3,5,5-trimethylcyclohexyl carbamic acid (diheptylphenyl) ester (including isomers), 3-((dioctylphenoxy)carbonylamino-methyl)-3,5,5-trimethylcyclohexyl carbamic acid (dioctylphenyl) ester (including isomers), 3-((dinonylphenoxy)carbonylamino-methyl)-3,5,5-trimethylcyclohexyl carbamic acid (dinonylphenyl) ester (including isomers), 3-((didecylphenoxy)carbonylamino-methyl)-3,5,5-trimethylcyclohexyl carbamic acid (didecylphenyl) ester (including isomers), 3-((didodecylphenoxy)carbonylamino-methyl)-3,5,5-trimethylcyclohexyl carbamic acid (didodecylphenyl) ester (including isomers), 3-((dioctadecylphenoxy)carbonylamino-methyl)-3,5,5-trimethylcyclohexyl carbamic acid (dioctadecylphenyl) ester (including isomers), toluene-di(carbamic acid phenyl ester) (including isomers), toluene-di(carbamic acid (methylphenyl) ester) (including isomers), toluene-di(carbamic acid (ethylphenyl) ester) (including isomers), toluene-di(carbamic acid (propylphenyl) ester) (including isomers), toluene-di(carbamic acid (butylphenyl) ester) (including isomers), toluene-di(carbamic acid (pentylphenyl) ester) (including isomers), toluene-di(carbamic acid (hexylphenyl) ester) (including isomers), toluene-di(carbamic acid (heptylphenyl) ester) (including isomers), toluene-di(carbamic acid (octylphenyl) ester) (including isomers), toluene-di(carbamic acid (nonylphenyl) ester) (including isomers), toluene-di(carbamic acid (decylphenyl) ester) (including isomers), toluene-di(carbamic acid (dodecylphenyl) ester) (including isomers), toluene-di(carbamic acid (octadecylphenyl) ester) (including isomers), toluene-bis(carbamic acid (dimethylphenyl) ester) (including isomers), toluene-bis(carbamic acid (diethylphenyl) ester) (including isomers), toluene-bis(carbamic acid (dipropylphenyl) ester) (including isomers), toluene-bis(carbamic acid (dibutylphenyl) ester) (including isomers), toluene-bis(carbamic acid (dipentylphenyl) ester) (including isomers), toluene-bis(carbamic acid (dihexylphenyl) ester) (including isomers), toluene-bis(carbamic acid (diheptylphenyl) ester) (including isomers), toluene-bis(carbamic acid (dioctylphenyl) ester) (including isomers), toluene-bis(carbamic acid (dinonylphenyl) ester) (including isomers), toluene-bis(carbamic acid (didecylphenyl) ester) (including isomers), toluene-bis(carbamic acid (didodecylphenyl) ester) (including isomers), toluene-bis(carbamic acid (dioctadecylphenyl) ester) (including isomers), N,N'-methylenedicyclohexyl-di(carbamic acid phenyl ester) (including isomers), N,N'-methylenedicyclohexyl-di(carbamic acid (methylphenyl) ester) (including isomers), N,N'-methylenedicyclohexyl-di(carbamic acid (ethylphenyl ester) (including isomers), N,N'-methylenedicyclohexyl-di(carbamic acid (propylphenyl) ester) (including isomers), N,N'-methylenedicyclohexyl-di(carbamic acid (butylphenyl) ester) (including isomers), N,N'-methylenedicyclohexyl-di(carbamic acid (pentylphenyl) ester) (including isomers), N,N'-methylenedicyclohexyl-di(carbamic acid (hexylphenyl) ester) (including isomers), N,N'-methylenedicyclohexyl-di(carbamic acid (heptylphenyl) ester) (including isomers), N,N'-methylenedicyclohexyl-di(carbamic acid (octylphenyl) ester) (including isomers), N,N'-methylenedicyclohexyl-di(carbamic acid (nonylphenyl) ester) (including isomers), N,N'-methylenedicyclohexyl-di(carbamic acid (decylphenyl) ester) (including isomers), N,N'-methylenedicyclohexyl-di(carbamic acid (dodecylphenyl) ester) (including isomers), N,N'-methylenedicyclohexyl-di(carbamic acid (octadecylphenyl) ester) (including isomers), N,N'-methylenedicyclohexyl-bis(carbamic acid (dimethylphenyl) ester) (including isomers), N,N'-methylenedicyclohexyl-bis(carbamic acid (diethylphenyl ester) (including isomers), N,N'-methylenedicyclohexyl-bis(carbamic acid (dipropylphenyl) ester) (including isomers), N,N'-methylenedicyclohexyl-bis(carbamic acid (dibutylphenyl) ester) (including isomers), N,N'-methylenedicyclohexyl-bis(carbamic acid (dipentylphenyl) ester) (including isomers), N,N'-methylenedicyclohexyl-bis(carbamic acid (dihexylphenyl) ester) (including isomers), N,N'-methylenedicyclohexyl-bis(carbamic acid (diheptylphenyl) ester) (including isomers), N,N'-methylenedicyclohexyl-bis(carbamic acid (dioctylphenyl) ester) (including isomers), N,N'-methylenedicyclohexyl-bis(carbamic acid (dinonylphenyl) ester) (including isomers), N,N'-methylenedicyclohexyl-bis(carbamic acid (didecylphenyl) ester) (including isomers), N,N'-methylenedicyclohexyl-bis(carbamic acid (didodecylphenyl) ester) (including isomers), N,N'-methylenedicyclohexyl-bis(carbamic acid (dioctadecylphenyl) ester) (including isomers), N-phenyl carbamic acid phenyl ester, N-phenyl carbamic acid (methylphenyl) ester (including isomers), N-phenyl carbamic acid (ethylphenyl) ester) (including isomers), N-phenyl carbamic acid (propylphenyl) ester (including isomers), N-phenyl carbamic acid (butylphenyl) ester (including isomers), N-phenyl carbamic acid (pentylphenyl) ester (including isomers), N-phenyl carbamic acid (hexylphenyl) ester (including isomers), N-phenyl carbamic acid (heptylphenyl) ester (including isomers), N-phenyl carbamic acid (octylphenyl) ester (including isomers), N-phenyl carbamic acid (nonylphenyl) ester (including isomers), N-phenyl carbamic acid (decylphenyl) ester (including isomers), N-phenyl carbamic acid (dodecylphenyl) ester (including isomers), N-phenyl carbamic acid (octadecylphenyl) ester (including isomers), N-phenyl carbamic acid (dimethylphenyl) ester (including isomers), N-phenyl carbamic acid (diethylphenyl) ester) (including isomers), N-phenyl carbamic acid (dipropylphenyl) ester (including isomers), N-phenyl carbamic acid (dibutylphenyl) ester (including isomers), N-phenyl carbamic acid (dipentylphenyl) ester (including isomers), N-phenyl carbamic acid (dihexylphenyl) ester (including isomers), N-phenyl carbamic acid (diheptylphenyl) ester (including isomers), N-phenyl carbamic acid (dioctylphenyl) ester (including isomers), N-phenyl carbamic acid (dinonylphenyl) ester (including isomers), N-phenyl carbamic acid (didecylphenyl) ester (including isomers), N-phenyl carbamic acid (didodecylphenyl) ester (including isomers), N-phenyl carbamic acid (dioctadecylphenyl) ester (including isomers), N-phenyl carbamic acid phenyl ester, N-phenyl carbamic acid (methylphenyl) ester (including isomers), N-phenyl carbamic acid (ethylphenyl) ester) (including isomers), N-phenyl carbamic acid (propylphenyl) ester (including isomers), N-phenyl carbamic acid (butylphenyl) ester (including isomers), N-phenyl carbamic acid (pentylphenyl) ester (including isomers), N-phenyl carbamic acid (hexylphenyl) ester (including isomers), N-phenyl carbamic acid (heptylphenyl) ester (including isomers), N-phenyl carbamic acid (octylphenyl) ester (including isomers), N-phenyl carbamic acid (nonylphenyl) ester (including isomers), N-phenyl carbamic acid (decylphenyl) ester (including isomers), N-phenyl carbamic acid (dodecylphenyl) ester (including isomers), N-phenyl carbamic acid (octadecylphenyl) ester (including isomers), N-phenyl carbamic acid (dimethylphenyl) ester (including isomers), N-phenyl carbamic acid (diethylphenyl) ester) (including isomers), N-phenyl carbamic acid (dipropylphenyl) ester (including isomers), N-phenyl carbamic acid (dibutylphenyl) ester (including isomers), N-phenyl carbamic acid (dipentylphenyl) ester (including isomers), N-phenyl carbamic acid (dihexylphenyl) ester (including isomers), N-phenyl carbamic acid (diheptylphenyl) ester (including isomers), N-phenyl carbamic acid (dioctylphenyl) ester (including isomers), N-phenyl carbamic acid (dinonylphenyl) ester (including isomers), N-phenyl carbamic acid (didecylphenyl) ester (including isomers), N-phenyl carbamic acid (didodecylphenyl) ester (including isomers), N-phenyl carbamic acid (dioctadecylphenyl) ester (including isomers), N-dimethylphenyl carbamic acid phenyl ester, N-dimethylphenyl carbamic acid (methylphenyl) ester (including isomers), N-dimethylphenyl carbamic acid (ethylphenyl) ester) (including isomers), N-dimethylphenyl carbamic acid (propylphenyl) ester (including isomers), N-dimethylphenyl carbamic acid (butylphenyl) ester (including isomers), N-dimethylphenyl carbamic acid (pentylphenyl) ester (including isomers), N-dimethylphenyl carbamic acid (hexylphenyl) ester (including isomers), N-dimethylphenyl carbamic acid (heptylphenyl) ester (including isomers), N-dimethylphenyl carbamic acid (octylphenyl) ester (including isomers), N-dimethylphenyl carbamic acid (nonylphenyl) ester (including isomers), N-dimethylphenyl carbamic acid (decylphenyl) ester (including isomers), N-dimethylphenyl carbamic acid (dodecylphenyl) ester (including isomers), N-dimethylphenyl carbamic acid (octadecylphenyl) ester (including isomers), N-dimethylphenyl carbamic acid (dimethylphenyl) ester (including isomers), N-dimethylphenyl carbamic acid (diethylphenyl) ester) (including isomers), N-dimethylphenyl carbamic acid (dipropylphenyl) ester (including isomers), N-dimethylphenyl carbamic acid (dibutylphenyl) ester (including isomers), N-dimethylphenyl carbamic acid (dipentylphenyl) ester (including isomers), N-dimethylphenyl carbamic acid (dihexylphenyl) ester (including isomers), N-dimethylphenyl carbamic acid (diheptylphenyl) ester (including isomers), N-dimethylphenyl carbamic acid (dioctylphenyl) ester (including isomers), N-dimethylphenyl carbamic acid (dinonylphenyl) ester (including isomers), N-dimethylphenyl carbamic acid (didecylphenyl) ester (including isomers), N-dimethylphenyl carbamic acid (didodecylphenyl) ester (including isomers) and N-dimethylphenyl carbamic acid (dioctadecylphenyl) ester (including isomers).

<Composition for Transfer and Storage of N-Substituted Carbamic Acid-O—Ar Ester>

Next, an explanation is given of the composition for transfer and storage of N-substituted carbamic acid O—Ar ester of the present embodiment. The N-substituted carbamic acid-O—Ar ester referred to here is an N-substituted carbamic acid-O—Ar ester represented by the above-mentioned formula (104).

In general, N-substituted carbamic acid-O—Ar esters easily form hydrogen bonds between molecules thereof by ester groups that compose the N-substituted carbamic acid-O—Ar ester. For this reason, there are many cases in which N-substituted carbamic acid-O—Ar esters have high melting points. In the case of transferring such an N-substituted carbamic acid-O—Ar ester, transfer is carried out by, for example, crushing a solid N-substituted carbamic acid-O—Ar ester or shaping such as by forming into pellets. Alternatively, methods are also employed in which an N-substituted carbamic acid-O—Ar ester is heated to a temperature higher than the melting point thereof to transfer the N-substituted carbamic acid-O—Ar ester in the form of a liquid.

In the case of transferring an N-substituted carbamic acid-O—Ar ester that has undergone shaping processing, there are cases in which this causes clogging of the transfer line since there is considerable variation in the shape of the N-substituted carbamic acid-O—Ar ester. Consequently, there are many cases in which complicated apparatuses are required to stably transfer a fixed amount of N-substituted carbamic acid-O—Ar ester or a step is required for aligning the shape of the N-substituted carbamic acid-O—Ar ester to within a certain range.

On the other hand, in the case of transferring an N-substituted carbamic acid-O—Ar ester in the form of a liquid, it is necessary to heat the N-substituted carbamic acid-O—Ar ester to a temperature higher than the melting point thereof in consideration of preventing clogging during transfer. In the case of holding an N-substituted carbamic acid-O—Ar ester under such high temperatures, there are frequently cases in which isocyanate may be formed at undesirable locations due to the occurrence of a thermal decomposition reaction of the N-substituted carbamic acid-O—Ar ester or the occurrence of a thermal denaturation reaction of the N-substituted carbamic acid-O—Ar ester. In particular, since N-substituted carbamic acid-O—Ar esters have a lower thermal decomposition temperature than N-substituted carbamic acid-O—$R^2$ esters, isocyanate groups are formed easily by thermal decomposition of these N-substituted carbamic acid-O—Ar esters.

The composition of the present embodiment demonstrates the effect of being able to maintain the stability of an N-substituted carbamic acid-O—Ar ester by inhibiting thermal denaturation of the N-substituted carbamic acid-O—Ar ester in the composition during transfer or storage of the composition. Although the mechanism by which the effect of inhibiting thermal denaturation of N-substituted carbamic acid-O—Ar ester is demonstrated is not clear, the inventors of the present invention presumed that, as a result of the aromatic hydroxy compound that composes the composition forming hydrogen bonds with urethane bonds (—NHCO—O—) of the N-substituted carbamic acid-O—Ar ester, a state is formed in which the urethane bonds have difficulty in approaching each other, thereby making it difficult for a reaction that forms ureylene groups to occur as in, for example, the following formula (116).

(116)

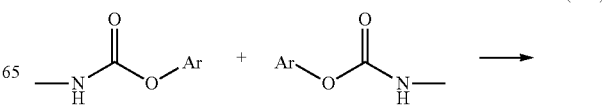

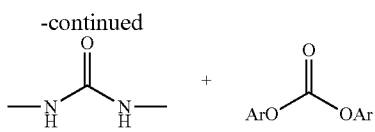

The composition for transfer and storage can be preferably used in the production of isocyanate in particular. More specifically, this method includes producing isocyanate by transferring the composition for transfer and storage to a thermal decomposition reactor and subjecting the N-substituted carbamic acid-O—Ar ester contained in the composition to a thermal decomposition reaction.

In the composition for transfer and storage of the present embodiment, the N-substituted carbamic acid-O—Ar ester contained in the composition is preferably an N-substituted carbamic acid-O—Ar ester obtained by reacting an organic amine, a carbonic acid derivative (to be explained in detail hereinafter) and an aromatic hydroxy composition.

In general, in the case the composition for transfer and storage contains urea, a compound having an ureido group (—NHCONH$_2$), a biuret, or a compound having a biuret terminal (—NHCONHCONH$_2$) (and particularly a compound derived from an organic amine that is formed in a reaction between an organic amine, a carbonic acid derivative and an aromatic hydroxy composition in the case where the N-substituted carbamic acid-O—Ar ester is an N-substituted carbamic acid-O—Ar ester obtained by reacting the organic amine, the carbonic acid derivative and the aromatic hydroxy composition) (to be referred to as "N-containing compounds"), there are many cases in which they react with isocyanate formed during thermal decomposition of the N-substituted carbamic acid ester resulting in polymers adhering to or solidifying in the reactor since these compounds have active hydrogens. In addition, there are also cases in which these N-containing compounds form thermal decomposition products such as ammonia and isocyanic acid due to thermal decomposition of these compounds themselves, thereby resulting in the formation of inactive polymers due to reaction with isocyanate.

However, the inventors of the present invention found that a composition containing a specific amount of N-containing compound contributes to inhibition of denaturation reactions of N-substituted carbamic acid-O—Ar ester during transfer and storage of the composition. Moreover, the inventors of the present invention also found that this composition has the effect of enhancing isocyanate yield when isocyanate is produced using the composition. Such an effect was heretofore unknown and is surprising. Although the mechanism by which this effect is demonstrated is unclear, the inventors of the present invention have surmised that, during transfer and storage of the composition, the N-containing compound traps minute amounts of water and oxygen present thereby inhibiting denaturation of N-substituted carbamic acid-O—Ar ester. In addition, the inventors of the present invention have also surmised that, during production of isocyanate using the composition, the N-containing compound functions as a thermal decomposition catalyst of N-substituted carbamic acid-O—Ar ester.

Thus, the composition for transfer and storage is preferably a composition in which the N-substituted carbamic acid-O—Ar ester is an N-substituted carbamic acid-O—Ar ester produced from the organic amine, the carbonic acid derivative and the aromatic hydroxy composition, and the composition for transfer and storage contains at least one type of urea and/or carbamic acid ester and/or biuret and/or compound having a terminal biuret group (—NH—(C=O)—NH—(C=O)—NH$_2$) derived from an organic amine that is formed in a reaction between the organic amine, the carbonic acid derivative and the aromatic hydroxy composition.

The components that compose the composition of the present embodiment as well as the composite ratios of each component are as indicated below.

In the composition for transfer and storage, the ratio the number of molecules (B) of an aromatic hydroxy compound that composes the aromatic hydroxy composition to the number of ester groups (A) that compose the N-substituted carbamic acid-O—Ar ester in the composition for transfer and storage is preferably within a range of from 1 to 100. In the case of assuming a mechanism like that described above, although B is preferably in large excess with respect to A since the concentrations of N-substituted carbamic acid-O—Ar ester and N-containing compounds contained in the composition are preferably as low as possible, on the other hand, if an overly excessive amount of aromatic hydroxy composition is used, the transfer efficiency of the N-substituted carbamic acid-O—Ar ester may decrease or the storage tank used during storage becomes excessively large. In addition, when isocyanate is produced using the composition for transfer and storage (to be described later), a reverse reaction between the aromatic hydroxy compound present in large excess and the isocyanate formed may occur easily, or the formation efficiency of isocyanate may decrease. In consideration of the above points, the ratio of B to A is more preferably from 2 to 50 and even more preferably from 3 to 20. The aromatic hydroxy compound that composes the aromatic hydroxy composition preferably contained in the composition is an aromatic hydroxy compound represented by the above-mentioned formula (46), (55), (56), (67), (70) or (79).

The N-containing compound is urea (H$_2$N—C(=O)—NH$_2$), carbamic acid ester, biuret (H$_2$N—C(=O)—NH—C(=O)—NH$_2$) or compound having a terminal biuret group (—NH—(C=O)—NH—(C=O)—NH$_2$) derived from an organic amine that is formed in a reaction between organic amine, carbonic acid derivative and aromatic hydroxy composition. The preferable content thereof in the composition is as indicated below.

The composition for transfer and storage is further a composition for transfer and storage in which the N-substituted carbamic acid-O—Ar ester is an N-substituted carbamic acid-O—Ar ester obtained by reacting an organic amine, a carbonic acid derivative and an aromatic hydroxy composition, wherein the total of the number of molecules of urea (H$_2$N—C(=O)—NH$_2$) (V), the number of molecules of carbamic acid ester (W), the number of molecules of biuret (H$_2$N—C(=O)—NH—C(=O)—NH$_2$)(X) and the total number of terminal biuret groups (—NH—(C=O)—NH—(C=O)—NH$_2$) of a compound having terminal biuret groups derived from an organic amine that is formed in a reaction between organic amine, carbonic acid derivative and aromatic hydroxy composition (Y), namely (V+W+X+Y), is preferably from 0.0001 to 0.05 based on the number of the N-substituted carbamic acid-O—Ar esters.

As has been described above, a certain amount of N-substituted compound is preferably contained in the composition in order to stabilize the N-substituted carbamic acid-O—Ar ester and improve the yield of isocyanate. On the other hand, however, if an excessively large amount of N-substituted compound is contained, polymers may form and adhere to or solidify in the reactor due to reaction with isocyanate formed during thermal decomposition. Thus, the above-mentioned total number (V+W+X+Y) is preferably within a range of from 0.0001 to 0.03 and more preferably within a range of from 0.0001 to 0.01 based on the N-substituted carbamic acid-O—Ar ester. The total number (V+W+X+Y) can be determined by known methods. For example, components contained in the composition can be identified and quantified by analyzing the composition by a method such as gas chromatography or liquid chromatography. Furthermore, although the lower limit was defined above as being 0.0001, this was set by the inventors of the present invention based on the lower detection limit when determining the total number (V+W+X+Y).

In addition, the composition for transfer and storage is preferably a composition that contains a carbonic acid ester derived from the aromatic hydroxy composition. The inventors of the present invention found that a composition containing a specific amount of a carbonic acid ester derived from the aromatic hydroxy composition contributes to stabilization of the N-substituted carbamic acid-O—Ar ester during transfer of the composition and during storage of the composition. Such an effect was heretofore unknown and is surprising. Although the mechanism by which this effect is demonstrated is unclear, the inventors of the present invention surmise that, similar to the case of N-containing compounds, the carbonic acid ester traps minute amounts of water and oxygen present during transfer and storage of the composition, thereby inhibiting denaturation of N-substituted carbamic acid-O—Ar ester. The preferable content of the carbonic acid ester is such that the number of carbonic acid esters derived from the aromatic hydroxy composition is within a range of from 0.0001 to 0.05 based on the number of the N-substituted carbamic acid-O—Ar ester. Although it is preferable that the carbonic acid ester be contained to a certain degree, since there are cases in which side reactions occur during thermal decomposition if the carbonic acid ester is contained in large excess, a range thereof is preferably from 0.0001 to 0.03 and more preferably from 0.0001 to 0.01. A carbonic acid ester preferably contained in the composition is a carbonic acid ester represented by the above-mentioned formula (44), and there are many cases in which the carbonic acid ester is a compound formed by a reaction with the above-mentioned carbonic acid derivative and hydroxy composition during the course of production of N-substituted carbamic acid-O—Ar ester.

The composition for transfer and storage may also contain a component other than the previously described compounds (N-substituted carbamic acid-O—Ar ester, aromatic hydroxy compound, N-containing compound and carbonic acid ester). Examples of such components may include compounds having a ureylene group (—NHCONH—) in a molecule thereof, Fries rearrangement products of N-substituted carbamic acid-O—Ar esters, non-N-substituted carbamic acid esters, compounds having a ureido group, water, alcohols and inert gases (such as nitrogen gas, carbon dioxide gas, argon gas or ammonia).

Furthermore, an ureylene group (—NHCONH—) may also be referred to as a ureine group in the explanation of the present embodiment.

Although there are no particular limitations on the amounts at which these components are contained, the amounts thereof are preferably adjusted as the occasion demands if it appears that undesirable side reactions occur depending on the storage temperature and the like. Particularly noteworthy components are oxygen, ammonia, water, oxidizing substances and reducing substances. There are many cases in which the composition for transfer and storage contains compounds containing nitrogen atoms, or the aromatic hydroxy compound may be denatured as a result of being oxidized by oxygen resulting in the occurrence of phenomena such as coloring. In addition, since the composition becomes a flammable composition in nearly all cases, oxygen gas is to be managed using known methods in the same manner as ordinary storage of organic chemical substances carried out in this technical field. For example, the concentration of gas-phase oxygen in a storage tank is controlled by purging with nitrogen so that the oxygen concentration is 10% or less, preferably 1% or less and more preferably 100 ppm or less. In the case of allowing an inert gas such as nitrogen to flow through gas-phase portions, the oxygen concentration of the insert gas is controlled to 10 ppm or less. The composition contains ammonia at from 1 to 1000 ppm, preferably from 1 to 300 ppm, more preferably from 1 to 100 ppm and most preferably from 1 to 10 ppm.

Moreover, the composition preferably does not contain a transesterification catalyst (the transesterification catalyst refers to a catalyst used in a reaction of a transesterification step to be described hereinafter). As a result of studies conducted by the inventors of the present invention, the transesterification catalyst was found to have the effect of facilitating the occurrence of reaction causing denaturation of the N-substituted carbamic acid-O—Ar ester. Thus, the content of the transesterification catalyst is preferably 2000 ppm or less, more preferably 600 ppm or less, even more preferably 200 ppm or less and most preferably 20 ppm or less.

Although the amount of ammonia is preferably as low as possible in consideration of equilibrium as is also known in the prior art, it was surprisingly found to have the effect of inhibiting reactions causing denaturation of the N-substituted carbamic acid-O—Ar ester by catalyst components in the composition (such as metal ions and transesterification catalysts dissolved therein) when present in small amounts. The amount of ammonia described above is the amount of ammonia at the start of transfer and storage, and as was previously explained, may be consumed during transfer and storage due to the effect of inhibiting the catalyst components. The composition for transfer and storage preferably has the amount of ammonia described above during production of the composition for transfer and storage, during preparation thereof, when placing the composition in a storage tank, or at the start of transfer. A known method may be carried out to adjust the amount of ammonia such as purging a liquid phase with an inert gas such as nitrogen.

Moreover, the ranges described above are preferable for the amount of transesterification catalyst contained in the composition as previously described. The transesterification catalyst refers to a Lewis acid or transition metal compound that forms a Lewis acid, organic tin compound, copper group metal, zinc or iron group metal compound. Specific examples may include Lewis acids and transition metal compounds that form a Lewis acid such as $AlX_3$, $TiX_3$, $TiX_4$, $VOX_3$, $VX_5$, $ZnX_2$, $FeX_3$ or $SnX_4$ (wherein X represents a halogen, an acetoxy group, an alkoxy group or an aryloxy group); organic tin compounds such as $(CH_3)_3SnOCHCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl$ or $BuSnO(OH)$; copper family metal compounds such as $CuCl$, $CuCl_2$, $CuBr$, $CuBr_2$, $CuI$, $CuI_2$, $Cu(OAc)_2$, $Cu(acac)_2$, copper olefinate, $Bu_2Cu$, $(CH_3O)_2Cu$, $AgNO_3$, $AgBr$, silver picrate or $AgC_6H_6ClO_4$; zinc compounds such as $Zn(acac)$; and, iron family metal compounds such as $Fe(C_{10}H_5)(CO)_5$, $Fe(CO)_5$, $Fe(C_4H_6)(CO)_3$, $Co(mesytilene)_2(Pet_2Ph_2)$, $COC_5F_5(CO)_7$ or ferrocene. (In the above listing of examples, Bu refers to a butyl group, Ph refers to a phenyl group, and acac refers to an acetyl acetone chelate ligand.)

Although varying according to the composition of the composition, the concentration of water is managed to 10% by weight or less and preferably 1% by weight or less since the presence of a large amount of water may cause phenomena that prevent the composition from being uniform, and in the case of using the composition as a raw material of an N-substituted carbamic acid-O—Ar ester, the concentration of water is more preferably controlled to 100 ppm or less since the presence of a large amount of water can cause side reactions derived from the water. The concentration of water may be controlled by a known method such as the use of a dehydrating agent or desiccant, distilling under reduced pressure, increased pressure or normal pressure, or purging a liquid phase with an inert gas to remove the water together with the inert gas. Since the presence of an oxidizing substance or reducing substance may cause denaturation of the aromatic hydroxy compound, these substances are controlled using a known method for controlling aromatic hydroxy compounds. Oxidizing substances refer to Bronsted acids such as organic acids or inorganic acids and Lewis acids, while reducing substances refer to Bronsted bases such as organic bases or inorganic bases, Lewis bases and hydrogen gas. Reducing substances do not include compounds derived from the composition, such as the above-mentioned ammonia, carbonic acid derivative or compounds that compose the composition.

Although there are no particular limitations on the conditions for storage and transfer of the composition, there are conditions at which a thermal decomposition reaction of the N-substituted carbamic acid-O—Ar ester occurs extremely easily at high temperatures. Although varying according to the storage period, although storage is carried out within a range of from −40 to 280° C., and in cases in which fluidity and stability are impaired, at from 0 to 260° C. and preferably from 40 to 260° C., storage temperature may be controlled corresponding to the application of the composition, the storage period and the handling ease of the composition. Although storage and transfer are carried out within their respective temperature ranges, when using the composition as a raw material for production of isocyanate and when transferring to a reactor for thermal decomposition of N-substituted carbamic acid-O—Ar ester, transfer may be carried out after confirming that transfer can be carried out safely according to the conditions of the thermal decomposition reaction and the equipment accompanying the thermal decomposition reactor since transfer to the thermal decomposition reactor is typically carried out after preheating to the reaction temperature. Generally, transfer is carried out within a range of from −40 to 280° C., and in cases in which fluidity and stability are impaired, is carried out at from 0 to 260° C. and preferably at from 40 to 260° C. Transfer may be controlled depending on the application of the composition, transfer time and handling ease of the composition as previously described. Although there are no particular limitations on pressure during transfer, storage may be carried out under conditions of reduced pressure to conditions of increased pressure. When storing under reduced pressure, since the aromatic hydroxy composition may be distilled off, the ratio of the N-substituted carbamic acid-O—Ar ester and aromatic hydroxy composition in the composition is controlled to be within the previously described range. There are no particular limitations on storage vessels, lines and the like during storage and transfer. A vessel is selected in accordance with applicable handling regulations in consideration of the handling of a flammable organic substance while paying attention to the flash point of the composition being handled. There are also no particular limitations on the material, and a known material can be used. Examples of materials may include glass, stainless steel, carbon steel, Hastelloy, glass-lined base materials and Teflon (registered trademark) coated materials. Known equipment may be incidentally provided as necessary as equipment for storage and transfer of the composition, such as pumps, temperature control equipment or instrumentation.

The composition for transfer and storage of N-substituted carbamic acid-O—Ar esters indicated above may be prepared by mixing an N-substituted carbamic acid-O—Ar ester, an aromatic hydroxy composition, a N-containing compound and a carbonic acid ester so as to be formulated in the ranges previously described, and is obtained in the production of N-substituted carbamic acid ester. The composition may also be prepared by adding and/or removing the aromatic hydroxy composition, N-containing compound and carbonic acid ester so as to be formulated in the ranges previously described by using a composition containing N-substituted carbamic acid-O—Ar ester as a base. The method for producing the N-substituted carbamic acid-O—Ar ester can be preferably carried out in the manner indicated below. It goes without saying that a composition containing N-substituted carbamic acid-O—Ar ester, which is obtained in the production of N-substituted carbamic acid-O—Ar ester, can also be used as is. The method for producing N-substituted carbamic acid-O—Ar ester can be preferably carried out according to a method indicated hereinafter.

<Reaction of Organic Amine, Carbonic Acid Derivative and Hydroxy Composition>

The following provides an explanation of a method for producing N-substituted carbamic acid ester from an organic amine, a carbonic acid derivative and a hydroxy composition.

The method for producing N-substituted carbamic acid ester of the present embodiment can be generally divided into the following two methods:

(1) a method in which a step (A) is carried out comprising the production of N-substituted carbamic acid-O-(Ar and/or $R^2$) ester by "simultaneously" reacting the organic amine, the carbonic acid derivative and the hydroxy composition, and (2) a method that separates the steps for producing N-substituted carbamic acid-O-(Ar and/or $R^2$) ester from the organic amine, the carbonic acid derivative and the hydroxy composition, in which a compound having an ureido group is produced by reacting the organic amine and the carbonic acid derivative in a step (a), and an N-substituted carbamic acid-O-(Ar and/or $R^2$) ester is produced by reacting the compound having an ureido group and the hydroxy composition in a subsequent step (b).

In the production method of the present embodiment, method (1) and (2) may also be combined. The above-mentioned N-substituted carbamic acid-O-(Ar and/or $R^2$) ester refers to an N-substituted carbamic acid-O—Ar ester and/or an N-substituted carbamic acid-O—$R^2$ ester.

Figure 2:
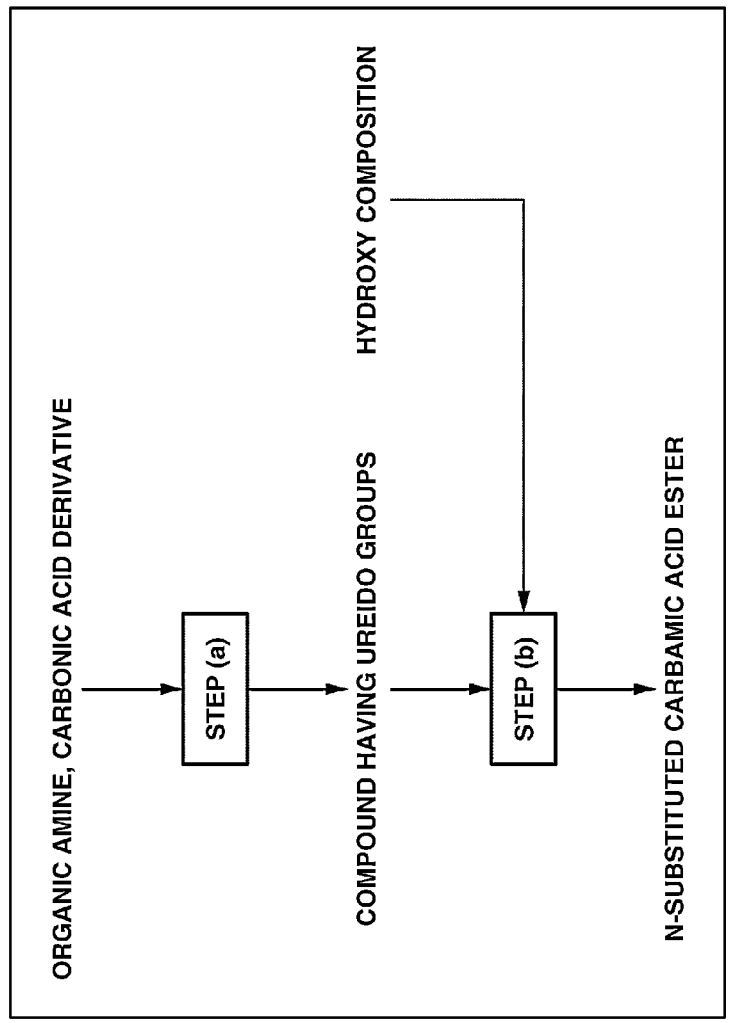
FIG. 2 shows a conceptual drawing depicting one aspect of the present embodiment in the form of a production method of N-substituted carbamic acid ester comprising step (a) and step (b)

FIG. 1 shows a conceptual drawing representing a production method of N-substituted carbamic acid ester according to step (A) in (1), while FIG. 2 shows a conceptual drawing representing a production method of N-substituted carbamic acid ester composed of step (a) and step (b) in (2).

<Step (A)>

A description is first provided of the method of (1) (Step (A)).

In contrast to "simultaneously" in the method of (1) referring to the steps for producing N-substituted carbamic acid ester being divided into two steps in the method of (2), these steps are not divided in the method of (1), and does not necessarily refer to reacting the organic amine, the carbonic acid derivative and the hydroxy composition at precisely the same time.

Step (A) is a step in which the organic amine, the carbonic acid derivative and the hydroxy composition are reacted using a urethane production reactor equipped with a condenser, the hydroxy composition, a compound having a carbonyl group derived from the carbonic acid derivative, and a gas containing ammonia produced as a by-product in the reaction are introduced into the condenser provided in the urethane production reactor, and an N-substituted carbamic acid ester is produced in which the hydroxy composition and the compound having the carbonyl group derived from the carbonic acid derivative are condensed. A urethane production reactor as referred to herein indicates a reactor in which production of N-substituted carbamic acid ester is carried out.

Although the reaction conditions for producing N-substituted carbamic acid ester by reacting the organic amine, the carbonic acid derivative and the hydroxy composition vary according to the reacted compounds, the amount of the hydroxy composition is within a range of a stoichiometric ratio of from 1 to 500 times the amino groups of the organic amine used. Although is preferable to use a large excess of the hydroxy composition since complexly substituted carbonyl compounds and the like are formed easily if the amount of the hydroxy composition used is excessively low, in consideration of the size of the reactor, it is preferably within a range of from 1 to 200 times, more preferably within a range of from 1.5 to 100 times, and even more preferably within a range of from 2 to 50 times.

The amount of the carbonic acid derivative is within a range of a stoichiometric ratio of from 1 to 10 times the amino groups of the organic amine used. Although it is preferable to use an excess of carbonic acid derivative since complexly substituted carbonyl compounds and the like are also formed easily if the amount of carbonic acid derivative used is low, if an overly excessive amount of carbonic acid derivative is used, complexly substituted carbonyl compounds may be conversely formed easily or unreacted carbonic acid derivative may remain resulting in excessive effort being required to separate and recover the carbonic acid derivative (to be described later). Consequently, the amount of carbonic acid derivative is preferably within a range of from 1.1 to 10 times and more preferably within a range of from 1.5 to 5 times.

Although varying according to the reactivities of the organic amine, carbonic acid derivative and hydroxy composition used, the reaction temperature is preferably within a range of from 100 to 350° C. If the temperature is lower than 100° C., the reaction slows or the reaction hardly proceeds at all due to strong bonding of the by-product ammonia to the hydroxy composition, or complexly substituted carbonyl compounds increase, thereby making this undesirable. On the other hand, at temperatures higher than 350° C., the carbonic acid derivative breaks down, the hydroxy composition is denatured by dehydrogenation or there is increased susceptibility to the occurrence of decomposition or denaturation of the product in the form of N-substituted carbamic acid ester, thereby making this undesirable. From such viewpoints, the reaction temperature is more preferably within a range of from 120 to 320° C. and even more preferably within a range of from 140 to 300° C.

Although the reaction pressure varies according to the composition of the reaction system, reaction temperature, method used to remove ammonia, reaction apparatus and the like and the reaction can be carried out at reduced pressure, normal pressure or increased pressure, generally it is preferably carried out within a range of from 0.01 kPa to 10 MPa (absolute pressure). In consideration of ease of industrial application, the reaction is preferably carried out at reduced pressure or normal pressure, and the reaction pressure is preferably within a range of from 0.1 kPa to 1.5 MPa (absolute pressure).

In the step (A), the reaction that forms N-substituted carbamic acid ester is frequently carried out mainly in the liquid phase. Thus, the hydroxy composition is preferably present in the form of a liquid phase component under the reaction conditions. On the other hand, as will be described later, since the hydroxy composition and the compound having carbonyl groups derived from the carbonic acid derivative (to be described in detail hereinafter) are introduced into the condenser in the form of a gaseous phase component and are condensed in the condenser, the hydroxy composition is preferably present as a gaseous phase component under the reaction conditions. Thus, the reaction conditions are set such that a portion of the hydroxy composition is present in a form of a liquid phase component, while a portion is also present in a form of a gaseous phase component. In the case of using a hydroxy composition composed of a plurality of hydroxy compounds, the reaction conditions are set such that at least one type of the hydroxy compounds is present as a liquid phase component. Since such reaction conditions (reaction temperature and pressure) are intimately related to the properties of the hydroxy composition used and particularly to the correlation between temperature and vapor pressure, the properties of the hydroxy composition used (correlation between temperature and vapor pressure) are measured or investigated and used as an indicator for determining the reaction conditions. Incidentally, it is a matter of common sense among persons with ordinary skill in the art that the correlation between the properties of temperature and vapor pressure differ greatly depending on the purity of the substance and the types and amounts of other compounds present, and when setting the reaction conditions as well, it is self-evident that not only the properties of the hydroxy composition (correlation between temperature and vapor pressure), but also the types and amounts of other compounds present should also be taken into consideration.

As a result of extensive studies conducted by the inventors of the present invention, the reaction that forms N-substituted carbamic acid ester from the organic amine, the carbonic acid derivative and the hydroxy compound was found to be an equilibrium reaction that is considerably biased towards the reactants side. Thus, in order to increase the yield of N-substituted carbamic acid ester, it is necessary to carry out the reaction while removing as much of the by-product ammonia as possible from the system. Ammonia is removed so that the concentration of ammonia in the reaction liquid is preferably 1000 ppm or less, more preferably 300 ppm or less, even more preferably 100 ppm or less and most preferably 10 ppm or less. Ammonia can be removed using methods such as reactive distillation, use of an inert gas, membrane separation and adsorptive separation. For example, the reactive distillation refers to a method for separating continuously formed ammonia during the reaction by distillation in the form of a gas. This can be carried out while boiling a solvent or hydroxy composition in order to increase the distillation efficiency of the ammonia. In addition, a method using an inert gas refers to a method for separating continuously formed ammonia during the reaction from the reaction system in the form of a gas along with the inert gas. Examples of inert gases used include nitrogen, helium, argon, carbon dioxide, methane, ethane and propane, these may be used alone or as a mixture, and a method in which the inert gas is introduced into the reaction system is preferable. Examples of adsorbents used in methods using adsorptive separation may include adsorbents able to be used under the temperature conditions at which the reaction is carried out, such as silica, alumina, various types of zeolite or diatomaceous earth. These methods for removing ammonia outside the system may be carried out alone or a plurality of types may be carried out in combination.

A catalyst can be used in the reaction for the purpose of increasing the reaction rate, for example. Examples of catalysts that are used preferably may include basic catalysts such as methylates, ethylates or butyrates (including isomers) of lithium, sodium, potassium, calcium or barium, rare earth elements, antimony or bismuth alone or oxides, sulfides and salts thereof, boron alone or boron compounds, metals of the copper family, zinc family, aluminum family, carbon family and titanium family in the periodic table as well as metal oxides and sulfides thereof, and carbides and nitrides of elements of the carbon family excluding carbon, titanium family, vanadium family and chromium family in the periodic table. Although there are no particular limitations on the amount of catalyst used in the case of using a catalyst, a catalyst can be used within a range of a stoichiometric ratio of from 0.0001 to 100 times the amino groups of the amine compound. Since there are many cases in which it is necessary to remove the catalyst if a catalyst is added, the reaction is preferably carried out without adding a catalyst. In the case of using a catalyst, the catalyst may be removed following the reaction. Since there are cases in which a catalyst may have a detrimental effect on compounds formed during the steps of the present embodiment, the catalyst is preferably separated or removed during the course of obtaining isocyanate by thermal decomposition of N-substituted carbamic acid-O—Ar ester and purification of the isocyanate. If the isocyanate is stored together with the catalyst, there are cases in which undesirable phenomena such as discoloration may occur. A known method can be used to remove the catalyst, and methods such as membrane separation, distillative separation and crystallization can be used. The catalyst is preferably removed for the reasons described above without being limited to step (A). More preferably, the catalyst is removed at completion of each step in which it is used. Known methods as previously described can be preferably used to remove the catalyst.

Although varying according to the composition of the reaction system, reaction temperature, method used to remove ammonia, reaction apparatus, reaction pressure and the like, the reaction time (residence time in the case of a continuous reaction) is generally from 0.01 to 100 hours. The reaction time can also be determined according to the formation amount of the target compound in the form of N-substituted carbamic acid ester. For example, the reaction may be stopped after having sampled the reaction liquid, determined the content of N-substituted carbamic acid ester in the reaction liquid and confirming that the N-substituted carbamic acid ester has been formed at a yield of 10% or more based on the organic amine used, or the reaction may be stopped after having confirmed that the yield is 90% or more. In the case of using an aromatic hydroxy composition for the hydroxy composition, the reaction liquid containing N-substituted carbamic acid-O—Ar ester obtained by the production method can be used as is as a transfer and storage composition for N-substituted carbamic acid-O—Ar ester as previously described, or can be used by preparing by adding and/or removing the aromatic hydroxy composition, N-containing compound and carbonic acid ester, and although the composition for transfer and storage of N-substituted carbamic acid-O—Ar ester can be preferably used to produce isocyanate, if the content of the N-substituted carbamic acid-O—Ar ester at that time is low (the yield is low), a decrease in the yield of isocyanate results.

In the case of using an alcohol for the hydroxy composition, although N-substituted carbamic acid-O—$R^2$ ester is obtained in the reaction of step (A), the N-substituted carbamic acid-O—$R^2$ ester is also used to produce isocyanate after having converted to an N-substituted carbamic acid-O—Ar ester by various steps to be described later. Thus, a decrease in the yield of isocyanate also results in the case of a low yield of N-substituted carbamic acid-O—$R^2$ ester.

From the above viewpoints, the yield is preferably 50% or more, more preferably 80% or more and even more preferably 90% or more.

Although the use of a reaction solvent is not necessarily required in the reaction, a suitable solvent is preferably used as a reaction solvent for the purpose of facilitating the reaction procedure, examples of which may include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and sulfoxides such as dimethylsulfoxide or diphenylsulfoxide. Naturally, a hydroxy composition used in excess in the reaction is also preferably used as a reaction solvent.

The reaction is carried out in a system having a gaseous phase containing a hydroxy composition, a compound having carbonyl groups derived from a carbonic acid derivative and ammonia produced as a by-product in the reaction, and a liquid phase in which the reaction is carried out. Although the reaction can also be carried out in the gaseous phase depending on the reaction conditions, the majority of the reaction is carried out in the liquid phase. At that time, the volumetric content of the liquid phase in the reaction in which the reaction is carried out is preferably 50% or less. In the case of carrying out the reaction continuously over a long period of time, although polymeric by-products may form due to fluctuations in operating conditions (such as temperature or pressure) and the like, if the volumetric content of the liquid phase in the reactor is high, adhesion and accumulation of such polymeric by-products in the reactor can be avoided. However, since the efficiency of removal of by-product ammonia may become poor and the yield of the N-substituted carbamic acid ester may decrease if the volumetric content of the liquid phase is excessively high, the volumetric content of the liquid phase based on the gaseous phase is preferably 50% or less, more preferably 30% or less and even more preferably 20% or less (the volumetric content of the liquid phase refers to volumetric ratio of the liquid phase based on the volume of the reaction tank in the case of a tank-type reactor, the volume of the stage lower than the feed stage (not including the tank bottom and reboiler) in the case of a column-type reactor, or the volume of the thin film distiller in the case of a thin film distiller).

There are no particular limitations on the reactor used when carrying out the reaction (namely, a urethane production reactor) provided it is equipped with a condenser, and although a known reactor can be used, a tank-type and/or a column-type reactor equipped with a condenser is used preferably.

As was previously described, the reaction is preferably carried out in a system having a gaseous phase containing a hydroxy composition, a compound having carbonyl groups derived from a carbonic acid derivative and ammonia produced as a by-product in the reaction, and a liquid phase in which the reaction is carried out under conditions such that the volumetric content of the liquid phase in the reactor is 50% or less, and a reactor that satisfies these conditions is selected for the reactor in which the reaction is carried out.

More specifically, conventionally known reactors can be suitably combined and used, examples of which may include a stirring tank, a pressurized stirring tank, a reduced pressure stirring tank, a column-type reactor, a distillation column, a packed column or a thin film distiller.

There are no particular limitations on the type of condenser provided in the reactor and a known condenser can be used. For example, conventionally known condensers such as a multitubular cylindrical condenser, double tube condenser, single tube condenser or air-cooled condenser can be suitably combined and used. The condenser may be provided inside the reactor or provided outside the reactor or may be connected with the reactor by a line, and various types can be employed in consideration of the forms of the reactor and condenser, the manner in which condensed liquid is handled and the like.

There are no particular limitations on the materials of the reactor and condenser and known materials can be used. Examples of materials that can be used may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Steps may also be added as necessary. For example, steps and apparatuses able to be conceived by a person or engineer with ordinary skill in the art may be added, such as a step of removing the ammonia formed, a step of purifying the organic primary amine, a step of dissolving the urea in the aromatic hydroxy compound, a step of dissolving the aromatic hydroxy compound, a step of separating the alcohol, a step of separating and/or purifying the aromatic hydroxy compound, a step of purifying the compound having ureido groups from the formed reaction liquid or a step of incinerating or discarding by-products and the like.

The N-substituted carbamic acid ester obtained by the reaction described above is an N-substituted carbamic acid-O—$R^2$ ester represented by the above-mentioned formula (92) in the case an alcohol is used for the hydroxy compound that composes the hydroxy composition. In addition, the resulting N-substituted carbamic acid ester is an N-substituted carbamic acid-O—Ar ester represented by the above-mentioned formula (104) in the case an aromatic hydroxy compound is used for the hydroxy compound that composes the hydroxy composition.

Although the production method of N-substituted carbamic acid ester of the present invention contains reacting an organic amine, a carbonic acid derivative and a hydroxy composition using a reactor equipped with a condenser to produce an N-substituted carbamic acid ester, the following provides an explanation of handling of gaseous components formed in the reaction containing the hydroxy composition, the compound having carbonyl groups derived from the carbonic acid derivative and the ammonia produced as a by-product.

In the method of the present embodiment, a gas containing the hydroxy composition, the compound having carbonyl groups derived from the carbonic acid derivative and the ammonia formed as a by-product in the reaction is introduced into a condenser provided in the reactor, all or a portion of the hydroxy composition and all or a portion of the compound having carbonyl groups derived from the carbonic acid derivative are condensed, the hydroxy compound contained in the condensed hydroxy composition is at a stoichiometric ratio of 1 or more based on the compound having carbonyl groups derived from the condensed carbonic acid, and the ratio of the number of carbonyl groups (—C(=O)—) contained in the compound having carbonyl groups derived from the carbonic acid derivative contained in ammonia recovered from the condenser in a form of a gas to the number of ammonia molecules is 1 or less.

Figure 3:
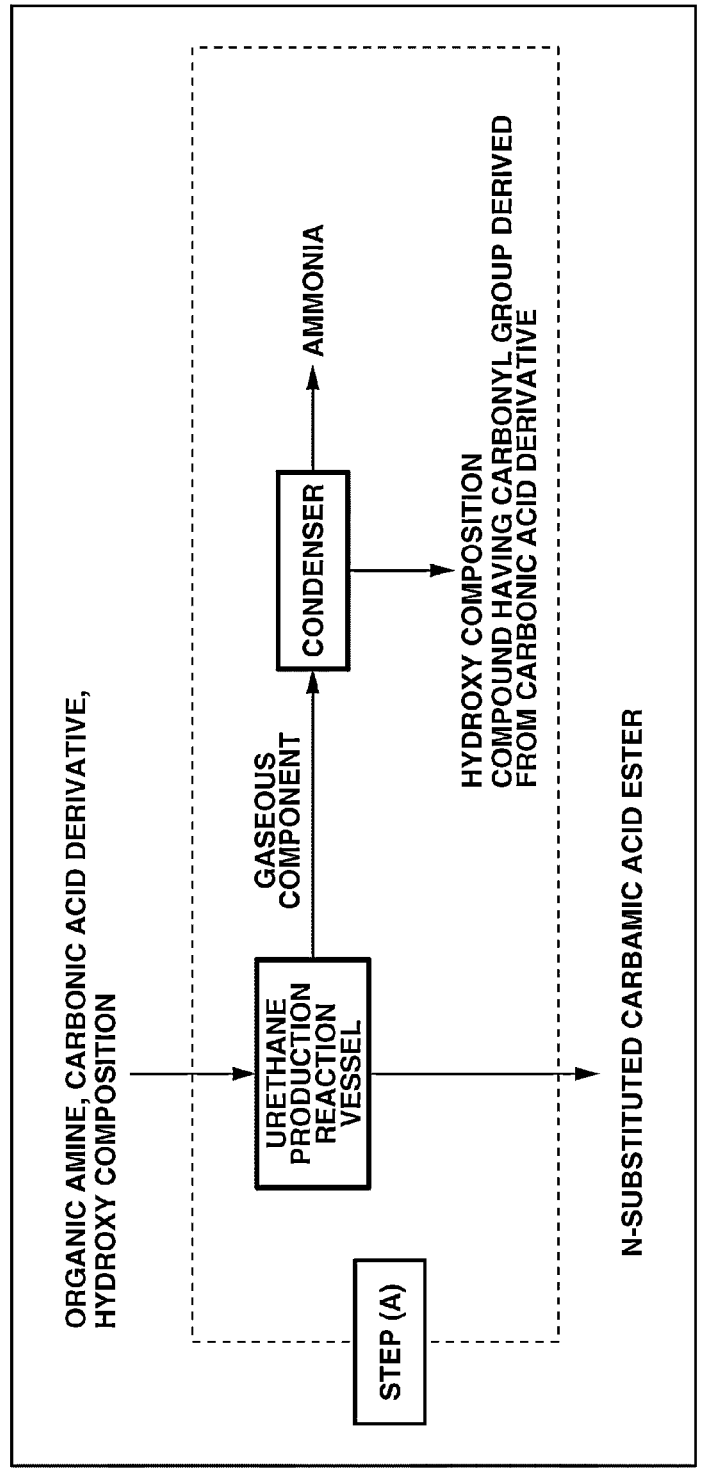
FIG. 3 shows a conceptual drawing depicting handling of gaseous components relating to a production method of N-substituted carbamic acid ester in the present embodiment.

FIG. 3 shows a conceptual drawing depicting handling of gaseous component relating to the production method of N-substituted carbamic acid ester of the present embodiment.

<Condensation of Gaseous Components>

In the reaction, a gas containing the hydroxy composition, the compound having carbonyl groups derived from the carbonic acid derivative, and ammonia formed as a by-product in the reaction is introduced into the condenser, and all or a portion of the hydroxy composition and the compound having carbonyl groups derived from the carbonic acid derivative are condensed (see FIG. 3). At that time, the hydroxy compound contained in the condensed hydroxy composition is at a stoichiometric ratio of 1 or more based on the condensed compound having carbonyl groups derived from the carbonic acid derivative.

The "compound containing carbonyl groups derived from the carbonic acid derivative" condensed in the condenser in the present embodiment refers to compounds having carbonyl groups derived from the carbonic acid derivative used in the reaction between the organic amine, carbonic acid derivative and hydroxy composition, and include the carbonic acid derivative itself used as a raw material (unreacted substance and/or excess portion in the case of using in excess based on the organic amine), compounds resulting from the reaction between the carbonic acid derivative and the hydroxy composition, and compounds resulting from the reaction of the same type or different types of carbonic acid derivatives. Although it is difficult to identify all compounds having carbonyl groups derived from carbonic acid derivatives, specific examples thereof may include the urea and carbamic acid ester used as raw materials, urea compounds such as isocyanic acid, urea, biurets (compounds on the right side of the above-mentioned formula (G)), nurates (compounds of the first parameter on the right side of the above-mentioned formula (K)) or urea polymers (compounds on the right side of the above-mentioned formula (L)) formed as by-products, carbamic acid esters in which the ester group is a group derived from the hydroxy composition, and carbonic acid esters in which the ester group is a group derived from the hydroxy composition. Compounds having carbonyl groups derived from the carbonic acid derivative can be quantified by methods in which carbonyl groups contained in the compound are detected by a method such as infrared spectroscopy, near infrared spectroscopy, Raman spectroscopy or ultraviolet spectroscopy, or can be quantified by a method that specifically analyzes compounds formed such as gas chromatography, liquid chromatography or NMR. These compounds having carbonyl groups derived from the carbonic acid derivative frequently have a high melting point and tend to precipitate easily. Among the compounds having carbonyl groups derived from the carbonic acid derivative listed above, urea in particular requires the greatest caution since it is formed in large amounts (detected in large amounts) and has a melting point of 135° C.

As a result of making the stoichiometric ratio of the hydroxy compound contained in the condensed hydroxy composition to be 1 or more based on the condensed compound having carbonyl groups derived from the carbonic acid derivative in the condensation procedure, a mixture thereof can be obtained in the form of a homogeneous liquid mixture in the condenser. Thus, not only does this facilitate handling of the mixture, but it is also possible to avoid the occurrence of problems such as adhesion and accumulation of solid components in the condenser. In addition, as will be described later, this is also effective for reducing the amount of compounds having carbonyl groups derived from the carbonic acid derivative contained in ammonia recovered from the condenser to equal to or less than a specific amount. The amount of the hydroxy compound contained in the condensed hydroxy composition based on the condensed compound having carbonyl groups derived from the carbonic acid derivative in terms of the stoichiometric ratio is more preferably 2 or more and even more preferably 3 or more. In order to ensure that the amount of the hydroxy compound contained in the condensed hydroxy composition based on the condensed compound having carbonyl groups derived from the carbonic acid derivative is within the above ranges, the condenser is preferably maintained at a temperature at least 90° C. lower than the standard boiling point of the hydroxy composition at which the hydroxy composition does not solidify.

<Carbonyl Compound Content in Ammonia>

Although ammonia is recovered from the condenser in a form of a gas, the compound having carbonyl groups derived from the carbonic acid derivative contained in the ammonia is present in an amount equal to or less than a specific amount. More specifically, the ratio of the number of carbonyl groups (—C(=O)—) contained in the compound having carbonyl groups derived from the carbonic acid derivative contained in the ammonia to the number of ammonia molecules is 1 or less, preferably 0.5 or less, more preferably 0.1 or less and even more preferably 0.02 or less. The reason for specifying a specific range for the amount of the compound having carbonyl groups derived from the carbonic acid derivative contained in the ammonia is to avoid adhesion and accumulation of solid components in a line for transferring the ammonia from the condenser.

Although all solid components that adhere and accumulate in the line for transferring ammonia cannot be identified, as a result of studies conducted by the inventors of the present invention, the majority were determined to be compounds having carbonyl groups. Although one possible method for avoiding adhesion and accumulation of such solid components contains heating the line for transferring ammonia to decompose compounds having carbonyl groups, according to studies conducted by the inventors of the present invention, there are many cases in which heating alone causes polymerization of decomposition products (such as isocyanic acid) or reaction with other compounds having carbonyl groups, thereby making it difficult to completely avoid adhesion and accumulation of solid components. In addition, in the case of simply heating the line, it was determined that compounds having carbonyl groups contained in the ammonia and their decomposition products solidify as a result of being rapidly cooled at the outlet of the line for transferring ammonia (such as the portion in contact with the atmosphere), thereby frequently resulting in prominent adhesion and accumulation of solid components. As a result of conducting extensive studies regarding this problem, the inventors of the present invention found that the problem of adhesion and accumulation of solid components can be solved by making the amount of the compound having carbonyl groups derived from the carbonic acid derivative contained in the ammonia to be equal to or less than the specific amount described above, thereby leading to completion of the present invention. Although the mechanism by which this effect is demonstrated is unclear, the inventors of the present invention surmised that adhesion and accumulation in the line is caused by the compound having carbonyl groups derived from the carbonic acid derivative itself as well as decomposition and/or polymerization products of the compound having carbonyl groups derived from the carbonic acid derivative, and that by making the amount of carbonyl groups contained in the compound having carbonyl groups derived from the carbonic acid derivative equal to or less than a specific concentration, adhesion of the compound having carbonyl groups derived from the carbonic acid derivative itself as well as the reaction rates of decomposition and/or polymerization of that compound are lowered considerably.

The "compound having carbonyl groups derived from the carbonic acid derivative" refers to compounds having carbonyl groups derived from the carbonic acid derivative used in the reaction between the organic amine, the carbonic acid derivative and the hydroxy composition, and include the carbonic acid derivative itself used as a raw material (unreacted substance and/or excess portion in the case of using in excess based on the organic amine), compounds resulting from the reaction between the carbonic acid derivative and the hydroxy composition, and compounds resulting from the reaction of the same type or different types of carbonic acid derivatives. Although it is difficult to identify all compounds having carbonyl groups derived from the carbonic acid derivative, specific examples thereof may include the urea and carbamic acid ester used as raw materials, urea compounds such as isocyanic acid, urea, biurets (compounds on the right side of the above-mentioned formula (G)), nurates (compounds of the first parameter on the right side of the above-mentioned formula (K)) or urea polymers (compounds on the right side of the above-mentioned formula (L)) formed as by-products, carbamic acid esters in which the ester group is a group derived from the hydroxy composition, and carbonic acid esters in which the ester group is a group derived from the hydroxy composition. Although varying according to the conditions for production of N-substituted carbamic acid ester, caution is required regarding the urea, isocyanic acid, carbamic acid ester and carbonic acid ester among the above-mentioned compounds since they are frequently contained in the ammonia and are present in large amounts. According to studies conducted by the inventors of the present invention, if the amounts of these compounds in the ammonia are controlled to be within the preferable ranges described above, the problem of adhesion and accumulation of solid components in the line for transferring ammonia can generally be avoided.

Compounds having carbonyl groups derived from the carbonic acid derivative in ammonia can be quantified by various known methods, and methods such as gas chromatography, liquid chromatography, NMR, (near) infrared spectroscopy or ultraviolet spectroscopy can be used. More specifically, these compounds may be measured by, for example, introducing the ammonia as a gas directly into a gas chromatograph (such as by connecting the line for transferring ammonia directly to a gas chromatograph and injecting ammonia trapped in a bag or container for trapping gas such as a Tedlar bag into the gas chromatograph with a gastight syringe), or by absorbing compounds having carbonyl groups derived from the carbonic acid derivative contained in the ammonia with water or an organic solvent and the like, followed by measuring by gas chromatography, liquid chromatography, NMR, (near) infrared spectroscopy or ultraviolet spectroscopy. Among these methods, a method is carried out preferably in which the ammonia is introduced directly in the form of a gas into a gas chromatograph equipped with a mass analyzer to identify compounds having carbonyl groups, and the total sum of the products of the amounts of compounds having carbonyl groups and the number of carbonyl groups contained in the compounds having carbonyl groups is taken to be the amount of compounds having carbonyl groups derived form the carbonic acid derivative contained in the ammonia.

Since compounds having carbonyl groups derived from the carbonic acid derivative contained in amounts below the detection limit of the methods indicated here are present in extremely low concentrations in the ammonia, there are hardly any cases in which they have an effect on adhesion and accumulation of solid components in the ammonia transfer line, thereby allowing them to not be included in the "amount of compounds having carbonyl groups derived from the carbonic acid derivative" and be ignored.

<Reuse of Condensed Components>

The mixture of the hydroxy composition and the compound having carbonyl groups derived from the carbonic acid derivative condensed by the condenser as described above may be circulated within the reactor and reused in the reaction between the organic amine, the carbonic acid derivative and the hydroxy composition, the mixture may be recovered and the hydroxy composition and/or the compound having carbonyl groups derived from the carbonic acid derivative may be reused in the reaction between the organic amine, the carbonic acid and the hydroxy composition, or the mixture may be reused in the step of producing non-N-substituted carbamic acid ester (referring to step (c) to be described later, step (c) being a step that is preferably carried out in the form of a step of producing non-N-substituted carbamic acid ester in the case of using a non-N-substituted carbamic acid ester for the carbonic acid derivative).

Figure 4:
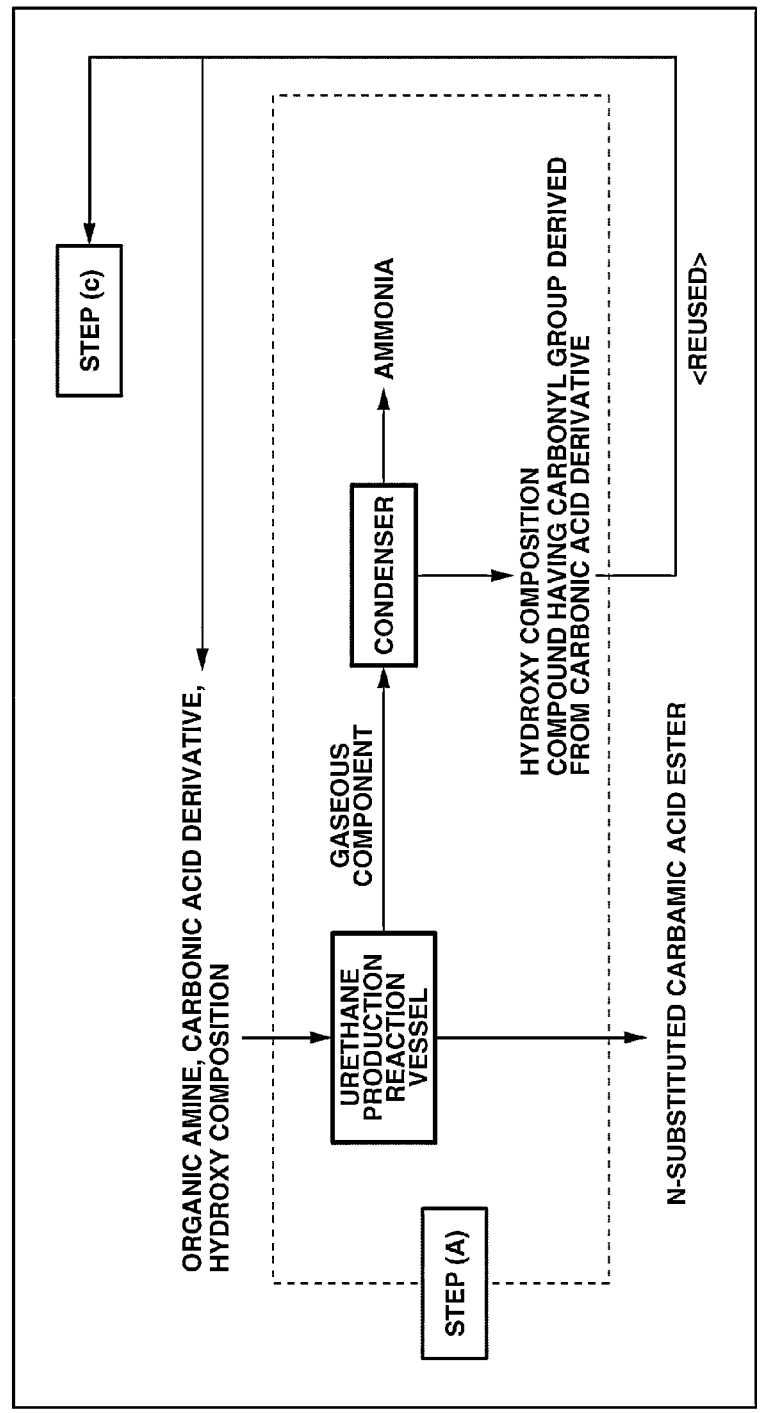
FIG. 4 shows a conceptual drawing depicting one aspect of the present embodiment in the form of reuse of condensed components.

FIG. 4 shows a conceptual drawing depicting one aspect of the present embodiment in the form of reuse of condensed components. When reusing condensed components, the amount of ammonia contained in the hydroxy composition and the compound having carbonyl groups derived from the carbonic acid derivative is preferably 5000 ppm or less. Although condensed components can be reused in the reaction between the organic amine, carbonic acid derivative and hydroxy composition even if ammonia is contained at greater than 5000 ppm, since the reaction between the organic amine, the carbonic acid derivative and the hydroxy composition is an equilibrium reaction as previously described, in order for the reaction to proceed efficiently, it is necessary to remove a product thereof in the form of the ammonia outside the system. If an overly excessive amount of ammonia is contained in the reused hydroxy composition and compound having carbonyl groups derived from the carbonic acid derivative, the amount of ammonia extracted from the reaction increases, thereby preventing the ammonia concentration in the reaction liquid from being lowered to the preferable range (range described above) as a result of exceeding the amount of ammonia able to be extracted per unit time (which is dependent on the capacity of the urethane production reactor, reaction conditions and the like), and causing a decrease in the yield of N-substituted carbamic acid ester. Thus, although it is preferable that the amount of ammonia contained in the hydroxy composition and compound having carbonyl groups derived from the carbonic acid derivative that are reused in the reaction be low, lowering the amount of ammonia to an extremely low level requires considerable effort. From this viewpoint, the amount of ammonia contained in the hydroxy composition and the compound having carbonyl groups derived from the carbonic acid derivative is more preferably 3000 ppm or less and even more preferably 2000 ppm or less.

As has been described above, although various compounds may be recovered as compounds having carbonyl groups derived from the carbonic acid derivative, the mixture of the hydroxy composition and compound having carbonyl groups derived from the carbonic acid derivative may be used for reuse of the condensed components even if it contains these compounds.

<Production Method of N-Substituted Carbamic Acid Ester Using an Aromatic Hydroxy Composition Containing a Plurality of Types of Aromatic Hydroxy Compounds>

The following provides an explanation of a production method of N-substituted carbamic acid ester that uses an aromatic hydroxy composition containing an active aromatic hydroxy compound and an inactive hydroxy compound for the hydroxy composition.

As has been previously described, in the production method of N-substituted carbamic acid ester of the present embodiment, a gas containing the aromatic hydroxy composition and a compound having carbonyl groups derived from the carbonic acid derivative is condensed in order to recover the compound having carbonyl groups derived from the carbonic acid derivative in a form of a homogeneous solution. Consequently, the aromatic hydroxy composition preferably contains an aromatic hydroxy compound that is easily vaporized to a certain degree under the reaction conditions. On the other hand, since the organic amine, the carbonic acid derivative and the aromatic hydroxy composition mainly react in the liquid phase to form N-substituted carbamic acid ester, the aromatic hydroxy composition preferably contains an aromatic hydroxy compound that is present as a liquid under the reaction conditions. Thus, an aromatic hydroxy composition that contains a plurality of types of aromatic hydroxy compounds having different standard boiling points can be preferably used for the aromatic hydroxy composition.

In this case, there are many cases in which, when any of the plurality of types of aromatic hydroxy compounds having different standard boiling points forms N-substituted carbamic acid ester by reacting with the organic amine and the carbonic acid derivative, a plurality of types of the aromatic hydroxyl compounds are formed together with isocyanate during production of isocyanate by thermal decomposition of the N-substituted carbamic acid ester, thereby making separation of the aromatic hydroxyl compounds complex. Therefore, a method for producing N-substituted carbamic acid ester having ester groups derived from an active aromatic hydroxyl compound with high selectivity is preferably carried out by using a combination of an active aromatic hydroxyl compound and an inactive aromatic hydroxyl compound. Moreover, if aromatic hydroxyl compounds are selected such that the standard boiling point of the active aromatic hydroxyl compound is the highest in the aromatic hydroxyl composition, the concentration of the active aromatic hydroxyl compound increases in the liquid phase in which the formation reaction of the N-substituted carbamic acid ester mainly takes place, thereby making it possible to form an N-substituted carbamic acid ester derived from the active aromatic hydroxyl compound with higher selectivity. An inactive aromatic hydroxyl compound having a standard boiling point lower than the standard boiling point of the active aromatic hydroxyl compound is preferably introduced into the condenser in the form of a gaseous phase component and condensed in the condenser together with the compound having carbonyl groups derived from the carbonic acid derivative. In the case of combining aromatic hydroxyl compounds having different standard boiling points in this manner, the difference in standard boiling points between the aromatic hydroxyl compound present mainly in the liquid phase and the aromatic hydroxyl compound condensed in the condenser together with the compound having carbonyl groups derived from the carbonic acid derivative is preferably 5° C. or more and more preferably 10° C. or more. In particular, it is effective to combine aromatic hydroxyl compounds such that the standard boiling point of the active aromatic hydroxyl compound is preferably 5° C. or more higher and more preferably 10° C. or more higher than the standard boiling point of the low activity aromatic hydroxyl compound.

Figure 5:
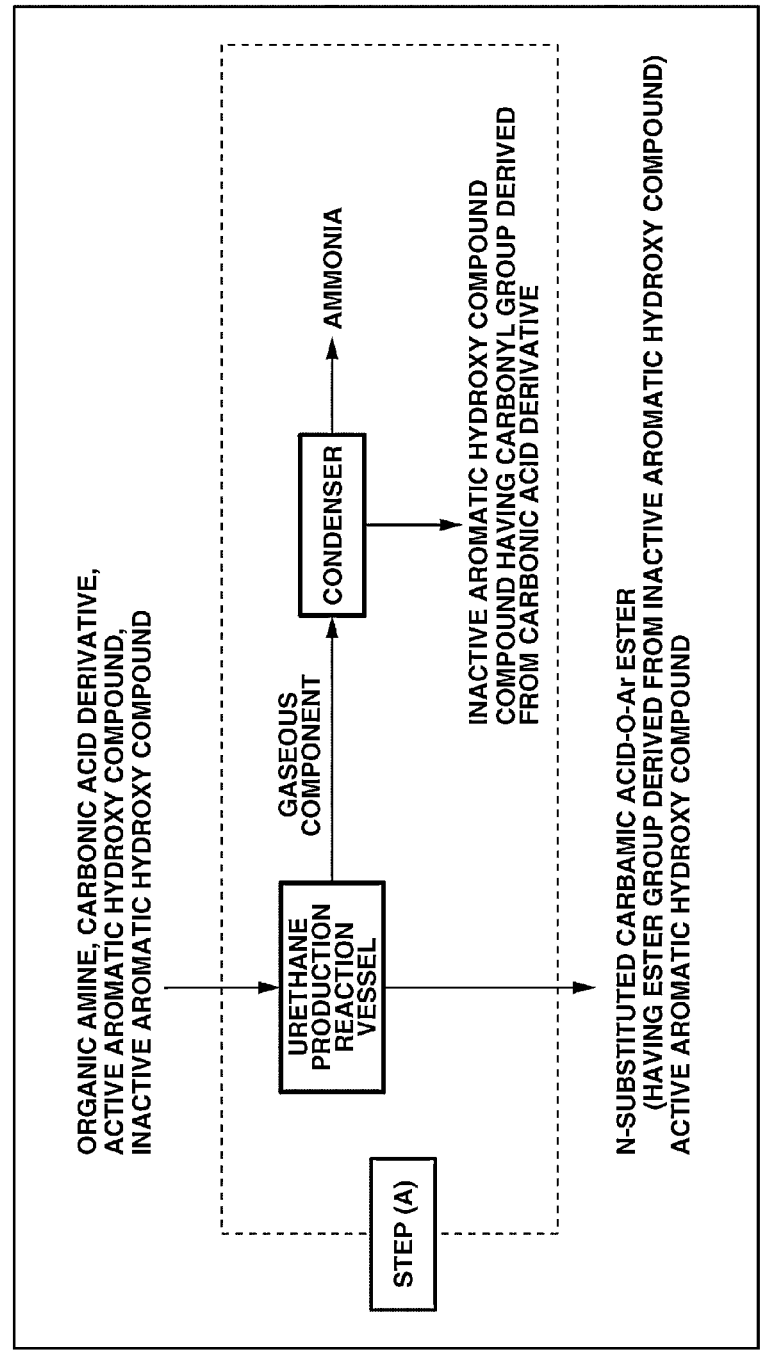
FIG. 5 shows a conceptual drawing depicting one aspect of the present invention in the form of a production method of N-substituted carbamic acid ester that uses an aromatic hydroxy composition containing an active aromatic hydroxy compound and an inactive aromatic hydroxy compound.

FIG. 5 shows a conceptual drawing of a production method of N-substituted carbamic acid ester that uses an aromatic hydroxyl composition composed of a plurality of types of the aromatic hydroxy compounds as described above (here, for the sake of simplicity of the explanation, an aromatic hydroxy composition is described that contains two types of aromatic hydroxy compounds comprising an active aromatic hydroxy compound and an inactive aromatic hydroxy compound).

In the case of using an aromatic hydroxy composition containing a plurality of types of aromatic hydroxy compounds in this manner, the amount of the active aromatic hydroxy compound to the amount of the inactive aromatic hydroxy compound in the aromatic hydroxy composition in terms of stoichiometric ratio is preferably from 0.01 to 100 times, more preferably from 0.05 to 20 times and even more preferably from 0.1 to 10 times.

<Urethane Production Method Using Compound Having Ureido Groups>

As was previously described, the method for producing N-substituted carbamic acid ester of the present embodiment can be generally divided into the following two methods:

(1) a method in which N-substituted carbamic acid ester is produced by "simultaneously" reacting the organic amine, the carbonic acid derivative and the hydroxy composition, and (2) a method that separates the steps for producing N-substituted carbamic ester by reacting the organic amine, the carbonic acid derivative and the hydroxy composition in which a compound having ureido groups is produced by reacting the organic amine and the carbonic acid derivative in the first step (step (a)), and an N-substituted carbamic acid ester is produced by reacting the compound having ureido groups and a hydroxy compound in a subsequent second step (step (b)). The following provides a description of the method of (2).

The inventors of the present invention believe that the reaction in which N-substituted carbamic acid ester is formed in step (A) takes place in the form of a combination of the various reactions indicated below. Furthermore, in the following explanation, for the sake of simplicity, an organic amine having two amino groups is used for the organic amine. Naturally, the explanation applies similarly to cases using organic amines other than that indicated herein.

The reaction is composed of a reaction in which a compound having ureido groups is formed from the organic amine and the carbonic acid derivative (for example, formula (117) below), and a reaction in which N-substituted carbamic acid ester is formed from the compound having ureido groups and the hydroxy compound (for example, formula (118) below):

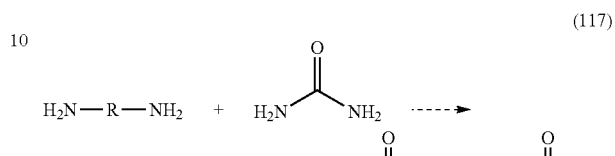

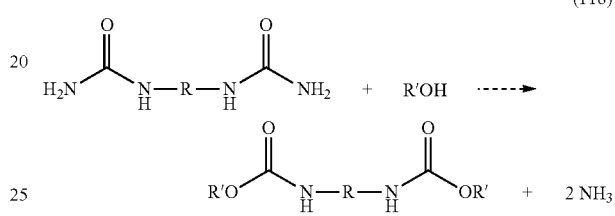

(wherein,

R respectively and independently represents an organic group substituted with two substituents).

In the reaction that forms a compound having ureido groups of formula (117) above, a reaction in which a compound having a ureylene group is formed from a compound having ureido groups and an organic amine represented by the following formula (119), or a reaction in which a compound having a biuret group is formed by condensing of a compound having ureido groups represented by the following formula (120), for example, may also occur as side reactions:

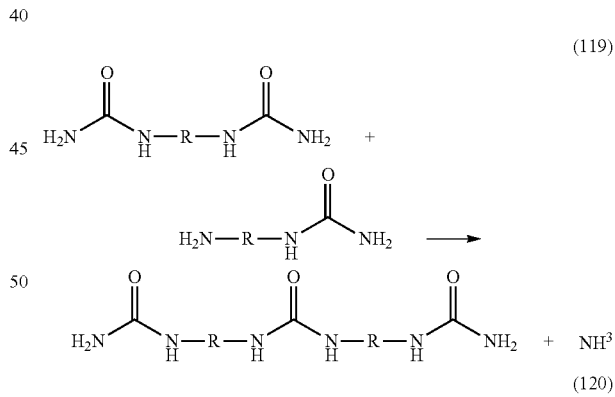

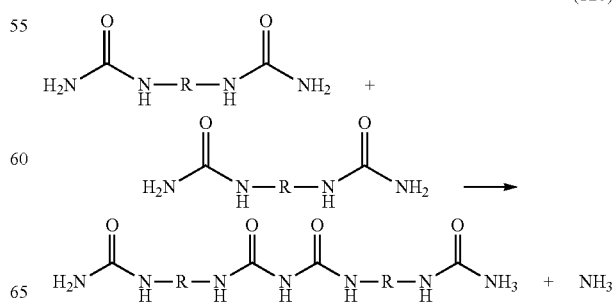

(wherein,

R respectively and independently represents an organic group substituted with two substituents).

The compound having a ureylene group reacts with carbonic acid derivative and hydroxy compound to form N-substituted carbamic acid ester as shown in formula (121) below, while for example, the compound having a biuret group and a hydroxy compound are presumed to react with a hydroxy compound to form N-substituted carbamic acid ester as in formula (122) below:

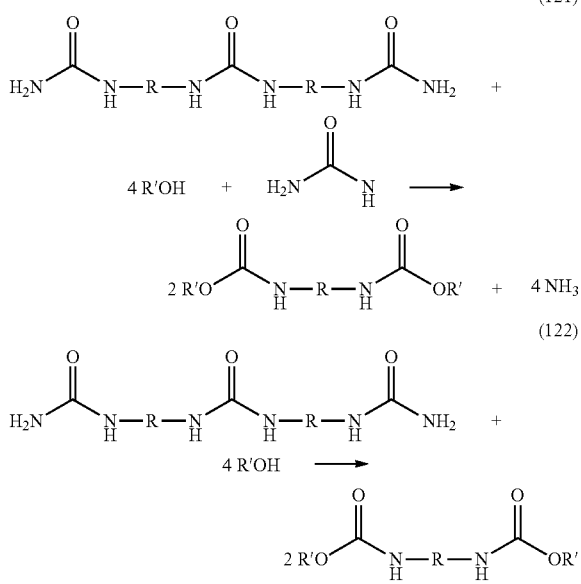

(wherein,

R respectively and independently represents an organic group substituted with two substituents, and R'OH represents a monovalent hydroxy compound).

Furthermore, the above formulas show the example of the case in which the organic amine is an organic amine having two amino groups and the carbonic acid derivative is urea.

In this manner, in the method of (1) above, N-substituted carbamic acid ester is produced by going through various intermediates. In particular, the formation rates of N-substituted carbamic acid ester according to the reactions of formulas (121) and (122) above were determined to be slower than the formation rate of N-substituted carbamic acid ester according to the reaction of formula (118) above. Namely, this means that when N-substituted carbamic acid ester is attempted to be obtained at a yield equal to or greater than a certain level, reaction time becomes longer due to the slow reactions of formulas (121) and (122) above, and if the reaction time becomes longer, there were cases in which the N-substituted carbamic acid ester formed first is held for a long time under reaction temperature conditions, thereby causing a denaturation reaction of the N-substituted carbamic acid ester and a decrease in the yield of N-substituted carbamic acid ester. In addition, in the case of ending the reaction in a short period of time in order to avoid denaturation of the N-substituted carbamic acid ester, large amounts of the compound having a ureylene group (compound on the right side of formula (119), for example) and the compound having a biuret group (compound on the right side of formula (120), for example) formed as intermediates remained, which frequently caused a decrease in the yield of N-substituted carbamic acid ester. In addition, there were cases in which N-substituted carbamic acid ester formed by the comparatively rapid reaction of formula (118) above reacted with amine terminals (—NH$_2$ groups) of unreacted organic amine resulting in the formation of a compound having a ureylene group (according to the reaction of formula (123) below, for example):

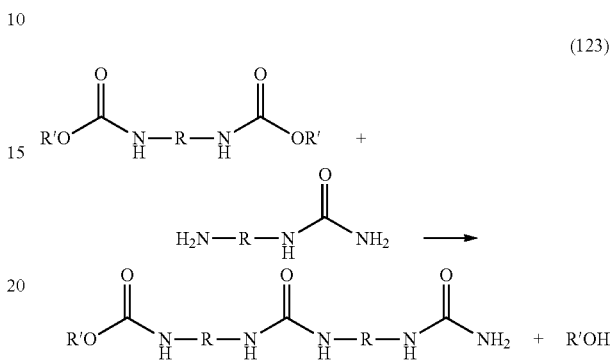

(wherein,

R respectively and independently represents an organic group substituted with two substituents, and R'OH represents a hydroxy compound).

In this manner, a method for producing N-substituted carbamic acid ester by "simultaneously" reacting the organic amine, the carbonic acid derivative and the hydroxy composition may not allow the obtaining of N-substituted carbamic acid ester at an adequate yield depending on the reaction conditions and the compounds used in the reaction.

As a result of extensive studies conducted by the inventors of the present invention, this problem was found to be solved by the method of (2) above, namely by dividing the step of producing N-substituted carbamic acid ester by reacting the organic amine, the carbonic acid derivative and the hydroxy compound, producing a compound having ureido groups by reacting the organic amine and the carbonic acid derivative in a first step (step (a)), and producing N-substituted carbamic acid ester by reacting the compound having ureido groups and the hydroxy compound in a subsequent second step (step (b)). This method can be used to produce N-substituted carbamic acid ester by inhibiting side reactions in the manner of formulas (119) and (120) above and selectively causing the occurrence of the reaction of formula (117) above while inhibiting a reaction (reaction of formula (118) above) that forms N-substituted carbamic acid ester by a reaction between the compound having ureido groups according to formula (117) above and the hydroxy compound to avoid a state in which N-substituted carbamic acid ester and unreacted organic amine are both present in the first step (step (a)), and then causing the occurrence of the reaction between the compound having ureido groups and the hydroxy compound (reaction of formula (118) above) in the subsequent second step (step (b)). According to this method, the problem with the method of (1) above can be solved.

Although naturally step (a) is important in this method, in this step (a), the inventors of the present invention surprisingly found that the compound having ureido groups can be selectively produced by selectively carrying out the reaction of formula (117) above by making the ratio between organic amine and the carbonic acid derivative to be within a specific range in a system in which organic amine, carbonic acid derivative and hydroxy composition are all present. This specific preferable range and the reason why it is preferable (presumed reason) is explained below along with the reaction conditions of each step.

The method corresponding to (2) above, which is carried out preferably in the method of the present embodiment, is a method for producing N-substituted carbamic acid ester by a process comprised by carrying out the following steps (a) and (b) in that order:

step (a): step of obtaining a reaction mixture containing a compound having ureido groups by reacting an organic amine and a carbonic acid derivative; and, step (b): step of producing N-substituted carbamic acid ester by reacting the compound having ureido groups obtained in step (a) and a hydroxy composition using a urethane production reactor equipped with a condenser, wherein a gas containing the hydroxy composition, a compound having carbonyl groups derived from the carbonic acid derivative and ammonia formed as a by-product in the reaction is introduced into the condenser provided in the urethane production reactor, and the hydroxy composition and the compound having carbonyl groups derived from the carbonic acid derivative are condensed.

The following provides an explanation of steps (a) and (b).
<Step (a)>

Figure 6:
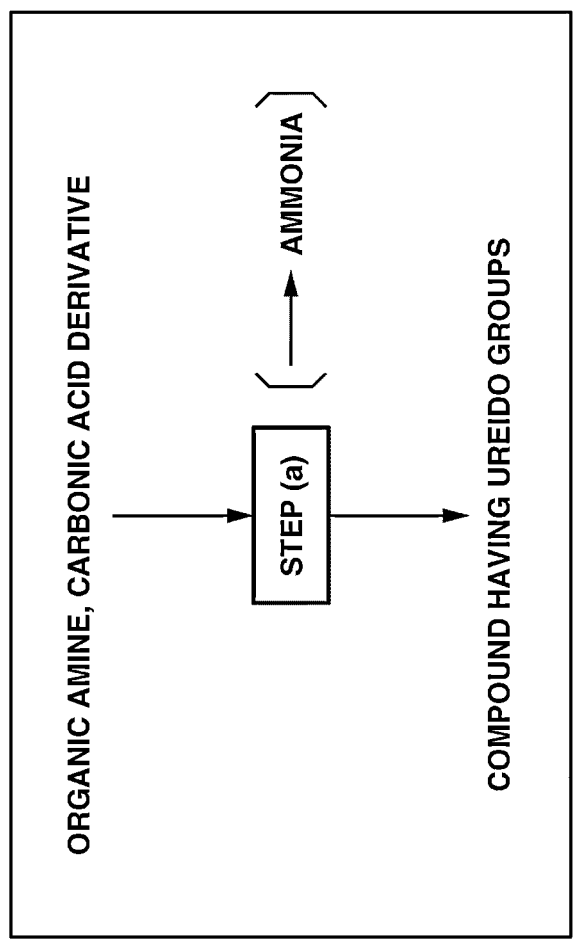
FIG. 6 shows a conceptual drawing depicting one aspect of the present embodiment in the form of step (a)

Step (a) is a step of obtaining a reaction mixture containing a compound containing ureido groups by reacting an organic amine and a carbonic acid derivative. FIG. 6 shows a conceptual drawing depicting step (a). Furthermore, ammonia may be formed in step (a) depending on the compound used for the carbonic acid derivative (and particularly in the case of using urea).

Although varying according to the reacted compounds, the reaction conditions for carrying out the reaction between the organic amine and the carbonic acid derivative are such that the number of carbonic acid derivatives to the number of amino groups of the organic amine is within a range of from 1 to 100 times. In the case of using a small amount of the carbonic acid derivative, complexly substituted carbonyl compounds such as compounds having ureylene groups presumed to be attributable to formula (119) above are formed easily. Thus, it is preferable to use an excess amount of the carbonic acid derivative.

In addition, an excess amount of carbonic acid derivative present in the reaction system of step (a) is presumed to have the effect of stabilizing the compound having ureido groups formed therein. According to studies conducted by the inventors of the present invention, compounds having a biuret bond (for example, the compound on the right side of the following formula (125)) and compounds having a biuret terminal (for example, the compound on the right side of the following formula (126)) were determined to be formed during the course of producing the compound having ureido groups depending on the reaction conditions. In order to form the target compound having ureido groups with high selectivity, it is necessary to inhibit the formation of such compounds. As a result of extensive studies conducted by the inventors of the present invention, it was surprisingly found that there is an intimate relationship between the amount of carbonic acid derivative in the reaction system and the amounts of such compounds formed, and that the formation of such compounds is reduced the larger the amount of carbonic acid derivative present. Although the mechanism by which carbonic acid derivative present in the reaction system demonstrates this effect is unclear, the inventors of the present invention made the presumptions indicated below regarding this mechanism.

Here, an example of a reaction in the case of using an organic amine having two primary amino groups is considered. This naturally also applies to the case of using an organic amine other than that indicated or a carbonic acid derivative.

First, the mechanism by which compounds having a biuret bond and compounds having a biuret terminal are formed is considered. The compound having ureido groups forms a compound having an isocyanate terminal (—NCO group) and ammonia due to thermal decomposition of the ureido groups depending on the reaction conditions (according to the following formula (124), for example).

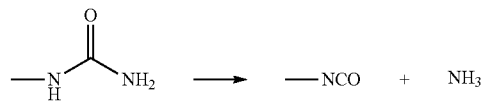

(124)

There is presumed to be cases in which the compound having an isocyanate terminal reacts with ureido groups (according to the following formula (125), for example), or in the case urea is present in the system, reacts with the urea (according to the following formula (126), for example) to form a compound having a biuret bond or compound having a biuret terminal:

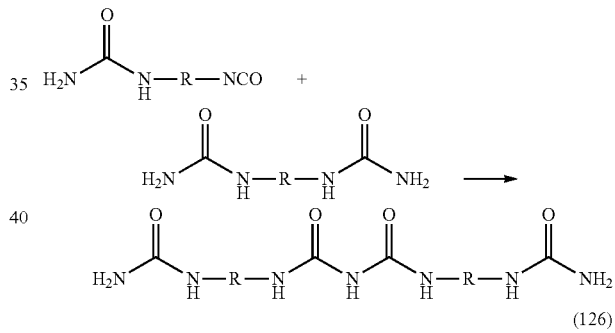

(125)

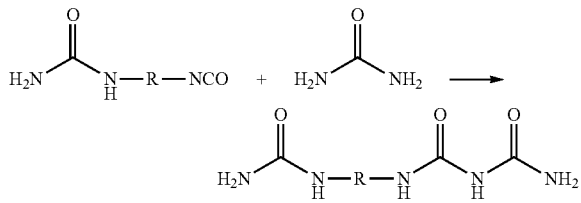

(126)

(wherein,
R represents an organic group substituted with two substituents).

The carbonic acid is presumed to stabilize the ureido groups by coordinating with the ureido groups by hydrogen bonding in the reaction liquid, and has the effect of inhibiting the first reaction in particular (namely the reaction represented by formula (124) above) among this series of reactions.

In addition, the inventors of the present invention also found that a carbonic acid derivative present in the reaction liquid has the effect of inhibiting the formation of N-substituted carbamic acid ester by inhibiting the reaction between the compound having ureido groups and a hydroxy compound. This effect is also thought to be the result of stabilization of the ureido groups by the carbonic acid derivative.

In this manner, the use of an excess amount of carbonic acid derivative is preferable since it allows the compound having ureido groups to be formed with high selectivity. However, the use of an overly excessive amount of carbonic acid derivative increases the size of the reactor making industrial application difficult, or as will be described later, may hinder separation and recovery of the carbonic acid derivative. Thus, the number of carbonic acid derivatives based on the number of amino groups of the organic amine is preferably within a range of from 1.1 to 10 times and more preferably within a range of from 1.5 to 5 times.

In addition, it is also necessary to pay attention to the procedure when carrying out the reaction in consideration of the role of the carbonic acid derivative as described above. Namely, a method is preferably carried out in which, for example, the entire amount of carbonic acid derivative used is dissolved in advance in a reaction solvent (the details of which will be described later) followed by addition of the organic amine to this mixed solution so as to continuously maintain the number of carbonic acid derivatives in the reaction system in a state of excess (and in a state of large excess if possible) based on the number of amino groups of the organic amine.

Next, an explanation is given of the ammonia concentration in the system. Furthermore, the preferable range of the ammonia concentration described here refers to the ammonia concentration in the reaction liquid after the compound having ureido groups has formed to a certain degree (such as at a yield of not less than 5% based on the organic amine), and does not refer to that at the start of the reaction.

The reaction in which N-substituted carbamic acid-O—($R^2$ and/or Ar) ester is formed (such as the reaction of the above-mentioned formula (118)) is an equilibrium reaction and the equilibrium is considerably biased towards the reactants side. However, as a result of studies conducted by the inventors of the present invention, the reaction in which the compound having ureido groups is formed (reaction of the above-mentioned formula (117)) was determined to be a reaction in which the equilibrium thereof is considerably biased towards the products side or be an irreversible reaction, and be virtually independent of the ammonia concentration in the system. Such a finding was heretofore unknown and is surprising. Thus, it was found that the compound having ureido groups can be formed selectively by maintaining the ammonia concentration in the reaction liquid of step (a) at a certain level or higher and inhibiting the formation of N-substituted carbamic acid ester by a reaction between the compound having ureido groups formed and the aromatic hydroxy compound (reaction of the above-mentioned formula (118)), and it was further found that the compound having ureido groups can be obtained with good selectivity by inhibiting side reactions by maintaining the ammonia concentration at a certain level or higher. In previously disclosed methods for producing compounds having ureido groups, side reaction products easily formed when obtaining a compound having ureido groups according to the above-mentioned reaction, and were contained within a range at which N-substituted carbamic acid ester formed in accordance with the above-mentioned formula (118) is simultaneously formed in large amounts, thus resulting in the serious problem of the concomitant occurrence of side reactions attributable to the N-substituted carbamic acid ester. In order to solve this problem, the amount of the urea and/or non-N-substituted carbamic acid ester used and/or the ammonia concentration is controlled. The ammonia concentration preferable for demonstrating such an effect is higher than 10 ppm, more preferably higher than 100 ppm, even more preferably higher than 300 ppm, and most preferably higher than 1000 ppm.

Step (a) can be carried out at a reaction temperature within a range of from 30 to 250° C. Although a high temperature is preferable to increase the reaction rate, on the other hand, since undesirable reactions occur at high temperatures (such as decomposition of the carbonic acid derivative) resulting in the formation of complexly substituted urea compounds and carbonyl compounds, the reaction temperature is preferably within a range of from 50 to 200° C. and more preferably within a range of from 70 to 180° C. A known cooling apparatus or heating apparatus may be installed in the reactor for carrying out step (a) to maintain a constant reaction temperature.

Although varying according to the types of compounds used, composition of the reaction system, reaction temperature, reaction apparatus and the like, normally the reaction is preferably carried out at a reaction pressure within a range of from 0.01 kPa to 10 MPa (absolute pressure), and in consideration of ease of industrial application, is preferably carried out at reaction pressure within a range of from 0.1 kPa to 5 MPa (absolute pressure).

There are no particular limitations on the reaction time (residence time in the case of a continuous method), and the reaction time is generally from 0.001 to 100 hours, preferably from 0.01 to 80 hours and more preferably from 0.1 to 50 hours. In addition, the reaction can be terminated after confirming that a desired amount of the compound having ureido groups has been formed by sampling the reaction liquid and determining the amount of the compound having ureido groups by liquid chromatography, for example. Although step (a) is a step of producing the compound having ureido groups, in step (a), if a large amount of amino groups derived from unreacted organic amine are present, compounds having ureylene groups and the like are formed in step (b) carried out after step (a), which frequently not only causes a decrease in the amount of N-substituted carbamic acid ester formed, but also causes adhesion and solidification in the reactor. Thus, in step (a), it is preferable to reduce the amount of amino groups derived from the organic amine by forming the compound having ureido groups at as high a yield as possible. More specifically, the reaction is preferably continued until the ratio of the number of amino groups derived from the organic amine to the number of ureido groups composing the compound having ureido groups becomes preferably 0.25 or less, more preferably 0.1 or less, and even more preferably 0.05 or less.

In the present embodiment, a catalyst can be used as necessary, and examples of catalysts that can be used may include organic metal compounds and inorganic metal compounds of tin, lead, copper or titanium, and basic catalysts such as alcoholates of alkaline metals or alkaline earth metals in the form of methylates, ethylates and butyrates (including isomers) of lithium, sodium, potassium, calcium or barium.

The reaction of step (a) is preferably carried out in the presence of a solvent from the viewpoint of lowering the viscosity of the reaction liquid and/or making the reaction system homogeneous. Examples of solvents that can be preferably used as reaction solvents may include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene;

nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; sulfoxides such as dimethylsulfoxide or diphenylsulfoxide, and hydroxy compounds such as water, alcohols or aromatic hydroxy compounds. However, from the viewpoint of solubility of the product in the form of the compound having ureido groups, the reaction solvent is preferably water or a hydroxy composition (alcohol and aromatic hydroxy compound), and more preferably a hydroxy composition (the hydroxy composition being a hydroxy composition composed of one type or a plurality of types of hydroxy compounds, and a hydroxy composition preferably used as a reaction solvent in step (a) is hereinafter referred to as "hydroxy composition a"). Furthermore, these solvents can be used alone or as a mixture of two or more types thereof.

Although hydroxy compounds that compose the hydroxy composition a may be completely identical, partially identical or different from the hydroxy compounds that compose the hydroxy composition used in step (b), in order to facilitate the procedure, the hydroxy composition a is preferably either the same as the hydroxy composition used in step (b) or is a composition composed of that hydroxy composition. Although an explanation thereof is provided to follow, the reaction of step (a) is more preferably either carried out in the presence of an aromatic hydroxy composition (at least one type of composition containing an aromatic hydroxy compound represented by the above-mentioned formula (46)), or the reaction of step (a) is carried out in the presence of an alcohol or aromatic hydroxy composition followed by the addition of an aromatic hydroxy composition (at least one type of composition containing an aromatic hydroxy compound represented by the above-mentioned formula (46)).

Although the reaction solvents indicated here can be used in an arbitrary amount, in the case of using an alcohol for the reaction solvent, it can be used at a stoichiometric ratio within a range of greater than 1 time to less than 100 times based on the amino groups of the organic primary amine. Although it is preferable to use an excess of alcohol based on the amino groups of the organic primary amine in order to improve the fluidity of the reaction liquid and allow the reaction to proceed efficiently, since problems may result such as an increase in the size of the reactor if an overly excessive amount of alcohol is used, the alcohol can be used at a stoichiometric ratio more preferably within a range of greater than 5 times to less than 50 times and even more preferably within a range of greater than 8 times to less than 20 times the amino groups of the organic primary amine.

In addition, in the case of using an aromatic hydroxy compound for the reaction solvent of step (A), it can be used at a stoichiometric ratio within a range of greater than 1 time to less than 10 times the amino groups of the organic primary amine. Although it is preferable to use an excess of aromatic hydroxyl compound based on the amino groups of the organic primary amine in order to improve the fluidity of the reaction liquid and allow the reaction to proceed efficiently, since problems may result such as an increase in the size of the reactor if an overly excessive amount of aromatic hydroxyl compound is used, the aromatic hydroxy compound can be used at a stoichiometric ratio more preferably within a range of greater than 2 times to less than 50 times and even more preferably within a range of greater than 3 times to less than 20 times the amino groups of the organic primary amine.

Among alcohols represented by the above-mentioned formula (45) and aromatic hydroxy compounds represented by the above-mentioned formula (46), an aromatic hydroxy compound in which $R^{29}$ is an aromatic group is used preferably in consideration of solubility of the compound having ureido groups formed. For example, although Japanese Patent Application Laid-open No. H6-41045 describes to the effect that polyhexamethylene-urea formed by a reaction between urea and hexamethylene diamine is poorly soluble in n-butanol, with respect to this point, aromatic hydroxy compounds frequently have superior solubility for various reaction products including compounds having ureido groups. Moreover, aromatic hydroxy compounds also demonstrate the effect of promoting the reaction between the organic amine and the carbonic acid derivative. Although the mechanism by which this effect is demonstrated is unclear, it has been surmised by the inventors of the present invention that, although carbonic acid derivatives generally tend to adopt an associated state, since aromatic hydroxy compounds have acidic hydroxy groups, the hydroxy groups inhibit association between carbonic acid derivatives thereby making it easier for amines to approach the reaction sites of the carbonic acid derivative (which are presumed to be carbons that compose the carbonyl groups of the carbonic acid derivative).

In the case of using an aromatic hydroxyl compound for the reaction solvent, although the aromatic hydroxy compound may be used alone or mixed with other solvents, the amount of the aromatic hydroxy compound used is within the range of the previously described values. Even in the case of adding an aromatic hydroxy composition (a composition containing at least one type of aromatic hydroxy compound represented by the above-mentioned formula (46)) after having carried out step (a) in the presence of alcohol, the aromatic hydroxy composition is used within the previously described ranges. At that time, the alcohol used during the reaction of step (a) is also used at the stoichiometric ratio indicated for the aromatic hydroxy compound based on the organic amine as previously described. In the case of using water in step (a), the water is preferably used together with an aromatic hydroxy composition and/or alcohol. Although water alone can be used as a solvent, it may be necessary to remove the water following completion of step (a). In addition, if an aromatic hydroxy compound is added in the amount described above following completion of step (a), the reaction liquid may separate into an aqueous phase and organic phase or the aromatic hydroxy composition and compound having ureido groups may solidify, thereby preventing transfer of a homogeneous liquid when carrying out step (b) or causing clogging of transfer pumps and lines. Thus, in the case of using water alone for the solvent of step (a), the water is removed before or after adding the aromatic hydroxy compound. Although varying according to the compounds used and composition, water is removed until the amount of water is within a range of from 10 ppm to 10% by weight, preferably from 10 ppm to 5% by weight and more preferably from 10 ppm to 2% by weight in the reaction liquid (or mixed liquid) following removal thereof. A known method for removing water can be used for the water removal method, and examples of methods that can be used preferably include removal by distillation at reduced pressure or normal pressure, the use of an adsorbent such as zeolite, the addition of a hydrolyzable compound such as an acetal followed by removal of water by a hydrolysis reaction, and removal of water with a compound that reacts with water in the manner of N,N-dicyclohexylcarbodiimide. Water is more preferably removed by distillation. In the case of using water together with an aromatic hydroxy composition and/or alcohol as a solvent in step (a), the amount of water in the reaction is within a range of from 10 ppm to 10% by weight, preferably from 10 ppm to 5% by weight, and more preferably from 10 ppm to 2% by weight. The inventors of the present invention surprisingly found that the reaction of step (a) demonstrates an improvement in reaction rate due to the presence of water. Thus, having water present during the reaction is a preferable method. Although the details of this effect have not been determined, it is presumed that the effect of enhancing nucleophilicity of the organic amine is demonstrated by the water.

There are no particular limitations on the reaction apparatus used when carrying out the reaction, and a known reactor can be used. For example, conventionally known reaction vessels can be suitably combined, such as a stirring tank, a pressurized stirring tank, a depressurized stirring tank, a column type reactor, a distillation column, a packed column or a thin film distiller. There are no particular limitations on the material of the reaction vessel, and known materials can be used. Examples thereof may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Steps may also be added as necessary. For example, steps and apparatuses able to be conceived by a person or engineer with ordinary skill in the art may be added, such as a step of removing the ammonia formed, a step of purifying the organic primary amine, a step of dissolving the urea in the aromatic hydroxy compound, a step of dissolving the aromatic hydroxy compound, a step of separating the alcohol, a step of separating and/or purifying the aromatic hydroxy compound, a step of purifying the compound having ureido groups from the formed reaction liquid or a step of incinerating or discarding by-products and the like.

A compound having ureido groups obtained according to the reaction described above is a compound represented by the above-mentioned formula (80).

In the case of using a reaction solvent in step (a), the reaction solvent may be removed from the reaction liquid of step (a) prior to carrying out step (b), or step (b) may be carried out without removing the reaction solvent. In particular, the hydroxy compound used as a reaction solvent is step (a) is preferably used as is as a portion of the hydroxy composition of step (b).

<Step (c)>

In the case of using the carbamic acid ester for the carbonic acid derivative in step (a) or in the previously explained step (A), the carbamic acid ester is preferably a carbamic acid ester produced by the following step (c):

step (c): a step in which a carbamic acid ester is produced by reacting a hydroxy composition c (the hydroxy composition c contains one type or a plurality of types of hydroxy compounds, may be the same as or different from the hydroxy composition a of step (a), may be the same as or different from the hydroxy composition of step (b), and may be the same as or different from the hydroxy composition of step (A)) and urea.

Figure 7:
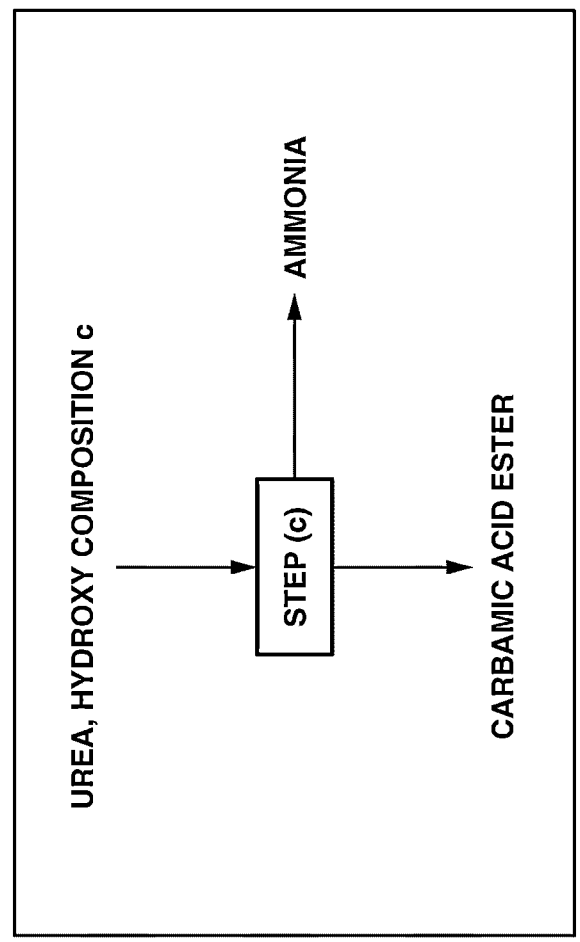
FIG. 7 shows a conceptual drawing depicting one aspect of the present embodiment in the form of step (c)

FIG. 7 shows a conceptual drawing depicting one aspect of the present embodiment in the form of the step (c).

The following provides an explanation of step (c).

The hydroxy composition c used in step (c) is a hydroxy composition that contains one type or a plurality of types of hydroxy compounds. An alcohol and/or aromatic hydroxy compound can be used for the hydroxy compound. In the case the hydroxy compound is an alcohol, an alcohol represented by the above-mentioned formula (45) is preferable, while in the case the hydroxy compound is an aromatic hydroxy compound, an aromatic hydroxy compound represented by the above-mentioned formula (46) is preferable. The hydroxy composition used herein has the role of a reaction solvent in step (c) and a role for forming carbamic acid ester by reacting with urea. In the case of an aromatic hydroxy compound in particular, the inventors of the present invention found that, similar to the formation reaction of N-substituted carbamic acid-O—Ar ester, the reaction rate of the formation reaction of the carbamic acid ester is also dependent on the structure of the aromatic hydroxy compound. Thus, in consideration of reactivity with urea, an aromatic hydroxy compound represented by the above-mentioned formula (56) is preferable, while an aromatic hydroxy compound represented by the above-mentioned formula (67) is more preferable.

The hydroxy composition c may be the same as or different from the hydroxy composition a of step (a), may be the same as or different from the hydroxy composition of step (b), and may be the same as or different from the hydroxy composition of step (A).

A known method (such as that disclosed in Japanese Patent Application Laid-open No. H5-310677) can be referred to regarding the reaction conditions of step (c).

Although varying according to the compounds used, the ratio of the amounts of urea and hydroxy composition used in the reaction of step (c) is preferably such that the stoichiometric ratio of the amount of the hydroxy composition to the amount of urea is 5 or more. In the case the stoichiometric ratio of the amount of the hydroxy composition to the amount of urea is less than 5, the yield of carbamic acid ester may decrease or a long period of time may be required for the reaction. Although there is no upper limit on the amount of the hydroxy composition based on the urea, since the use of an overly excessive amount of the hydroxy composition leads to a decrease in the production efficiency of carbamic acid ester, the stoichiometric ratio described above is generally 100 or less.

Since the reaction between the hydroxy composition and the urea is such that the equilibrium thereof is biased towards the reactants, ammonia formed as a by-product of the reaction is preferably removed outside the system. One preferable aspect of the method for removing ammonia is reactive distillation. The reaction can also be carried out while boiling the hydroxy composition to increase the removal efficiency of the ammonia. The reaction can also be carried out at the boiling point of a solvent for the same purpose by using a solvent having lower standard boiling point than the hydroxy composition used. The boiled hydroxy composition or solvent is separated from the ammonia by a known method such as distillation, and the ammonia is removed outside the system. Examples of such solvents may include hydrocarbons such as pentane, hexane, cyclohexane, heptane, benzene, toluene or xylene, halogenated hydrocarbons such as dichloromethane, chloroform or carbon tetrachloride, ketones such as acetone or methyl ethyl ketone, and ethers such as tetrahydrofuran or dioxane.

A preferable aspect for removing ammonia formed as a by-product in the reaction system is a method that uses an inert gas. Namely, ammonia that is continuously formed during the reaction is combined with an inert gas in a gaseous state to separate from the reaction system. Examples of such inert gases may include nitrogen, helium, argon, carbon dioxide, methane, ethane and propane.

Another example of a preferable aspect of removing ammonia formed as a by-product in the reaction system is a method in which the ammonia is separated by adsorbing with an adsorbent. The adsorbent used is that which has the ability to adsorb ammonia at the temperature and under the conditions used, and examples thereof may include silica, alumina, zeolite and diatomaceous earth.

The reaction temperature of step (c) is preferably within a range of from 120 to 250° C. and more preferably within a range of from 130 to 240° C. If the temperature is lower than these ranges, the reaction rate slows and considerable time is required for obtaining a high yield, thereby making this unsuitable for industrial application. On the other hand, if the temperature is higher than the above ranges, yield may decrease due to the occurrence of side reactions, thereby making this undesirable.

Although varying according to conditions such as the composition of the reaction system, reaction temperature, ammonia removal method or reaction apparatus, the reaction pressure is normally within a range of from 0.01 kPa to 5 MPa (absolute pressure).

There are no particular limitations on the reaction apparatus used when carrying out the reaction, and a known reactor can be used. For example, conventionally known reaction vessels can be suitably combined, such as a stirring tank, a pressurized stirring tank, a depressurized stirring tank, a column type reactor, a distillation column, a packed column or a thin film distiller. There are no particular limitations on the material of the reaction vessel, and known materials can be used. Examples may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Steps may also be added as necessary. For example, steps and apparatuses able to be conceived by a person or engineer with ordinary skill in the art may be added, such as a step of removing the ammonia formed, a step of purifying the organic primary amine, a step of dissolving the urea in the aromatic hydroxy compound, a step of dissolving the aromatic hydroxy compound, a step of separating the alcohol, a step of separating and/or purifying the aromatic hydroxy compound, a step of purifying the compound having ureido groups from the formed reaction liquid or a step of incinerating or discarding by-products and the like. Moreover, an apparatus provided with a distillation column or a partial condenser and the like that separates the ammonia, hydroxy composition and solvent followed by returning the hydroxy composition and solvent to the reaction system is used preferably.

Although the use of a catalyst is not required in the reaction of step (c), a catalyst can be used for the purpose of lowering the reaction temperature or increasing the reaction rate. Examples of such catalysts that are used preferably may include rare earth elements, antimony and bismuth alone as well as oxides, sulfides and chlorides of these elements; boron and boron compounds; metals belonging to the copper, zinc, aluminum, carbon and titanium families of the periodic table as well as oxides and sulfides of these metals; and, carbides and nitrides of elements belonging to the carbon family (excluding carbon) and titanium, vanadium and chromium families of the periodic table. In the case of using a catalyst, although any ratio may be adopted for the ratio of the amounts of the catalyst and urea, the catalyst is generally used at 0.0001 to 0.1 times the amount of urea in terms of the weight ratio thereof.

A reaction solvent may also be used in the reaction of step (c) for the purpose of lowering the viscosity of the reaction liquid and/or making the reaction system homogeneous. Examples of solvents that can be preferably used as reaction solvents may include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and sulfoxides such as dimethylsulfoxide or diphenylsulfoxide. Naturally, the excess hydroxy composition c used in step (c) is also preferably used as a reaction solvent.

The reaction liquid of step (c) that contains carbamic acid ester produced in this manner can be used directly in the reaction of step (a) or the reaction of step (A), or the carbamic acid ester can be used in the reaction of step (a) or the reaction of step (A) by separating the carbamic acid ester. In addition, after adding a reaction solvent and the like used in step (a) to the reaction liquid of step (c), all or a portion of the reaction solvent used in step (c), excess or unreacted hydroxy compound and excess or unreacted urea and the like may be extracted from the reaction liquid of step (c) and used in step (a). Separation of the carbamic acid ester, reaction solvent, hydroxy composition, urea and the like can be carried out using a known method such as distillative separation, precipitation or membrane separation.

<Step (b)>

Figure 8:
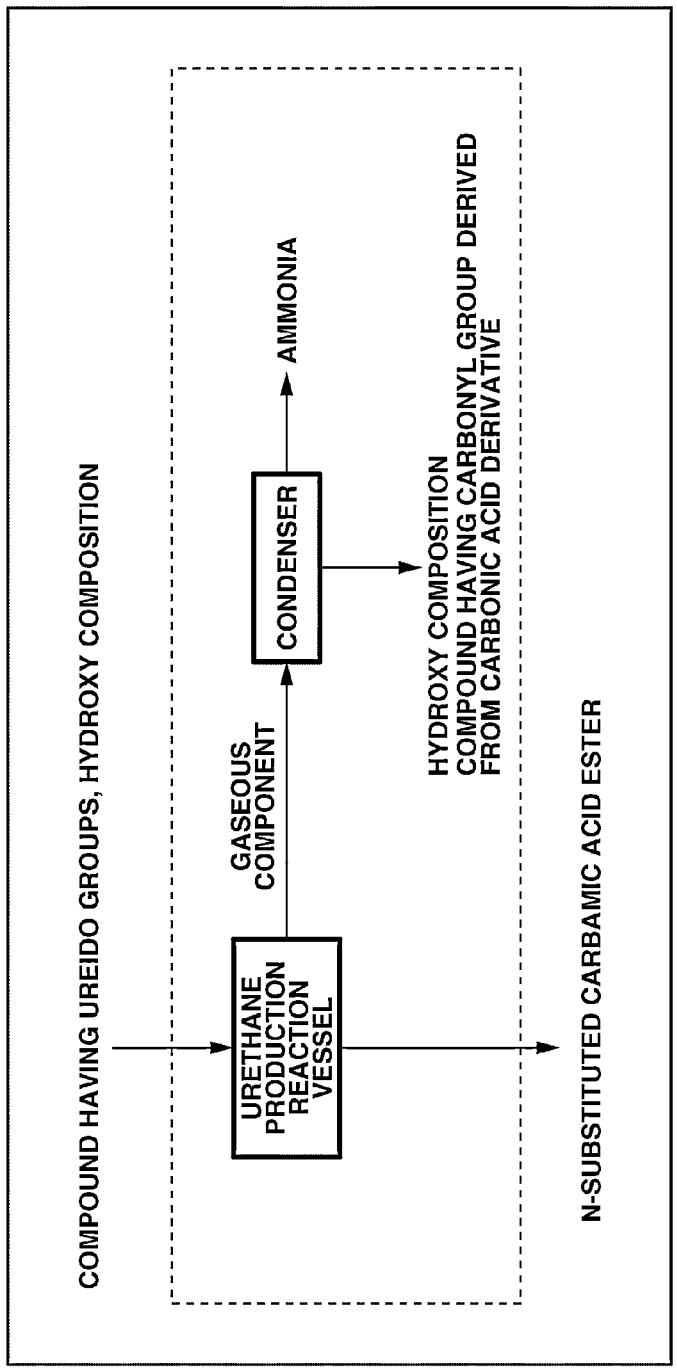
FIG. 8 shows a conceptual drawing depicting one aspect of the present embodiment in the form of step (b) for producing N-substituted carbamic acid ester by reacting a compound having ureido groups obtained in step (a) and a hydroxy composition.

Step (b) is a step of producing N-substituted carbamic acid ester by reacting a compound having ureido groups obtained in step (a) with the hydroxy composition. FIG. 8 shows a conceptual drawing depicting the step (b).

In the case of using hydroxy composition a for the reaction solvent of step (a) and the hydroxy composition a is the same as the hydroxy composition of step (b), step (b) can be carried out directly using the reaction liquid obtained in step (a). In the case the reaction solvent of step (a) differs from the hydroxy composition of step (b), step (b) may also be carried out by newly adding a hydroxy compound to the reaction liquid obtained in step (a). One or more types of hydroxy compounds may be newly added to the reaction liquid obtained in step (a), and continuinglly, step (b) may be carried out after separating all or a portion of the reaction solvent of step (a). Step (b) may also be carried out after newly adding the hydroxy compound after having removed all or a portion of the reaction solvent of step (a). The hydroxy composition added here is a hydroxy composition containing at least one type of an alcohol represented by the above-mentioned formula (45) or aromatic hydroxy compound represented by the above-mentioned formula (46). Among the hydroxy compositions, an aromatic hydroxy composition containing at least one type of aromatic hydroxy compound represented by formula (46) is preferable, an aromatic hydroxy composition containing an active aromatic hydroxy compound represented by the above-mentioned formula (56) is more preferable, and an aromatic hydroxy composition containing an active aromatic hydroxy compound represented by the above-mentioned formula (67) is even more preferable. There are no particular limitations on the method used to separate the reaction solvent used in step (a), and although a known method such as distillative separation, membrane separation or extraction separation can be used, distillative separation is preferable.

The hydroxy composition used in step (b) is preferably an aromatic hydroxy composition that contains an aromatic hydroxy compound represented by formula (46), and more preferably an aromatic hydroxy composition that contains an active aromatic hydroxy compound represented by formula (56) or (67).

Although varying according to the compounds reacted, the reaction conditions for producing N-substituted carbamic acid ester by reacting the compound having ureido groups and the hydroxy composition in step (b) are those in which the amount of the hydroxy composition is such that the stoichiometric ratio of the number of hydroxy compounds that compose the hydroxy composition to the number of ureido groups of the compound having ureido groups used is within a range of from 1 to 500 times. Although it is preferable to use an excess of hydroxy compound since complexly substituted carbonyl compounds and high molecular weight compounds having carbonyl bonds in molecules thereof form easily if the stoichiometric ratio is less than 1 time, in consideration of the size of the reactor, the stoichiometric ratio is preferably within a range of from 1 to 100 times, more preferably within a range of from 2 to 50 times and even more preferably within a range of from 3 to 20 times.

Although varying according to the compounds used, the reaction temperature is preferably within a range of from 100 to 350° C. Since the hydroxy composition and ammonia formed as a by-product form strong bonds if the temperature is lower than 100° C., the reaction slows, the reaction hardly proceeds at all, or complexly substituted carbonyl compounds increase, thereby making this undesirable. On the other hand, if the temperature is higher than 350° C., the carbonic acid derivative decomposes, the hydroxy composition is denatured by dehydration, or decomposition and denaturation of the product in the form of N-substituted carbamic acid ester occur easily, thereby making this undesirable. From these viewpoints, the reaction temperature is preferably within of from 120 to 320° C. and more preferably within a range of from 140 to 300° C.

Although varying according to the composition of the reaction system, reaction temperature, ammonia removal method and reaction apparatus and the like, generally the reaction pressure is preferably within a range of from 0.01 Pa to 10 MPa (absolute pressure), is preferably within a range of from 0.1 Pa to 5 MPa (absolute pressure) in consideration of ease of industrial application, and is more preferably within a range of from 0.1 Pa to 1.5 MPa (absolute pressure) in consideration of removal of gaseous ammonia outside the system.

In the step (b), the reaction that forms N-substituted carbamic acid ester is frequently carried out mainly in the liquid phase. Thus, the hydroxy composition is preferably present in the form of a liquid phase component under the reaction conditions. On the other hand, as will be described later, since the hydroxy composition and the compound having carbonyl groups derived from the carbonic acid derivative (to be described in detail hereinafter) are introduced into the condenser in the form of a gaseous phase component and are condensed in the condenser, the hydroxy composition is preferably present as a gaseous phase component under the reaction conditions. Thus, the reaction conditions are set such that a portion of the hydroxy composition is present in the form of a liquid phase component, while a portion is also present in the form of a gaseous phase component. In the case of using a hydroxy composition composed of a plurality of hydroxy compounds, the reaction conditions are set such that at least one type of the hydroxy compounds is present as a liquid phase component. Since such reaction conditions (reaction temperature and pressure) are intimately related to the properties of the hydroxy composition used and particularly to the correlation between temperature and vapor pressure, the properties of the hydroxy composition used (correlation between temperature and vapor pressure) are measured or investigated and used as an indicator for determining the reaction conditions. Incidentally, it is a matter of common sense among persons with ordinary skill in the art that the correlation between the properties of temperature and vapor pressure differ greatly depending on the purity of the substance and the types and amounts of other compounds present, and when setting the reaction conditions as well, it is self-evident that not only the properties of the hydroxy composition (correlation between temperature and vapor pressure), but also the types and amounts of other compounds present should also be taken into consideration.

As has been previously described, since the reaction that forms N-substituted carbamic acid ester is an equilibrium reaction that is biased towards the reactants side, the reaction is preferably carried out while removing as much of the by-product ammonia as possible from the system. Ammonia is removed so that the concentration of ammonia in the reaction liquid is preferably 1000 ppm or less, more preferably 300 ppm or less, even more preferably 100 ppm or less and most preferably 10 ppm or less. Ammonia can be removed using methods such as reactive distillation, use of an inert gas, membrane separation and adsorptive separation. For example, the reactive distillation refers to a method for separating continuously formed ammonia during the reaction by distillation in the form of a gas. This can be carried out while boiling a solvent or hydroxy composition in order to increase the distillation efficiency of the ammonia. In addition, a method using an inert gas refers to a method for separating continuously formed ammonia during the reaction from the reaction system in the form of a gas along with the inert gas. Examples of inert gases used may include nitrogen, helium, argon, carbon dioxide, methane, ethane and propane, these may be used alone or as a mixture, and a method in which the inert gas is introduced into the reaction system is preferable.

These methods for removing ammonia outside the system may be carried out alone or a plurality of types may be carried out in combination.

A catalyst can be used in the reaction for the purpose of increasing the reaction rate, for example. Examples of catalysts that are used preferably may include basic catalysts such as methylates, ethylates or butyrates (including isomers) of lithium, sodium, potassium, calcium or barium, rare earth elements, antimony or bismuth alone or oxides, sulfides and salts thereof, boron alone or boron compounds, metals of the copper family, zinc family, aluminum family, carbon family and titanium family of the periodic table as well as metal oxides and sulfides thereof, and carbides and nitrides of elements of the carbon family excluding carbon, titanium family, vanadium family and chromium family of the periodic table. Although there are no particular limitations on the amount of catalyst used in the case of using a catalyst, a catalyst can be used within a range of a stoichiometric ratio of from 0.0001 to 100 times the ureido groups of the compound having ureido groups.

Although varying according to the composition of the reaction system, reaction temperature, method used to remove ammonia, reaction apparatus, reaction pressure and the like, the reaction time (residence time in the case of a continuous reaction) is generally from 0.01 to 100 hours. The reaction time can also be determined according to the formation amount of the target compound in the form of N-substituted carbamic acid ester. For example, the reaction may be stopped after having sampled the reaction liquid, determined the content of N-substituted carbamic acid ester in the reaction liquid and confirming that the N-substituted carbamic acid ester has been formed at a yield of 10% or more based on the compound having ureido groups, or the reaction may be stopped after having confirmed that the yield is 90% or more. In the case of using an aromatic hydroxy composition for the hydroxy composition, the reaction liquid containing N-substituted carbamic acid-O—Ar ester obtained by the reaction of step (b) can be used as is as a transfer and storage composition for N-substituted carbamic acid-O—Ar ester as previously described, or can be used by preparing by adding and/or removing the aromatic hydroxy composition, N-containing compound and carbonic acid ester, and although the composition for transfer and storage of N-substituted carbamic acid-O—Ar ester can be preferably used to produce isocyanate, if the content of the N-substituted carbamic acid-O—Ar ester at that time is low (the yield is low), a decrease in the yield of isocyanate results. In the case of using an alcohol for the hydroxy composition, although N-substituted carbamic acid-O—$R^2$ ester is obtained in the reaction of step (b), the N-substituted carbamic acid-O—$R^2$ ester is also used to produce isocyanate after having converted to an N-substituted carbamic acid-O—Ar ester by various steps to be described later. Thus, a decrease in the yield of isocyanate also results in the case of a low yield of N-substituted carbamic acid-O—$R^2$ ester.

From the above viewpoints, the yield is preferably 50% or more, more preferably 80% or more and even more preferably 90% or more.

Although the use of a reaction solvent is not necessarily required in the reaction, a suitable solvent is preferably used as a reaction solvent for the purpose of facilitating the reaction procedure, examples of which include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and sulfoxides such as dimethylsulfoxide or diphenylsulfoxide. These solvents can be used alone or two or more types can be used as a mixture. Naturally, a hydroxy composition used in excess in the reaction is preferably used for the reaction solvent. In particular, the step (b) is preferably carried out in the presence of an aromatic hydroxy compound represented by the above-mentioned formula (46). The aromatic hydroxy compound may be an aromatic hydroxy compound in the case a hydroxy compound that composes the hydroxy composition used in step (b) is an aromatic hydroxy compound, or may be an aromatic hydroxy compound that is added separately from the hydroxy composition used in step (b).

The reaction is carried out in a system having a gaseous phase containing a hydroxy composition, a compound having carbonyl groups derived from a carbonic acid derivative and ammonia produced as a by-product in the reaction, and a liquid phase in which the reaction is carried out. Although the majority of the reaction is carried out in the liquid phase, the reaction may also occur in the gaseous phase depending on the reaction conditions. At that time, the volumetric content of the liquid phase in the reaction in which the reaction is carried out is preferably 50% or less. In the case of carrying out the reaction continuously over a long period of time, although polymeric by-products may form due to fluctuations in operating conditions (such as temperature or pressure) and the like, if the volumetric content of the liquid phase in the reactor is high, adhesion and accumulation of such polymeric by-products in the reactor can be avoided. However, since the efficiency of removal of by-product ammonia may become poor and the yield of the N-substituted carbamic acid ester may decrease if the volumetric content of the liquid phase is excessively high, the volumetric content of the liquid phase based on the gaseous phase is preferably 50% or less, more preferably 30% or less and even more preferably 20% or less (the volumetric content of the liquid phase refers to volumetric ratio of the liquid phase based on the volume of the reaction tank in the case of a tank-type reactor, the volume of the stage lower than the feed stage (not including the tank bottom and reboiler) in the case of a column-type reactor, or the volume of the thin film distiller in the case of a thin film distiller).

There are no particular limitations on the reactor used when carrying out the reaction provided it is equipped with a condenser, and although a known reactor can be used, a tank-type and/or a column-type reactor equipped with a condenser is used preferably.

As was previously described, the reaction is preferably carried out in a system having a gaseous phase containing a hydroxy composition, a compound having carbonyl groups derived from a carbonic acid derivative and ammonia produced as a by-product in the reaction, and a liquid phase in which the reaction is carried out under conditions such that the volumetric content of the liquid phase in the reactor is 50% or less, and a reactor that satisfies these conditions is selected for the reactor in which the reaction is carried out. More specifically, conventionally known reactors can be suitably combined and used, examples of which may include a stirring tank, a pressurized stirring tank, a reduced pressure stirring tank, a column-type reactor, a distillation column, a packed column or a thin film distiller.

There are no particular limitations on the type of condenser provided in the reactor and a known condenser can be used. For example, conventionally known condensers such as a multitubular cylindrical condenser, a double tube condenser, a single tube condenser or an air-cooled condenser can be suitably combined and used. The condenser may be provided inside the reactor or provided outside the reactor or may be connected with the reactor by a line, and various types can be employed in consideration of the forms of the reactor and condenser, the manner in which condensed liquid is handled and the like.

There are no particular limitations on the materials of the reactor and condenser and known materials can be used. Examples of materials that can be used may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, a cooling water or a brine can be used for cooling. Steps may also be added as necessary. For example, steps and apparatuses able to be conceived by a person or engineer with ordinary skill in the art may be added, such as a step of removing the ammonia formed, a step of purifying the organic primary amine, a step of dissolving the urea in the aromatic hydroxy compound, a step of dissolving the aromatic hydroxy compound, a step of separating the alcohol, a step of separating and/or purifying the aromatic hydroxy compound, a step of purifying the compound having ureido groups from the formed reaction liquid or a step of incinerating or discarding by-products and the like.

The N-substituted carbamic acid ester obtained by the reaction described above is an N-substituted carbamic acid-O—$R^2$ ester represented by the above-mentioned formula (92) in the case an alcohol is used for the hydroxy compound that composes the hydroxy composition. In addition, the resulting N-substituted carbamic acid ester is an N-substituted carbamic acid-O—Ar ester represented by the above-mentioned formula (104) in the case an aromatic hydroxy compound is used for the hydroxy compound that composes the hydroxy composition.

<Condensation of Gaseous Components>

In the reaction, a gas containing the hydroxy composition, the compound having carbonyl groups derived from the carbonic acid derivative, and ammonia formed as a by-product in the reaction is introduced into the condenser, and all or a portion of the hydroxy composition and the compound having carbonyl groups derived from the carbonic acid derivative are condensed (see FIG. 8).

At that time, the hydroxy compound contained in the condensed hydroxy composition is at a stoichiometric ratio of 1 or more based on the condensed compound having carbonyl groups derived from the carbonic acid derivative.

The "compound containing carbonyl groups derived from the carbonic acid derivative" condensed in the condenser in the present embodiment refers to compounds having carbonyl groups derived from the carbonic acid derivative used in the reaction between the organic amine, the carbonic acid derivative and the hydroxy composition, and include the carbonic acid derivative itself used as a raw material (unreacted substance and/or excess portion in the case of using in excess based on the organic amine), compounds resulting from the reaction between the carbonic acid derivative and the hydroxy composition, and compounds resulting from the reaction of the same type or different types of carbonic acid derivatives. Although it is difficult to identify all compounds having carbonyl groups derived from carbonic acid derivatives, specific examples thereof may include urea compounds such as isocyanic acid, urea, biurets or nurates, carbamic acid esters in which the ester group is a group derived from the hydroxy composition, carbamic acid esters in which the ester group is a group derived from the hydroxy composition, and carbonic acid esters in which the ester group is a group derived from the hydroxy composition. Compounds having carbonyl groups derived from the carbonic acid derivative can be quantified by methods in which carbonyl groups contained in the compound are detected by a method such as infrared spectroscopy, near infrared spectroscopy, Raman spectroscopy or ultraviolet spectroscopy, or can be quantified by a method that specifically analyzes compounds formed such as gas chromatography, liquid chromatography or NMR. These compounds having carbonyl groups derived from the carbonic acid derivative frequently have a high melting point and tend to precipitate easily. Among the compounds having carbonyl groups derived from the carbonic acid derivative listed above, urea in particular requires the greatest caution since it is formed in large amounts (detected in large amounts) and has a melting point of 135° C.

As a result of making the stoichiometric ratio of the hydroxy compound contained in the condensed hydroxy composition to be 1 or more based on the condensed compound having carbonyl groups derived from the carbonic acid derivative in the condensation procedure, a mixture thereof can be obtained in the form of a homogeneous liquid mixture in the condenser. Thus, not only does this facilitate handling of the mixture, but it is also possible to avoid the occurrence of problems such as adhesion and accumulation of solid components in the condenser. In addition, as will be described later, this is also effective for reducing the amount of compounds having carbonyl groups derived from the carbonic acid derivative contained in ammonia recovered from the condenser to equal to or less than a specific amount. The amount of the hydroxy compound contained in the condensed hydroxy composition based on the condensed compound having carbonyl groups derived from the carbonic acid derivative in terms of the stoichiometric ratio is more preferably 2 or more and even more preferably 3 or more. In order to ensure that the amount of the hydroxy compound contained in the condensed hydroxy composition based on the condensed compound having carbonyl groups derived from the carbonic acid derivative is within the above ranges, the condenser is preferably maintained at a temperature at least 90° C. lower than the standard boiling point of the hydroxy composition.

<Carbonyl Compound Content in Ammonia>

Although ammonia is recovered from the condenser in the form of a gas, the compound having carbonyl groups derived from the carbonic acid derivative contained in the ammonia is present in an amount equal to or less than a specific amount. More specifically, the ratio of the number of carbonyl groups (—C(=O)—) contained in the compound having carbonyl groups derived from the carbonic acid derivative contained in the ammonia to the number of ammonia molecules is 1 or less, preferably 0.5 or less, more preferably 0.1 or less and even more preferably 0.02 or less. The reason for specifying a specific range for the amount of the compound having carbonyl groups derived from the carbonic acid derivative contained in the ammonia is to avoid adhesion and accumulation of solid components in a line for transferring the ammonia from the condenser.

Although all solid components that adhere and accumulate in the line for transferring ammonia cannot be identified, as a result of studies conducted by the inventors of the present invention, the majority were determined to be compounds having carbonyl groups. Although one possible method for avoiding adhesion and accumulation of such solid components consists of heating the line for transferring ammonia to decompose compounds having carbonyl groups, according to studies conducted by the inventors of the present invention, there are many cases in which heating alone causes polymerization of decomposition products (such as isocyanic acid) or reaction with other compounds having carbonyl groups, thereby making it difficult to completely avoid adhesion and accumulation of solid components. In addition, in the case of simply heating the line, it was determined that compounds having carbonyl groups contained in the ammonia and their decomposition products solidify as a result of being rapidly cooled at the outlet of the line for transferring ammonia (such as the portion in contact with the atmosphere), thereby frequently resulting in prominent adhesion and accumulation of solid components. As a result of conducting extensive studies regarding this problem, the inventors of the present invention found that the problem of adhesion and accumulation of solid components can be solved by making the amount of the compound having carbonyl groups derived from the carbonic acid derivative contained in the ammonia to be equal to or less than the specific amount described above, thereby leading to completion of the present invention. Although the mechanism by which this effect is demonstrated is unclear, the inventors of the present invention surmised that adhesion and accumulation in the line is caused by the compound having carbonyl groups derived from the carbonic acid derivative itself as well as decomposition and/or polymerization products of the compound having carbonyl groups derived from the carbonic acid derivative, and that by making the amount of carbonyl groups contained in the compound having carbonyl groups derived from the carbonic acid derivative equal to or less than a specific concentration, adhesion of the compound having carbonyl groups derived from the carbonic acid derivative itself as well as the reaction rates of decomposition and/or polymerization of that compound are lowered considerably.

Examples of the compound having carbonyl groups derived from the carbonic acid derivative may include compounds such as urea or carbamic acid ester defined as the above-mentioned carbonic acid derivatives, reaction products of isocyanic acid and carbonic acid derivatives formed by thermal decomposition of the carbonic acid derivative in the form of compounds such as biurets and triurets (compounds on the right side of the above-mentioned formula (L)), nurates (compounds on the right side of the above-mentioned formula (K)), and compounds such as the reaction products of carbonic acid derivatives and aromatic hydroxy compounds in the form of carbonic acid esters. Although varying according to the conditions for production of N-substituted carbamic acid ester, caution is required regarding the urea, isocyanic acid, carbamic acid ester and carbonic acid ester among the above-mentioned compounds since they are frequently contained in the ammonia and are present in large amounts. According to studies conducted by the inventors of the present invention, if the amounts of these compounds in the ammonia are controlled to be within the preferable ranges described above, the problem of adhesion and accumulation of solid components in the line for transferring ammonia can generally be avoided.

Compounds having carbonyl groups derived from the carbonic acid derivative contained in the ammonia can be quantified by various known methods, and methods such as gas chromatography, liquid chromatography, NMR, (near) infrared spectroscopy or ultraviolet spectroscopy can be used. More specifically, these compounds may be measured by, for example, introducing the ammonia as a gas directly into a gas chromatograph (such as by connecting the line for transferring ammonia directly to a gas chromatograph and injecting ammonia trapped in a bag or container for trapping gas such as a Tedlar bag into the gas chromatograph with a gastight syringe), or by absorbing compounds having carbonyl groups derived from the carbonic acid derivative contained in the ammonia with water or an organic solvent and the like, followed by measuring by gas chromatography, liquid chromatography, NMR, (near) infrared spectroscopy or ultraviolet spectroscopy. Among these methods, a method is carried out preferably in which the ammonia is introduced directly in the form of a gas into a gas chromatograph equipped with a mass analyzer to identify compounds having carbonyl groups, and the total sum of the products of the amounts of compounds having carbonyl groups and the number of carbonyl groups contained in the compounds having carbonyl groups is taken to be the amount of compounds having carbonyl groups derived form the carbonic acid derivative contained in the ammonia.

Since compounds having carbonyl groups derived from the carbonic acid derivative contained in amounts below the detection limit of the methods indicated here are present in extremely low concentrations in the ammonia, there are hardly any cases in which they have an effect on adhesion and accumulation of solid components in the ammonia transfer line, thereby allowing them to not be included in the "amount of compounds having carbonyl groups derived from the carbonic acid derivative" and be ignored.

<Reuse of Condensed Components>

The mixture of the aromatic hydroxy composition and the compound having carbonyl groups derived from the carbonic acid derivative condensed by the condenser as described above may be circulated within the reactor and reused in the reaction between the compound having ureido groups and the hydroxy composition, the mixture may be recovered and the hydroxy composition and/or the compound having carbonyl groups derived from the carbonic acid derivative may be reused in step (a), or the mixture may be reused in the step of producing carbamic acid ester of step (c).

At that time, the amount of ammonia contained in the hydroxy composition and the compound having carbonyl groups derived from the carbonic acid derivative is preferably 5000 ppm or less. Although condensed components can be reused in the reaction between the organic amine, the carbonic acid derivative and the hydroxy composition even if ammonia is contained at greater than 5000 ppm, since the reaction between the organic amine, the carbonic acid derivative and the hydroxy composition is an equilibrium reaction as previously described, in order for the reaction to proceed efficiently, it is necessary to remove a product thereof in the form of the ammonia outside the system. If an overly excessive amount of ammonia is contained in the reused hydroxy composition and compound having carbonyl groups derived from the carbonic acid derivative, the amount of ammonia extracted from the reaction increases, thereby preventing the ammonia concentration in the reaction liquid from being lowered to the preferable range (range described above) as a result of exceeding the amount of ammonia able to be extracted per unit time (which is dependent on the capacity of the urethane production reactor), and causing a decrease in the yield of N-substituted carbamic acid ester. Thus, although it is preferable that the amount of ammonia contained in the hydroxy composition and compound having carbonyl groups derived from the carbonic acid derivative that are reused in the reaction be low, lowering the amount of ammonia to an extremely low level requires considerable effort. From this viewpoint, the amount of ammonia contained in the hydroxy composition and the compound having carbonyl groups derived from the carbonic acid derivative is more preferably 3000 ppm or less and even more preferably 2000 ppm or less.

As has been described above, although various compounds may be recovered as compounds having carbonyl groups derived from the carbonic acid derivative, the mixture of the hydroxy composition and compound having carbonyl groups derived from the carbonic acid derivative may contain these compounds.

Incidentally, ammonia is produced as a by-product in the previously described step (c), and depending on the case, in step (a) as well as (particularly in the case urea is used as a carbonic acid derivative). When discharging this ammonia, the ratio of the number of carbonyl groups (—C(=O)—) contained in the compound having carbonyl groups derived from the carbonic acid derivative contained in the ammonia to the number of ammonia molecules is 1 or less, preferably 0.5 or less, more preferably 0.1 or less and even more preferably 0.02 or less from the viewpoint of preventing clogging of the ammonia discharge line in the same manner as in step (b).

In addition, although a portion of the reaction solvent and carbonic acid derivative in step (a) and/or step (c) depending on the reaction conditions, and a portion of the hydroxy composition c in step (c), may be extracted from the reaction system and recovered, these compounds can also be reused in steps (a) and/or (c).

<Production Method of N-Substituted Carbamic Acid Ester Using an Aromatic Hydroxy Composition Containing a Plurality of Types of Aromatic Hydroxy Compounds>

Although an explanation was given of a production method of N-substituted carbamic acid-O—Ar ester that uses an aromatic hydroxy composition that contains a plurality of aromatic hydroxy compounds, and particularly one type or a plurality of types of an active aromatic hydroxy compound and one type or a plurality of types of an inactive aromatic hydroxy compound for the aromatic hydroxy composition, in the above-mentioned step (A), N-substituted carbamic acid-O—Ar ester can also be produced in the step (b) by using an aromatic hydroxy composition containing a plurality of types of aromatic hydroxy compounds.

As has been previously described, in the production method of N-substituted carbamic acid ester of the present embodiment, a gas containing the aromatic hydroxy composition and a compound having carbonyl groups derived from the carbonic acid derivative is condensed in a condenser in order to recover the compound having carbonyl groups derived from the carbonic acid derivative in the form of a homogeneous solution. Consequently, the aromatic hydroxy composition preferably contains an aromatic hydroxy compound that is easily vaporized to a certain degree under the reaction conditions. On the other hand, since the compound having ureido groups, the carbonic acid derivative and the aromatic hydroxy composition mainly react in the liquid phase to form N-substituted carbamic acid ester, the aromatic hydroxy composition preferably contains an aromatic hydroxy compound that is present as a liquid under the reaction conditions. Thus, an aromatic hydroxy composition that contains a plurality of types of aromatic hydroxy compounds having different standard boiling points can be preferably used for the aromatic hydroxy composition.

In this case, there are many cases in which, when any of the plurality of types of aromatic hydroxy compounds having different standard boiling points forms N-substituted carbamic acid ester by reacting with the compound having ureido groups and carbonic acid derivative, a plurality of types of aromatic hydroxy compounds are formed together with isocyanate during production of isocyanate by thermal decomposition of the N-substituted carbamic acid ester, thereby making separation of the aromatic hydroxy compounds complex. Therefore, a method for producing N-substituted carbamic acid ester having ester groups derived from an active aromatic hydroxy compound with high selectivity is preferably carried out by using a combination of an active aromatic hydroxy compound and an inactive aromatic hydroxy compound. Moreover, if aromatic hydroxy compounds are selected such that the standard boiling point of the active aromatic hydroxy compound is the highest in the aromatic hydroxy composition, the concentration of the active aromatic hydroxy compound increases in the liquid phase in which the formation reaction of the N-substituted carbamic acid ester mainly takes place, thereby making it possible to form an N-substituted carbamic acid ester derived from the active aromatic hydroxy compound with higher selectivity. An inactive aromatic hydroxy compound having a standard boiling point lower than the standard boiling point of the active aromatic hydroxy compound is preferably introduced into the condenser in the form of a gaseous phase component and condensed in the condenser together with the compound having carbonyl groups derived from the carbonic acid derivative. In the case of combining aromatic hydroxy compounds having different standard boiling points in this manner, the difference in standard boiling points between the aromatic hydroxy compound present mainly in the liquid phase and the aromatic hydroxy compound condensed in the condenser together with the compound having carbonyl groups derived from the carbonic acid derivative is preferably 5° C. or more and more preferably 10° C. or more. In particular, it is effective to combine aromatic hydroxy compounds such that the standard boiling point of the active aromatic hydroxy compound is preferably 5° C. or more higher and more preferably 10° C. or more higher than the standard boiling point of the low activity aromatic hydroxy compound.

Figure 9:
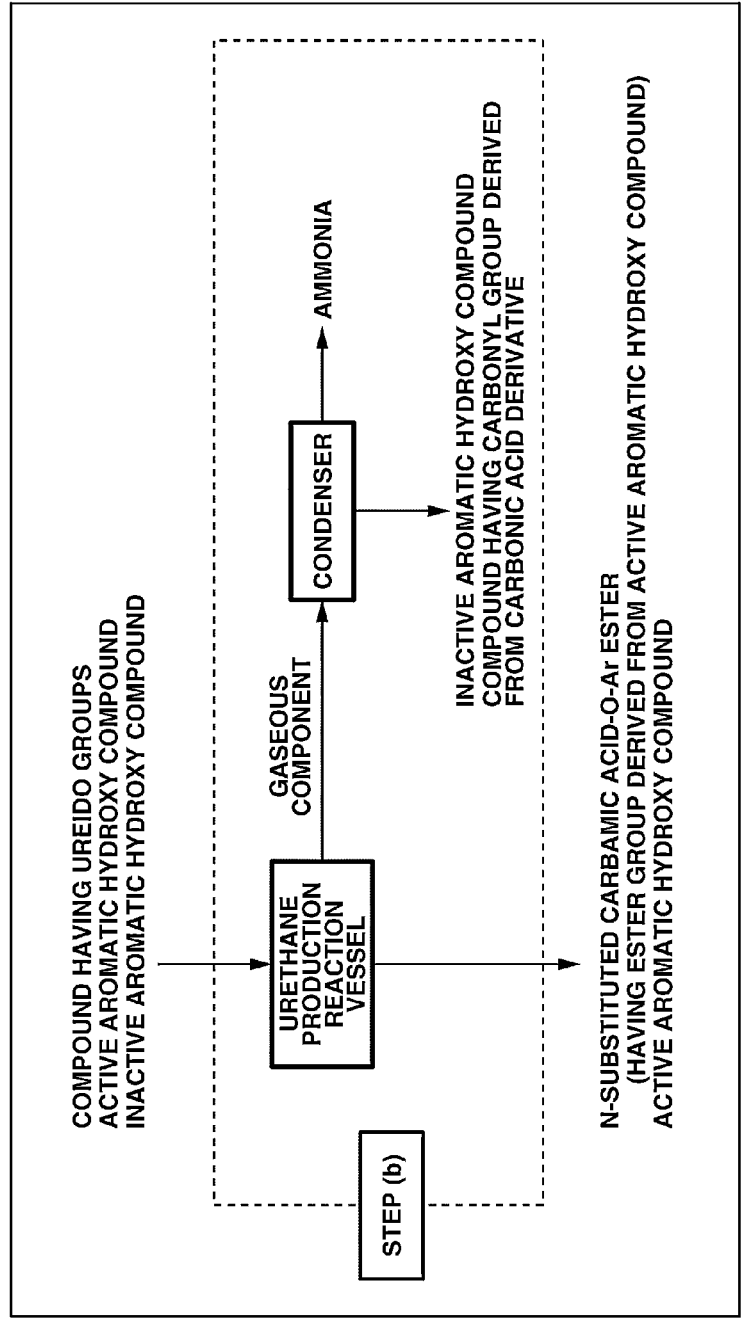
FIG. 9 shows a conceptual drawing depicting one aspect of the present embodiment in the form of a production method of N-substituted carbamic acid ester that uses an aromatic hydroxy composition containing an active aromatic hydroxy compound and an inactive aromatic hydroxy compound.

FIG. 9 shows a conceptual drawing of a production method of N-substituted carbamic acid ester that uses an aromatic hydroxy composition containing a plurality of types of aromatic hydroxy compounds as described above (herein, for the sake of simplicity of the explanation, an aromatic hydroxy composition is described that contains two types of aromatic hydroxy compounds containing an active aromatic hydroxy compound and an inactive aromatic hydroxy compound).

In the case of using an aromatic hydroxy composition containing a plurality of types of aromatic hydroxy compounds in this manner, the amount of the active aromatic hydroxy compound to the amount of the inactive aromatic hydroxy compound in the aromatic hydroxy composition in terms of stoichiometric ratio is preferably from 0.01 to 100 times, more preferably from 0.05 to 20 times and even more preferably from 0.1 to 10 times.

<Step (Y): Transesterification Step>

Although an N-substituted carbamic acid ester produced according to the above method (step (A) and/or step (a) and step (b)) is preferably used to produce isocyanate by thermal decomposition of the N-substituted carbamic acid ester, an N-substituted carbamic acid ester preferably used in the production of the isocyanate is an N-substituted carbamic acid-O—Ar ester. This is because an N-substituted carbamic acid-O—Ar ester allows the thermal decomposition reaction to occur more easily than an N-substituted carbamic acid-O—$R^2$ ester, and demonstrates a greater tendency to easily dissolve in the corresponding isocyanate and aromatic hydroxy compound.

Although the N-substituted carbamic acid ester obtained in the production method described above can be used to produce N-substituted carbamic acid-O—Ar ester or produce N-substituted carbamic acid-O—$R^2$ ester depending on the type of hydroxy composition used, in the case of obtain N-substituted carbamic acid-O—$R^2$ ester according to the above-mentioned production method, the N-substituted carbamic acid-O—$R^2$ ester is converted to an N-substituted carbamic acid-O—Ar ester that is more easily thermally decomposed according the following step (Y) followed by use in a reaction of isocyanate. Furthermore, since this step is a step of converting the ester group of N-substituted carbamic acid-O—$R^2$ ester, this step is also referred to as a "transesterification step" in the present embodiment.

Step (Y): a step in which N-substituted carbamic acid-O—$R^2$ ester is reacted with an aromatic hydroxy compound to produce N-substituted carbamic acid-O—Ar ester having an ester group derived from the aromatic hydroxy compound.

Furthermore, an alcohol is formed that is derived from the N-substituted carbamic acid-O—$R^2$ ester in the step (Y). The following provides an explanation of the step (Y).

Here, the subject N-substituted carbamic acid-O—$R^2$ ester refers to an N-substituted carbamic acid-O—$R^2$ ester represented by the above-mentioned formula (92), an N-substituted carbamic acid mono(—O—$R^2$ ester) represented by the following formula (120) to be described later, or an N-substituted carbamic acid poly(—O—$R^2$ ester) represented by the following formula (130) to be described later.

Any of the aromatic hydroxy compounds represented by the above-mentioned formula (46), (55), (56), (67), (70) or (79) may be used for the reacted aromatic hydroxy compound. In addition, the aromatic hydroxy compound may be used alone or a plurality of types may be used in combination.

Step (Y) can be carried out using various methods corresponding to the compounds used with reference to known methods (such as WO 2008/059953).

Although varying according to the reacted compounds, the reaction conditions of step (Y) are such that the aromatic hydroxy compound is used based on the ester groups that compose the raw material N-substituted carbamic acid-O—$R^2$ ester at a stoichiometric ratio within a range of from 2 to 1000. Although the aromatic hydroxy compound is preferably in excess based on the ester groups that compose the raw material N-substituted carbamic acid-O—$R^2$ ester in order to complete the reaction more quickly, in consideration of the size of the reactor, the stoichiometric ratio thereof is preferably within a range of from 2 to 100 times and more preferably within a range of from 5 to 50 times.

The reaction temperature is generally within a range of from 100 to 300° C., and although a high temperature is preferable for increasing the reaction rate, since there are cases in which side reactions occur easily at high temperatures, the reaction temperature is preferably within a range of from 150 to 250° C. A known cooling apparatus or heat apparatus may be installed in the reactor to maintain a constant reaction temperature. In addition, although varying according to the types of compounds used and the reaction temperature, the reaction may be carried out at reduced pressure, normal pressure or increased pressure and normally at a reaction pressure within a range of from 20 to $1 \times 10^6$ Pa. There are no particular limitations on the reaction time (residence time in the case of a continuous method), and is generally from 0.001 to 100 hours, preferably from 0.01 to 50 hours and more preferably from 0.1 to 30 hours. In addition, the reaction can be terminated after confirming that a desired amount of the target N-substituted carbamic acid-O—Ar ester has been formed by sampling the reaction liquid and determining the amount formed by liquid chromatography, for example.

Although a catalyst is not necessarily required in step (Y), a catalyst may be used without problem to lower the reaction temperature or complete the reaction more quickly. The catalyst is used at from 0.01 to 30% by weight and preferably at from 0.5 to 20% by weight based on the weight of the N-substituted carbamic acid-O—$R^2$ ester. Examples of catalysts may include Lewis acids as well as transition metal compounds that form a Lewis acid, organic tin compounds, copper group metals, zinc or iron group metal compounds, and more specifically, Lewis acids and transition metal compounds that form a Lewis acid represented by $AlX_3$, $TiX_3$, $TiX_4$, $VOX_3$, $VX_5$, $ZnX_2$, $FeX_3$ or $SnX_4$ (wherein X represents a halogen, an acetoxy group, an alkoxy group or an aryloxy group); organic tin compounds represented by $(CH_3)_3SnOCOCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$ or $BuSnO(OH)$; copper family metal compounds represented by $CuCl$, $CuCl_2$, $CuBr$, $CuBr_2$, $CuI$, $CuI_2$, $Cu(OAc)_2$, $Cu(acac)_2$, copper olefinate, $Bu_2Cu$, $(CH_3O)_2Cu$, $AgNO_3$, $AgBr$, silver picrate or $AgC_6H_6ClO_4$; zinc compounds represented by $Zn(acac)_2$; and, iron family metal compounds represented by $Fe(C_{10}H_5)(CO)_5$, $Fe(CO)_5$, $Fe(C_4H_6)(CO)_3$, $Co(mesitylene)_2(PEt_2Ph_2)$, $CoC_5F_5(CO)_7$ or ferrocene. (In the above listing of examples, Bu refers to a butyl group, Ph refers to a phenyl group, and acac refers to an acetyl acetone chelate ligand.) Amines such as 1,4-diazabicyclo[2,2,2]octane, triethylenediamine or triethylamine are suitable for use as catalysts, while organic metal catalysts such as dibutyl tin dilaurate, ferrous octoate or stannous octoate are particularly preferable. These compounds may be used alone or two or more types may be used as a mixture.

Although the use of a reaction solvent is not necessarily required in the present embodiment, a suitable inert solvent can be preferably used as a reaction solvent for the purpose of facilitating the reaction procedure and the like, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; and sulfoxides such as dimethylsulfoxide or diphenylsulfoxide. These solvents can be used alone or two or more types can be used as a mixture.

The transesterification reaction in the present embodiment is an equilibrium reaction. Thus, it is preferable to allow the reaction to proceed while removing a product in the form of alcohol (alcohol derived from the raw material N-substituted carbamic acid-O—$R^2$ ester) from the reaction system in order to carrying out transesterification efficiently. Thus, if the aromatic hydroxy compound is selected such that the standard boiling point of the aromatic hydroxy compound used in transesterification is higher than the standard boiling point of the alcohol derived from the raw material N-substituted carbamic acid-O—$R^2$ ester, the compound having the lowest standard boiling point in the reaction system becomes the alcohol derived from the raw material N-substituted carbamic acid-O—$R^2$ ester, thereby facilitating removal of products from the reaction system.

In addition, transesterification is preferably carried out by a continuous method to allow transesterification to proceed efficiently. Namely, the raw material N-substituted carbamic acid-O—$R^2$ ester and the aromatic hydroxy compound are continuously supplied to a reactor, transesterification is carried out, alcohol derived from the raw material N-substituted carbamic acid-O—$R^2$ ester that is formed is extracted from the reactor, and a reaction liquid containing the N-substituted carbamic acid-O—Ar ester formed and the aromatic hydroxy compound is continuously extracted from the bottom of the reactor.

Although the material of the reactor and lines used to carry out transesterification may be known materials provided they do not have a detrimental effect on the starting substances and reactants, materials such as SUS304, SUS316 or SUS316L are inexpensive and can be used preferably. There are no particular limitations on the type of a reactor, and a known tank-type or a column-type reactor can be used. Various known methods are used for such a reactor, examples of which may include types using reactors containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a thin film evaporator or a column-type reactor are preferable from the viewpoint of efficiently shifting the equilibrium to the products side, while a structure having a large gas-liquid contact area is preferable for being able to rapidly transfer the alcohol derived from the raw material N-substituted carbamic acid-O—$R^2$ ester formed to the gaseous phase.

A multistage distillation column refers to a distillation column having multiple stages in which the number of theoretical plates of distillation is 2 or more, and any multistage distillation column may be used provided it allows continuous distillation. Any multistage distillation column can be used for the multistage distillation column provided it is ordinarily used as a multistage distillation column, examples of which may include tray column types using a tray such as a bubble tray, a porous plate tray, a valve tray or a countercurrent tray, and packed column types packed with various types of packing materials such as a raschig ring, a lessing ring, a pole ring, a Berl saddle, an Interlock saddle, a Dixon packing, a McMahon packing, Helipack, a Sulzer packing or Mellapak. Any packed column can be used provided the column is packed with a known packing material as described above. Moreover, a combination tray-packed column type is also used preferably that combines a tray portion with a portion packed with a packing material.

A line for supplying inert gas and/or liquid inert solvent from the lower portion of the reactor may be separately attached, and in the case the mixture of the target N-substituted carbamic acid-O—Ar ester and aromatic hydroxy compound contains raw material N-substituted carbamic acid-O—$R^2$ ester, a line may be attached for re-circulating all or a portion of the mixture to the reactor. Furthermore, in the case of using the above-mentioned inert solvent, the inert solvent may be in the form of a gas and/or a liquid.

The gaseous component extracted from the reactor containing alcohol derived from the raw material N-substituted carbamic acid-O—$R^2$ ester is preferably purified using a known method such as that which uses a distillation column, and can be reused as an alcohol of step (A) and/or step (a) and/or step (b) and/or step (c).

Figure 10:
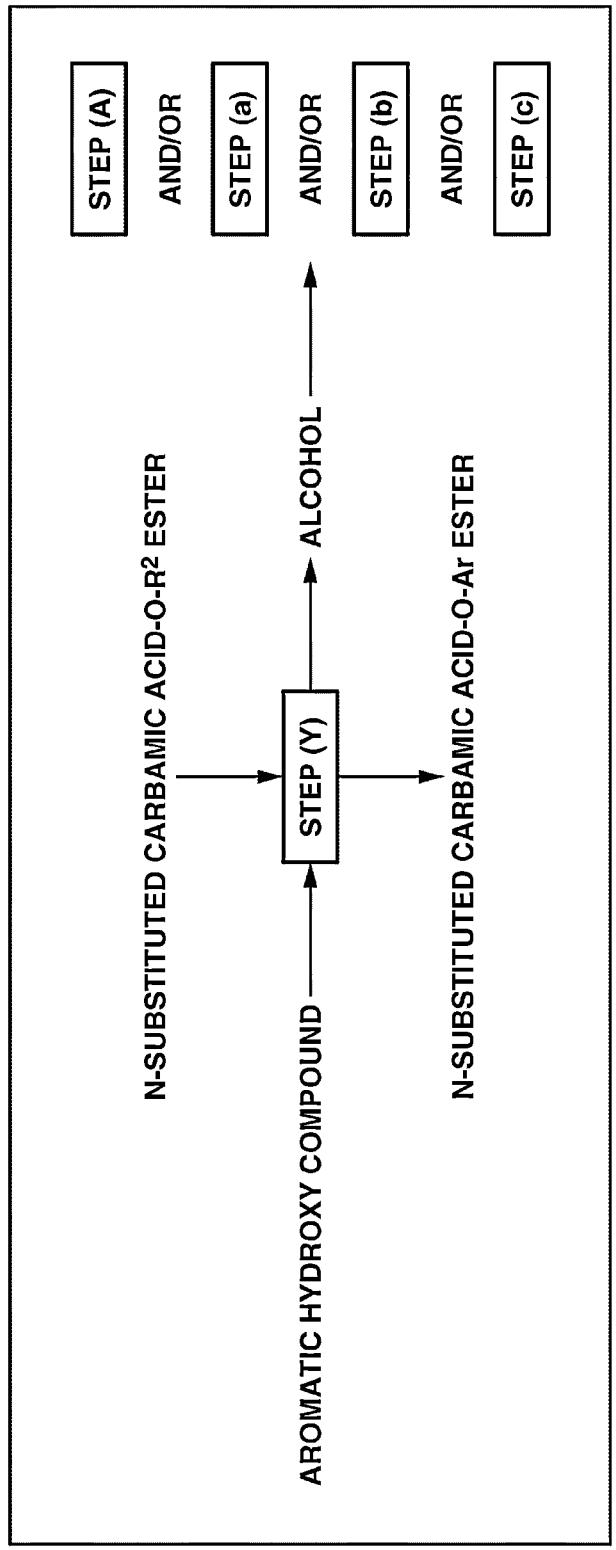
FIG. 10 shows a conceptual drawing depicting one aspect of the present embodiment in the form of step (Y) and reuse of an alcohol formed in the step (Y)

FIG. 10 shows a conceptual drawing representing step (Y) and reuse of an alcohol formed in the step (Y).

<Step (Z): Use of Recovered Ammonia for Urea Synthesis>

In the present embodiment, although ammonia discharged from the condenser in the above-mentioned step (A), step (a) and/or step (b) and/or step (c) can be converted to aqueous ammonia by absorbing water and used in the production of absorption refrigerator refrigerant, oil-based detergents for woolen fabrics, raw rubber coagulants and various types of ammonia salts, the treatment of nitrogen oxides (NOx) generated at thermal power generation plants and the like, or the production of photographic emulsions, or can be converted to liquid ammonia by a method such as cryogenic separation and used for nitrogen fertilizer raw materials, synthetic fiber raw materials (such as caprolactam or acrylonitrile), treatment of nitrogen oxides (NOx) generated thermal power generation plants, or refrigeration refrigerants, it is preferably used in the synthesis of urea. The following provides an explanation of this urea synthesis step (to be referred to as step (Z)).

A conventionally known method can be employed to produce urea by reacting ammonia and carbon dioxide, an example of which contain reacting ammonia and carbon dioxide at a pressure within a range of from 20 to 40 MPa and temperature within a range of from 190 to 200° C. such that the ratio of ammonia to carbon dioxide is within a range of a stoichiometric ratio of from 3 to 5.

The urea produced by such a method may be used in the reaction of step (a) or used as the urea of step (c).

Figure 11:
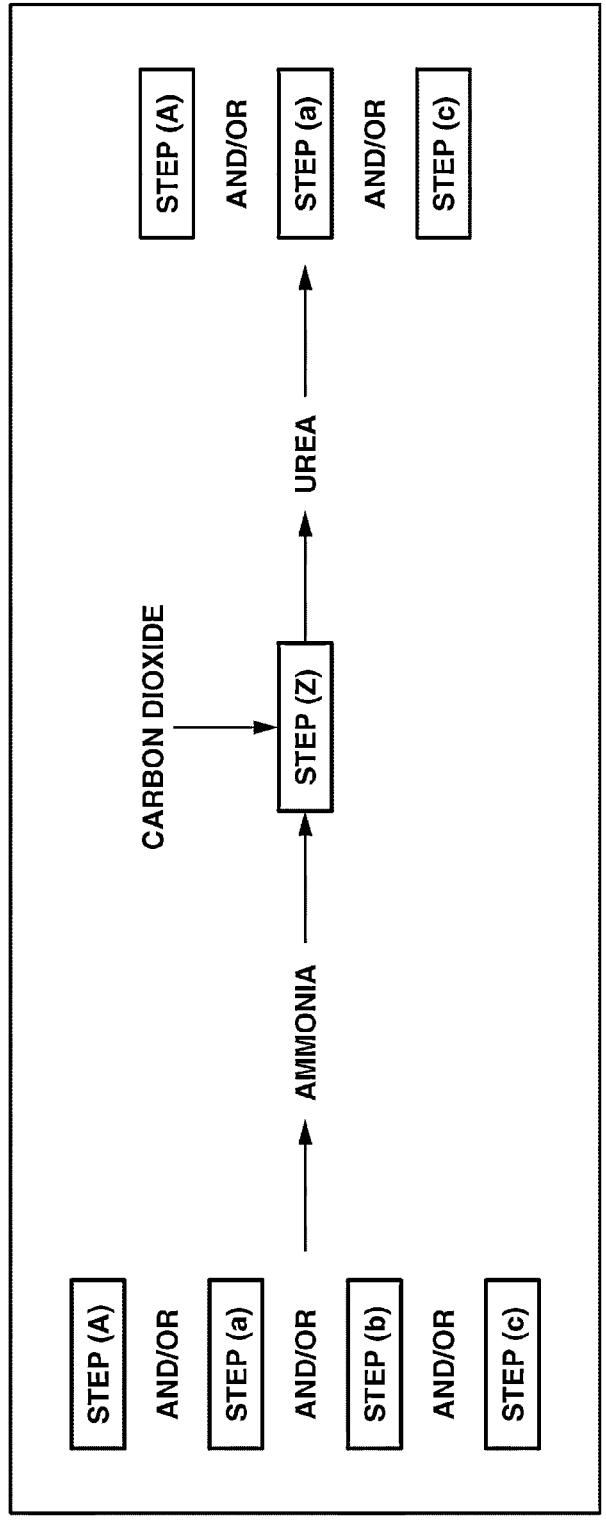
FIG. 11 shows a conceptual drawing depicting one aspect of the present embodiment in the form of a urea synthesis step and reuse of urea produced in the urea synthesis step.

FIG. 11 shows a conceptual drawing representing the urea synthesis step and the reuse of urea produced in the urea synthesis step.

<Step (F): Production of Isocyanate by Thermal Decomposition Reaction of N-Substituted Carbamic Acid-O—Ar Ester>

The following provides an explanation of step (F).

Step (F) is a step of producing isocyanate by applying N-substituted carbamic acid-O—Ar ester to a thermal decomposition reaction.

Although the N-substituted carbamic acid-O—Ar ester produced according to the method described above is preferably used to produce isocyanate, the N-substituted carbamic acid-O—Ar ester is preferably supplied to a thermal decomposition reactor (a "thermal decomposition reactor" as referred to herein indicates the reactor in which step (F) is carried out) in the form of a composition for transfer and storage of N-substituted carbamic acid-O—Ar ester as previously explained. As a result of supplying the N-substituted carbamic acid-O—Ar ester in the form of the composition for transfer and storage, not only can thermal denaturation reactions of the N-substituted carbamic acid-O—Ar ester be inhibited, but the yield of isocyanate can also be enhanced.

The reaction temperature is generally within a range of from 100 to 300° C., and although a high temperature is preferable for increasing the reaction rate, since there are cases in which side reactions as previously described occur easily at high temperatures due to the N-substituted carbamic acid-O—Ar ester and/or isocyanate, the reaction temperature is preferably within a range of from 150 to 250° C. A known cooling apparatus or heat apparatus may be installed in the reactor to maintain a constant reaction temperature. In addition, although varying according to the types of compounds used and the reaction temperature, the reaction may be carried out at reduced pressure, normal pressure or increased pressure and normally at a reaction pressure within a range of from 20 to $1 \times 10^6$ Pa. There are no particular limitations on the reaction time (residence time in the case of a continuous method), and is generally from 0.001 to 100 hours, preferably from 0.005 to 50 hours and more preferably from 0.01 to 10 hours.

Although a catalyst is not necessarily in the present embodiment, a catalyst may be used without problem to lower the reaction temperature or complete the reaction more quickly. The catalyst is used at from 0.01 to 30% by weight and preferably at from 0.5 to 20% by weight based on the weight of the N-substituted carbamic acid-O—Ar ester. Examples of catalysts may include Lewis acids as well as transition metal compounds that form a Lewis acid, organic tin compounds, copper group metals, zinc or iron group metal compounds, and more specifically, Lewis acids and transition metal compounds that form a Lewis acid represented by $AlX_3$, $TiX_3$, $TiX_4$, $VOX_3$, $VX_5$, $ZnX_2$, $FeX_3$ or $SnX_4$ (wherein X represents a halogen, an acetoxy group, an alkoxy group or an aryloxy group); organic tin compounds represented by $(CH_3)_3SnOCHCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$ or $BuSnO(OH)$; copper family metal compounds represented by $CuCl$, $CuCl_2$, $CuBr$, $CuBr_2$, $CuI$, $CuI_2$, $Cu(OAc)_2$, $Cu(acac)_2$, copper olefinate, $Bu_2Cu$, $(CH_3O)_2Cu$, $AgNO_3$, $AgBr$, silver picrate or $AgC_6H_6ClO_4$; zinc compounds represented by $Zn(acac)_2$; and, iron family metal compounds represented by $Fe(C_{10}H_8)(CO)_5$, $Fe(CO)_5$, $Fe(C_4H_6)(CO)_3$, $Co(mesitylene)_2(PEt_2Ph_2)$, $CoC_5F_5(CO)_7$ or ferrocene. (In the above listing of examples, Bu refers to a butyl group, Ph refers to a phenyl group, and acac refers to an acetyl acetone chelate ligand.) Amines such as 1,4-diazabicyclo[2,2,2]octane, triethylenediamine or triethylamine are suitable for use as catalysts, while organic metal catalysts such as dibutyl tin dilaurate, ferrous octoate or stannous octoate are particularly preferable. These compounds may be used alone or two or more types may be used as a mixture.

In addition, in the case of using a catalyst in any of the steps during production of the N-substituted carbamic acid-O—Ar ester, although the catalyst residue may be supplied to the thermal decomposition step, the presence of such a catalyst residue does not present a problem in many cases.

Although the use of a reaction solvent other than the aromatic hydroxy compound is not necessarily required in step (F), a suitable inert solvent can be preferably used as a reaction solvent for the purpose of facilitating the reaction procedure and the like, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; sulfoxides such as dimethylsulfoxide or diphenylsulfoxide; and silicone oils. These solvents can be used alone or two or more types can be used as a mixture.

In the case of having stored an N-substituted carbamic acid-O—Ar ester at a high temperature for a long period of time, there are cases in which side reactions occur such as a reaction by which urea bond-containing compounds are formed by an ester decarboxylation reaction of two molecules of N-substituted carbamic acid-O—Ar ester, or a reaction by which allophanate groups are formed by a reaction with isocyanate formed by thermal decomposition of N-substituted carbamic acid-O—Ar ester. Thus, the amount of time during which the N-substituted carbamic acid-O—Ar ester and the isocyanate are held at a high temperature is preferably as short as possible. Thus, the thermal decomposition reaction is preferably carried out in the form of a continuous method. A continuous method refers to a method in which a mixture containing the N-substituted carbamic acid-O—Ar ester is continuously supplied to a reactor where it is subjected to a thermal decomposition reaction, and the isocyanate and aromatic hydroxy compound formed are continuously extracted from the thermal decomposition reactor. In this continuous method, low boiling point components formed by thermal decomposition of urethane are preferably recovered from the upper portion of the thermal decomposition reactor in the form of gaseous phase components, while the remainder is recovered from the bottom of the thermal decomposition reactor in the form of liquid phase components. Although all compounds present in the thermal decomposition reactor can be recovered as gaseous phase components, the presence of liquid phase components in the thermal decomposition reactor has the effect of dissolving polymeric substances formed by side reactions caused by the N-substituted carbamic acid-O—Ar ester and/or isocyanate, thereby preventing adhesion and solidification of the polymeric substances in the thermal decomposition reactor. Although isocyanate and aromatic hydroxy compound are formed by thermal decomposition of N-substituted carbamic acid-O—Ar ester, at least one of these compounds is recovered in the form of a gaseous phase component. Which compound is recovered as a gaseous phase component is dependent upon such factors as the conditions of the thermal decomposition reaction.

Here, although the term "low boiling point component formed by thermal decomposition of N-substituted carbamic acid-O—Ar ester" used in the present embodiment is equivalent to the aromatic hydroxy compound and/or isocyanate formed by thermal decomposition of the N-substituted carbamic acid-O—Ar ester, it particularly refers to a compound that is able to be present as a gas under the conditions in which the thermal decomposition reaction is carried out.

For example, a method can be employed in which the isocyanate and aromatic hydroxy compound formed by the thermal decomposition reaction can be recovered in the form of gaseous phase components, while a liquid phase component is recovered that contains N-substituted carbamic acid-O—Ar ester. In this method, the isocyanate and aromatic hydroxy compound may be recovered separately in the thermal decomposition reactor. The recovered gaseous phase component that contains isocyanate is preferably supplied to a distillation apparatus for separating and purifying the isocyanate in the gaseous phase. Although the recovered gaseous phase component that contains isocyanate can be supplied to a distillation apparatus after converting to a liquid phase with a condenser and the like, there are many cases in which the apparatus becomes complex and the amount of energy used becomes large, thereby making this undesirable. In the case the liquid phase component contains N-substituted carbamic acid-O—Ar ester, all or a portion of the liquid phase component is preferably supplied to the upper portion of the thermal decomposition reactor where the N-substituted carbamic acid-O—Ar ester is again subjected to a thermal decomposition reaction. The upper portion of the thermal decomposition reactor as referred to herein indicates the portion two or more stages above the bottom of the column in terms of the number of theoretical plates in the case of the thermal decomposition reactor being a distillation column, while in the case the thermal decomposition reactor is a thin film distiller, indicates the portion above the heated transfer surface portion. When supplying all or a portion of the liquid phase component to the upper portion of the thermal decomposition reactor, the liquid phase component is transferred while holding at a temperature of preferably from 50 to 180° C., more preferably from 70 to 170° C. and even more preferably from 100 to 150° C.

In addition, a method can also be employed in which, for example, the isocyanate and aromatic hydroxy compound formed by the thermal decomposition reaction are recovered in the form of gaseous phase components, while a liquid phase component containing N-substituted carbamic acid-O—Ar ester is recovered from the bottom of the thermal decomposition reactor. In this method as well, the recovered gaseous component that contains isocyanate is preferably supplied to a distillation apparatus for separating and purifying the isocyanate in the gaseous phase. On the other hand, all or a portion of the liquid phase component that contains N-substituted carbamic acid-O—Ar ester is supplied to the upper portion of the thermal decomposition reactor where the N-substituted carbamic acid-O—Ar ester is again subjected to a thermal decomposition reaction. When supplying all or a portion of the liquid phase component to the upper portion of the thermal decomposition reactor, the liquid phase component is transferred while holding at a temperature of preferably from 50 to 180° C., more preferably from 70 to 170° C. and even more preferably from 100 to 150° C.

Moreover, a method can also be employed in which, for example, the aromatic hydroxy compound among the isocyanate and aromatic hydroxy compound formed by the thermal decomposition reaction is recovered in the form of a gaseous phase component, while a mixture containing the isocyanate is recovered in the form of a liquid phase component from the bottom of the thermal decomposition reactor. In this case, the liquid phase component is supplied to a distillation apparatus to recover the isocyanate. In the case N-substituted carbamic acid-O—Ar ester is contained in the liquid phase component, all or a portion of the mixture containing N-substituted carbamic acid-O—Ar ester is preferably supplied to the upper portion of the thermal decomposition reactor and the N-substituted carbamic acid-O—Ar ester is again subjected to a thermal decomposition reaction. When supplying all or a portion of the liquid phase component to the thermal decomposition reactor, the liquid phase component is transferred while holding at a temperature of preferably from 50 to 180° C., more preferably from 70 to 170° C. and even more preferably from 100 to 150° C.

Although previously described, in the thermal decomposition reaction, the liquid phase component is preferably recovered from the bottom of the thermal decomposition reactor. This is because the presence of a liquid phase component in the thermal decomposition reactor has the effect of dissolving polymeric substances formed by side reactions caused by the N-substituted carbamic acid-O—Ar ester and/or isocyanate as previously described, thereby enabling the polymeric substances to be discharged from the thermal decomposition reactor and preventing adhesion and solidification of the polymeric substances in the thermal decomposition reactor.

In the case the liquid phase component contains N-substituted carbamic acid-O—Ar ester, although all or a portion of the liquid phase component is supplied to the upper portion of the thermal decomposition reactor where the N-substituted carbamic acid-O—Ar ester is again subjected to a thermal decomposition reaction, polymeric by-products may accumulate in the liquid phase component if this step is repeated. In this case, all or a portion of the liquid phase component can be removed from the reaction system or held to a fixed concentration to reduce accumulation of polymeric by-products. Although the liquid phase component removed from the reaction system frequently contains aromatic hydroxy compound, the aromatic hydroxy compound can be recovered from the liquid phase component by a method such as distillation and reused in step (A) and/or step (a) and/or step (b) and/or step (c) and/or step (Y).

The recovered isocyanate may contain aromatic hydroxy compound and the like depending on the reaction conditions, the conditions under which the isocyanate is recovered, the reaction apparatus and the like. In such cases, a desired purity of isocyanate may be obtained by further carrying out distillation or other procedure.

The isocyanate produced in this manner preferably contains 1 to 1000 ppm of aromatic hydroxy compound present together with isocyanate in the thermal decomposition reactor based on the amount of isocyanate.

In general, although isocyanate has the property of easily yellowing, an aromatic hydroxy compound, and particularly 2,6-(di-tert-butyl)-p-cresol (BHT), which has substituents having steric hindering action at both ortho positions of an aromatic hydroxy group, is frequently added as an additive. Conventional stabilizers are in the form of an isocyanate composition as a result of being added following production of isocyanate. The inventors of the present invention found that by adjusting the conditions under which isocyanate is recovered, reaction conditions, reaction apparatus and the like during production of isocyanate using the method described above, an isocyanate containing an aromatic hydroxy compound, and particularly an aromatic hydroxy compound represented by the above-mentioned formula (56), together with isocyanate in the thermal decomposition reactor in an amount within the above-mentioned range is effective in preventing coloring in particular. In the past, aromatic hydroxy compounds having substituents having steric hindering action at both ortho positions of the aromatic hydroxy group were considered to be effective as stabilizers, and it is therefore surprising that an aromatic hydroxy compound formed in the isocyanate production step of the present embodiment (an aromatic hydroxy compound not having substituents having steric hindering action at both ortho positions of the aromatic hydroxy group as represented by the above-mentioned formula (56)) demonstrates such an effect. In addition, it is also surprising that there are many cases in which such an effect is not obtained simply by adding an aromatic hydroxy compound represented by the above-mentioned formula (56) to an isocyanate.

Although there are no particular limitations on the type of the thermal decomposition reactor, a known distillation apparatus is used preferably in order to efficiently recover gaseous phase components. Various known methods are used for such a reaction vessel, examples of which may include types using reaction vessels containing a distillation column, a multistage distillation column, a multitubular reactor, a continuous multistage distillation column, a packed column, a thin film evaporator, a reactor provided with a support inside, a forced circulation reactor, a falling film evaporator or a falling drop evaporator, and types using combinations thereof. From the viewpoint of rapidly removing low boiling point components from the reaction system, a method using a tubular reactor is preferable, while a method using a reactor such as a tubular thin film evaporator or tubular falling film evaporator is more preferable, and a structure having a large gas-liquid contact area is preferable for being able to rapidly transfer the low boiling point components formed to the gaseous phase.

Although a known material may be used for the material of the thermal decomposition reactor and lines provided it does not have a detrimental effect on the urethane or products in the form of the aromatic hydroxy compound and isocyanate, SUS304, SUS316 or SUS316L are inexpensive and can be used preferably.

The aromatic hydroxy compounds contained in the gaseous phase components and/or liquid phase component obtained in the thermal decomposition reaction as described above can each be separated, recovered and reused. More specifically, aromatic hydroxy compounds can be reused as aromatic hydroxy compounds used in step (A) and/or step (a) and/or step (b) and/or step (c) and/or step (Y).

Figure 12:
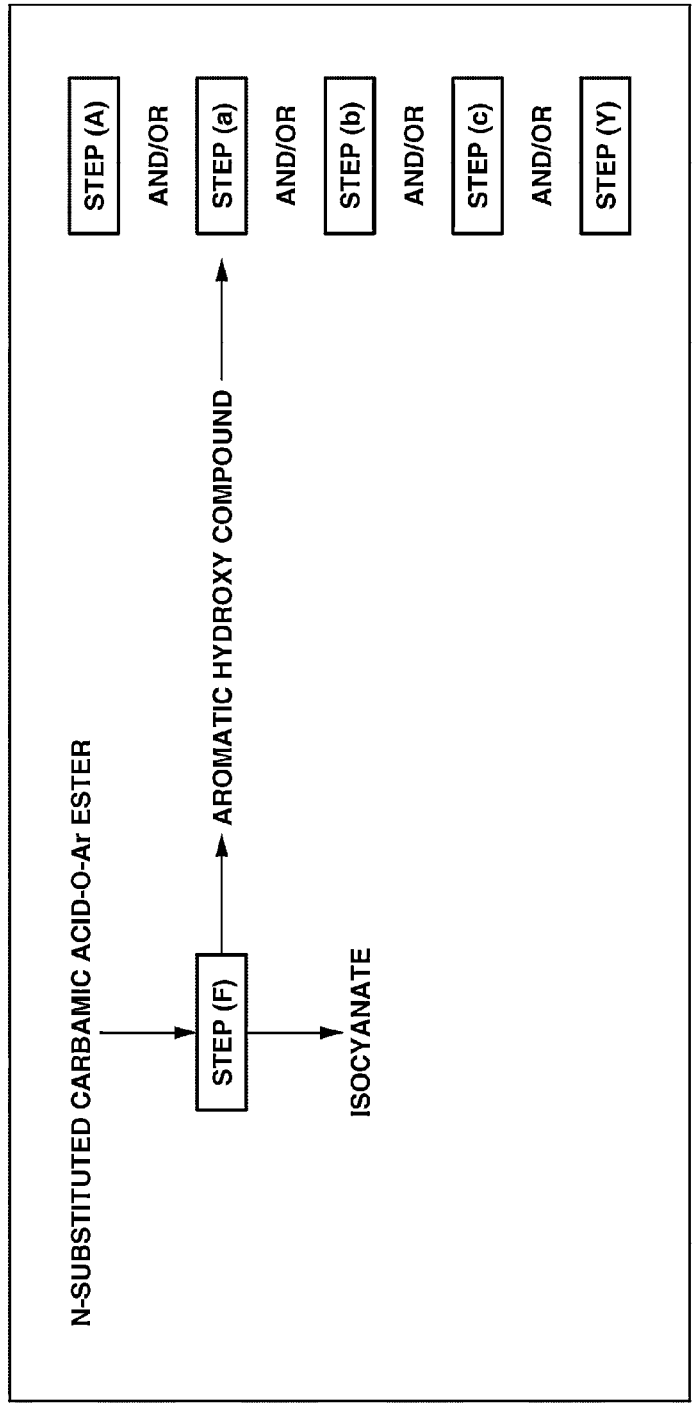
FIG. 12 shows a conceptual drawing depicting one aspect of the present embodiment in the form of step (F) and reuse of an aromatic hydroxy compound formed in the step (F)

FIG. 12 shows a conceptual drawing depicting the step (F) and reuse of aromatic hydroxy compound formed in the step (F).

<Cleaning the Reactor>

There are cases in which polymeric side-reaction products may be formed, albeit in minute amounts, in the production N-substituted carbamic acid-O—Ar ester and the production of isocyanate using the N-substituted carbamic acid-O—Ar ester of the present embodiment. Since these polymeric side-reaction products have a high solubility with respect to aromatic hydroxy compounds used in the present embodiment, they are removed from the reactor in the form of a solution of the aromatic hydroxy compounds. However, in cases of fluctuations in reaction apparatus operating conditions or cases of long-term operation, the polymeric side-reaction products may adhere to the reactor.

In such cases, the inside (and particularly the inner walls) of the reactor can be cleaned with an acid that is a good solvent of the polymeric side-reaction products to keep the inside of the reactor clean.

There are no particular limitations on the cleaning acid provided it dissolves the polymeric side-reaction products, and although both organic acids and inorganic acids may be used, organic acids are used preferably. Although examples of organic acids that can be used may include carboxylic acid, sulfonic acid, sulfinic acid, phenols, enols, thiophenols, imides, oximes and aromatic sulfonamides, carboxylic acid and phenols are used preferably. Examples of such compounds may include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (including isomers), octanoic acid (including isomers), nonanoic acid (including isomers), decanoic acid (including isomers), undecanoic acid (including isomers), dodecanoic acid (including isomers), tetradecanoic acid (including isomers), hexadecanoic acid (including isomers), acrylic acid, crotic acid, isocrotic acid, vinylacetic acid, methacrylic acid, angelic acid, tiglic acid, arylacetate or undecenoic acid (including isomers); saturated or unsaturated aliphatic dicarboxylic acids such as oxalic acid, malonic acid, succinic acid, glutaric acid, adipic acid, heptanedioic acid (including isomers), octanedioic acid (including isomers), nonanedioic acid (including isomers), decanedioic acid (including isomers), maleic acid, fumaric acid, methylmaleic acid, methylfumaric acid, pentenedioic acid (including isomers), itaconic acid or allylmalonic acid; saturated or unsaturated aliphatic tricarboxylic acid compounds such as 1,2,3-propanetricarboxylic acid, 1,2,3-propenetricarboxylic acid or 2,3-dimethylbutane-1,2,3-tricarboxylic acid; aromatic carboxylic acid compounds such as benzoic acid, methylbenzoic acid (including isomers), ethylbenzoic acid (including isomers), propylbenzoic acid (including isomers), dimethylbenzoic acid (including isomers) or trimethylbenzoic acid (including isomers); aromatic dicarboxylic acid compounds such as phthalic acid, isophthalic acid, terephthalic acid or methylisophthalic acid; aromatic tricarboxylic acid compounds such as hemimellitic acid, trimellitic acid or trimesic acid; phenol; mono-substituted phenols such as methyl phenol (including isomers), ethyl phenol (including isomers), propyl phenol (including isomers), butyl phenol (including isomers), pentyl phenol (including isomers), hexyl phenol (including isomers), heptyl phenol (including isomers), octyl phenol (including isomers), nonyl phenol (including isomers), decyl phenol (including isomers), dodecyl phenol (including isomers), phenyl phenol (including isomers), phenoxyphenol (including isomers) or cumyl phenol (including isomers); and di-substituted phenols such as dimethyl phenol (including isomers), diethyl phenol (including isomers), dipropyl phenol (including isomers), dibutyl phenol (including isomers), dipentyl phenol (including isomers), dihexyl phenol (including isomers), diheptyl phenol (including isomers), dioctyl phenol (including isomers), dinonyl phenol (including isomers), didecyl phenol (including isomers), didodecyl phenol (including isomers), diphenyl phenol (including isomers), diphenoxyphenol (including isomers) or dicumyl phenol (including isomers). In consideration of effects in the case of the cleaning solvent remaining after cleaning the thermal decomposition reactor, more preferable examples of these organic acids may include aromatic hydroxy compounds, while even more preferable examples may include compounds of the same types as aromatic hydroxy compounds formed in the production method of N-substituted carbamic acid-O—Ar ester and/or thermal decomposition reaction of N-substituted carbamic acid-O—Ar ester of the present embodiment.

Furthermore, in the case of using an aromatic hydroxy compound for the cleaning acid, the standard boiling point of the aromatic hydroxy compound preferably has a difference in boiling point of 10° C. or more from the standard boiling point of isocyanate formed by the thermal decomposition reaction of N-substituted carbamic acid-O—Ar ester described above from the viewpoint of cleaning effects.

Various methods can be used to clean the reactor using the above-mentioned cleaning solvent, examples of which may include a method in which the reactor is cleaned by introducing the cleaning solvent from the upper portion of the reactor, and a method in which the inside of the reactor is cleaned by introducing the cleaning agent into the bottom of the reactor and then boiling the cleaning reagent up through the reactor.

It is not necessary to carry out the cleaning procedure each time the reaction is carried out, but rather can be determined arbitrarily based on the compounds used, operating rate and the like, and the cleaning procedure is preferably carried out once every 1 to 20000 hours of operating time, more preferably once every one day to one year of operating time, and even more preferably once every one month to one year of operating time. The reactor may be equipped with a line for introducing the cleaning agent.

<Example of Preferable Aspects>

The preceding has provided an explanation of a production method of N-substituted carbamic acid ester, a composition for transfer and storage of N-substituted carbamic acid ester, and an isocyanate production method using the N-substituted carbamic acid ester. As has been previously indicated, the production method of N-substituted carbamic acid ester can be carried out diversely by combining the above-mentioned steps in various ways. The following provides an explanation of particularly preferable aspects of these various combinations. Furthermore, the production method of N-substituted carbamic acid ester, the composition for transfer and storage of N-substituted carbamic acid ester, and the isocyanate production method using the N-substituted carbamic acid ester are not limited to the methods explained here.

<Preferable Aspect (I)>

Figure 13:
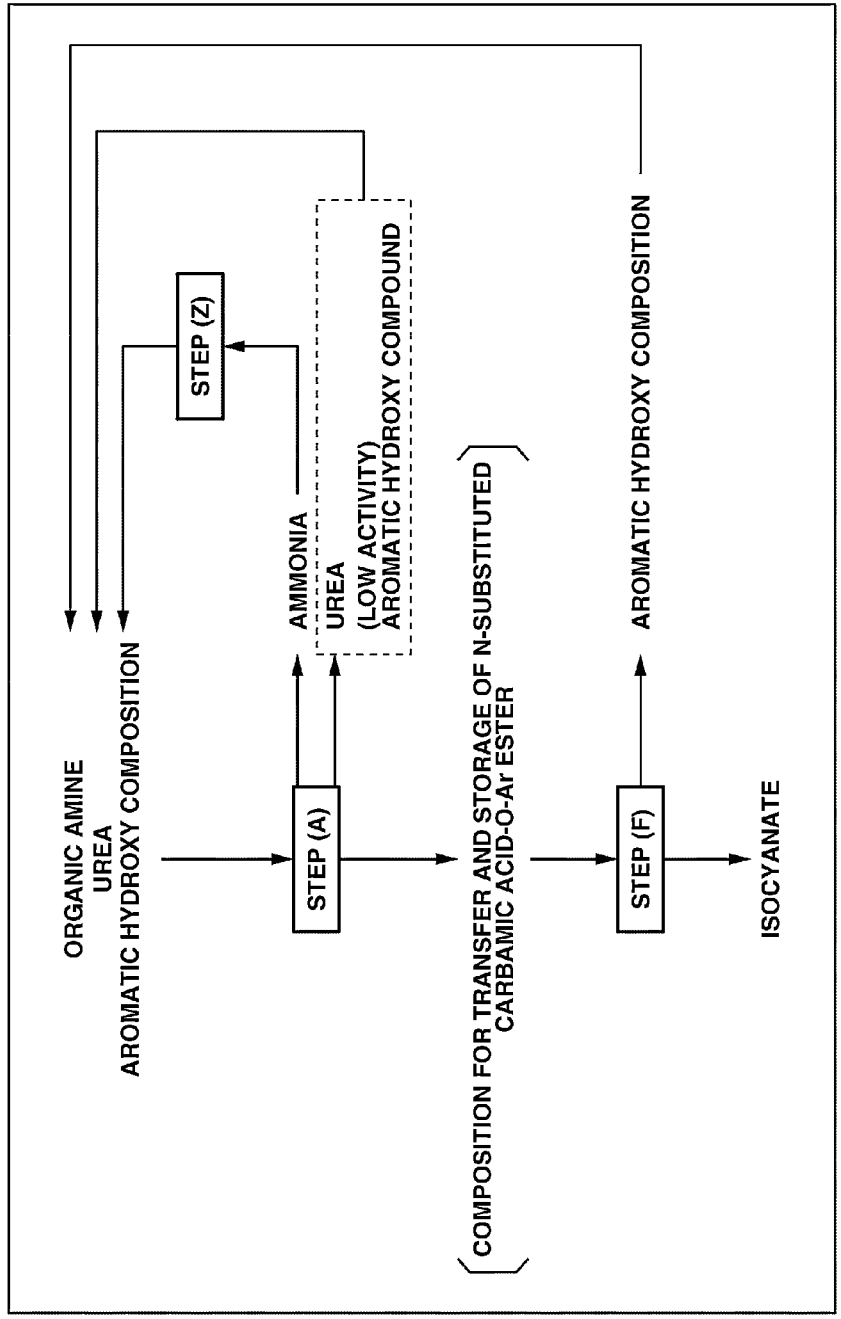
FIG. 13 shows a conceptual drawing depicting a preferable aspect (I) of the present embodiment.

A preferable aspect (I) is first indicated in the form of a method for producing isocyanate by using urea as a carbonic acid derivative, using an aromatic hydroxy composition containing an active aromatic hydroxy compound and a low activity aromatic hydroxy compound (that has a standard boiling point lower than the standard boiling point of the active aromatic hydroxy compound), and producing isocyanate from an organic amine, the urea and the aromatic hydroxy composition by going through an N-substituted carbamic acid-O—Ar ester. FIG. 13 shows a conceptual drawing depicting the preferable aspect (I).

First, in step (A), the organic amine, urea and aromatic hydroxy composition are reacted to obtain N-substituted carbamic acid-O—Ar ester. In step (A), a mixture of the organic amine, urea and aromatic hydroxy composition is reacted by introducing into a urethane production reactor for carrying out the reaction of step (A). Ammonia formed as a by-product of this reaction is introduced into a condenser provided in the urethane production reactor together with unreacted or excess urea, the low activity aromatic hydroxy compound (which may also contain the active aromatic hydroxy compound) and the like, the urea and the low activity aromatic hydroxy compound (which may contain the active aromatic hydroxy compound) and the like are condensed in the condenser, and the ammonia is extracted in the form of a gas. The urea and low activity aromatic hydroxy compound (which may contain the active aromatic hydroxy compound) condensed in the condenser are reused as raw materials for carrying out step (A). On the other hand, the ammonia extracted in the form of a gas is used in step (Z), and the urea produced in step (Z) is reused as a raw material for carrying out step (A). A mixture containing N-substituted carbamic acid-O—Ar ester and the aromatic hydroxy composition is recovered from the urethane production reactor in the form of a liquid phase component. The mixture may be a composition for transfer and storage of N-substituted carbamic acid-O—Ar ester of the present embodiment depending on the raw materials used, composite ratios of the raw materials, reaction conditions and the like.

The subsequent step (F) is carried out using the mixture obtained in step (A). Step (F) is a step of producing a corresponding isocyanate and aromatic hydroxy compound by a thermal decomposition reaction of N-substituted carbamic acid ester, and isocyanate is obtained in this step (F). In step (F), the aromatic hydroxy compound separated from the isocyanate is reused as a raw material for carrying out step (A).

<Preferable Aspect (II)>

Figure 14:
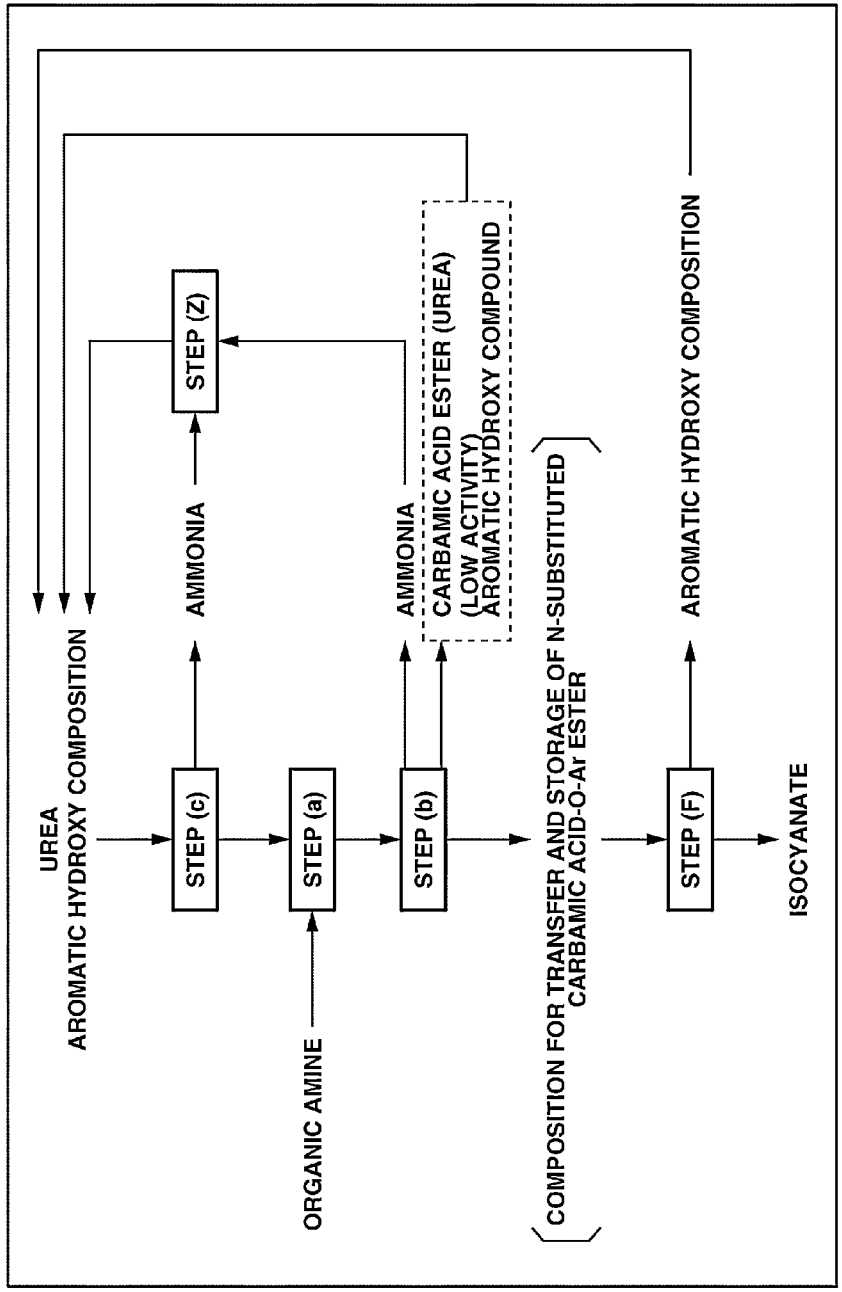
FIG. 14 shows a conceptual drawing depicting a preferable aspect (II) of the present embodiment.

Next, a preferable aspect (II) is indicated in the form of a method for producing isocyanate by producing a carbamic acid ester from an aromatic hydroxy composition containing an active aromatic hydroxy compound and a low activity aromatic hydroxy compound (having a standard boiling point lower than the standard boiling point of the active aromatic hydroxy compound) and urea, using the carbamic acid ester as a carbonic acid derivative, and producing isocyanate from an organic amine, the carbonic acid derivative and the aromatic hydroxy composition by going through an N-substituted carbamic acid-O—Ar ester. FIG. 14 shows a conceptual drawing depicting the preferable aspect (II).

First, in step (c), urea and aromatic hydroxy composition are reacted to produce a non-N-substituted carbamic acid ester. Ammonia formed as a by-product of the reaction of the urea and the aromatic hydroxy composition is used in step (Z). If a large excess of the aromatic hydroxy composition is used in step (c), the reaction liquid obtained in the step (c) is a mixture containing the aromatic hydroxy composition and a carbamic acid ester (which may also contain unreacted urea), and this can be used as is in the reaction of step (a). The following indicates an example of the case of having used a large excess of the aromatic hydroxy composition in step (c).

In step (a), the carbamic acid ester obtained in step (c) is reacted with organic amine to obtain a compound having ureido groups. In the case a large excess of aromatic hydroxy composition based on the urea is used in step (c) to obtain a mixture containing aromatic hydroxy composition and carbamic acid ester as the reaction liquid of step (c) (which may also contain unreacted urea), step (a) can be carried out by a method containing adding organic amine to the reaction liquid, and a reaction liquid is obtained that contains the compound having ureido groups, the aromatic hydroxy composition and unreacted carbamic acid ester.

Next, the reaction liquid obtained in step (a) is introduced into a urethane production reactor for carrying out step (b), and the compound having ureido groups and the aromatic hydroxy composition are allowed to react. Ammonia formed as a by-product of this reaction is introduced into a condenser provided in the urethane production reactor together with unreacted or excess carbamic acid ester, the low activity aromatic hydroxy compound (which may contain the active aromatic hydroxy compound) and the like, the carbamic acid ester and the low activity aromatic hydroxy compound (which may contain the active aromatic hydroxy compound) and the like are condensed in the condenser, and the ammonia is extracted in the form of a gas. The carbamic acid ester and the low activity aromatic hydroxy compound (which may contain the active aromatic hydroxy compound) and the like condensed in the condenser are reused as raw materials for carrying out step (c). On the other hand, the ammonia extracted in the form of a gas is used in step (Z) together with the ammonia obtained in step (c). The urea produced in step (Z) is reused as a raw material for carrying out step (c). A mixture composed of N-substituted carbamic acid-O—Ar ester and aromatic hydroxy composition is recovered from the urethane production reactor in the form of a liquid phase component. This mixture may be the composition for transfer and storage of N-substituted carbamic acid-O—Ar ester of the present embodiment depending on the raw materials used, the composite ratios of the raw materials, the reaction conditions and the like.

The subsequent step (F) is carried out using the mixture obtained in step (b). Step (F) is a step of producing a corresponding isocyanate and aromatic hydroxy compound by a thermal decomposition reaction of N-substituted carbamic acid-O—Ar ester, and isocyanate is obtained in the step (F). The aromatic hydroxy compound separated from the isocyanate in step (F) is reused as a raw material for carrying out step (c).

<Preferable Aspect (III)>

Figure 15:
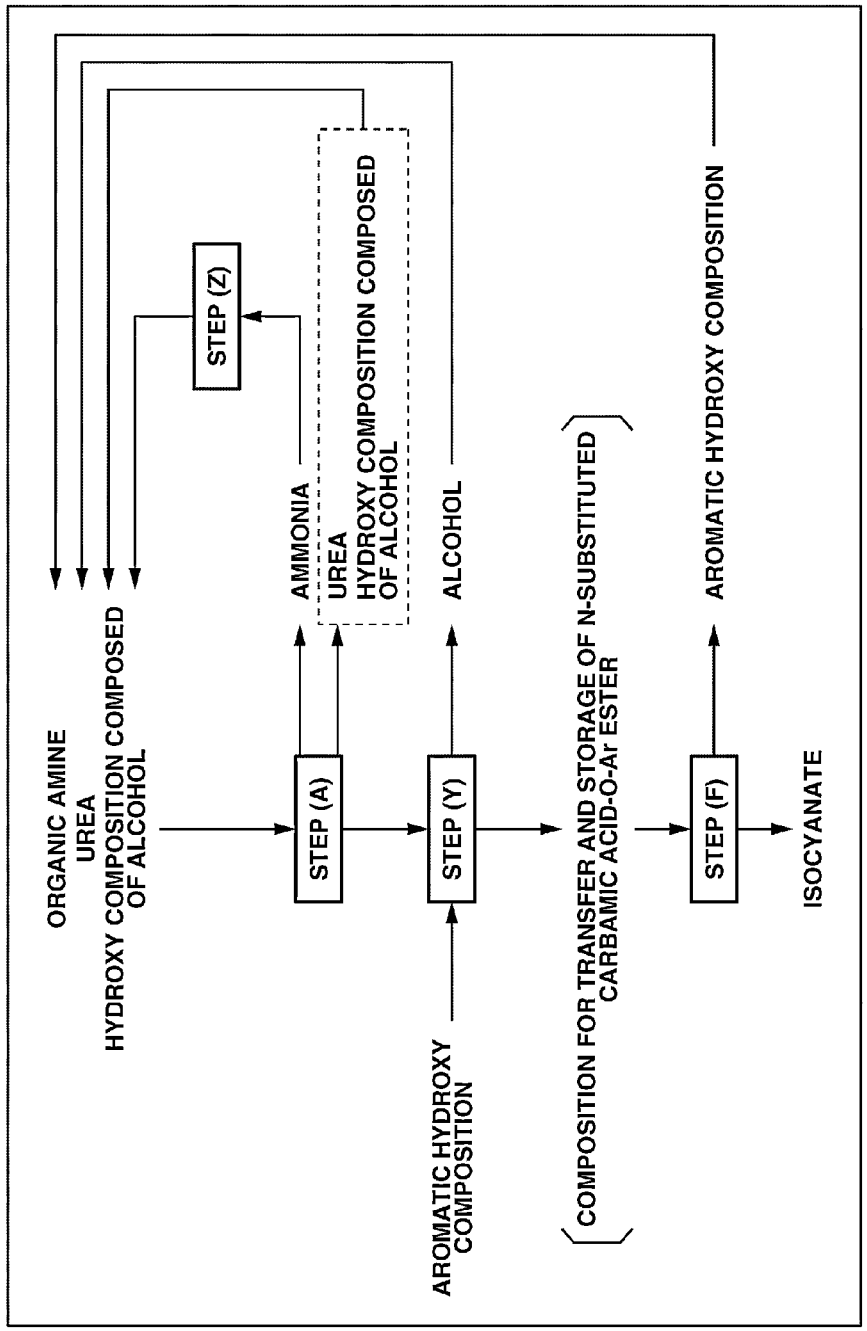
FIG. 15 shows a conceptual drawing depicting a preferable aspect (III) of the present embodiment.

Next, a preferable aspect (III) is indicated in the form of a method for producing isocyanate from a hydroxy composition composed of an alcohol, urea and organic amine by going through N-substituted carbamic acid-O—$R^2$ ester and N-substituted carbamic acid-O—Ar ester. FIG. 15 shows a conceptual drawing depicting the preferable aspect (III).

First, in step (A) an organic amine, urea and hydroxy composition containing an alcohol are introduced into a urethane production reactor for carrying out the reaction of step (a) to produce N-substituted carbamic acid-O—$R^2$ ester. Ammonia formed as a by-product of the reaction is introduced into a condenser provided in the urethane production reactor together with unreacted or excess urea, alcohol and the like, the urea, alcohol and the like are condensed in the condenser, and the ammonia is extracted in the form of a gas. The urea, alcohol and the like condensed in the condenser are reused as raw materials of step (A). On the other hand, the ammonia extracted in the form of a gas is used in step (Z). The urea produced in step (Z) is reused as a raw material of step (A). A mixture containing N-substituted carbamic acid-O—$R^2$ ester and alcohol is obtained from the urethane production reactor. An aromatic hydroxy composition is added to the mixture and used as a raw material liquid of step (Y).

In Step (Y), N-substituted carbamic acid-O—$R^2$ ester and aromatic hydroxy composition are reacted to produce N-substituted carbamic acid-O—Ar ester. The alcohol formed in the reaction is separated from the N-substituted carbamic acid-O—Ar ester and recovered together with the alcohol contained in the raw material liquid of step (Y), and then reused as raw materials of step (A). The other product in the form of the N-substituted carbamic acid-O—Ar ester is recovered in the form of a mixture with the aromatic hydroxy composition. This mixture may be a composition for transfer and storage of N-substituted carbamic acid-O—Ar ester depending on the raw materials used, composite ratios of the raw materials, reaction conditions and the like.

The subsequent step (F) is carried out by using the mixture obtained in step (Y). Step (F) is a step of producing a corresponding isocyanate and aromatic hydroxy compound by a thermal decomposition reaction of N-substituted carbamic acid-O—Ar ester, and isocyanate is obtained in the step (F). In step (F), the aromatic hydroxy compound separated from the isocyanate is reused as a raw material of step (A).

<Preferable Aspect (IV)>

Figure 16:
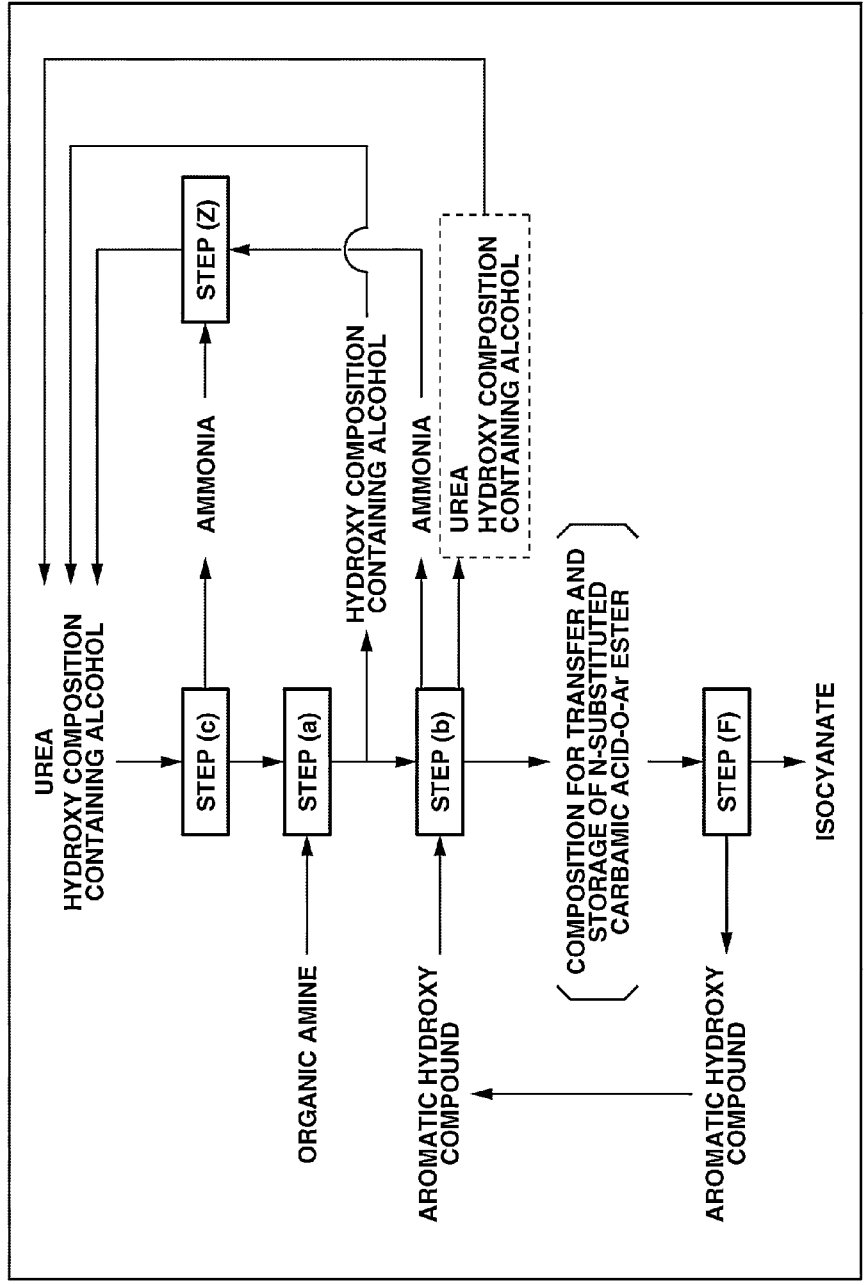
FIG. 16 shows a conceptual drawing depicting a preferable aspect (IV) of the present embodiment.

Next, a preferable aspect (IV) is indicated in the form of a method for producing isocyanate by producing carbamic acid ester from a hydroxy composition containing alcohol and urea, using the carbamic acid ester as a carbonic acid derivative, and producing the isocyanate from an organic amine, the carbonic acid derivative and an aromatic hydroxy composition by going through a compound having ureido groups and N-substituted carbamic acid-O—Ar ester. FIG. 16 shows a conceptual drawing depicting the preferable aspect (IV).

First, in step (c), urea and a hydroxy composition containing alcohol are reacted to produce non-N-substituted carbamic acid ester. Ammonia formed as a by-product of the reaction between the urea and the hydroxy composition containing alcohol is used in step (Z). If a large excess of hydroxy composition is used in step (c), the reaction liquid obtained in the step (c) is a mixture containing the hydroxy composition and carbamic acid ester (which may also contain unreacted urea), and can be used as is in the reaction of step (a).

In step (a), the carbamic acid ester obtained in step (c) is reacted with an organic amine to obtain a compound having ureido groups. In the case a large excess of hydroxy composition based on the urea is used in step (c) to obtain a mixture containing hydroxy composition and carbamic acid ester as the reaction liquid of step (c) (which may also contain unreacted urea), step (a) can be carried out by a method containing adding organic amine to the reaction liquid, and a reaction liquid is obtained that contains the compound having ureido groups, alcohol and unreacted carbamic acid ester and the like.

Next, an aromatic hydroxy compound (preferably an active aromatic hydroxy compound having a standard boiling point higher than the standard boiling point of the alcohol) is added to the reaction liquid obtained in step (a) to obtain a mixture, this mixture is introduced into a urethane production reactor for carrying out step (b), and the compound having ureido groups and the aromatic hydroxy compound are allowed to react. Ammonia formed as a by-product of this reaction is introduced into a condenser provided in the urethane production reactor together with unreacted or excess carbamic acid ester, hydroxy composition containing alcohol (which may contain an aromatic hydroxy compound) and the like, the carbamic acid ester and the hydroxy compound containing alcohol (which may contain an aromatic hydroxy compound) and the like are condensed in the condenser, and the ammonia is extracted in the form of a gas. The carbamic acid ester and the hydroxy compound containing alcohol and the like condensed in the condenser are reused as raw materials of step (c). On the other hand, the ammonia extracted in the form of a gas is used in step (Z) together with the ammonia obtained in step (c). The urea produced in step (Z) is reused as a raw material of step (c). A mixture containing N-substituted carbamic acid-O—Ar ester and aromatic hydroxy compound is recovered from the urethane production reactor in the form of a liquid phase component. This mixture may be the composition for transfer and storage of N-substituted carbamic acid-O—Ar ester of the present embodiment depending on the raw materials used, the composite ratios of the raw materials, the reaction conditions and the like.

The subsequent step (F) is carried out using the mixture obtained in step (b). Step (F) is a step of producing a corresponding isocyanate and aromatic hydroxy compound by a thermal decomposition reaction of N-substituted carbamic acid-O—Ar ester, and isocyanate is obtained in the step (F). The aromatic hydroxy compound separated from the isocyanate in step (F) is reused as an aromatic hydroxy compound added to the reaction liquid obtained in step (a).

<Case of Using Organic Monoamine>

<Step (X): Condensation of N-Substituted Carbamic Acid Mono(—O-(Ar and/or $R^2$) Ester)>

The following provides an explanation of the case of using an organic monoamine represented by the above-mentioned formula (39) for the organic amine in particular. An N-substituted carbamic acid mono(—O-(Ar and/or $R^2$) ester) refers to an N-substituted carbamic acid mono-O-aryl ester and/or an N-substituted carbamic acid —O—$R^2$ ester, and respectively represent an N-substituted carbamic acid-O-ester having a single carbamic acid-O-aryl ester group and/or a single carbamic acid-O—$R^2$ ester group in a molecule thereof.

The above-mentioned step (A) or the above-mentioned steps (a) and (b) can be carried out using an organic monoamine represented by formula (39) in the same manner as other organic amines. In the case a hydroxy compound that composes the hydroxy composition used in the reaction with the organic monoamine is an aromatic hydroxy compound, an N-substituted carbamic acid mono(—O—Ar ester) represented by the following formula (127) is produced, while in the case a hydroxy compound that composes the hydroxy composition is an aromatic hydroxy compound, an N-substituted carbamic acid mono(—O—$R^2$ ester) represented by the following formula (128) is produced:

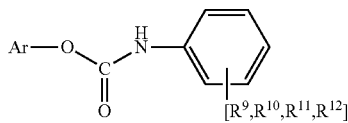
(127)

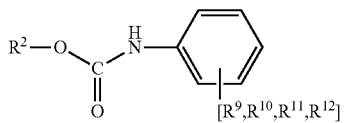
(128)

(wherein groups $R^9$ to $R^{12}$ respectively and independently may substitute the aromatic ring, groups $R^9$ to $R^{12}$ may bond to form a ring together with the aromatic ring, and respectively and independently represent hydrogen atoms or groups composed of groups in which an alkyl group, a cycloalkyl group, an aryl group or a group selected from the group consisting of these groups is bonded by saturated hydrocarbon bonds and/or ether bonds, $R^2$ represents a group derived from an alcohol that is a residue in which a single hydroxy group bonded to a saturated carbon atom of the alcohol has been removed from the alcohol, and Ar represents a group derived from an aromatic hydroxy compound that is a residue in which a single hydroxy group bonded to an aromatic ring of the aromatic hydroxy compound has been removed from the aromatic hydroxy compound).

Furthermore, although the term "N-substituted carbamic acid mono(—O—Ar ester) has been used here, this refers to an N-substituted carbamic acid-O—Ar ester having a single carbamic acid ester group from among of N-substituted carbamic acid —O—Ar esters. In the subsequent explanation, although there are cases in which the term "N-substituted carbamic acid poly(—O—Ar ester)" is used in addition to the term "N-substituted carbamic acid mono(—O—Ar ester)", this refers to an N-substituted carbamic acid-O—Ar ester having an integral number of carbamic acid ester groups of 2 or more from among N-substituted carbamic acid —O—Ar esters.

The term "N-substituted carbamic acid mono(—O—$R^2$ ester)" similarly refers to an N-substituted carbamic acid-O—$R^2$ ester having a single carbamic acid ester group, while the term "N-substituted carbamic acid poly(—O—$R^2$ ester)" refers to an N-substituted carbamic acid-O—$R^2$ ester having an integral number of carbamic acid ester groups of 2 or more from among N-substituted carbamic acid —O—Ar esters.

In addition, an N-substituted carbamic acid mono(—O—Ar ester) and an N-substituted carbamic acid mono(—O—$R^2$ ester) may collectively be referred to as simply an N-substituted carbamic acid monoester. Similarly, an N-substituted carbamic acid poly(—O—Ar ester) and an N-substituted carbamic acid poly(—O—$R^2$ ester) may be collectively referred to as simply an N-substituted carbamic acid polyester.

Although the N-substituted carbamic acid monoesters represented by the above-mentioned formulas (127) and (128) can be applied directly to a thermal decomposition reaction to produce monoisocyanate, when considering that typical applications of isocyanates are for paints and polyurethane, the isocyanate is preferably a polyfunctional isocyanate. Thus, a preferable example of a method for producing polyfunctional isocyanate from N-substituted carbamic acid monoester contains polymerizing the N-substituted carbamic acid monoester in advance to obtain an N-substituted carbamic acid polyester, followed by applying the N-substituted carbamic acid polyester to a thermal decomposition reaction to obtain polyfunctional isocyanate.

The following step (X) can be carried out as a method for polymerizing the N-substituted carbamic acid monoester:

Step (X): the N-substituted carbamic acid monoester is reacted with a methylenating agent, and aromatic groups derived from an organic monoamine contained in the N-substituted carbamic acid monoester are crosslinked with methylene (—$CH_2$—) groups to obtain N-substituted carbamic acid polyester.

Figure 17:
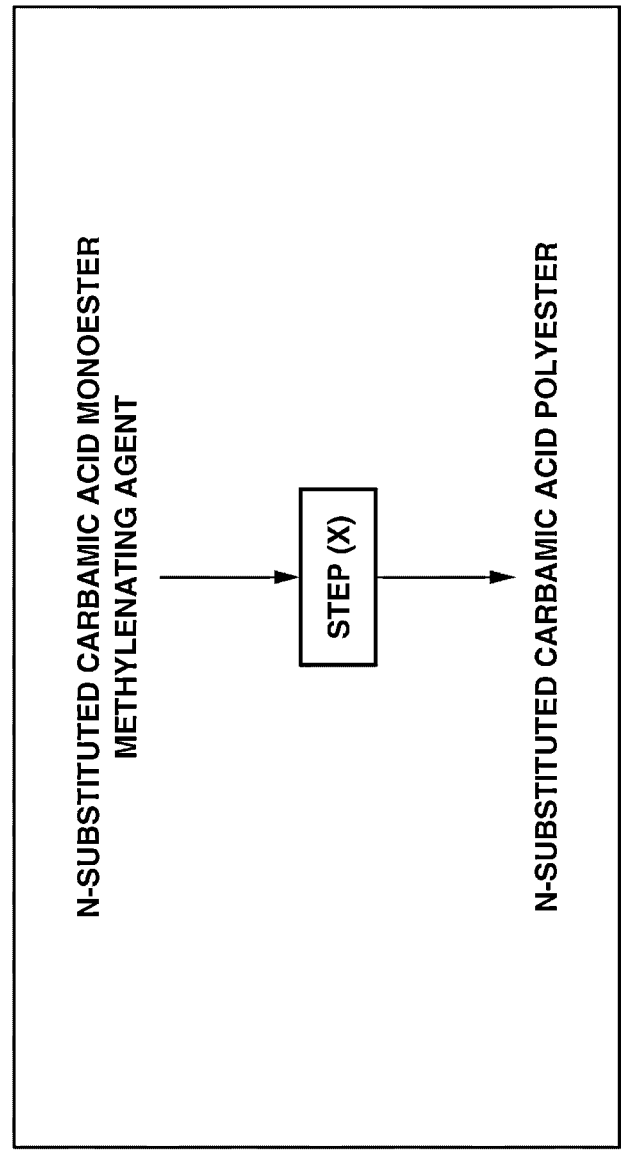
FIG. 17 shows a conceptual drawing of one aspect of the present embodiment in the form of step (X)

FIG. 17 shows a conceptual drawing of the step (X).

The step (X) can be carried out in the same manner whether the N-substituted carbamic acid monoester is an N-substituted carbamic acid mono(—O—Ar ester) or an N-substituted carbamic acid mono(—O—$R^2$ ester). An N-substituted carbamic acid poly(—O—Ar ester) represented by the following formula (129) is obtained from an N-substituted carbamic acid mono(—O—Ar ester) represented by the above-mentioned formula (127), while an N-substituted carbamic acid poly(—O—$R^2$ ester) represented by the following formula (130) is obtained from an N-substituted carbamic acid mono(—O—$R^2$ ester) represented by the above-mentioned formula (128).

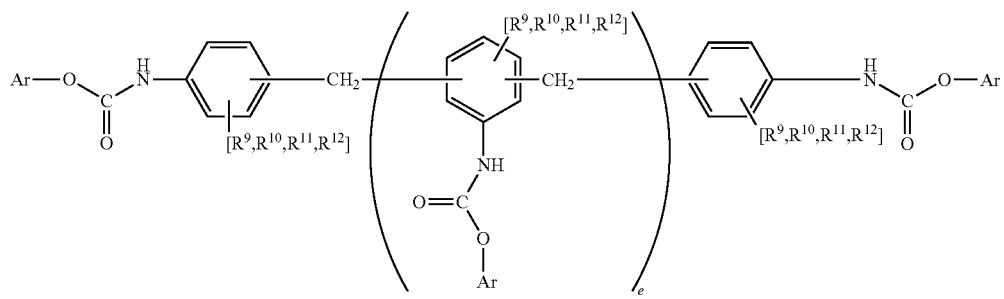
(129)

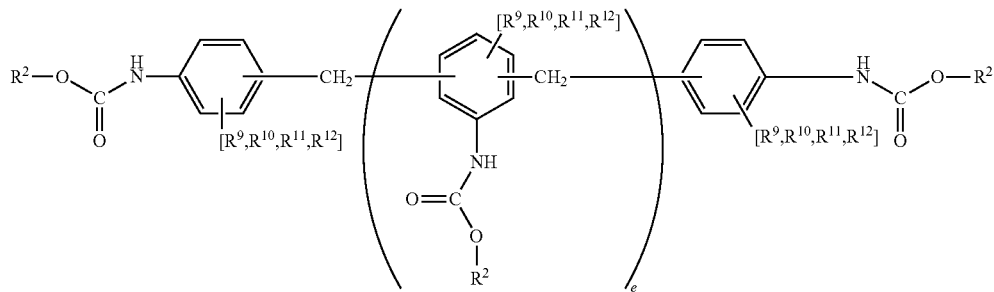
(130)

(wherein groups $R^9$ to $R^{12}$ respectively and independently may substitute the aromatic ring, groups $R^9$ to $R^{12}$ may bond to form a ring together with the aromatic ring, and respectively and independently represent hydrogen atoms or groups composed of groups in which an alkyl group, a cycloalkyl group, an aryl group or a group selected from the group consisting of these groups is bonded by saturated hydrocarbon bonds and/or ether bonds, $R^2$ represents a group derived from an alcohol that is a residue in which a single hydroxy group bonded to a saturated carbon atom of the alcohol has been removed from the alcohol, Ar represents a group derived from an aromatic hydroxy compound that is a residue in which a single hydroxy group bonded to an aromatic ring of the aromatic hydroxy compound has been removed from the aromatic hydroxy compound, and e represents 0 or a positive integer).

The following provides an explanation of the step (X).

The step (X) can be carried out by a known method (refer to, for example, Federal Republic of Germany Patent No. 1042891).

Examples of methylenating agents preferably used in the step (X) may include formaldehyde, paraformaldehyde, trioxane, dialkoxymethanes having a lower alkyl group having 1 to 6 carbon atoms (such as dimethoxymethane, diethoxymethane, dipropoxymethane, dipentanoxymethane or dihexyloxymethane), and diacyloxymethanes having a lower acyl group such as diacetoxymethane or dipropionyloxymethane. These may be used alone or two or more types may be used as a mixture. Among these methylenating agents, aqueous solutions of formaldehyde are particularly preferable in consideration of cases of industrial application, ease of handling of the methylenating agent and the like.

In carrying out the reaction of the step (X), although there are no particular limitations on the ratio of N-substituted carbamic acid monoester to methylenating agent, the N-substituted carbamic acid monoester is preferably used at a stoichiometric ratio of from 2 to 20 times the methylenating agent. Although the formation of polynuclear forms (referring to N-substituted carbamic acid monoesters in which three or more aromatic rings are bonded by a methylene crosslinked structure, or in other words, compounds in which e is an integer of 1 or more in the above-mentioned formulas (129) and (130)) is inhibited the greater the amount of N-substituted carbamic acid monoester used, if an overly excessive amount of N-substituted carbamic acid monoester is used, there are many cases in which the remaining amount of raw material N-substituted carbamic acid monoester increases. Thus, the amount of N-substituted carbamic acid monoester used in terms of the stoichiometric ratio with the methylenating agent is more preferably within a range of from 3 to 15 times and even more preferably within a range of from 5 to 10 times.

An acid catalyst is preferably used as a catalyst in the condensation reaction. Examples of acid catalysts may include inorganic acids such as hydrochloric acid, sulfuric acid, phosphoric acid or boric acid, and organic acids such as formic acid, acetic acid, oxalic acid or toluenesulfonic acid. In addition, acids referred to as super strong acids such as hydrobromic acid, perchloric acid, chlorosulfonic acid or trifluoromethanesulfonic acid are also effective. In addition, ion exchange resins having acidic groups such as carboxyl groups or sulfonate groups as well as acids referred to as Lewis acids, such as trifluoroboric acid, iron chloride, aluminum chloride, zinc chloride or titanium chloride, are also effective.

In the case of a protonic acid such as the above-mentioned inorganic acids, organic acids or super strong acids, the amount of these acids used is within a range of a stoichiometric ratio of from 0.001 to 10, and preferably within a range of from 0.01 to 5, based on the raw material N-substituted carbamic acid monoester. In addition, in the case these acids are used in the form of aqueous solutions, they can be used at a concentration within a range of from 10 to 95% by weight and preferably within a range of from 20 to 80% by weight based on the amount of water in the reaction system. If the concentration is less than 10% by weight, the reaction rate of the condensation reaction becomes extremely slow, while if the concentration exceeds 95% by weight, hydrolysis of the raw material and other undesirable side reactions may occur.

The condensation reaction can be carried out in the presence or absence of solvent.

Examples of solvents that are used preferably may include linear, branched or cyclic hydrocarbons such as pentane, hexane, heptane, octane, nonane, decane, hexadecane, cyclopentane or cyclohexane; aromatic hydrocarbons such as benzene, toluene or xylene and their alkyl-, halogen- and nitro-substituted forms; halogenated hydrocarbons such as chloroform, methylene chloride, carbon tetrachloride, dichloroethane, trichloroethane or tetrachloroethane; aliphatic alkyl esters such as methyl acetate or ethyl acetate; and ethers such as diethyl ether, diisopropyl ether, dioxane or tetrahydrofuran. In addition, thioacetals, acetals or acylals are used preferably since they do not form free formaldehyde under the reaction conditions and do not substantially form water by reacting with formed as a by-product in the reaction. Acetals and acylals are used particularly preferably. In addition, the above-mentioned acids themselves are also preferably used as solvents. These solvents may be used alone or two or more types may be used as a mixture.

These solvents can be used at a weight ratio within a range of from 0.1 to 100 times and preferably within a range of from 0.2 to 50 times based on the raw material N-substituted carbamic acid monoester.

The N-substituted carbamic acid monoester used in the step (X) is an N-substituted carbamic acid monoester obtained by the methods of step (A) and/or steps (a) and (b) using an organic monoamine. In any of these methods, there are many cases in which the N-substituted carbamic acid monoester is obtained in the form of a reaction liquid of step (A) and/or step (b). Since a hydroxy composition used in step (A) and/or step (b), and a catalyst and reaction solvent depending on the case, are contained in the reaction liquid, in the case of adding a methylenating agent, catalyst or reaction solvent used in step (X), unintended reactions may occur, the solution may undergo phase separation, the N-substituted carbamic acid monoester may solidify, or it may become difficult to carry out step (X) itself. Thus, it is preferable to remove all or a portion of the hydroxy composition used in step (A) and/or step (b) prior to or after adding the methylenating agent, catalyst or reaction solvent used in step (X). Although the amount removed is arbitrary and is determined in consideration of the compounds used and composition thereof, the hydroxy compound is removed to a stoichiometric ratio based on the N-substituted carbamic acid monoester of 1 time or less and more preferably 0.1 times or less. A known removal method can be used for removal, examples of which may include distillative separation and membrane separation, and distillative separation can be used preferably.

The reaction temperature is preferably from 10 to 160° C., more preferably from 20 to 140° C. and even more preferably from 50 to 120° C. Although the reaction is advantageously carried out at a high temperature in order to increase the reaction rate and complete the reaction quickly, an excessive high temperature may cause undesirable side reactions such as hydrolysis.

Although varying according to the reaction method, compounds used and reaction conditions, the reaction time can be within a range of from 1 minute to 20 hours. In addition, the reaction may be terminated when the reduction in the amount of raw material N-substituted carbamic acid monoester has reached a certain level by sampling the reaction liquid and using a known analytical method such as liquid chromatography, or the reaction may be terminated when the average molecular weight of the product in the form of N-substituted carbamic acid polyester has reached a certain level by using a known analytical method such as gel permeation chromatography. There are no particular limitations on the reaction apparatus used when carrying out the reaction, and although a known reactor can be used, a tank-type and/or a column-type reactor equipped with a condenser is used preferably.

More specifically, conventionally known reactors can be suitably combined and used, examples of which may include a stirring tank, a pressurized stirring tank, a reduced pressure stirring tank, a column-type reactor, a distillation column, a packed column or a thin film distiller.

There are no particular limitations on the type of condenser provided in the reactor and a known condenser can be used. For example, conventionally known condensers such as a multitubular cylindrical condenser, a double tube condenser, a single tube condenser or an air-cooled condenser can be suitably combined and used. The condenser may be provided inside the reactor or provided outside the reactor or may be connected with the reactor by a line, and various types can be employed in consideration of the forms of the reactor and condenser, the manner in which condensate is handled and the like.

Since an acid is used in step (X), although caution is required with respect to the materials of the reactor and the condenser, there are no particular limitations on the materials provided they do not cause problems such as corrosion attributable to the compounds used in step (X), and known materials can be used. Examples of materials that can be used may include glass, stainless steel, carbon steel, Hastelloy, glass-lined base materials and Teflon (registered trademark) coated materials. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Steps may also be added as necessary, and for example, steps and apparatuses able to be conceived by a person or engineer with ordinary skill in the art may be added.

The N-substituted carbamic acid polyester obtained according to the above-mentioned method is an N-substituted carbamic acid poly(—O—Ar-ester) represented by the above-mentioned formula (129) in the case the N-substituted carbamic acid monoester is N-substituted carbamic acid mono(—O—Ar ester) represented by the above-mentioned formula (127), or is an N-substituted carbamic acid poly(—O—$R^2$ ester) represented by the above-mentioned formula (130) in the case the N-substituted carbamic acid monoester is an N-substituted carbamic acid mono(—O—$R^2$ ester) represented by the above-mentioned formula (128). Among these N-substituted carbamic acid polyesters, although compounds in which e is an integer of from 0 to 3 and preferably 0 are preferable in consideration of handling ease and solution viscosity in particular, the presence of hexanuclear forms and larger polynuclear forms (namely compounds in which e is 4 or more in the above-mentioned formulas (129) and (130)) does not present any problems whatsoever provided they do not deviate from the gist of the present embodiment.

Although N-substituted carbamic acid polyester is produced from N-substituted carbamic acid monoester by the previously indicated step (X), in the case of obtaining the N-substituted carbamic acid poly(—O—$R^2$ ester) represented by formula (130) in the step (X) (namely, in the case of carrying out step (X) using an N-substituted carbamic acid mono(—O—$R^2$ ester) represented by formula (130)), further carrying out the above-mentioned step (Y) following step (X) allows conversion to an N-substituted carbamic acid poly(—O—Ar ester) preferable for production of isocyanate, thereby enabling the production of isocyanate using the N-substituted carbamic acid poly(—O—Ar ester).

When carrying out the step (Y) after the step (X), the reaction liquid obtained in step (X) contains unreacted or excess methylenating agent, catalyst, reaction solvent and the like in addition to the N-substituted carbamic acid poly(—O—$R^2$ ester). In the case of having added an aromatic hydroxy compound used in step (Y) to the reaction liquid obtained in step (X) (and there are also cases in which catalyst or reaction solvent is added), unintended reactions may occur, the solution may undergo phase separation, the N-substituted carbamic acid poly(—O—$R^2$ ester) may solidify, or it may become difficult to carry out step (Y) as is. In such cases, all or a portion of the above-mentioned compounds contained in the reaction liquid of step (X) are removed before or after addition of the aromatic hydroxy composition, catalyst or solvent used in step (Y). The amount removed is arbitrary and is determined in consideration of the compounds used and composition thereof. A known removal method can be used for removal, examples of which may include distillative separation and membrane separation, and distillative separation can be used preferably.

Figure 18:
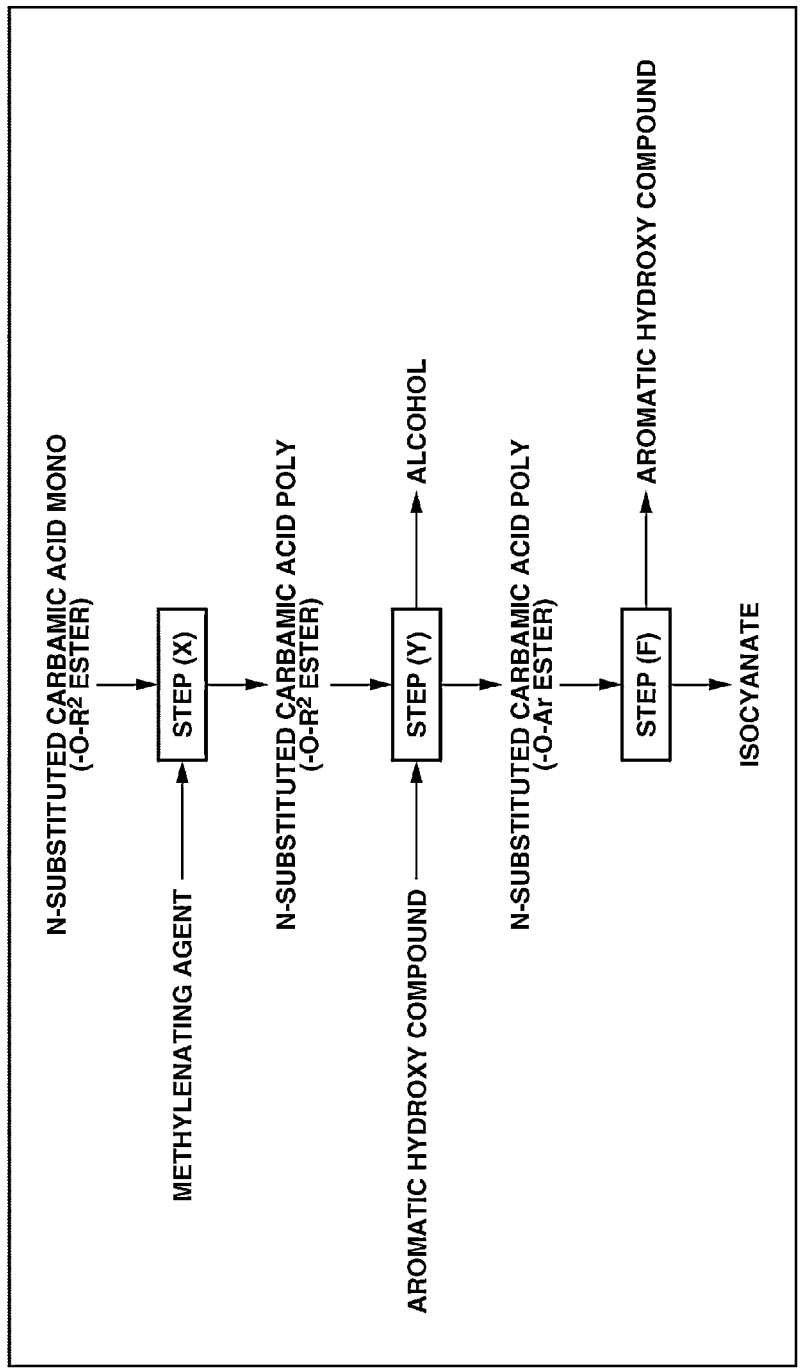
FIG. 18 shows a conceptual drawing depicting one aspect of the present embodiment in the form of a method for producing polyfunctional isocyanate from N-substituted carbamic acid mono (—O—$R^2$ ester) that combines step (X), step (Y) and step (F)

FIG. 18 shows a conceptual drawing depicting a preferable aspect of a method for producing polyfunctional isocyanate from N-substituted carbamic acid mono(—O—$R^2$ ester) that combines the steps (X), (Y) and (F).

In addition, another preferable aspect of a method for producing polyfunctional isocyanate from N-substituted carbamic acid mono(—O—$R^2$ ester) is a method in which after first converting the N-substituted carbamic acid mono(—O—$R^2$ ester) to an N-substituted carbamic acid mono(—O—Ar ester) with step (Y), polymerization is carried out according to step (X) to obtain N-substituted carbamic acid-O—Ar ester, and polyfunctional isocyanate is then obtained by thermal decomposition of the N-substituted carbamic acid-O—Ar ester in Step (F).

Similar to that when carrying out step (F) after step (X), the reaction liquid obtained in step (X) contains unreacted or excess methylenating agent, catalyst or reaction solvent and the like in addition to N-substituted carbamic acid poly(—O—Ar ester). As was previously described, when supplying N-substituted carbamic acid-O—Ar ester to step (F), it is preferably supplied to the step (F) in the form of a composition for transfer and storage of N-substituted carbamic acid-O—Ar ester as previously described. Thus, although the aromatic hydroxy compound used in step (F) is added to the reaction liquid obtained in step (X) to obtain a mixture, if this mixture is used directly in step (F), unintended reactions may occur, the solution may undergo phase separation, or the N-substituted carbamic acid poly-O—Ar ester may solidify. In such cases, all or a portion of the above-mentioned compounds contained in the reaction liquid of step (X) are removed before or after addition of the aromatic hydroxy compound, catalyst or solvent used in step (F). The amount removed is arbitrary and is determined in consideration of the compounds used and composition thereof. A known removal method can be used for removal, examples of which may include distillative separation and membrane separation, and distillative separation can be used preferably. Naturally, the procedure described above does not have to be carried out in the case the unreacted or excess methylenating agent, catalyst or reaction solvent and the like contained in the reaction liquid of step (X) do not have an effect on step (F).

Figure 19:
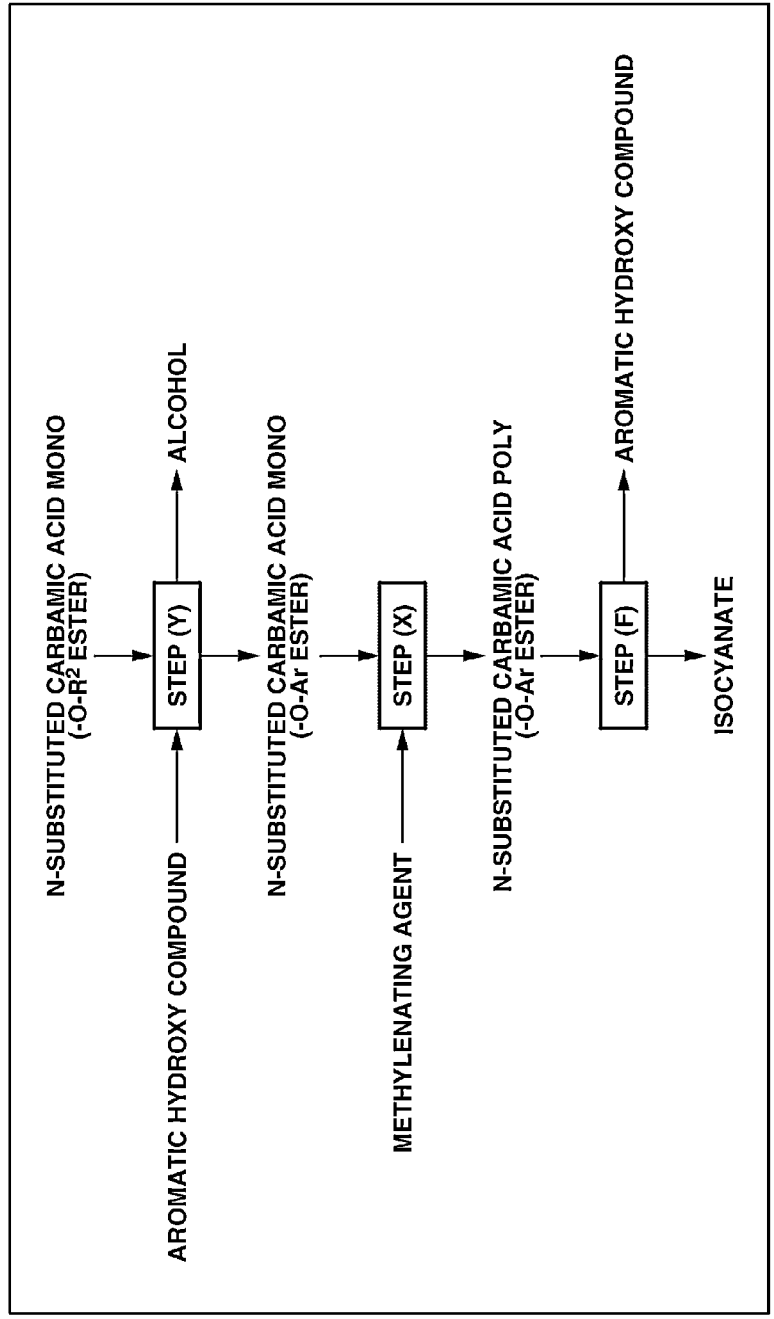
FIG. 19 shows a conceptual drawing depicting one aspect of the present embodiment in the form of another method for producing polyfunctional isocyanate from N-substituted carbamic acid mono (—O—$R^2$ ester) that combines step (X), step (Y) and step (F)

FIG. 19 shows a conceptual drawing depicting another preferable aspect of a method for producing polyfunctional isocyanate from N-substituted carbamic acid mono(—O—$R^2$ ester) that combines the steps (X), (Y) and (F).

Furthermore, in the case of obtaining N-substituted carbamic acid poly(—O—Ar ester) by carrying step (X) using N-substituted carbamic acid mono(—O—Ar ester), polyfunctional isocyanate can be obtained by thermal decomposition of the N-substituted carbamic acid poly(—O—Ar ester) in step (F). In this case as well, it is preferable to remove all or a portion of the above-mentioned compounds contained in the reaction liquid of step (X) before or after addition of the aromatic hydroxy compound, catalyst or solvent used in step (F) for the same reasons as described above. The amount removed is arbitrary and is determined in consideration of the compounds used and composition thereof. A known removal method can be used for removal, examples of which may include distillative separation and membrane separation, and distillative separation can be used preferably.

Figure 20:
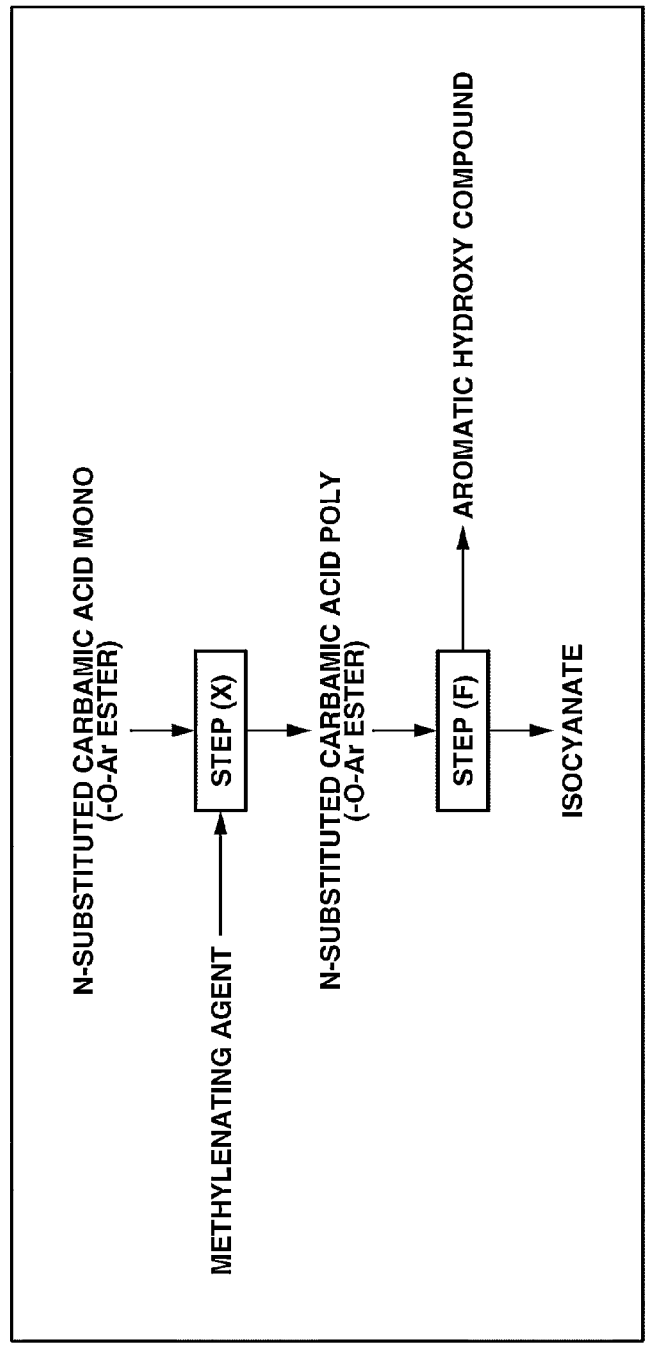
FIG. 20 shows a conceptual drawing depicting a preferable aspect of a method for producing polyfunctional isocyanate from N-substituted carbamic acid mono (—O—Ar ester) of the present embodiment.

FIG. 20 shows a conceptual drawing depicting a preferable aspect of a method for producing polyfunctional isocyanate from N-substituted carbamic acid mono(—O—Ar ester).

Since the N-substituted carbamic acid ester production method of the present embodiment efficiently recovers and reuses carbonic acid derivative and the like used in excess in the reaction, N-substituted carbamic acid ester can be produced without losing original units of the carbonic acid derivative. In addition, since clogging of discharge lines for ammonia formed as a by-product during production of N-substituted carbamic acid ester can be inhibited, operation is possible over a long period of time. Moreover, N-substituted carbamic acid ester and the composition for transfer and storage of the N-substituted carbamic acid ester can be preferably used as raw materials for production of isocyanate. Thus, the present invention is extremely important industrially.

EXAMPLES

Although the following provides a detailed explanation of the present invention based on examples thereof, the scope of the present invention is not limited by these examples.

<Analytical Methods>
1) NMR Analysis
   Apparatus: JNM-A400 FT-NMR system, JEOL Ltd., Japan
(1) Preparation of $^1$H- and $^{13}$C-NMR Analysis Samples
   About 0.3 g of sample solution were weighed followed by the addition of about 0.7 g of heavy chloroform (99.8%, Aldrich Corp., USA) and 0.05 g of internal standard in the form of tetramethyl tin (guaranteed reagent, Wako Pure Chemical Industries, Ltd., Japan) and mixing to uniformity to obtain solutions used as NMR analysis samples.
(2) Quantitative Analysis
   Analyses were performed for each standard and quantitative analyses were performed on the analysis sample solutions based on the resulting calibration curve.
2) Liquid Chromatography
   Apparatus: LC-10AT system, Shimadzu Corp., Japan
   Column: Inertsil-ODS column, GL Sciences Inc., Japan, two columns connected in series
   Developing solvent: Mixed liquid of 5 mmol/L aqueous ammonium acetate solution (solution A) and acetonitrile (solution B)
   Developing solvent flow rate: 2 mL/min
   Column temperature: 35° C.
   Detector: R.I. detector (refractometer) and PDA detector (photodiode array detector, measuring wavelength range: 200 to 300 nm)

(1) Liquid Chromatography Analysis Samples

About 0.1 g of sample were weighed followed by the addition of about 1 g of tetrahydrofuran (dehydrated, Wako Pure Chemical Industries, Ltd., Japan) and about 0.02 g of internal standard in the form of 1,1-diethyl urea (Tokyo Chemical Industry Co., Ltd., Japan) and mixing to uniformity to obtain solutions used as liquid chromatography analysis samples.

(2) Quantitative Analysis

Analyses were performed for each standard and quantitative analyses were performed on the analysis sample solutions based on the resulting calibration curve.

3) Gas Chromatography

Apparatus: GC-14B, Shimadzu Corp., Japan
Column: Porapack N, inner diameter: 3 mm, length: 3 m, SUS
Column temperature: 60° C.
Injection port temperature: 120° C.
Carrier gas: Helium
Carrier gas flow rate: 40 mL/min
Detector: TCD (thermal conductivity detector)

(1) Gas Chromatography Analysis Samples

Gas samples captured in a Tedlar bag were collected and injected with a gastight syringe.

(2) Quantitative Analysis

Analyses were performed for each standard and quantitative analyses were performed on the analysis sample solutions based on the resulting calibration curve.

4) GC-MS Analysis

Apparatus: Apparatus connecting GC17A and GCMS-QP5050A, Shimadzu Corp., Japan
Column: DB-1, Agilent Technologies Corp., USA, length: 30 m, inner diameter: 0.250 mm, film thickness: 1.00 μm
Column temperature: Held at 50° C. for 5 minutes followed by increasing at the rate of 10° C./min to 200° C.; held at 200° C. for 5 minutes followed by increasing at the rate of 10° C./min to 300° C.
Injection port temperature: 300° C.
Interface temperature: 300° C.

(1) GC-MS Analysis Samples

Gas samples captured in a Tedlar bag were collected and injected with a gastight syringe.

(2) Quantitative Analysis

Analyses were performed for each standard and quantitative analyses were performed on the analysis sample solutions based on the resulting calibration curve. Furthermore, the detection lower limit was about 1 ppm in terms of the concentrations in the samples.

In the following descriptions, although the term "N-containing compound" is used and mention is made regarding the amount of this N-containing compound, the amount of N-containing compound refers to the total of the number of molecules of urea ($H_2N-C(=O)-NH_2$) (V), the number of molecules of carbamic acid ester (W), the number of molecules of biuret ($H_2N-C(=O)-NH-C(=O)-NH_2$)(X) and the total number of terminal biuret groups ($-NH-C(=O)-NH-C(=O)-NH_2$) of a compound having terminal biuret groups derived from an organic amine that is formed in a reaction between organic amine, carbonic acid derivative and aromatic hydroxy composition (Y), namely (V+W+X+Y), and is represented as the amount (multiple) based on the number of N-substituted carbamic acid-O—Ar esters.

In addition, in the following descriptions, although mention is made regarding the amount of "carbonyl groups contained in compounds having carbonyl groups contained in ammonia", this amount is an amount calculated according to the procedure described below.

i) GC-MS analysis is carried out according to the method described above on a gas containing the ammonia.

ii) The number of carbonyl groups contained in one molecule of compounds detected by GC-MS is determined.

iii) The total sum (units: mmol) of the products of the amount (units: mmol) of each compound detected by GC-MS and the number of carbonyl groups contained in the compounds is calculated, and that total sum is taken to be the amount of "carbonyl groups contained in compounds having carbonyl groups contained in ammonia". Thus, although the amount of carbonyl groups contained in compounds having carbonyl groups in an amount below the detection lower limit of GC-MS are not included in this amount, since the total amount of these carbonyl groups that are not included is extremely low, there are no problems whatsoever in discussing the weight ratio between "carbonyl groups contained in compound having carbonyl groups contained in ammonia" and the ammonia in the examples.

5) Sample Water Content Analysis

Apparatus: Micro Water Content Analyzer Model CA-21, Mitsubishi Chemical Analytech Co., Ltd., Japan (1) Quantitative Analysis About 1 g of sample was weighed out and injected into the micro water content analyzer to determine the water content of the sample.

Example 1

Step (1-1): Production of N-Substituted Carbamic Acid-O—Ar Ester

Figure 21:
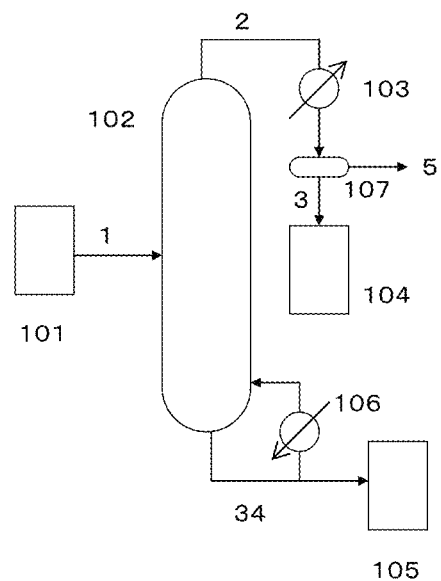
FIG. 21 shows a conceptual drawing depicting an N-substituted carbamic acid ester production apparatus used in an example of the present embodiment.

Production of urethane was carried out in a reactor as shown in FIG. 21.

240 g of hexamethylenediamine (Aldrich Corp., USA), 8510 g of 4-(1,1,3,3-tetramethylbutyl) phenol (Tokyo Chemical Industry Co., Ltd., Japan) and 496 g of urea (ultra pure, by Wako Pure Chemical Industries, Ltd., Japan) were mixed to prepare a raw material solution. A packed column 102 packed with a packing (Helipack No. 3) and having an inner diameter of 20 mm was heated to 240° C. and the pressure inside the column was set to about 20 kPa. A mixed liquid having the same composition as the raw material solution was introduced through a line 1 provided in the upper portion of the packed column 102, and after operating conditions had stabilized, the raw material solution was introduced at about 1.0 g/min, and the reaction liquid was recovered in a storage tank 105 via a line 4 provided in the bottom of the packed column 102. A gaseous phase component was recovered from a line 2 provided in the top of the packed column 102, condensed in a condenser 103 held at about 85° C., and the resulting component was recovered in a storage tank 104. The amount of reaction liquid recovered in a storage tank 105 was 4.69 kg. When the reaction liquid was analyzed by liquid chromatography and $^1$H-NMR, the reaction liquid was found to be a composition that contained 4-(1,1,3,3-tetramethylbutyl) phenol at a stoichiometric ratio of 8.8 times and bis(4-(1,1,3,3-tetramethylbutyl)phenyl) carbonate at a stoichiometric ratio of 0.0008 times based on N,N'-hexanediyl-di(carbamic acid (4-(1,1,3,3-tetramethylbutyl)phenyl)ester), and contained 0.0023 times an N-containing compound based on the number of N,N'-hexanediyl-di(carbamic acid(4-(1,1,3,3-tetramethylbutyl)phenyl)esters), and contained 8.0 ppm ammonia. In addition, the yield of N,N'-hexanediyl-di(carbamic acid (4-(1,1,3,3-tetramethylbutyl)phenyl)ester) based on hexamethylenediamine was about 92%.

On the other hand, when $^1$H-NMR and $^{13}$C-NMR measurements were carried out on the component recovered in the storage tank 104, it was found to be a mixture of 4-(1,1,3,3-tetramethylbutyl) phenol and urea, the content of urea was about 286 g (4.77 mol) and the content of 4-(1,1,3,3-tetramethylbutyl) phenol was 4.25 kg (20.7 mol). In addition, a gas containing ammonia was discharged from a line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.162 g (9.56 mmol). In addition, when the gas was analyzed by GC-MS, the amount of carbonyl groups contained in compounds having carbonyl groups contained in the ammonia was 0.0025 mmol.

Step (1-2): Reuse of Mixture Obtained in Condenser

Production of N-substituted carbamic acid-O—Ar ester was carried out using the mixture recovered in the storage tank 104 in step (1-1).

The ammonia concentration in the mixture recovered in the storage tank 104 in step (1-1) was 580 ppm. 225 g of hexamethylenediamine, 5680 g of 4-(1,1,3,3-tetramethylbutyl) phenol and 179 g of urea were added to the mixture to obtain a raw material solution. 6228 g of a reaction liquid were recovered in the storage tank 105 by using the raw material solution and carrying out the same method as step (1-1). The reaction liquid recovered in the storage tank 105 contained N,N'-hexanediyl-dicarbamic acid-bis(4-t-octylphenyl), and the yield of N,N'-hexanediyl-dicarbamic acid-bis(4-t-octylphenyl) based on hexamethylenediamine was about 92%.

When the step (1-1) was continued to be carried out, clogging of the ammonia discharge line was not observed even after operating time had exceeded 380 days. Furthermore, operating time referred to here indicates the total net time during which the reaction of step (1-1) was carried out using the apparatus described above, and does not include the amount of time during which the reaction was not carried out, such as the amount of time during which preparations were carried out for operating the above-mentioned apparatus.

Step (1-3): Production of Isocyanate by Thermal Decomposition of N-Substituted Carbamic Acid-O—Ar Ester Production of isocyanate was carried out using the apparatus shown in FIG. 26.

A thin film distillation apparatus 702 (Kobelco Eco-Solutions Co., Ltd., Japan) having a heat-conducting surface area of 0.2 m² was heated to 220° C. and the pressure within the thin film distillation apparatus was set to about 1.3 kPa. The reaction liquid recovered in the storage tank 105 in Example 1 was placed in a storage tank 701 and supplied to the thin film distillation apparatus at the rate of about 1800 g/hr via a line 70. A liquid component was extracted from a line 72 provided in the bottom of thin film distillation apparatus 702 and recovered in a storage tank 703. The liquid component recovered in the storage tank 703 was again supplied to the thin film distillation apparatus 702 through a line 73. A gaseous component containing hexamethylene diisocyanate and 4-(1,1,3,3-tetramethylbutyl) phenol was extracted from a line 71 provided in the upper portion of the thin film distillation apparatus 702. The gaseous component was introduced into a distillation column 704, and the hexamethylene diisocyanate and 4-(1,1,3,3-tetramethylbutyl) phenol were separated by distillation. A portion of a high boiling component containing the 4-(1,1,3,3-tetramethylbutyl) phenol was returned to the storage tank 703 through a line 76 provided in the bottom of the distillation column 704, a portion was again supplied to the distillation column 704 through a reboiler 708, and the remainder was recovered in a storage tank 709. A gaseous phase component containing hexamethylene diisocyanate was extracted from the top of the distillation column 704 via a line 74, condensed in a condenser 705, and a portion of the condensate was returned to the distillation column 704. The condensate was obtained in a storage tank 707 at the rate of about 83 g/hr.

When the condensate recovered in the storage tank 707 was analyzed by $^1$H-NMR and gas chromatography, it was found to be hexamethylene diisocyanate containing 200 ppm of 4-(1,1,3,3-tetramethylbutyl) phenol.

Although the hexamethylene diisocyanate was stored for 630 days at normal temperatures in a nitrogen atmosphere, discoloration was not observed.

Example 2

Step (2-1): Production of N-Substituted Carbamic Acid-O—Ar Ester

The same method as Example 1 was carried out with the exception of mixing 255 g of 4,4'-methylenedianiline (Aldrich Corp., USA), 5063 g of p-dodecyl phenol (Tokyo Chemical Industry Co., Ltd., Japan) and 193 g of urea to obtain a raw material solution, heating the packed column 102 to 240° C., setting the internal pressure to about 20 kPa, holding the condenser at about 60° C. and introducing the condensate at the rate of about 1.0 g/min. 4564 g of reaction liquid were recovered in the storage tank 105. When the reaction liquid was analyzed by liquid chromatography and $^1$H-NMR, the reaction liquid was found to be a composition that contained p-dodecyl phenol at a stoichiometric ratio of 11.5 times and di(p-dodecylphenyl) carbonate at a stoichiometric ratio of 0.0010 times based on N,N'-(4,4'-methanediyl-diphenyl)-di(carbamic acid(p-dodecylphenyl) ester), and contained 0.013 times an N-containing compound based on the number of N,N'-(4,4'-methanediyl-diphenyl)-di(carbamic acid(p-dodecylphenyl) esters). In addition, the yield of N,N'-(4,4'-methanediyl-diphenyl)-di(carbamic acid(p-dodecylphenyl) ester) based on 4,4'-methylenedianiline was about 92%. In addition, the amount of ammonia contained in the reaction liquid was 6.0 ppm. On the other hand, when $^1$H-NMR and $^{13}$C-NMR measurements were carried out on the component recovered in the storage tank 104, it was found to be a mixture of p-dodecyl phenol and urea, the content of urea was about 62.4 g (1.04 mol) and the content of p-dodecyl phenol was 861 g (3.28 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.16 g (9.6 mmol). In addition, when the gas was analyzed by GC-MS, the amount of carbonyl groups contained in compounds having carbonyl groups contained in the ammonia was 0.015 mmol.

When the step (2-1) was continued to be carried out, clogging of the ammonia discharge line was not observed even after operating time had exceeded 380 days.

Step (2-2): Reuse of Mixture Obtained in Condenser

Production of N-substituted carbamic acid-O—Ar ester was carried out using the mixture recovered in the storage tank 104 in step (2-1).

The ammonia concentration in the mixture recovered in the storage tank 104 in step (2-1) was 630 ppm. 260 g of 4,4'-methylenedianiline, 4300 g of p-dodecyl phenol and 134 g of urea were added to the mixture to obtain a raw material solution. 4600 g of a reaction liquid were recovered in the storage tank 105 by using the raw material solution and carrying out the same method as step (2-1). The reaction liquid recovered in the storage tank 105 contained N,N'-(4,4'-methanediyl-diphenyl)-di(carbamic acid(p-dodecylphenyl)ester), and the yield of N,N'-(4,4'-methanediyl-diphenyl)-di(carbamic acid(p-dodecylphenyl)ester) based on 4,4'-methylenedianiline was about 91%.

Step (2-3): Production of Isocyanate by Thermal Decomposition of N-Substituted Carbamic Acid-O—Ar Ester The same method as Example 1 was carried out with the exception of heating the thin film distillation apparatus 702 to 220° C., setting the pressure within the thin film distillation apparatus to about 1.3 kPa and supplying the reaction liquid recovered in the storage tank 105 in Example 2 instead of the reaction liquid recovered in storage tank 105 in Example 1 to the thin film distillation apparatus at the rate of about 2250 g/hr.

A condensate was obtained in the storage tank 707 at the rate of about 82 g/hr, and when the condensate recovered in the storage tank 707 was analyzed by $^1$H-NMR and gas chromatography, it was found to be 4,4'-diphenylmethane diisocyanate containing 100 ppm of p-dodecyl phenol.

Although the isocyanate was stored for 630 days at normal temperatures in a nitrogen atmosphere, discoloration was not observed.

Example 3

Step (3-1): Production of N-Substituted Carbamic Acid-O—Ar Ester

The same method as step (1-1) of Example 1 was carried out with the exception of mixing 220 g of 2,4-toluenediamine (Aldrich Corp., USA), 9274 g of 4-(1,1,3,3-tetramethylbutyl) phenol and 541 g of urea to obtain a raw material solution, heating the packed column 102 to 240° C., setting the internal pressure to about 52 kPa, holding the condenser at 120° C. and introducing the condensate at the rate of about 1.0 g/min. 5512 g of reaction liquid were recovered in the storage tank 105. When the reaction liquid was analyzed by liquid chromatography and $^1$H-NMR, the reaction liquid was found to be a composition that contained 4-(1,1,3,3-tetramethylbutyl) phenol at a stoichiometric ratio of 13.0 times and bis(4-(1,1,3,3-tetramethylbutyl)phenyl) carbonate at a stoichiometric ratio of 0.022 times based on toluene-2,4-di(carbamic acid (4-(1,1,3,3-tetramethylbutyl)phenyl) ester), and contained 0.028 times an N-containing compound based on the number of toluene-2,4-di(carbamic acid (4-(1,1,3,3-tetramethylbutyl)phenyl) esters). In addition, the yield of toluene-2,4-di (carbamic acid (4-(1,1,3,3-tetramethylbutyl)phenyl) ester) based on 2,4-toluenediamine was about 91%. The amount of ammonia contained in the reaction liquid was 8.3 ppm. On the other hand, when $^1$H-NMR and $^{13}$C-NMR measurements were carried out on the component recovered in the storage tank 104, it was found to be a mixture of 4-(1,1,3,3-tetramethylbutyl) phenol and urea, the content of urea was about 361 g (6.02 mol) and the content of 4-(1,1,3,3-tetramethylbutyl) phenol was 4173 g (20.3 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.134 g (7.9 mmol). When the gas was analyzed by GC-MS, the amount of carbonyl groups contained in compounds having carbonyl groups contained in the ammonia was 0.0237 mmol.

When the step (3-1) was continued to be carried out, clogging of the ammonia discharge line was not observed even after operating time had exceeded 380 days.

Step (3-2): Reuse of Mixture Obtained in Condenser

Production of N-substituted carbamic acid-O—Ar ester was carried out using the mixture recovered in the storage tank 104 in step (3-1).

The ammonia concentration in the mixture recovered in the storage tank 104 in step (3-1) was 2100 ppm. 310 g of 2,4-toluenediamine, 8895 g of 4-(1,1,3,3-tetramethylbutyl) phenol and 400 g of urea were added to the mixture to obtain a raw material solution. 10624 g of a reaction liquid were recovered in the storage tank 105 by using the raw material solution and carrying out the same method as step (2-1). The reaction liquid recovered in the storage tank 105 contained toluene-2,4-di(carbamic acid(4-(1,1,3,3-tetramethylbutyl) phenyl) ester), and the yield of toluene-2,4-di(carbamic acid (4-(1,1,3,3-tetramethylbutyl)phenyl) ester) based on 2,4-toluenediamine was about 81%.

Example 4

Step (4-1): Production of N-Substituted Carbamic Acid-O—Ar Ester

The same method as step (1-1) of Example 1 was carried out with the exception of mixing 321 g of 3-aminomethyl-3,5,5-trimethylcyclohexylamine (Aldrich Corp., USA), 3518 g of 4-phenyl phenol (Tokyo Chemical Industry Co., Ltd., Japan) and 339 g of urea to obtain a raw material solution, heating the packed column 102 to 240° C., setting the internal pressure to about 26 kPa, holding the condenser at about 150° C. and introducing the raw material solution at the rate of about 1.2 g/min. 1971 g of reaction liquid were recovered in the storage tank 105. When the reaction liquid was analyzed by liquid chromatography and $^1$H-NMR, the reaction liquid was found to be a composition that contained 4-phenyl phenol at a stoichiometric ratio of 2.7 times and di(4-phenylphenyl) carbonate at a stoichiometric ratio of 0.0009 times based on 3-((4-phenylphenoxy)carbonylamino-methyl)-3,5,5-trimethylcyclohexyl carbamic acid (4-phenylphenyl) ester, and contained 0.008 times an N-containing compound based on the number of 3-((4-phenylphenoxy)carbonylamino-methyl)-3,5,5-trimethylcyclohexyl carbamic acid (4-phenylphenyl) esters. In addition, 3-((4-phenylphenoxy)carbonylamino-methyl)-3,5,5-trimethylcyclohexyl carbamic acid (4-phenylphenyl) ester was detected, and the yield based on 3-aminomethyl-3,5,5-trimethylcyclohexylamine was about 93%. The amount of ammonia contained in the reaction liquid was 7.7 ppm. On the other hand, when $^1$H-NMR and $^{13}$C-NMR measurements were carried out on the component recovered in the storage tank 104, it was found to be a mixture of 4-phenyl phenol and urea, the content of urea was about 143 g (2.39 mol) and the content of 4-phenyl phenol was 2111 g (12.4 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.36 g (21.2 mmol). In addition, when the gas was analyzed by GC-MS, the amount of carbonyl groups contained in compounds having carbonyl groups contained in the ammonia was 0.263 mmol.

When the step (4-1) was continued to be carried out, clogging of the ammonia discharge line was not observed even after operating time had exceeded 380 days.

Step (4-2): Reuse of Mixture Obtained in Condenser

Production of N-substituted carbamic acid-O—Ar ester was carried out using the mixture recovered in the storage tank 104 in step (4-1).

The ammonia concentration in the mixture recovered in the storage tank 104 in step (4-1) was 3200 ppm. 310 g of 3-aminomethyl-3,5,5-trimethylcyclohexylamine, 2451 g of 4-phenyl phenol and 178 g of urea were added to the mixture to obtain a raw material solution. 2913 g of a reaction liquid were recovered in the storage tank 105 by using the raw material solution and carrying out the same method as step (2-1). The reaction liquid recovered in the storage tank 105 contained 3-((4-phenylphenoxy)carbonylamino-methyl)-3,5,5-trimethylcyclohexyl carbamic acid(4-phenylphenyl) ester, and the yield of 3-((4-phenylphenoxy)carbonylamino-methyl)-3,5,5-trimethylcyclohexyl carbamic acid(4-phenylphenyl) ester based on 3-aminomethyl-3,5,5-trimethylcyclohexylamine was about 74%.

Step (4-3): Production of Isocyanate by Thermal Decomposition of N-substituted Carbamic Acid-O—Ar Ester The same method as Example 1 was carried out with the exception of heating the thin film distillation apparatus 702 to 220° C., setting the pressure within the thin film distillation apparatus to about 1.3 kPa and supplying the reaction liquid recovered in the storage tank 105 in Example 4 instead of the reaction liquid recovered in storage tank 105 in Example 1 to the thin film distillation apparatus at the rate of about 660 g/hr.

A condensate was obtained in the storage tank 707 at the rate of about 104 g/hr, and when the condensate recovered in the storage tank 707 was analyzed by $^1$H-NMR and gas chromatography, it was found to be isophorone diisocyanate containing 130 ppm of 4-phenyl phenol. Although the isocyanate was stored for 630 days at normal temperatures in a nitrogen atmosphere, discoloration was not observed.

Example 5

Step (5-1): Production of N-Substituted Carbamic Acid-O—Ar Ester

The same method as step (1-1) of Example 1 was carried out with the exception of mixing 315 g of 4,4'-methylenebis(cyclohexylamine) (Aldrich Corp., USA), 7074 g of p-dodecyl phenol and 216 g of urea to obtain a raw material solution, heating the packed column 102 to 240° C., setting the internal pressure to about 26 kPa, holding the condenser at about 60° C. and introducing the raw material solution at the rate of about 1.5 g/min. 6655 g of reaction liquid were recovered in the storage tank 105. When the reaction liquid was analyzed by liquid chromatography and $^1$H-NMR, the reaction liquid was found to be a composition that contained p-dodecyl phenol at a stoichiometric ratio of 15.0 times and di(p-dodecylphenyl) carbonate at a stoichiometric ratio of 0.016 times based on N,N'-(4,4'-methanediyl-diphenyl)-di(carbamic acid (p-dodecylphenyl) ester), and contained 0.008 times an N-containing compound based on the number of N,N'-(4,4'-methanediyl-diphenyl)-di(carbamic acid(p-dodecylphenyl) esters). In addition, the yield of N,N'-(4,4'-methanediyl-diphenyl)-di(carbamic acid(p-dodecylphenyl) ester) based on 4,4'-methylenebis(cyclohexylamine) was about 93%. The amount of ammonia contained in the reaction liquid was 6.9 ppm. On the other hand, when $^1$H-NMR and $^{13}$C-NMR measurements were carried out on the component recovered in the storage tank 104, it was found to be a mixture of p-dodecyl phenol and urea, the content of urea was about 60.3 g (1.00 mol) and the content of p-dodecyl phenol was 848 g (3.23 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.20 g (12.0 mmol). When the gas was analyzed by GC-MS, the amount of carbonyl groups contained in compounds having carbonyl groups contained in the ammonia was 0.011 mmol.

When the step (5-1) was continued to be carried out, clogging of the ammonia discharge line was not observed even after operating time had exceeded 380 days.

Step (5-2): Reuse of Mixture Obtained in Condenser

Production of N-substituted carbamic acid-O—Ar ester was carried out using the mixture recovered in the storage tank 104 in step (5-1).

The ammonia concentration in the mixture recovered in the storage tank 104 in step (5-1) was 1910 ppm. 290 g of 4,4'-methylenebis(cyclohexylamine), 5663 g of p-dodecyl phenol and 134 g of urea were added to the mixture to obtain a raw material solution. 2913 g of a reaction liquid were recovered in the storage tank 105 by using the raw material solution and carrying out the same method as step (5-1). The reaction liquid recovered in the storage tank 105 contained N,N'-(4,4'-methanediyl-diphenyl)-di(carbamic acid(p-dodecylphenyl) ester), and the yield of N,N'-(4,4'-methanediyl-diphenyl)-di(carbamic acid(p-dodecylphenyl) ester) based on 4,4'-methylenebis(cyclohexylamine)3-((4-phenylphenoxy)carbonylamino-methyl)-3,5,5-trimethylcyclohexyl carbamic was about 93%.

Step (5-3): Production of Isocyanate by Thermal Decomposition of N-Substituted Carbamic Acid-O—Ar Ester Production of isocyanate was carried out using the apparatus shown in FIG. 28.

A thin film distillation apparatus 802 (Kobelco Eco-Solutions Co., Ltd., Japan) having a heat-conducting surface area of 0.2 m$^2$ was heated to 220° C. and the pressure within the thin film distillation apparatus was set to about 1.3 kPa. The reaction liquid recovered in the storage tank 105 in Example 5 was placed in a storage tank 801 and supplied to the thin film distillation apparatus at the rate of about 1690 g/hr via a line 80. A liquid component was extracted from a line 82 provided in the bottom of thin film distillation apparatus 802 and recovered in a storage tank 803. The liquid component recovered in the storage tank 803 was again supplied to the thin film distillation apparatus 802 through a line 83. A gaseous component containing diphenylmethane diisocyanate and p-dodecyl phenol was extracted from a line 81 provided in the upper portion of the thin film distillation apparatus 802. The gaseous component was introduced into a distillation column

804, the p-dodecyl phenol was separated by distillation, and a liquid phase was fed to a distillation column 809 from the feed port of the distillation column 804 through a line 88 provided in the lower portion thereof. In the distillation column 809, a gaseous phase component containing diphenylmethane diisocyanate was extracted, condensed in a condenser 810, and a portion of the condensate was returned to the distillation column 809. The condensate was obtained in a storage tank 812 at the rate of about 85 g/hr.

When the condensate recovered in the storage tank 812 was analyzed by $^1$H-NMR and gas chromatography, it was found to be diphenylmethane diisocyanate containing 720 ppm of p-dodecyl phenol. Although the isocyanate was stored for 630 days at normal temperatures in a nitrogen atmosphere, discoloration was not observed.

Example 6

Step (6-1): Production of (4-phenylphenyl) Carbamate 6298 g of 4-phenyl phenol and 444 g of urea were charged into an autoclave (Toyo Koatsu Inc., Japan) equipped with a thermometer, stirrer, reflux condenser and gas feed tube and having an internal volume of 12 L followed by stirring at normal pressure while bubbling nitrogen gas with a capillary tube at the rate of 100 L/hr and carrying out the reaction at 140° C. When a portion of the reaction liquid was removed 10 hours later and analyzed by liquid chromatography, the formation of (4-phenylphenyl) carbamate was confirmed. The yield was about 90% based on the charged amount of urea.

Step (6-2): Production of N-Substituted Carbamic Acid-O—Ar Ester 215 g of hexamethylenediamine were added to the solution obtained in step (6-1) followed by stirring to obtain a raw material solution. The same method as step (1-1) of Example 1 was carried out with the exception of using this raw material solution, heating the packed column 102 to 240° C., setting the internal pressure to 26 kPa, holding the condenser at 150° C. and introducing the raw material solution at the rate of about 1.0 g/min. 2688 g of reaction liquid were recovered in the storage tank 105. When the reaction liquid was analyzed by liquid chromatography and $^1$H-NMR, the reaction liquid was found to be a composition that contained 4-phenyl phenol at a stoichiometric ratio of 6.1 times and di(p-dodecylphenyl) carbonate at a stoichiometric ratio of 0.0010 times based on N,N'-hexanediyl-di(carbamic acid(4-phenylphenyl) ester), and contained 0.044 times an N-containing compound based on the number of N,N'-hexanediyl-di(carbamic acid(4-phenylphenyl) esters). In addition, the yield of N,N'-hexanediyl-di(carbamic acid(4-phenylphenyl) ester) based on hexamethylenediamine was about 90%. The amount of ammonia contained in the reaction liquid was 10 ppm. On the other hand, when $^1$H-NMR and $^{13}$C-NMR measurements were carried out on the component recovered in the storage tank 104, it was found to be a mixture of 4-phenyl phenol, urea and (4-phenylphenyl) carbamate, the content of urea was about 31 g (0.52 mol), the content of (4-phenylphenyl) carbamate was 828 g (3.89 mol), and the content of 4-phenyl phenol was 2840 g (16.7 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.094 g (5.5 mmol).

When the gas was analyzed by GC-MS, the amount of carbonyl groups contained in compounds having carbonyl groups contained in the ammonia was 0.025 mmol.

When the steps (6-1) to (6-2) were continued to be carried out, clogging of the ammonia discharge line was not observed even after operating time had exceeded 380 days.

Step (6-3): Production of N-Substituted Carbamic Acid-O—Ar Ester by Reusing Mixture Obtained in Condenser The ammonia concentration in the mixture recovered in the storage tank 104 in step (6-2) was 5200 ppm. The same method as step (6-1) was carried out by adding 5225 g of 4-phenyl phenol and 170 g of urea to the mixture. The same method as step (6-2) was carried out by adding 210 g of hexamethylenediamine to the resulting reaction liquid to obtain a raw material solution. 4408 g of a reaction liquid were recovered in the storage tank 105. The reaction liquid contained N,N'-hexanediyl-di(carbamic acid(4-phenylphenyl) ester), and the yield of N,N'-hexanediyl-di(carbamic acid (4-phenylphenyl) ester) based on hexamethylenediamine was about 63%.

Step (6-4): Production of Isocyanate by Thermal Decomposition of N-Substituted Carbamic Acid-O—Ar Ester The same method as Example 1 was carried out with the exception of heating the thin film distillation apparatus 702 to 220° C., setting the pressure within the thin film distillation apparatus to about 1.3 kPa and supplying the reaction liquid recovered in the storage tank 105 in step (6-2) of Example 6 instead of the reaction liquid recovered in storage tank 105 in Example 1 to the thin film distillation apparatus at the rate of about 1410 g/hr. A condensate was obtained in the storage tank 707 at the rate of about 84 g/hr, and when the condensate recovered in the storage tank 707 was analyzed by $^1$H-NMR and gas chromatography, it was found to be hexamethylene diisocyanate containing 130 ppm of 4-phenyl phenol. Although the isocyanate was stored for 630 days at normal temperatures in a nitrogen atmosphere, discoloration was not observed.

Example 7

Step (7-1): Production of (4-nonylphenyl) Carbamate

The same method as step (6-1) of Example 6 was carried out with the exception of using 11003 g of 4-nonyl phenol (Tokyo Chemical Industry Co., Ltd., Japan) instead of 4-phenyl phenol, using 499 g of urea and carrying out the reaction for 15 hours. When a portion of the reaction liquid was removed and analyzed by liquid chromatography, the formation of (4-nonylphenyl) carbamate was confirmed. The yield was about 85% based on the charged amount of urea.

Step (7-2): Production of N-Substituted Carbamic Acid-O—Ar Ester 330 g of 4,4'-methylenedianiline were added to the solution obtained in step (7-1) followed by stirring to obtain a raw material solution. The same method as step (1-1) of Example 1 was carried out with the exception of using this raw material solution, heating the packed column 102 to 240° C., setting the internal pressure to about 26 kPa, holding the condenser at 60° C. and introducing the raw material solution at the rate of about 2.0 g/min. 8078 g of reaction liquid were recovered in the storage tank 105. When the reaction liquid was analyzed by liquid chromatography and $^1$H-NMR, the reaction liquid was found to be a composition that contained 4-nonyl phenol at a stoichiometric ratio of 22.1 times and di(4-nonylphenyl) carbonate at a stoichiometric ratio of 0.0039 times based on N,N'-(4,4'-methanediyl-diphenyl)-di(carbamic acid(4-nonylphenyl) ester), and contained 0.036 times an N-containing compound based on the number of N,N'-(4,4'-methanediyl-diphenyl)-di(carbamic acid(4-nonylphenyl) esters). In addition, the yield of N,N'-(4,4'-methanediyl-diphenyl)-di(carbamic acid(4-nonylphenyl) ester) based on 4,4'-methylenedianiline was about 85%. The amount of ammonia contained in the reaction liquid was 7.3 ppm. On the other hand, when $^1$H-NMR and $^{13}$C-NMR measurements were carried out on the component recovered in the storage tank 104, it was found to be a mixture of 4-nonyl phenol, urea and (4-nonylphenyl) carbamate, the content of urea was about 52 g (0.87 mol), the content of (4-nonylphenyl) carbamate was 1328 g (5.04 mol), and the content of 4-nonyl phenol was 1889 g (8.57 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.101 g (5.9 mmol). When the gas was analyzed by GC-MS, the amount of carbonyl groups contained in compounds having carbonyl groups contained in the ammonia was 2.42 mmol.

When the steps (7-1) to (7-2) were continued to be carried out, the line 5 clogged when the operating time had exceeded 220 days.

Step (7-3): Production of N-Substituted Carbamic Acid-O—Ar Ester by Reusing Mixture Obtained in Condenser The ammonia concentration in the mixture recovered in the storage tank 104 in step (7-2) was 2200 ppm. When the mixture was heated to 120° C. and held for 3 hours at 50 kPa, the ammonia concentration in the mixture was 150 ppm. The same method as step (7-1) was carried out by adding 9280 g of 4-nonyl phenol and 152 g of urea to the mixture. The same method as step (7-2) was carried out by adding 335 g of 4,4'-methylenedianiline to the resulting reaction liquid to obtain a raw material solution. 8125 g of a reaction liquid were recovered in the storage tank 105. The reaction liquid contained N,N'-(4,4'-methanediyl-diphenyl)-di(carbamic acid(4-nonylphenyl) ester), and the yield of N,N'-(4,4'-methanediyl-diphenyl)-di(carbamic acid(4-nonylphenyl) ester) based on 4,4'-methylenedianiline was about 88%.

Step (7-4): Production of Isocyanate by Thermal Decomposition of N-Substituted Carbamic Acid-O—Ar Ester The apparatus shown in FIG. 28 was used.
The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 7 instead of the reaction liquid recovered in storage tank 105 in Example 5, and supplying to the thin film distillation apparatus via the line 80 at the rate of about 1910 g/hr.

A condensate was obtained in the storage tank 812 at the rate of about 75 g/hr, and when the condensate recovered in the storage tank 812 was analyzed by $^1$H-NMR and gas chromatography, it was found to be diphenylmethane diisocyanate containing 220 ppm of 4-nonyl phenol. Although the isocyanate was stored for 630 days at normal temperatures in a nitrogen atmosphere, discoloration was not observed.

Example 8

Step (8-1): Production of (4-ethylphenyl) Carbamate

The same method as step (6-1) of Example 6 was carried out with the exception of using 39.0 kg of 4-ethyl phenol (Tokyo Chemical Industry Co., Ltd., Japan) instead of 4-phenyl phenol, using 1057 g of urea and carrying out the reaction for 12 hours. When a portion of the reaction liquid was removed and analyzed by liquid chromatography, the formation of (4-ethylphenyl) carbamate was confirmed. The yield was about 88% based on the charged amount of urea.

Step (8-2): Production of N-Substituted Carbamic Acid-O—Ar Ester 215 g of 2,4-toluenediamine were added to the solution obtained in step (8-1) followed by stirring to obtain a raw material solution. The same method as step (1-1) of Example 1 was carried out with the exception of using this raw material solution, heating the packed column 102 to 240° C., setting the internal pressure to atmospheric pressure (nitrogen atmosphere), holding the condenser at 60° C. and introducing the raw material solution at the rate of about 2.8 g/min. 20.8 kg of reaction liquid were recovered in the storage tank 105. When the reaction liquid was analyzed by liquid chromatography and $^1$H-NMR, the reaction liquid was found to be a composition that contained 4-ethyl phenol at a stoichiometric ratio of 105 times and di(4-ethylphenyl) carbonate at a stoichiometric ratio of 0.0026 times based on toluene-2,4-di(carbamic acid(4-ethylphenyl) ester), and contained 0.015 times an N-containing compound based on the number of toluene-2,4-di(carbamic acid(4-ethylphenyl) esters). In addition, the yield of toluene-2,4-di(carbamic acid(4-ethylphenyl) ester) based on 2,4-toluenediamine was about 84%. The amount of ammonia contained in the reaction liquid was 3.2 ppm. On the other hand, when $^1$H-NMR and $^{13}$C-NMR measurements were carried out on the component recovered in the storage tank 104, it was found to be a mixture of 4-ethyl phenol, urea and (4-ethylphenyl) carbamate, the content of urea was about 88 g (1.48 mol), the content of (4-ethylphenyl) carbamate was 2253 g (13.6 mol), and the content of 4-ethyl phenol was 19.5 kg (159 mol). In addition, a gas containing ammonia was discharged from the line 5 provided in the upper portion of the storage tank 105. The gas was recovered in a Tedlar bag and injected into a gas chromatograph with a gastight syringe to analyze the gas components. As a result, the amount of ammonia recovered per 10 minutes was 0.0986 g (5.80 mmol). When the gas was analyzed by GC-MS, the amount of carbonyl groups contained in compounds having carbonyl groups contained in the ammonia was 0.0055 mmol.

When the steps (8-1) to (8-2) were continued to be carried out, clogging of the ammonia discharge line was not observed even after operating time had exceeded 380 days.

Step (8-3): Production of N-Substituted Carbamic Acid-O—Ar Ester by Reusing Mixture Obtained in Condenser The ammonia concentration in the mixture recovered in the storage tank 104 in step (8-2) was 80 ppm. The same method as step (8-1) was carried out by adding 19.5 kg of 4-ethyl phenol and 237 g of urea to the mixture. The same method as step (8-2) was carried out by adding 215 g of 2,4-toluenediamine to the resulting reaction liquid to obtain a raw material solution. 2230 g of a reaction liquid were recovered in the storage tank 105. The reaction liquid contained toluene-2,4-di(carbamic acid(4-ethylphenyl) ester), and the yield of toluene-2,4-di(carbamic acid(4-ethylphenyl) ester) based on 2,4-toluenediamine was about 85%.

Step (8-4): Production of Isocyanate by Thermal Decomposition of N-Substituted Carbamic Acid-O—Ar Ester The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 8 instead of the reaction liquid recovered in storage tank 105 in Example 1, and supplying to the thin film distillation apparatus via the line 80 at the rate of about 2580 g/hr.

A condensate was obtained in the storage tank 812 at the rate of about 19 g/hr, and when the condensate recovered in the storage tank 812 was analyzed by $^1$H-NMR and gas chromatography, it was found to be diphenylmethane diisocyanate containing 20 ppm of 4-ethyl phenol. Although the isocyanate was stored for 630 days at normal temperatures in a nitrogen atmosphere, discoloration was not observed.

Example 9

Step (9-1): Production of (p-heptylphenyl) Carbamate

The same method as step (6-1) of Example 6 was carried out with the exception of using 8040 g of p-heptyl phenol instead of 4-phenyl phenol, using 378 g of urea and carrying out the reaction for 16 hours. When a portion of the reaction liquid was removed and analyzed by liquid chromatography, the formation of (p-pentylphenyl) carbamate was confirmed. The yield was about 90% based on the charged amount of urea.

Step (9-2): Production of N-Substituted Carbamic Acid-O—Ar Ester 356 g of 3-aminomethyl-3,5,5-trimethylcyclohexylamine were added to the solution obtained in step (9-1) followed by stirring to obtain a raw material solution. The same method as step (1-1) of Example 1 was carried out with the exception of using this raw material solution, heating the packed column 102 to 240° C., setting the internal pressure to 26 kPa, holding the condenser at 60° C. and introducing the raw material solution at the rate of about 1.4 g/min. 6134 g of reaction liquid were recovered in the storage tank 105. When the reaction liquid was analyzed by liquid chromatography and $^1$H-NMR, the reaction liquid was found to be a composition that contained p-heptyl phenol at a stoichiometric ratio of 13.3 times and di(p-heptylphenyl) carbonate at a stoichiometric ratio of 0.013 times based on 3-((p-heptylphenoxy)carbonylamino-methyl)-3,5,5-trimethylcyclohexyl carbamic acid (p-heptylphenyl) ester, and contained 0.022 times an N-containing compound based on the number of 3-((p-heptylphenoxy)carbonylamino-methyl)-3,5,5-trimethylcyclohexyl carbamic acid(p-heptylphenyl) esters. In addition, the yield of 3-((p-heptylphenoxy)carbonylamino-methyl)-3,5,5-trimethylcyclohexyl carbamic acid(p-heptylphenyl) ester based on 3-aminomethyl-3,5,5-trimethylcyclohexylamine was about 90%. The amount of ammonia contained in the reaction liquid was 4.9 ppm. On the other hand, when $^1$H-NMR and $^{13}$C-NMR measurements were carried out on the component recovered in the storage tank 104, it was found to be a mixture of p-heptyl phenol, urea and (p-heptylphenyl) carbamate, the content of urea was about 26.4 g (0.44 mol), the content of (p-heptylphenyl) carbamate was 575 g (2.45 mol), and the content of p-heptyl phenol was 1390 g (7.23 mol). In addition, a gas containing ammonia was discharged from the line 5 provided in the upper portion of the storage tank 105. The gas was recovered in a Tedlar bag and injected into a gas chromatograph with a gastight syringe to analyze the gas components. As a result, the amount of ammonia recovered per 10 minutes was 0.121 g (7.10 mmol). When the gas was analyzed by GC-MS, the amount of carbonyl groups contained in compounds having carbonyl groups contained in the ammonia was 0.056 mmol.

When the steps (9-1) to (9-2) were continued to be carried out, the line 5 clogged when operating time had exceeded 380 days.

Step (9-3): Production of N-Substituted Carbamic Acid-O—Ar Ester by Reusing Mixture Obtained in Condenser The ammonia concentration in the mixture recovered in the storage tank 104 in step (9-2) was 120 ppm. The same method as step (9-1) was carried out by adding 6287 g of p-heptyl phenol and 186 g of urea to the mixture. The same method as step (9-2) was carried out by adding 340 g of 3-aminomethyl-3,5,5-trimethylcyclohexylamine to the resulting reaction liquid to obtain a raw material solution. 5850 g of a reaction liquid were recovered in the storage tank 105. The reaction liquid contained 3-((p-heptylphenoxy)carbonylamino-methyl-3,5,5-trimethylcyclohexyl carbamic acid(p-heptylphenyl) ester, and the yield of 3-((p-heptylphenoxy)carbonylamino-methyl-3,5,5-trimethylcyclohexyl carbamic acid(p-heptylphenyl) ester based on 3-aminomethyl-3,5,5-trimethylcyclohexylamine was about 89%.

Example 10

Step (10-1): Production of (2,6-dimethoxyphenylphenyl) Carbamate

The same method as step (6-1) of Example 6 was carried out with the exception of using 6155 g of 2,6-dimethoxy phenol (Aldrich Corp., USA) instead of 4-phenyl phenol, using 420 g of urea and carrying out the reaction for 13 hours. When a portion of the reaction liquid was removed and analyzed by liquid chromatography, the formation of (2,6-dimethoxyphenyl) carbamate was confirmed. The yield was about 81% based on the charged amount of urea.

Step (10-2): Production of N-Substituted Carbamic Acid-O—Ar Ester 420 g of 4,4'-methylenebis(cyclohexylamine) were added to the solution obtained in step (10-1) followed by stirring to obtain a raw material solution. The same method as step (1-1) of Example 1 was carried out with the exception of using this raw material solution, heating the packed column 102 to 240° C., setting the internal pressure to about 26 kPa, holding the condenser at 60° C. and introducing the raw material solution at the rate of about 1.4 g/min. 2364 g of reaction liquid were recovered in the storage tank 105. When the reaction liquid was analyzed by liquid chromatography and $^1$H-NMR, the reaction liquid was found to be a composition that contained 2,6-dimethoxy phenol at a stoichiometric ratio of 4.46 times and di(2,6-dimethoxyphenyl) carbonate at a stoichiometric ratio of 0.0002 times based on N,N'-(4,4'-methanediyl-dicyclohexyl)-di(carbamic acid(2,6-dimethoxyphenyl) ester), and contained 0.081 times an N-containing compound based on the number of N,N'-(4,4'-methanediyl-dicyclohexyl)-di(carbamic acid(2,6-dimethoxyphenyl) esters). In addition, the yield of N,N'-(4,4'-methanediyl-dicyclohexyl)-di(carbamic acid(2,6-dimethoxyphenyl) ester) based on 4,4'-methylenebis(cyclohexylamine) was about 86%. The amount of ammonia contained in the reaction liquid was 9.3 ppm. On the other hand, when $^1$H-NMR and $^{13}$C-NMR measurements were carried out on the component recovered in the storage tank 104, it was found to be a mixture of 2,6-dimethoxy phenol, urea and (2,6-dimethoxyphenyl) carbamate, the content of urea was about 56 g (0.93 mol), the content of (2,6-dimethoxyphenyl) carbamate was 69 g (4.05 mol), and the content of 2,6-dimethoxy phenol was 3539 g (23.0 mol). In addition, a gas containing ammonia was discharged from the line 5 provided in the upper portion of the storage tank 105. The gas was recovered in a Tedlar bag and injected into a gas chromatograph with a gastight syringe to analyze the gas components. As a result, the amount of ammonia recovered per 10 minutes was 0.149 g (8.81 mmol). When the gas was analyzed by GC-MS, the amount of carbonyl groups contained in compounds having carbonyl groups contained in the ammonia was 0.0078 mmol.

When the steps (10-1) to (10-2) were continued to be carried out, clogging of the ammonia discharge line was not observed even after operating time had exceeded 380 days.

Step (10-3): Production of N-Substituted Carbamic Acid-O—Ar Ester by Reusing Mixture Obtained in Condenser The same method as step (10-1) was carried out by adding 2616 g of 2,6-dimethoxy phenol and 177 g of urea to the mixture recovered in the storage tank 104 in step (10-2). The same method as step (10-2) was carried out by adding 423 g of 4,4'-methylenebis(cyclohexylamine) to the resulting reaction liquid to obtain a raw material solution. 2328 g of a reaction liquid were recovered in the storage tank 105. The reaction liquid contained N,N'-(4,4'-methanediyl-cyclohexyl)-di(carbamic acid(2,6-dimethoxyphenyl) ester), and the yield of N,N'-(4,4'-methanediyl-cyclohexyl)-di(carbamic acid(2,6-dimethoxyphenyl) ester) based on 4,4'-methylenebis(cyclohexylamine) was about 85%.

Step (10-4): Production of Isocyanate by Thermal Decomposition of N-Substituted Carbamic Acid-O—Ar Ester The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 10 instead of the reaction liquid recovered in storage tank 105 in Example 5, and supplying to the thin film distillation apparatus via the line 80 at the rate of about 680 g/hr.

A condensate was obtained in the storage tank 812 at the rate of about 114 g/hr, and when the condensate recovered in the storage tank 812 was analyzed by $^1$H-NMR and gas chromatography, it was found to be dicyclohexylmethane diisocyanate containing 29 ppm of 2,6-dimethoxy phenol. Although the isocyanate was stored for 630 days at normal temperatures in a nitrogen atmosphere, discoloration was not observed.

Example 11

Step (11-1): Production of N-Substituted Carbamic Acid-O—Ar Ester

The same method as step (1-1) of Example 1 was carried out with the exception of mixing 273 g of hexamethylenediamine, 13766 g of 2,4-di-tert-amyl phenol (Tokyo Chemical Industry Co., Ltd., Japan) and 381 g of urea to obtain a raw material solution, heating the packed column 102 to 240° C., setting the internal pressure to 26 kPa, setting the temperature of the condenser to 85° C., and introducing the raw material solution at the rate of about 1.4 g/min. The amount of reaction liquid recovered in the storage tank 105 was 11599 g. When the reaction liquid was analyzed by liquid chromatography and $^1$H-NMR, the reaction liquid was found to be a composition that contained 2,4-di-tert-amyl phenol at a stoichiometric ratio of 35.9 times based on N,N'-hexanediyl-di(carbamic acid(2,4-di-tert-amylphenyl) ester), and contained 0.0058 times an N-containing compound based on the number of N,N'-hexanediyl-di(carbamic acid(2,4-di-tert-amylphenyl) esters). The amount of bis(2,4-di-tert-amylphenyl) carbonate was below the detection lower limit. In addition, the yield of N,N'-hexanediyl-di(carbamic acid(2,4-di-tert-amylphenyl) ester) based on hexamethylenediamine was about 53%. On the other hand, when $^1$H-NMR and $^{13}$C-NMR measurements were carried out on the component recovered in the storage tank 104, it was found to be a mixture of 4-tert-amyl phenol and urea, the content of urea was about 261 g (4.36 mol) and the content of 4-tert-amyl phenol was 2615 g (11.2 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.14 g (8.0 mmol). In addition, when the gas was analyzed by GC-MS, the amount of carbonyl groups contained in compounds having carbonyl groups contained in the ammonia was 0.76 mmol.

When the step (11-1) was continued to be carried out, the line 5 became clogged when operating time had exceeded 310 days.

Step (11-2): Production of Isocyanate by Thermal Decomposition of N-Substituted Carbamic Acid-O—Ar Ester The same method as Example 1 was carried out with the exception of heating the thin film distillation apparatus 702 to 220° C., setting the pressure within the thin film distillation apparatus to about 1.3 kPa, and supplying the reaction liquid recovered in the storage tank 105 in step (11-1) of Example 11 instead of the reaction liquid recovered in the storage tank 105 in Example 1 to the thin film distillation apparatus at the rate of about 1230 g/hr.

A condensate was obtained in the storage tank 707 at the rate of about 25 g/hr, and when the condensate recovered in the storage tank 707 was analyzed by $^1$H-NMR and gas chromatography, it was found to be isophorone diisocyanate containing 3 ppm of 4-phenyl phenol. Although the hexamethylene diisocyanate was stored for 630 days at normal temperatures in a nitrogen atmosphere, discoloration was not observed.

Example 12

Step (12-1): Production of N-Substituted Carbamic Acid-O—Ar Ester

The same method as step (1-1) of Example 1 was carried out with the exception of mixing 287 g of 3-aminomethyl-3,5,5-trimethylcyclohexylamine, 9013 g of 2,6-diisopropyl phenol (Tokyo Chemical Industry Co., Ltd., Japan) and 354 g of urea to obtain a raw material solution, heating the packed column 102 to 240° C., setting the internal pressure to 26 kPa, holding the condenser at 60° C., and introducing the raw material solution at the rate of about 1.7 g/min. The amount of reaction liquid recovered in the storage tank 105 was 2393 g. When the reaction liquid was analyzed by liquid chromatography and $^1$H-NMR, the reaction liquid was found to be a composition that contained 2,6-diisopropyl phenol at a stoichiometric ratio of 10.2 times based on 3-((2,6-diisopropylphenoxy)carbonylamino-methyl)-3,5,5-trimethylcyclohexyl carbamic acid(2,6-diisopropylphenyl) ester, and contained 0.028 times an N-containing compound based on the number of 3-((2,6-diisopropylphenoxy)carbonylaminomethyl)-3,5,5-trimethylcyclohexyl carbamic acid(2,6-diisopropylphenyl) esters. The amount of bis(2,6-diisopropylphenyl) carbonate was below the detection lower limit. In addition, the yield of 3-((2,6-diisopropylphenoxy)carbonylamino-methyl)-3,5,5-trimethylcyclohexyl carbamic acid(2,6-diisopropylphenyl) ester based on 3-aminomethyl-3,5,5-trimethylcyclohexylamine was about 55%. The reaction liquid contained 9.8 ppm of ammonia. On the other hand, when $^1$H-NMR and $^{13}$C-NMR measurements were carried out on the component recovered in the storage tank 104, it was found to be a mixture of 2,6-diisopropyl phenol and urea, the content of urea was about 293 g (4.88 mol) and the content of 2,6-diisopropyl phenol was 6940 g (38.9 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.17 g (9.7 mmol). In addition, when the gas was analyzed by GC-MS, the amount of carbonyl groups contained in compounds having carbonyl groups contained in the ammonia was 0.008 mmol.

When the step (12-1) was continued to be carried out, clogging of the ammonia discharge line was not observed even after operating time had exceeded 380 days.

Example 13

Step (13-1): Production of N-Substituted Carbamic Acid-O—Ar Ester

The same method as step (1-1) of Example 1 was carried out with the exception of mixing 255 g of hexamethylenediamine, 14015 g of hydroquinone (Wako Pure Chemical Industries, Ltd., Japan) and 527 g of urea to obtain a raw material solution, heating the packed column 102 to 240° C., setting the internal pressure to 26 kPa, holding the condenser at 180° C., and introducing the raw material solution at the rate of about 1.7 g/min. The amount of reaction liquid recovered in the storage tank 105 was 9757 g. When the reaction liquid was analyzed by liquid chromatography and $^1$H-NMR, the reaction liquid was found to be a composition that contained hydroquinone at a stoichiometric ratio of 57.3 times based on N,N'-hexanediyl-di(carbamic acid(hydroxyphenyl) ester), and contained 0.027 times an N-containing compound based on the number of N,N'-hexanediyl-di(carbamic acid (hydroxyphenyl) esters). Carbonic acid ester derived from the hydroquinone was not detected. In addition, the yield of N,N'-hexanediyl-di(carbamic acid(hydroxyphenyl) ester) based on hexamethylenediamine was about 63%. The reaction liquid contained 7.9 ppm of ammonia. On the other hand, when $^1$H-NMR and $^{13}$C-NMR measurements were carried out on the component recovered in the storage tank 104, it was found to be a mixture of hydroquinone and urea, the content of urea was about 422 g (7.04 mol) and the content of hydroquinone was 4905 g (44.6 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.20 g (11.6 mmol). In addition, when the gas was analyzed by GC-MS, the amount of carbonyl groups contained in compounds having carbonyl groups contained in the ammonia was 0.489 mmol.

When the step (13-1) was continued to be carried out, clogging of the ammonia discharge line was not observed even after operating time had exceeded 380 days.

Example 14

Step (14-1): Production of N-Substituted Carbamic Acid-O—Ar Ester

The same method as step (1-1) of Example 1 was carried out with the exception of mixing 210 g of 4,4'-methylenebis(cyclohexylamine), 11395 g of bisphenol A (Wako Pure Chemical Industries, Ltd., Japan) and 210 g of urea to obtain a raw material solution, heating the packed column 102 to 240° C., setting the internal pressure to 26 kPa, holding the condenser at 165° C., and introducing the raw material solution at the rate of about 1.7 g/min. The amount of reaction liquid recovered in the storage tank 105 was 9520 g. When the reaction liquid was analyzed by liquid chromatography and $^1$H-NMR, the reaction liquid was found to be a composition that contained bisphenol A at a stoichiometric ratio of 66.4 times based on N,N'-(4,4'-methanediyl-cyclohexyl)-di(carbamic acid(4-hydroxyphenyl-isopropyl)phenyl ester), and contained 0.037 times an N-containing compound based on the number of N,N'-(4,4'-methanediyl-cyclohexyl)-di(carbamic acid(4-hydroxyphenyl-isopropyl)phenyl esters). Carbonic acid ester derived from the bisphenol A was not detected. In addition, the yield of N,N'-(4,4'-methanediyl-cyclohexyl)-di(carbamic acid(4-hydroxyphenyl-isopropyl) phenyl ester) based on hexamethylenediamine was about 58%. The reaction liquid contained 4.9 ppm of ammonia. On the other hand, when $^1$H-NMR and $^{13}$C-NMR measurements were carried out on the component recovered in the storage tank 104, it was found to be a mixture of bisphenol A and urea, the content of urea was about 169.5 g (2.82 mol) and the content of bisphenol A was 2280 g (10.0 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.10 g (5.9 mmol). In addition, when the gas was analyzed by GC-MS, the amount of carbonyl groups contained in compounds having carbonyl groups contained in the ammonia was 0.057 mmol.

When the step (14-1) was continued to be carried out, clogging of the ammonia discharge line was not observed even after operating time had exceeded 380 days.

Example 15

Step (15-1): Production of N-Substituted Carbamic Acid-O—Ar Ester

Figure 22:
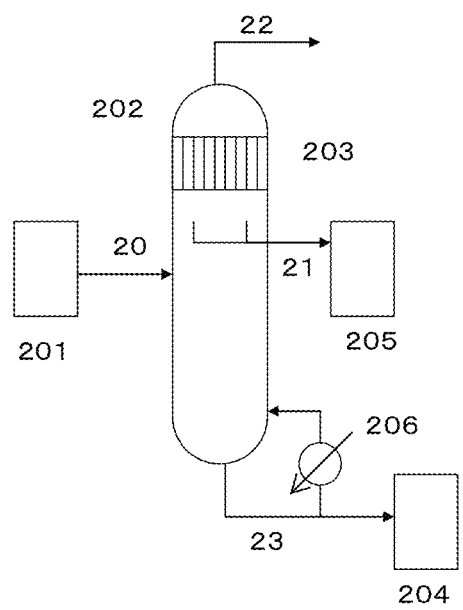
FIG. 22 shows a conceptual drawing depicting an N-substituted carbamic acid ester production apparatus used in an example of the present embodiment.

Production of urethane was carried out with an apparatus as shown in FIG. 22.

422 g of 4,4'-methylenebis(cyclohexylamine), 4942 g of 4-tert-amyl phenol (Aldrich Corp., USA) and 337 g of urea were mixed to prepare a raw material solution. A packed column 202 packed with a packing (Helipack No. 3), having an inner diameter of 20 mm and having a height of 2000 mm was heated to 240° C. and the pressure inside the column was set to 26 kPa. A mixed liquid having the same composition as the raw material solution was introduced through a line 20 provided in the upper portion of the packed column 202 (but lower than the condenser provided within the packed column 202), and after operating conditions had stabilized, the raw material solution was introduced at about 1.5 g/min, and the reaction liquid was recovered in a storage tank 204 via a line 23 provided in the bottom of the packed column 202. A gaseous phase component within the packed column 202 was condensed in a condenser 203 held at about 100° C., and the resulting component was recovered in a storage tank 205 from a line 21. The amount of reaction liquid recovered in a storage tank 204 was 3588 g. When the reaction liquid was analyzed by liquid chromatography and $^1$H-NMR, the reaction liquid was found to be a composition that contained 4-tert-amyl phenol at a stoichiometric ratio of 7.9 times and di(4-tert-amylphenyl) carbonate at a stoichiometric ratio of 0.013 times based on N,N'-(4,4'-methanediyl-diphenyl)-di (carbamic acid(4-tert-amylphenyl) ester), and contained 0.038 times an N-containing compound based on the number of N,N'-(4,4'-methanediyl-diphenyl)-di(carbamic acid(4-tert-amylphenyl) esters). In addition, the yield of N,N'-(4,4'-methanediyl-diphenyl)-di(carbamic acid(4-tert-amylphenyl) ester) based on 4,4'-methylenebis(cyclohexylamine) was about 90%. On the other hand, when $^1$H-NMR and $^{13}$C-NMR measurements were carried out on the component recovered in the storage tank 205, it was found to be a mixture of 4-tert-amyl phenol and urea, the content of urea was about 142 g (2.37 mol) and the content of 4-tert-amyl phenol was 1977 g (12.0 mol). In addition, a gas containing ammonia discharged from a line 22 provided in the top of the packed column 202 was recovered in a Tedlar bag and injected into a gas chromatograph with a gastight syringe to analyze the gas components. As a result, the amount of ammonia recovered per 10 minutes was 0.42 g (24.7 mmol). When the gas was analyzed by GC-MS, the amount of carbonyl groups contained in compounds having carbonyl groups contained in the ammonia was 0.003 mmol.

When the step (15-1) was continued to be carried out, clogging of the ammonia discharge line was not observed even after operating time had exceeded 380 days.

Step (15-2): Production of Isocyanate by Thermal Decomposition of N-Substituted Carbamic Acid-O—Ar Ester The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 15 instead of the reaction liquid recovered in the storage tank 105 in Example 5 into the storage tank 801, and supplying to the thin film distillation apparatus from the line 80 at the rate of about 860 g/hr.

A condensate was obtained in the storage tank 812 at the rate of about 99 g/hr, and when the condensate recovered in the storage tank 812 was analyzed by $^1$H-NMR and gas chromatography, it was found to be dicyclohexylmethane diisocyanate containing 30 ppm of 4-tert-amyl phenol. Although the isocyanate was stored for 630 days at normal temperatures in a nitrogen atmosphere, discoloration was not observed.

Example 16

Step (16-1): Production of N-Substituted Carbamic Acid-O—Ar Ester 445 g of 3-aminomethyl-3,5,5-trimethylcyclohexylamine, 5579 g of 4-tert-amyl phenol and 502 g of urea were mixed to prepare a raw material solution. The same method as Example 15 was carried out with the exception of heating the packed column 202 to 240° C., setting the internal pressure to 13 kPa, holding the condenser at 100° C., and introducing the raw material solution at the rate of about 1.5 g/min. The amount of reaction liquid recovered in the storage tank 204 was 4025 g. When the reaction liquid was analyzed by liquid chromatography and $^1$H-NMR, the reaction liquid was found to be a composition that contained 4-tert-amyl phenol at a stoichiometric ratio of 6.39 times and di(4-tert-amylphenyl) carbonic acid at a stoichiometric ratio of 0.011 times based on 3-((4-tert-amylphenoxy)carbonylamino-methyl)-3,5,5-trimethylcyclohexyl carbamic acid(4-tert-amylphenyl) ester, and contained 0.040 times an N-containing compound based on the number of 3-((4-tert-amylphenoxy)carbonylamino-methyl)-3,5,5-trimethylcyclohexyl carbamic acid(4-tert-amylphenyl) esters. In addition, the yield of 3-((4-tert-amylphenoxy)carbonylamino-methyl)-3,5,5-trimethylcyclohexyl carbamic acid(4-tert-amylphenyl) ester based on 3-aminomethyl-3,5,5-trimethylcyclohexylamine was about 92%. The amount of ammonia contained in the reaction liquid was 4.9 ppm. On the other hand, when $^1$H-NMR and $^{13}$C-NMR measurements were carried out on the component recovered in the storage tank 205, it was found to be a mixture of 4-tert-amyl phenol and urea, the content of urea was about 236 g (3.94 mol) and the content of 4-tert-amyl phenol was 2231 g (13.6 mol). In addition, a gas containing ammonia discharged from the line 22 provided in the top of the packed column 202 was recovered in a Tedlar bag and injected into a gas chromatograph with a gastight syringe to analyze the gas components. As a result, the amount of ammonia recovered per 10 minutes was 0.42 g (24.9 mmol). In addition, when the gas was analyzed by GC-MS, the amount of carbonyl groups contained in compounds having carbonyl groups contained in the ammonia was 0.01 mmol.

When the step (16-1) was continued to be carried out, clogging of the ammonia discharge line was not observed even after operating time had exceeded 380 days.

Step (16-2): Production of Isocyanate by Thermal Decomposition of N-Substituted Carbamic Acid-O—Ar Ester The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 16 instead of the reaction liquid recovered in the storage tank 105 in Example 5 into the storage tank 801, and supplying to the thin film distillation apparatus via the line 80 at the rate of about 910 g/hr.

A condensate was obtained in the storage tank 812 at the rate of about 106 g/hr, and when the condensate recovered in the storage tank 812 was analyzed by $^1$H-NMR and gas chromatography, it was found to be dicyclohexylmethane diisocyanate containing 1100 ppm of 4-tert-amyl phenol. Discoloration was observed when the isocyanate was stored for 630 days at normal temperatures in a nitrogen atmosphere.

Example 17

Step (17-1): Production of N-Substituted Carbamic Acid-O—Ar Ester 397 g of 4,4'-methylenedianiline, 8250 g of 4-(1,1,3,3-tetramethylbutyl) phenol and 601 g of urea were mixed to prepare a raw material solution. The same method as Example 15 was carried out with the exception of heating the packed column 202 to 260° C., setting the internal pressure to 13 kPa, holding the condenser at 90° C., and introducing the raw material solution at the rate of about 1.3 g/min. The amount of reaction liquid recovered in the storage tank 204 was 4025 g. When the reaction liquid was analyzed by liquid chromatography and $^1$H-NMR, the reaction liquid was found to be a composition that contained 4-(1,1,3,3-tetramethylbutyl) phenol at a stoichiometric ratio of 12.2 times and di(4-(1,1,3,3-tetramethylbutyl)phenyl) carbonic acid at a stoichiometric ratio of 0.0083 times based on N,N'-(4,4'-methanediyl-diphenyl)-di(carbamic acid(4-(1,1,3,3-tetramethylbutyl)phenyl) ester, and contained 0.046 times an N-containing compound based on the number of N,N'-(4,4'-methanediyl-diphenyl)-di(carbamic acid(4-(1,1,3,3-tetramethylbutyl)phenyl) esters. In addition, the yield of N,N'-(4,4'-methanediyl-diphenyl)-di(carbamic acid(4-(1,1,3,3-tetramethylbutyl)phenyl) ester based on 4,4'-methylenedianiline was about 91%. On the other hand, when $^1$H-NMR and $^{13}$C-NMR measurements were carried out on the component recovered in the storage tank 205, it was found to be a mixture of 4-(1,1,3,3-tetramethylbutyl) phenol and urea, the content of urea was about 402 g (6.70 mol) and the content of 4-(1,1,3,3-tetramethylbutyl) phenol was 2887 g (14.0 mol). In addition, a gas containing ammonia discharged from the line 22 provided in the top of the packed column 202 was recovered in a Tedlar bag and injected into a gas chromatograph with a gastight syringe to analyze the gas components. As a result, the amount of ammonia recovered per 10 minutes was 0.24 g (14.2 mmol). In addition, when the gas was analyzed by GC-MS, the amount of carbonyl groups contained in compounds having carbonyl groups contained in the ammonia was 5.68 mmol.

When the step (17-1) was continued to be carried out, the line 5 clogged after 202 days.

Step (17-2): Production of Isocyanate by Thermal Decomposition of N-Substituted Carbamic Acid-O—Ar Ester The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 17 instead of the reaction liquid recovered in the storage tank 105 in Example 5 into the storage tank 801, and supplying to the thin film distillation apparatus via the line 80 at the rate of about 1480 g/hr.

A condensate was obtained in the storage tank 812 at the rate of about 92 g/hr, and when the condensate recovered in the storage tank 812 was analyzed by $^1$H-NMR and gas chromatography, it was found to be diphenylmethane diisocyanate containing 40 ppm of 4-(1,1,3,3-tetramethylbutyl) phenol. Although the isocyanate was stored for 630 days at normal temperatures in a nitrogen atmosphere, discoloration was not observed.

Example 18

Step (18-1): Production of (p-Heptylphenyl) Carbamate

The same method as step (6-1) of Example 6 was carried out with the exception of using 14629 g of p-heptyl phenol instead of 4-phenyl phenol, using 959 g of urea and carrying out the reaction for 17 hours. When a portion of the reaction liquid was removed and analyzed by liquid chromatography, the formation of (p-heptylphenyl) carbamate was confirmed. The yield was about 78% based on the charged amount of urea.

Step (18-2): Production of N-Substituted Carbamic Acid-O—Ar Ester 442 g of hexamethylenediamine were added to the solution obtained in step (18-1) followed by stirring to obtain a raw material solution. The same method as Example 15 was carried out with the exception of using this raw material solution, heating the packed column 202 to 220° C., setting the internal pressure to about 10 kPa, holding the condenser at 60° C. and introducing the raw material solution at the rate of about 1.5 g/min. 8953 g of reaction liquid were recovered in the storage tank 204. When the reaction liquid was analyzed by liquid chromatography and $^1$H-NMR, the reaction liquid was found to be a composition that contained p-heptyl phenol at a stoichiometric ratio of 10.9 times and di(p-heptylphenyl) carbonate at a stoichiometric ratio of 0.0076 times based on N,N'-hexanediyl-di(carbamic acid(p-heptylphenyl) ester), and contained 0.310 times an N-containing compound based on the number of N,N'-hexanediyl-di(carbamic acid(p-heptylphenyl) esters). In addition, the yield of N,N'-hexanediyl-di(carbamic acid(p-heptylphenyl) ester) based on hexamethylenediamine was about 86%. The amount of ammonia contained in the reaction liquid was 9.7 ppm. On the other hand, when $^1$H-NMR and $^{13}$C-NMR measurements were carried out on the component recovered in the storage tank 205, it was found to be a mixture of p-heptyl phenol and urea, the content of urea was about 147 g (2.46 mol), and the content of p-heptyl phenol was 4036 g (21.0 mol). In addition, a gas containing ammonia discharged from the line 22 provided in the top of the storage tank 205 was recovered in a Tedlar bag and injected into a gas chromatograph with a gastight syringe to analyze the gas components. As a result, the amount of ammonia recovered per 10 minutes was 0.12 g (7.3 mmol). When the gas was analyzed by GC-MS, the amount of carbonyl groups contained in compounds having carbonyl groups contained in the ammonia was 0.66 mmol.

When the steps (18-1) and (18-2) were continued to be carried out, the line 5 clogged after 298 days.

Example 19

Step (19-1): Production of (p-Heptylphenyl) Carbamate

Figure 23:
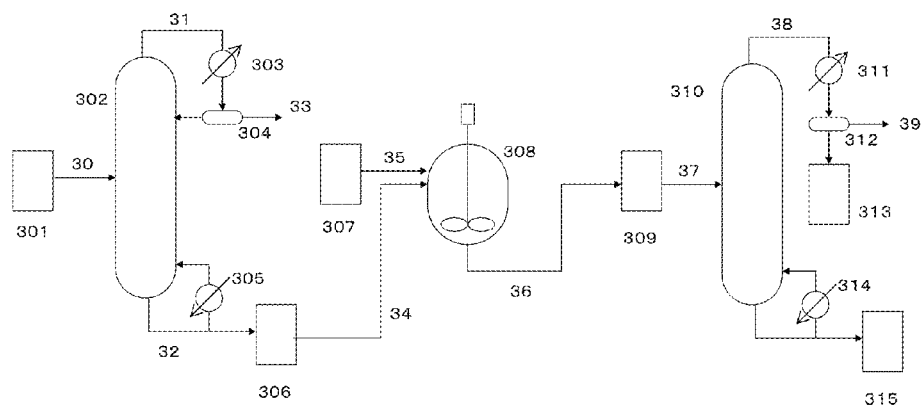
FIG. 23 shows a conceptual drawing depicting an N-substituted carbamic acid ester production apparatus used in an example of the present embodiment.

The apparatus shown in FIG. 23 was used.

A mixed liquid of 3.29 kg of urea and 54.2 kg of p-heptyl phenol was charged into a storage tank 401. A packed column 302 packed with a packing (Helipack No. 3), having an inner diameter of 20 mm and having a height of 1500 mm was heated to 150° C. and the pressure inside the column was set to 50 kPa. The mixture of urea and p-heptyl phenol was fed from the storage tank 401 to the packed column 302, and the reaction liquid was recovered in a storage tank 306 through a line 32 provided in the bottom of the packed column 302. A gaseous phase component was introduced into a condenser 303 through a line 31 from the top of the packed column 302, the condensate was refluxed to a packed column 402, and gaseous ammonia was recovered from a line 43. When the reactant recovered in the storage tank 306 was analyzed by liquid chromatography, the reactant was found to be a mixture containing 22.8% by weight of (p-heptylphenyl) carbamate.

Step (19-2): Production of Compound Having Ureido Groups

The apparatus shown in FIG. 23 was continued to be used.

The mixture in the storage tank 306 was charged into a stirring tank 308 heated to 120° C. with a line 36 closed. While stirring the stirring tank 308, 1.82 kg of hexamethylenediamine were supplied from a storage tank 307 to the stirring tank 308 through a line 35 at the rate of about 20 g/min. After finishing supplying the hexamethylenediamine, stirring was carried out for about 2 hours followed by sampling the reaction liquid. As a result of analyzing the reaction liquid by liquid chromatography, the reaction liquid was found to contain 5.3% by weight of 1,6-hexanebisurea.

The line 36 was then opened and the reaction liquid was transferred to a storage tank 309 through the line 36.

Step (19-3): Production of N-Substituted Carbamic Acid-O—Ar Ester

The apparatus shown in FIG. 23 was continued to be used.
A packed column 310 packed with a packing (Helipack No. 3), having an inner diameter of 40 mm and having a height of 4000 mm was heated to 240° C., the pressure inside the column was set to 26 kPa, and the reaction liquid obtained in step (19-2) was fed at the rate of about 2.0 g/min from a line 37 provided in the packed column 310. Since the reaction is initially in an unsteady state, the sample at that time was discarded. The amount of reaction liquid after the reaction had reached a steady state was about 55.5 kg. The reaction liquid was recovered in a storage tank 315 through a line 320 provided in the bottom of the packed column 310. A gaseous phase component was condensed from a line 38 provided in the top of the packed column 310 with a condenser 311 held at about 85° C., and the resulting liquid phase component was recovered in a storage tank 313 via a gas-liquid separator 312. The amount of reaction liquid recovered in the storage tank 313 was about 12.0 kg. When reaction liquid recovered in the storage tank 315 was analyzed by liquid chromatography and $^1$H-NMR, the reaction liquid was found to be a composition that contained p-heptyl phenol at a stoichiometric ratio of 13.8 times and di(p-heptylphenyl) carbonate at a stoichiometric ratio of 0.0021 times based on N,N'-hexanediyl-di(carbamic acid(p-heptylphenyl) ester), and contained 0.0089 times an N-containing compound based on the number of N,N'-hexanediyl-di(carbamic acid(p-heptylphenyl) esters). In addition, the yield of N,N'-hexanediyl-di(carbamic acid-bis(p-heptylphenyl) based on hexamethylenediamine was about 97%. The amount of ammonia contained in the reaction liquid was 6.7 ppm. On the other hand, when $^1$H-NMR and $^{13}$C-NMR measurements were carried out on the component recovered in the storage tank 313, it was found to be a mixture of p-heptyl phenol, urea and p-(heptylphenyl) carbamate, the content of p-heptyl phenol was 6.82 kg (35.5 mol), the content of urea was about 108 g (1.80 mol), and the content of (p-heptylphenyl) carbamate was 5.13 kg (21.8 mol).

A gas containing ammonia discharged from the gas-liquid separator 312 via a line 39 was recovered in a Tedlar bag and injected into a gas chromatograph with a gastight syringe to analyze the gas components. As a result, the amount of ammonia recovered per 10 minutes was 0.176 g (10.3 mmol). When the gas was analyzed by GC-MS, the amount of carbonyl groups contained in compounds having carbonyl groups contained in the ammonia was 2.06 mmol.

When the steps (19-1) to (19-3) were continued to be carried out, the line 5 clogged after 241 days.

Step (19-4): Production of N-Substituted Carbamic Acid-O—Ar Ester by Reusing Mixture Obtained in Condenser The ammonia concentration of the mixture recovered in the storage tank 313 in step (19-3) was 120 ppm. 2.65 kg of p-heptyl phenol and 0.64 kg of urea were added to the mixture and the same method as step (19-1) was carried out. 1.12 kg of hexamethylenediamine were added to the reaction liquid followed by carrying out the same method as step (19-2) to obtain a solution containing 5.35% by weight of hexamethylenebisurea. The same method as step (19-3) was carried out using this solution instead of the solution of step (19-2). The reaction liquid recovered in the storage tank 315 contained N,N'-hexanediyl-di(carbamic acid(p-heptylphenyl) ester), and the yield of N,N'-hexanediyl-di(carbamic acid(p-heptylphenyl) ester) based on hexamethylenediamine was about 97%.

Step (19-5): Production of Isocyanate by Thermal Decomposition of N-Substituted Carbamic Acid-O—Ar Ester The same method as Example 1 was carried out with the exception of heating the thin film distillation apparatus 702 to 220° C., setting the pressure within the thin film distillation apparatus to about 1.3 kPa, and supplying the reaction liquid recovered in the storage tank 105 in Example 19 instead of the reaction liquid recovered in storage tank 105 in Example 1 to the thin film distillation apparatus at the rate of about 1770 g/hr.

A condensate was obtained in the storage tank 707 at the rate of about 104 g/hr, and when the condensate recovered in the storage tank 707 was analyzed by $^1$H-NMR and gas chromatography, it was found to be hexamethylene diisocyanate containing 210 ppm of 4-heptyl phenol. Although the isocyanate was stored for 630 days at normal temperatures in a nitrogen atmosphere, discoloration was not observed.

Example 20

Step (20-1): Production of (4-cumylphenyl) Carbamate

The apparatus shown in FIG. 23 was used.
The same method as step (19-1) of Example 19 was used with the exception of using 41.9 kg of 4-cumyl phenol instead of p-heptyl phenol and using 1.85 kg of urea. When the reactant recovered in the storage tank 306 was analyzed by liquid chromatography, the reactant was found to be a mixture containing 18.2% by weight of (4-cumylphenyl) carbamate.

Step (20-2): Production of Compound Having Ureido Groups

The same method as step (19-2) of Example 19 was carried out with the exception of using the mixture obtained in step (20-2) instead of the mixture obtained in step (19-1), and supplying 2.10 kg of 3-aminomethyl-3,5,5-trimethylcyclohexylamine instead of hexamethylenediamine at the rate of about 17 g/min.

As a result of analyzing the reaction liquid by liquid chromatography, it was found to contain 6.8% by weight of 3-(ureidomethyl)-3,5,5-trimethylcyclohexylurea.

Step (20-3): Production of N-Substituted Carbamic Acid-O—Ar Ester

The same method as step (19-3) was carried out with the exception of heating the packed column 310 to 240° C., setting the internal pressure to 26 kPa, holding the condenser at 120° C., and feeding the reaction liquid obtained in step (20-2) instead of the reaction liquid obtained in step (19-2) at the rate of about 2.2 g/min. The amount of reaction liquid fed after the reaction had reached a steady state was about 34.6 kg. The amount of reaction liquid recovered in the storage tank 315 was 38.4 kg. When reaction liquid recovered in the storage tank 315 was analyzed by liquid chromatography and $^1$H-NMR, the reaction liquid was found to be a composition that contained 3-((4-cumylphenoxy)carbonylamino-methyl)-3,5,5-trimethylcyclohexyl carbamic acid(4-cumylphenyl) ester, and 4-cumyl phenol at a stoichiometric ratio of 11.9 times and di(4-heptylphenyl) carbonate at a stoichiometric ratio of 0.0015 times based on 3-((4-cumylphenoxy)carbonylamino-methyl)-3,5,5-trimethylcyclohexyl carbamic acid (4-cumylphenyl) ester, and contained 0.010 times an N-containing compound based on the number of 3-((4-cumylphenoxy)carbonylamino-methyl)-3,5,5-trimethylcyclohexyl carbamic acid(4-cumylphenyl) esters. In addition, the yield of 3-((4-cumylphenoxy)carbonylamino-methyl)-3,5,5-trimethylcyclohexyl carbamic acid(4-cumylphenyl) ester based on 3-aminomethyl-3,5,5-trimethylcyclohexylurea was about 96%. The amount of ammonia contained in the reaction liquid was 5.7 ppm. On the other hand, when $^1$H-NMR and $^{13}$C-NMR measurements were carried out on the component recovered in the storage tank 313, it was found to be a mixture of 4-cumyl phenol, urea and (4-cumylphenyl) carbamate, the content of 4-cumyl phenol was 5.73 kg (27.0 mol), the content of urea was about 32 g (0.54 mol), and the content of (4-cumylphenyl) carbamate was 1.50 kg (5.91 mol).

A gas containing ammonia discharged from the gas-liquid separator 312 via the line 39 was recovered in a Tedlar bag and injected into a gas chromatograph with a gastight syringe to analyze the gas components. As a result, the amount of ammonia recovered per 10 minutes was 0.180 g (10.6 mmol). When the gas was analyzed by GC-MS, the amount of carbonyl groups contained in compounds having carbonyl groups contained in the ammonia was 0.0985 mmol.

When the steps (20-1) to (20-3) were continued to be carried out, clogging of the ammonia discharge line was not observed even after operating time had exceeded 380 days.

Step (20-4): Production of N-Substituted Carbamic Acid-O—Ar Ester by Reusing Mixture Obtained in Condenser The mixture recovered in the storage tank 313 in step (20-3) contained 1900 ppm of ammonia. The same method as step (20-1) was carried out with the exception of adding 36.2 kg of 4-cumyl phenol and 1.50 kg of urea to the mixture to obtain a solution containing (4-cumylphenyl) carbamate. The same method as step (20-2) was carried out by adding the mixture recovered in the storage tank 313 in step (20-3) to the solution followed and further adding 2.10 kg of 3-aminomethyl-3,5,5-trimethylcyclohexylamine to obtain a solution containing 5.3% by weight of 3-(ureidomethyl)-3,5,5-trimethylcyclohexylurea. The same method as step (19-3) was carried out using this solution instead of the solution of step (19-2). The reaction liquid recovered in the storage tank 315 contained 3-((4-cumylphenoxy)carbonylamino-methyl)-3,5,5-trimethylcyclohexyl carbamic acid(4-cumylphenyl) ester, and the yield of 3-((4-cumylphenoxy)carbonylamino-methyl)-3,5,5-trimethylcyclohexyl carbamic acid(4-cumylphenyl) ester based on 3-aminomethyl-3,5,5-trimethylcyclohexylamine was about 97%.

Step (20-5): Production of Isocyanate by Thermal Decomposition of N-Substituted Carbamic Acid-O—Ar Ester The same method as Example 1 was carried out with the exception of heating the thin film distillation apparatus 702 to 220° C., setting the pressure within the thin film distillation apparatus to about 1.3 kPa, and supplying the reaction liquid recovered in the storage tank 105 in Example 20 instead of the reaction liquid recovered in storage tank 105 in Example 1 to the thin film distillation apparatus at the rate of about 1430 g/hr.

A condensate was obtained in the storage tank 707 at the rate of about 87 g/hr, and when the condensate recovered in the storage tank 707 was analyzed by $^1$H-NMR and gas chromatography, it was found to be isophorone diisocyanate containing 90 ppm of 4-cumyl phenol. Although the isocyanate was stored for 630 days at normal temperatures in a nitrogen atmosphere, discoloration was not observed.

Example 21

Step (21-1): Production of (4-dodecylphenyl) Carbamate

The apparatus shown in FIG. 23 was used.

The same method as step (19-1) of Example 19 was used with the exception of using 44.0 kg of p-dodecyl phenol instead of 4-heptyl phenol and using 1.57 kg of urea. When the reactant recovered in the storage tank 306 was analyzed by liquid chromatography, the reactant was found to be a mixture containing 17.7% by weight of (p-dodecylphenyl) carbamate.

Step (21-2): Production of Compound Having Ureido Groups

The same method as step (19-2) of Example 19 was carried out with the exception of using the mixture obtained in step (21-1) instead of the mixture obtained in step (19-1), and supplying 1.28 kg of 2,4-toluenediamine instead of hexamethylenediamine at the rate of about 12 g/min.

As a result of analyzing the reaction liquid by liquid chromatography, it was found to contain 4.2% by weight of 2,4-toluenediamine.

Step (21-3): Production of N-Substituted Carbamic Acid-O—Ar Ester

The same method as step (19-3) was carried out with the exception of heating the packed column 310 to 210° C., setting the internal pressure to 33 kPa, holding the condenser at 60° C., and feeding the reaction liquid obtained in step (21-2) instead of the reaction liquid obtained in step (19-2) at the rate of about 2.5 g/min. The amount of reaction liquid fed after the reaction had reached a steady state was 31.4 kg. The amount of reaction liquid recovered in the storage tank 315 was 37.0 kg. When reaction liquid recovered in the storage tank 315 was analyzed by liquid chromatography and $^1$H-NMR, the reaction liquid was found to be a composition that contained toluene-2,4-di(carbamic acid (p-dodecylphenyl) ester), and p-dodecyl phenol at a stoichiometric ratio of 14.7 times and di(p-dodecylphenyl) carbonate at a stoichiometric ratio of 0.0005 times based on toluene-2,4-di(carbamic acid (p-dodecylphenyl) ester), and contained 0.020 times an N-containing compound based on the number of toluene-2,4-di(carbamic acid (p-dodecylphenyl) esters). In addition, the yield of toluene-2,4-di(carbamic acid (p-dodecylphenyl) ester) based on 2,4-toluenediamine was about 81%. The amount of ammonia contained in the reaction liquid was 5.9 ppm. On the other hand, when $^1$H-NMR and $^{13}$C-NMR measurements were carried out on the component recovered in the storage tank 313, it was found to be a mixture of 4-dodecyl phenol, urea and (p-dodecylphenyl) carbamate, the content of 4-dodecyl phenol was 7.57 kg (28.9 mol), the content of urea was about 67.5 g (1.12 mol), and the content of (p-dodecylphenyl) carbamate was 1.89 kg (6.20 mol).

A gas containing ammonia discharged from the gas-liquid separator 312 via the line 39 was recovered in a Tedlar bag and injected into a gas chromatograph with a gastight syringe to analyze the gas components. As a result, the amount of ammonia recovered per 10 minutes was 0.138 g (8.10 mmol). In addition, when the gas was analyzed by GC-MS, the amount of carbonyl groups contained in compounds having carbonyl groups contained in the ammonia was 0.0024 mmol.

When the steps (21-1) to (21-3) were continued to be carried out, clogging of the ammonia discharge line was not observed even after operating time had exceeded 380 days.

Step (21-4): Production of N-Substituted Carbamic Acid-O—Ar Ester by Reusing Mixture Obtained in Condenser The ammonia concentration of the mixture recovered in the storage tank 313 in step (21-3) was 2200 ppm. The same method as step (21-1) was carried out by adding 37.2 kg of p-dodecyl phenol and 1.16 kg of urea to the mixture. 1.30 kg of 2,4-toluenediamine were added to the resulting reaction liquid followed by carrying out the same method as step (21-2) to obtain a solution containing 4.2% by weight of 2,4-toluenediurea. The same method as step (21-3) was carried out by using this solution instead of the solution of step (21-2). The reaction liquid recovered in the storage tank 315 contained toluene-2,4-dicarbamic acid di(p-dodecylphenyl) ester, and the yield of 2,4-toluene-di(carbamic acid(p-dodecylphenyl) ester) based on 2,4-toluenediamine was about 73%.

Step (21-5): Production of Isocyanate by Thermal Decomposition of N-Substituted Carbamic Acid-O—Ar Ester The same method as Example 1 was carried out with the exception of heating the thin film distillation apparatus 702 to 220° C., setting the pressure within the thin film distillation apparatus to about 1.3 kPa, and supplying the reaction liquid recovered in the storage tank 105 in Example 21 instead of the reaction liquid recovered in storage tank 105 in Example 1 to the thin film distillation apparatus at the rate of about 2350 g/hr.

A condensate was obtained in the storage tank 707 at the rate of about 68 g/hr, and when the condensate recovered in the storage tank 707 was analyzed by $^1$H-NMR and gas chromatography, it was found to be 2,4-tolylene diisocyanate containing 25 ppm of p-dodecyl phenol. Although the isocyanate was stored for 630 days at normal temperatures in a nitrogen atmosphere, discoloration was not observed.

Although the above-mentioned steps (21-1) to (21-3) were repeated five times, clogging of the line 39 did not occur.

Example 22

Step (22-1): Production of (4-dodecylphenyl) Carbamate

The apparatus shown in FIG. 23 was used.

The same method as step (19-1) of Example 19 was used with the exception of using 161.8 kg of 4-(1,1,3,3-tetramethylbutyl) phenol instead of 4-heptyl phenol and using 1.29 kg of urea. When the reactant recovered in the storage tank 306 was analyzed by liquid chromatography, the reactant was found to be a mixture containing 1.90% by weight of (4-(1,1,3,3-tetramethylbutyl)phenyl) carbamate.

Step (22-2): Production of Compound Having Ureido Groups

The same method as step (19-2) of Example 19 was carried out with the exception of using the mixture obtained in step (22-1) instead of the mixture obtained in step (19-1), and supplying 1.42 kg of 4,4'-methylenedianiline instead of hexamethylenediamine at the rate of about 17 g/min.

As a result of analyzing the reaction liquid by liquid chromatography, it was found to contain 0.64% by weight of 4,4'-methanediyl-diphenylurea.

Step (22-3): Production of N-Substituted Carbamic Acid-O—Ar Ester

The same method as step (19-3) was carried out with the exception of heating the packed column 310 to 210° C., setting the internal pressure to 33 kPa, holding the condenser at 90° C., and feeding the reaction liquid obtained in step (22-2) instead of the reaction liquid obtained in step (19-2) at the rate of about 25 g/min. The amount of reaction liquid fed after the reaction had reached a steady state was about 65.2 kg. The amount of reaction liquid recovered in the storage tank 315 was 51.1 kg. When reaction liquid recovered in the storage tank 315 was analyzed by liquid chromatography and $^1$H-NMR, the reaction liquid was found to be a composition that contained N,N'-(4,4'-methanediyl-diphenyl)-di(carbamic acid(4-(1,1,3,3-tetramethylbutyl)phenyl) ester), and 4-(1,1,3,3-tetramethylbutyl) phenol at a stoichiometric ratio of 210 times and di(4-(1,1,3,3-tetramethylbutyl)phenyl carbonate at a stoichiometric ratio of 0.0011 times based on N,N'-(4,4'-methanediyl-diphenyl)-di(carbamic acid(4-(1,1,3,3-tetramethylbutyl)phenyl) ester), and contained 0.013 times an N-containing compound based on the number of N,N'-(4,4'-methanediyl-diphenyl)-di(carbamic acid(4-(1,1,3,3-tetramethylbutyl) esters). In addition, the yield of N,N'-(4,4'-methanediyl-diphenyl)-di(carbamic acid(4-(1,1,3,3-tetramethylbutyl)phenyl) ester) based on 4,4'-methylenedianiline was about 79%. On the other hand, when $^1$H-NMR and $^{13}$C-NMR measurements were carried out on the component recovered in the storage tank 313, it was found to be a mixture of 4-(1,1,3,3-tetramethylbutyl) phenol, urea and (4-(1,1,3,3-tetramethylbutyl)phenyl) carbamate, the content of 4-(1,1,3,3-tetramethylbutyl) phenol was 13.5 kg (65.6 mol), the content of urea was about 61.5 g (1.02 mol), and the content of (4-(1,1,3,3-tetramethylbutyl)phenyl) carbamate was 1.91 kg (7.68 mol).

A gas containing ammonia discharged from the gas-liquid separator 312 via the line 39 was recovered in a Tedlar bag and injected into a gas chromatograph with a gastight syringe to analyze the gas components. As a result, the amount of ammonia recovered per 10 minutes was 0.068 g (4.02 mmol). In addition, when the gas was analyzed by GC-MS, the amount of carbonyl groups contained in compounds having carbonyl groups contained in the ammonia was 0.0624 mmol.

When the steps (22-1) to (22-3) were continued to be carried out, clogging of the ammonia discharge line was not observed even after operating time had exceeded 380 days.

Step (22-4): Production of N-Substituted Carbamic Acid-O—Ar Ester by Reusing Mixture Obtained in Condenser The ammonia concentration of the mixture recovered in the storage tank 313 in step (22-3) was 33 ppm. The same method as step (22-1) was carried out by adding 148.9 kg of 4-(1,1, 3,3-tetramethylbutyl) phenol and 0.27 kg of urea to the mixture. 1.29 kg of 4,4'-methylenedianiline were added to the resulting reaction liquid followed by carrying out the same method as step (22-2) to obtain a solution containing 0.064% by weight of 4,4'-methanediylphenylurea. The same method as step (22-3) was carried out by using this solution instead of the solution of step (22-2). The reaction liquid recovered in the storage tank 315 contained N,N'-(4,4'-methanediyl-diphenyl)-biscarbamic acid di(4-(1,1,3,3-tetramethylbutyl) phenyl) ester, and the yield of N,N'-(4,4'-methanediyl-diphenyl)-biscarbamic acid di(4-(1,1,3,3-tetramethylbutyl) phenyl)ester based on 4,4'-methylenedianiline was about 80%.

Step (22-5): Production of Isocyanate by Thermal Decomposition of N-Substituted Carbamic Acid-O—Ar Ester The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 22 instead of the reaction liquid recovered in storage tank 105 in Example 5 to the storage tank 801, and supplying to the thin film distillation apparatus via the line 80 at the rate of about 6500 g/hr.

A condensate was obtained in the storage tank 812 at the rate of about 17 g/hr, and when the condensate recovered in the storage tank 812 was analyzed by $^1$H-NMR and gas chromatography, it was found to be diphenylmethane diisocyanate containing 160 ppm of 4-(1,1,3,3-tetramethylbutyl) phenol. Although the isocyanate was stored for 630 days at normal temperatures in a nitrogen atmosphere, discoloration was not observed.

Example 23

Step (23-1): Production of (4-dodecylphenyl) Carbamate

The apparatus shown in FIG. 23 was used.

The same method as step (19-1) of Example 19 was used with the exception of using 43.3 kg of 4-ethyl phenol instead of 4-heptyl phenol and using 2.13 kg of urea. When the reactant recovered in the storage tank 306 was analyzed by liquid chromatography, the reactant was found to be a mixture containing 13.0% by weight of (4-ethylphenyl) carbamate.

Step (23-2): Production of Compound Having Ureido Groups

The same method as step (19-2) of Example 19 was carried out with the exception of using the mixture obtained in step (23-1) instead of the mixture obtained in step (19-1), and supplying 2.20 kg of aniline instead of hexamethylenediamine at the rate of about 10 g/min.

As a result of analyzing the reaction liquid by liquid chromatography, it was found to contain 8.0% by weight of N-phenylurea.

Step (23-3): Production of N-Substituted Carbamic Acid-O—Ar Ester

The same method as step (19-3) was carried out with the exception of heating the packed column 310 to 220° C., setting the internal pressure to atmospheric pressure (nitrogen atmosphere), holding the condenser at 60° C., and feeding the reaction liquid obtained in step (23-2) instead of the reaction liquid obtained in step (19-2) at the rate of about 1.5 g/min. The amount of reaction liquid fed after the reaction had reached a steady state was about 45.2 kg. The amount of reaction liquid recovered in the storage tank 315 was 29.9 kg. When reaction liquid recovered in the storage tank 315 was analyzed by liquid chromatography and $^1$H-NMR, the reaction liquid was found to be a composition that contained N-phenylcarbamic acid (4-ethylphenyl) ester, and 4-ethyl phenol at a stoichiometric ratio of 11.9 times and di(4-ethylphenyl) carbonate at a stoichiometric ratio of 0.0001 times based on N-phenylcarbamic acid (4-ethylphenyl) ester, and contained 0.0082 times an N-containing compound based on the number of N-phenylcarbamic acid (4-ethylphenyl) esters. In addition, the yield of N-phenylcarbamic acid (4-ethylphenyl) ester based on aniline was about 80%. The reaction liquid contained 6.1 ppm ammonia. On the other hand, when $^1$H-NMR and $^{13}$C-NMR measurements were carried out on the component recovered in the storage tank 313, it was found to be a mixture of 4-ethyl phenol, urea and (4-ethylphenyl) carbamate, the content of 4-ethyl phenol was 13.8 kg (113 mol), the content of urea was about 161 g (2.68 mol), and the content of (4-ethylphenyl) carbamate was 2.06 kg (12.5 mol).

A gas containing ammonia discharged from the gas-liquid separator 312 via the line 39 was recovered in a Tedlar bag and injected into a gas chromatograph with a gastight syringe to analyze the gas components. As a result, the amount of ammonia recovered per 10 minutes was 0.195 g (11.5 mmol). In addition, when the gas was analyzed by GC-MS, the amount of carbonyl groups contained in compounds having carbonyl groups contained in the ammonia was 0.0007 mmol.

When the steps (23-1) to (23-3) were continued to be carried out, clogging of the ammonia discharge line was not observed even after operating time had exceeded 380 days.

Step (23-4): Condensation of N-Substituted Carbamic Acid Mono(—O—Ar Ester)

Figure 30:
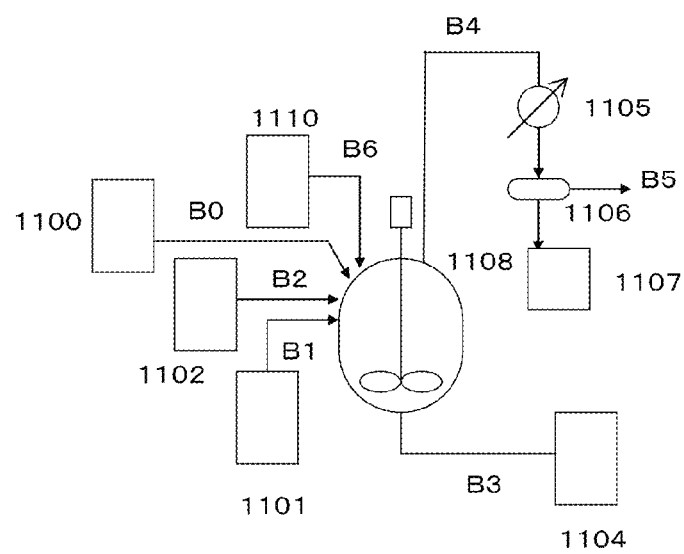
FIG. 30 shows a conceptual drawing of condensation reaction apparatus for an N-substituted carbamic acid monoester used in an example of the present embodiment.

The apparatus shown in FIG. 30 was used.

The reaction liquid recovered in the storage tank 313 in step (23-3) was charged into a stirring tank 1108. The stirring tank 1108 was heated to 160° C. and the internal pressure was set to 2 kPa to remove aromatic hydroxy compounds. An aromatic hydroxy compound in the form of 4-ethyl phenol was condensed in a condenser 1105 via a line B4 and recovered in a storage tank 1107. Next, 1.14 kg of methylal (formaldehyde dimethyl acetal) from a storage tank 1100, 4.70 kg of nitrobenzole from a storage tank 1101 and 5.6 kg of sulfuric acid from a storage tank 1102 were added to the stirring tank 1108 followed by heating for 10 hours at 100° C. while stirring the stirring tank 1108. The inside of the stirring tank 1108 was then maintained at 100° C. and the internal pressure was reduced to 1 kPa to distill off solvent and unreacted substances. When the resulting compound was analyzed by liquid chromatography, it was found to be a mixture containing about 55% by weight of N,N'-(methanediyl-diphenyl)-di(carbamic acid(4-ethylphenyl) ester). About 5.1 kg of 4-tert-amyl phenol were added to this compound to obtain a homogeneous solution, and the solution was transferred to a storage tank 1104.

Step (23-5): Production of Isocyanate by Thermal Decomposition of N-Substituted Carbamic Acid-O-Aryl Ester The apparatus shown in FIG. 29 was used.

A thin film distillation apparatus 1002 (Kobelco Eco-Solutions Co., Ltd., Japan) having a heat-conducting surface area of 0.2 m$^2$ was heated to 260° C. and the pressure within the thin film distillation apparatus was set to about 1.5 kPa. The reaction liquid recovered in the storage tank 1104 in step (23-4) was placed in a storage tank 1001 and supplied to the thin film distillation apparatus at the rate of about 1200 g/hr via a line A1. A liquid component was extracted from a line A2 provided in the bottom of thin film distillation apparatus 1002 and recovered in a storage tank 1003. The liquid component recovered in the storage tank 1003 was again supplied to the thin film distillation apparatus 1002 through a line A3. A gaseous component was extracted from a line A4 provided in the upper portion of the thin film distillation apparatus 1002. The gaseous component was introduced into a distillation column 1004, and low boiling components were separated by distillation. A liquid phase component was supplied to a distillation column 1009 from a line A8 provided at a portion of the distillation column 1004 lower than the feed line and further subjected to distillative separation. The liquid phase component was supplied to a distillation column 1014 from a line A12 provided at a portion of the distillation column 1009 lower than the feed line and further subjected to distillative separation.

A gaseous component was extracted from a line A13 provided in the top of the distillation column 1014 and condensed in a condenser 1015, and the condensate was recovered in a storage tank 1019. When the condensate was analyzed by $^1$H-NMR, it was found to be a solution containing about 99% by weight of 4,4'-diphenylmethane diisocyanate (MDI). The yield based on aniline was about 48%.

Example 24

Step (24-1): Production of (4-nonylphenyl) Carbamate

The apparatus shown in FIG. 23 was used.

The same method as step (19-1) of Example 19 was used with the exception of using 38.3 kg of 4-nonyl phenol instead of p-heptyl phenol and using 2.19 kg of urea. When the reactant recovered in the storage tank 306 was analyzed by liquid chromatography, the reactant was found to be a mixture containing 24.1% by weight of (4-nonylphenyl) carbamate.

Step (24-2): Production of Compound Having Ureido Groups

The same method as step (19-2) of Example 19 was carried out with the exception of using the mixture obtained in step (24-1) instead of the mixture obtained in step (19-1), and supplying 1.83 kg of 4,4'-methylenebis(cyclohexylamine) instead of hexamethylenediamine at the rate of about 12 g/min.

As a result of analyzing the reaction liquid by liquid chromatography, it was found to contain 6.0% by weight of 4,4'-methanediyl-dicyclohexyldiurea.

Step (24-3): Production of N-Substituted Carbamic Acid-O—Ar Ester

The same method as step (19-3) was carried out with the exception of heating the packed column 310 to 250° C., setting the internal pressure to 20 kPa, holding the condenser at 60° C., and feeding the reaction liquid obtained in step (24-2) instead of the reaction liquid obtained in step (19-2) at the rate of about 1.9 g/min. The amount of reaction liquid fed after the reaction had reached a steady state was about 39.8 kg. The amount of reaction liquid recovered in the storage tank 315 was 24.8 kg. When reaction liquid recovered in the storage tank 315 was analyzed by liquid chromatography and $^1$H-NMR, the reaction liquid was found to be a composition that contained N,N'-(4,4'-methanediyl-dicyclohexyl)-di(carbamic acid(4-nonylphenyl) ester), and 4-nonyl phenol at a stoichiometric ratio of 11.6 times and di(4-nonylphenyl) carbonate at a stoichiometric ratio of 0.005 times based on N,N'-(4,4'-methanediyl-dicyclohexyl)-di(carbamic acid(4-nonylphenyl) ester), and contained 0.011 times an N-containing compound based on the number of di(4-nonylphenyl)-4,4'-methylene dicyclohexyl carbamate. In addition, the yield of N,N'-(4,4'-methanediyl-dicyclohexyl)-di(carbamic acid(4-nonylphenyl) ester) based on 4,4'-methylenebis(cyclohexylamine) was about 94%. The reaction liquid contained 9.8 ppm of ammonia.

On the other hand, when $^1$H-NMR and $^{13}$C-NMR measurements were carried out on the component recovered in the storage tank 313, it was found to be a mixture of 4-nonyl phenol, urea and (4-nonylphenyl) carbamate, the content of 4-nonyl phenol was 9.93 kg (45.1 mol), the content of urea was about 70.8 g (1.18 mol), and the content of (4-nonylphenyl) carbamate was 4.69 kg (17.8 mol).

A gas containing ammonia discharged from the gas-liquid separator 312 via the line 39 was recovered in a Tedlar bag and injected into a gas chromatograph with a gastight syringe to analyze the gas components. As a result, the amount of ammonia recovered per 10 minutes was 0.119 g (7.01 mmol). In addition, when the gas was analyzed by GC-MS, the amount of carbonyl groups contained in compounds having carbonyl groups contained in the ammonia was 0.070 mmol.

Step (24-4): Production of Isocyanate by Thermal Decomposition of N-Substituted Carbamic Acid-O—Ar Ester The same method as Example 5 was carried out with the exception of heating the thin film distillation apparatus 802 to 220° C., setting the pressure inside the thin film distillation apparatus to about 1.3 kPa, charging the reaction liquid recovered in the storage tank 105 in Example 24 instead of the reaction liquid recovered in the storage tank 105 in Example 5, and supplying to the thin film distillation apparatus via the line 80 at the rate of about 1330 g/hr.

A condensate was obtained in the storage tank 812 at the rate of about 87 g/hr, and when the condensate recovered in the storage tank 812 was analyzed by $^1$H-NMR and gas chromatography, it was found to be dicyclohexylmethane diisocyanate containing 160 ppm of 4-nonyl phenol.

When the steps (24-1) and (24-2) were continued to be carried out, clogging of the ammonia discharge line was not observed even after operating time had exceeded 380 days.

Example 25

Step (25-1): Production of Compound Having Ureido Groups

Figure 24:
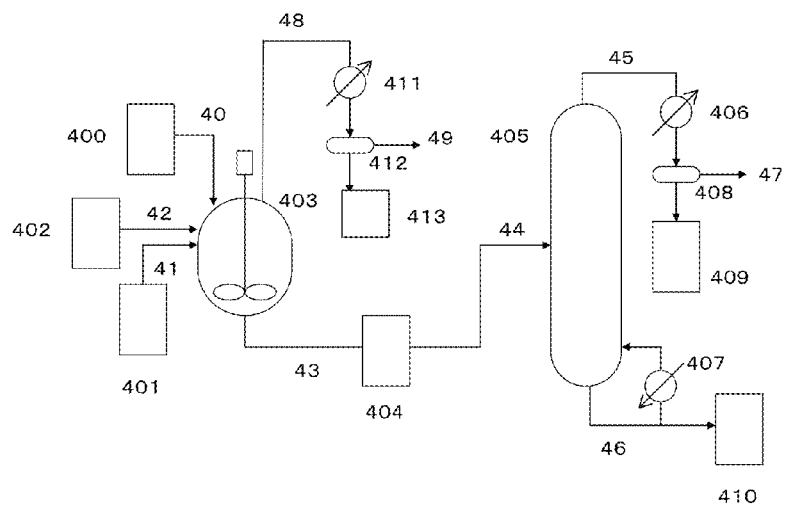
FIG. 24 shows a conceptual drawing of an N-substituted carbamic acid ester production apparatus used in an example of the present embodiment.

The apparatus shown in FIG. 24 was used.

A mixture of 3.00 kg of phenyl carbamate (Wako Pure Chemical Industries, Ltd., Japan) and 15.3 kg of 1-hexanol (Wako Pure Chemical Industries, Ltd., Japan) was fed from a storage tank 400 into a stirring tank 403 with the line 43 and a line 48 closed. The stirring tank 403 was heated to 100° C. and stirring was started. 1.38 kg of 3-aminomethyl-3,5,5-trimethylcyclohexylamine were supplied from the storage tank 401 to the stirring tank 403 through a line 41 at the rate of about 20 g/min. After finishing supplying the 3-aminomethyl-3,5,5-trimethylcyclohexylamine, the reaction liquid was stirred for about 2 hours, and as a result of sampling the reaction liquid and analyzing by liquid chromatography, it was found that 3-(ureidomethyl)-3,5,5-triethylcyclohexylurea had been formed.

Next, 33.3 kg of 4-(1,1,3,3-tetramethylbutyl) phenol were fed from a storage tank 402 to the stirring tank 403. The line 48 was opened to reduce the pressure of the stirring tank 403 to about 6 kPa to distill off 1-hexanol under reduced pressure from a line 49. The distilled 1-hexanol was condensed in a condenser 411 through the line 48 and recovered in a storage tank 413.

Following distillation of the 1-hexanol, the solution in the stirring tank 403 was transferred to a storage tank 404.

Step (25-2): Production of N-Substituted Carbamic Acid-O—Ar Ester

The apparatus shown in FIG. 24 was continued to be used.

A packed column 405 packed with a packing (Helipack No. 3) and having an inner diameter of 40 mm was heated to 240° C., the pressure inside the column was set to 26 kPa, and the condenser was held to 60° C. The reaction liquid obtained in step (25-1) was fed at the rate of about 1.8 g/min from a line 44 provided in the packed column 405. Since the reaction is initially in an unsteady state, the sample at that time was discarded. The amount of reaction liquid after the reaction had reached a steady state was about 32.9 kg. The reaction liquid was recovered in a storage tank 410 through a line 46 provided in the bottom of the packed column 405. A gaseous phase component was condensed from a line 45 provided in the top of the packed column 405 with a condenser 406 held at about 85° C., and the resulting liquid phase component was recovered in a storage tank 409 via a gas-liquid separator 408. The amount of reaction liquid recovered in the storage tank 410 was about 19.9 kg. When reaction liquid recovered in the storage tank 410 was analyzed by liquid chromatography and $^1$H-NMR, the reaction liquid was found to be a composition that contained 3-((4-(1,1,3,3-tetramethylbutyl)phenoxy)carbonylamino-methyl)-3,5,5-trimethylcyclohexyl carbamic acid (4-(1,1,3,3-tetramethylbutyl)phenyl) ester, and 4-(1,1,3,3-tetramethylbutyl) phenol at a stoichiometric ratio of 10.0 times and di(4-(1,1,3,3-tetramethylbutyl)phenyl) carbonate at a stoichiometric ratio of 0.0015 times based on 3-((4-(1,1,3,3-tetramethylbutyl)phenoxy) carbonylamino-methyl)-3,5,5-trimethylcyclohexyl carbamic acid (4-(1,1,3,3-tetramethylbutyl)phenyl) ester, and contained 0.010 times an N-containing compound based on the number of 3-((4-(1,1,3,3-tetramethylbutyl)phenoxy)carbonylamino-methyl)-3,5,5-trimethylcyclohexyl carbamic acid (4-(1,1,3,3-tetramethylbutyl)phenyl) esters. In addition, the yield of 3-((4-(1,1,3,3-tetramethylbutyl)phenoxy)carbonylamino-methyl)-3,5,5-trimethylcyclohexyl carbamic acid (4-(1,1,3,3-tetramethylbutyl)phenyl) ester based on 3-aminomethyl-3,5,5-trimethylcyclohexylamine was about 91%. The amount of ammonia contained in the reaction liquid was 8.2 ppm. On the other hand, when $^1$H-NMR and $^{13}$C-NMR measurements were carried out on the component recovered in the storage tank 409, it was found to be a mixture of 4-(1,1,3,3-tetramethyl butyl) phenol, urea, (4-(1,1,3,3-tetramethylbutyl)phenyl) carbamate and phenyl carbamate, the content of 4-(1,1,3,3-tetramethylbutyl) phenol was 12.7 kg (61.7 mol), the content of urea was about 32.4 g (0.54 mol), the content of (4-(1,1,3,3-tetramethylbutyl)phenyl) carbamate was 0.357 kg (1.43 mol) and the content of phenyl carbamate was 0.337 kg (2.46 mol). A gas containing ammonia discharged from the gas-liquid separator 408 via a line 47 was recovered in a Tedlar bag and injected into a gas chromatograph with a gastight syringe to analyze the gas components. As a result, the amount of ammonia recovered per 10 minutes was 0.121 g (7.10 mmol). When the gas was analyzed by GC-MS, the amount of carbonyl groups contained in compounds having carbonyl groups contained in the ammonia was 0.0030 mmol.

When the steps (25-1) and (25-2) were continued to be carried out, clogging of the ammonia discharge line was not observed even after operating time had exceeded 380 days.

Example 26

Step (26-1): Production of Carbamic Acid Ester

Figure 25:
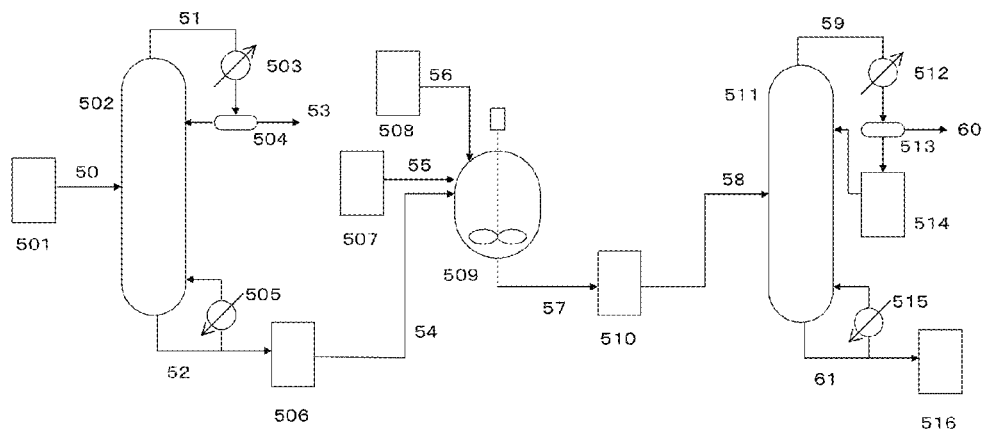
FIG. 25 shows a conceptual drawing of an N-substituted carbamic acid ester production apparatus used in an example of the present embodiment.

The apparatus shown in FIG. 25 was used.

A mixed liquid of 2.84 kg of urea and 48.7 kg of 4-(1,1,3,3-tetramethylbutyl) phenol was charged into a storage tank 501. A packed column 502 packed with a packing (Helipack No. 3) and having an inner diameter of 20 mm was heated to 150° C. and the pressure inside the column was set to 50 kPa. The mixture of urea and 4-(1,1,3,3-tetramethylbutyl) phenol was fed from the storage tank 501 to the packed column 502, and the reaction liquid was recovered in a storage tank 506 through a line 52 provided in the bottom of the packed column 502. A gaseous phase component was introduced into a condenser 503 through a line 51 from the top of the packed column 502, the condensate was refluxed to the packed column 502, and gaseous ammonia was recovered from a line 53. When the reactant recovered in the storage tank 506 was analyzed by liquid chromatography, the reactant was found to be a mixture containing 23.2% by weight of (4-(1,1,3,3-tetramethylbutyl)phenyl) carbamate.

Step (26-2): Production of Compound Having Ureido Groups

The apparatus shown in FIG. 25 was continued to be used.

The mixture in the storage tank 506 was charged into a stirring tank 509 heated to 120° C. with a line 57 closed. 6.34 kg of 2-isopropyl phenol were supplied from a storage tank 508 to the stirring tank 509 through a line 56. While stirring the stirring tank 509, 1.83 kg of hexamethylenediamine were supplied from the storage tank 507 to the stirring tank 509 through a line 55 at the rate of about 20 g/min. After finishing supplying the hexamethylenediamine, stirring was carried out for about 2 hours followed by sampling the reaction liquid. As a result of analyzing the reaction liquid by liquid chromatography, the reaction liquid was found to contain 5.2% by weight of 1,6-hexamethylenediurea.

The line 57 was then opened and the reaction liquid was transferred to a storage tank 510 through the line 57.

Step (26-3): Production of N-Substituted Carbamic Acid-O—Ar Ester

The apparatus shown in FIG. 25 was continued to be used.

A packed column 511 packed with a packing (Helipack No. 3) and having an inner diameter of 40 mm was heated to 240° C., the pressure inside the column was set to 26 kPa, and a condenser was held at 90° C. The reaction liquid obtained in step (26-2) was fed at the rate of about 2.2 g/min from a line 58 provided in the packed column 511. Since the reaction is initially in an unsteady state, the sample at that time was discarded. The amount of reaction liquid fed after the reaction had reached a steady state was about 39.8 kg. The reaction liquid was recovered in a storage tank 516 through a line 61 provided in the bottom of the packed column 511. A gaseous phase component was condensed from a line 59 provided in the top of the packed column 511 with a condenser 513 held at about 85° C., and the resulting liquid phase component was recovered in a storage tank 514 via a gas-liquid separator 513. The amount of reaction liquid recovered in the storage tank 516 was 31.2 kg. When reaction liquid recovered in the storage tank 516 was analyzed by liquid chromatography and $^1$H-NMR, the reaction liquid was found to be a composition that contained N,N'-hexanediyl-di(carbamic acid(4-(1,1,3,3-tetramethylbutyl)phenyl) ester), and 4-(1,1,3,3-tetramethylbutyl) phenol at a stoichiometric ratio of 12.5 times and di(4-(1,1,3,3-tetramethylbutyl)phenyl) carbonate at a stoichiometric ratio of 0.0033 times based on N,N'-hexanediyl-di(carbamic acid(4-(1,1,3,3-tetramethylbutyl)phenyl) ester), and contained 0.0012 times an N-containing compound based on the number of N,N'-hexanediyl-di(carbamic acid(4-(1,1,3,3-tetramethylbutyl)phenyl) esters). In addition, the yield of N,N'-hexanediyl-di(carbamic acid(4-(1,1,3,3-tetramethylbutyl)phenyl) ester) based on hexamethylenediamine was about 94%. The amount of ammonia contained in the reaction liquid was 6.9 ppm. On the other hand, when $^1$H-NMR and $^{13}$C-NMR measurements were carried out on the component recovered in the storage tank 514, it was found to be a mixture of 2-isopropyl phenol, urea and (4-(1,1,3,3-tetramethylbutyl)phenyl carbamate, the content of 2-isopropyl phenol was 3.91 kg (28.7 mol), the content of 4-(1,1,3,3-tetramethylbutyl) phenol was 1.64 kg (7.97 mol), the content of urea was about 52.4 g (0.87 mol), and the content of (4-(1,1,3,3-tetramethylbutyl)phenyl) carbamate was 2.67 kg (10.7 mol).

A gas containing ammonia discharged from the gas-liquid separator 513 via a line 60 was recovered in a Tedlar bag and injected into a gas chromatograph with a gastight syringe to analyze the gas components. As a result, the amount of ammonia recovered per 10 minutes was 0.140 g (8.25 mmol). In addition, when the gas was analyzed by GC-MS, the amount of carbonyl groups contained in compounds having carbonyl groups contained in the ammonia was 0.0032 mmol.

When the steps (26-1) to (26-3) were continued to be carried out, clogging of the ammonia discharge line was not observed even after operating time had exceeded 380 days.

Step (26-4): Production of Isocyanate by Thermal Decomposition of N-Substituted Carbamic Acid-O—Ar Ester Production of isocyanate was carried out using the apparatus shown in FIG. 28.

The thin film distillation apparatus 802 was heated to 220° C. and the pressure within the thin film distillation apparatus was set to about 1.3 kPa. The reaction liquid recovered in the storage tank 105 in Example 26 was placed in the storage tank 801 and supplied to the thin film distillation apparatus at the rate of about 1770 g/hr via the line 80. A liquid component was extracted from the line 82 provided in the bottom of thin film distillation apparatus 802 and recovered in the storage tank 803. The liquid component recovered in the storage tank 803 was again supplied to the thin film distillation apparatus 802 through the line 83. A gaseous component containing hexamethylene diisocyanate, 2-isopropyl phenol and 4-heptyl phenol was extracted from the line 81 provided in the upper portion of the thin film distillation apparatus 802. The gaseous component was introduced into the distillation column 804, the 2-isopropyl phenol was separated by distillation, and a liquid phase was fed to the distillation column 809 through the line 88 provided in a portion of the distillation column 804 lower than the feed portion thereof. A gaseous phase component containing hexamethylene diisocyanate was extracted in the distillation column 809, condensed in the condenser 810, and a portion of the condensate was returned to the distillation column 809. Condensate was obtained in the storage tank 812 at the rate of about 90 g/hr.

When the condensate recovered in the storage tank 812 was analyzed by $^1$H-NMR and gas chromatography, it was found to be hexamethylene diisocyanate containing 90 ppm of 4-heptyl phenol. Although the hexamethylene diisocyanate was stored for 630 days at normal temperatures in a nitrogen atmosphere, discoloration was not observed.

Example 27

Step (27-1): Production of Carbamic Acid Ester

The same method as step (26-1) of Example 26 was carried out with the exception of using 2.26 kg of urea and 41.1 kg of 4-cumyl phenol instead of 4-(1,1,3,3-tetramethylbutyl) phenol. When the reactant recovered in the storage tank 506 was analyzed by liquid chromatography, the reactant was found to be a mixture that contained 22.5% by weight of (4-cumylphenyl) carbamate.

Step (27-2): Production of Compound Having Ureido Groups

The same method as step (26-2) of Example 26 was carried out with the exception of using the reaction liquid obtained in step (27-1) instead of the reaction liquid obtained in step (26-1), using 8.82 kg of 2-tert-amyl phenol instead of 2-isopropyl phenol, and supplying 1.84 kg of 3-aminomethyl-3,5,5-trimethylcyclohexylamine instead of hexamethylenediamine at the rate of about 21 g/min. After finishing supplying the 3-aminomethyl-3,5,5-trimethylcyclohexylamine, stirring was carried out for about 3 hours followed by sampling of the reaction liquid. When the reaction liquid was analyzed by liquid chromatography, it was found to contain 5.1% by weight of 3-(ureidomethyl)-3,5,5-trimethylcyclohexylurea.

The line 57 was then opened and the reaction liquid was transferred to the storage tank 510 through the line 57.

Step (27-3): Production of N-Substituted Carbamic Acid-O—Ar Ester

The same method as step (26-3) of Example 26 was carried out with the exception of heating the packed column 511 to 240° C., setting the internal pressure to 26 kPa, holding the condenser at 60° C., and feeding the reaction liquid obtained in step (27-2) instead of the reaction liquid obtained in step (26-2) at the rate of about 1.9 g/min. Since the reaction is initially in an unsteady state, the sample at that time was discarded. The amount of reaction liquid fed after the reaction had reached a steady state was about 51.1 kg. The amount of reaction liquid recovered in the storage tank 516 was 38.1 kg. When the reaction liquid recovered in the storage tank 516 was analyzed by liquid chromatography and $^1$H-NMR, the reaction liquid was found to be a composition that contained 3-((4-cumylphenoxy)carbonylamino-methyl)-3,5,5-trimethylcyclohexyl carbamic acid (4-cumylphenyl) ester, and 4-cumyl phenol at a stoichiometric ratio of 15.3 times and di(4-cumylphenyl) carbonate at a stoichiometric ratio of 0.0024 times based on 3-((4-cumylphenoxy)carbonylamino-methyl)-3,5,5-trimethylcyclohexyl carbamic acid (4-cumylphenyl) ester, and contained 0.0010 times an N-containing compound based on the number of 3-((4-cumylphenoxy)carbonylamino-methyl)-3,5,5-trimethylcyclohexyl carbamic acid (4-cumylphenyl) esters. In addition, the yield of 3-((4-cumylphenoxy)carbonylamino-methyl)-3,5,5-trimethylcyclohexyl carbamic acid (4-cumylphenyl) ester based on 3-aminomethyl-3,5,5-trimethylcyclohexylamine was about 95%. The amount of ammonia contained in the reaction liquid was 4.9 ppm. On the other hand, when $^1$H-NMR and $^{13}$C-NMR measurements were carried out on the component recovered in the storage tank 514, it was found to be a mixture of 2-tert-amyl phenol, 4-cumyl phenol, urea and (4-cumylphenyl) carbamate, the content of 2-tert-amyl phenol was 8.20 kg (49.9 mol), the content of 4-cumyl phenol was 0.526 kg (2.48 mol), the content of urea was about 62.3 g (1.04 mol), and the content of (4-cumylphenyl) carbamate was 3.79 kg (14.8 mol).

A gas containing ammonia discharged from the gas-liquid separator 513 via the line 60 was recovered in a Tedlar bag and injected into a gas chromatograph with a gastight syringe to analyze the gas components. As a result, the amount of ammonia recovered per 10 minutes was 0.141 g (8.31 mmol). In addition, when the gas was analyzed by GC-MS, the amount of carbonyl groups contained in compounds having carbonyl groups contained in the ammonia was 0.0025 mmol.

When the steps (27-1) to (27-3) were continued to be carried out, clogging of the ammonia discharge line was not observed even after operating time had exceeded 380 days.

Step (27-4): Production of N-Substituted Carbamic Acid-O—Ar Ester by Reusing Mixture Obtained in Condenser The ammonia concentration in the mixture recovered in the storage tank 514 in step (27-3) was 2900 ppm. The same method as step (27-1) was carried out by adding 37.6 kg of 4-cumyl phenol and 1.14 kg of urea to the mixture. The same method as step (27-2) was carried out by adding 1.70 kg of 3-aminomethyl-3,5,5-trimethylcyclohexylamine to the resulting reaction liquid to obtain a solution containing 5.1% by weight of isophorone bisurea. The same method as step (27-3) was carried out using this solution instead of the solution of step (27-2). The reaction liquid recovered in the storage tank 516 contained 3-((4-cumylphenoxy)carbonylamino-methyl)-3,5,5-trimethylcyclohexyl carbamic acid (4-cumylphenyl) ester, and the yield of 3-((4-cumylphenoxy)carbonylamino-methyl)-3,5,5-trimethylcyclohexyl carbamic acid (4-cumylphenyl) ester based on 3-aminomethyl-3,5,5-trimethylcyclohexylamine was about 64%.

Step (27-5): Production of Isocyanate by Thermal Decomposition of N-Substituted Carbamic Acid-O—Ar Ester Production of isocyanate was carried out using the apparatus shown in FIG. 28.

The thin film distillation apparatus 802 was heated to 220° C. and the pressure within the thin film distillation apparatus was set to about 1.3 kPa. The reaction liquid recovered in the storage tank 516 in Example 27 was placed in the storage tank 801 and supplied to the thin film distillation apparatus at the rate of about 1830 g/hr via the line 80. A liquid component was extracted from the line 82 provided in the bottom of thin film distillation apparatus 802 and recovered in the storage tank 803. The liquid component recovered in the storage tank 803 was again supplied to the thin film distillation apparatus 802 through the line 83. A gaseous component containing isophorone diisocyanate, 2-tert-amyl phenol and 4-cumyl phenol was extracted from the line 81 provided in the upper portion of the thin film distillation apparatus 802. The gaseous component was introduced into the distillation column 804, the 2-tert-amyl phenol was separated by distillation, and a liquid phase was fed to the distillation column 809 through the line 88 provided in a portion of the distillation column 804 lower than the feed portion thereof. A gaseous phase component containing isophorone diisocyanate was extracted in the distillation column 809, condensed in the condenser 810, and a portion of the condensate was returned to the distillation column 809. Condensate was obtained in the storage tank 812 at the rate of about 90 g/hr.

When the condensate recovered in the storage tank 812 was analyzed by $^1$H-NMR and gas chromatography, it was found to be isophorone diisocyanate containing 1 ppm of 4-cumyl phenol. Although the hexamethylene diisocyanate was stored for 630 days at normal temperatures in a nitrogen atmosphere, discoloration was not observed.

Example 28

Step (28-1): Production of Carbamic Acid Ester

The same method as step (26-1) of Example 26 was carried out with the exception of using 2.67 kg of urea and 42.7 kg of p-heptyl phenol instead of 4-(1,1,3,3-tetramethylbutyl) phenol. When the reactant recovered in the storage tank 506 was analyzed by liquid chromatography, the reactant was found to be a mixture containing 23.4% by weight of (p-heptylphenyl) carbamate.

Step (28-2): Production of Compound Having Ureido Groups

The same method as step (26-2) of Example 26 was carried out with the exception of using the reaction liquid obtained in step (28-1) instead of the reaction liquid obtained in step (26-1), using 19.8 kg of 2,6-diisopropyl phenol instead of 2-isopropyl phenol, and supplying 2.20 kg of 4,4'-methylenedianiline instead of hexamethylenediamine at the rate of about 15 g/min. After finishing supplying the 4,4'-methylenedianiline, stirring was carried out for about 1 hour followed by sampling of the reaction liquid. When the reaction liquid was analyzed by liquid chromatography, it was found to contain 4.4% by weight of 4,4'-diphenylmethanebisurea.

The line 57 was then opened and the reaction liquid was transferred to the storage tank 510 through the line 57.

Step (28-3): Production of N-Substituted Carbamic Acid-O—Ar Ester

The same method as step (26-3) of Example 26 was carried out with the exception of heating the packed column 511 to 240° C., setting the internal pressure to 26 kPa, holding the condenser at 60° C., and feeding the reaction liquid obtained in step (28-2) instead of the reaction liquid obtained in step (26-2) at the rate of about 3.5 g/min. Since the reaction is initially in an unsteady state, the sample at that time was discarded. The amount of reaction liquid fed after the reaction had reached a steady state was about 63.4 kg. The amount of reaction liquid recovered in the storage tank 516 was 38.9 kg. When the reaction liquid recovered in the storage tank 516 was analyzed by liquid chromatography and $^1$H-NMR, the reaction liquid was found to be a composition that contained N,N'-(4,4'-methanediyl-diphenyl)-di(carbamic acid (4-heptylphenyl) ester), and 4-heptyl phenol at a stoichiometric ratio of 21.0 times, 2,6-diisopropyl phenol at a stoichiometric ratio of 0.39 times, and di(p-heptylphenyl) carbonate at a stoichiometric ratio of 0.0007 times based on N,N'-(4,4'-methanediyl-diphenyl)-di(carbamic acid (4-heptylphenyl) ester), and contained 0.0092 times an N-containing compound based on the number of N,N'-(4,4'-methanediyl-diphenyl)-di(carbamic acid (4-heptylphenyl) esters). In addition, the yield of N,N'-(4,4'-methanediyl-diphenyl)-di(carbamic acid (4-heptylphenyl) ester) based on 4,4'-methylenedianiline was about 83%. The amount of ammonia contained in the reaction liquid was 7.6 ppm. On the other hand, when $^1$H-NMR and $^{13}$C-NMR measurements were carried out on the component recovered in the storage tank 514, it was found to be a mixture of 2,6-diisopropyl phenol, p-heptyl phenol, urea and (p-heptylphenyl) carbamate, the content of 2,6-diisopropyl phenol was 18.3 kg (103 mol), the content of p-heptyl phenol was 0.582 kg (3.03 mol), the content of urea was about 118 g (1.97 mol), and the content of (p-heptylphenyl) carbamate was 5.10 kg (21.7 mol).

A gas containing ammonia discharged from the gas-liquid separator 513 via the line 60 was recovered in a Tedlar bag and injected into a gas chromatograph with a gastight syringe to analyze the gas components. As a result, the amount of ammonia recovered per 10 minutes was 0.157 g (9.25 mmol). In addition, when the gas was analyzed by GC-MS, the amount of carbonyl groups contained in compounds having carbonyl groups contained in the ammonia was 0.0009 mmol.

When the steps (28-1) to (28-3) were continued to be carried out, clogging of the ammonia discharge line was not observed even after operating time had exceeded 380 days.

Step (28-4): Production of Isocyanate by Thermal Decomposition of N-Substituted Carbamic Acid-O—Ar Ester The apparatus shown in FIG. 29 was used.

The thin film distillation apparatus 1002 was heated to 220° C. and the pressure within the thin film distillation apparatus was set to about 1.3 kPa. The reaction liquid recovered in the storage tank 105 in Example 28 was placed in the storage tank 1001 and supplied to the thin film distillation apparatus at the rate of about 2140 g/hr via the line A1. A liquid component was extracted from the line A2 provided in the bottom of thin film distillation apparatus 1002 and recovered in the storage tank 1003. The liquid component recovered in the storage tank 1003 was again supplied to the thin film distillation apparatus 1002 through the line A3. A gaseous component containing diphenylmethane diisocyanate, 2,6-diisopropyl phenol and p-heptyl phenol was extracted from the line A4 provided in the upper portion of the thin film distillation apparatus 1002. The gaseous component was introduced into the distillation column 1004, the 2,6-diisopropyl phenol was separated by distillation, and a liquid phase was fed to the distillation column 1009 through the line A8 provided in a portion of the distillation column 1004 lower than the feed portion thereof. The p-heptyl phenol was separated by distillation in the distillation column 1009, and a liquid phase was fed to the distillation column 1014 through the line A12 provided at a portion of the distillation column 1009 lower than the feed portion thereof. A gaseous phase component containing diphenylmethane diisocyanate was extracted in the distillation column 1014, condensed in the condenser 1015, and a portion of the condensate was returned to the distillation column 1014. Condensate was obtained in the storage tank 1019 at the rate of about 92 g/hr.

When the condensate recovered in the storage tank 812 was analyzed by $^1$H-NMR and gas chromatography, it was found to be diphenylmethane diisocyanate containing 190 ppm of p-heptyl phenol.

Example 29

Step (29-1): Production of Carbamic Acid Ester

The same method as step (26-1) of Example 26 was carried out with the exception of using 2.39 kg of urea and 23.7 kg of 4-phenyl phenol instead of 4-(1,1,3,3-tetramethylbutyl) phenol. When the reactant recovered in the storage tank 506 was analyzed by liquid chromatography, the reactant was found to be a mixture containing 33.5% by weight of (4-phenylphenyl) carbamate.

Step (29-2): Production of Compound Having Ureido Groups

The same method as step (26-2) of Example 26 was carried out with the exception of using the reaction liquid obtained in step (29-1) instead of the reaction liquid obtained in step (26-1), using 5.74 kg of 2,4-di-tert-butyl phenol instead of 2-isopropyl phenol, and supplying 1.95 kg of 4,4'-methylenebis(cyclohexylamine) instead of hexamethylenediamine at the rate of about 20 g/min. After finishing supplying the 4,4'-methylenebis(cyclohexylamine), stirring was carried out for about 2 hours followed by sampling of the reaction liquid. When the reaction liquid was analyzed by liquid chromatography, it was found to contain 7.89% by weight of 4,4'-methanediyldicyclohexylurea.

The line 57 was then opened and the reaction liquid was transferred to the storage tank 510 through the line 57.

Step (29-3): Production of N-Substituted Carbamic Acid-O—Ar Ester

The same method as step (26-3) of Example 26 was carried out with the exception of heating the packed column 511 to 240° C., setting the internal pressure to 26 kPa, holding the condenser at 60° C., and feeding the reaction liquid obtained in step (29-2) instead of the reaction liquid obtained in step (26-2) at the rate of about 1.7 g/min. Since the reaction is initially in an unsteady state, the sample at that time was discarded. The amount of reaction liquid fed after the reaction had reached a steady state was about 30.5 kg. The amount of reaction liquid recovered in the storage tank 516 was 38.9 kg. When the reaction liquid recovered in the storage tank 516 was analyzed by liquid chromatography and $^1$H-NMR, the reaction liquid was found to be a composition that contained N,N'-(4,4'-methanediyl-diphenyl)-di(carbamic acid (4-phenylphenyl) ester), and 4-phenyl phenol at a stoichiometric ratio of 12.5 times, 2,4-di-tert-butyl phenol at a stoichiometric ratio of 0.11 times, and di(4-phenylphenyl) carbonate at a stoichiometric ratio of 0.0010 times based on N,N'-(4,4'-methanediyl-diphenyl)-di(carbamic acid (4-phenylphenyl) ester), and contained 0.011 times an N-containing compound based on the number of N,N'-(4,4'-methanediyl-diphenyl)-di(carbamic acid (4-phenylphenyl) esters). In addition, the yield of N,N'-(4,4'-methanediyl-diphenyl)-di(carbamic acid (4-phenylphenyl) ester) based on 4,4'-methylenebis(cyclohexylamine) was about 90%. The amount of ammonia contained in the reaction liquid was 9.1 ppm. On the other hand, when $^1$H-NMR and $^{13}$C-NMR measurements were carried out on the component recovered in the storage tank 514, it was found to be a mixture of 2,4-di-tert-butyl phenol, 4-phenyl phenol, urea and (4-phenylphenyl) carbamate, the content of 2,4-di-tert-butyl phenol was 5.13 kg (24.9 mol), the content of 4-phenyl phenol was 0.358 kg (2.10 mol), the content of urea was about 86 g (1.43 mol), and the content of (4-phenylphenyl) carbamate was 4.16 kg (19.5 mol).

A gas containing ammonia discharged from the gas-liquid separator 513 via the line 60 was recovered in a Tedlar bag and injected into a gas chromatograph with a gastight syringe to analyze the gas components. As a result, the amount of ammonia recovered per 10 minutes was 0.132 g (7.77 mmol). In addition, when the gas was analyzed by GC-MS, the amount of carbonyl groups contained in compounds having carbonyl groups contained in the ammonia was 5.44 mmol.

When the steps (29-1) to (29-3) were continued to be carried out, the ammonia discharge line became clogged when operating time had exceeded 183 days.

Step (29-4): Production of N-Substituted Carbamic Acid-O—Ar Ester by Reusing Mixture Obtained in Condenser The ammonia concentration in the mixture recovered in the storage tank 514 in step (29-3) was 21 ppm. The same method as step (29-1) was carried out by adding 42.1 kg of 4-phenyl phenol and 1.39 kg of urea to the mixture. The same method as step (29-2) was carried out by adding 1.90 kg of 4,4'-methylenebis(cyclohexylamine) to the resulting reaction liquid to obtain a solution containing 5.1% by weight of 4,4'-methanediyldicyclohexyldiurea. The same method as step (29-3) was carried out using this solution instead of the solution of step (29-2). The reaction liquid recovered in the storage tank 516 contained N,N'-(4,4'-methanediyl-diphenyl)-di(carbamic acid (4-phenylphenyl) ester), and the yield of N,N'-(4,4'-methanediyl-diphenyl)-di(carbamic acid (4-phenylphenyl) ester) based on 4,4'-methylenebis(cyclohexylamine) was about 80%.

Step (29-5): Production of Isocyanate by Thermal Decomposition of N-Substituted Carbamic Acid-O—Ar Ester The apparatus shown in FIG. 29 was used.
The thin film distillation apparatus 1002 was heated to 220° C. and the pressure within the thin film distillation apparatus was set to about 1.3 kPa. The reaction liquid recovered in the storage tank 105 in Example 29 was placed in the storage tank 1001 and supplied to the thin film distillation apparatus at the rate of about 1370 g/hr via the line A1. A liquid component was extracted from the line A2 provided in the bottom of thin film distillation apparatus 1002 and recovered in the storage tank 1003. The liquid component recovered in the storage tank 1003 was again supplied to the thin film distillation apparatus 1002 through the line A3. A gaseous component containing dicyclohexylmethane diisocyanate, 2,4-di-tert-butyl phenol and 4-phenyl phenol was extracted from the line A4 provided in the upper portion of the thin film distillation apparatus 1002. The gaseous component was introduced into the distillation column 1004, the 2,4-di-tert-butyl phenol was separated by distillation, and a liquid phase was fed to the distillation column 1009 through the line A8 provided in a portion of the distillation column 1004 lower than the feed portion thereof. The 4-phenyl phenol was separated by distillation in the distillation column 1009, and a liquid phase was fed to the distillation column 1014 through the line A12 provided at a portion of the distillation column 1009 lower than the feed portion thereof. A gaseous phase component containing diphenylmethane diisocyanate was extracted in the distillation column 1014, condensed in the condenser 1015, and a portion of the condensate was returned to the distillation column 1014. Condensate was obtained in the storage tank 1019 at the rate of about 115 g/hr.

When the condensate recovered in the storage tank 1019 was analyzed by $^1$H-NMR and gas chromatography, it was found to be dicyclohexylmethane diisocyanate containing 230 ppm of 4-phenyl phenol. Although the isocyanate was stored for 630 days at normal temperatures in a nitrogen atmosphere, discoloration was not observed.

Example 30

Step (30-1): Production of N-Substituted Carbamic Acid-O—Ar Ester

The same method as Example 1 was carried out with the exception of mixing 2.28 kg of hexamethylenediamine, 75.5 kg of p-heptyl phenol, 13.4 kg of 2-isopropyl phenol and 4.71 g of urea to obtain a raw material solution, heating the packed column 102 to 240° C., setting the internal pressure to 26 kPa, holding the condenser at 60° C., and introducing the raw material solution at the rate of about 1.0 g/min. The amount of reaction liquid recovered in the storage tank 105 was 77.6 kg. When the reaction liquid was analyzed by liquid chromatography and $^1$H-NMR, the reaction liquid was found to be a composition that contained N,N'-hexanediyl-di(carbamic acid) (p-heptylphenyl) ester), p-heptyl phenol at a stoichiometric ratio of 19.0 times, 2-isopropyl phenol at a stoichiometric ratio of 0.109 times and di(p-heptylphenyl) carbonate at a stoichiometric ratio of 0.0022 times based on N,N'-hexanediyl-di(carbamic acid(p-heptylphenyl) ester), and contained 0.008 times an N-containing compound based on the number of N,N'-hexanediyl-di(carbamic acid(p-heptylphenyl) esters). In addition, the yield of N,N'-hexanediyl-di(carbamic acid(p-heptylphenyl) ester) based on hexamethylenediamine was about 92%. The amount of ammonia contained in the reaction liquid was 9.5 ppm. On the other hand, when $^1$H-NMR and $^{13}$C-NMR measurements were carried out on the component recovered in the storage tank 104, it was found to be a mixture of 2-isopropyl phenol, p-heptyl phenol, urea and (p-heptylphenyl) carbamate, the content of 2-isopropyl phenol was 13.1 kg (96.1 mol), the content of p-heptyl phenol was 2.26 kg (11.7 mol), the content of urea was about 2.66 g (44.4 mol), and the content of (p-heptylphenyl) carbamate was 171 g (0.91 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.16 g (9.6 mmol). In addition, when the gas was analyzed by GC-MS, the amount of carbonyl groups contained in compounds having carbonyl groups contained in the ammonia was 0.480 mmol.

When the step (30-1) was continued to be carried out, the line 5 became clogged when operating time had exceeded 309 days.

Step (30-2): Production of N-Substituted Carbamic Acid-O—Ar Ester by Reusing Mixture Obtained in Condenser The ammonia concentration in the mixture recovered in the storage tank 104 in step (30-1) was 40 ppm. The same method as step (30-1) was carried out by adding 73.2 kg of 4-heptyl phenol, 1.99 kg of urea and 2.28 kg of hexamethylenediamine to the mixture to obtain a raw material solution. The amount of reaction liquid recovered in the storage tank 105 was 77.6 kg. The reaction liquid contained N,N'-hexanediyl-dicarbamic acid-bis(4-heptylphenyl), and the yield of N,N'-hexanediyl-dicarbamic acid-bis(4-heptylphenyl) based on hexamethylenediamine was about 86%.

Step (30-3): Production of Isocyanate by Thermal Decomposition of N-Substituted Carbamic Acid-O—Ar Ester Production of isocyanate was carried out by using the apparatus shown in FIG. 27.

The thin film distillation apparatus 802 was heated to 220° C. and the pressure within the thin film distillation apparatus was set to about 1.3 kPa. The reaction liquid recovered in the storage tank 105 in Example 30 was placed in the storage tank 801 and supplied to the thin film distillation apparatus at the rate of about 2430 g/hr via the line 80. A liquid component was extracted from the line 82 provided in the bottom of thin film distillation apparatus 802 and recovered in the storage tank 803. The liquid component recovered in the storage tank 803 was again supplied to the thin film distillation apparatus 802 through the line 83. A gaseous component containing hexamethylene diisocyanate, 2-isopropyl phenol and 4-heptyl phenol was extracted from the line 81 provided in the upper portion of the thin film distillation apparatus 802. The gaseous component was introduced into the distillation column 804, the 2-isopropyl phenol was separated by distillation, and a liquid phase was fed to the distillation column 809 through the line 88 provided in a portion of the distillation column 804 lower than the feed portion thereof. A gaseous phase component containing hexamethylene diisocyanate was extracted in the distillation column 809, condensed in the condenser 810, and a portion of the condensate was returned to the distillation column 809. Condensate was obtained in the storage tank 812 at the rate of about 90 g/hr.

When the condensate recovered in the storage tank 812 was analyzed by $^1$H-NMR and gas chromatography, it was found to be hexamethylene diisocyanate containing 89 ppm of 4-heptyl phenol. Although the isocyanate was stored for 630 days at normal temperatures in a nitrogen atmosphere, discoloration was not observed.

Example 31

Step (31-1): Production of N-Substituted Carbamic Acid-O—Ar Ester

The same method as Example 1 was carried out with the exception of mixing 2.32 kg of 3-aminomethyl-3,5,5-trimethylcyclohexylamine, 35.8 kg of p-dodecyl phenol, 12.1 kg of 2,6-diisopropyl phenol and 3.27 g of urea to obtain a raw material solution, heating the packed column 102 to 270° C., setting the internal pressure to 74 kPa, holding the condenser at 60° C., and introducing the raw material solution at the rate of about 1.2 g/min. The amount of reaction liquid recovered in the storage tank 105 was 40.1 kg. When the reaction liquid was analyzed by liquid chromatography and $^1$H-NMR, the reaction liquid was found to be a composition that contained 3-((p-dodecylphenoxy)carbonylamino-methyl)-3,5,5-trimethylcyclohexylcarbamic acid (p-dodecylphenyl) ester, and p-dodecyl phenol at a stoichiometric ratio of 8.4 times, 2,6-diisopropyl phenol at a stoichiometric ratio of 0.968 times and di(p-dodecylphenyl) carbonate at a stoichiometric ratio of 0.0001 times based on 3-((p-dodecylphenoxy)carbonylamino-methyl)-3,5,5-trimethylcyclohexylcarbamic acid (p-dodecylphenyl) ester, and contained 0.0001 times an N-containing compound based on the number of 3-((p-dodecylphenoxy)carbonylamino-methyl)-3,5,5-trimethylcyclohexylcarbamic acid (p-dodecylphenyl) ester. In addition, the yield of 3-((p-dodecylphenoxy)carbonylamino-methyl)-3,5,5-trimethylcyclohexylcarbamic acid (p-dodecylphenyl) ester based on 3-aminomethyl-3,5,5-trimethylcyclohexylamine was about 93%. The amount of ammonia contained in the reaction liquid was 8.8 ppm. On the other hand, when $^1$H-NMR and $^{13}$C-NMR measurements were carried out on the component recovered in the storage tank 104, it was found to be a mixture of 2,6-diisopropyl phenol, p-dodecyl phenol, urea and (p-dodecylphenyl) carbamate, the content of 2,6-diisopropyl phenol was 9.96 kg (55.9 mol), the content of p-dodecyl phenol was 1.07 kg (4.09 mol), the content of urea was about 1.82 kg (30.3 mol), and the content of (p-dodecylphenyl) carbamate was 162 g (0.62 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.209 g (12.3 mmol). In addition, when the gas was analyzed by GC-MS, the amount of carbonyl groups contained in compounds having carbonyl groups contained in the ammonia was 9.84 mmol.

When the step (31-1) was continued to be carried out, the line 5 became clogged when operating time had exceeded 171 days.

Step (31-2): Production of N-Substituted Carbamic Acid-O—Ar Ester by Reusing Mixture Obtained in Condenser The ammonia concentration in the mixture recovered in the storage tank 104 in step (31-1) was 4500 ppm. The same method as step (31-1) was carried out by adding 28.4 kg of p-dodecyl phenol, 0.84 kg of urea and 1.91 kg of 3-aminomethyl-3,5,5-trimethylcyclohexylamine to the mixture to obtain a raw material solution. The amount of reaction liquid recovered in the storage tank 105 was 33.0 kg. The reaction liquid contained 3-((p-dodecylphenoxy)carbonylamino-methyl)-3,5,5-trimethylcyclohexylcarbamic acid (p-dodecylphenyl) ester, and the yield of 3-((p-dodecylphenoxy)carbonylamino-methyl)-3,5,5-trimethylcyclohexylcarbamic acid (p-dodecylphenyl) ester based on 3-aminomethyl-3,5,5-trimethylcyclohexylamine was about 72%.

Step (31-3): Production of Isocyanate by Thermal Decomposition of N-Substituted Carbamic Acid-O—Ar Ester Production of isocyanate was carried out by using the apparatus shown in FIG. 27.

The thin film distillation apparatus 802 was heated to 220° C. and the pressure within the thin film distillation apparatus was set to about 1.3 kPa. The reaction liquid recovered in the storage tank 105 in Example 31 was placed in the storage tank 801 and supplied to the thin film distillation apparatus at the rate of about 1220 g/hr via the line 80. A liquid component was extracted from the line 82 provided in the bottom of thin film distillation apparatus 802 and recovered in the storage tank 803. The liquid component recovered in the storage tank 803 was again supplied to the thin film distillation apparatus 802 through the line 83. A gaseous component containing isophorone diisocyanate, 2,6-diisopropyl phenol and p-dodecyl phenol was extracted from the line 81 provided in the upper portion of the thin film distillation apparatus 802. The gaseous component was introduced into the distillation column 804, the 2,6-diisopropyl phenol was separated by distillation, and a liquid phase was fed to the distillation column 809 through the line 88 provided in a portion of the distillation column 804 lower than the feed portion thereof. A gaseous phase component containing isophorone diisocyanate was extracted in the distillation column 809, condensed in the condenser 810, and a portion of the condensate was returned to the distillation column 809. Condensate was obtained in the storage tank 812 at the rate of about 81 g/hr.

When the condensate recovered in the storage tank 812 was analyzed by $^1$H-NMR and gas chromatography, it was found to be isophorone diisocyanate containing 53 ppm of p-dodecyl phenol. Although the isocyanate was stored for 630 days at normal temperatures in a nitrogen atmosphere, discoloration was not observed.

Example 32

Step (32-1): Production of N-Substituted Carbamic Acid-O—Ar Ester

The same method as Example 1 was carried out with the exception of mixing 1.22 kg of 2,4-toluenediamine, 21.2 kg of 4-cumyl phenol, 7.50 kg of 2-tert-butyl phenol and 1.56 kg of urea to obtain a raw material solution, heating the packed column 102 to 240° C., setting the internal pressure to atmospheric pressure (nitrogen atmosphere), and introducing the raw material solution at the rate of about 1.3 g/min. The amount of reaction liquid recovered in the storage tank 105 was 23.6 kg. When the reaction liquid was analyzed by liquid chromatography and $^1$H-NMR, the reaction liquid was found to be a composition that contained toluene-2,4-di(carbamic acid(2-tert-butylphenyl) ester), and 4-cumyl phenol at a stoichiometric ratio of 9.8 times, 2-tert-butyl phenol at a stoichiometric ratio of 1.10 times and di(4-cumylphenyl) carbonate at a stoichiometric ratio of 0.0009 times based on toluene-2,4-di(carbamic acid(2-tert-butylphenyl) ester), and contained 0.022 times an N-containing compound based on the number of toluene-2,4-di(carbamic acid(2-tert-butylphenyl) esters). In addition, the yield of toluene-2,4-di(carbamic acid(2-tert-butylphenyl) ester) based on 2,4-toluenediamine was about 82%. The amount of ammonia contained in the reaction liquid was 7.5 ppm. On the other hand, when $^1$H-NMR and $^{13}$C-NMR measurements were carried out on the component recovered in the storage tank 104, it was found to be a mixture of 2,4-toluenediamine phenol, 4-cumyl phenol, urea and (4-cumylphenyl) carbamate, the content of 2-tert-butyl phenol was 6.15 kg (40.9 mol), the content of 4-cumyl phenol was 0.636 kg (3.00 mol), the content of urea was about 0.738 kg (12.3 mol), and the content of (4-cumylphenyl) carbamate was 53.2 g (0.25 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.251 g (14.8 mmol). In addition, when the gas was analyzed by GC-MS, the amount of carbonyl groups contained in compounds having carbonyl groups contained in the ammonia was 1.33 mmol.

When the step (32-1) was continued to be carried out, the line 5 became clogged when operating time had exceeded 301 days.

Step (32-2): Production of N-Substituted Carbamic Acid-O—Ar Ester by Reusing Mixture Obtained in Condenser The ammonia concentration in the mixture recovered in the storage tank 104 in step (32-1) was 63 ppm. The same method as step (32-1) was carried out by adding 19.9 kg of 4-cumyl phenol, 0.76 kg of urea and 1.18 kg of 2,4-toluenediamine to the mixture to obtain a raw material solution. The amount of reaction liquid recovered in the storage tank 105 was 33.0 kg. The reaction liquid contained toluene-2,4-di(carbamic acid (2-tert-butylphenyl) ester), and the yield of toluene-2,4-di (carbamic acid (2-tert-butylphenyl) ester) based on 2,4-toluenediamine was about 94%.

Step (32-3): Production of Isocyanate by Thermal Decomposition of N-Substituted Carbamic Acid-O—Ar Ester Production of isocyanate was carried out by using the apparatus shown in FIG. 27.

The thin film distillation apparatus 802 was heated to 220° C. and the pressure within the thin film distillation apparatus was set to about 1.3 kPa. The reaction liquid recovered in the storage tank 105 in Example 32 was placed in the storage tank 801 and supplied to the thin film distillation apparatus at the rate of about 2190 g/hr via the line 80. A liquid component was extracted from the line 82 provided in the bottom of thin film distillation apparatus 802 and recovered in the storage tank 803. The liquid component recovered in the storage tank 803 was again supplied to the thin film distillation apparatus 802 through the line 83. A gaseous component containing 2,4-tolylene diisocyanate, 2-tert-butyl phenol and 4-cumyl phenol was extracted from the line 81 provided in the upper portion of the thin film distillation apparatus 802. The gaseous component was introduced into the distillation column 804, the 2-tert-butyl phenol was separated by distillation, and a liquid phase was fed to the distillation column 809 through the line 88 provided in a portion of the distillation column 804 lower than the feed portion thereof. A gaseous phase component containing 2,4-tolylene diisocyanate was extracted in the distillation column 809, condensed in the condenser 810, and a portion of the condensate was returned to the distillation column 809. Condensate was obtained in the storage tank 812 at the rate of about 115 g/hr.

When the condensate recovered in the storage tank 812 was analyzed by $^1$H-NMR and gas chromatography, it was found to be 2,4-tolylene diisocyanate containing 80 ppm of 4-cumyl phenol. Although the isocyanate was stored for 630 days at normal temperatures in a nitrogen atmosphere, discoloration was not observed.

Example 33

Step (33-1): Production of N-Substituted Carbamic Acid-O—Ar Ester

The same method as Example 1 was carried out with the exception of mixing 1.76 kg of 4,4'-methylenedianiline, 15.1 kg of 4-phenyl phenol, 4.37 kg of 2-tert-amyl phenol and 1.33 kg of urea to obtain a raw material solution, heating the packed column 102 to 260° C., setting the internal pressure to 52 kPa, holding the condenser at 60° C., and introducing the raw material solution at the rate of about 2.0 g/min. The amount of reaction liquid recovered in the storage tank 105 was 17.6 kg. When the reaction liquid was analyzed by liquid chromatography and $^1$H-NMR, the reaction liquid was found to be a composition that contained N,N'-4,4'-methanediyl-diphenyl)-di(carbamic acid (4-phenylphenyl) ester), and 4-phenyl phenol at a stoichiometric ratio of 9.8 times, 2-tert-amyl phenol at a stoichiometric ratio of 0.659 times and di(4-phenylphenyl) carbonate at a stoichiometric ratio of 0.0011 times based on N,N'-4,4'-methanediyl-diphenyl)-di(carbamic acid (4-phenylphenyl) ester), and contained 0.0039 times an N-containing compound based on the number of N,N'-4,4'-methanediyl-diphenyl)-di(carbamic acid (4-phenylphenyl) esters). In addition, the yield of N,N'-4,4'-methanediyl-diphenyl)-di(carbamic acid (4-phenylphenyl) ester) based on 4,4'-methylenedianiline was about 82%. The amount of ammonia contained in the reaction liquid was 4.6 ppm. On the other hand, when $^1$H-NMR and $^{13}$C-NMR measurements were carried out on the component recovered in the storage tank 104, it was found to be a mixture of 2-tert-amyl phenol, 4-phenyl phenol, urea and (4-phenylphenyl) carbamate, the content of 2-tert-amyl phenol was 3.59 kg (21.7 mol), the content of 4-phenyl phenol was 0.453 kg (2.66 mol), the content of urea was about 0.603 kg (10.0 mol), and the content of (4-phenylphenyl) carbamate was 34.9 g (0.21 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.479 g (21.2 mmol). In addition, when the gas was analyzed by GC-MS, the amount of carbonyl groups contained in compounds having carbonyl groups contained in the ammonia was 4.24 mmol.

When the steps (33-1) was continued to be carried out, the line 5 became clogged when operating time had exceeded 254 days.

Step (33-2): Production of N-Substituted Carbamic Acid-O—Ar Ester by Reusing Mixture Obtained in Condenser The ammonia concentration in the mixture recovered in the storage tank 104 in step (33-1) was 710 ppm. The same method as step (33-1) was carried out by adding 11.9 kg of 4-phenyl phenol, 0.47 kg of urea and 1.44 kg of 4,4'-methylenedianiline to the mixture to obtain a raw material solution. The amount of reaction liquid recovered in the storage tank 105 was 14.4 kg. The reaction liquid contained N,N'-4,4'-methanediyl-diphenyl)-di(carbamic acid (4-phenylphenyl) ester), and the yield of N,N'-4,4'-methanediyl-diphenyl)-di(carbamic acid (4-phenylphenyl) ester) based on 4,4'-methylenedianiline was about 93%.

Step (33-3): Production of Isocyanate by Thermal Decomposition of N-Substituted Carbamic Acid-O—Ar Ester Production of isocyanate was carried out by using the apparatus shown in FIG. 29.

The thin film distillation apparatus 1002 was heated to 220° C. and the pressure within the thin film distillation apparatus was set to about 1.3 kPa. The reaction liquid recovered in the storage tank 105 in Example 33 was placed in the storage tank 1001 and supplied to the thin film distillation apparatus at the rate of about 1140 g/hr via the line A1. A liquid component was extracted from the line A2 provided in the bottom of thin film distillation apparatus 1002 and recovered in the storage tank 1003. The liquid component recovered in the storage tank 1003 was again supplied to the thin film distillation apparatus 1002 through the line A3. A gaseous component containing diphenylmethane diisocyanate, 2-tert-amyl phenol and 4-phenyl phenol was extracted from the line A4 provided in the upper portion of the thin film distillation apparatus 1002. The gaseous component was introduced into the distillation column 1004, the 2-tert-amyl phenol was separated by distillation, and a liquid phase was fed to the distillation column 1009 through the line A8 provided in a portion of the distillation column 1004 lower than the feed portion thereof. The 4-phenyl phenol was separated by distillation in the distillation column 1009, and a liquid phase was fed to the distillation column 1014 through the line A12 provided in a portion of the distillation column 1009 lower than the feed portion thereof. A gaseous phase component containing diphenylmethane diisocyanate was extracted in the distillation column 1014, condensed in the condenser 1015, and a portion of the condensate was returned to the distillation column 1014. Condensate was obtained in the storage tank 1019 at the rate of about 100 g/hr.

When the condensate recovered in the storage tank 1019 was analyzed by $^1$H-NMR and gas chromatography, it was found to be diphenylmethane diisocyanate containing 110 ppm of 4-phenyl phenol. Although the isocyanate was stored for 630 days at normal temperatures in a nitrogen atmosphere, discoloration was not observed.

Example 34

Step (34-1): Production of N-Substituted Carbamic Acid-O—Ar Ester

The same method as Example 1 was carried out with the exception of mixing 1.11 kg of 4,4'-methylenebis(cyclohexylamine), 11.6 kg of 4-nonyl phenol, 1.59 kg of 2-tert-butyl phenol and 0.824 kg of urea to obtain a raw material solution, heating the packed column 102 to 280° C., setting the internal pressure to 78 kPa, holding the condenser at 60° C., and introducing the raw material solution at the rate of about 1.5 g/min. The amount of reaction liquid recovered in the storage tank 105 was 13.1 kg. When the reaction liquid was analyzed by liquid chromatography and $^1$H-NMR, the reaction liquid was found to be a composition that contained N,N'-(4,4'-methanediyl-cyclohexyl)-di(carbamic acid (4-nonylphenyl) ester), and 4-nonyl phenol at a stoichiometric ratio of 9.2 times, 2-tert-butyl phenol at a stoichiometric ratio of 0.227 times and di(4-nonylphenyl) carbonate at a stoichiometric ratio of 0.0035 times based on N,N'-(4,4'-methanediyl-cyclohexyl)-di(carbamic acid (4-nonylphenyl) ester), and contained 0.0077 times an N-containing compound based on the number of N,N'-(4,4'-methanediyl-cyclohexyl)-di(carbamic acid (4-nonylphenyl) esters). In addition, the yield of N,N'-(4,4'-methanediyl-cyclohexyl)-di(carbamic acid (4-nonylphenyl) ester) based on 4,4'-methylenebis(cyclohexylamine) was about 88%. The amount of ammonia contained in the reaction liquid was 6.3 ppm. On the other hand, when $^1$H-NMR and $^{13}$C-NMR measurements were carried out on the component recovered in the storage tank 104, it was found to be a mixture of 2-tert-butyl phenol, 4-nonyl phenol, urea and (4-nonylphenyl) carbamate, the content of 2-tert-butyl phenol was 1.42 kg (9.50 mol), the content of 4-nonyl phenol was 0.116 kg (0.53 mol), the content of urea was about 0.326 kg (5.43 mol), and the content of (4-nonylphenyl) carbamate was 24.4 g (0.11 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.339 g (20.0 mmol). In addition, when the gas was analyzed by GC-MS, the amount of carbonyl groups contained in compounds having carbonyl groups contained in the ammonia was 0.033 mmol.

When the step (34-1) was continued to be carried out, clogging of the ammonia discharge line was not observed even when operating time had exceeded 380 days.

Step (34-2): Production of N-Substituted Carbamic Acid-O—Ar Ester by Reusing Mixture Obtained in Condenser The ammonia concentration in the mixture recovered in the storage tank 104 in step (34-1) was 510 ppm. The same method as step (34-1) was carried out by adding 10.5 kg of 4-nonyl phenol, 0.41 kg of urea and 1.01 kg of 4,4'-methylenebis(cyclohexylamine) to the mixture to obtain a raw material solution. The amount of reaction liquid recovered in the storage tank 105 was 11.9 kg. The reaction liquid contained N,N'-(4,4'-methanediyl-cyclohexyl)-di(carbamic acid (4-nonylphenyl) ester), and the yield of N,N'-(4,4'-methanediyl-cyclohexyl)-di(carbamic acid (4-nonylphenyl) ester) based on 4,4'-methylenebis(cyclohexylamine) was about 92%.

Step (34-3): Production of Isocyanate by Thermal Decomposition of N-Substituted Carbamic Acid-O—Ar Ester Production of isocyanate was carried out by using the apparatus shown in FIG. 29.

The thin film distillation apparatus 1002 was heated to 220° C. and the pressure within the thin film distillation apparatus was set to about 1.3 kPa. The reaction liquid recovered in the storage tank 105 in Example 34 was placed in the storage tank 1001 and supplied to the thin film distillation apparatus at the rate of about 1240 g/hr via the line A1. A liquid component was extracted from the line A2 provided in the bottom of thin film distillation apparatus 1002 and recovered in the storage tank 1003. The liquid component recovered in the storage tank 1003 was again supplied to the thin film distillation apparatus 1002 through the line A3. A gaseous component containing dicyclohexylmethane diisocyanate, 2-tert-butyl phenol and 4-nonyl phenol was extracted from the line A4 provided in the upper portion of the thin film distillation apparatus 1002. The gaseous component was introduced into the distillation column 1004, the 2-tert-butyl phenol was separated by distillation, and a liquid phase was fed to the distillation column 1009 through the line A8 provided in a portion of the distillation column 1004 lower than the feed portion thereof. The 4-nonyl phenol was separated by distillation in the distillation column 1009, and a liquid phase was fed to the distillation column 1014 through the line A12 provided in a portion of the distillation column 1009 lower than the feed portion thereof. A gaseous phase component containing dicyclohexylmethane diisocyanate was extracted in the distillation column 1014, condensed in the condenser 1015, and a portion of the condensate was returned to the distillation column 1014. Condensate was obtained in the storage tank 1019 at the rate of about 93 g/hr.

When the condensate recovered in the storage tank 1019 was analyzed by $^1$H-NMR and gas chromatography, it was found to be dicyclohexylmethane diisocyanate containing 110 ppm of 4-nonyl phenol. Although the isocyanate was stored for 630 days at normal temperatures in a nitrogen atmosphere, discoloration was not observed.

Example 35

Step (35-1): Production of Compound Having Ureido Groups

Figure 26:
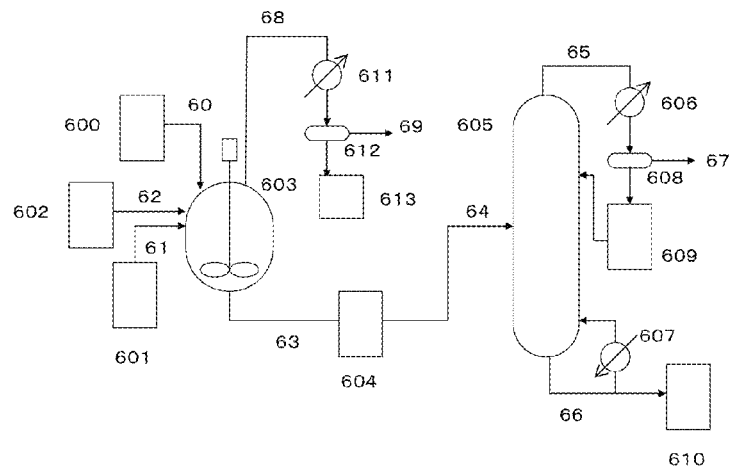
FIG. 26 shows a conceptual drawing of an N-substituted carbamic acid ester production apparatus used in an example of the present embodiment.

The apparatus shown in FIG. 26 was used.

41.84 kg of p-heptyl phenol and 3101 g of urea were mixed in a storage tank 601 heated to 120° C. with a line 63 closed, and the mixture was transferred to a stirring tank 603 (internal liquid volume: 80 L, equipped with baffles) heated to 120° C. While stirring the stirring tank 603, 1.50 kg of hexamethylenediamine were supplied from a storage tank 602 to the stirring tank 604 through a line 62 at the rate of about 20 g/min. After finishing supplying the hexamethylenediamine, stirring was carried out for about 2 hours followed by sampling the reaction liquid. As a result of analyzing the reaction liquid by liquid chromatography, the reaction liquid was found to contain 6.3% by weight of 1,6-hexamethylenediurea.

The line 63 was then opened and the reaction liquid was transferred to a storage tank 604 through the line 63.

Step (35-2): Production of N-Substituted Carbamic Acid-O—Ar Ester

The apparatus shown in FIG. 26 was continued to be used.

A packed column 605 packed with a packing (Helipack No. 3) was heated to 240° C., the pressure inside the column was set to 26 kPa, and the condenser was held at 60° C. The reaction liquid obtained in step (35-1) was fed at the rate of about 1.5 g/min from a line 64 provided in the packed column 605. Since the reaction is initially in an unsteady state, the sample at that time was discarded. The amount of reaction liquid after the reaction had reached a steady state was about 35.1 kg. The reaction liquid was recovered in a storage tank 610 through a line 66 provided in the bottom of the packed column 605. A gaseous phase component was condensed from a line 65 provided in the top of the packed column 605 with a condenser 606 held at about 85° C., and the resulting liquid phase component was recovered in a storage tank 609 via a gas-liquid separator 608. The amount of reaction liquid recovered in a storage tank 610 was about 23.0 kg. When reaction liquid was analyzed by liquid chromatography and $^1$H-NMR, the reaction liquid was found to be a composition that contained N,N'-hexanediyl-di(carbamic acid (p-heptylphenyl) ester), and p-heptyl phenol at a stoichiometric ratio of 8.4 times and di(p-heptylphenyl) carbonate at a stoichiometric ratio of 0.0053 times based on N,N'-hexanediyl-di (carbamic acid (p-heptylphenyl) ester), and contained 0.0132 times an N-containing compound based on the number of N,N'-hexanediyl-di(carbamic acid (p-heptylphenyl) esters). In addition, the yield of N,N'-hexanediyl-dicarbamic acid-bis (p-heptylphenyl) based on hexamethylenediamine was about 97%. The amount of ammonia contained in the reaction liquid was 6.9 ppm. On the other hand, when $^1$H-NMR and $^{13}$C-NMR measurements were carried out on the component recovered in the storage tank 409, it was found to be a mixture of p-heptyl phenol, urea and p-(heptylphenyl) carbamate, the content of p-heptyl phenol was 10.0 kg (52.0 mol), the content of urea was about 1.19 kg (19.9 mol), and the content of (p-heptylphenyl) carbamate was 0.515 kg (2.91 mol). In addition, gas containing ammonia was discharged from the gas-liquid separator 608 via a line 67. The gas was recovered in a Tedlar bag and injected into a gas chromatograph with a gastight syringe to analyze the gas components. As a result, the amount of ammonia recovered per 10 minutes was 0.14 g (8.5 mmol). When the gas was analyzed by GC-MS, the amount of carbonyl groups contained in compounds having carbonyl groups contained in the ammonia was 0.085 mmol.

When the steps (35-1) and (35-2) were continued to be carried out, clogging of the ammonia discharge line was not observed even after operating time had exceeded 380 days.

Step (35-3): Production of N-Substituted Carbamic Acid-O—Ar Ester by Reusing Mixture Obtained in Condenser The ammonia concentration in the mixture recovered in the storage tank 609 in step (35-2) was 70 ppm. The same method as step (35-1) was carried out by adding 12.8 kg of p-heptyl phenol and 0.578 kg of urea to the mixture, transferring to the stirring tank 603 and using 0.92 kg of hexamethylenediamine. A solution containing 6.3% by weight of 1,6-hexanebisdiurea was obtained. The same method as step (35-2) was carried out by using this solution instead of the solution of step (35-1). The reaction liquid recovered in the storage tank 610 contained N,N'-hexanediyl-di(carbamic acid (p-heptylphenyl) ester), and the yield of N,N'-hexanediyl-di (carbamic acid (p-heptylphenyl) ester) based on hexamethylenediamine was about 97%.

Step (35-4): Production of Isocyanate by Thermal Decomposition of N-Substituted Carbamic Acid-O—Ar Ester The same method as Example 1 was carried out with the exception of heating the thin film distillation apparatus 702 to 220° C., setting the pressure within the thin film distillation apparatus to about 1.3 kPa, and supplying the reaction liquid recovered in the storage tank 105 in Example 35 instead of the reaction liquid recovered in storage tank 105 in Example 1 to the thin film distillation apparatus at the rate of about 1790 g/hr.

Condensate was obtained in the storage tank 707 at the rate of about 125 g/hr, and when the condensate recovered in the storage tank 707 was analyzed by $^1$H-NMR and gas chromatography, it was found to be hexamethylene diisocyanate containing 5 ppm of p-heptyl phenol. Although the isocyanate was stored for 630 days at normal temperatures in a nitrogen atmosphere, discoloration was not observed.

Example 36

Step (36-1): Production of Compound Having Ureido Groups 45.4 kg of 4-cumyl phenol and 2.25 kg of urea were mixed in the storage tank 601 heated to 110° C. with the line 63 closed, and the mixture was transferred to the stirring tank 603 heated to 100° C. While stirring the stirring tank 603, 1.82 kg of 3-aminomethyl-3,5,5-trimethylcyclohexylamine were supplied from the storage tank 602 to the stirring tank 303 through the line 62 at the rate of about 20 g/min. After finishing supplying the 3-aminomethyl-3,5,5-trimethylcyclohexylamine, stirring was carried out for about 8 hours followed by sampling the reaction liquid. As a result of analyzing the reaction liquid by liquid chromatography, the reaction liquid was found to contain 5.6% by weight of 3-ureidomethyl-3,5, 5-trimethylcyclohexylurea.

The line 63 was then opened and the reaction liquid was transferred to the storage tank 604 through the line 63.

Step (36-2): Production of N-Substituted Carbamic Acid-O—Ar Ester

The same method as step (35-2) of Example 35 was carried out with the exception of heating the packed column 605 to 220° C., setting the pressure inside the column to 8 kPa, holding the condenser at 80° C., and feeding the reaction liquid obtained in step (36-1) instead of the reaction liquid obtained in step (35-1) at the rate of about 1.7 g/min. The amount of reaction liquid fed after the reaction had reached a steady state was about 40.5 kg. The amount of reaction liquid recovered in the storage tank 610 was 27.1 kg. When reaction liquid was analyzed by liquid chromatography and $^1$H-NMR, the reaction liquid was found to be a composition that contained 3-((4-phenylphenoxy) carbonylamino-methyl)-3,5,5-trimethylcyclohexyl carbamic acid (4-cumylphenyl) ester, and 4-cumyl phenol at a stoichiometric ratio of 12.8 times and di(4-cumylphenyl) carbonate at a stoichiometric ratio of 0.0066 times based on 3-((4-phenylphenoxy) carbonylamino-methyl)-3,5,5-trimethylcyclohexyl carbamic acid (4-cumylphenyl) ester, and contained 0.0211 times an N-containing compound based on the number of 3-((4-phenylphenoxy) carbonylamino-methyl)-3,5,5-trimethylcyclohexyl carbamic acid (4-cumylphenyl) esters. In addition, the yield of 3-((4-phenylphenoxy) carbonylamino-methyl)-3,5,5-trimethylcyclohexyl carbamic acid (4-cumylphenyl) ester based on 3-aminomethyl-3,5,5-trimethylcyclohexylamine was about 90%. The amount of ammonia contained in the reaction liquid was 10.5 ppm. On the other hand, when $^1$H-NMR and $^{13}$C-NMR measurements were carried out on the component recovered in the storage tank 609, it was found to be a mixture of 4-cumyl phenol, urea and (4-cumylphenyl) carbamate, the content of 4-cumyl phenol was 12.2 kg (57.5 mol), the content of urea was about 0.765 kg (12.7 mol), and the content of (4-cumylphenyl) carbamate was 0.169 kg (0.66 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.092 g (5.4 mmol). When the gas was analyzed by GC-MS, the amount of carbonyl groups contained in compounds having carbonyl groups contained in the ammonia was 0.0033 mmol.

When the steps (36-1) and (36-2) were continued to be carried out, clogging of the ammonia discharge line was not observed even after operating time had exceeded 380 days.

Step (36-3): Production of N-Substituted Carbamic Acid-O—Ar Ester by Reusing Mixture Obtained in Condenser The ammonia concentration in the mixture recovered in the storage tank 609 in step (36-2) was 59 ppm. The same method as step (36-1) was carried out by adding 10.7 kg of 4-cumyl phenol and 0.330 kg of urea to the mixture, transferring to the stirring tank 603 and using 0.920 kg of 3-aminomethyl-3,5, 5-trimethylcyclohexylamine. A solution containing 5.6% by weight of 3-ureidomethyl-3,5,5-trimethylcyclohexylurea was obtained. The same method as step (36-2) was carried out by using this solution instead of the solution of step (36-1). The reaction liquid recovered in the storage tank 610 contained 3-((4-phenylphenoxy) carbonylamino-methyl)-3,5,5-trimethylcyclohexyl carbamic acid (4-cumylphenyl) ester, and the yield of 3-((4-phenylphenoxy) carbonylamino-methyl)-3,5,5-trimethylcyclohexyl carbamic acid (4-cumylphenyl) ester based on 3-aminomethyl-3,5,5-trimethylcyclohexylamine was about 90%. The ammonia concentration in the reaction liquid was 11 ppm.

Step (36-4): Production of Isocyanate by Thermal Decomposition of N-Substituted Carbamic Acid-O—Ar Ester The same method as Example 1 was carried out with the exception of heating the thin film distillation apparatus 702 to 230° C., setting the pressure within the thin film distillation apparatus to about 0.8 kPa, and supplying the reaction liquid recovered in the storage tank 105 in Example 36 instead of the reaction liquid recovered in storage tank 105 in Example 1 to the thin film distillation apparatus at the rate of about 1910 g/hr.

Condensate was obtained in the storage tank 707 at the rate of about 118 g/hr, and when the condensate recovered in the storage tank 707 was analyzed by $^1$H-NMR and gas chromatography, it was found to be isophorone diisocyanate containing 10 ppm of p-cumyl phenol.

Example 37

Step (37-1): Production of Compound Having Ureido Groups 49.3 kg of p-dodecyl phenol and 3.38 kg of urea were mixed in the storage tank 601 heated to 90° C. with the line 63 closed, and the mixture was transferred to the stirring tank 603 heated to 90° C. While stirring the stirring tank 603, 1.53 kg of 2,4-toluenediamine were supplied from the storage tank 62 to the stirring tank 603 through the line 62 at the rate of about 15 g/min. After finishing supplying the 2,4-toluenediamine, stirring was carried out for about 1 hour followed by sampling the reaction liquid. As a result of analyzing the reaction liquid by liquid chromatography, the reaction liquid was found to contain 4.9% by weight of 2,4-toluenediurea.

The line 63 was then opened and the reaction liquid was transferred to the storage tank 604 through the line 63.

Step (37-2): Production of N-Substituted Carbamic Acid-O—Ar Ester

The same method as step (35-2) of Example 35 was carried out with the exception of heating the packed column 605 to 210° C., setting the pressure inside the column to 8 kPa, holding the condenser at 80° C., and feeding the reaction liquid obtained in step (37-1) instead of the reaction liquid obtained in step (35-1) at the rate of about 2.0 g/min. The amount of reaction liquid fed after the reaction had reached a steady state was about 48.2 kg. The amount of reaction liquid recovered in the storage tank 610 was 36.1 kg. When reaction liquid was analyzed by liquid chromatography and $^1$H-NMR, the reaction liquid was found to be a composition that contained toluene-2,4-di(carbamic acid (p-dodecylphenyl) ester), and p-dodecyl phenol at a stoichiometric ratio of 9.11 times and di(p-dodecylphenyl) carbonate at a stoichiometric ratio of 0.0035 times based on toluene-2,4-di(carbamic acid (p-dodecylphenyl) ester), and contained 0.0012 times an N-containing compound based on the number of toluene-2, 4-di(carbamic acid (p-dodecylphenyl) esters). In addition, the yield of toluene-2,4-di(carbamic acid (p-dodecylphenyl) ester) based on 2,4-toluenediamine was about 90%. The amount of ammonia contained in the reaction liquid was 29 ppm. On the other hand, when $^1$H-NMR and $^{13}$C-NMR measurements were carried out on the component recovered in the storage tank 609, it was found to be a mixture of p-dodecyl phenol, urea and (p-dodecylphenyl) carbamate, the content of p-dodecyl phenol was 14.2 kg (54.2 mol), the content of urea was about 1.62 kg (27.1 mol), and the content of (p-dodecylphenyl) carbamate was 0.428 kg (1.40 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.108 g (6.38 mmol). In addition, when the gas was analyzed by GC-MS, the amount of carbonyl groups contained in compounds having carbonyl groups contained in the ammonia was 0.572 mmol.

When the steps (37-1) and (37-2) were continued to be carried out, the ammonia discharge line became clogged after operating time had exceeded 303 days.

Step (37-3): Production of N-Substituted Carbamic Acid-O—Ar Ester by Reusing Mixture Obtained in Condenser The ammonia concentration in the mixture recovered in the storage tank 609 in step (37-2) was 86 ppm. The same method as step (37-1) was carried out by adding 12.2 kg of p-dodecyl phenol and 0.105 kg of urea to the mixture, transferring to the stirring tank 603 and using 0.820 kg of 2,4-toluenediamine. A solution containing 4.9% by weight of 2,4-toluenediurea was obtained. The same method as step (37-2) was carried out by using this solution instead of the solution of step (35-2). The reaction liquid recovered in the storage tank 610 contained toluene-2,4-di(carbamic acid (p-dodecylphenyl) ester), and the yield of toluene-2,4-di(carbamic acid (p-dodecylphenyl) ester) based on 2,4-toluenediamine was about 89%. The ammonia concentration in the reaction liquid was 27 ppm.

Although the steps (37-1) and (37-2) were repeated five times, clogging of the line 67 did not occur.

Step (37-4): Production of Isocyanate by Thermal Decomposition of N-Substituted Carbamic Acid-O—Ar Ester The same method as Example 1 was carried out with the exception of heating the thin film distillation apparatus 702 to 210° C., setting the pressure within the thin film distillation apparatus to about 1.3 kPa, and supplying the reaction liquid recovered in the storage tank 105 in Example 37 instead of the reaction liquid recovered in storage tank 105 in Example 1 to the thin film distillation apparatus at the rate of about 2020 g/hr.

Condensate was obtained in the storage tank 707 at the rate of about 102 g/hr, and when the condensate recovered in the storage tank 707 was analyzed by $^1$H-NMR and gas chromatography, it was found to be 2,4-tolylene diisocyanate containing 15 ppm of p-dodecyl phenol. Although the isocyanate was stored for 630 days at normal temperatures in a nitrogen atmosphere, discoloration was not observed.

Example 38

Step (38-1): Production of Compound Having Ureido Groups 110.8 kg of 4-(1,1,3,3-tetramethylbutyl) phenol and 0.99 kg of urea were mixed in the storage tank 601 heated to 90° C. with the line 63 closed, and the mixture was transferred to the stirring tank 603 heated to 90° C. While stirring the stirring tank 603, 0.820 kg of 4,4'-methylenedianiline were supplied from the storage tank 602 to the stirring tank 603 through the line 62 at the rate of about 10 g/min. After finishing supplying the 4,4'-methylenedianiline, stirring was carried out for about 1 hour followed by sampling the reaction liquid. As a result of analyzing the reaction liquid by liquid chromatography, the reaction liquid was found to contain 1.05% by weight of 4,4'-methanediyldiphenyldiurea.

The line 63 was then opened and the reaction liquid was transferred to the storage tank 604 through the line 63.

Step (38-2): Production of N-Substituted Carbamic Acid-O—Ar Ester

The same method as step (35-2) of Example 35 was carried out with the exception of heating the packed column 605 to 200° C., setting the pressure inside the column to 8 kPa, holding the condenser at 90° C., and feeding the reaction liquid obtained in step (38-1) instead of the reaction liquid obtained in step (35-1) at the rate of about 13.2 g/min. The amount of reaction liquid fed after the reaction had reached a steady state was about 47.7 kg. The amount of reaction liquid recovered in the storage tank 610 was 31.9 kg. When reaction liquid was analyzed by liquid chromatography and $^1$H-NMR, the reaction liquid was found to be a composition that contained N,N'-(4,4'-methanediyl-diphenyl)-di(carbamic acid (4-(1,1,3,3-tetramethylbutyl)phenyl) ester), and 4-(1,1,3,3-tetramethylbutyl) phenol at a stoichiometric ratio of 8.4 times and di(4-(1,1,3,3-tetramethylbutyl)phenyl) carbonate at a stoichiometric ratio of 0.0046 times based on N,N'-(4,4'-methanediyl-diphenyl)-di(carbamic acid (4-(1,1,3,3-tetramethylbutyl)phenyl) ester), and contained 0.0132 times an N-containing compound based on the number of N,N'-(4,4'-methanediyl-diphenyl)-di(carbamic acid (4-(1,1,3,3-tetramethylbutyl)phenyl) esters). In addition, the yield of N,N'-(4,4'-methanediyl-diphenyl)-di(carbamic acid (4-(1,1,3,3-tetramethylbutyl)phenyl) ester) based on 4,4'-methylenedianiline was about 90%. On the other hand, when $^1$H-NMR and $^{13}$C-NMR measurements were carried out on the component recovered in the storage tank 609, it was found to be a mixture of 4-(1,1,3,3-tetramethylbutyl) phenol and urea, the content of 4-(1,1,3,3-tetramethylbutyl) phenol was 15.5 kg (75.8 mol), and the content of urea was about 0.679 kg (11.3 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.0667 g (3.23 mmol). In addition, when the gas was analyzed by GC-MS, the amount of carbonyl groups contained in compounds having carbonyl groups contained in the ammonia was 0.291 mmol.

When the steps (38-1) and (38-2) were continued to be carried out, the ammonia discharge line became clogged after operating time had exceeded 300 days.

Step (38-3): Production of N-Substituted Carbamic Acid-O—Ar Ester by Reusing Mixture Obtained in Condenser The ammonia concentration in the mixture recovered in the storage tank 609 in step (38-2) was 50 ppm. The same method as step (38-1) was carried out by adding 95.2 kg of 4-(1,1,3,3-tetramethylbutyl) phenol and 0.778 kg of urea to the mixture, transferring to the stirring tank 603 and using 0.776 kg of 4,4'-methylenedianiline. A solution containing 1.1% by weight of 4,4'-methanediyldiphenyldiurea was obtained. The same method as step (38-2) was carried out by using this solution instead of the solution of step (35-2). The reaction liquid recovered in the storage tank 610 contained N,N'-(4,4'-methanediyl-diphenyl)-di(carbamic acid (4-(1,1,3,3-tetramethylbutyl)phenyl) ester), and the yield of N,N'-(4,4'-methanediyl-diphenyl)-di(carbamic acid (4-(1,1,3,3-tetramethylbutyl)phenyl) ester) based on 4,4'-methylenedianiline was about 90%.

Step (38-4): Production of Isocyanate by Thermal Decomposition of N-Substituted Carbamic Acid-O—Ar Ester The apparatus shown in FIG. 28 was used.

The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 38 instead of the reaction liquid recovered in the storage tank 105 in Example 5 to the storage tank 801, and supplying to the thin film distillation apparatus via the line 80 at the rate of about 2580 g/hr.

Condensate was obtained in the storage tank 812 at the rate of about 23 g/hr, and when the condensate recovered in the storage tank 812 was analyzed by $^1$H-NMR and gas chromatography, it was found to be 4,4'-diphenylmethane diisocyanate containing 120 ppm of 4-(1,1,3,3-tetramethylbutyl) phenol. Although the isocyanate was stored for 630 days at normal temperatures in a nitrogen atmosphere, discoloration was not observed.

Example 39

Step (39-1): Production of Compound Having Ureido Groups 43.5 kg of 4-tert-amyl phenol and 3.61 kg of urea were mixed in the storage tank 601 heated to 80° C. with the line 63 closed, and the mixture was transferred to the stirring tank 603 heated to 80° C. While stirring the stirring tank 603, 1.12 kg of aniline were supplied from the storage tank 602 to the stirring tank 603 through the line 62 at the rate of about 10 g/min. After finishing supplying the aniline, stirring was carried out for about 28 hours followed by sampling the reaction liquid. As a result of analyzing the reaction liquid by liquid chromatography, the reaction liquid was found to contain 4.5% by weight of N-phenylurea.

The line 63 was then opened and the reaction liquid was transferred to the storage tank 604 through the line 63.

Step (39-2): Production of N-Substituted Carbamic Acid-O—Ar Ester

The same method as step (35-2) of Example 35 was carried out with the exception of heating the packed column 605 to 200° C., setting the pressure inside the column to 8 kPa, holding the condenser at 100° C., and feeding the reaction liquid obtained in step (39-1) instead of the reaction liquid obtained in step (35-1) at the rate of about 1.6 g/min. The amount of reaction liquid fed after the reaction had reached a steady state was about 42.6 kg. The amount of reaction liquid recovered in the storage tank 610 was 27.2 kg. When reaction liquid was analyzed by liquid chromatography and $^1$H-NMR, the reaction liquid was found to be a composition that contained N-phenylcarbamic acid-(4-tert-amylphenyl), and 4-tert-amyl phenol at a stoichiometric ratio of 13.8 times and di(4-tert-amylphenyl) carbonate at a stoichiometric ratio of 0.0046 times based on N-phenylcarbamic acid-(4-tert-amylphenyl), and contained 0.0189 times an N-containing compound based on the number of N-phenylcarbamic acid-(4-tert-amylphenyl). In addition, the yield of N-phenylcarbamic acid-(4-tert-amylphenyl) based on aniline was about 93%. The reaction liquid contained 4.9 ppm of ammonia. On the other hand, when $^1$H-NMR and $^{13}$C-NMR measurements were carried out on the component recovered in the storage tank 609, it was found to be a mixture of 4-tert-amyl phenol and urea, the content of 4-tert-amyl phenol was 12.7 kg (77.9 mol), and the content of urea was about 1.95 kg (32.4 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.117 g (6.87 mmol). In addition, when the gas was analyzed by GC-MS, the amount of carbonyl groups contained in compounds having carbonyl groups contained in the ammonia was 0.206 mmol.

When the steps (39-1) and (39-2) were continued to be carried out, the ammonia discharge line became clogged after operating time had exceeded 308 days.

Step (39-3): Production of N-Substituted Carbamic Acid-O—Ar Ester by Reusing Mixture Obtained in Condenser The same method as step (39-1) was carried out in step (39-2) by adding 19.0 kg of 4-tert-amyl phenol and 0.690 kg of urea to the mixture, transferring to the stirring tank 603 and using 0.820 kg of aniline. A solution containing 4.5% by weight of phenylurea was obtained. The same method as step (39-2) was carried out by using this solution instead of the solution of step (35-2). The reaction liquid recovered in the storage tank 610 contained N-phenylcarbamic acid-(4-tert-amylphenyl), and the yield of N-phenylcarbamic acid-(4-tert-amylphenyl) based on aniline was about 93%.

Step (39-4): Condensation of N-Substituted Carbamic Acid Mono(—O—Ar Ester

The apparatus shown in FIG. 30 was used.
The reaction liquid recovered in the storage tank 610 in step (39-3) was charged into the stirring tank 1108. The stirring tank 1108 was heated to 160° C. and the internal pressure was set to 2 kPa to remove aromatic hydroxy compounds. An aromatic hydroxy compound in the form of 4-tert-amyl phenol was condensed in the condenser 1105 via the line B4 and recovered in the storage tank 1107. Next, 1.14 kg of methylal (formaldehyde dimethyl acetal) from the storage tank 1100, 4.70 kg of nitrobenzole from the storage tank 1101 and 5.6 kg of sulfuric acid from the storage tank 1102 were added to the stirring tank 1108 followed by heating for 10 hours at 100° C. while stirring the stirring tank 1108. The inside of the stirring tank 1108 was then maintained at 100° C. and the internal pressure was reduced to 1 kPa to distill off solvent and unreacted substances. When the resulting compound was analyzed by liquid chromatography, it was found to be a mixture containing about 55% by weight of N,N'-(methanediyl-diphenyl)-bis(carbamic acid(4-tert-amylphenyl) ester). About 5.1 kg of an aromatic hydroxy compound (4-tert-amyl phenol) were added to this compound to obtain a homogeneous solution, and the solution was transferred to the storage tank 1104.

Step (39-5): Production of Isocyanate by Thermal Decomposition of N-Substituted Carbamic Acid-O-Aryl Ester The apparatus shown in FIG. 29 was used.
A thin film distillation apparatus 1002 (Kobelco Eco-Solutions Co., Ltd., Japan) having a heat-conducting surface area of 0.2 m$^2$ was heated to 260° C. and the pressure within the thin film distillation apparatus was set to about 1.5 kPa. The reaction liquid recovered in the storage tank 1104 in step (39-4) was placed in the storage tank 1001 and supplied to the thin film distillation apparatus at the rate of about 1200 g/hr via the line A1. A liquid component was extracted from the line A4 provided in the bottom of thin film distillation apparatus 1002 and recovered in the storage tank 1003. The liquid component recovered in the storage tank 1003 was again supplied to the thin film distillation apparatus 1002 through the line A3. A gaseous component was extracted from the line A4 provided in the upper portion of the thin film distillation apparatus 1002. The gaseous component was introduced into the distillation column 1004, and low boiling components were separated by distillation. A liquid phase component was supplied to the distillation column 1009 from the line A8 provided at a portion of the distillation column 1004 lower than the feed line and further subjected to distillative separation. The liquid phase component was supplied to the distillation column 1014 from the line A12 provided at a portion of the distillation column 1009 lower than the feed line and further subjected to distillative separation.

A gaseous component was extracted from the line A13 provided in the top of the distillation column 1014 and condensed in the condenser 1015, and the condensate was recovered in the storage tank 1019. When the condensate was analyzed by $^1$H-NMR, it was found to be a solution containing about 99% by weight of 4,4'-diphenylmethane diisocyanate (MDI). The yield based on aniline was about 50%.

Example 40

Step (40-1): Production of Compound Having Ureido Groups 51.1 kg of 4-ethyl phenol and 0.43 kg of urea were mixed in the storage tank 601 heated to 110° C. with the line 63 closed, and the mixture was transferred to the stirring tank 603 heated to 100° C. While stirring the stirring tank 603, 0.43 kg of 4,4'-methylenebis(cyclohexylamine) were supplied from the storage tank 602 to the stirring tank 603 through the line 62 at the rate of about 20 g/min. After finishing supplying the 4,4'-methylenebis(cyclohexylamine), stirring was carried out for about 8 hours followed by sampling the reaction liquid. As a result of analyzing the reaction liquid by liquid chromatography, the reaction liquid was found to contain 1.17% by weight of 4,4'-methanediyldicyclohexyldiurea.

The line 63 was then opened and the reaction liquid was transferred to the storage tank 604 through the line 63.

Step (40-2): Production of N-Substituted Carbamic Acid-O—Ar Ester

The same method as step (35-2) of Example 35 was carried out with the exception of heating the packed column 605 to 220° C., setting the pressure inside the column to 13 kPa, holding the condenser at 60° C., and feeding the reaction liquid obtained in step (40-1) instead of the reaction liquid obtained in step (35-1) at the rate of about 1.4 g/min. The amount of reaction liquid fed after the reaction had reached a steady state was about 48.6 kg. The amount of reaction liquid recovered in the storage tank 610 was 32.5 kg. When reaction liquid was analyzed by liquid chromatography and $^1$H-NMR, the reaction liquid was found to be a composition that contained N,N'-(4,4'-methanediyl-dicyclohexyl)-di(carbamic acid) (4-ethylphenyl) ester), and 4-ethyl phenol at a stoichiometric ratio of 149 times and di(4-ethylphenyl) carbonate at a stoichiometric ratio of 0.0039 times based on N,N'-(4,4'-methanediyl-dicyclohexyl)-di(carbamic acid) (4-ethylphenyl) ester), and contained 0.0155 times an N-containing compound based on the number of N,N'-(4,4'-methanediyl-dicyclohexyl)-di(carbamic acid) (4-ethylphenyl) esters). In addition, the yield of N,N'-(4,4'-methanediyl-dicyclohexyl)-di(carbamic acid) (4-ethylphenyl) ester) based on 4,4'-methylenebis(cyclohexylamine) was about 91%. On the other hand, when $^1$H-NMR and $^{13}$C-NMR measurements were carried out on the component recovered in the storage tank 609, it was found to be a mixture of 4-ethyl phenol and urea, the content of 4-ethyl phenol was 15.8 kg (129 mol), and the content of urea was about 0.168 kg (2.81 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.025 g (1.46 mmol). In addition, when the gas was analyzed by GC-MS, the amount of carbonyl groups contained in compounds having carbonyl groups contained in the ammonia was 0.0014 mmol.

When the steps (40-1) and (40-2) were continued to be carried out, clogging of the ammonia extraction line was not observed even after operating time had exceeded 380 days.

Step (40-3): Production of N-Substituted Carbamic Acid-O—Ar Ester by Reusing Mixture Obtained in Condenser The ammonia concentration in the mixture recovered in the storage tank 609 in step (40-2) was 2 ppm. The same method as step (40-1) was carried out by adding 36.7 kg of 4-ethyl phenol and 0.252 kg of urea to the mixture, transferring to the stirring tank 603 and using 0.43 kg of 4,4'-methylenebis(cyclohexylamine). A solution containing 1.14% by weight of 4,4'-methanediyldicyclohexyldiurea was obtained. The same method as step (40-2) was carried out by using this solution instead of the solution of step (40-1). The reaction liquid recovered in the storage tank 610 contained N,N'-(4,4'-methanediyl-dicyclohexyl)-di(carbamic acid) (4-ethylphenyl) ester), and the yield of N,N'-(4,4'-methanediyl-dicyclohexyl)-di(carbamic acid) (4-ethylphenyl) ester) based on 4,4'-methylenebis(cyclohexylamine) was about 91%.

Step (40-4): Production of Isocyanate by Thermal Decomposition of N-Substituted Carbamic Acid-O—Ar Ester The apparatus shown in FIG. 28 was used.
The same method as Example 5 was carried out with the exception of heating the thin film distillation apparatus 802 to 220° C., setting the pressure within the thin film distillation apparatus to about 1.3 kPa, charging the reaction liquid recovered in the storage tank 105 in Example 40 instead of the reaction liquid recovered in the storage tank 105 in Example 5 to the storage tank 801, and supplying to the thin film distillation apparatus via the line 80 at the rate of about 1880 g/hr.

Condensate was obtained in the storage tank 812 at the rate of about 16 g/hr, and when the condensate recovered in the storage tank 812 was analyzed by $^1$H-NMR and gas chromatography, it was found to be 4,4'-dicyclohexylmethane)diisocyanate containing 230 ppm of 4-ethyl phenol. Although the isocyanate was stored for 630 days at normal temperatures in a nitrogen atmosphere, discoloration was not observed.

Example 41

Step (41-1): Production of Compound Having Ureido Groups

The apparatus shown in FIG. 26 was used.
8.44 kg of 2-isopropyl phenol and 7.03 kg of urea were mixed in the storage tank 601 heated to 120° C. with the line 63 closed, and the mixture was transferred to the stirring tank 603 (internal liquid volume: 80 L, equipped with baffles) heated to 120° C. While stirring the stirring tank 603, 1.50 kg of hexamethylenediamine were supplied from the storage tank 602 to the stirring tank 603 through the line 62 at the rate of about 20 g/min. After finishing supplying the hexamethylenediamine, stirring was carried out for about 2 hours. After adding 13.3 kg of 4-(1,1,3,3-tetramethylbutyl) phenol from the storage tank 600, the line 63 was opened and the reaction liquid was transferred to the storage tank 604 through the line 63. As a result of analyzing the reaction liquid by liquid chromatography, the reaction liquid was found to contain 8.1% by weight of 1,6-hexanebisurea.

Step (41-2): Production of N-Substituted Carbamic Acid-O—Ar Ester

The apparatus shown in FIG. 26 was continued to be used.
A packed column 605 packed with a packing (Helipack No. 3) and having an inner diameter of 40 mm and height of 4000 mm was heated to 240° C., and the pressure inside the column was set to 26 kPa. The reaction liquid obtained in step (41-1) was fed at the rate of about 1.8 g/min from the line 64 provided in the packed column 605. Since the reaction is initially in an unsteady state, the sample at that time was discarded. The amount of reaction liquid fed after the reaction had reached a steady state was about 21.3 kg. The reaction liquid was recovered in the storage tank 610 through the line 66 provided in the bottom of the packed column 605. A gaseous phase component was condensed from the line 65 provided in the top of the packed column 605 with the condenser 606 held at about 60° C., and the resulting liquid phase component was recovered in the storage tank 609 via the gas-liquid separator 608. The amount of reaction liquid recovered in the storage tank 610 was 11.9 kg. When the reaction liquid was analyzed by liquid chromatography and $^1$H-NMR, the reaction liquid was found to be a composition that contained N,N'-hexanediyl-di(carbamic acid (4-(1,1,3,3-tetramethylbutyl)phenyl) ester), and 4-(1,1,3,3-tetramethylbutyl) phenol at a stoichiometric ratio of 4.1 times and bis((4-(1,1,3,3-tetramethylbutyl)phenyl) carbonate at a stoichiometric ratio of 0.039 times based on N,N'-hexanediyl-di(carbamic acid (4-(1,1,3,3-tetramethylbutyl)phenyl) ester), and contained 0.0035 times an N-containing compound based on the number of N,N'-hexanediyl-di(carbamic acid (4-(1,1,3,3-tetramethylbutyl)phenyl) esters). In addition, the yield of N,N'-hexanediyl-di(carbamic acid (4-(1,1,3,3-tetramethylbutyl)phenyl) ester) based on hexamethylenediamine was about 77%. The amount of ammonia contained in the reaction liquid was 9.3 ppm. On the other hand, when $^1$H-NMR and $^{13}$C-NMR measurements were carried out on the component recovered in the storage tank 609, it was found to be a mixture of 4-(1,1,3,3-tetramethylbutyl) phenol, 2-isopropyl phenol, urea and (4-(1,1,3,3-tetramethylbutyl)phenyl) carbamate, the content of 4-(1,1,3,3-tetramethylbutyl) phenol was about 0.11 kg (0.51 mol), the content of 2-isopropyl phenol was about 6.86 kg (50.4 mol), the content of urea was about 933 g (15.5 mol), and the content of (4-(1,1,3,3-tetramethylbutyl)phenyl) carbamate was about 521 g (2.09 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.225 g (13.2 mmol). When the gas was analyzed by GC-MS, the amount of carbonyl groups contained in compounds having carbonyl groups contained in the ammonia was 0.0013 mmol.

When the steps (41-1) and (41-2) were continued to be carried out, clogging of the ammonia discharge line was not observed even after operating time had exceeded 380 days.

Step (41-3): Production of N-Substituted Carbamic Acid-O—Ar Ester by Reusing Mixture Obtained in Condenser The same method as step (41-1) was carried out in step (41-2) by adding 2.35 kg of urea to the mixture recovered in the storage tank 609, transferring to the stirring tank 603 and using 1.650 kg of hexamethylenediamine and 14.2 kg of 4-(1,1,3,3-tetramethylbutyl) phenol. A solution containing 8.1% by weight of 1,6-hexamethylenediurea was obtained. The same method as step (41-2) was carried out by using this solution instead of the solution of step (41-1). The reaction liquid recovered in the storage tank 610 contained N,N'-hexanediyl-dicarbamic acid di(4-(1,1,3,3-tetramethylbutyl) phenyl)ester, and the yield of N,N'-hexanediyl-dicarbamic acid di(4-(1,1,3,3-tetramethylbutyl)phenyl)ester, based on hexamethylenediamine was about 77%.

Step (41-4): Production of Isocyanate by Thermal Decomposition of N-Substituted Carbamic Acid-O—Ar Ester Production of isocyanate was carried out using the apparatus shown in FIG. 28.

The thin film distillation apparatus 802 was heated to 220° C. and the pressure within the thin film distillation apparatus was set to about 1.3 kPa. The reaction liquid recovered in the storage tank 105 in Example 41 was placed in the storage tank 801 and supplied to the thin film distillation apparatus at the rate of about 890 g/hr via the line 80. A liquid component was extracted from the line 82 provided in the bottom of the thin film distillation apparatus 802 and recovered in the storage tank 803. The liquid component recovered in the storage tank 803 was again supplied to the thin film distillation apparatus 802 through the line 83. A gaseous component containing hexamethylene diisocyanate, 2-isopropyl phenol and 4-(1,1,3,3-tetramethylbutyl) phenol was extracted from the line 81 provided in the upper portion of the thin film distillation apparatus 802. The gaseous component was introduced into the distillation column 804, the 2-isopropyl phenol was separated by distillation, and a liquid phase was fed to the distillation column 809 from the line 88 provided at a portion of the distillation column 804 lower than the feed portion thereof. A gaseous phase component containing hexamethylenediisocyanate was extracted in the distillation column 809, condensed in the condenser 810, and a portion of the condensate was returned to the distillation column 809. Condensate was obtained in the storage tank 812 at the rate of about 86.5 g/hr.

When the condensate recovered in the storage tank 812 was analyzed by $^1$H-NMR and gas chromatography, it was found to be hexamethylene diisocyanate containing 15 ppm of 4-(1,1,3,3-tetramethylbutyl) phenol. Although the isocyanate was stored for 630 days at normal temperatures in a nitrogen atmosphere, discoloration was not observed.

Example 42

Step (42-1): Production of Compound Having Ureido Groups

The same method as step (41-1) of Example 41 was carried out with the exception of using 7.74 kg of 2-isopropyl phenol and 1.71 kg of urea, and using 1.21 kg of 3-aminomethyl-3,5,5-trimethylcyclohexylamine instead of hexamethylenediamine. As a result of adding 9.67 kg of 4-phenyl phenol instead of 4-(1,1,3,3-tetramethylbutyl) phenol and analyzing the reaction liquid by liquid chromatography, the mixture was found to contain 9.1% by weight of 3-(ureidomethyl)-3,5,5-trimethylcyclohexylurea.

Step (42-2): Production of N-Substituted Carbamic Acid-O—Ar Ester

The packed column 605 was heated to 240° C., the internal pressure was set to 26 kPa and the condenser was held at 60° C. The same method as step (42-1) of Example 41 was carried out with the exception of feeding the reaction liquid obtained in step (42-1) instead of the reaction liquid obtained in step (41-1) at the rate of about 1.6 g/min. The amount of reaction liquid fed after the reaction had reached a steady state was about 16.2 kg. The amount of reaction liquid recovered in the storage tank 610 was 8.52 kg. When reaction liquid was analyzed by liquid chromatography and $^1$H-NMR, the reaction liquid was found to be a composition that contained 3-((4-(phenylphenoxy)carbonylamino-methyl)-3,5,5-trimethylcyclohexyl carbamic acid (4-phenylphenyl) ester, and 4-phenyl phenol at a stoichiometric ratio of 5.57 times, 2-isopropyl phenol at a stoichiometric ratio of 0.082 times, and bis((4-(1,1,3,3-tetramethylbutyl)phenyl) carbonate at a stoichiometric ratio of 0.029 times based on 3-((4-(phenylphenoxy)carbonylamino-methyl)-3,5,5-trimethylcyclohexyl carbamic acid (4-phenylphenyl) ester, and contained 0.0011 times an N-containing compound based on the number of 3-((4-(phenylphenoxy)carbonylamino-methyl)-3,5,5-trimethylcyclohexyl carbamic acid (4-phenylphenyl) esters. In addition, the yield of 3-((4-(phenylphenoxy)carbonylamino-methyl)-3,5,5-trimethylcyclohexyl carbamic acid (4-phenylphenyl) ester based on 3-aminomethyl-3,5,5-trimethylcyclohexylamine was about 97%. The amount of ammonia contained in the reaction liquid was 8.5 ppm. On the other hand, when $^1$H-NMR and $^{13}$C-NMR measurements were carried out on the component recovered in the storage tank 609, it was found to be a mixture of 4-phenyl phenol, 2-isopropyl phenol, urea and (4-phenylphenyl) carbamate, the content of 4-phenyl phenol was about 0.43 kg (2.52 mol), the content of 2-isopropyl phenol was about 6.18 kg (45.4 mol), the content of urea was about 625 g (10.4 mol), and the content of (4-phenylphenyl) carbamate was about 244 g (1.15 mol). In addition, a gas containing ammonia discharged from the gas-liquid separator 608 via the line 67 was recovered in a Tedlar bag and injected into a gas chromatograph with a gastight syringe to analyze the gas components. As a result, the amount of ammonia recovered per 10 minutes was 0.166 g (9.87 mmol). When the gas was analyzed by GC-MS, the amount of carbonyl groups contained in compounds having carbonyl groups contained in the ammonia was 0.0011 mmol.

When the steps (42-1) and (42-2) were continued to be carried out, clogging of the ammonia discharge line was not observed even after operating time had exceeded 380 days.

Step (42-3): Production of N-Substituted Carbamic Acid-O—Ar Ester by Reusing Mixture Obtained in Condenser The ammonia concentration in the mixture recovered in the storage tank 609 in step (42-2) was 75 ppm. The same method as step (42-1) was carried out by adding 0.788 kg of urea and 0.538 kg of 2-isopropyl phenol to the mixture, transferring to the stirring tank 603 and using 1.05 kg of 3-aminomethyl-3, 5,5-trimethylcyclohexylamine. A solution containing 9.1% by weight of isophorone bisurea was obtained. The same method as step (42-2) was carried out by using this solution instead of the solution of step (42-1). The reaction liquid recovered in the storage tank 610 contained 3-((4-(phenylphenoxy)carbonylamino-methyl)-3,5,5-trimethylcyclohexyl carbamic acid (4-phenylphenyl) ester, and the yield of 3-((4-(phenylphenoxy)carbonylamino-methyl)-3,5,5-trimethylcyclohexyl carbamic acid (4-phenylphenyl) ester based on 3-aminomethyl-3,5,5-trimethylcyclohexylamine was about 96%.

Step (42-4): Production of Isocyanate by Thermal Decomposition of N-Substituted Carbamic Acid-O—Ar Ester Production of isocyanate was carried out using the apparatus shown in FIG. 28.

The thin film distillation apparatus 802 was heated to 220° C. and the pressure within the thin film distillation apparatus was set to about 1.3 kPa. The reaction liquid recovered in the storage tank 105 in Example 42 was placed in the storage tank 801 and supplied to the thin film distillation apparatus at the rate of about 790 g/hr via the line 80. A liquid component was extracted from the line 82 provided in the bottom of the thin film distillation apparatus 802 and recovered in the storage tank 803. The liquid component recovered in the storage tank 803 was again supplied to the thin film distillation apparatus 802 through the line 83. A gaseous component containing isophorone diisocyanate, 2-isopropyl phenol and 4-phenyl phenol was extracted from the line 81 provided in the upper portion of the thin film distillation apparatus 802. The gaseous component was introduced into the distillation column 804, the 2-isopropyl phenol was separated by distillation, and a liquid phase was fed to the distillation column 809 from the line 88 provided at a portion of the distillation column 804 lower than the feed portion thereof. A gaseous phase component containing isophorone diisocyanate was extracted in the distillation column 809, condensed in the condenser 810, and a portion of the condensate was returned to the distillation column 809. Condensate was obtained in the storage tank 812 at the rate of about 94 g/hr.

When the condensate recovered in the storage tank 812 was analyzed by $^1$H-NMR and gas chromatography, it was found to be isophorone diisocyanate containing 11 ppm of 4-phenyl phenol. Although the isocyanate was stored for 630 days at normal temperatures in a nitrogen atmosphere, discoloration was not observed.

Example 43

Step (43-1): Production of Compound Having Ureido Groups

The same method as step (41-1) of Example 41 was carried out with the exception of using 3.86 kg of 2-tert-butyl phenol instead of 2-isopropyl phenol, using 2.30 kg of urea, and using 1.04 kg of 2,4-toluenediamine instead of hexamethylenediamine. As a result of analyzing the reaction liquid by liquid chromatography, the mixture was found to contain 5.1% by weight of 2,4-tolylenebisurea. 16.4 kg of p-heptyl phenol were added instead of 4-(1,1,3,3-tetramethylbutyl) phenol, and the mixture was transferred to the storage tank 604.

Step (43-2): Production of N-Substituted Carbamic Acid-O—Ar Ester

The packed column 605 was heated to 280° C., the internal pressure was set to 35 kPa and the condenser was held at 60° C. The same method as step (41-2) of Example 41 was carried out with the exception of feeding the reaction liquid obtained in step (43-1) instead of the reaction liquid obtained in step (41-1) at the rate of about 2.4 g/min. The amount of reaction liquid fed after the reaction had reached a steady state was about 21.4 kg. The amount of reaction liquid recovered in the storage tank 610 was 14.8 kg. When reaction liquid was analyzed by liquid chromatography and $^1$H-NMR, the reaction liquid was found to be a composition that contained toluene-2,4-di(carbamic acid (p-heptylphenyl) ester), and p-heptyl phenol at a stoichiometric ratio of 13.0 times, 2-tert-butyl phenol at a stoichiometric ratio of 0.054 times, and bis(p-heptylphenyl) carbonate at a stoichiometric ratio of 0.043 times based on toluene-2,4-di(carbamic acid (p-heptylphenyl) ester), and contained 0.0023 times an N-containing compound based on the number of toluene-2,4-di(carbamic acid (p-heptylphenyl) esters). In addition, the yield of toluene-2,4-di(carbamic acid (p-heptylphenyl) ester) based on 2,4-toluenediamine was about 60%. On the other hand, when $^1$H-NMR and $^{13}$C-NMR measurements were carried out on the component recovered in the storage tank 609, it was found to be a mixture of p-heptyl phenol, 2-tert-butyl phenol, urea and (p-heptylphenyl) carbamate, the content of p-heptyl phenol was about 0.154 kg (0.80 mol), the content of 2-tert-butyl phenol was about 3.58 kg (23.9 mol), the content of urea was about 1.14 kg (19.0 mol), and the content of (p-heptylphenyl) carbamate was about 493 g (2.09 mol). In addition, a gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.210 g (12.3 mmol). In addition, when the gas was analyzed by GC-MS, the amount of carbonyl groups contained in compounds having carbonyl groups contained in the ammonia was 0.0023 mmol.

When the steps (43-1) and (43-2) were continued to be carried out, clogging of the ammonia discharge line was not observed even after operating time had exceeded 380 days.

Step (43-3): Production of Isocyanate by Thermal Decomposition of N-Substituted Carbamic Acid-O—Ar Ester Production of isocyanate was carried out using the apparatus shown in FIG. 28.

The thin film distillation apparatus 802 was heated to 220° C. and the pressure within the thin film distillation apparatus was set to about 1.3 kPa. The reaction liquid recovered in the storage tank 105 in Example 43 was placed in the storage tank 801 and supplied to the thin film distillation apparatus at the rate of about 1430 g/hr via the line 80. A liquid component was extracted from the line 82 provided in the bottom of the thin film distillation apparatus 802 and recovered in the storage tank 803. The liquid component recovered in the storage tank 803 was again supplied to the thin film distillation apparatus 802 through the line 83. A gaseous component containing 2,4-tolylene diisocyanate, 2-tert-butyl phenol and p-heptyl phenol was extracted from the line 81 provided in the upper portion of the thin film distillation apparatus 802. The gaseous component was introduced into the distillation column 804, the 2-tert-butyl phenol was separated by distillation, and a liquid phase was fed to the distillation column 809 from the line 88 provided at a portion of the distillation column 804 lower than the feed portion thereof. A gaseous phase component containing 2,4-tolylene diisocyanate was extracted in the distillation column 809, condensed in the condenser 810, and a portion of the condensate was returned to the distillation column 809. Condensate was obtained in the storage tank 812 at the rate of about 73 g/hr.

When the condensate recovered in the storage tank 812 was analyzed by $^1$H-NMR and gas chromatography, it was found to be 2,4-tolylene diisocyanate containing 80 ppm of p-heptyl phenol. Although the isocyanate was stored for 630 days at normal temperatures in a nitrogen atmosphere, discoloration was not observed.

Example 44

Step (44-1): Production of Compound Having Ureido Groups

The same method as step (41-1) of Example 41 was carried out with the exception of using 4.19 kg of 2,6-diisopropyl phenol instead of 2-isopropyl phenol, using 1.17 kg of urea, and using 1.33 kg of 4,4'-methylenedianiline instead of hexamethylenediamine. 16.4 kg of p-nonyl phenol were added instead of 4-(1,1,3,3-tetramethylbutyl) phenol and the mixture was transferred to the storage tank 604. As a result of analyzing the reaction liquid by liquid chromatography, the mixture was found to contain 10.4% by weight of 4,4'-methanediyldiphenyldiurea.

Step (44-2): Production of N-Substituted Carbamic Acid-O—Ar Ester

The packed column 605 was heated to 280° C., the internal pressure was set to 26 kPa and the condenser was held at 60° C. The same method as step (41-2) was carried out with the exception of feeding the reaction liquid obtained in step (44-1) instead of the reaction liquid obtained in step (41-1) at the rate of about 1.6 g/min. The amount of reaction liquid fed after the reaction had reached a steady state was about 17.2 kg. The amount of reaction liquid recovered in the storage tank 610 was 12.3 kg. When reaction liquid was analyzed by liquid chromatography and $^1$H-NMR, the reaction liquid was found to be a composition that contained N,N'-(4,4'-methanediyl-diphenyl)-di(carbamic acid (p-nonylphenyl) ester), and p-nonyl phenol at a stoichiometric ratio of 6.38 times, 2,6-diisopropyl phenol at a stoichiometric ratio of 0.40 times, and bis(p-nonylphenyl) carbonate at a stoichiometric ratio of 0.038 times based on N,N'-(4,4'-methanediyl-diphenyl)-di(carbamic acid (p-nonylphenyl) ester), and contained 0.0078 times an N-containing compound based on the number of N,N'-(4,4'-methanediyl-diphenyl)-di(carbamic acid (p-nonylphenyl) esters). In addition, the yield of N,N'-(4,4'-methanediyl-diphenyl)-di(carbamic acid (p-nonylphenyl) ester) based on 4,4'-methylenedianiline was about 88%. The amount of ammonia contained in the reaction liquid was 4.9 ppm. On the other hand, when $^1$H-NMR and $^{13}$C-NMR measurements were carried out on the component recovered in the storage tank 609, it was found to be a mixture of p-nonyl phenol, 2,6-diisopropyl phenol, urea and (p-nonylphenyl) carbamate, the content of p-nonyl phenol was about 0.240 kg (1.05 mol), the content of 2,6-diisopropyl phenol was about 3.54 kg (19.9 mol), the content of urea was about 340 g (5.66 mol), and the content of (p-nonylphenyl) carbamate was about 105 g (0.40 mol). In addition, a gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.180 g (10.6 mmol). In addition, when the gas was analyzed by GC-MS, the amount of carbonyl groups contained in compounds having carbonyl groups contained in the ammonia was 0.0069 mmol.

When the steps (44-1) and (44-2) were continued to be carried out, clogging of the ammonia discharge line was not observed even after operating time had exceeded 380 days.

Step (44-3): Production of N-Substituted Carbamic Acid-O—Ar Ester by Reusing Mixture Obtained in Condenser The ammonia concentration in the mixture recovered in the storage tank 609 in step (44-2) was 43 ppm. The same method as step (44-1) was carried out by adding 0.884 kg of urea and 0.925 kg of 2,6-diisopropyl phenol to the mixture, transferring to the stirring tank 603 and using 1.42 kg of 4,4'-methylenedianiline. A solution containing 10.1% by weight of 4,4'-methanediyldiphenyldiurea was obtained. The same method as step (44-2) was carried out by using this solution instead of the solution of step (44-1). The reaction liquid recovered in the storage tank 610 contained N,N'-(4,4'-methanediyl-diphenyl)-di(carbamic acid (p-nonylphenyl) ester), and the yield of N,N'-(4,4'-methanediyl-diphenyl)-di(carbamic acid (p-nonylphenyl) ester) based on 4,4'-methylenedianiline was about 88%.

Step (44-4): Production of Isocyanate by Thermal Decomposition of N-Substituted Carbamic Acid-O—Ar Ester The apparatus shown in FIG. 29 was used.

The thin film distillation apparatus 1002 was heated to 220° C. and the pressure within the thin film distillation apparatus was set to about 1.3 kPa. The reaction liquid recovered in the storage tank 105 in Example 44 was placed in the storage tank 1001 and supplied to the thin film distillation apparatus at the rate of about 1090 g/hr via the line A1. A liquid component was extracted from the line A2 provided in the bottom of the thin film distillation apparatus 1002 and recovered in the storage tank 1003. The liquid component recovered in the storage tank 1003 was again supplied to the thin film distillation apparatus 1002 through the line A3. A gaseous component containing 4,4'-diphenylmethane diisocyanate, 2,6-diisopropyl phenol and 4-nonyl phenol was extracted from the line A4 provided in the upper portion of the thin film distillation apparatus 1002. The gaseous component was introduced into the distillation column 1004, the 2,6-diisopropyl phenol was separated by distillation, and a liquid phase was fed to the distillation column 1009 from the line A8 provided at a portion of the distillation column 1004 lower than the feed portion thereof. 4-nonyl phenol was separated by distillation in the distillation column 1009, and the liquid phase was fed to the distillation column 1014 through the line A12 provided at a portion of the distillation column 1009 lower than the feed portion thereof. A gaseous phase component containing 4,4'-diphenylmethane diisocyanate was extracted in the distillation column 1014, condensed in the condenser 1015, and a portion of the condensate was returned to the distillation column 1014. Condensate was obtained in the storage tank 1019 at the rate of about 110 g/hr.

When the condensate recovered in the storage tank 1019 was analyzed by $^1$H-NMR and gas chromatography, it was found to be 4,4'-diphenylmethane diisocyanate containing 105 ppm of 4-nonyl phenol. Although the isocyanate was stored for 630 days at normal temperatures in a nitrogen atmosphere, discoloration was not observed.

Example 45

Step (45-1): Production of Compound Having Ureido Groups

The same method as step (41-1) of Example 41 was carried out with the exception of using 6.23 kg of 2-tert-amyl phenol instead of 2-isopropyl phenol, using 1.44 kg of urea, and using 1.33 kg of 4,4'-methylenebis(cyclohexylamine) instead of hexamethylenediamine. 11.8 kg of 4-phenyl phenol were added instead of 4-(1,1,3,3-tetramethylbutyl) phenol and the mixture was transferred to the storage tank 604. As a result of analyzing the reaction liquid by liquid chromatography, the mixture was found to contain 9.0% by weight of 4,4'-methanediyldicyclohexyldiurea.

Step (45-2): Production of N-Substituted Carbamic Acid-O—Ar Ester

The packed column 605 was heated to 270° C., the internal pressure was set to 13 kPa and the condenser was held at 60° C. The same method as step (41-2) of Example 41 was carried out with the exception of feeding the reaction liquid obtained in step (45-1) instead of the reaction liquid obtained in step (41-1) at the rate of about 1.7 g/min. The amount of reaction liquid fed after the reaction had reached a steady state was about 19.1 kg. The amount of reaction liquid recovered in the storage tank 610 was 11.8 kg. When reaction liquid was analyzed by liquid chromatography and $^1$H-NMR, the reaction liquid was found to be a composition that contained N,N'-(4,4'-methanediyl-dicyclohexyl)-di(carbamic acid (4-phenylphenyl) ester), and 4-phenyl phenol at a stoichiometric ratio of 9.56 times, 2-tert-amyl phenol at a stoichiometric ratio of 0.068 times, and bis(4-phenylphenyl) carbonate at a stoichiometric ratio of 0.088 times based on N,N'-(4, 4'-methanediyl-dicyclohexyl)-di(carbamic acid (4-phenylphenyl) ester), and contained 0.0094 times an N-containing compound based on the number of N,N'-(4,4'-methanediyl-dicyclohexyl)-di(carbamic acid (4-phenylphenyl) esters). In addition, the yield of N,N'-(4,4'-methanediyl-dicyclohexyl)-di(carbamic acid (4-phenylphenyl) ester) based on 4,4'-methylenebis(cyclohexylamine) was about 88%. The amount of ammonia contained in the reaction liquid was 8.9 ppm. On the other hand, when $^1$H-NMR and $^{13}$C-NMR measurements were carried out on the component recovered in the storage tank 609, it was found to be a mixture of 4-phenyl phenol, 2-tert-amyl phenol, urea and (4-phenylphenyl) carbamate, the content of 4-phenyl phenol was about 0.275 kg (1.62 mol), the content of 2-tert-amyl phenol was about 5.71 kg (34.1 mol), the content of urea was about 590 g (9.84 mol), and the content of (4-phenylphenyl) carbamate was about 180 g (0.84 mol). In addition, a gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.164 g (9.67 mmol). In addition, when the gas was analyzed by GC-MS, the amount of carbonyl groups contained in compounds having carbonyl groups contained in the ammonia was 0.0033 mmol.

When the steps (45-1) and (45-2) were continued to be carried out, clogging of the ammonia discharge line was not observed even after operating time had exceeded 380 days.

Step (45-3): Production of N-Substituted Carbamic Acid-O—Ar Ester by Reusing Mixture Obtained in Condenser The ammonia concentration in the mixture recovered in the storage tank 609 in step (45-2) was 42 ppm. The same method as step (45-1) was carried out by adding 1.32 kg of urea to the mixture, transferring to the stirring tank 603 and using 1.22 kg of 4,4'-methylenebis(cyclohexylamine). A solution containing 9.2% by weight of 4,4'-methanediyldicyclohexyldiurea was obtained. The same method as step (45-2) was carried out by using this solution instead of the solution of step (45-1). The reaction liquid recovered in the storage tank 610 contained N,N'-(4,4'-methanediyl-dicyclohexyl)-di(carbamic acid (4-phenylphenyl) ester), and the yield of N,N'-(4,4'-methanediyl-dicyclohexyl)-di(carbamic acid (4-phenylphenyl) ester) based on 4,4'-methylenebis(cyclohexylamine) was about 88%.

Step (45-4): Production of Isocyanate by Thermal Decomposition of N-Substituted Carbamic Acid-O—Ar Ester The apparatus shown in FIG. 29 was used.

The thin film distillation apparatus 1002 was heated to 220° C. and the pressure within the thin film distillation apparatus was set to about 1.3 kPa. The reaction liquid recovered in the storage tank 105 in Example 45 was placed in the storage tank 1001 and supplied to the thin film distillation apparatus at the rate of about 1120 g/hr via the line A1. A liquid component was extracted from the line A2 provided in the bottom of the thin film distillation apparatus 1002 and recovered in the storage tank 1003. The liquid component recovered in the storage tank 1003 was again supplied to the thin film distillation apparatus 1002 through the line A3. A gaseous component containing dicyclohexylmethane diisocyanate, 2-tert-amyl phenol and 4-phenyl phenol was extracted from the line A4 provided in the upper portion of the thin film distillation apparatus 1002. The gaseous component was introduced into the distillation column 1004, the 2-tert-amyl phenol was separated by distillation, and a liquid phase was fed to the distillation column 1009 from the line A8 provided at a portion of the distillation column 1004 lower than the feed portion thereof. 4-phenyl phenol was separated by distillation in the distillation column 1009, and the liquid phase was fed to the distillation column 1014 through the line A12 provided at a portion of the distillation column 1009 lower than the feed portion thereof. A gaseous phase component containing dicyclohexylmethane diisocyanate was extracted in the distillation column 1014, condensed in the condenser 1015, and a portion of the condensate was returned to the distillation column 1014. Condensate was obtained in the storage tank 1019 at the rate of about 111 g/hr.

When the condensate recovered in the storage tank 1019 was analyzed by $^1$H-NMR and gas chromatography, it was found to be dicyclohexylmethane diisocyanate containing 80 ppm of 4-phenyl phenol. Although the isocyanate was stored for 630 days at normal temperatures in a nitrogen atmosphere, discoloration was not observed.

Example 46

Step (46-1): Production of Compound Having Ureido Groups

The apparatus used in FIG. 24 was used.

16.7 kg of a solvent (1-nonanol) and 3.34 kg of urea were mixed in the storage tank 401 heated to 90° C. with the line 43 closed, and the mixed liquid was transferred to the stirring tank 403 heated to 90° C. While stirring the stirring tank 403, 1.08 kg of aniline were supplied from the storage tank 402 to the stirring tank 403 through a line 42 at the rate of about 12 g/min. After finishing supplying the aniline, stirring was carried out for about 28 hours followed by sampling the reaction liquid. As a result of analyzing the reaction liquid by liquid chromatography, the reaction liquid was found to contain about 6.8% by weight of phenylurea. The ammonia concentration in the reaction liquid was 7900 ppm. Unreacted amino groups were not detected. After the reaction, 25.9 kg of an aromatic hydroxy compound in the form of 2-phenyl phenol were added to obtain a mixed liquid. The ratio of the number of aromatic hydroxy compounds to the number of ureido groups in the mixed liquid was 6.6. The line 43 was then opened and the mixed liquid was transferred to the storage tank 404 through the line 43.

Step (46-2): Production of N-Substituted Carbamic Acid Mono(—O—R$^2$ Ester)

The packed column 405 packed with a packing (Helipack No. 3) was heated to 210° C., and the pressure inside the column was set to 50 kPa. The reaction liquid obtained in step (46-1) was fed at the rate of about 1.2 g/min from the line 44 provided in the packed column 405. Since the reaction is initially in an unsteady state, the sample at that time was discarded. The amount of reaction liquid fed after the reaction had reached a steady state was about 29.6 kg. The reaction liquid was recovered in the storage tank 410 through the line 46 provided in the bottom of the packed column 405. A gaseous phase component was condensed from the line 45 provided in the top of the packed column 405 with the condenser 406, and the resulting liquid phase component was recovered in the storage tank 409 via the gas-liquid separator 408. When the condensed component recovered in the storage tank 409 was analyzed by $^1$H-NMR, the condensed component was found to contain urea and 1-nonanol. The stoichiometric ratio of 1-nonanol to urea was 3.4. The amount of reaction liquid recovered in a storage tank 410 was 15.7 kg. When the reaction liquid was analyzed by liquid chromatography and $^1$H-NMR, it was found to contain N-phenyl carbamic acid-(nonylester), and the yield of N-phenyl carbamic acid-(nonylester) based on aniline was about 91%. On the other hand, a gas containing ammonia was discharged from the gas-liquid separator 408 via the line 47. The gas was recovered in a Tedlar bag and injected into a gas chromatograph with a gastight syringe to analyze the gas components. As a result, the amount of ammonia recovered per 10 minutes was 0.139 g (8.2 mmol). In addition, when the gas was analyzed by GC-MS, the amount of carbonyl groups contained in compounds having carbonyl groups contained in the ammonia was 0.0022 mmol.

Step (46-3): Production of N-Substituted Carbamic Acid Mono(—O—Ar Ester) by a Transesterification Reaction The apparatus shown in FIG. 31 was used.

The mixture obtained in step (46-2) was recovered in a storage tank 1201. A packed column 1202 packed with a packing (Helipack No. 3), having an inner diameter of 20 mm and having a height of 4000 mm was heated to 260° C., and the pressure inside the column was set to 26 kPa. The reaction liquid obtained in step (46-2) was fed from a line C1 provided in a packed column 1202 at the rate of about 1.9 g/min. The reaction liquid was recovered in a storage tank 1205 through a line C4 provided in the bottom of the packed column 1202. A gaseous phase component was introduced into a condenser 1203 from a line C3 provided in the top of the packed column 1202, and the resulting liquid phase component was recovered in a storage tank 1204 through a gas-liquid separator 1207. The amount of reaction liquid recovered in the storage tank 1205 was 26.8 kg. When the reaction liquid was analyzed by liquid chromatography and $^1$H-NMR, the reaction liquid was found to be a solution that contained N-phenyl carbamic acid-((2-phenylphenyl) ester), and the yield of N-phenyl carbamic acid-((2-phenylphenyl) ester) based on aniline was about 89%.

When the steps (46-1) and (46-3) were continued to be carried out, clogging of the ammonia discharge line was not observed even after operating time had exceeded 380 days.

Step (46-4): Condensation of N-Substituted Carbamic Acid Mono(—O—Ar Ester)

The apparatus shown in FIG. 30 was used.

The reaction liquid recovered in the storage tank 1205 in step (46-3) was charged into the stirring tank 1108. The stirring tank 1108 was heated to 160° C. and the internal pressure was set to 1 kPa to distill 2-phenyl phenol. The 2-phenyl phenol was condensed in the condenser 1105 via the line B4 and recovered in the storage tank 1107. Next, 2.04 kg of methylal from the storage tank 1100, 1.94 kg of nitrobenzole from the storage tank 1101 and 1.02 kg of sulfuric acid from the storage tank 1102 were added to the stirring tank 1108 followed by heating for 24 hours at 90° C. while stirring the stirring tank 1108. The pressure inside the stirring tank 1108 was then reduced to distill off solvent and unreacted substances. When the resulting compound was analyzed by liquid chromatography, it was found to be a mixture containing about 53% by weight of N,N'-(methanediyl-diphenyl)-bis(carbamic acid(2-phenylphenyl) ester).

Step (46-5): Production of Isocyanate by Thermal Decomposition of N-Substituted Carbamic Acid-O-Aryl Ester The apparatus shown in FIG. 29 was used.
A thin film distillation apparatus 1002 (Kobelco Eco-Solutions Co., Ltd., Japan) having a heat-conducting surface area of 0.2 m$^2$ was heated to 260° C. and the pressure within the thin film distillation apparatus was set to about 1.5 kPa. The reaction liquid recovered in the storage tank 1104 in step (46-4) was placed in the storage tank 1001 and supplied to the thin film distillation apparatus at the rate of about 1200 g/hr via the line A1. A liquid component was extracted from the line A4 provided in the bottom of thin film distillation apparatus 1002 and recovered in the storage tank 1003. The liquid component recovered in the storage tank 1003 was again supplied to the thin film distillation apparatus 1002 through the line A3. A gaseous component was extracted from the line A4 provided in the upper portion of the thin film distillation apparatus 1002. The gaseous component was introduced into the distillation column 1004, and low boiling components were separated by distillation. A liquid phase component was supplied to the distillation column 1009 from the line A8 provided at a portion of the distillation column 1004 lower than the feed line and further subjected to distillative separation. The liquid phase component was supplied to the distillation column 1014 from the line A12 provided at a portion of the distillation column 1009 lower than the feed line and further subjected to distillative separation.

A gaseous component was extracted from the line A13 provided in the top of the distillation column 1014 and condensed in the condenser 1015, and the condensate was recovered in the storage tank 1019. When the condensate was analyzed by $^1$H-NMR, it was found to be a solution containing about 99% by weight of 4,4'-diphenylmethane diisocyanate (MDI). The yield based on aniline was about 54%.

Example 47

Step (47-1): Production of Compound Having Ureido Groups

The apparatus used in FIG. 24 was used.
25.4 kg of a solvent (1-heptanol) and 3.50 kg of urea were mixed in the storage tank 401 heated to 90° C. with the line 43 closed, and the mixed liquid was transferred to the stirring tank 403 heated to 90° C. While stirring the stirring tank 403, 1.13 kg of aniline were supplied from the storage tank 402 to the stirring tank 403 through the line 42 at the rate of about 18 g/min. After finishing supplying the aniline, stirring was carried out for about 28 hours followed by sampling the reaction liquid. As a result of analyzing the reaction liquid by liquid chromatography, the reaction liquid was found to contain about 7.4% by weight of phenylurea. The ammonia concentration in the reaction liquid was 8300 ppm. Unreacted amino groups were not detected.

The line 43 was then opened and the reaction liquid was transferred to the storage tank 404 through the line 43.

Step (47-2): Production of N-Substituted Carbamic Acid Mono(—O—R$^2$ Ester)

The packed column 405 packed with a packing (Helipack No. 3) and having an inner diameter of 40 mm and height of 4000 mm was heated to 190° C., and the pressure inside the column was set to 50 kPa. The reaction liquid obtained in step (47-1) was fed at the rate of about 1.0 g/min from the line 44 provided in the packed column 405. Since the reaction is initially in an unsteady state, the sample at that time was discarded. The amount of reaction liquid fed after the reaction had reached a steady state was about 28.0 kg. The reaction liquid was recovered in the storage tank 410 through the line 46 provided in the bottom of the packed column 405. A gaseous phase component was condensed from the line 45 provided in the top of the packed column 405 with the condenser 406, and the resulting liquid phase component was recovered in the storage tank 409 via the gas-liquid separator 408. When the condensed component recovered in the storage tank 409 was analyzed by $^1$H-NMR, the condensed component was found to contain urea and 1-heptanol. The stoichiometric ratio of 1-heptanol to urea was 4.2. The amount of reaction liquid recovered in a storage tank 410 was 13.8 kg. When the reaction liquid was analyzed by liquid chromatography and $^1$H-NMR, it was found to contain N-phenyl carbamic acid-(1-heptyl) ester, and the yield of N-phenyl carbamic acid-(1-heptyl) ester based on aniline was about 90%. On the other hand, a gas containing ammonia was discharged from the gas-liquid separator 408 via the line 47. The gas was recovered in a Tedlar bag and injected into a gas chromatograph with a gastight syringe to analyze the gas components. As a result, the amount of ammonia recovered per 10 minutes was 0.151 g (8.9 mmol). In addition, when the gas was analyzed by GC-MS, the amount of carbonyl groups contained in compounds having carbonyl groups contained in the ammonia was 0.0022 mmol.

When the steps (47-1) and (47-2) were continued to be carried out, clogging of the ammonia discharge line was not observed even after operating time had exceeded 380 days.

Step (47-3): Condensation of N-Substituted Carbamic Acid Mono(—O—R$^2$ Ester)

The apparatus shown in FIG. 30 was used.
The reaction liquid recovered in the storage tank 410 in step (47-2) was charged into the stirring tank 1108. The stirring tank 1108 was heated to 160° C. and the internal pressure was set to 10 kPa to distill 1-heptanol. The 1-heptanol was condensed in the condenser 1105 via the line B4 and recovered in the storage tank 1107. Next, 1.30 kg of methylal from the storage tank 1100, 7.34 kg of nitrobenzole from the storage tank 1101 and 13.3 kg of sulfuric acid from the storage tank 1102 were added to the stirring tank 1108 followed by heating for 10 hours at 100° C. while stirring the stirring tank 1108. The pressure inside the stirring tank 1008 was then reduced to distill off solvent and unreacted substances. When the resulting compound was analyzed by liquid chromatography, it was found to be a mixture containing about 63% by weight of N,N'-(methanediyl-diphenyl)-bis(carbamic acid octyl ester).

Step (47-4): Production of N-Substituted Carbamic Acid-O—Ar Ester by a Transesterification Reaction The apparatus shown in FIG. 31 was used.
The mixture obtained in step (47-3) was mixed with 24.2 kg of 2,4-di-tert-amyl phenyl (Tokyo Chemical Industry Co., Ltd., Japan) and charged into the storage tank 1201. A packed column 1202 packed with a packing (Helipack No. 3), having an inner diameter of 20 mm and having a height of 4000 mm was heated to 250° C., and the pressure inside the column was set to 20 kPa. The reaction liquid obtained in step (47-3) was fed from the line C1 provided in the packed column 1202 at the rate of about 1.3 g/min. The reaction liquid was recovered in the storage tank 1205 through the line C4 provided in the bottom of the packed column 1202. A gaseous phase component was introduced into the condenser 1203 from the line C3 provided in the top of the packed column 1202, and the resulting liquid phase component was recovered in the storage tank 1204 through the gas-liquid separator 1207. The amount of reaction liquid recovered in the storage tank 1205 was 25.0 kg. When the reaction liquid was analyzed by liquid chromatography and $^1$H-NMR, the reaction liquid was found to be a solution that contained N,N'-(methanediyl-diphenyl)-bis(carbamic acid-(2,4-di-tert-amylphenyl) ester).

Step (47-5): Production of Isocyanate by Thermal Decomposition of N-Substituted Carbamic Acid-O-Aryl Ester The apparatus shown in FIG. 29 was used.

The thin film distillation apparatus 1002 (Kobelco Eco-Solutions Co., Ltd., Japan) having a heat-conducting surface area of 0.2 m$^2$ was heated to 260° C. and the pressure within the thin film distillation apparatus was set to about 1.5 kPa. The reaction liquid recovered in the storage tank 1204 in step (47-4) was placed in the storage tank 1001 and supplied to the thin film distillation apparatus at the rate of about 1200 g/hr via the line A1. A liquid component was extracted from the line A2 provided in the bottom of thin film distillation apparatus 1002 and recovered in the storage tank 1003. The liquid component recovered in the storage tank 1003 was again supplied to the thin film distillation apparatus 1002 through the line A3. A gaseous component was extracted from the line A4 provided in the upper portion of the thin film distillation apparatus 1002. The gaseous component was introduced into the distillation column 1004, and low boiling components were separated by distillation. A liquid phase component was supplied to the distillation column 1009 from the line A8 provided at a portion of the distillation column 1004 lower than the feed line and further subjected to distillative separation. The liquid phase component was supplied to the distillation column 1014 from the line A12 provided at a portion of the distillation column 1009 lower than the feed line and further subjected to distillative separation.

A gaseous component was extracted from the line A13 provided in the top of the distillation column 1014 and condensed in the condenser 1015, and the condensate was recovered in the storage tank 1019. When the condensate was analyzed by $^1$H-NMR, it was found to be a solution containing about 47% by weight of 4,4'-diphenylmethane diisocyanate. The yield based on aniline was about 47%.

Example 48

Step (48-1): Urea Regeneration Step

Example 1 was carried out repeatedly, and ammonia obtained from the line 5 in step (1-1) was recovered in the form of liquid ammonia by using a liquefaction apparatus.

The liquid ammonia pressurized to 17.6 MPa and heated to 150° C. at 3.44 kg/hr, carbon dioxide pressurized to 17.6 MPa at 2.20 kg/hr, and a condensate to be described later were supplied to a urea synthesis tube 1401 and reacted at 190° C.

The urea synthesis solution discharged from the urea synthesis tube was supplied to a high-pressure disintegrator 1402 while simultaneously contacting with carbon dioxide supplied at the rate of 2.20 kg/hr from a line 21 to decompose unconverted substances at 195° C., and a gaseous mixture containing ammonia at 4.26 kg/hr, carbon dioxide at 2.43 kg/hr and water at 0.50 kg/hr was separated from an aqueous urea solution containing urea at 6.0 kg/hr, ammonia at 2.88 kg/hr, carbon dioxide at 2.34 kg/hr and water at 3.01 kg/hr. The aqueous urea solution was depressurized to 1.76 MPa and further depressurized to 0.20 MPa to separate residual unconverted substances and then applied to final treatment to obtain urea at the rate of 6.0 kg/hr. The separated unconverted substances were adsorbed by water to obtain an aqueous ammonium carbamate solution at 1.76 MPa containing ammonia at 2.84 kg/hr, carbon dioxide at 2.34 kg/hr and water at 1.21 kg/hr.

The aforementioned gaseous mixture was supplied to a condenser 1403 to aspirate and pressurize the aqueous ammonium carbamate solution pressurized to 17.6 MPa. The resulting condensate was recirculated to the urea synthesis tube 1401.

Step (48-2): Reuse of Regenerated Urea

The same method as step (1-1) of Example 1 was carried out with the exception of using 240 g of hexamethylenediamine, 8510 g of 4-(1,1,3,3-tetramethylbutyl) phenol and 501 g of the urea produced in step (48-1). The yield of N,N'-hexanediyl-dicarbamic acid-bis(4-(1,1,3,3-tetramethylbutyl) phenyl) ester based on hexamethylenediamine was about 92%.

Example 49

Step (49-1): Production of N-Substituted Carbamic Acid-O—Ar Ester

Production of urethane was carried out in a reactor as shown in FIG. 21.

1.22 kg of hexamethylenediamine, 43.3 kg of 4-(1,1,3,3-tetramethylbutyl) phenol and 2.40 kg of urea were mixed to prepare a raw material solution. The packed column 102 was heated to 240° C. and the pressure inside the column was set to about 60 kPa. A mixed liquid having the same composition as the raw material solution was introduced through the line 1 provided in the upper portion of the packed column 102, and after operating conditions had stabilized, the raw material solution was introduced at about 1.5 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 90° C., and the resulting component was recovered in the storage tank 104. When 10 hours had elapsed after operating conditions had stabilized, the component recovered in the storage tank 104 was sampled, and when $^1$H-NMR and $^{13}$C-NMR measurements were carried out on the sampled component, it was found to be a mixture of 4-(1,1,3,3-tetramethylbutyl) phenol and urea, and the stoichiometric ratio of 4-(1,1,3,3-tetramethylbutyl) phenol to urea was 2.5. A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.253 g (14.9 mmol). In addition, when the gas was analyzed by GC-MS, the amount of carbonyl groups contained in compounds having carbonyl groups contained in the ammonia was 0.447 mmol. The reaction liquid obtained in the storage tank 105 contained N,N'-hexanediyl-di(carbamic acid (4-(1,1,3,3-tetramethylbutyl)phe-

249 nyl) ester), and the yield of N,N'-hexanediyl-di(carbamic acid (4-(1,1,3,3-tetramethylbutyl)phenyl) ester) based on hexamethylenediamine was about 90%. The reaction liquid contained 8.8 ppm of ammonia.

When the above step was continued to be carried out, the ammonia discharge line became clogged after operating time had exceeded 330 days.

Example 50

Step (50-1): Production of N-Substituted Carbamic Acid-O—Ar Ester

The same method as step (49-1) of Example 49 was carried out with the exception of using 1.33 kg of hexamethylenediamine, 47.2 kg of 4-(1,1,3,3-tetramethylbutyl) phenol and 2.61 kg of urea, and holding the condenser 103 to about 105° C. When 10 hours had elapsed after operating conditions had stabilized, the component recovered in the storage tank 104 was sampled, and when $^1$H-NMR and $^{13}$C-NMR measurements were carried out on the sampled component, it was found to be a mixture of 4-(1,1,3,3-tetramethylbutyl) phenol and urea, and the stoichiometric ratio of 4-(1,1,3,3-tetramethylbutyl) phenol to urea was 3.1. A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.251 g (14.8 mmol). In addition, when the gas was analyzed by GC-MS, the amount of carbonyl groups contained in compounds having carbonyl groups contained in the ammonia was 1.33 mmol. The reaction liquid obtained in the storage tank 105 contained N,N'-hexanediyl-di(carbamic acid (4-(1,1,3,3-tetramethylbutyl)phenyl) ester), and the yield of N,N'-hexanediyl-di(carbamic acid (4-(1,1,3,3-tetramethylbutyl)phenyl) ester) based on hexamethylenediamine was about 90%. The reaction liquid contained 8.8 ppm of ammonia.

When the above step was continued to be carried out, the ammonia discharge line became clogged after operating time had exceeded 302 days.

Example 51

Step (51-1): Production of N-Substituted Carbamic Acid-O—Ar Ester

The same method as step (49-1) of Example 49 was carried out with the exception of using 1.23 kg of hexamethylenediamine, 43.6 kg of 4-(1,1,3,3-tetramethylbutyl) phenol and 2.42 kg of urea, and holding the condenser 103 to about 110° C. When 10 hours had elapsed after operating conditions had stabilized, the component recovered in the storage tank 104 was sampled, and when $^1$H-NMR and $^{13}$C-NMR measurements were carried out on the sampled component, it was found to be a mixture of 4-(1,1,3,3-tetramethylbutyl) phenol and urea, and the stoichiometric ratio of 4-(1,1,3,3-tetramethylbutyl) phenol to urea was 3.2. A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.255 g (15.0 mmol). In addition, when the gas was analyzed by GC-MS, the amount of carbonyl groups contained in compounds having carbonyl groups contained in the ammonia was 2.89 mmol.

250

The reaction liquid obtained in the storage tank 105 contained N,N'-hexanediyl-di(carbamic acid (4-(1,1,3,3-tetramethylbutyl)phenyl) ester), and the yield of N,N'-hexanediyl-di(carbamic acid (4-(1,1,3,3-tetramethylbutyl)phenyl) ester) based on hexamethylenediamine was about 90%. The reaction liquid contained 8.8 ppm of ammonia.

When the above step was continued to be carried out, the ammonia discharge line became clogged after operating time had exceeded 245 days.

Example 52

Step (52-1): Production of N-Substituted Carbamic Acid-O—Ar Ester

Production of urethane was carried out in a reactor as shown in FIG. 21.

1.14 kg of hexamethylenediamine, 40.4 kg of 4-(1,1,3,3-tetramethylbutyl) phenol and 2.24 kg of urea were mixed to prepare a raw material solution. The packed column 102 was heated to 240° C. and the pressure inside the column was set to about 60 kPa. A mixed liquid having the same composition as the raw material solution was introduced through the line 1 provided in the upper portion of the packed column 102, and after operating conditions had stabilized, the raw material solution was introduced at about 1.5 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 125° C., and the resulting component was recovered in the storage tank 104. When 10 hours had elapsed after operating conditions had stabilized, the component recovered in the storage tank 104 was sampled, and when $^1$H-NMR and $^{13}$C-NMR measurements were carried out on the sampled component, it was found to be a mixture of 4-(1,1,3,3-tetramethylbutyl) phenol and urea, and the stoichiometric ratio of 4-(1,1,3,3-tetramethylbutyl) phenol to urea was 2.56. A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.24 g (14.4 mmol). In addition, when the gas was analyzed by GC-MS, the amount of carbonyl groups contained in compounds having carbonyl groups contained in the ammonia was 5.76 mmol.

The reaction liquid obtained in the storage tank 105 contained N,N'-hexanediyl-di(carbamic acid (4-(1,1,3,3-tetramethylbutyl)phenyl) ester), and the yield of N,N'-hexanediyl-di(carbamic acid (4-(1,1,3,3-tetramethylbutyl)phenyl) ester) based on hexamethylenediamine was about 90%. The reaction liquid contained 8.8 ppm of ammonia.

When the above step was continued to be carried out, the ammonia discharge line became clogged after operating time had exceeded 221 days.

Example 53

Step (53-1): Production of N-Substituted Carbamic Acid-O—Ar Ester

Production of urethane was carried out in a reactor as shown in FIG. 1.

1.38 kg of 3-aminomethyl-3,5,5-trimethylcyclohexylamine, 42.5 kg of p-dodecyl phenol and 1.85 kg of urea were mixed to prepare a raw material solution. The packed column 102 was heated to 255° C. and the pressure inside the column was set to 30 kPa. A mixed liquid having the same composition as the raw material solution was introduced through the line 1 provided in the upper portion of the packed column 102, and after operating conditions had stabilized, the raw material solution was introduced at about 1.5 g/min, and the reaction liquid was recovered in the storage tank 105 via the line 4 provided in the bottom of the packed column 102. The solution recovered in the storage tank 105 contained 3-((p-dodecylphenoxy)carbonylamino-methyl)-3,5,5-trimethylcyclohexylcarbamic acid (p-dodecylphenyl) ester, and the yield of 3-((p-dodecylphenoxy)carbonylamino-methyl)-3,5,5-trimethylcyclohexylcarbamic acid (p-dodecylphenyl) ester based on 3-aminomethyl-3,5,5-tricyclohexylamine was about 91%. The reaction liquid contained 8.8 ppm of ammonia. A gaseous phase component was recovered from the line 2 provided in the top of the packed column 102, condensed in the condenser 103 held at about 60° C., and the resulting component was recovered in the storage tank 104. When 10 hours had elapsed after operating conditions had stabilized, the component recovered in the storage tank 104 was sampled, and when $^1$H-NMR and $^{13}$C-NMR measurements were carried out on the sampled component, it was found to be a mixture of p-dodecyl phenol and urea, and the stoichiometric ratio of p-dodecyl phenol to urea was 2.23. A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.24 g (13.7 mmol). In addition, when the gas was analyzed by GC-MS, the amount of carbonyl groups contained in compounds having carbonyl groups contained in the ammonia was 0.34 mmol.

When the above step was continued to be carried out, the ammonia discharge line became clogged after operating time had exceeded 311 days.

Example 54

Step (54-1): Production of N-Substituted Carbamic Acid-O—Ar Ester

Production of urethane was carried out in a reactor as shown in FIG. 21.

1.22 kg of 3-aminomethyl-3,5,5-trimethylcyclohexylamine, 37.6 kg of p-dodecyl phenol and 1.64 kg of urea were mixed to prepare a raw material solution. The packed column 102 was heated to 240° C. and the pressure inside the column was set to 35 kPa. A mixed liquid having the same composition as the raw material solution was introduced through the line 1 provided in the upper portion of the packed column 102, and after operating conditions had stabilized, the raw material solution was introduced at about 1.5 g/min, and the reaction liquid was recovered in the storage tank 105 via the line 4 provided in the bottom of the packed column 102. The solution recovered in the storage tank 105 contained 3-((p-dodecylphenoxy)carbonylamino-methyl)-3,5,5-trimethylcyclohexylcarbamic acid (p-dodecylphenyl) ester, and the yield of 3-((p-dodecylphenoxy)carbonylamino-methyl)-3,5,5-trimethylcyclohexylcarbamic acid (p-dodecylphenyl) ester based on 3-aminomethyl-3,5,5-trimethylcyclohexylamine was about 91%. The reaction liquid contained 7.9 ppm of ammonia. A gaseous phase component was recovered from the line 2 provided in the top of the packed column 102, condensed in the condenser 103 held at about 50° C., and the resulting component was recovered in the storage tank 104. When 10 hours had elapsed after operating conditions had stabilized, the component recovered in the storage tank 104 was sampled, and when $^1$H-NMR and $^{13}$C-NMR measurements were carried out on the sampled component, it was found to be a mixture of p-dodecyl phenol and urea, and the stoichiometric ratio of p-dodecyl phenol to urea was 2.23. A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.19 g (11.3 mmol). In addition, the amount of carbonyl groups contained in compounds having carbonyl groups contained in the ammonia was 0.170 mmol.

When the above step was continued to be carried out, clogging of the ammonia discharge line was not observed even after operating time had exceeded 380 days.

Example 55

Step (55-1): Production of N-Substituted Carbamic Acid-O—Ar Ester

Production of urethane was carried out in a reactor as shown in FIG. 21.

1.10 kg of hexamethylenediamine, 33.0 kg of 1-nonanol and 2.10 kg of urea were mixed to prepare a raw material solution. The packed column 102 was heated to 220° C., the pressure inside the column was set to about 50 kPa, a mixed liquid having the same composition as the raw material solution was introduced through the line 1 provided in the upper portion of the packed column 102, and after operating conditions had stabilized, the raw material solution was introduced at about 1.8 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 50° C., and the resulting component was recovered in the storage tank 104. The amount of reaction liquid recovered in the storage tank 105 was 31.3 kg. When the reaction liquid was analyzed by liquid chromatography and $^1$H-NMR, the reaction liquid was found to contain N,N'-hexanediyl-di(carbamic acid nonyl ester), and the yield of N,N'-hexanediyl-di (carbamic acid nonyl ester) based on hexamethylenediamine was about 91%. The reaction liquid contained 7.5 ppm of ammonia. On the other hand, when $^1$H-NMR and $^{13}$C-NMR measurements were carried out on the component recovered in the storage tank 104, it was found to be a mixture of 1-nonanol and urea, the content of urea was about 1.47 kg (24.5 mol), and the content of 1-nonanol was 4.13 kg (28.6 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.42 g (23.6 mmol). In addition, the amount of carbonyl groups contained in compounds having carbonyl groups contained in the ammonia was 22.4 mmol.

When the above step (55-1) was continued to be carried out, the ammonia discharge line became clogged after operating time had exceeded 172 days.

Step (55-2): Reuse of Mixture Obtained in Condenser

Production of N-substituted carbamic acid-O—Ar ester was carried out using the mixture recovered in the storage tank 104 in step (55-1).

1.33 kg of hexamethylenediamine, 29.0 kg of 1-nonanol and 1.14 kg of urea were added to the mixture recovered in the storage tank 104 in step (55-1) to obtain a raw material solution. The same method as step (55-1) was carried out using this raw material solution. The yield of N,N'-hexanediyl-di (carbamic acid nonyl ester) based on hexamethylenediamine was about 91%.

Step (55-3): Transesterification Reaction

Figure 31:
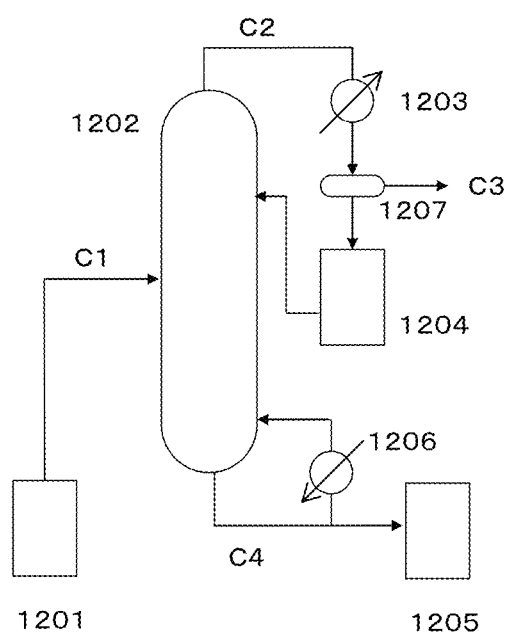
FIG. 31 shows a conceptual drawing of a transesterification reaction apparatus used in an example of the present embodiment.

The apparatus shown in FIG. 31 was used.
21.5 kg of 4-(1,1,3,3-tetramethylbutyl) phenol were added to the mixture obtained in step (55-2) to obtain a homogeneous solution and then charged into the storage tank 1201. A packed column 1202 packed with a packing (Helipack No. 3), having an inner diameter of 20 mm and having a height of 4000 mm was heated to 260° C., and the pressure inside the column was set to 26 kPa. The reaction liquid stored in the storage tank 1204 was fed from the line C1 provided in the packed column 1202 at the rate of about 2.0 g/min. The reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained N,N'-hexanediyl-di(carbamic acid (4-(1,1,3,3-tetramethylbutyl) phenyl ester, and the yield of N,N'-(hexanediyl-di(carbamic acid (4-(1,1,3,3-tetramethylbutyl)phenyl) ester based on hexamethylenediamine was about 89%.

Step (55-4): Production of Isocyanate

The same method as Example 1 was carried out with the exception of heating the thin film distillation apparatus 702 to 220° C., setting the pressure within the thin film distillation apparatus to about 1.3 kPa and supplying the reaction liquid recovered in step (55-3) instead of the reaction liquid recovered in storage tank 105 in Example 1 to the thin film distillation apparatus at the rate of about 1790 g/hr. A condensate was obtained in the storage tank 707 at the rate of about 101 g/hr. The condensate was hexamethylene diisocyanate. The hexamethylene diisocyanate was further purified by distillation, and hexamethylene diisocyanate was obtained in which 4-(1,1,3,3-tetramethylbutyl) phenol was not detected (below the detection limit) by gas chromatography analysis. Although the isocyanate was stored for 630 days at normal temperatures in a nitrogen atmosphere, discoloration was not observed.

Example 56

Step (56-1): Production of N-Substituted Carbamic Acid-O—Ar Ester

Production of urethane was carried out in a reactor as shown in FIG. 21.
0.630 kg of hexamethylenediamine, 53.0 kg of 2-phenylethanol and 1.30 kg of urea were mixed to prepare a raw material solution. The packed column 102 was heated to 220° C., the pressure inside the column was set to about 50 kPa, a mixed liquid having the same composition as the raw material solution was introduced through the line 1 provided in the upper portion of the packed column 102, and after operating conditions had stabilized, the raw material solution was introduced at about 1.8 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 40° C., and the resulting component was recovered in the storage tank 104. The amount of reaction liquid recovered in the storage tank 105 was 43.3 kg. When the reaction liquid was analyzed by liquid chromatography and $^1$H-NMR, the reaction liquid was found to contain N,N'-hexanediyl-di(carbamic acid (2-phenylethyl) ester), and the yield of N,N'-hexanediyl-di(carbamic acid (2-phenylethyl) ester) based on hexamethylenediamine was about 91%. The reaction liquid contained 5.5 ppm of ammonia. On the other hand, when $^1$H-NMR and $^{13}$C-NMR measurements were carried out on the component recovered in the storage tank 104, it was found to be a mixture of 2-phenylethanol and urea, the content of urea was about 0.763 kg (12.7 mol), and the content of 2-phenylethanol was 11.7 kg (95.4 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.182 g (10.7 mmol). In addition, the amount of carbonyl groups contained in compounds having carbonyl groups contained in the ammonia was 0.755 mmol.

When the above step (56-1) was continued to be carried out, the ammonia discharge line became clogged after operating time had exceeded 320 days.

Step (56-2): Reuse of Mixture Obtained in Condenser

Production of N-substituted carbamic acid-O—Ar ester was carried out using the mixture recovered in the storage tank 104 in step (56-1).

0.63 kg of hexamethylenediamine, 47.1 kg of 2-phenylethanol and 1.10 kg of urea were added to the mixture recovered in the storage tank 104 in step (56-1) to obtain a raw material solution. The same method as step (56-1) was carried out using this raw material solution. The yield of N,N'-hexanediyl-di(carbamic acid (2-phenylethyl) ester) based on hexamethylenediamine was about 91%.

Step (56-3): Transesterification Reaction

The apparatus shown in FIG. 31 was used.
21.0 kg of p-dodecyl phenol were added to the mixture obtained in step (56-2) to obtain a homogeneous solution and then charged into the storage tank 1201. A packed column 1202 packed with a packing (Helipack No. 3), having an inner diameter of 20 mm and having a height of 4000 mm was heated to 250° C., and the pressure inside the column was set to 26 kPa. The solution in the storage tank 1201 was fed from the line C1 provided in the packed column 1205 at the rate of about 2.0 g/min. The reaction liquid was recovered in the storage tank 1202 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained N,N'-hexanediyl-di(carbamic acid (p-dodecylphenyl) ester), and the yield of N,N'-hexanediyl-di(carbamic acid (p-dodecylphenyl) ester) based on hexamethylenediamine was about 88%.

Step (56-4): Production of Isocyanate

The same method as Example 1 was carried out with the exception of heating the thin film distillation apparatus 702 to 220° C., setting the pressure within the thin film distillation apparatus to about 1.3 kPa and supplying the solution obtained in step (56-3) instead of the reaction liquid recovered in storage tank 105 in Example 1 to the thin film distillation apparatus at the rate of about 1620 Or. A condensate was obtained in the storage tank 707 at the rate of about 87 pr. The condensate was hexamethylene diisocyanate. The hexamethylene diisocyanate was further purified by distillation, and hexamethylene diisocyanate was obtained in which p-dodecyl phenol was not detected (below the detection limit) by gas chromatography analysis. Subsequently, p-dodecyl phenol was added so that the concentration of p-dodecyl phenol in the isocyanate was 15 ppm to obtain a mixture, and discoloration was observed when the mixture was stored for 630 days at normal temperatures in a nitrogen atmosphere.

Example 57

Step (57-1): Production of N-Substituted Carbamic Acid-O—Ar Ester

Production of urethane was carried out in a reactor as shown in FIG. 21.

1.28 kg of hexamethylenediamine, 26.9 kg of 2-phenylethanol and 2.64 kg of urea were mixed to prepare a raw material solution. The packed column 102 was heated to 220° C., the pressure inside the column was set to about 20 kPa, a mixed liquid having the same composition as the raw material solution was introduced through the line 1 provided in the upper portion of the packed column 102, and after operating conditions had stabilized, the raw material solution was introduced at about 1.8 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 40° C., and the resulting component was recovered in the storage tank 104. The amount of reaction liquid recovered in the storage tank 105 was 31.3 kg. When the reaction liquid was analyzed by liquid chromatography and $^1$H-NMR, the reaction liquid was found to contain N,N'-hexanediyl-di(carbamic acid (2-phenylethyl) ester), and the yield of N,N'-hexanediyl-di(carbamic acid (2-phenylethyl) ester) based on hexamethylenediamine was about 91%. The reaction liquid contained 3.9 ppm of ammonia. On the other hand, when $^1$H-NMR and $^{13}$C-NMR measurements were carried out on the component recovered in the storage tank 104, it was found to be a mixture of 2-phenylethanol and urea, the content of urea was about 1.55 kg (25.8 mol), and the content of 2-phenylethanol was 8.07 kg (66.1 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.46 g (27.3 mmol). In addition, the amount of carbonyl groups contained in compounds having carbonyl groups contained in the ammonia was 0.041 mmol.

When the above step (57-1) was continued to be carried out, clogging of the ammonia discharge line was not observed even after operating time had exceeded 380 days.

Step (57-2): Reuse of Mixture Obtained in Condenser

Production of N-substituted carbamic acid-O—Ar ester was carried out using the mixture recovered in the storage tank 104 in step (57-1).

1.28 kg of hexamethylenediamine, 21.0 kg of 2-phenylethanol and 1.10 kg of urea were added to the mixture recovered in the storage tank 104 in step (57-1) to obtain a raw material solution. The same method as step (57-1) was carried out using this raw material solution. The yield of N,N'-hexanediyl-di(carbamic acid (2-phenylethyl) ester) based on hexamethylenediamine was about 91%.

Step (57-3): Transesterification Reaction

The apparatus shown in FIG. 31 was used.

18.8 kg of p-dodecyl phenol and 1.10 kg of urea were added to the mixture obtained in step (57-2) to obtain a homogeneous solution and then charged into the storage tank 1201. A packed column 1202 packed with a packing (Helipack No. 3), having an inner diameter of 20 mm and having a height of 4000 mm was heated to 250° C., and the pressure inside the column was set to 26 kPa. The solution obtained in the storage tank 1201 was fed from the line C1 provided in the packed column 1202 at the rate of about 2.0 g/min. The reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained N,N'-hexanediyl-di(carbamic acid (p-dodecylphenyl) ester), and the yield of N,N'-hexanediyl-di(carbamic acid (p-dodecylphenyl) ester) based on hexamethylenediamine was about 88%.

Step (57-4): Production of Isocyanate

The same method as Example 1 was carried out with the exception of heating the thin film distillation apparatus 702 to 220° C., setting the pressure within the thin film distillation apparatus to about 1.3 kPa and supplying the solution obtained in step (57-3) instead of the reaction liquid recovered in storage tank 105 in Example 1 to the thin film distillation apparatus at the rate of about 1620 g/hr. A condensate was obtained in the storage tank 707 at the rate of about 87 g/hr. The condensate was hexamethylene diisocyanate that contained 5 ppm of p-dodecyl phenol. Although the isocyanate was stored for 630 days at normal temperatures in a nitrogen atmosphere, discoloration was not observed.

Example 58

Step (58-1): Production of N-Substituted Carbamic Acid-O—Ar Ester 1.19 kg of 3-aminomethyl-3,5,5-trimethylcyclohexylamine, 31.5 kg of ethylene glycol mono-2-ethyl hexyl ether and 1.76 kg of urea were mixed to prepare a raw material solution. The packed column 102 was heated to 220° C., the pressure inside the column was set to about 50 kPa, a mixed liquid having the same composition as the raw material solution was introduced through the line 1 provided in the upper portion of the packed column 102, and after operating conditions had stabilized, the raw material solution was introduced at about 2.3 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 70° C., and the resulting component was recovered in the storage tank 104. The amount of reaction liquid recovered in the storage tank 105 was 26.6 kg. When the reaction liquid was analyzed by liquid chromatography and $^1$H-NMR, the reaction liquid was found to contain 3-((2-(2-ethylhexyloxy)ethyloxy) carbonylamino-methyl)-3,5,5-trimethylcyclohexyl carbamic acid (2-(2-ethyl hexyloxy)ethyl) ester, and the yield of 3-((2-(2-ethyl hexyloxy)ethyloxy) carbonylamino-methyl)-3,5,5-trimethylcyclohexyl carbamic acid (2-(2-ethyl hexyloxy)ethyl) ester based on 3-aminomethyl-3,5,5-trimethylcyclohexylamine was about 90%. The reaction liquid contained 6.9 ppm of ammonia. On the other hand, when $^1$H-NMR and $^{13}$C-NMR measurements were carried out on the component recovered in the storage tank 104, it was found to be a mixture of ethylene glycol mono-2-ethyl hexyl ether and urea, the content of urea was about 1.08 kg (18.0 mol), and the content of ethylene glycol mono-2-ethyl hexyl ether was 6.93 kg (40.0 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.35 g (20.4 mmol). In addition, the amount of carbonyl groups contained in compounds having carbonyl groups contained in the ammonia was 0.51 mmol.

When the above step (58-1) was continued to be carried out, the ammonia discharge line clogged after operating time had exceeded 355 days.

Step (58-2): Reuse of Mixture Obtained in Condenser

Production of N-substituted carbamic acid-O—Ar ester was carried out using the mixture recovered in the storage tank 104 in step (58-1).

1.19 kg of 3-aminomethyl-3,5,5-trimethylcyclohexylamine, 24.6 kg of ethylene glycol mono-2-ethyl hexyl ether and 0.68 kg of urea were added to the mixture recovered in the storage tank 104 in step (58-1) to obtain a raw material solution. The same method as step (58-1) was carried out using this raw material solution. The yield of 3-((2-(2-ethylhexyloxy)ethyloxy) carbonylamino-methyl)-3,5,5-trimethylcyclohexyl carbamic acid (2-(2-ethyl hexyloxy)ethyl) ester based on 3-aminomethyl-3,5,5-trimethylcyclohexylamine was about 90%.

Step (58-3): Transesterification Reaction

The apparatus shown in FIG. 31 was used.

16.5 kg of p-dodecyl phenol were added to the mixture obtained in step (58-2) to obtain a homogeneous solution and then charged into the storage tank 1201. The packed column 1202 packed with a packing (Helipack No. 3), having an inner diameter of 20 mm and having a height of 4000 mm was heated to 250° C., and the pressure inside the column was set to 26 kPa. The solution obtained in the storage tank 1201 was fed from the line C1 provided in the packed column 1202 at the rate of about 2.0 g/min. The reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained 3-((p-dodecylphenoxy)carbonylamino-methyl)-3,5,5-trimethylcyclohexyl carbamic acid (p-dodecylphenyl) ester, and the yield of 3-((p-dodecylphenoxy)carbonylamino-methyl)-3,5,5-trimethylcyclohexyl carbamic acid (p-dodecylphenyl) ester based on 3-aminomethyl-3,5,5-trimethylcyclohexylamine was about 86%.

Step (58-4): Production of Isocyanate

The same method as Example 1 was carried out with the exception of heating the thin film distillation apparatus 702 to 220° C., setting the pressure within the thin film distillation apparatus to about 1.3 kPa and supplying the solution obtained in step (58-3) instead of the reaction liquid recovered in storage tank 105 in Example 1 to the thin film distillation apparatus at the rate of about 1820 g/hr. A condensate was obtained in the storage tank 707 at the rate of about 104 g/hr. The condensate was isophorone diisocyanate that contained 10 ppm of p-dodecyl phenol. Although the isocyanate was stored for 630 days at normal temperatures in a nitrogen atmosphere, discoloration was not observed.

Example 59

Step (59-1): Production of N-Substituted Carbamic Acid-O—Ar Ester 1.20 kg of 3-aminomethyl-3,5,5-trimethylcyclohexylamine, 28.1 kg of decyl alcohol and 1.79 kg of urea were mixed to prepare a raw material solution. The packed column 102 was heated to 220° C., the pressure inside the column was set to about 50 kPa, a mixed liquid having the same composition as the raw material solution was introduced through the line 1 provided in the upper portion of the packed column 102, and after operating conditions had stabilized, the raw material solution was introduced at about 2.3 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 70° C., and the resulting component was recovered in the storage tank 104. The amount of reaction liquid recovered in the storage tank 105 was 22.8 kg. When the reaction liquid was analyzed by liquid chromatography and $^1$H-NMR, the reaction liquid was found to contain 3-(decyloxycarbonylamino-methyl)-3,5,5-trimethylcyclohexyl carbamic acid decyl ester, and the yield of 3-(decyloxycarbonylamino-methyl)-3,5,5-trimethylcyclohexyl carbamic acid decyl ester based on 3-aminomethyl-3,5,5-trimethylcyclohexylamine was about 90%. The reaction liquid contained 9.0 ppm of ammonia. On the other hand, when $^1$H-NMR and $^{13}$C-NMR measurements were carried out on the component recovered in the storage tank 104, it was found to be a mixture of decyl alcohol and urea, the content of urea was about 1.10 kg (18.3 mol), and the content of decyl alcohol was 7.30 kg (46.2 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.39 g (22.9 mmol). In addition, when the gas was analyzed by GC-MS, the amount of carbonyl groups contained in compounds having carbonyl groups contained in the ammonia was 0.229 mmol.

When the above step (59-1) was continued to be carried out, the ammonia discharge line did not become clogged even after operating time had exceeded 380 days.

Step (59-2): Reuse of Mixture Obtained in Condenser

The ammonia concentration in the mixture recovered in the storage tank 104 in step (59-1) was 39 ppm. Production of N-substituted carbamic acid-O—Ar ester was carried out using this mixture.

1.21 kg of 3-aminomethyl-3,5,5-trimethylcyclohexylamine, 20.6 kg of decyl alcohol and 0.69 kg of urea were added to the mixture recovered in the storage tank 104 in step (59-1) to obtain a raw material solution. The same method as step (59-1) was carried out using this raw material solution. The yield of 3-(decyloxycarbonylamino-methyl)-3,5,5-trimethylcyclohexyl carbamic acid decyl ester based on 3-aminomethyl-3,5,5-trimethylcyclohexylamine was about 90%.

Step (59-3): Transesterification Reaction

The apparatus shown in FIG. 31 was used.

16.5 kg of p-dodecyl phenol were added to the mixture obtained in step (59-2) to obtain a homogeneous solution and then charged into the storage tank 1201. The packed column 1202 packed with a packing (Helipack No. 3), having an inner diameter of 20 mm and having a height of 4000 mm was heated to 250° C., and the pressure inside the column was set to 26 kPa. The solution obtained in the storage tank 1201 was fed from the line C1 provided in the packed column 1202 at the rate of about 2.0 g/min. The reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained 3-((p-dodecylphenoxy)carbonylamino-methyl)-3,5,5-trimethylcyclohexyl carbamic acid (p-dodecylphenyl) ester, and the yield of 3-((p-dodecylphenoxy)carbonylamino-methyl)-3,5,5-trimethylcyclohexyl carbamic acid (p-dodecylphenyl) ester based on 3-aminomethyl-3,5,5-trimethylcyclohexylamine was about 86%.

Step (59-4): Production of Isocyanate

The same method as Example 1 was carried out with the exception of heating the thin film distillation apparatus 702 to 220° C., setting the pressure within the thin film distillation apparatus to about 1.3 kPa and supplying the solution obtained in step (59-3) instead of the reaction liquid recovered in storage tank 105 in Example 1 to the thin film distillation apparatus at the rate of about 1820 g/hr. A condensate was obtained in the storage tank 707 at the rate of about 104 g/hr. The condensate was isophorone diisocyanate that contained 13.3 ppm of p-dodecyl phenol. Although the isocyanate was stored for 630 days at normal temperatures in a nitrogen atmosphere, discoloration was not observed.

Example 60

Step (60-1): Production of N-Substituted Carbamic Acid-O—Ar Ester

Production of urethane was carried out in a reactor as shown in FIG. 21.

1050 g of 2,4-toluenediamine, 37.2 g of 1-nonanol and 2.17 kg of urea were mixed to prepare a raw material solution. The packed column 102 was heated to 200° C., and the pressure inside the column was set to about 50 kPa. A mixed liquid having the same composition as the raw material solution was introduced through the line 1 provided in the upper portion of the packed column 102, and after operating conditions had stabilized, the raw material solution was introduced at about 2.3 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 40° C., and the resulting component was recovered in the storage tank 104. The amount of reaction liquid recovered in the storage tank 105 was 29.2 kg. When the reaction liquid was analyzed by liquid chromatography and $^1$H-NMR, the reaction liquid was found to be a composition that contained 1-nonanol at a stoichiometric ratio of 22.2 times and dinonyl carbonate at a stoichiometric ratio of 0.011 times based on toluene-2,4-di(carbamic acid nonyl ester), 0.035 times an N-containing compound based on the number of toluene-2,4-di(carbamic acid nonyl esters), and 5.9 ppm of ammonia. In addition, the yield of toluene-2,4-di(carbamic acid nonyl ester) based on 2,4-toluenediamine was about 90%. On the other hand, when $^1$H-NMR and $^{13}$C-NMR measurements were carried out on the component recovered in the storage tank 104, it was found to be a mixture of 1-nonanol and urea, the content of urea was about 1.33 kg (22.2 mol), and the content of 1-nonanol was 10.0 kg (69.6 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.374 g (22.0 mmol). In addition, when the gas was analyzed by GC-MS, the amount of carbonyl groups contained in compounds having carbonyl groups contained in the ammonia was 0.044 mmol.

When the above step (60-1) was continued to be carried out, the ammonia discharge line did not become clogged even after operating time had exceeded 380 days.

Step (60-2): Reuse of Mixture Obtained in Condenser

Production of N-substituted carbamic acid-O—Ar ester was carried out using the mixture recovered in the storage tank 104 in step (60-1).

1.05 kg of 2,4-toluenediamine, 27.2 kg of 1-nonanol and 0.84 kg of urea were added to the mixture recovered in the storage tank 104 in step (60-1) to obtain a raw material solution. The same method as step (60-1) was carried out using this raw material solution. The yield of toluene-2,4-di(carbamic acid nonyl ester) based on 2,4-toluenediamine was about 90%.

Step (60-3): Transesterification Reaction

The apparatus shown in FIG. 31 was used.

18.1 kg of 2,4-di-tert-amyl phenol and 2.3 kg of dibutyl tin dilaurate were added to the mixture obtained in step (60-2) to obtain a homogeneous solution and then charged into the storage tank 1201. The packed column 1202 was heated to 250° C., and the pressure inside the column was set to 26 kPa. The solution obtained in the storage tank 1201 was fed from the line C1 provided in the packed column 1202 at the rate of about 2.0 g/min. The reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained toluene-2,4-di(carbamic acid (2,4-di-tert-amylphenyl) ester), and the yield of toluene-2,4-di(carbamic acid (2,4-di-tert-amylphenyl) ester) based on 2,4-toluenediamine was about 86%.

Step (60-4): Production of Isocyanate

The same method as Example 1 was carried out with the exception of heating the thin film distillation apparatus 702 to 220° C., setting the pressure within the thin film distillation apparatus to about 1.3 kPa and supplying the solution obtained in step (60-3) instead of the reaction liquid recovered in storage tank 105 in Example 1 to the thin film distillation apparatus at the rate of about 1820 g/hr. A condensate was obtained in the storage tank 707 at the rate of about 91 g/hr. The condensate was 2,4-tolylene diisocyanate that contained 23 ppm of 4-di-tert-amyl phenol. Although the isocyanate was stored for 630 days at normal temperatures in a nitrogen atmosphere, discoloration was not observed.

Example 61

Step (61-1): Production of N-Substituted Carbamic Acid-O—Ar Ester

Production of urethane was carried out in a reactor as shown in FIG. 21.

1080 g of 2,4-toluenediamine, 39.8 kg of 4-phenyl-1-butanol and 2.23 kg of urea were mixed to prepare a raw material solution. The packed column 102 was heated to 200° C., and the pressure inside the column was set to about 50 kPa. A mixed liquid having the same composition as the raw material solution was introduced through the line 1 provided in the upper portion of the packed column 102, and after operating conditions had stabilized, the raw material solution was introduced at about 1.8 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 90° C., and the resulting component was recovered in the storage tank 104. The amount of reaction liquid recovered in the storage tank 105 was 29.2 kg. When the reaction liquid was analyzed by liquid chromatography and $^1$H-NMR, the reaction liquid was found to be a composition that contained 4-phenyl-1-butanol at a stoichiometric ratio of 25.2 times and bis(4-phenylbutyl) carbonate at a stoichiometric ratio of 0.003 times based on toluene-2,4-di(carbamic acid(4-phenylbutyl) ester), 0.033 times an N-containing compound based on the number of toluene-2,4-di(carbamic acid(4-phenylbutyl) esters), and 8.4 ppm of ammonia. In addition, the yield of toluene-2,4-di(carbamic acid(4-phenylbutyl) ester) based on 2,4-toluenediamine was about 90%. On the other hand, when $^1$H-NMR and $^{13}$C-NMR measurements were carried out on the component recovered in the storage tank 104, it was found to be a mixture of 4-phenyl-1-butanol and urea, the content of urea was about 1.37 kg (22.8 mol), and the content of 4-phenyl-1-butanol was 7.17 kg (47.7 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.282 g (16.6 mmol). In addition, when the gas was analyzed by GC-MS, the amount of carbonyl groups contained in compounds having carbonyl groups contained in the ammonia was 15.2 mmol.

When the above step (61-1) was continued to be carried out, the ammonia discharge line became clogged after operating time had exceeded 160 days.

Step (61-2): Reuse of Mixture Obtained in Condenser

Production of N-substituted carbamic acid-O—Ar ester was carried out using the mixture recovered in the storage tank 104 in step (61-1).

The ammonia concentration in the mixture recovered in the storage tank 104 in step (61-1) was 53 ppm. 1.08 kg of 2,4-toluenediamine, 32.7 kg of 4-phenyl-1-butanol and 0.86 kg of urea were added to this mixture to obtain a raw material solution. The same method as step (61-1) was carried out using this raw material solution. The yield of toluene-2,4-di (carbamic acid(4-phenylbutyl) ester) based on 2,4-toluenediamine was about 90%.

Step (61-3): Transesterification Reaction

The apparatus shown in FIG. 31 was used.

20.3 kg of 4-phenyl phenol and 1.3 kg of dibutyl tin dilaurate were added to the mixture obtained in step (61-2) to obtain a homogeneous solution and then charged into the storage tank 1201. The packed column 1202 was heated to 260° C., and the pressure inside the column was set to 30 kPa. The solution obtained in the storage tank 1201 was fed from the line C1 provided in the packed column 1202 at the rate of about 2.0 g/min. The reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained toluene-2,4-di(carbamic acid (4-phenylphenyl) ester), and the yield of toluene-2,4-di(carbamic acid (4-phenylphenyl) ester) based on 2,4-toluenediamine was about 88%.

Step (61-4): Production of Isocyanate

The same method as Example 1 was carried out with the exception of heating the thin film distillation apparatus 702 to 220° C., setting the pressure within the thin film distillation apparatus to about 1.3 kPa and supplying the solution obtained in step (61-3) instead of the reaction liquid recovered in storage tank 105 in Example 1 to the thin film distillation apparatus at the rate of about 1620 g/hr. A condensate was obtained in the storage tank 707 at the rate of about 81 g/hr. The condensate was 2,4-tolylene diisocyanate that contained 923 ppm of 4-phenyl phenol. Although the isocyanate was stored for 630 days at normal temperatures in a nitrogen atmosphere, discoloration was not observed.

Example 62

Step (62-1): Production of N-Substituted Carbamic Acid-O—Ar Ester

Production of urethane was carried out in a reactor as shown in FIG. 21.

1340 g of hexamethylenediamine, 42.1 kg of 2-ethyl-1-hexanol and 3.12 kg of urea were mixed to prepare a raw material solution. The packed column 102 was heated to 200° C., and the pressure inside the column was set to about 50 kPa. A mixed liquid having the same composition as the raw material solution was introduced through the line 1 provided in the upper portion of the packed column 102, and after operating conditions had stabilized, the raw material solution was introduced at about 1.8 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 30° C., and the resulting component was recovered in the storage tank 104. The amount of reaction liquid recovered in the storage tank 105 was 15.3 kg. When the reaction liquid was analyzed by liquid chromatography and $^1$H-NMR, the reaction liquid was found to be a composition that contained 2-ethyl-1-hexanol at a stoichiometric ratio of 7.0 times and bis(2-ethylhexyl) carbonate at a stoichiometric ratio of 0.022 times based on toluene-2,4-di(carbamic acid (4-phenylphenyl) ester), 0.023 times an N-containing compound based on the number of toluene-2,4-di(carbamic acid (4-phenylphenyl) esters), and 8.9 ppm of ammonia. In addition, the yield of toluene-2,4-di(carbamic acid (4-phenylphenyl) ester) based on hexamethylenediamine was about 90%. On the other hand, when $^1$H-NMR and $^{13}$C-NMR measurements were carried out on the component recovered in the storage tank 104, it was found to be a mixture of 2-ethyl-1-hexanol and urea, the content of urea was about 1.94 kg (32.4 mol), and the content of 2-ethyl-1-hexanol was 29.4 kg (226 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.342 g (20.2 mmol). In addition, when the gas was analyzed by GC-MS, the amount of carbonyl groups contained in compounds having carbonyl groups contained in the ammonia was 0.0033 mmol.

When the above step (62-1) was continued to be carried out, the ammonia discharge line did not become clogged even after operating time had exceeded 380 days.

Step (62-2): Reuse of Mixture Obtained in Condenser

Production of N-substituted carbamic acid-O—Ar ester was carried out using the mixture recovered in the storage tank 104 in step (62-1).

The ammonia concentration in the mixture recovered in the storage tank 104 in step (62-1) was 72 ppm. 1.34 kg of hexamethylenediamine, 12.6 kg of 2-ethyl-1-hexanol and 1.17 kg of urea were added to this mixture to obtain a raw material solution. The same method as step (62-1) was carried out using this raw material solution. The yield of N,N'-hexanediyl-di(carbamic acid (2-ethylhexyl) ester) based on hexamethylenediamine was about 92%.

Step (62-3): Transesterification Reaction

The apparatus shown in FIG. 31 was used.

12.2 kg of 2-naphthol and 1.2 kg of dibutyl tin dilaurate were added to the mixture obtained in step (62-2) to obtain a homogeneous solution and then charged into the storage tank 1201. The packed column 1202 was heated to 260° C., and the pressure inside the column was set to 30 kPa. The solution obtained in the storage tank 1201 was fed from the line C1 provided in the packed column 1202 at the rate of about 2.1 g/min. The reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained N,N'-hexanediyl-di(carbamic acid (2-naphthyl) ester), and the yield of N,N'-hexanediyl-di(carbamic acid (2-naphthyl) ester) based on hexamethylenediamine was about 89%.

Step (62-4): Production of Isocyanate

The same method as Example 1 was carried out with the exception of heating the thin film distillation apparatus 702 to 220° C., setting the pressure within the thin film distillation apparatus to about 1.3 kPa and supplying the solution obtained in step (62-3) instead of the reaction liquid recovered in storage tank 105 in Example 1 to the thin film distillation apparatus at the rate of about 1220 g/hr. A condensate was obtained in the storage tank 707 at the rate of about 113 g/hr. The condensate was hexamethylene diisocyanate that contained 20 ppm of 2-naphthol. Although the isocyanate was stored for 630 days at normal temperatures in a nitrogen atmosphere, discoloration was not observed.

Example 63

Step (63-1): Production of N-Substituted Carbamic Acid-O—Ar Ester

Production of urethane was carried out in a reactor as shown in FIG. 21.

1220 g of 3-aminomethyl-3,5,5-trimethylcyclohexylamine, 28.0 kg of 1-octanol and 1.76 kg of urea were mixed to prepare a raw material solution. The packed column 102 was heated to 190° C., and the pressure inside the column was set to about 30 kPa. A mixed liquid having the same composition as the raw material solution was introduced through the line 1 provided in the upper portion of the packed column 102, and after operating conditions had stabilized, the raw material solution was introduced at about 2.2 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 30° C., and the resulting component was recovered in the storage tank 104. The amount of reaction liquid recovered in the storage tank 105 was 21.3 kg. When the reaction liquid was analyzed by liquid chromatography and $^1$H-NMR, the reaction liquid was found to be a composition that contained 1-octanol at a stoichiometric ratio of 20.0 times and dioctyl carbonate at a stoichiometric ratio of 0.0043 times based on 3-((1-octyloxy)carbonylamino-methyl)-3,5,5-tricyclohexyl carbamic acid (1-octyl) ester, 0.039 times an N-containing compound based on the number of t3-((1-octyloxy)carbonylamino-methyl)-3,5,5-tricyclohexyl carbamic acid (1-octyl) esters, and 4.9 ppm of ammonia. In addition, the yield of 3-((1-octyloxy)carbonylamino-methyl)-3,5,5-tricyclohexyl carbamic acid (1-octyl) ester based on 3-aminomethyl-3,5,5-trimethylcyclohexylamine was about 92%. On the other hand, when $^1$H-NMR and $^{13}$C-NMR measurements were carried out on the component recovered in the storage tank 104, it was found to be a mixture of 1-octanol and urea, the content of urea was about 1.04 kg (17.2 mol), and the content of 1-octanol was 8.96 kg (68.8 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.402 g (23.3 mmol). In addition, when the gas was analyzed by GC-MS, the amount of carbonyl groups contained in compounds having carbonyl groups contained in the ammonia was 0.0028 mmol.

When the above step (63-1) was continued to be carried out, the ammonia discharge line did not become clogged even after operating time had exceeded 380 days.

Step (63-2): Reuse of Mixture Obtained in Condenser

Production of N-substituted carbamic acid-O—Ar ester was carried out using the mixture recovered in the storage tank 104 in step (63-1).

The ammonia concentration in the mixture recovered in the storage tank 104 in step (63-1) was 59 ppm. 1.22 kg of 3-aminomethyl-3,5,5-trimethylcyclohexylamine, 19.0 kg of 1-octanol and 0.73 kg of urea were added to this mixture to obtain a raw material solution. The same method as step (63-1) was carried out using this raw material solution. The yield of 3-((1-octyloxy)carbonylamino-methyl)-3,5,5-tricyclohexyl carbamic acid (1-octyl) ester based on 3-aminomethyl-3,5,5-trimethylcyclohexylamine was about 92%.

Step (63-3): Transesterification Reaction

The apparatus shown in FIG. 31 was used.
11.2 kg of 4-cumyl phenol and 1.3 kg of dibutyl tin dilaurate were added to the mixture obtained in step (63-2) to obtain a homogeneous solution and then charged into the storage tank 1201. The packed column 1202 was heated to 260° C., and the pressure inside the column was set to 30 kPa. The solution obtained in the storage tank 1201 was fed from the line C1 provided in the packed column 1202 at the rate of about 2.2 g/min. The reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. When the reaction liquid was analyzed by liquid chromatography and $^1$H-NMR, the reaction liquid was found to be a solution that contained 3-((4-cumylphenoxy)carbonylamino-methyl)-3,5,5-trimethylcyclohexyl carbamic acid (4-cumylphenyl) ester, and the yield of 3-((4-cumylphenoxy)carbonylamino-methyl)-3,5,5-trimethylcyclohexyl carbamic acid (4-cumylphenyl) ester based on 3-aminomethyl-3,5,5-trimethylcyclohexylamine was about 87%.

Step (63-4): Production of Isocyanate

The same method as Example 1 was carried out with the exception of heating the thin film distillation apparatus 702 to 220° C., setting the pressure within the thin film distillation apparatus to about 1.3 kPa and supplying the solution obtained in step (63-3) instead of the reaction liquid recovered in storage tank 105 in Example 1 to the thin film distillation apparatus at the rate of about 1380 g/hr. A condensate was obtained in the storage tank 707 at the rate of about 113 g/hr. The condensate was isophorone diisocyanate that contained 2 ppm of 4-cumyl phenol. Although the isocyanate was stored for 630 days at normal temperatures in a nitrogen atmosphere, discoloration was not observed.

Example 64

Step (64-1): Production of Compound Having Ureido Groups

The apparatus shown in FIG. 26 was used.
21.7 kg of 2-ethyl-1-hexanol and 2.50 kg of urea were mixed in the storage tank 601 heated to 120° C. with the line 63 closed, and the mixture was transferred to the stirring tank 603 heated to 120° C. While stirring the stirring tank 603, 1.42 kg of 3-aminomethyl-3,5,5-trimethylcyclohexylamine were supplied from the storage tank 602 to the stirring tank 603 through the line 62 at the rate of about 10 g/min. After finishing supplying the 3-aminomethyl-3,5,5-trimethylcyclohexylamine, stirring was carried out for about 2 hours followed by sampling the reaction liquid. As a result of analyzing the reaction liquid by liquid chromatography, the reaction liquid was found to contain about 7.9% by weight of 3-(ureidomethyl)-3,5,5-trimethylcyclohexylurea. In addition, the ammonia concentration in the reaction liquid was 6600 ppm. 21.8 kg of an aromatic hydroxy compound in the form of p-dodecyl phenol were added from the storage tank 601 to obtain a homogeneous solution. The line 63 was then opened and the reaction liquid was transferred to the storage tank 604 through the line 63.

Step (64-2): Production of N-Substituted Carbamic Acid-O—R$^2$ Ester and Recovery of Urea The packed column 605 was heated to 190° C. Dibutyl tin dilaurate was added at 0.1% by weight to the reaction liquid obtained in step (64-1) from the line 64 provided in the packed column 605 to obtain a mixed liquid. The mixed liquid was fed at the rate of about 2.2 g/min. The mixed liquid was recovered in the storage tank 610 through the line 66 provided n the bottom of the packed column 605. A gaseous phase component was condensed in the condenser 606 (held at about 30° C.) from the line 65 provided in the top of the packed column 605, and the resulting liquid phase component was recovered in the storage tank 609 through the gas-liquid separator 608. When the condensed component recovered in the storage tank 609 was analyzed by $^1$H-NMR, the condensed component was found to contain 2-ethyl-1-hexanol, urea and (2-ethylbutylethylhexyl) carbamate, and the condensed component contained 11.2 kg (86.1 mol) of 2-ethyl-1-hexanol, 1.51 kg (23.9 mol) of urea and 0.24 kg (1.26 mol) of (2-ethylhexyl) carbamate. The amount of reaction liquid recovered in the storage tank 610 was 45.4 kg. When the reaction liquid was analyzed by liquid chromatography and $^1$H-NMR, the reaction liquid was found to contain 3-((2-ethylhexyloxy)carbonylaminomethyl)-3,5,5-trimethylcyclohexyl carbamic acid (2-ethylhexyl) ester, and the yield of 3-((2-ethylhexyloxy)carbonylamidomethyl)-3,5,5-trimethylcyclohexyl carbamic acid (2-ethylhexyl) ester based on 3-aminomethyl-3,5,5-trimethylcyclohexylamine was about 83%. In addition, the reaction liquid contained 10 ppm of ammonia.

In addition, a gas containing ammonia was discharged from the line 67. The gas was recovered in a Tedlar bag and injected into a gas chromatograph with a gastight syringe to analyze the gas components. As a result, the amount of ammonia recovered per 10 minutes was 0.111 g (6.51 mmol). In addition, when the gas was analyzed by GC-MS, the amount of carbonyl groups contained in compounds having carbonyl groups contained in the ammonia was 0.0022 mmol.

When the above steps (64-1) and (64-2) were continued to be carried out, clogging of the ammonia discharge line was not observed even after operating time had exceeded 380 days.

Step (64-3): Transesterification Reaction

The apparatus shown in FIG. 31 was used.

The packed column 1202 packed with a packing (Helipack No. 3) was heated to 260° C. and the internal pressure was set to 26 kPa. The mixed liquid in the storage tank 1201 was fed from the line C1 provided in the packed column 1202 at the rate of about 1.9 g/min. Reaction liquid was recovered in the storage tank 1205 through the line C4 provided in the bottom of the packed column 1202. A gaseous phase component was introduced into the condenser 1203 from the line C2 provided in the top of the packed column 1202, and the resulting liquid phase component was recovered in the storage tank 1204 through the gas-liquid separator 1207. The amount of reaction liquid recovered in the storage tank 1205 was 25.0 kg. When the reaction liquid was analyzed by liquid chromatography and $^1$H-NMR, the reaction liquid was found to be a solution that contained 3-((p-dodecylphenoxy)carbonylaminomethyl)-3,5,5-trimethylcyclohexyl carbamic acid (p-dodecylphenyl) ester, and the yield of 3-((p-dodecylphenoxy)carbonylamidomethyl)-3,5,5-trimethylcyclohexyl carbamic acid (p-dodecylphenyl) ester based on 3-aminomethyl-3,5,5-trimethylcyclohexylamine was about 78%.

Step (64-4): Production of Isocyanate by Thermal Decomposition of N-Substituted Carbamic Acid-O—Ar Ester The apparatus shown in FIG. 28 was used.

The thin film distillation apparatus 802 having a heat-conducting surface area of 0.2 m$^2$ was heated to 220° C. and the pressure within the thin film distillation apparatus was set to about 1.3 kPa. The reaction liquid recovered in the storage tank 1210 in step (64-3) was placed in the storage tank 801 and supplied to the thin film distillation apparatus at the rate of about 1790 g/hr via the line 80. A liquid component was extracted from the line 82 provided in the bottom of thin film distillation apparatus 802 and recovered in the storage tank 803. The liquid component recovered in the storage tank 803 was again supplied to the thin film distillation apparatus 802 through the line 83. A gaseous component containing isophorone diisocyanate and p-dodecyl phenol was extracted from the line 81 provided in the upper portion of the thin film distillation apparatus 802. The gaseous component was introduced into the distillation column 804, and low boiling components were separated by distillation. A liquid phase component was supplied to the distillation column 809 from the line 88 provided in the distillation column 804 at a portion lower than the feed line, and further subjected to distillative separation. The gaseous phase component was condensed in the condenser 810 through the line 89 and recovered in the storage tank 812 through the gas-liquid separator 811.

When the condensate was analyzed by $^1$H-NMR and gas chromatography, it was found to contain about 99% by weight of isophorone diisocyanate. The yield based on organic amine (3-aminomethyl-3,5,5-trimethylcyclohexylamine) was about 70%.

Example 65

Step (65-1): Production of Compound Having Ureido Groups

The same method as step (64-1) of Example 64 was carried out with the exception of using 15.2 kg of 2-phenylethanol instead of 2-ethyl-1-hexanol using 2.29 kg of urea, using 1.11 kg of hexamethylenediamine instead of 3-aminomethyl-3,5,5-trimethylcyclohexylamine, and setting the temperature of the stirring tank 603 to 100° C. As a result of analyzing the reaction liquid by liquid chromatography, the reaction liquid was found to contain about 8.0% by weight of N,N'-hexamethylenediurea. In addition, the ammonia concentration in the reaction liquid was 7700 ppm. 19.7 kg of 4-(1,1,3,3-tetramethylbutyl) phenol were added instead of p-dodecyl phenol to obtain a homogeneous solution.

Step (65-2): Production of N-Substituted Carbamic Acid-O—R$^2$ Ester and Recovery of Urea The same method as step (64-2) of Example 64 was carried out with the exception of using the reaction liquid obtained in step (65-1) instead of the reaction liquid obtained in step (64-1) and heating the packed column 605 to 240° C. When the resulting reaction liquid was analyzed by liquid chromatography and $^1$H-NMR, it was found to contain N,N'-hexanediyl-di(carbamic acid (4-(1,1,3,3-tetramethylbutyl)phenyl) ester), and the yield based on hexamethylenediamine was about 73%. The ammonia concentration in the reaction liquid was 9 ppm.

When the condensed component recovered in the storage tank 609 was analyzed by $^1$H-NMR, the condensed component was found to contain 2-phenylethanol, urea and (2-phenylethyl) carbamate, and the condensed component contained 7.96 kg (65.2 mol) of 2-phenylethanol, 1.19 kg (18.8 mol) of urea and 0.18 kg (0.99 mol) of (2-phenylethyl) carbamate. The amount of reaction liquid recovered in the storage tank 610 was 23.8 kg.

In addition, a gas containing ammonia was discharged from the line 67. The gas was recovered in a Tedlar bag and injected into a gas chromatograph with a gastight syringe to analyze the gas components. As a result, the amount of ammonia recovered per 10 minutes was 0.137 g (8.10 mmol). In addition, when the gas was analyzed by GC-MS, the amount of carbonyl groups contained in compounds having carbonyl groups contained in the ammonia was 0.0013 mmol.

When the above steps (65-1) and (65-2) were continued to be carried out, clogging of the ammonia discharge line was not observed even after operating time had exceeded 380 days.

Step (65-3): Transesterification Reaction

The same method as step (64-3) of Example 64 was carried out with the exception of heating the packed column 1202 to 220° C. and setting the internal pressure to 20 kPa. When the resulting reaction liquid was analyzed by liquid chromatography and $^1$H-NMR, the reaction liquid was found to contain N,N'-hexanediyl-di(carbamic acid(4-(1,1,3,3-tetramethylbutyl)phenyl) ester), and the yield based on hexamethylenediamine was 68%.

Step (65-4): Production of Isocyanate by Thermal Decomposition of N-Substituted Carbamic Acid-O—Ar Ester The same method as step (64-4) of Example 64 was carried out with the exception of heating the thin film distillation apparatus 802 to 220° C. and setting the pressure within the thin film distillation apparatus to about 1.3 kPa. Hexamethylene diisocyanate was obtained in the storage tank 812, and the yield based on hexamethylenediamine was about 65%.

Example 66

Step (66-1): Production of Compound Having Ureido Groups

The same method as step (64-1) of Example 64 was carried out with the exception of using 18.9 kg of diethylene glycol monobutyl ether instead of 2-ethyl-1-hexanol, and setting the temperature of the stirring tank 603 to 120° C. As a result of analyzing the reaction liquid by liquid chromatography, the reaction liquid was found to contain about 7.0% by weight of 3-(ureidomethyl)-3,5,5-trimethylcyclohexylurea. In addition, the ammonia concentration in the reaction liquid was 5800 ppm. 18.1 kg of 2,4-di-tert-amyl phenol were added instead of p-dodecyl phenol to obtain a homogeneous solution.

Step (66-2): Production of N-Substituted Carbamic Acid-O—R² Ester and Recovery of Urea The same method as step (64-2) of Example 64 was carried out with the exception of using the reaction liquid obtained in step (66-1) instead of the reaction liquid obtained in step (64-1) and heating the packed column 605 to 240° C. When the resulting reaction liquid was analyzed by liquid chromatography and $^1$H-NMR, it was found to contain 3-(((2-(2-butyloxy)ethyloxy)ethyloxy)carbonylamino-methyl)-3,5,5-trimethylcyclohexyl carbamic acid (2-(2-butyloxy)ethyloxy)ethyloxy) ester, and the yield based on 3-aminomethyl-3,5,5-trimethylcyclohexylamine was about 75%. The ammonia concentration in the reaction liquid was 6.2 ppm.

When the condensed component recovered in the storage tank 609 was analyzed by $^1$H-NMR, the condensed component was found to contain diethylene glycol monobutyl ether and urea, and the condensed component contained 12.8 kg (79.0 mol) of diethylene glycol monobutyl ether and 1.62 kg (25.7 mol) of urea.

In addition, a gas containing ammonia was discharged from the line 67. The gas was recovered in a Tedlar bag and injected into a gas chromatograph with a gastight syringe to analyze the gas components. As a result, the amount of ammonia recovered per 10 minutes was 0.109 g (6.42 mmol). In addition, when the gas was analyzed by GC-MS, the amount of carbonyl groups contained in compounds having carbonyl groups contained in the ammonia was 0.0018 mmol.

When the above steps (66-1) and (66-2) were continued to be carried out, clogging of the ammonia discharge line was not observed even after operating time had exceeded 380 days.

Step (66-3): Transesterification Reaction

The same method as step (64-3) of Example 64 was carried out with the exception of heating the packed column 1202 to 240° C. and setting the internal pressure to 20 kPa. When the resulting reaction liquid was analyzed by liquid chromatography and $^1$H-NMR, the reaction liquid was found to contain 3-((2,4-di-tert-amylphenoxy)carbonylamino-methyl)-3,5,5-trimethylcyclohexyl carbamic acid (2,4-di-tert-amylphenyl) ester, and the yield based on 3-aminomethyl-3,5,5-trimethylcyclohexylamine was 71%.

Step (66-4): Production of Isocyanate by Thermal Decomposition of N-Substituted Carbamic Acid-O—Ar Ester The same method as step (64-4) of Example 64 was carried out with the exception of heating the thin film distillation apparatus 802 to 230° C. and setting the pressure within the thin film distillation apparatus to about 1.5 kPa. Isophorone diisocyanate was obtained in the storage tank 812, and the yield based on 3-aminomethyl-3,5,5-trimethylcyclohexylamine was about 64%.

Example 67

Step (67-1): Production of Compound Having Ureido Groups

The same method as step (64-1) of Example 64 was carried out with the exception of using 11.3 kg of 2-ethyl-1-hexanol, using 3.29 kg of urea, using 1.33 kg of 2,4-toluenediamine instead of 3-aminomethyl-3,5,5-trimethylcyclohexylamine, and setting the temperature of the stirring tank 603 to 70° C. The resulting reaction liquid was a slurry. As a result of analyzing the reaction liquid by liquid chromatography, the reaction liquid was found to contain about 8.1% by weight of 2,4-toluenediurea. In addition, the ammonia concentration in the reaction liquid was 3400 ppm. 16.7 kg of p-heptyl phenol were added instead of p-dodecyl phenol to obtain a homogeneous solution.

Step (67-2): Production of N-Substituted Carbamic Acid-O-Alkyl Ester and Recovery of Urea The same method as step (64-2) of Example 64 was carried out with the exception of using the reaction liquid obtained in step (67-1) instead of the reaction liquid obtained in step (64-1) and heating the packed column 605 to 210° C. When the resulting reaction liquid was analyzed by liquid chromatography and $^1$H-NMR, it was found to contain toluene-2,4-di(carbamic acid (2-ethylhexyl) ester), and the yield based on 2,4-toluenediamine was about 52%. The ammonia concentration in the reaction liquid was 8 ppm.

When the condensed component recovered in the storage tank 609 was analyzed by $^1$H-NMR, the condensed component was found to contain 2-ethyl-1-hexanol and urea, and the condensed component contained 6.93 kg (53.2 mol) of 2-ethyl-1-hexanol and 1.88 kg (29.5 mol) of urea.

In addition, a gas containing ammonia was discharged from the line 67. The gas was recovered in a Tedlar bag and injected into a gas chromatograph with a gastight syringe to analyze the gas components. As a result, the amount of ammonia recovered per 10 minutes was 0.134 g (7.87 mmol). In addition, when the gas was analyzed by GC-MS, the amount of carbonyl groups contained in compounds having carbonyl groups contained in the ammonia was 0.701 mmol.

When the above steps (67-1) and (67-2) were continued to be carried out, clogging of the ammonia discharge line was observed when operating time had exceeded 320 days.

Step (67-3): Transesterification Reaction

The same method as step (64-3) of Example 64 was carried out with the exception of heating the packed column 1202 to 220° C. and setting the internal pressure to 15 kPa. When the resulting reaction liquid was analyzed by liquid chromatography and $^1$H-NMR, the reaction liquid was found to contain toluene-2,4-di(carbamic acid (p-heptylphenyl) ester), and the yield based on 2,4-toluenediamine was 49%.

Step (67-4): Production of Isocyanate by Thermal Decomposition of N-Substituted Carbamic Acid-O—Ar Ester The same method as step (64-4) of Example 64 was carried out with the exception of heating the thin film distillation apparatus 802 to 210° C. and setting the pressure within the thin film distillation apparatus to about 0.8 kPa. 2,4-tolylene diisocyanate was obtained in the storage tank 812, and the yield based on 2,4-toluenediamine was about 44%.

Example 68

Step (68-1): Production of Compound Having Ureido Groups

The same method as step (64-1) of Example 64 was carried out with the exception of using 31.6 kg of cyclohexanol instead of 2-ethyl-1-hexanol, using 6.34 kg of urea, using 1.29 kg of 2,4-toluenediamine instead of 3-aminomethyl-3,5,5-trimethylcyclohexylamine, and setting the temperature of the stirring tank 603 to 90° C. As a result of analyzing the reaction liquid by liquid chromatography, the reaction liquid was found to contain about 6.6% by weight of 2,4-toluenediurea. In addition, the ammonia concentration in the reaction liquid was 7300 ppm. 17.9 kg of 2-phenyl phenol were added instead of p-dodecyl phenol to obtain a homogeneous solution.

Step (68-2): Production of N-Substituted Carbamic Acid-O—R$^2$ Ester and Recovery of Urea The same method as step (64-2) of Example 64 was carried out with the exception of using the reaction liquid obtained in step (68-1) instead of the reaction liquid obtained in step (64-1) and heating the packed column 605 to 220° C. When the resulting reaction liquid was analyzed by liquid chromatography and $^1$H-NMR, it was found to contain toluene-2,4-di(carbamic acid cyclohexyl ester), and the yield based on 2,4-toluenediamine was about 82%. The ammonia concentration in the reaction liquid was 5.4 ppm.

When the condensed component recovered in the storage tank 609 was analyzed by $^1$H-NMR, the condensed component was found to contain cyclohexanol, urea and dicyclohexyl carbonate, and the condensed component contained 13.0 kg (129 mol) of cyclohexanol, 4.71 kg (73.5 mol) of urea and 0.75 kg (3.92 mol) of dicyclohexyl carbonate.

In addition, a gas containing ammonia was discharged from the line 67. The gas was recovered in a Tedlar bag and injected into a gas chromatograph with a gastight syringe to analyze the gas components. As a result, the amount of ammonia recovered per 10 minutes was 0.147 g (8.64 mmol). In addition, when the gas was analyzed by GC-MS, the amount of carbonyl groups contained in compounds having carbonyl groups contained in the ammonia was 0.216 mmol.

When the above steps (68-1) and (68-2) were continued to be carried out, clogging of the ammonia discharge line was observed when operating time had exceeded 340 days.

Step (68-3): Transesterification Reaction

The same method as step (64-3) of Example 64 was carried out with the exception of heating the packed column 1202 to 220° C. and setting the internal pressure to 25 kPa. When the resulting reaction liquid was analyzed by liquid chromatography and $^1$H-NMR, the reaction liquid was found to contain toluene-2,4-di(carbamic acid (2-phenylphenyl) ester), and the yield based on 2,4-toluenediamine was 79%.

Step (68-4): Production of Isocyanate by Thermal Decomposition of N-Substituted Carbamic Acid-O—Ar Ester The same method as step (64-4) of Example 64 was carried out with the exception of heating the thin film distillation apparatus 802 to 200° C. and setting the pressure within the thin film distillation apparatus to about 0.5 kPa. 2,4-tolylene diisocyanate was obtained in the storage tank 812, and the yield based on 2,4-toluenediamine was about 71%.

Example 69

Step (69-1): Production of Compound Having Ureido Groups

The same method as step (64-1) of Example 64 was carried out with the exception of using 29.7 kg of 2-phenylethanol instead of 2-ethyl-1-hexanol, using 3.89 kg of urea, using 1.32 kg of 2,4-toluenediamine instead of 3-aminomethyl-3,5,5-trimethylcyclohexylamine, and setting the temperature of the stirring tank 603 to 90° C. As a result of analyzing the reaction liquid by liquid chromatography, the reaction liquid was found to contain about 6.1% by weight of 2,4-toluenediurea. In addition, the ammonia concentration in the reaction liquid was 2800 ppm. 22.3 kg of 4-(1,1,3,3-tetramethylbutyl) phenol were added instead of p-dodecyl phenol to obtain a homogeneous solution.

Step (69-2): Production of N-Substituted Carbamic Acid-O—R² Ester and Recovery of Urea The same method as step (64-2) of Example 64 was carried out with the exception of using the reaction liquid obtained in step (69-1) instead of the reaction liquid obtained in step (64-1) and heating the packed column 605 to 220° C. When the resulting reaction liquid was analyzed by liquid chromatography and ¹H-NMR, it was found to contain toluene-2,4-di(carbamic acid (2-phenylethyl) ester), and the yield based on 2,4-toluenediamine was about 88%. The ammonia concentration in the reaction liquid was 5 ppm.

When the condensed component recovered in the storage tank 609 was analyzed by ¹H-NMR, the condensed component was found to contain 2-phenylethanol, urea and bis(2-phenylether) carbonate, and the condensed component contained 13.9 kg (114 mol) of 2-phenylethanol, 2.10 kg (33.3 mol) of urea and 0.32 kg (1.75 mol) of bis(2-phenylethyl) carbonate.

In addition, a gas containing ammonia was discharged from the line 67. The gas was recovered in a Tedlar bag and injected into a gas chromatograph with a gastight syringe to analyze the gas components. As a result, the amount of ammonia recovered per 10 minutes was 0.124 g (7.31 mmol). In addition, when the gas was analyzed by GC-MS, the amount of carbonyl groups contained in compounds having carbonyl groups contained in the ammonia was 6.21 mmol.

When the above steps (69-1) and (69-2) were continued to be carried out, the line 67 became clogged after 162 days.

Step (69-3): Transesterification Reaction

The same method as step (64-3) of Example 64 was carried out with the exception of heating the packed column 1202 to 220° C. and setting the internal pressure to 25 kPa. When the resulting reaction liquid was analyzed by liquid chromatography and ¹H-NMR, the reaction liquid was found to contain toluene-2,4-di(carbamic acid (2-phenylphenyl) ester), and the yield based on 2,4-toluenediamine was 79%.

Step (69-4): Production of Isocyanate by Thermal Decomposition of N-Substituted Carbamic Acid-O—Ar Ester The same method as step (64-4) of Example 64 was carried out with the exception of heating the thin film distillation apparatus 802 to 200° C. and setting the pressure within the thin film distillation apparatus to about 0.5 kPa. 2,4-tolylene diisocyanate was obtained in the storage tank 812, and the yield based on 2,4-toluenediamine was about 74%.

Example 70

Step (70-1): Production of Compound Having Ureido Groups

The same method as step (64-1) of Example 64 was carried out with the exception of using 29.0 kg of isodecyl alcohol instead of 2-ethyl-1-hexanol, using 4.54 kg of urea, using 1.32 kg of 2,4-toluenediamine instead of 3-aminomethyl-3,5,5-trimethylcyclohexylamine, and setting the temperature of the stirring tank 603 to 90° C. As a result of analyzing the reaction liquid by liquid chromatography, the reaction liquid was found to contain about 6.2% by weight of 2,4-toluenediurea. In addition, the ammonia concentration in the reaction liquid was 3200 ppm. 23.8 kg of p-nonyl phenol were added instead of p-dodecyl phenol to obtain a homogeneous solution.

Step (70-2): Production of N-Substituted Carbamic Acid-O—R² Ester and Recovery of Urea The same method as step (64-2) of Example 64 was carried out with the exception of using the reaction liquid obtained in step (70-1) instead of the reaction liquid obtained in step (64-1), heating the packed column 605 to 220° C., and setting the temperature of the condenser to 50° C. When the resulting reaction liquid was analyzed by liquid chromatography and ¹H-NMR, it was found to contain toluene-2,4-di(carbamic acid isodecyl ester), and the yield based on 2,4-toluenediamine was about 88%. The ammonia concentration in the reaction liquid was 6.4 ppm.

When the condensed component recovered in the storage tank 609 was analyzed by ¹H-NMR, the condensed component was found to contain isodecyl alcohol, urea and di(isodecyl) carbonate, and the condensed component contained 20.8 kg (132 mol) of isodecyl alcohol, 3.15 kg (49.8 mol) of urea and 0.57 kg (2.62 mol) of di(isodecyl) carbonate.

In addition, a gas containing ammonia was discharged from the line 67. The gas was recovered in a Tedlar bag and injected into a gas chromatograph with a gastight syringe to analyze the gas components. As a result, the amount of ammonia recovered per 10 minutes was 0.122 g (7.20 mmol). In addition, when the gas was analyzed by GC-MS, the amount of carbonyl groups contained in compounds having carbonyl groups contained in the ammonia was 0.061 mmol.

When the above steps (70-1) and (70-2) were continued to be carried out, clogging of the ammonia discharge line was not observed even after operating time had exceeded 380 days.

Step (70-3): Transesterification Reaction

The same method as step (64-3) of Example 64 was carried out with the exception of heating the packed column 1202 to 220° C. and setting the internal pressure to 25 kPa. When the resulting reaction liquid was analyzed by liquid chromatography and ¹H-NMR, the reaction liquid was found to contain toluene-2,4-di(carbamic acid (p-nonylphenyl) ester), and the yield based on 2,4-toluenediamine was 83%.

Step (70-4): Production of Isocyanate by Thermal Decomposition of N-Substituted Carbamic Acid-O—Ar Ester The same method as step (64-4) of Example 64 was carried out with the exception of heating the thin film distillation apparatus 802 to 200° C. and setting the pressure within the thin film distillation apparatus to about 0.5 kPa. 2,4-tolylene diisocyanate was obtained in the storage tank 812, and the yield based on 2,4-toluenediamine was about 75%.

Example 71

Step (71-1): Production of N-Substituted Carbamic Acid-O—Ar Ester

The same method as step (1-1) of Example 1 was carried out with the exception of mixing 0.830 kg of hexamethylenediamine, 27.5 kg of p-heptyl phenol and 1.72 kg of urea to obtain a raw material solution, heating the packed column 102 to 240° C., setting the internal pressure to about 20 kPa, holding the condenser at about 60° C. and introducing the raw material solution at the rate of about 1.0 g/min. When the reaction liquid recovered in the storage tank 105 was analyzed by liquid chromatography and $^1$H-NMR, the reaction liquid was found to be a composition that contained N,N'-hexanediyl-di(carbamic acid (p-heptylphenyl) ester), and p-heptyl phenol at a stoichiometric ratio of 10.8 times and di(p-heptylphenyl) carbonate at a stoichiometric ratio of 0.016 times based on N,N'-hexanediyl-di(carbamic acid (p-heptylphenyl) ester), and contained 0.035 times an N-containing compound based on the number of N,N'-hexanediyl-di(carbamic acid (p-heptylphenyl) esters). In addition, the yield of N,N'-hexanediyl-di(carbamic acid (p-heptylphenyl) ester) based on hexamethylenediamine was about 85%. On the other hand, when $^1$H-NMR and $^{13}$C-NMR measurements were carried out on the component recovered in the storage tank 104, it was found to be a mixture of p-heptyl phenol and urea, the content of urea was about 1.09 kg (18.3 mol) and the content of p-heptyl phenol was about 9.06 kg (47.1 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.162 g (9.5 mmol). When the gas was analyzed by GC-MS, the amount of carbonyl groups contained in compounds having carbonyl groups contained in the ammonia was 0.075 mmol.

When the step (71-1) was continued to be carried out, clogging of the ammonia discharge line was not observed even after operating time had exceeded 380 days.

Example 72

Step (72-1): Production of Compound Having Ureido Groups 39.6 kg of 4-tert-amyl phenol and 3.29 kg of urea were mixed in the storage tank 601 heated to 80° C. with the line 63 closed, and the mixture was transferred to the stirring tank 603 heated to 80° C. While stirring the stirring tank 603, 1.02 kg of aniline were supplied from the storage tank 602 to the stirring tank 603 through the line 62 at the rate of about 10 g/min. After finishing supplying the aniline, stirring was carried out for about 28 hours followed by sampling the reaction liquid. As a result of analyzing the reaction liquid by liquid chromatography, the reaction liquid was found to contain 4.5% by weight of N-phenylurea.

The line 63 was then opened and the reaction liquid was transferred to the storage tank 604 through the line 63.

Step (72-2): Production of N-Substituted Carbamic Acid-O—Ar Ester

The same method as step (35-2) of Example 35 was carried out with the exception of heating the packed column 605 to 200° C., setting the pressure inside the column to 10 kPa, holding the condenser at 100° C., and feeding the reaction liquid obtained in step (72-1) instead of the reaction liquid obtained in step (35-1) at the rate of about 1.6 g/min. The amount of reaction liquid fed after the reaction had reached a steady state was about 41.2 kg. The amount of reaction liquid recovered in the storage tank 610 was 26.4 kg. When reaction liquid was analyzed by liquid chromatography and $^1$H-NMR, the reaction liquid was found to be a composition that contained N-phenyl (4-tert-amylphenyl) carbamate, and 4-tert-amyl phenol at a stoichiometric ratio of 15.9 times and di(4-tert-amylphenyl) carbonate at a stoichiometric ratio of 0.0044 times based on N-phenyl (4-tert-amylphenyl) carbamate, and contained 0.0191 times an N-containing compound based on the number of N-phenyl (4-tert-amylphenyl) carbamates. In addition, the yield of N-phenyl (4-tert-amylphenyl) carbamate based on aniline was about 82%. The reaction liquid contained 35 ppm of ammonia. On the other hand, when $^1$H-NMR and $^{13}$C-NMR measurements were carried out on the component recovered in the storage tank 609, it was found to be a mixture of 4-tert-amyl phenol and urea, the content of 4-tert-amyl phenol was 12.7 kg (77.9 mol), and the content of urea was about 1.95 kg (32.4 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.117 g (6.88 mmol). In addition, when the gas was analyzed by GC-MS, the amount of carbonyl groups contained in compounds having carbonyl groups contained in the ammonia was 0.106 mmol.

When the steps (72-1) and (72-2) were continued to be carried out, the ammonia extraction line did not become clogged even after operating time had exceeded 380 days.

Example 73

Step (73-1): Production of Compound Having Ureido Groups

The same method as step (41-1) of Example 41 was carried out with the exception of using 6.46 kg of 2-isopropyl phenol and 1.42 kg of urea, and using 1.01 kg of 3-aminomethyl-3, 5,5-trimethylcyclohexylamine instead of hexamethylenediamine. 8.08 kg of 4-phenyl phenol were added instead of 4-(1,1,3,3-tetramethylbutyl) phenol, and as a result of analyzing the reaction liquid by liquid chromatography, the reaction liquid was found to contain 9.1% by weight of 3-(ureidomethyl)-3,5,5-trimethylcyclohexylurea.

Step (73-2): Production of N-Substituted Carbamic Acid-O—Ar Ester

The packed column 605 was heated to 210° C., the pressure inside the column was set to 26 kPa, and the condenser was held at 60° C. The same method as step (41-1) of Example 41 was carried out with the exception of feeding the reaction liquid obtained in step (73-1) instead of the reaction liquid obtained in step (41-1) at the rate of about 1.6 g/min. The amount of reaction liquid fed after the reaction had reached a steady state was about 15.8 kg. The amount of reaction liquid recovered in the storage tank 610 was 8.3 kg. When reaction liquid was analyzed by liquid chromatography and $^1$H-NMR, the reaction liquid was found to be a composition that contained 3-((4-phenylphenoxy) carbonylamino-methyl)-3,5,5-trimethylcyclohexyl carbamic acid (4-phenylphenyl) ester, and 4-phenyl phenol at a stoichiometric ratio of 7.08 times and bis(4-phenyl phenyl) carbonate at a stoichiometric ratio of 0.023 times based on 3-((4-phenylphenoxy)carbonylamino-methyl)-3,5,5-trimethylcyclohexyl carbamic acid (4-phenylphenyl) ester, and contained 0.0021 times an N-containing compound based on the number of 3-((4-phenylphenoxy) carbonylamino-methyl)-3,5,5-trimethylcyclohexyl carbamic acid (4-phenylphenyl) esters. In addition, the yield of 3-((4-phenylphenoxy)carbonylamino-methyl)-3,5, 5-trimethylcyclohexyl carbamic acid (4-phenylphenyl) ester based on 3-aminomethyl-3,5,5-tricyclohexylamine was about 80%. The reaction liquid contained 95 ppm of ammonia. On the other hand, when $^1$H-NMR and $^{13}$C-NMR measurements were carried out on the component recovered in the storage tank 609, it was found to be a mixture of 4-phenyl phenol, 2-isopropyl phenol, urea and (4-phenylphenyl) carbamate, the content of 4-phenyl phenol was about 0.42 kg (2.46 mol), the content of 2-isopropyl phenol was about 6.03 kg (44.3 mol), the content of urea was about 637 g (10.6 mol), and the content of (4-phenylphenyl) carbamate was about 244 g (1.15 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.179 g (10.5 mmol). In addition, when the gas was analyzed by GC-MS, the amount of carbonyl groups contained in compounds having carbonyl groups contained in the ammonia was 0.0011 mmol.

When the steps (73-1) and (73-2) were continued to be carried out, clogging of the ammonia extraction line was not observed even after operating time had exceeded 380 days.

Example 74

Step (74-1): Production of Compound Having Ureido Groups

The same method as step (41-1) of Example 41 was carried out with the exception of using 4.44 kg of 2,6-diisopropyl phenol instead of 2-isopropyl phenol, using 1.24 kg of urea, and using 1.41 kg of 4,4'-methylenedianiline instead of hexamethylenediamine. 12.5 kg of p-nonyl phenol were added instead of 4-(1,1,3,3-tetramethylbutyl) phenol, and then transferred to the storage tank 604. As a result of analyzing the reaction liquid by liquid chromatography, the reaction liquid was found to contain 10.4% by weight of 4,4'-methanediyl-diphenyldiurea.

Step (74-2): Production of N-Substituted Carbamic Acid-O—Ar Ester

The packed column 605 was heated to 200° C., the pressure inside the column was set to 26 kPa, and the condenser was held at 60° C. The same method as step (41-2) of Example 41 was carried out with the exception of feeding the reaction liquid obtained in step (74-1) instead of the reaction liquid obtained in step (41-1) at the rate of about 1.6 g/min. The amount of reaction liquid fed after the reaction had reached a steady state was about 17.2 kg. The amount of reaction liquid recovered in the storage tank 610 was 12.9 kg. When reaction liquid was analyzed by liquid chromatography and $^1$H-NMR, the reaction liquid was found to be a composition that contained N,N'-(4,4'-methanediyl-diphenyl)-di(carbamic acid (p-nonylphenyl) ester), and p-nonyl phenol at a stoichiometric ratio of 8.83 times, 2,6-diisopropyl phenol at a stoichiometric ratio of 0.041 times based on N,N'-(4,4'-methanediyl-diphenyl)-di(carbamic acid (p-nonylphenyl) ester), and contained 0.0082 times an N-containing compound based on the number of N,N'-(4,4'-methanediyl-diphenyl)-di(carbamic acid (p-nonylphenyl) esters). In addition, the yield of N,N'-(4,4'-methanediyl-diphenyl)-di(carbamic acid (p-nonylphenyl) ester) based on 4,4'-methylenedianiline was about 71%. The reaction liquid contained 110 ppm of ammonia. On the other hand, when $^1$H-NMR and $^{13}$C-NMR measurements were carried out on the component recovered in the storage tank 609, it was found to be a mixture of 2,6-diisopropyl phenol, urea and (p-nonylphenyl) carbamate, the content of 2,6-diisopropyl phenol was about 3.54 kg (19.9 mol), the content of urea was about 370 g (6.20 mol), and the content of (p-nonylphenyl) carbamate was about 105 g (0.40 mol). In addition, gas containing ammonia was discharged from the gas-liquid separator 608 via the line 67. The gas was recovered in a Tedlar bag and injected into a gas chromatograph with a gastight syringe to analyze the gas components. As a result, the amount of ammonia recovered per 10 minutes was 0.155 g (9.12 mmol). In addition, when the gas was analyzed by GC-MS, the amount of carbonyl groups contained in compounds having carbonyl groups contained in the ammonia was 0.0059 mmol.

When the steps (74-1) and (74-2) were continued to be carried out, clogging of the ammonia extraction line was not observed even after operating time had exceeded 380 days.

Example 75

Step (75-1): Production of (4-dodecylphenyl) Carbamate

The apparatus shown in FIG. 23 was used.
The same method as step (19-1) of Example 19 was carried out with the exception of using 44.0 kg of p-dodecyl phenol instead of 4-heptyl phenol and using 1.57 kg of urea. When the reactant recovered in the storage tank 306 was analyzed by liquid chromatography, the reactant was found to be a mixture containing 17.7% by weight of (p-dodecylphenyl) carbamate.

Step (75-2): Production of Compound Having Ureido Groups

The same method as step (19-2) of Example 19 was carried out with the exception of using the mixture obtained in step (75-1) instead of the mixture obtained in step (19-1), and supplying 1.28 kg of 2,4-toluenediamine instead of hexamethylenediamine at the rate of about 12 g/min.

As a result of analyzing the reaction liquid by liquid chromatography, the reaction liquid was found to contain 4.2% by weight of 2,4-toluenediurea.

Step (75-3): Production of N-Substituted Carbamic Acid-O—Ar Ester

The same method as step (19-3) of Example 19 was carried out with the exception of heating the packed column 310 to 210° C., setting the pressure inside the column to 40 kPa, holding the condenser at 60° C., and feeding the reaction liquid obtained in step (75-2) instead of the reaction liquid obtained in step (19-2) at the rate of about 2.5 g/min. The amount of reaction liquid fed after the reaction had reached a steady state was about 41.3 kg. The amount of reaction liquid recovered in the storage tank 315 was 31.4 kg. When reaction liquid recovered in the storage tank 315 was analyzed by liquid chromatography and $^1$H-NMR, the reaction liquid was found to be a composition that contained toluene-2,4-di(carbamic acid (p-dodecylphenyl) ester), and p-dodecyl phenol at a stoichiometric ratio of 24.2 times and di(p-dodecylphenyl) carbonate at a stoichiometric ratio of 0.0002 times based on toluene-2,4-di(carbamic acid (p-dodecylphenyl) ester), and contained 0.021 times an N-containing compound based on the number of toluene-2,4-di(carbamic acid (p-dodecylphenyl) esters). In addition, the yield of toluene-2,4-di(carbamic acid (p-dodecylphenyl) ester) based on 2,4-toluenediamine was about 61%. The reaction liquid contained 310 ppm of ammonia. On the other hand, when $^1$H-NMR and $^{13}$C-NMR measurements were carried out on the component recovered in the storage tank 313, it was found to be a mixture of 4-dodecyl phenol, urea and (p-dodecylphenyl) carbamate, the content of p-dodecyl phenol was 7.57 kg (28.9 mol), the content of urea was about 67.5 g (1.12 mol), and the content of (p-dodecylphenyl) carbamate was 1.89 kg (6.20 mol).

Ammonia discharged from the gas-liquid separator 312 through the line 39 was recovered in a Tedlar bag and injected into a gas chromatograph with a gastight syringe to analyze the gas components. As a result, the amount of ammonia recovered per 10 minutes was 0.138 g (8.10 mmol). In addition, when the gas was analyzed by GC-MS, the amount of carbonyl groups contained in compounds having carbonyl groups contained in the ammonia was 0.0020 mmol.

When the steps (75-1) to (75-3) were continued to be carried out, clogging of the ammonia extraction line was not observed even after operating time had exceeded 380 days.

Example 76

Step (76-1): Production of (4-ethylphenyl) Carbamate

The apparatus shown in FIG. 23 was used.

The same method as step (19-1) of Example 19 was carried out with the exception of using 42.3 kg of 4-ethyl phenol instead of 4-heptyl phenol and using 2.08 kg of urea. When the reactant recovered in the storage tank 306 was analyzed by liquid chromatography, the reactant was found to be a mixture containing 13.0% by weight of (4-ethylphenyl) carbamate.

Step (76-2): Production of Compound Having Ureido Groups

The same method as step (19-2) of Example 19 was carried out with the exception of using the mixture obtained in step (76-1) instead of the mixture obtained in step (19-1), and supplying 2.15 kg of aniline instead of hexamethylenediamine at the rate of about 10 g/min.

As a result of analyzing the reaction liquid by liquid chromatography, the reaction liquid was found to contain 8.0% by weight of N-phenylurea.

Step (76-3): Production of N-Substituted Carbamic Acid-O—Ar Ester

The same method as step (19-3) of Example 19 was carried out with the exception of heating the packed column 310 to 200° C., setting the pressure inside the column to atmospheric pressure (nitrogen atmosphere), holding the condenser at 60° C., and feeding the reaction liquid obtained in step (76-2) instead of the reaction liquid obtained in step (19-2) at the rate of about 1.5 g/min. The amount of reaction liquid fed after the reaction had reached a steady state was about 45.2 kg. The amount of reaction liquid recovered in the storage tank 315 was 29.9 kg. When reaction liquid recovered in the storage tank 315 was analyzed by liquid chromatography and $^1$H-NMR, the reaction liquid was found to be a composition that contained N-phenyl carbamic acid (4-ethylphenyl) ester, and 4-ethyl phenol at a stoichiometric ratio of 24.7 times and di(4-ethylphenyl) carbonate at a stoichiometric ratio of 0.0011 times based on N-phenyl carbamic acid (4-ethylphenyl) ester, and contained 0.052 times an N-containing compound based on the number of N-phenyl carbamic acid (4-ethylphenyl) esters. In addition, the yield of N-phenyl carbamic acid (4-ethylphenyl) ester based on aniline was about 36%. The reaction liquid contained 1010 ppm of ammonia. On the other hand, when $^1$H-NMR and $^{13}$C-NMR measurements were carried out on the component recovered in the storage tank 313, it was found to be a mixture of 4-ethyl phenol, urea and (4-ethylphenyl) carbamate, the content of 4-ethyl phenol was 13.8 kg (113 mol), the content of urea was about 161 g (2.68 mol), and the content of (4-ethylphenyl) carbamate was 2.06 kg (12.5 mol).

Ammonia discharged from the gas-liquid separator 312 through the line 39 was recovered in a Tedlar bag and injected into a gas chromatograph with a gastight syringe to analyze the gas components. As a result, the amount of ammonia recovered per 10 minutes was 0.155 g (9.14 mmol). In addition, when the gas was analyzed by GC-MS, the amount of carbonyl groups contained in compounds having carbonyl groups contained in the ammonia was 0.0007 mmol.

When the steps (76-1) to (76-3) were continued to be carried out, clogging of the ammonia extraction line was not observed even after operating time had exceeded 380 days.

Example 77

Step (77-1): Production of (4-nonylphenyl) Carbamate

The apparatus shown in FIG. 23 was used.

The same method as step (19-1) of Example 19 was carried out with the exception of using 38.0 kg of 4-nonyl phenol instead of p-heptyl phenol and using 2.19 kg of urea. When the reactant recovered in the storage tank 306 was analyzed by liquid chromatography, the reactant was found to be a mixture containing 23.9% by weight of (4-nonylphenyl) carbamate.

Step (77-2): Production of Compound Having Ureido Groups

The same method as step (19-2) of Example 19 was carried out with the exception of using the mixture obtained in step (77-1) instead of the mixture obtained in step (19-1), and supplying 1.83 kg of 4,4'-methylenebis(cyclohexylamine) instead of hexamethylenediamine at the rate of about 12 g/min.

As a result of analyzing the reaction liquid by liquid chromatography, the reaction liquid was found to contain 6.0% by weight of 4,4'-methanediyl-dicyclohexyldiurea.

Step (77-3): Production of N-Substituted Carbamic Acid-O—Ar Ester

The same method as step (19-3) of Example 19 was carried out with the exception of heating the packed column 310 to 250° C., setting the pressure inside the column to 20 kPa, holding the condenser at 60° C., and feeding the reaction liquid obtained in step (77-2) instead of the reaction liquid obtained in step (19-2) at the rate of about 1.9 g/min. The amount of reaction liquid fed after the reaction had reached a steady state was about 39.2 kg. The amount of reaction liquid recovered in the storage tank 315 was 24.5 kg. When reaction liquid recovered in the storage tank 315 was analyzed by liquid chromatography and $^1$H-NMR, the reaction liquid was found to be a composition that contained N,N'-(4,4'-methanediyl-dicyclohexyl)-di(carbamic acid (4-nonylphenyl) ester), and 4-nonyl phenol at a stoichiometric ratio of 14.7 times and di(4-nonylphenyl) carbonate at a stoichiometric ratio of 0.008 times based on N,N'-(4,4'-methanediyl-dicyclohexyl)-di(carbamic acid (4-nonylphenyl) ester), and contained 0.022 times an N-containing compound based on the number of N,N'-(4,4'-methanediyl-dicyclohexyl)-di(carbamic acid (4-nonylphenyl) esters). In addition, the yield of N,N'-(4,4'-methanediyl-dicyclohexyl)-di(carbamic acid (4-nonylphenyl) ester) based on 4,4'-methyenebis(cyclohexylamine) was about 73%. The reaction liquid contained 290 ppm of ammonia. On the other hand, when $^1$H-NMR and $^{13}$C-NMR measurements were carried out on the component recovered in the storage tank 313, it was found to be a mixture of 4-nonyl phenol, urea and (4-nonylphenyl) carbamate, the content of 4-nonyl phenol was 9.79 kg (44.4 mol), the content of urea was about 101 g (1.68 mol), and the content of (4-nonylphenyl) carbamate was 4.58 kg (17.4 mol).

Ammonia discharged from the gas-liquid separator 312 through the line 39 was recovered in a Tedlar bag and injected into a gas chromatograph with a gastight syringe to analyze the gas components. As a result, the amount of ammonia recovered per 10 minutes was 0.107 g (6.28 mmol). In addition, when the gas was analyzed by GC-MS, the amount of carbonyl groups contained in compounds having carbonyl groups contained in the ammonia was 0.070 mmol.

When the steps (77-1) to (77-3) were continued to be carried out, clogging of the ammonia extraction line was not observed even after operating time had exceeded 380 days.

Comparative Example 1

Step (A-1): Production of N-Substituted Carbamic Acid-O—Ar Ester

Production of urethane was carried out in a reactor as shown in FIG. 21.

1.21 kg of hexamethylenediamine, 42.9 kg of 4-(1,1,3,3-tetramethylbutyl) phenol and 2.38 kg of urea were mixed to prepare a raw material solution. The packed column 102 was heated to 240° C., and the pressure inside the column was set to 40 kPa. A mixed liquid having the same composition as the raw material solution was introduced through the line 1 provided in the upper portion of the packed column 102, and after operating conditions had stabilized, the raw material solution was introduced at about 1.5 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 190° C., and the resulting component was recovered in the storage tank 104. When 10 hours had elapsed after operating conditions had stabilized, the component recovered in the storage tank 104 was sampled and $^1$H-NMR and $^{13}$C-NMR measurements were carried out on the sample, the component was found to be a mixture of 4-(1,1,3,3-tetramethylbutyl) phenol and urea, the content of urea was about 25.5 g (0.42 mol) and the content of 4-(1,1,3,3-tetramethylbutyl) phenol was 83.1 g (0.40 mol). A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.24 g (14.4 mmol). In addition, when the gas was analyzed by GC-MS, the amount of carbonyl groups contained in compounds having carbonyl groups contained in the ammonia was 16.2 mmol. The reaction liquid obtained in the storage tank 105 contained N,N'-hexanediyl-di(carbamic acid (4-(1,1,3,3-tetramethylbutyl) phenyl) ester), and the yield of N,N'-hexanediyl-di(carbamic acid (4-(1,1,3,3-tetramethylbutyl) phenyl) ester) based on hexamethylenediamine was about 90%. The reaction liquid contained 9.1 ppm of ammonia.

When the reaction was continued, the line 5 became clogged 34 days after operating conditions had stabilized, and N-substituted carbamic acid-O—Ar ester was unable to be produced.

Comparative Example 2

Step (B-1): Production of N-Substituted Carbamic Acid-O—Ar Ester

Production of urethane was carried out in a reactor as shown in FIG. 21.

1.32 kg of hexamethylenediamine, 42.9 kg of p-heptyl phenol and 2.38 kg of urea were mixed to prepare a raw material solution. The packed column 102 was heated to 240° C., and the pressure inside the column was set to 20 kPa. A mixed liquid having the same composition as the raw material solution was introduced through the line 1 provided in the upper portion of the packed column 102, and after operating conditions had stabilized, the raw material solution was introduced at about 1.5 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 130° C., and the resulting component was recovered in the storage tank 104. When 10 hours had elapsed after operating conditions had stabilized, the component recovered in the storage tank 104 was sampled and $^1$H-NMR and $^{13}$C-NMR measurements were carried out on the sample, the component was found to be a mixture of p-heptyl phenol and urea, the content of urea was about 1.71 g (28.5 mol) and the content of p-heptyl phenol was 14.2 g (73.8 mol). A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.22 g (12.8 mmol). In addition, when the gas was analyzed by GC-MS, the amount of carbonyl groups contained in compounds having carbonyl groups contained in the ammonia was 14.8 mmol. The reaction liquid obtained in the storage tank 105 contained N,N'-hexanediyl-di(carbamic acid (p-heptylphenyl) ester), and the yield of N,N'-hexanediyl-di(carbamic acid (p-heptylphenyl) ester) based on hexamethylenediamine was about 90%. The reaction liquid contained 8.8 ppm of ammonia.

When the reaction was continued, the line 5 became clogged 30 days after operating conditions had stabilized, and N-substituted carbamic acid-O—Ar ester was unable to be produced.

Comparative Example 3

Step (C-1): Production of N-Substituted Carbamic Acid-O—Ar Ester

Production of urethane was carried out in a reactor as shown in FIG. 21.

1.32 kg of hexamethylenediamine, 64.1 kg of p-dodecyl phenol and 3.08 kg of urea were mixed to prepare a raw material solution. The packed column 102 was heated to 250° C., and the pressure inside the column was set to 60 kPa. A mixed liquid having the same composition as the raw material solution was introduced through the line 1 provided in the upper portion of the packed column 102, and after operating conditions had stabilized, the raw material solution was introduced at about 1.5 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 50° C., and the resulting component was recovered in the storage tank 104. When 10 hours had elapsed after operating conditions had stabilized, the component recovered in the storage tank 104 was sampled and $^1$H-NMR and $^{13}$C-NMR measurements were carried out on the sample, the component was found to be a mixture of p-dodecyl phenol and urea, the content of urea was about 1.84 g (30.6 mol) and the content of p-dodecyl phenol was 7.69 g (29.3 mol). A gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.19 g (11.4 mmol). In addition, when the gas was analyzed by GC-MS, the amount of carbonyl groups contained in compounds having carbonyl groups contained in the ammonia was 15.1 mmol.

When the reaction was continued, the line 5 became clogged 21 days after operating conditions had stabilized, and N-substituted carbamic acid-O—Ar ester was unable to be produced.

Comparative Example 4

Step (D-1): Production of Compound having Ureido Groups

The apparatus shown in FIG. 26 was used.

22.5 kg of 1-octanol and 2.27 kg of urea were mixed in the storage tank 601 heated to 120° C. with the line 63 closed, and the mixed liquid was transferred to the stirring tank 603 heated to 120° C. While stirring the stirring tank 603, 1.34 kg of organic amine in the form of 3-aminomethyl-3,5,5-trimethylcyclohexylamine were supplied from the storage tank 602 to the stirring tank 603 through the line 62 at the rate of about 10 g/min. After finishing supplying the 3-aminomethyl-3,5,5-trimethylcyclohexylamine, stirring was carried out for about 2 hours followed by sampling the reaction liquid. As a result of analyzing the reaction liquid by liquid chromatography, the reaction liquid was found to contain about 7.8% by weight of 3-(ureidomethyl)-3,5,5-trimethylcyclohexylurea. In addition, the ammonia concentration in the reaction liquid was 6800 ppm. The line 63 was then opened and the solution was transferred to the storage tank 604 through the line 63.

Step (D-2): Production of N-Substituted Carbamic Acid-O—R² Ester and Recovery of Urea Next, the apparatus shown in FIG. 26 was used.

The packed column 605 packed with a packing (Helipack No. 3) was heated to 190° C. The reaction liquid obtained in step (D-1) was fed at the rate of about 1.1 g/min from the line 64 provided in the packed column 605. Since the reaction is initially in an unsteady state, the sample at that time was discarded. The amount of reaction liquid fed after the reaction had reached a steady state was about 23.4 kg. The reaction liquid was recovered in the storage tank 610 through the line 66 provided in the bottom of the packed column 605. A gaseous phase component was condensed from the line 65 provided in the top of the packed column 605 with the condenser 606, and the resulting liquid phase component was recovered in the storage tank 609 via the gas-liquid separator 608. When condensed component recovered in the storage tank 609 was analyzed by $^1$H-NMR, the condensed component was found to contain 1-octanol and urea. The amount of reaction liquid recovered in the storage tank 610 was 8.80 kg. When the reaction liquid was analyzed by liquid chromatography and $^1$H-NMR, the reaction liquid was found to contain 3-((1-octyloxy)carbonylaminomethyl)-3,5,5-trimethylcyclohexyl carbamic acid (1-octyl) ester, and the yield of 3-((1-octyloxy)carbonylamidomethyl)-3,5,5-trimethylcyclohexyl carbamic acid (1-octyl) ester based on 3-aminomethyl-3,5,5-trimethylcyclohexylamine was about 90%. The reaction liquid contained 7.1 ppm of ammonia.

Step (D-3): Production of Isocyanate by Thermal Decomposition of N-Substituted Carbamic Acid-O—R² Ester The apparatus shown in FIG. 28 was used.

The thin film distillation apparatus 802 having a heat-conducting surface area of 0.2 m² was heated to 250° C. and the pressure within the thin film distillation apparatus was set to about 0.8 kPa. The reaction liquid recovered in the storage tank 610 in step (D-2) was placed in the storage tank 801 and supplied to the thin film distillation apparatus at the rate of about 890 g/hr via the line 80. A liquid component was extracted from the line 82 provided in the bottom of thin film distillation apparatus 802 and recovered in the storage tank 803. The liquid component recovered in the storage tank 803 was again supplied to the thin film distillation apparatus 802 through the line 83. A gaseous component containing isophorone diisocyanate and 1-octanol was extracted from the line 81 provided in the upper portion of the thin film distillation apparatus 802. The gaseous component was introduced into the distillation column 604, and low boiling components were separated by distillation. A liquid phase component was supplied to the distillation column 809 from the line 88 provided in the distillation column 804 at a portion lower than the feed line, and further subjected to distillative separation. The gaseous phase component was condensed in the condenser 810 through the line 89 and recovered in the storage tank 812 through the gas-liquid separator 811.

When the condensate was analyzed by $^1$H-NMR and gas chromatography, it was found to contain about 93% by weight of isophorone diisocyanate and about 4% by weight of 3-((1-octyloxy)carbonylaminomethyl)-3,5,5-trimethylcyclohexyl carbamic acid (1-octyl) ester. The yield based on 3-aminomethyl-3,5,5-trimethylcyclohexylamine was about 53%.

Comparative Example 5

Step (E-1): Production of N-Substituted Carbamic Acid-O—Ar Ester

Production of urethane was carried out in a reactor as shown in FIG. 21.

1.20 kg of hexamethylenediamine, 29.8 kg of 1-nonanol and 2.36 kg of urea were mixed to prepare a raw material solution. The packed column 102 was heated to 220° C., the pressure inside the column was set to 50 kPa, a mixed liquid having the same composition as the raw material solution was introduced through the line 1 provided in the upper portion of the packed column 102, and after operating conditions had stabilized, the raw material solution was introduced at about 1.8 g/min, and the reaction liquid was recovered in the storage tank 105 via the line 4 provided in the bottom of the packed column 102. A gaseous phase component was recovered from the line 2 provided in the top of the packed column 102, condensed in the condenser 103 held at about 85° C., and the resulting component was recovered in the storage tank 104. The amount of reaction liquid recovered in the storage tank 105 was 28.2 kg. When the reaction liquid was analyzed by liquid chromatography and $^1$H-NMR, the reaction liquid was found to contain N,N'-hexanediyl-di(carbamic acid nonylphenyl ester), and the yield of N,N'-hexanediyl-di(carbamic acid nonylphenyl ester) based on hexamethylenediamine was about 91%. The reaction liquid contained 6.9 ppm of ammonia. On the other hand, when $^1$H-NMR and $^{13}$C-NMR measurements were carried out on the component recovered in the storage tank 104, it was found to be a mixture of 1-nonanol and urea, the content of urea of about 1.33 kg (22.1 mol), and the content of 1-nonanol was 3.72 kg (25.8 mol). In addition, a gas containing ammonia was discharged from the line 5 provided in the upper portion of the storage tank 104. The gas was recovered in a Tedlar bag and injected into a gas chromatograph with a gastight syringe to analyze the gas components. As a result, the amount of ammonia recovered per 10 minutes was 0.40 g (23.6 mmol). In addition, when the gas was analyzed by GC-MS, the amount of carbonyl groups contained in compounds having carbonyl groups contained in the ammonia was 0.039 mmol.

Step (E-2): Production of Isocyanate

The same method as Example 1 was carried out with the exception of heating the thin film distillation apparatus 702 to 220° C., setting the pressure within the thin film distillation apparatus to about 1.3 kPa, and supplying the solution obtained in step (E-1) instead of the reaction liquid recovered in the storage tank 105 in Example 1 to the thin film distillation apparatus at the rate of about 1790 pr. A condensate was obtained in the storage tank 707 at the rate of about 61 g/hr. The condensate was hexamethylene diisocyanate. The yield of hexamethylene diisocyanate based on hexamethylenediamine was about 54%.

Example 78

A composition containing 21.5% by weight of an N-substituted carbamic acid-O—Ar ester in the form of bis(4-(2,4,4-trimethylpentan-2-yl)phenyl)hexan-1,6-diyl dicarbamate, 78% by weight of an aromatic hydroxy composition in the form of 4-(2,4,4-trimethylpentan-2-yl) phenol and 12 ppm of ammonia was placed in a 100 L SUS storage vessel to about ½ the volume thereof, followed by replacing the inside of the storage vessel with nitrogen, and storing for 1095 days in a storage environment found in the Kojima district of Kurashiki City in Okayama Prefecture, Japan. During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the bis(4-(2,4,4-trimethylpentan-2-yl)phenyl)hexan-1,6-diyl dicarbamate was contained at 99 mol % as compared with prior to storage. Following the storage period, the composition was heated to 180° C. and transferred through a preheater (device for preheating the composition to 230° C.) to a thin film distiller using a liquid pump. A thermal decomposition reaction was carried out while confirming operating conditions containing a temperature of the thin film distiller of 230° C., residence time within a range of from 60 to 120 seconds, and pressure within a range of from 0.3 to 1 kPa, the gaseous phase was introduced into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of from 150 to 300° C. and confirming operating conditions; the minimum pressure during operation was about 0.3 KPa). Isocyanate derived from the bis(4-(2,4,4-trimethylpentan-2-yl)phenyl)hexan-1,6-diyl dicarbamate in the form of hexane 1,6-diisocyanate was obtained from the upper portion of the distillation column. Although the yield changed from the start to completion of operation due to fluctuations in operating conditions, at the highest level of performance during the operating period, the yield of the hexane 1,6-diisocyanate based on bis(4-(2,4,4-trimethylpentan-2-yl)phenyl)hexan-1,6-diyl dicarbamate was 92.9 mol %. There was no clogging of lines during both storage and transport, and formation of solid within the distillation column was not observed.

Examples 79 to 122 and Comparative Examples 6 and 7

Storage and thermal decomposition were carried out on compositions in the same manner as Example 78 with the exception of the composition ratios of the N-substituted carbamic acid-O—Ar ester, aromatic hydroxy composition, ammonia and carbonic acid derivative and the like, and the results of distillation are shown in Tables 2 to 8. When using an aromatic hydroxy compound having a standard boiling point lower than the standard boiling point of hexane 1,6-diisocyanate, a packed distillation column having an inner diameter of 2.5 inches and 20 theoretical plates (packing: Metal Gauze CY Packing manufactured by Sulzer Chemtech Ltd.) was installed along with the previously described distillation column, and a gaseous phase extracted from the upper portion of the sieve plate distillation column was introduced into the vicinity of the middle of the packed distillation column to separate the hexane 1,6-diisocyanate and aromatic hydroxy compound (the yield of hexane 1,6-diisocyanate is shown as the value obtained by analyzing the gaseous phase in the upper portion of the sieve plate distillation column; the packed distillation column was installed for the purpose of industrial purification).

In the tables, an Ar—O— group represents an Ar—O— group that composes a carbamic acid-O—Ar group in the N-substituted carbamic acid-O—Ar ester (namely, the Ar—O group in the following formula (131)), and ArOH represents an aromatic hydroxy compound that composes the aromatic hydroxy composition. The content of each component in the composition is represented as a weight percentage (wt %) obtained by rounding the contents of N-substituted carbamic acid-O—Ar ester, aromatic hydroxy composition and water to the number of significant digits of the analysis apparatus or less, ammonia and metal components are expressed in ppm, while other components (such as carbonic acid derivative) are indicated as the ratio of the number of molecules to carbamic acid-O—Ar groups of the N-substituted carbamic acid-O—Ar ester.

Figure 32:
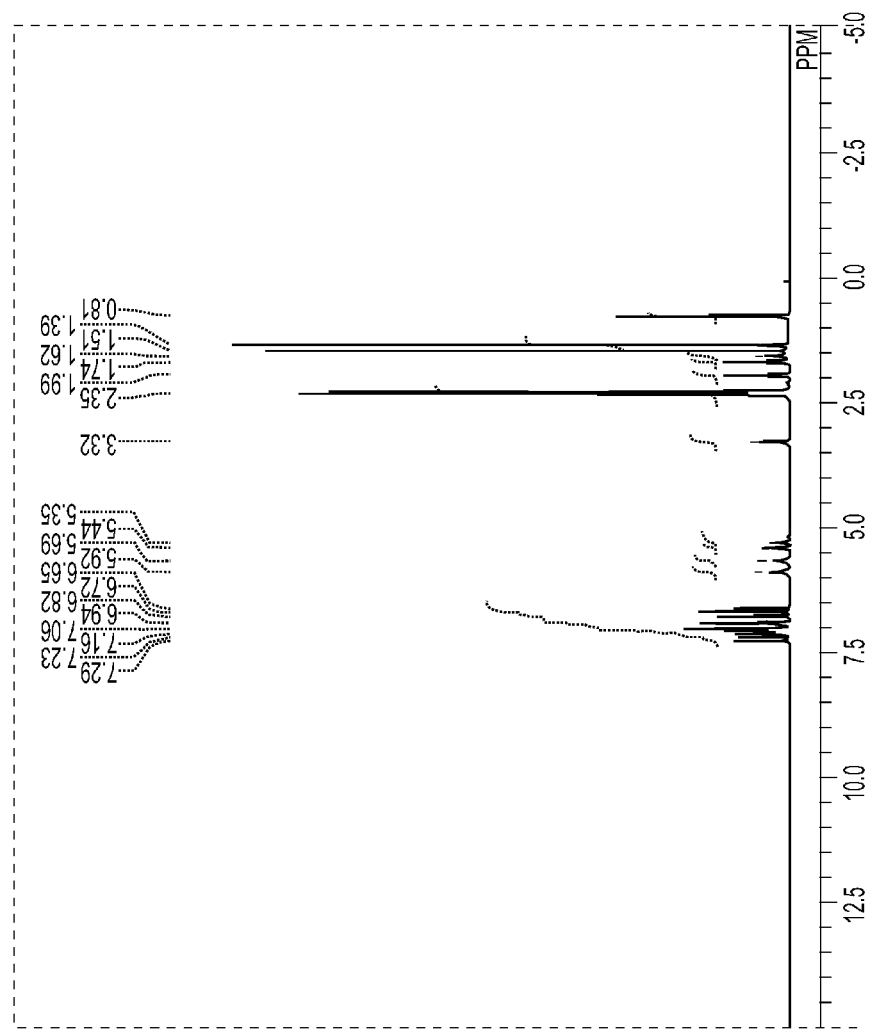
FIG. 32 shows the $^1$H-NMR spectrum of a composition for transfer and storage of N-substituted carbamic acid ester of an Example 84 of the present embodiment.
Figure 33:
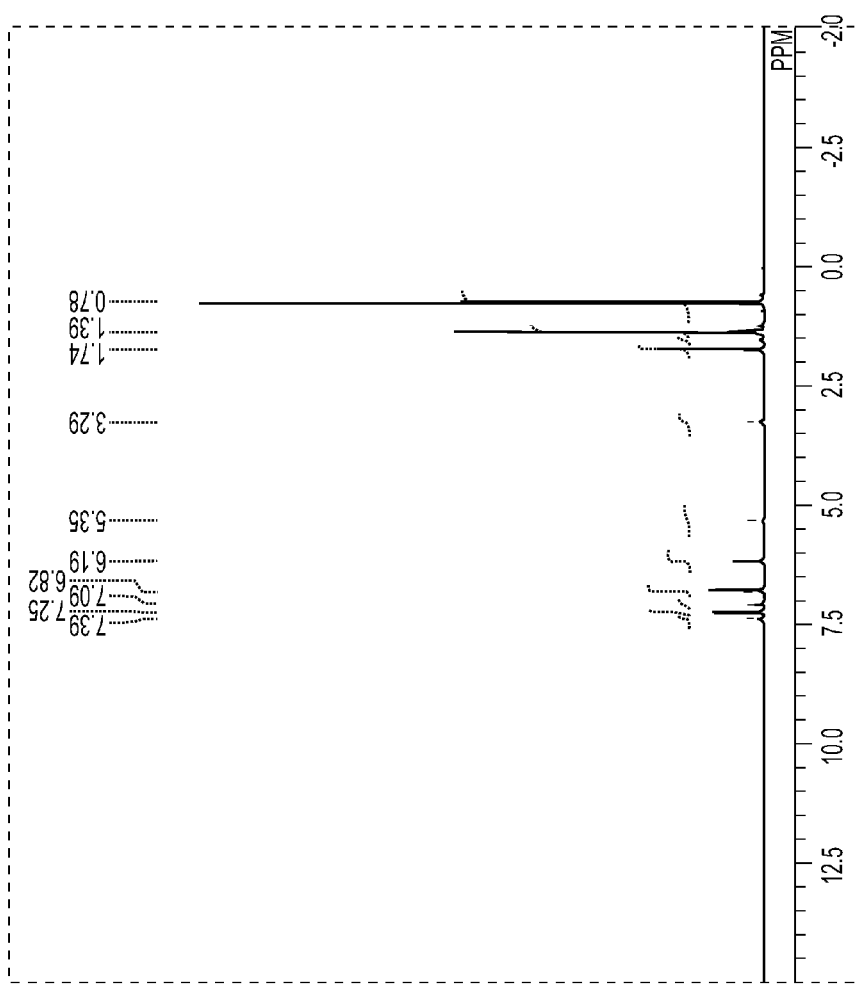
FIG. 33 shows the $^1$H-NMR spectrum of a composition for transfer and storage of N-substituted carbamic acid ester of an Example 104 of the present embodiment.
Figure 34:
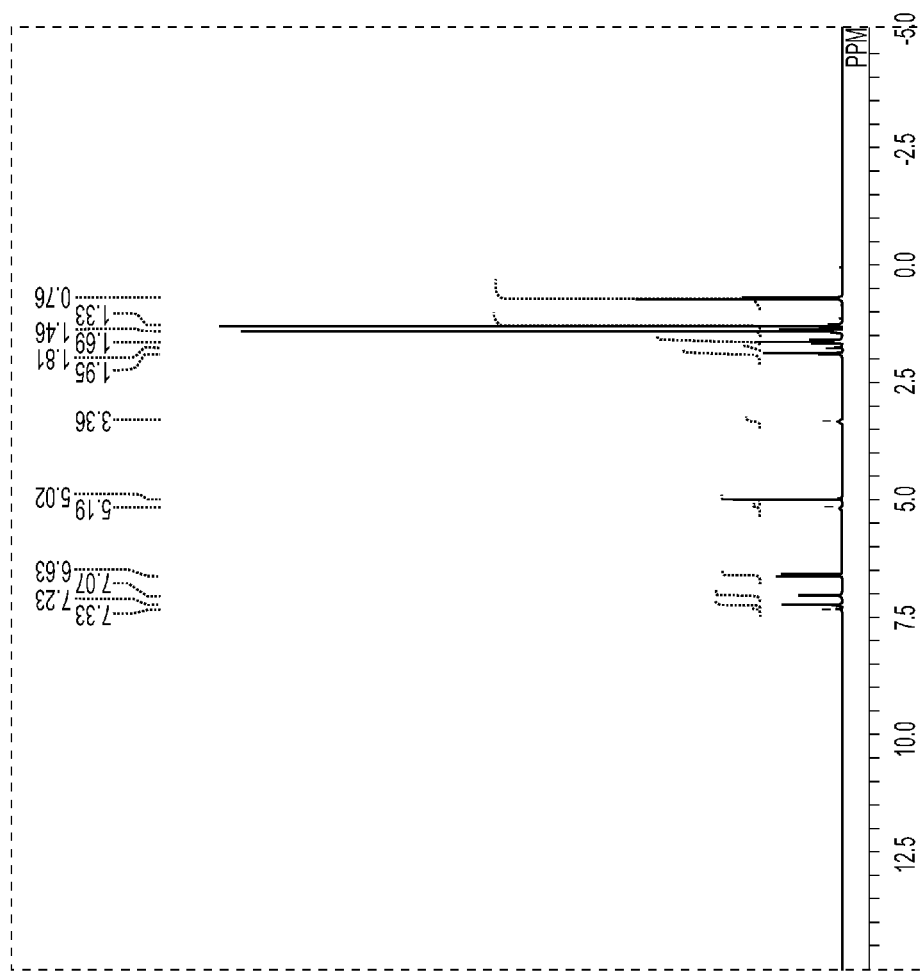
FIG. 34 shows the $^1$H-NMR spectrum of a composition for transfer and storage of N-substituted carbamic acid ester of an Example 120 of the present embodiment.

The $^1$H-NMR spectra of the compositions of Examples 84, 104 and 120 are shown in FIGS. 32, 33 and 35, respectively. (Unless indicated otherwise, phenomena such as clogging or solid formation did not occur during storage or transfer.)

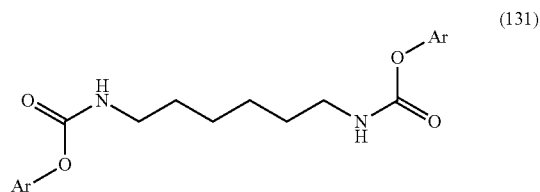

(131)

TABLE 2

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 79 | phenyl-O | 27.2 | phenol, 2-naphthol | 42.5 / 30 | 5 | Fe ion: 20 ppm, Ni ion: 15 ppm | 98.5 | 93.7 |
| Comparative Example 6 | phenyl-O | 99 | | | 5 | | 12.6 | (Solid formed, pump clogged) |
| Comparative Example 7 | phenyl-O | 25.5 | | | 5 | Methanol: 72.5 wt %, Dibutyl tin dilaurate: 2010 ppm | 12.4 | (Solid formed, pump clogged) |
| Example 80 | phenyl-O | 1.5 | phenol, 2-naphthol | 86 / 10 | 100 | Fe ion: 20 ppm, Ni ion: 15 ppm, Dibutyl tin dilaurate: 2010 ppm | 19.3 | 2.0 |
| Example 81 | 2-methylphenyl-O | 25.5 | 2-methylphenol, 4-(1,1,3,3-tetramethylbutyl)phenol | 37 / 36 | 80 | Dibutyl tin dilaurate: 10 ppm, Total carbonic acid ester: 0.001 | 85.5 | 81.4 |

TABLE 2-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 82 | 3-methylphenyl-O- | 46 | 3-methylphenol; 4-(1,1,3,3-tetramethylbutyl)phenol | 40<br>13.8 | 295 | Water: 90 ppm | 70.6 | 66.9 |
| Example 83 | 4-methylphenyl-O- | 26.2 | 4-methylphenol; 4-octylphenol | 43<br>30 | 350 | Fe ion: 20 ppm<br>Ni ion: 30 ppm<br>Dibutyl tin dilaurate: 300 ppm | 73.7 | 65.8 |

TABLE 3

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 84 | 2,4-dimethylphenoxy | 24.8 | 2,4-dimethylphenol; 2,4-di-tert-pentylphenol | 48 / 24.8 | 15 | Total compounds having biuret groups: 0.005, Al ion: 40 ppm | 76.2 | 71.2 |
| Example 85 | 2,6-dimethylphenoxy | 25.2 | 2,6-dimethylphenol; 2-naphthol | 23 / 50 | 11 | Urea: 0.001, Al ion: 40 ppm | 94.4 | 89.7 |
| Example 86 | 2,5-dimethylphenoxy | 24.2 | 2,5-dimethylphenol; 2-phenoxyphenol | 33 / 41.3 | 950 | Urea: 0.005, dibutyl tin dilaurate: 590 ppm | 76.4 | 60.5 |

TABLE 3-continued

| | Ar—O group | Content of N-substituted carbamic acid- O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid- O—Ar ester after storage versus before storage (mol %) | Yield of hexane 1,6-diisocyanate (mol %) (molar yield versus N-substituted carbamic acid- O—Ar ester before storage) |
|---|---|---|---|---|---|---|---|---|
| Example 87 | 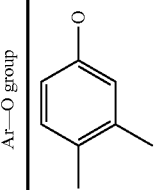 | 2.5 | 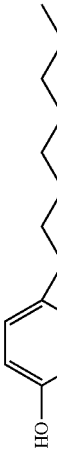 | 31<br>65 | 900 | Total ureylene group-containing compounds: 0.005, dibutyl tin dilaurate: 290 ppm | 88.4 | 22.5 |
| Example 88 | 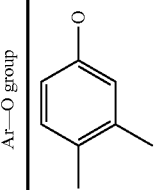 | 5.5 | 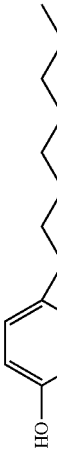 | 31<br>62 | 1050 | Total terminal biuret group-containing compounds: 0.005, dibutyl tin dilaurate: 60 ppm | 89.7 | 45.2 |
| Example 89 | 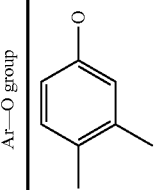 | 24 | 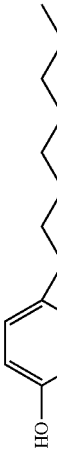 | 23<br>50 | 80 | Total ureylene group-containing compounds: 0.005, dibutyl tin dilaurate: 30 ppm, water: 0.5 wt % | 94.7 | 82.3 |

TABLE 3-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 90 |  | 24.3 | 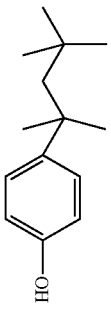 | 37 35.6 | 800 | Total ureylene group-containing compounds: 0.005, terminal biuret group-containing compounds: 0.005, dibutyl tin dilaurate: 60 ppm, water: 0.5 wt % | 73.3 | 65.4 |

TABLE 4

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 91 | [2-propylphenoxy] | 24 | [2-propylphenol and 4-(1,1,3,3-tetramethylbutyl)phenol] | 14 / 60 | 20 | Total ureylene group-containing compounds: 0.005 | 96.0 | 93.0 |
| Example 92 | [2-isopropylphenoxy] | 40 | [2-isopropylphenol and 2-naphthol] | 17 / 40 | 10 | Total ureylene group-containing compounds: 0.005 | 80.5 | 78.4 |
| Example 93 | [4-isopropylphenoxy] | 24.3 | [4-isopropylphenol and 4-octylphenol] | 23 / 50 | 5 | Urea: 0.005, dibutyl tin dilaurate: 40 ppm, water: 0.5 wt % | 90.5 | 85.9 |

TABLE 4-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 94 | 3-isopropylphenoxy | 24 | 3-isopropylphenol; 4-(1,1,3,3-tetramethylbutyl)phenol | 20<br>53 | 15 | Total ureylene group-containing compounds: 0.005, terminal biuret group-containing compounds: 0.005 | 90.6 | 88.7 |
| Example 95 | 2-isopropylphenoxy | 22 | 2-isopropylphenol; 4-phenoxyphenol | 15<br>60 | 5 | Total ureylene group-containing compounds: 0.005, terminal biuret group-containing compounds: 0.005 | 98.5 | 97.0 |

TABLE 4-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 96 | (4-butylphenoxy) | 20 | 4-butylphenol; 2,4-di-tert-pentylphenol | 26; 52 | 10 | Total ureylene group-containing compounds: 0.005, terminal biuret group-containing compounds: 0.005, dibutyl tin dilaurate: 60 ppm | 75.0 | 71.3 |
| Example 97 | (2-tert-pentylphenoxy) | 23.2 | 2-tert-pentylphenol | 75.5 | | Total ureylene group-containing compounds: 0.005, terminal biuret group-containing compounds: 0.005 | 96.1 | 92.9 |

TABLE 5

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 98 | 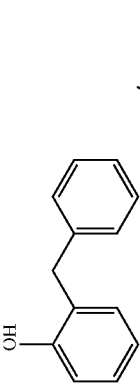 | 22 | 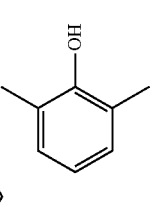 | 68 8 | 18 | Total ureylene group-containing compounds: 0.005, terminal biuret group-containing compounds: 0.005 | 95.8 | 93.2 |
| Example 99 | 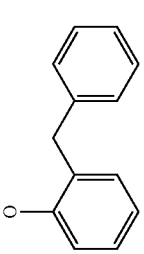 | 6 |  | 22 71 | 480 | Total ureylene group-containing compounds: 0.015, terminal biuret group-containing compounds: 0.015 | 88.5 | 32.0 |

TABLE 5-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 100 | 2-ethoxyphenoxy | 20.5 | 2-ethoxyphenol; 2,4-di-tert-pentylphenol | 38.2 / 40 | 290 | Total ureylene group-containing compounds: 0.020, terminal biuret group-containing compounds: 0.015 | 91.2 | 87.5 |
| Example 101 | 4-octylphenoxy | 22.3 | geranyl-type phenol; 4-isopropylphenol; 2-isopropylphenol | 64.3 / 6 / 6 | 11 | Total ureylene group-containing compounds: 0.002, terminal biuret group-containing compounds: 0.005, urea: 1 | 88.0 | 86.0 |

TABLE 5-continued

| Example | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (molar yield versus N-substituted carbamic acid-O—Ar ester before storage) |
|---|---|---|---|---|---|---|---|---|
| Example 102 | (4-octylphenoxy) | 22 | (4-octylphenol) | 55 | 11 | Naphthalene: 20 wt %, total ureylene group-containing compounds: 0.002, terminal biuret group-containing compounds: 0.005 | 94.9 | 88.6 |
| Example 103 | (4-butoxyphenoxy) | 23 | (4-butoxyphenol), phenol | 65, 10 | 250 | Total ureylene group-containing compounds: 0.002, terminal biuret group-containing compounds: 0.005 | 97.4 | 92.6 |
| Example 104 | (4-(2,4,4-trimethylpentan-2-yl)phenoxy) | 21 | (4-(2,4,4-trimethylpentan-2-yl)phenol) | 71.5 | 11 | Total ureylene group-containing compounds: 0.002, terminal biuret group-containing compounds: 0.005, urea: 1 | 99.5 | 94.8 |

TABLE 6

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 105 | 2-naphthyl-O | 23 | 2-naphthol | 75 | 12 | Total ureylene group-containing compounds: 0.002, terminal biuret group-containing compounds: 0.005 | 99.2 | 97.2 |
| Example 106 | 1-naphthyl-O | 23 | 1-naphthol / 2,6-dimethylphenol | 56 / 18.7 | 13 | Total ureylene group-containing compounds: 0.002, terminal biuret group-containing compounds: 0.005 | 98.8 | 97.5 |
| Example 107 | 4-phenoxyphenyl-O | 1.5 | 4-phenoxyphenol | 97 | 25 | Total ureylene group-containing compounds: 0.002, terminal biuret group-containing compounds: 0.005 | 75.0 | 15.0 |
| Example 108 | 4-phenoxyphenyl-O | 2.5 | 4-phenoxyphenol | 95 | 25 | Total ureylene group-containing compounds: 0.002, terminal biuret group-containing compounds: 0.005 | 94.6 | 16.0 |

TABLE 6-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 109 | (4-phenoxyphenoxy group) | 11.2 | (4-phenoxyphenol) | 87 | 14 | Total ureylene group-containing compounds: 0.002, terminal biuret group-containing compounds: 0.005 | 96.4 | 90.0 |
| Example 110 | (4-chlorophenoxy group) | 24.8 | (4-chlorophenol) and (2-naphthol) | 20 53 | 350 | Total ureylene group-containing compounds: 0.022, terminal biuret group-containing compounds: 0.015 | 78.0 | 45.5 |

TABLE 7

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 111 | 4-(dimethylamino)phenoxy | 24.4 | 4-(dimethylamino)phenol | 20 | 310 | Total ureylene group-containing compounds: 0.022, terminal biuret group-containing compounds: 0.015 | 76.0 | 47.3 |
| Example 112 (aromatic hydroxy compound partially removed from stored composition of Example 108) | 4-phenoxyphenoxy | 11.2 | 2,6-dimethylphenol / 4-phenoxyphenol | 54.5 / 87 | 1 | Total ureylene group-containing compounds: 0.002, terminal biuret group-containing compounds: 0.005 | 94.5 | 87.0 |
| Example 113 | 2-(cyclohexylmethyl)phenoxy | 22 | 2-(cyclohexylmethyl)phenol / 2,6-dimethylphenol | 60 / 16 | 13 | Total ureylene group-containing compounds: 0.002, terminal biuret group-containing compounds: 0.005 | 99.6 | 92.6 |

TABLE 7-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|---|
| Example 114 | 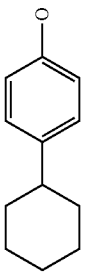 | 22.8 | 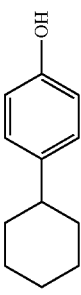<br>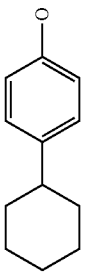 | 65<br><br>10 | 14 | Total ureylene group-containing compounds: 0.002, terminal biuret group-containing compounds: 0.005, ditolyl carbonate: 0.01 | 98.7 | 92.5 |
| Example 115 | 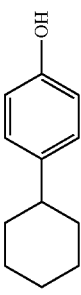 | 22 | 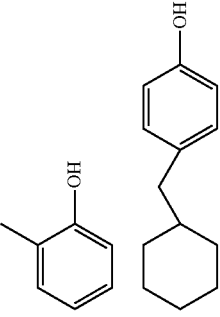<br> | 65<br><br>9.8 | 75 | Total ureylene group-containing compounds: 0.002, terminal biuret group-containing compounds: 0.005, ditolyl carbonate: 0.01 | 96.7 | 92.8 |

TABLE 7-continued

| Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of hexane 1,6-diisocyanate (mol %) (molar yield versus N-substituted carbamic acid-O—Ar ester before storage) |
|---|---|---|---|---|---|---|---|
| Example 116 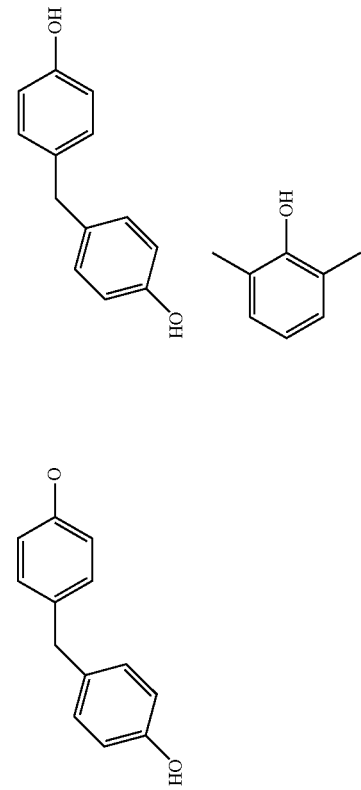 | 10 | | 73 | 500 | Urea: 0.05, terminal biuret group-containing compounds: 0.05, dixylyl carbonate: 0.06, dibutyl tin dilaurate: 650 ppm | 27.0 | 17.8 |

Example 123

A composition containing 26% by weight of an N-substituted carbamic acid-O—Ar ester in the form of the N-substituted carbamic acid-O—Ar ester represented by the following formula (132), 72% by weight of an aromatic hydroxy composition in the form of 2,4,6-trimethyl phenol, 80 ppm of ammonia, 0.1 of urea (ratio of the number of urea molecules to the number of carbamic acid-O—Ar ester groups in the N-substituted carbamic acid-O—Ar ester) and 0.001 of mesityl carbamate (ratio of number of moles of mesityl carbamate to number of carbamic acid-O—Ar ester groups in the N-substituted carbamic acid-O—Ar ester) was placed in a 100 L SUS storage vessel to about ½ the volume thereof, followed by replacing the inside of the storage vessel with nitrogen, and storing for 1095 days in a storage environment found in the Kojima district of Kurashiki City in Okayama Prefecture, Japan. During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the N-substituted carbamic acid-O—Ar ester was contained at 97 mol % as compared with prior to storage. Following the storage period, the composition was heated to 180° C. and transferred through a preheater (device for preheating the composition to 230° C.) to a thin film distiller using a liquid pump. A thermal decomposition reaction was carried out while confirming operating conditions containing a temperature of the thin film distiller of 230° C., residence time within a range of from 60 to 120 seconds, and pressure within a range of from 0.1 to 1 kPa, the gaseous phase was introduced into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of from 150 to 300° C. and confirming operating conditions; the minimum pressure during operation was about 0.5 KPa). Isocyanate derived from the N-substituted carbamic acid-O—Ar ester in the form of 5-isocyanato-1-(isocyanatomethyl)-1,3,3-trimethylcyclohexane (isophorone diisocyanate) was obtained from the bottom of the distillation column. Although the yield changed from the start to completion of operation due to fluctuations in operating conditions, at the highest level of performance during the operating period, the yield of the isophorone diisocyanate based on the N-substituted carbamic acid-O—Ar ester at the start of storage was 90 mol %. There was no clogging of lines during both storage and transport, and formation of solid within the distillation column was not observed.

Examples 124 to 145 and Comparative Example 8

Storage and thermal decomposition were carried out on compositions under the same conditions as Example 123 with the exception of the composite ratios of the N-substituted carbamic acid-O—Ar ester, aromatic hydroxy composition, ammonia and carbonic acid derivative and the like, and the results of distillation are shown in Tables 9 to 12. When using an aromatic hydroxy compound having a standard boiling point lower than the standard boiling point of isophorone diisocyanate, a packed distillation column having an inner diameter of 2.5 inches and 20 theoretical plates (packing: Metal Gauze CY Packing manufactured by Sulzer Chemtech Ltd.) was installed along with the previously described distillation column, and a liquid phase extracted from the bottom of the sieve plate distillation column was introduced into the vicinity of the middle of the packed distillation column to separate the isophorone diisocyanate and aromatic hydroxy compound (the yield of isophorone diisocyanate is shown as the value obtained by analyzing the liquid phase in the bottom of the sieve plate distillation column; the packed distillation column was installed for the purpose of industrial purification).

In the tables, an Ar—O— group represents an Ar—O group that composes a carbamic acid-O—Ar group in the N-substituted carbamic acid-O—Ar ester (namely, the Ar—O group in the following formula (133)), and ArOH represents an aromatic hydroxy compound that composes the aromatic hydroxy composition. The content of each component in the composition is represented as a weight percentage (wt %) obtained by rounding the contents of N-substituted carbamic acid-O—Ar ester, aromatic hydroxy composition and water to the number of significant digits of the analysis apparatus or less, ammonia and metal components are expressed in ppm, while other components (such as carbonic acid derivative) are indicated as the ratio of the number of molecules to carbamic acid-O—Ar groups of the N-substituted carbamic acid-O—Ar ester. (Unless indicated otherwise, phenomena such as clogging or solid formation did not occur during storage or transfer.)

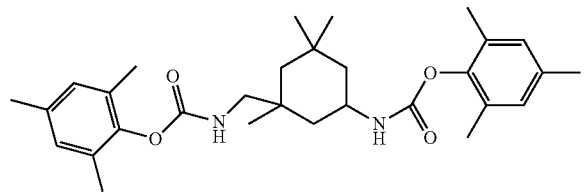

(132)

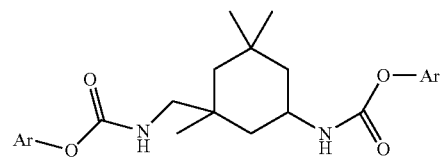

(133)

TABLE 9

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 124 | 2,4,6-trimethylphenoxy | 26.6 | 2,4,6-trimethylphenol | 68.0 | 10 | Urea: 0.001, mesityl carbamate: 0.001 | 98.0 | 94.2 |
| Example 125 | 2,4,6-trimethylphenoxy | 42.1 | 2,4,6-trimethylphenol | 55.0 | 50 | Urea: 0.001, mesityl carbamate: 0.001 | 98.0 | 94.8 |
| Example 126 | 2,4,6-trimethylphenoxy | 67.0 | 2,4,6-trimethylphenol | 32.0 | 60 | Urea: 0.001, mesityl carbamate: 0.001, water: 100 ppm | 80.5 | 85.7 |
| Example 127 | 2,4,6-trimethylphenoxy | 7.0 | 2,4,6-trimethylphenol | 92.0 | 80 | Urea: 0.005, mesityl carbamate: 0.001, Fe ion: 50 ppm, Ni ion: 60 ppm | 54.5 | 32.0 |
| Example 128 | phenoxy | 60.0 | phenol | 35.0 | 10 | Urea: 0.001, phenyl N-substituted carbamate: 0.001 | 92.2 | 87.5 |
| Comparative Example 8 | phenoxy | 97.3 | — | — | 5 | Dibutyl tin dilaurate: 2010 ppm | 12.4 | (solid formation, pump clogging) |

TABLE 10

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 129 | phenoxy | 30.0 | phenol | 38.0 | 50 | Fe ion: 20 ppm, Ni ion: 15 ppm | 93.5 | 88.7 |
| Example 130 | 2-methylphenoxy | 28.9 | 2-isopropylphenol | 30.0 | 80 | Dibutyl tin dilaurate: 10 ppm, total carbonic acid ester: 0.001 | 96.0 | 91.1 |
| Example 131 | 4-propylphenoxy | 26.2 | 2-methylphenol | 68.0 | 50 | Butylphenyl N-substituted carbamate: 0.005, dibutyl tin dilaurate: 20 ppm, water: 0.5 wt % | 96.8 | 92.2 |
| | | | 4-propylphenol | 40.0 | | | | |
| | | | 2-benzylphenol | 31.0 | | | | |
| Example 132 | 2-propylphenoxy | 35.0 | 2-propylphenol | 50.0 | 20 | Butylphenyl N-substituted carbamate: 0.005, terminal biuret group-containing compounds: 0.004, oxygen: 5 ppm | 92.0 | 88.5 |

TABLE 10-continued

| Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|
| | | 2-isopropylphenol | 10.0 | | | | |
| Example 133 | 1.3 | 4-isopropylphenol | 30.0 | 500 | Total ureylene group-containing compounds: 0.01, dibutyl tin dilaurate: 600 ppm, water: 0.5 wt % | 60.2 | 5.6 |
| | | 4-nonylphenol | 68.0 | | | | |
| Example 134 | 8.8 | 4-isopropylphenol | 91.0 | 11 | Total ureylene group-containing compounds: 0.005 | 96.0 | 93.0 |
| Example 135 | 2.0 | 3-isopropylphenol | 97.0 | 100 | Fe ion: 5 ppm, Ni ion: 15 ppm, oxygen: 50 ppm | 70.9 | 16.5 |

TABLE 11

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 136 | (2-benzylphenoxy structure) | 35.0 | (2-benzylphenol) | 65.0 | 5 | | 99.7 | 97.0 |
| Example 137 | (2-ethoxyphenoxy structure) | 24.0 | (2-ethoxyphenol) | 53.1 | 310 | Total ureylene group-containing compounds: 0.005, terminal biuret group-containing compounds: 0.005, dibutyl tin dilaurate: 60 ppm | 95.8 | 88.2 |
| | | | (4-phenoxyphenol) | 20.0 | | | | |
| Example 138 | (4-phenoxyphenoxy structure) | 24.2 | (4-phenoxyphenol) | 75.6 | 10 | | 99.6 | 94.5 |
| Example 139 | (bisphenol A mono-ether structure) | 5.0 | (bisphenol A) | 94.0 | 10 | Fe ion: 5 ppm, Ni ion: 5 ppm, oxygen: 50 ppm | 97.3 | 31.2 |

TABLE 11-continued

| Ar—O group | | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 140 | (2-hydroxyphenoxy structure) | 6.5 | catechol | 92.0 | 1050 | Total ureylene group-containing compounds: 0.005, terminal biuret group-containing compounds: 0.005, dibutyl tin dilaurate: 60 ppm | 81.1 | 36.4 |
| Example 141 | (3'-methylbiphenyl-3-yloxy structure) | 4.0 | 3'-methylbiphenyl-3-ol / 4-isopropylphenol | 46.0 / 50.0 | 20 | | 89.0 | 32.0 |

Example 146

A composition containing 28% by weight of an N-substituted carbamic acid-O—Ar ester in the form of the N-substituted carbamic acid-O—Ar ester represented by the following formula (134), 70% by weight of an aromatic hydroxy composition in the form of 2,4,6-trimethyl phenol, 12 ppm of ammonia, 0.1 of urea (ratio of the number of urea molecules to the number of carbamic acid-O—Ar ester groups in the N-substituted carbamic acid-O—Ar ester) and 0.001 of mesityl carbamate (ratio of number of moles of mesityl carbamate to number of carbamic acid-O—Ar ester groups in the N-substituted carbamic acid-O—Ar ester) was placed in a 100 L SUS storage vessel, followed by replacing the inside of the storage vessel with nitrogen, and storing for 1095 days in a storage environment found in the Kojima district of Kurashiki City in Okayama Prefecture, Japan. During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the N-substituted carbamic acid-O—Ar ester was contained at 96 mol % as compared with prior to storage. Following the storage period, the composition was heated to 180° C. and transferred through a preheater (device for preheating the composition to 230° C.) to a thin film distiller using a liquid pump. A thermal decomposition reaction was carried out while confirming operating conditions containing a temperature of the thin film distiller of 230° C., residence time within a range of from 60 to 120 seconds, and pressure within a range of from 0.1 to 1 kPa, the gaseous phase was introduced into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of from 150 to 300° C. and confirming operating conditions; the minimum pressure during operation was about 0.5 KPa). Isocyanate derived from the N-substituted carbamic acid-O—Ar ester in the form of 4,4'-methylenebis(cyclohexylisocyanate) was obtained from the bottom of the distillation column. Although the yield changed from the start to completion of operation due to fluctuations in operating conditions, at the highest level of performance during the operating period, the yield of the 4,4'-methylenebis(cyclohexylisocyanate) based on the N-substituted carbamic acid-O—Ar ester at the start of storage was 92 mol %. There was no clogging of lines during both storage and transport, and formation of solid within the distillation column was not observed.

Examples 147 to 164 and Comparative Example 9

Storage and thermal decomposition were carried out on compositions under the same conditions as Example 146 with the exception of the composite ratios of the N-substituted carbamic acid-O—Ar ester, aromatic hydroxy composition, ammonia and carbonic acid derivative and the like, and the results of distillation are shown in Tables 13 to 15. When using an aromatic hydroxy compound having a standard boiling point higher than the standard boiling point of 4,4'-methylenebis(cyclohexylisocyanate), a packed distillation column having an inner diameter of 2.5 inches and 20 theoretical plates (packing: Metal Gauze CY Packing manufactured by Sulzer Chemtech Ltd.) was installed along with the previously described distillation column, and a liquid phase extracted from the bottom of the sieve plate distillation column was introduced into the vicinity of the middle of the packed distillation column to separate the 4,4'-methylenebis(cyclohexylisocyanate) and aromatic hydroxy compound (the yield of 4,4'-methylenebis(cyclohexylisocyanate) is shown as the value obtained by analyzing the liquid phase in the bottom of the sieve plate distillation column; the packed distillation column was installed for the purpose of industrial purification).

In the tables, an Ar—O— group represents an Ar—O group that composes a carbamic acid-O—Ar group in the N-substituted carbamic acid-O—Ar ester (namely, the Ar—O group in the following formula (135)), and ArOH represents an aromatic hydroxy compound that composes the aromatic hydroxy composition. The content of each component in the composition is represented as a weight percentage (wt %) obtained by rounding the contents of N-substituted carbamic acid-O—Ar ester, aromatic hydroxy composition and water to the number of significant digits of the analysis apparatus or less, ammonia and metal components are expressed in ppm, while other components (such as carbonic acid derivative) are indicated as the ratio of the number of molecules to carbamic acid-O—Ar groups of the N-substituted carbamic acid-O—Ar ester. (Unless indicated otherwise, phenomena such as clogging or solid formation did not occur during storage or transfer.)

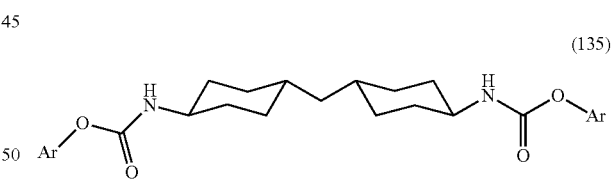

(135)

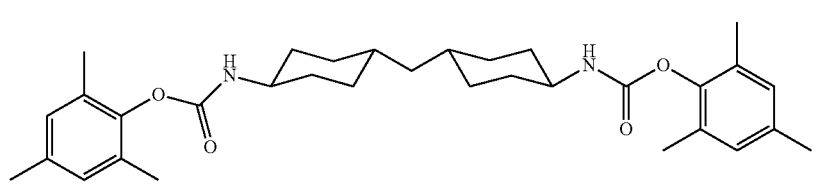

(134)

TABLE 13

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 147 | phenyl-O- | 32.4 | phenol | 65 | 8 | Urea: 0.001, phenyl non-N-substituted carbamate: 0.001 | 97.0 | 92.0 |
| Comparative Example 9 | phenyl-O- | 31.2 | phenol | | 5 | Methanol: 65 wt %, Dibutyl tin dilaurate: 2010 ppm | 12.5 | (Solid formation, pump clogging) |
| Example 148 | phenyl-O- | 52.0 | 2-isopropylphenol | 27 | 48 | Fe ion: 20 ppm Ni ion: 15 ppm | 88.0 | 85.0 |
| Example 149 | 2-methylphenyl-O- | 25.0 | 2-methylphenol | 65 | 73 | Dibutyl tin dilaurate: 10 ppm, Total carbonic acid ester: 0.001 | 96.0 | 91.0 |
| Example 150 | 4-propylphenyl-O- | 27.0 | 4-propylphenol; 2-benzylphenol | 50 / 15 | 35 | Butylphenyl non-N-substituted carbamate: 0.005 | 94.0 | 90.0 |

TABLE 13-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 151 | 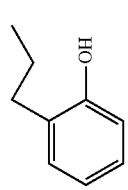 | 35.0 | 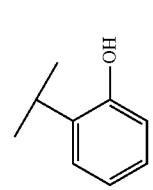 | 50 | 18 | Butylphenyl non-N-substituted carbamate: 0.005, terminal biuret group-containing compounds: 0.04, oxygen: 5 ppm | 92.0 | 88.0 |
| Example 152 | | 1.4 | | 30 | 480 | Total ureylene group-containing compounds: 0.01, dibutyl tin dilaurate: 600 ppm, water: 0.5 wt % | 60.0 | 5.6 |
| | | | | 68 | | | | |

Example 165

A composition containing 24% by weight of an N-substituted carbamic acid-O—Ar ester in the form of the N-substituted carbamic acid-O—Ar ester represented by the following formula (136), 74% by weight of an aromatic hydroxy composition in the form of 2,4,6-trimethyl phenol, 10 ppm of ammonia, 0.01 of urea (ratio of the number of urea molecules to the number of carbamic acid-O—Ar ester groups in the N-substituted carbamic acid-O—Ar ester) and 0.001 of mesityl carbamate (ratio of number of moles of mesityl carbamate to number of carbamic acid-O—Ar ester groups in the N-substituted carbamic acid-O—Ar ester) was placed in a 100 L SUS storage vessel, followed by replacing the inside of the storage vessel with nitrogen, and storing for 1095 days in a storage environment found in the Kojima district of Kurashiki City in Okayama Prefecture, Japan. During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the N-substituted carbamic acid-O—Ar ester was contained at 96 mol % as compared with prior to storage. Following the storage period, the composition was heated to 180° C. and transferred through a preheater (device for preheating the composition to 230° C.) to a thin film distiller using a liquid pump. A thermal decomposition reaction was carried out while confirming operating conditions containing a temperature of the thin film distiller of 230° C., residence time within a range of from 60 to 120 seconds, and pressure within a range of from 0.3 to 1 kPa, the gaseous phase was introduced into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of from 150 to 300° C. and confirming operating conditions; the minimum pressure during operation was about 0.3 KPa). Isocyanate derived from the N-substituted carbamic acid-O—Ar ester in the form of 2,4-diisocyanato-1-methylbenzene (2,4-TDI) was obtained from the bottom of the distillation column. Although the yield changed from the start to completion of operation due to fluctuations in operating conditions, at the highest level of performance during the operating period, the yield of the 2,4-TDI based on the N-substituted carbamic acid-O—Ar ester at the start of storage was 93 mol %. There was no clogging of lines during both storage and transport, and formation of solid within the distillation column was not observed.

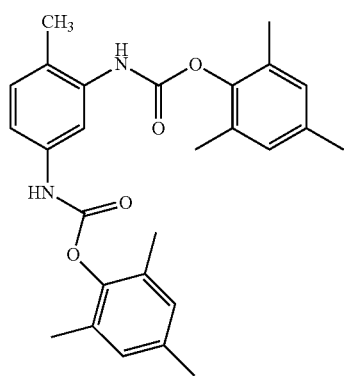

(136)

Examples 166 to 183 and Comparative Example 10

Storage and thermal decomposition were carried out on compositions under the same conditions as Example 165 with the exception of the composite ratios of the N-substituted carbamic acid-O—Ar ester, aromatic hydroxy composition, ammonia and carbonic acid derivative and the like, and the results of distillation are shown in Tables 16 to 18. When using an aromatic hydroxy compound having a standard boiling point higher than the standard boiling point of 2,4-TDI, a packed distillation column having an inner diameter of 2.5 inches and 20 theoretical plates (packing: Metal Gauze CY Packing manufactured by Sulzer Chemtech Ltd.) was installed along with the previously described distillation column, and a liquid phase extracted from the upper portion of the sieve plate distillation column was introduced into the vicinity of the middle of the packed distillation column to separate the 2,4-TDI and aromatic hydroxy compound (the yield of 2,4-TDI is shown as the value obtained by analyzing the liquid phase in the upper portion of the sieve plate distillation column; the packed distillation column was installed for the purpose of industrial purification).

In the tables, an Ar—O— group represents an Ar—O group that composes a carbamic acid-O—Ar group in the N-substituted carbamic acid-O—Ar ester (namely, the Ar—O group in the following formula (137)), and ArOH represents an aromatic hydroxy compound that composes the aromatic hydroxy composition. The content of each component in the composition is represented as a weight percentage (wt %) obtained by rounding the contents of N-substituted carbamic acid-O—Ar ester, aromatic hydroxy composition and water to the number of significant digits of the analysis apparatus or less, ammonia and metal components are expressed in ppm, while other components (such as carbonic acid derivative) are indicated as the ratio of the number of molecules to carbamic acid-O—Ar groups of the N-substituted carbamic acid-O—Ar ester. (Unless indicated otherwise, phenomena such as clogging or solid formation did not occur during storage or transfer.)

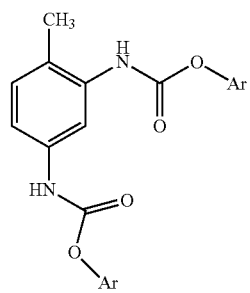

(137)

TABLE 17

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 172 | 4-isopropylphenoxy | 24.7 | 4-isopropylphenol | 73.0 | 16 | Total ureylene group-containing compounds: 0.005 | 100 | 95 |
| Example 173 | 3-isopropylphenoxy | 24.7 | 3-isopropylphenol | 75.0 | 90 | Fe ion: 5 ppm, Ni ion: 15 ppm, oxygen: 50 ppm | 97 | 92 |
| Example 174 | 2-benzylphenoxy | 32.0 | 2-benzylphenol | 68.0 | 5 | | 99 | 95 |
| Example 175 | 2-ethoxyphenoxy | 24.6 | 2-ethoxyphenol | 23.0 | 305 | Total ureylene group-containing compounds: 0.005, terminal biuret group-containing compounds: 0.005, dibutyl tin dilaurate: 60 ppm | 96 | 91 |
| | | | 4-phenoxyphenol | 50.1 | | | | |

TABLE 17-continued

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 176 | (4-phenoxyphenyl structure) | 22.0 | (4-phenoxyphenol) | 75.0 | 12 | Total ureylene group-containing compounds: 0.005, terminal biuret group-containing compounds: 0.005 | 100 | 94 |
| Example 177 | (bisphenol A structure) | 22.3 | (bisphenol A) | 76.0 | 11 | Fe ion: 5 ppm, Ni ion: 5 ppm, oxygen: 50 ppm | 97 | 31 |

Example 184

A composition containing 26% by weight of an N-substituted carbamic acid-O—Ar ester in the form of the N-substituted carbamic acid-O—Ar ester represented by the following formula (138), 67% by weight of an aromatic hydroxy composition in the form of 2,4,6-trimethyl phenol, 10 ppm of ammonia, 1 of urea (ratio of the number of urea molecules to the number of carbamic acid-O—Ar ester groups in the N-substituted carbamic acid-O—Ar ester) and 0.001 of mesityl carbamate (ratio of number of moles of mesityl carbamate to number of carbamic acid-O—Ar ester groups in the N-substituted carbamic acid-O—Ar ester) was placed in a 100 L SUS storage vessel, followed by replacing the inside of the storage vessel with nitrogen, and storing for 1095 days in a storage environment found in the Kojima district of Kurashiki City in Okayama Prefecture, Japan. During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the N-substituted carbamic acid-O—Ar ester was contained at 98 mol % as compared with prior to storage. Following the storage period, the composition was heated to 180° C. and transferred through a preheater (device for preheating the composition to 230° C.) to a thin film distiller using a liquid pump. A thermal decomposition reaction was carried out while confirming operating conditions containing a temperature of the thin film distiller of 230° C., residence time within a range of from 60 to 120 seconds, and pressure within a range of from 0.1 to 1 kPa, the gaseous phase was introduced into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of from 150 to 300° C. and confirming operating conditions; the minimum pressure during operation was about 0.5 KPa). Isocyanate derived from the N-substituted carbamic acid-O—Ar ester in the form of bis(4-isocyanatophenyl) methane was obtained from the bottom of the distillation column. Although the yield changed from the start to completion of operation due to fluctuations in operating conditions, at the highest level of performance during the operating period, the yield of the bis(4-isocyanatophenyl) methane based on the N-substituted carbamic acid-O—Ar ester at the start of storage was 97 mol %. There was no clogging of lines during both storage and transport, and formation of solid within the distillation column was not observed.

Examples 185 to 192 and Comparative Example 11

Storage and thermal decomposition were carried out on compositions under the same conditions as Example 184 with the exception of the composite ratios of the N-substituted carbamic acid-O—Ar ester, aromatic hydroxy composition, ammonia and carbonic acid derivative and the like, and the results of distillation are shown in Tables 19 and 20. When using an aromatic hydroxy compound having a standard boiling point higher than the standard boiling point of bis(4-isocyanatophenyl) methane, a packed distillation column having an inner diameter of 2.5 inches and 20 theoretical plates (packing: Metal Gauze CY Packing manufactured by Sulzer Chemtech Ltd.) was installed along with the previously described distillation column, and a liquid phase extracted from the bottom of the sieve plate distillation column was introduced into the vicinity of the middle of the packed distillation column to separate the bis(4-isocyanatophenyl) methane and aromatic hydroxy compound (the yield of bis(4-isocyanatophenyl) methane is shown as the value obtained by analyzing the liquid phase in the bottom of the sieve plate distillation column; the packed distillation column was installed for the purpose of industrial purification).

In the tables, an Ar—O— group represents an Ar—O group that composes a carbamic acid-O—Ar group in the N-substituted carbamic acid-O—Ar ester (namely, the Ar—O group in the following formula (139)), and ArOH represents an aromatic hydroxy compound that composes the aromatic hydroxy composition. The content of each component in the composition is represented as a weight percentage (wt %) obtained by rounding the contents of N-substituted carbamic acid-O—Ar ester, aromatic hydroxy composition and water to the number of significant digits of the analysis apparatus or less, ammonia and metal components are expressed in ppm, while other components (such as carbonic acid derivative) are indicated as the ratio of the number of molecules to carbamic acid-O—Ar groups of the N-substituted carbamic acid-O—Ar ester. (Unless indicated otherwise, phenomena such as clogging or solid formation did not occur during storage or transfer.)

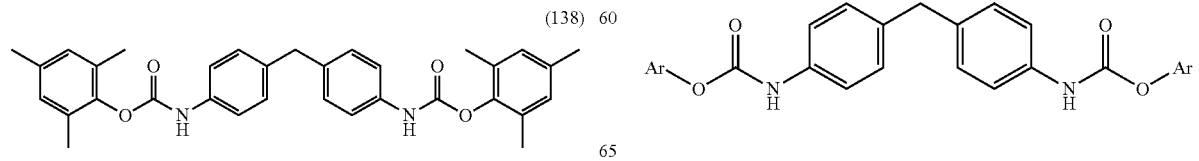

TABLE 19

| | Ar—O group | Content of N-substituted carbamic acid-O—Ar ester in composition (wt %) | ArOH | Content of aromatic hydroxy compound in composition (wt %) | Content of ammonia in composition (ppm) | Other components and contents thereof in composition (%) | Amount of N-substituted carbamic acid-O—Ar ester after storage versus before storage (mol %) | Yield of isocyanate (mol %) (molar yield versus N-substituted carbamic acid-O—Ar ester before storage) |
|---|---|---|---|---|---|---|---|---|
| Example 185 | phenyl-O- | 11.0 | phenol | 88.0 | 8 | Urea: 0.001, phenyl non-N-substituted carbamate: 0.001 | 92.2 | 87.5 |
| Comparative Example 11 | phenyl-O- | 97.6 | | | | | 12.5 | (Solid formation, pump clogging) |
| Example 186 | 2,6-dimethylphenyl-O- | 38.0 | 2,6-dimethylphenol | 61.0 | 12 | Dibutyl tin dilaurate: 2010 ppm | 97.0 | 94.5 |
| Example 187 | 2-ethoxyphenyl-O- | 22.0 | 2-ethoxyphenol | 17.0 | 29 | Total ureylene group-containing compounds: 0.005, terminal biuret group-containing compounds: 0.005 | 96.0 | 92.2 |
| | 4-phenoxyphenyl-O- | | 4-phenoxyphenol | 55.0 | | Total ureylene group-containing compounds: 0.005, terminal biuret group-containing compounds: 0.005, dibutyl tin dilaurate: 60 ppm | | |
| Example 188 | 4-(1,1,3,3-tetramethylbutyl)phenyl-O- | 23.0 | 4-(1,1,3,3-tetramethylbutyl)phenol | 74.0 | 15 | Total ureylene group-containing compounds: 0.005, terminal biuret group-containing compounds: 0.005 | 97.0 | 93.7 |

Example 193

A composition containing 36% by weight of an N-substituted carbamic acid-O—Ar ester in the form of the N-substituted carbamic acid-O—Ar ester represented by the following formula (140) (having different methylene group crosslinked positions, and having a trimer structure as shown in the following formula for the average structure thereof),

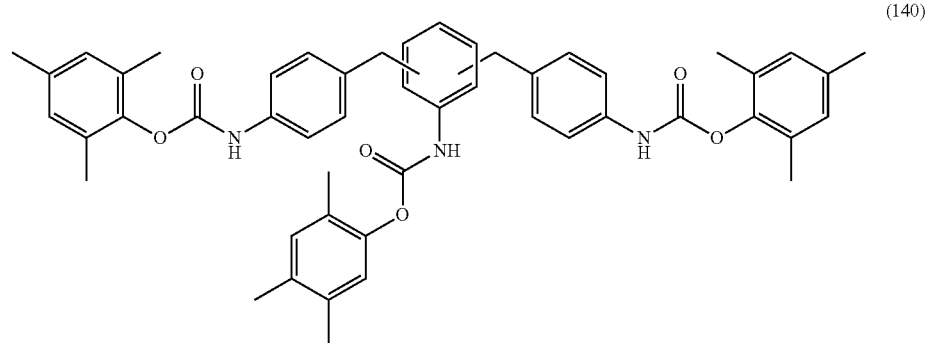

(140)

61% by weight of an aromatic hydroxy composition in the form of 2,4,6-trimethyl phenol, 10 ppm of ammonia, 0.01 of urea (ratio of the number of urea molecules to the number of carbamic acid-O—Ar ester groups in the N-substituted carbamic acid-O—Ar ester) and 0.001 of mesityl carbamate (ratio of number of moles of mesityl carbamate to number of carbamic acid-O—Ar ester groups in the N-substituted carbamic acid-O—Ar ester) was placed in a 100 L SUS storage vessel, followed by replacing the inside of the storage vessel with nitrogen, and storing for 1095 days in a storage environment found in the Kojima district of Kurashiki City in Okayama Prefecture, Japan. During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the N-substituted carbamic acid-O—Ar ester was contained at 99 mol % as compared with prior to storage. Following the storage period, the composition was heated to 180° C. and transferred through a preheater (device for preheating the composition to 230° C.) to a thin film distiller using a liquid pump. A thermal decomposition reaction was carried out while confirming operating conditions containing a temperature of the thin film distiller of 230° C., residence time within a range of from 60 to 120 seconds, and pressure within a range of from 0.1 to 1 kPa, the gaseous phase was introduced into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of 150 to 300° C. and confirming operating conditions; the minimum pressure during operation was about 0.5 KPa). Isocyanate derived from the N-substituted carbamic acid-O—Ar ester (compound in which the carbamic acid ester group of the N-substituted carbamic acid-O—Ar ester had become isocyanate groups) was obtained from the bottom of the distillation column. Although the yield changed from the start to completion of operation due to fluctuations in operating conditions, at the highest level of performance during the operating period, the yield of the isocyanate based on the N-substituted carbamic acid-O—Ar ester at the start of storage was 95 mol %. There was no clogging of lines during both storage and transport, and formation of solid within the distillation column was not observed.

Example 194

A composition containing 26% by weight of an N-substituted carbamic acid-O—Ar ester in the form of the N-substituted carbamic acid-O—Ar ester represented by the following formula (141) (having different methylene group crosslinked positions, and having a trimer structure as shown in the following formula for the average structure thereof), 72% by weight of an aromatic hydroxy composition in the form of phenol, 11 ppm of ammonia, 0.01 of urea (ratio of the number of urea molecules to the number of carbamic acid-O—Ar ester groups in the N-substituted carbamic acid-O—Ar ester) and 0.001 of phenyl carbamate (ratio of number of moles of phenyl carbamate to number of carbamic acid-O—Ar ester groups in the N-substituted carbamic acid-O—Ar ester) was placed in a 100 L SUS storage vessel, followed by replacing the inside of the storage vessel with nitrogen, and storing for 1095 days in a storage environment found in the Kojima district of Kurashiki City in Okayama Prefecture, Japan. During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the N-substituted carbamic acid-O—Ar ester was contained at 97 mol % as compared with prior to storage. Following the storage period, the composition was heated to 180° C. and transferred through a preheater (device for preheating the composition to 230° C.) to a thin film distiller using a liquid pump. A thermal decomposition reaction was carried out while confirming operating conditions containing a temperature of the thin film distiller of 230° C., residence time within a range of from 60 to 120 seconds, and pressure within a range of from 0.1 to 1 kPa, the gaseous phase was introduced into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of from 150 to 300° C. and confirming operating conditions; the minimum pressure during operation was about 0.5 KPa). Isocyanate derived from the N-substituted carbamic acid-O—Ar ester (compound in which the carbamic acid ester group of the N-substituted carbamic acid-O—Ar ester had become isocyanate groups) was obtained from the bottom of the distillation column. Although the yield changed from the start to completion of operation due to fluctuations in operating conditions, at the highest level of performance during the operating period, the yield of the isocyanate based on the N-substituted carbamic acid-O—Ar ester at the start of storage was 97 mol %. There was no clogging of lines during both storage and transport, and formation of solid within the distillation column was not observed.

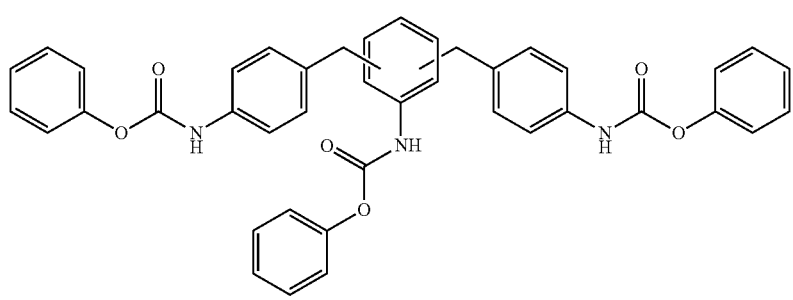

(141)

The present application claims priority based on Japanese patent applications (Japanese Patent Application No. 2009-192250 and Japanese Patent Application No. 2009-192268) filed with the Japanese Patent Office on Aug. 21, 2009, the content of which is incorporated herein by reference.

INDUSTRIAL APPLICABILITY

The production method of the present embodiment enables N-substituted carbamic acid ester to be produced without exacerbating original units of urea. In addition, since N-substituted carbamic acid ester obtained with the production method of the present embodiment is preferable as a raw material for the production of isocyanate without using extremely toxic phosgene, the production method as claimed in the present embodiment is extremely industrially useful. Moreover, according to the present invention, production of N-substituted carbamic acid ester can be realized over a long period of time by being able to avoid adhesion and accumulation of polymeric by-products to the reaction vessel during production of N-substituted carbamic acid ester, thereby having high commercial value.

DESCRIPTION OF REFERENCE NUMERICALS

[FIG. 21]
101, 104, 105: storage tank, 102: packed column, 103: condenser, 106: reboiler, 107: gas-liquid separator, 1, 2, 3, 4, 5: line
[FIG. 22]
201, 205, 204: storage tank, 202: packed column, 203: condenser, 206: reboiler, 20, 21, 22, 23: line
[FIG. 23]
301, 306, 307, 309, 313, 315: storage tank, 302, 310: packed column, 308: stirring tank, 303, 311: condenser, 305, 314: reboiler, 304, 312: gas-liquid separator, 30, 31, 32, 33, 34, 35, 36, 37, 38, 39: line

[FIG. 24]
400, 401, 402, 404, 409, 410, 413: storage tank, 403: stirring tank, 406, 411: condenser, 407: reboiler, 408, 412: gas-liquid separator, 40, 41, 42, 43, 44, 45, 46, 47, 48, 49: line, 405: packed column
[FIG. 25]
501, 506, 507, 508, 510, 514, 516: storage tank, 502, 511: packed column, 509: stirring tank, 503, 512: condenser, 505, 515: reboiler, 504, 513: gas-liquid separator, 50, 51, 52, 53, 54, 55, 56, 57, 58, 59, 60, 61: line
[FIG. 26]
600, 601, 602, 604, 609, 610, 613: storage tank, 603: stirring tank, 606, 611: condenser, 605: packed column, 607: reboiler, 608, 612: gas-liquid separator, 60, 61, 62, 63, 64, 65, 66, 67, 68, 69: line

Figure 27:
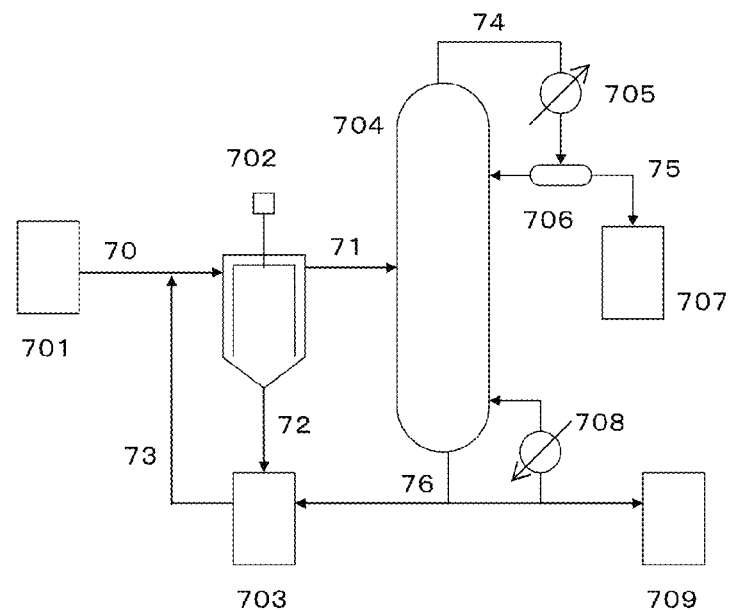
FIG. 27 shows a conceptual drawing of an isocyanate production apparatus used in an example of the present embodiment.
Figure 28:
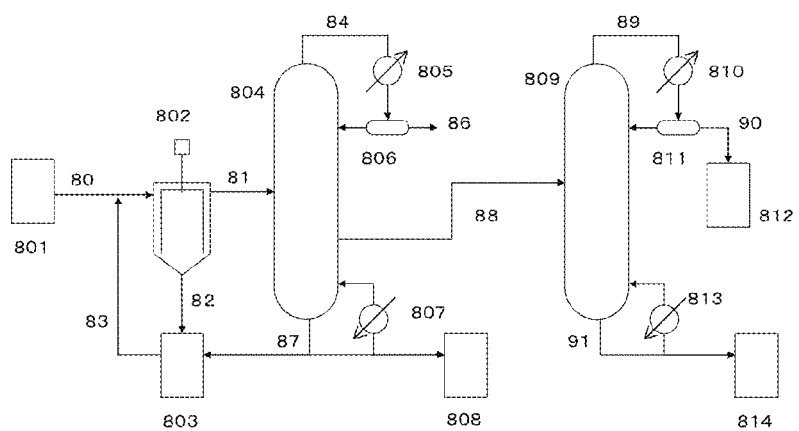
FIG. 28 shows a conceptual drawing of an isocyanate production apparatus used in an example of the present embodiment.
Figure 29:
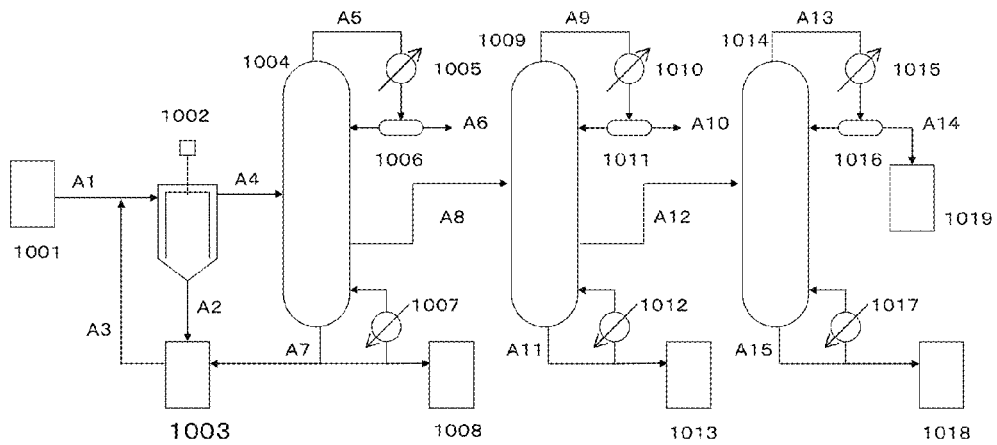
FIG. 29 shows a conceptual drawing of an isocyanate production apparatus used in an example of the present embodiment.

[FIG. 27]
701, 703, 707, 709: storage tank, 702: thin film evaporator, 704: packed column, 705: condenser, 706: gas-liquid separator, 708: reboiler, 70, 71, 72, 73, 74, 75, 76: line
[FIG. 28]
801, 803, 808, 812, 814: storage tank, 802: thin film evaporator, 804, 809: packed column, 805, 810: condenser, 807, 813: reboiler, 806, 811: gas-liquid separator, 80, 81, 82, 83, 84, 86, 87, 88, 89, 90, 91: line
[FIG. 29]
1001, 1003, 1008, 1013, 1018, 1019: storage tank, 1002: thin film evaporator, 1004, 1009, 1014: distillation column, 1108: stirring tank, 1005, 1010, 1015: condenser, 1007, 1012, 1017: reboiler, 1006, 1011, 1016: gas-liquid separator, A1, A2, A3, A4, A5, A6, A7, A8, A9, A10, A11, A12, A13, A14, A15: line
[FIG. 30]
1100, 1101, 1102, 1104, 1107, 1110: storage tank, 1108: stirring tank, 1105: condenser, 1106: gas-liquid separator, B0, B1, B2, B3, B4, B5, B6: line
[FIG. 31]
1201, 1204, 1205: storage tank, 1202: packed column, 1203: condenser, 1206: reboiler, 1207: gas-liquid separator, C1, C2, C3, C4: line

We claim:
1. A method for producing an isocyanate, comprising: recovering an isocyanate and an aromatic hydroxy compound formed by subjecting an N-substituted carbamic acid-O—Ar ester to a thermal decomposition reaction, wherein the N-substituted carbamic acid-O—Ar ester is represented by the following formula (2)

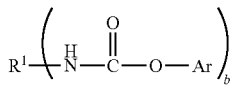

formula (2)

wherein:
R¹ represents an organic group which has 1 to 85 carbon atoms and which is substituted with amino groups,
Ar represents a group derived from an aromatic hydroxy compound that is a residue in which a single hydroxy group bonded to an aromatic ring of the aromatic hydroxy compound has been removed, and
b represents an integer of from 1 to 10; or
wherein the N-substituted carbamic acid-O—Ar ester is represented by the following formula (11)

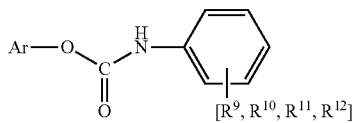

formula (11)

wherein:
R⁹ to R¹² may respectively and independently substitute the aromatic ring, R⁹ to R¹² may mutually bond to form a ring with the aromatic ring, and represent a hydrogen atom or a group composed of groups in which an alkyl group, cycloalkyl group, aryl group or group selected from the group consisting of these groups is bonded by saturated hydrocarbon bonds and/or ether bonds, and
Ar represents a group derived from an aromatic hydroxy compound that is a residue in which a single hydroxy group bonded to an aromatic ring of the aromatic hydroxy compound has been removed.

2. A method for producing an isocyanate, comprising: recovering an isocyanate and an aromatic hydroxy compound formed by transferring a composition for transfer and storage of an N-substituted carbamic acid-O—Ar ester to a thermal decomposition reaction vessel, and subjecting the N-substituted carbamic acid ester to a thermal decomposition reaction,
wherein the N-substituted carbamic acid-O—Ar ester is represented by the following formula (6)

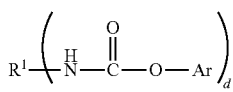

formula (6)

wherein:
R¹ represents an organic group which has 1 to 85 carbon atoms and which is substituted with amino groups,
Ar represents a residue in which a single hydroxy group bonded to an aromatic ring of an aromatic hydroxy compound has been removed from the aromatic hydroxy compound, wherein the aromatic hydroxy compound may be the same or different from the aromatic hydroxy compound that composes the aromatic hydroxy composition), and
d represents an integer of from 1 to 10.

3. The method according to claim 1, wherein the recovered aromatic hydroxy compound is reused.

4. The production method according to claim 1, wherein a residual liquid containing unreacted N-substituted carbamic acid-O—Ar ester recovered from a bottom of the thermal decomposition reaction vessel is again transferred to the thermal decomposition reaction vessel, and the N-substituted carbamic acid-O—Ar ester is subjected to a thermal decomposition reaction.

5. The production method according to claim 1, wherein the isocyanate produced in the production method according to claim 1 contains 1 to 1000 ppm of the aromatic hydroxy compound that composes the aromatic hydroxy composition based on the isocyanate.

6. A method for producing an isocyanate, comprising: recovering an isocyanate and an aromatic hydroxy compound formed by subjecting an N-substituted carbamic acid-O—Ar ester to a thermal decomposition reaction,
wherein the N-substituted carbamic acid-O—Ar ester is represented by the following formula (5)

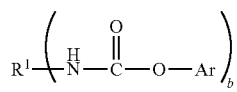

formula (5)

wherein:
R¹ represents an organic group which has 1 to 85 carbon atoms and which is substituted with amino groups,
Ar represents a residue in which a single hydroxy group bonded to an aromatic ring of an aromatic hydroxy compound has been removed from the aromatic hydroxy compound, wherein the aromatic hydroxy compound may be the same or different from the aromatic hydroxy compound that composes the aromatic hydroxy composition), and
b represents an integer of from 1 to 10.

7. The method according to claim 1, wherein the N-substituted carbamic acid-O—Ar ester is represented by the formula (11).

8. A method for producing an isocyanate, comprising: recovering an isocyanate and an aromatic hydroxy compound formed by subjecting the N-substituted carbamic acid-O—Ar ester to a thermal decomposition reaction,
wherein the N-substituted carbamic acid-O—Ar ester is represented by the following formula (14)

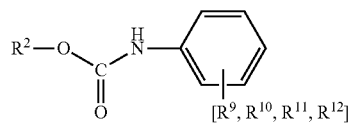

formula (14)

wherein:
R⁹ to R¹² may respectively and independently substitute the aromatic ring, R⁹ to R¹² may mutually bond to form a ring with the aromatic ring, and represent hydrogen atoms or groups composed of groups in which an alkyl group, cycloalkyl group, aryl group or group selected from the group consisting of these groups is bonded by saturated hydrocarbon bonds and/or ether bonds, $R^2$ represents a group derived from an alcohol that is a residue in which a single hydroxy group bonded to a saturated carbon atom of the alcohol has been removed from the alcohol, and Ar represents a group derived from an aromatic hydroxy compound that is a residue in which a single hydroxy group bonded to an aromatic ring of the aromatic hydroxy compound has been removed from the aromatic hydroxy compound.

9. The method according to claim 2, wherein the recovered aromatic hydroxy compound is reused.

10. The method according to claim 2, wherein a residual liquid containing unreacted N-substituted carbamic acid-O—Ar ester recovered from a bottom of the thermal decomposition reaction vessel is again transferred to the thermal decomposition reaction vessel, and the N-substituted carbamic acid-O—Ar ester is subjected to a thermal decomposition reaction.

11. The method according to claim 2, wherein the isocyanate produced in the production method contains 1 to 1000 ppm of the aromatic hydroxy compound that comprises the aromatic hydroxy composition based on the isocyanate.

* * * * *